United States Patent
Caulfield et al.

(10) Patent No.: US 8,569,535 B2
(45) Date of Patent: Oct. 29, 2013

(54) SUBSTITUTED BENZOYLAMINO-INDAN-2-CARBOXYLIC ACIDS AND RELATED COMPOUNDS

(75) Inventors: Thomas Joseph Caulfield, Lebanon, NJ (US); Jennifer Williford Clemens, Somerset, NJ (US); Robert S. Francis, Easton, PA (US); Brian Scott Freed, Phillipsburg, NJ (US); Stanly John, Basking Ridge, NJ (US); Tieu-Binh Le, Bridgewater, NJ (US); Brian Pedgrift, Flemington, NJ (US); Antonio Daniel Ramos, Flemington, NJ (US); Gerard Charles Rosse, Exton, PA (US); Martin Smrcina, Tucson, AZ (US); David Squire Thorpe, Tucson, AZ (US); William Shelly Wire, Tucson, AZ (US); Jianhong Zhao, Annadale, NJ (US)

(73) Assignee: Sanofi, Paris (FR)

( * ) Notice: Subject to any disclaimer, the term of this patent is extended or adjusted under 35 U.S.C. 154(b) by 222 days.

(21) Appl. No.: 12/627,546

(22) Filed: Nov. 30, 2009

(65) Prior Publication Data
US 2010/0113462 A1   May 6, 2010

Related U.S. Application Data

(63) Continuation of application No. PCT/US2008/065711, filed on Jun. 4, 2008.

(60) Provisional application No. 60/942,169, filed on Jun. 5, 2007.

(51) Int. Cl.
C07C 229/00 (2006.01)

(52) U.S. Cl.
USPC .......................................................... 560/44

(58) Field of Classification Search
None
See application file for complete search history.

(56) References Cited

U.S. PATENT DOCUMENTS

2009/0018145 A1* 1/2009 Kanne et al. ............. 514/255.06

FOREIGN PATENT DOCUMENTS

| FR | 2701480 | | 8/1994 |
| WO | WO 98/53818 | | 12/1998 |
| WO | WO 2005044975 | * | 4/2006 |
| WO | WO 2008/151211 A1 | | 12/2008 |

OTHER PUBLICATIONS

Lohmar al. (STN abstract, Accession No. 1981:156251 of Chemische Berichte, 1980, 113(12), 3706).*
Lohmar al. (Chemische Berichte, 1980, 113(12), 3706).*
Silverman (The Organic Chemistry of Drug Design and Drug Action, 1992, Academic Press Inc.).*
Bundgaard, H., et. al., (C) Means to Enhance Penetration, Advanced Drug Delivery Reviews, vol. 8, (1992), pp. 1-38.
Dorner, T., et al., Crossroads of B Cell Activation in Autoimmunity: Rationale of Targeting B Cell Rheumatol Suppl., (2006), vol. 77, pp. 3-11.
Farooq O., et. al., Oxidation of Aromatic 1,2-Dimethanols by Activated Dimethyl Sulfoxide, Synthesis, (1994), pp. 1035-1036.
Hennessy, E. J., et. al., Synthesis of 4,5-Dianilinophthalimide and Related Analogues for Potential Treatment of Alzheimer's Disease Via Palladium-Catalyzed Amination, J. Org. Chem., vol. 70, pp. 7371-7375, (2005).
Krumbholz, M., et. al., Chemokines in Multiple Sclerosis: CXCL12 and CXCL13 Up-Regulation is Differently Linked to CNS Immune Cell Recruitment, Brain, (2006), vol. 129, pp. 200-211.
Levy, L. A., et. al., The Synthesis of 2,3,6,7-Tetrasubstituted Naphthalenes: 2,3.6,7-Tetrachloronaphthalene, Synthetic Communications, vol. 13, No. 8, pp. 639-648, (1983).
Lohmar, R., et. al., Synthese Symmetrischer Ketone Unter Verwendung Von 2-Phenyl-2-Oxazolin-5-on, Chemische Berichte, vol. 113, No. 12, pp6. 3706-3715, (1980).
Meijer, J., et. al., The CXCR5 Chemokine Receptor is Expressed by Carcinoma Cells and Promotes Growth of Colon Carcinoma in the Liver, Cancer Res., (2006), vol. 66, No. 19, pp. 9576-9582.
Rice, J. E., et. al., Synthesis of Fluorinated Derivatives of Benzo[k]Fluoranthene and Indeno[1,2,3-cd] Pyrene and 8,9-Dihydro-8,9-Epoxybenzo[k]Fluoranthene. J. Org. Chem., (1988), vol. 53, pp. 1775-1779.
Rosowsky, A., et. al., Analogues of Na—(4-Amino-4-Deoxypteroyl)-N6-Hemiphthaloyl-L-Omithine (PT523) Modified in the Side Chain: Synthesis and Biological Evaluation, J. Med. Chem., (1997), vol. 40, pp. 286-299.
Saito, R., et. al., Altered Expression of Chemokine Receptor CXCR5 on T Cells of Myasthenia Gravis Patients, Journal of Neuroimmunology, vol. 170, pp. 172-178, (2005).
Aitken, R. A., et, al., Flash Vacuum Pyrolysis Over Magnesium. Part 1. Pyrolysis of Benzylic, Other Aryl/Alkyl and Aliphatic Halides, J. Chem. Soc., Perkin Trans. 1, (2002), pp. 402-415.

(Continued)

*Primary Examiner* — Johann R Richter
*Assistant Examiner* — Jennifer C Sawyer
(74) *Attorney, Agent, or Firm* — Ronald G. Ort

(57) ABSTRACT

The present invention relates to novel compounds of the formula Ia:

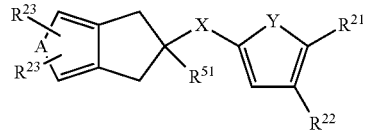

in any of its stereoisomeric forms or a mixture of stereoisomeric forms in any ratio, or a physiologically acceptable salt thereof, wherein the substituents are as described herein. The inventive compounds have CXCR5 inhibitory activity, and are particularly useful in treating or preventing various inflammatory diseases, such as rheumatoid arthritis, multiple sclerosis, lupus, Crohn's Disease, associated with the modulation of the human CXCR5 receptor.

20 Claims, No Drawings

(56) References Cited

OTHER PUBLICATIONS

Schmutz, C., et al., Chemokine Receptors in the Rheumatoid Synovium: Upregulation of CXCR5, Arthritis Research & Therapy, vol. 7, No. 2, pp. R217-229, (2005).

Amft, N., et. al., Ectopic Expression of the B Cell-Attracting Chemokine BCA-1 (CXCL13) On Endothelial Cells and Within Lymphoid Follicles Contributes to the Establishment of Germinal Center-Like Structures in Structures in Sjogren's Syndrome, Arthritis & Rheumatism, (2001), pp. 2633-2641, vol. 44, No. 11.

Nielsen, N. M., et. al., Glycolamide Esters as Biolabile Prodrugs of Carboxylic Acid Agents: Synthesis, Stability, Bioconversion, and Physicochemical Properties, Journal of Pharmaceutical Sciences, vol. 77. No. 4, (1988), pp. 285-298.

Kakeya, N., et. al., Studies on Prodrugs of Cephalosporins. I. Synthesis and Biological Properties of Glycyloxybenzoyloxymethyl and Glycylaminobenzoyloxymethyl Esters of 7B-[2-(2-Aminothiazol-4-yl)(2)-2-Methoxylminoacetamido]-3-Methyl-3-Cephem-4-Carboxylic Acid, Chem. Pharm. Bull., vol. 32, No. 2, pp. 692-698, (1984).

Bird, R. F., et. al., The Reduction of 3-Chlorophthalic Acid and of its Three Methyl Esters, J. Chem. Soc., (1952), pp. 5050-5051.

Lyon, D. R., et. al., The Preparation and Properties of 2-Substituted IsoArsindolines and of As-Spiro-Bisisoarsindolinium Salts, J. Chem. Soc., (1947), pp. 662-670.

* cited by examiner

SUBSTITUTED BENZOYLAMINO-INDAN-2-CARBOXYLIC ACIDS AND RELATED COMPOUNDS

FIELD OF THE INVENTION

The present invention is directed to substituted benzoylamino-indan-2-carboxylic acids and related compounds and intermediates thereto, their preparation including stereoselective synthetic processes to intermediates, pharmaceutical compositions containing the compounds, and the use of the compounds or compositions thereof having the ability to block the CXCR5 receptor and inhibit B cell function associated with receptor activation. The compounds having CXCR5 inhibitory activity are particularly useful in treating or preventing various inflammatory diseases, such as rheumatoid arthritis, multiple sclerosis, lupus, Crohn's Disease, associated with the modulation of the human CXCR5 receptor.

BACKGROUND OF THE INVENTION

CXCR5 is a non-promiscuous chemokine receptor belonging to the family of G-Coupled Protein receptors (GPCRs). Specifically, the CXCR5 receptor interacts with its CXCL13 ligand—which is constitutively expressed on stromal cells, such as follicular dendritic cells, and in lymphoid tissues. The CXCL13 ligand specifically attracts B cells and a small subset of T cells called B helper follicular T cells ($T_{FH}$). When the CXCR5/CXCL13 interaction is blocked by an antagonist, patients with Rheumatoid Arthritis (RA) and other autoimmune or inflammatory diseases in which the up-regulation of CXCR5 and/or its ligand CXCL13 are responsible for the pathogenesis or exacerbation of the disease, can be treated. While B cell depletion therapy with anti-CD20 monoclonal antibody (Rituximab) has shown as efficacious in the treatment of RA, blocking of B cells, such as CXCR5-expressing cells, is known to be of therapeutic benefit in experimental murine models of arthritis.

Furthermore, CXCR5 and/or CXCL13 is known to be up-regulated in patients with Rheumatoid Arthritis [*Arthritis Res Ther.* 2005; 7(2):R217-29. Epub 2004 Dec. 16.], Sjogren's syndrome [*Arthritis Rheum.* 2001 November; 44(11):2633-41.], myasthenia gravis [*J Neuroimmunol.* 2005 Dec. 30; 170(1-2):172-8. Epub 2005 Oct. 7] and multiple sclerosis [*Brain.* 2006 January; 129(Pt 1):200-11. Epub 2005 Nov. 9]. A linkage between CXCR5 and pancreatic carcinoma [*Cancer Res.* 2006 Oct. 1; 66(19):9576-82.] is also known. By blocking the receptor/ligand interaction with a CXCR5 antagonist, therapeutic benefits can be realized in the diseases mentioned above, and in other diseases in which B cell infiltration (or other lymphocyte subsets expressing the CXCR5 receptor) is responsible for the pathogenesis of the disease [*Front Biosci.* 2007 Jan. 1; 12:2194-2006, *J Rheumatol Suppl.* 2006 May; 77:3-11].

Infiltration of lymphocytes into tertiary ectopic germinal centers (GCs) is known to correlate well with increased disease severity and tolerance breakdown. By using in vivo murine models, such as CXCR5$^{-/-}$ and CXCL13$^{-/-}$ mice, for example, the absence of either the receptor or the ligand, results in an altered GC fine architecture caused by changed T and B cell localization. These mice are known to be protected against developing severe collagen-induced arthritis (CIA). Thus, since CXCR5 is selectively expressed on mature B cells, which are linked to the pathogenesis of RA, an antagonist that capable of blocking this receptor can modulate the arthritogenic response in affected individuals. Presently, Rheumatoid arthritis treatment with anti-CD20 antibodies has shown to be clinically effective; such as with patients on B cell directed therapy, who have shown long-lasting improvements in clinical signs and symptoms. The selective targeting of CXCR5, which is only expressed on mature B cells and B helper T cells is, therefore, not expected to affect B cell development or immuno-compromise the patient Thus, an unmet need exists for CXCR5 antagonists for treatment of Rheumatoid Arthritis and other inflammatory, autoimmune diseases and cancers caused by the interaction of B cells expressing CXCR5 in response to CXCL13 expression.

SUMMARY OF THE INVENTION

The present invention is directed to antagonist compounds of the formula I, which have been found to block B cell migration in response to a ligand gradient, without peripheral B cell depletion. These compounds, therefore, provide a safety profile for the long-term treatment of inflammatory diseases.

The present invention relates to novel compounds of the formula I:

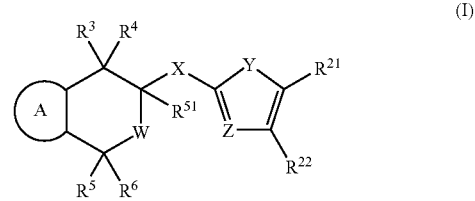

wherein:
ring A is a benzene ring or a monocyclic 5-membered or 6-membered aromatic heterocyclic ring comprising 1 or 2 identical or different hetero ring members chosen from the group consisting of N, N($R^1$), O and S, which rings can all be substituted by one or more identical or different substituents chosen from the group consisting of halogen, ($C_1$-$C_4$)-alkyl, ($C_1$-$C_4$)-alkyloxy, ($C_1$-$C_4$)-alkyl-S(O)$_m$—, cyano and nitro;
W is chosen from the group consisting of a bond or CH2;
X is chosen from the group consisting of N($R^7$)C═O, N($R^7$)S(O)$_m$, N($R^7$)C$R^8$($R^9$), C═ON($R^7$), S(O)$_m$N($R^7$), C$R^8$($R^9$)N($R^7$), C$R^8$($R^9$)N($R^7$)C═O, C$R^8$($R^9$)N($R^7$)S(O)$_m$;
Y is chosen from the group consisting of N($R^{11}$), S, O, C($R^{12}$)═C($R^{13}$), N═C($R^{14}$) and C($R^{15}$)═N;
C($R^{12}$)═C($R^{13}$) can be a 5-7 membered carbocycle or heterocycle with any substitution;
Z is chosen from the group consisting of N and C($R^{16}$);
$R^1$ is chosen from the group consisting of hydrogen and ($C_1$-$C_4$)-alkyl;
$R^3$ and $R^4$ are independently of each other chosen from the group consisting of hydrogen, ($C_1$-$C_4$)-alkyl;
$R^5$ and $R^6$ are independently of each other chosen from the group consisting of hydrogen and ($C_1$-$C_4$)-alkyl;
$R^7$ is chosen from the group consisting of hydrogen, ($C_1$-$C_4$)-alkyl and ($C_1$-$C_6$)-cycloalkyl;
$R^8$ and $R^9$ are independently of each other chosen from the group consisting of hydrogen and ($C_1$-$C_4$)-alkyl or together as ($C_1$-$C_6$)-cycloalkyl;
$R^{11}$ is chosen from the group consisting of hydrogen, ($C_1$-$C_{10}$)-alkyl, hydroxy-($C_1$-$C_{10}$)-alkyl-, ($C_1$-$C_{10}$)-alkyloxy, ($C_1$-$C_{10}$)-alkyl-S(O)$_m$—, ($C_1$-$C_{10}$)-alkylcarbonyl-, amino, ($C_1$-$C_{10}$)-alkylamino, di(($C_1$-$C_{10}$)-alkyl)amino;

$R^{12}$, $R^{15}$ and $R^{16}$ are independently of each other chosen from the group consisting of hydrogen, halogen, $(C_1-C_{10})$-alkyl, hydroxy-$(C_1-C_{10})$-alkyl-, $(C_1-C_{10})$-alkyloxy, $(C_1-C_{10})$-alkyl-S(O)$_m$—, cyano, $(C_1-C_{10})$-alkylcarbonyl-, amino, $(C_1-C_{10})$-alkylamino, di($(C_1-C_{10})$-alkyl)amino and nitro;

$R^{13}$, $R^{14}$, $R^{21}$ and $R^{22}$ are independently of each other chosen from the group consisting of hydrogen, halogen, $(C_1-C_4)$-alkyl, hydroxy-$(C_1-C_3)$-alkyl-, $(C_1-C_3)$-alkyloxy, $(C_1-C_3)$-alkyl-S(O)$_m$—, cyano, $(C_1-C_2)$-alkylcarbonyl-, amino, $(C_1-C_3)$-alkylamino, di($(C_1-C_3)$-alkyl)amino and nitro;

provided that the total number of C, N, O and S atoms which is present in any one of the groups $R^{13}$, $R^{14}$, $R^{21}$ and $R^{22}$, does not exceed 4;

$R^{51}$ is chosen from the group consisting of COOR$^{52}$, CONR$^{53}$($R^{54}$), and 5-6 membered heterocycles containing 3 or more heteroatoms;

$R^{52}$ is chosen from the group consisting of hydrogen and $(C_1-C_4)$-alkyl;

$R^{53}$ is chosen from the group consisting of hydrogen, hydroxyl, $(C_1-C_4)$-alkyloxy, $(C_1-C_4)$-alkyl, cyano and $R^{55}$—SO$_2$—;

$R^{54}$ is chosen from the group consisting of hydrogen, $(C_1-C_4)$-alkyl, $(C_1-C_2)$-alkylcarbonyl-, $(C_1-C_3)$-alkyl-S(O)$_m$—;

$R^{55}$ is chosen from the group consisting of $(C_1-C_4)$-alkyl and phenyl;

$R^{61}$ is chosen from the group consisting of hydrogen and $(C_1-C_4)$-alkyl;

$R^{62}$ is chosen from the group consisting of hydrogen and $(C_1-C_4)$-alkyl;

heteroaryl is a monocyclic 5-membered or 6-membered aromatic heterocyclic ring which comprises 1, 2 or 3 identical or different hetero ring members chosen from the group consisting of N, N($R^{61}$), O and S;

heterocyclyl is a monocyclic 4-membered to 7-membered heterocyclic ring which comprises 1 or 2 identical or different hetero ring members chosen from the group consisting of N, N($R^{62}$), O, S, SO and SO$_2$ but two hetero ring members from the series consisting of N($R^{62}$), O and S cannot be present in adjacent ring positions, which ring is saturated or partially unsaturated and can be substituted by one or more identical or different substituents chosen from the group consisting of $(C_1-C_4)$-alkyl;

m is an integer chosen from the group consisting of 0, 1 and 2, where all numbers m are independent of each other and can be identical or different;

all phenyl and heteroaryl groups in the compound of the formula Ia can independently of each other be substituted by one or more identical or different substituents chosen from the group consisting of halogen, $(C_1-C_4)$-alkyl, $(C_1-C_4)$-alkyloxy, $(C_1-C_4)$-alkylsulfonyl and cyano;

all alkyl groups in the compound of the formula Ia can independently of each other be substituted by one or more fluorine atoms;

in any of its stereoisomeric forms or a mixture of stereoisomeric forms in any ratio, or a physiologically acceptable salt thereof.

DETAILED DESCRIPTION OF THE INVENTION

The contents of each of the patent documents and other references cited herein are herein incorporated by reference in their entirety.

In a particular embodiment, the present invention includes the compound of formula Ia wherein:

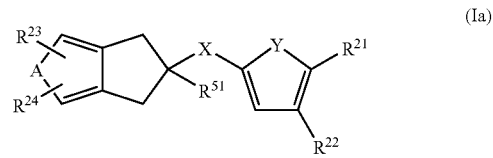

wherein:

A is CH═CH or S;

$R^{23}$ is hydrogen, halogen, $(C_1-C_4)$-alkyl, $(C_1-C_4)$-alkyloxy, $(C_1-C_4)$-alkyl-S—, or nitro;

$R^{24}$ is hydrogen or halogen when A is CH═CH, or is hydrogen, halogen, $(C_1-C_4)$-alkyl, $(C_1-C_4)$-alkyloxy, $(C_1-C_4)$-alkyl-S—, or nitro when A is S;

X is N(H)C═O, N(H)S(O)$_2$, C═ON(H), or S(O)$_2$N(H);

Y is N($R^{11}$), S, O, C($R^{12}$)═C($R^{13}$), N═C($R^{14}$), or C($R^{15}$)═N, or fused optionally substituted 5-7 membered carbocyclyl;

$R^{11}$ is hydrogen, $(C_1-C_{10})$-alkyl, hydroxy-$(C_1-C_{10})$-alkyl-, $(C_1-C_{10}$-alkyloxy, $(C_1-C_{10})$-alkyl-S(O)$_m$—, $(C_1-C_{10}$-alkylcarbonyl-, phenyl, amino, $(C_1-C_{10}$-alkylamino, or di($(C_1-C_{10}$-alkyl)amino;

$R^{12}$ is hydrogen, halogen, $(C_1-C_{10}$-alkyl, $(C_2-C_{10})$-alkenyl, $(C_3-C_6)$-cycloalkyloxy, $(C_3-C_{10})$-cycloalkenyloxy, $(C_3-C_6)$-cycloalkyl, $(C_3-C_{10})$-cycloalkenyl, $(C_3-C_6)$-cycloalkyl[$(C_1-C_4)$-alkyl or $(C_2-C_4)$-alkenyl], $(C_3-C_6)$-cycloalkyl$(C_1-C_4)$-alkyloxy, hydroxy-$(C_1-C_{10}$-alkyl-, $(C_1-C_{10}$-alkyloxy, $(C_2-C_{10})$-alkenyloxy, $(C_1-C_{10})$-alkyl-S—, cyano, $(C_1-C_{10})$-alkylcarbonyl-, phenyl, or nitro;

$R^{13}$ is hydrogen, halogen, or $(C_1)$-alkyl;

$R^{14}$ is hydrogen, halogen, $(C_1-C_4)$-alkyl, hydroxy-$(C_1-C_3)$-alkyl-, $(C_1-C_3)$-alkyloxy, $(C_1-C_3)$-alkyl-S(O)$_m$—, cyano, $(C_1-C_2)$-alkylcarbonyl-, amino, $(C_1-C_3)$-alkylamino, di($(C_1-C_3)$-alkyl)amino or nitro, provided that the total number of C, N, O and S atoms which is present in $R^{14}$ does not exceed 4;

$R^{15}$ is hydrogen, halogen, $(C_1-C_{10})$-alkyl, $(C_2-C_{10})$-alkenyl, $(C_3-C_6)$-cycloalkyl, $(C_3-C_6)$-cycloalkenyl, $(C_3-C_6)$-cycloalkyl[$(C_1-C_4)$-alkyl or $(C_2-C_4)$-alkenyl], hydroxy-$(C_1-C_{10})$-alkyl-, cyano, $(C_1-C_{10})$-alkylcarbonyl-, phenyl, amino, [$(C_1-C_{10})$-alkyl or $(C_2-C_{10})$-alkenyl]amino, [$(C_1-C_{10})$-alkyl or $(C_2-C_{10})$-alkenyl]($(C_1-C_{10})$-alkyl)amino or nitro;

$R^{21}$ is hydrogen when Y is C($R^{12}$)═C($R^{13}$), N═C($R^{14}$), C($R^{15}$)═N, and is hydrogen, halogen, $(C_1-C_4)$-alkyl, hydroxy-$(C_1-C_3)$-alkyl-, $(C_1-C_3)$-alkyloxy, $(C_1-C_3)$-alkyl-S(O)$_m$—, cyano, $(C_1-C_2)$-alkylcarbonyl-, amino, $(C_1-C_3)$-alkylamino, di($(C_1-C_3)$-alkyl)amino or nitro when Y is N($R^{11}$), S, or O, provided that the total number of C, N, O and S atoms which is present in $R^{21}$ does not exceed 4;

$R^{22}$ is hydrogen, halogen, $(C_1)$-alkyl when Y is C($R^{12}$)═C($R^{13}$), N═C $R^{14}$), or C($R^{15}$)═N, or is hydrogen, hydroxy-$(C_1-C_3)$-alkyl-, $(C_1-C_3)$-alkyloxy, $(C_1-C_3)$-alkyl-S(O)$_m$—, cyano, $(C_1-C_2)$-alkylcarbonyl-, amino, $(C_1-C_3)$-alkylamino, di($(C_1-C_3)$-alkyl)amino or nitro when Y is N($R^{11}$), S, or O, provided that the total number of C, N, O and S atoms which is present in $R^{22}$ does not exceed 4;

$R^{51}$ is COOH or CONH($R^{53}$);

$R^{53}$ is $R^{55}$—SO$_2$— or tetrazolyl;

$R^{55}$ is $(C_1-C_4)$-alkyl or phenyl optionally substituted by one or more identical or different substituents chosen from the group consisting of halogen, $(C_1-C_4)$-alkyl, $(C_1-C_4)$-alkyloxy, $(C_1-C_4)$-alkyl-sulfonyl and cyano; and m is 0, 1, or 2;
  wherein all phenyl groups herein can independently of each other be optionally substituted by one or more identical or different substituents chosen from the group consisting of halogen, $(C_{1-4})$-alkyl, $(C_{1-4})$-alkyloxy, $(C_{1-4})$-alkylsulfonyl and cyano;
  wherein all alkyl groups herein can independently of each other be optionally substituted by one or more fluorine atoms; or
  a stereoisomeric form thereof, mixture of stereoisomeric forms thereof in any ratio, or a physiologically acceptable salt thereof.

Another particular embodiment according to the invention is the compound according to formula Ia wherein
  $R^{23}$ is hydrogen, halogen, $(C_1-C_4)$-alkyl, or $(C_1-C_4)$-alkyloxy;
  $R^{24}$ is hydrogen or halogen when A is CH=CH, or is hydrogen, halogen, or $(C_1-C_4)$-alkyl when A is S;
  X is N(H)C=O, N(H)S(O)$_2$, or C=ON(H);
  Y is $C(R^{12})$=$C(R^{13})$, or $C(R^{15})$=N, or fused optionally substituted 5-6 membered carbocyclyl;
  $R^{12}$ is $(C_1-C_6)$-alkyl, $(C_3-C_6)$-alkenyl, $(C_4-C_6)$-cycloalkyloxy, $(C_5-C_6)$-cycloalkyl, $(C_5-C_6)$-cycloalkenyl, $(C_3)$-cycloalkyl[$(C_2)$-alkyl or $(C_2)$-alkenyl], $(C_3)$-cycloalkyl$(C_1)$-alkyloxy, $(C_3-C_4)$-alkyloxy, $(C_3)$-alkenyloxy, $(C_1-C_3)$-alkyl-S—, or $(C_3)$-alkylcarbonyl-, phenyl;
  $R^{13}$ is hydrogen, halogen, or $(C_1)$-alkyl;
  $R^{15}$ is $(C_1-C_6)$-alkyl, $(C_2-C_6)$-alkenyl, or [$(C_2-C_3)$-alkyl or $(C_3)$-alkenyl]$((C_1)$-alkyl)amino;
  $R^{21}$ is hydrogen when Y is $C(R^{12})$=$C(R^{13})$, or $C(R^{15})$=N;
  $R^{22}$ is hydrogen or halogen, $(C_1)$-alkyl when Y is $C(R^{12})$=$C(R^{13})$, or $C(R^{15})$=N;
  $R^{51}$ is COOH;
  wherein all phenyl groups herein can independently of each other be optionally substituted by one or more identical or different substituents chosen from the group consisting of halogen, $(C_{1-4})$-alkyl, $(C_{1-4})$-alkyloxy, $(C_{1-4})$-alkylsulfonyl and cyano;
  wherein all alkyl groups herein can independently of each other be optionally substituted by one or more fluorine atoms; or
  a stereoisomeric form thereof, mixture of stereoisomeric forms thereof in any ratio, or a physiologically acceptable salt thereof.

Another particular embodiment according to the invention is the compound according to formula Ia wherein
  A is CH=CH.

Another particular embodiment according to the invention is the compound according to formula Ia wherein
  $R^{23}$ is hydrogen or halogen.

Another particular embodiment according to the invention is the compound according to formula Ia wherein
  $R^{24}$ is hydrogen or halogen when A is CH=CH;

Another particular embodiment according to the invention is the compound according to formula Ia wherein
  X is N(H)C=O.

Another particular embodiment according to the invention is the compound according to formula Ia wherein
  Y is $C(R^{12})$=$C(R^{13})$.

Another particular embodiment according to the invention is the compound according to formula Ia wherein
  Y is $C(R^{15})$=N.

Another particular embodiment according to the invention is the compound according to formula Ia wherein
  Y is fused optionally substituted 5-6 membered carbocyclyl.

Another particular embodiment according to the invention is the compound according to formula Ia wherein
  $R^{12}$ is $(C_4-C_6)$-alkyl, or more particularly isobutyl or propyl.

Another particular embodiment according to the invention is the compound according to formula Ia wherein
  $R^{12}$ is $(C_{3-5})$alkenyl, or more particularly penten-1-yl, isobutene-1-yl or propen-1-yl.

Another particular embodiment according to the invention is the compound according to formula Ia wherein
  $R^{12}$ is $(C_4)$-cycloalkyloxy (cyclobutyloxy).

Another particular embodiment according to the invention is the compound according to formula Ia wherein
  $R^{12}$ is $(C_5-C_6)$-cycloalkyl.

Another particular embodiment according to the invention is the compound according to formula Ia wherein
  $R^{12}$ is $(C_5-C_6)$-cycloalkenyl, or more particularly cyclopenten-1-yl.

Another particular embodiment according to the invention is the compound according to formula Ia wherein
  $R^{12}$ is $(C_3)$-cycloalkyl[$(C_2)$-alkyl or $(C_2)$-alkenyl], or more particularly cyclopropylethyl.

Another particular embodiment according to the invention is the compound according to formula Ia wherein
  $R^{12}$ is $(C_3)$-cycloalkyl$(C_1)$-alkyloxy (cyclopropylmethyl).

Another particular embodiment according to the invention is the compound according to formula Ia wherein
  $R^{12}$ is $(C_3-C_4)$-alkyloxy.

Another particular embodiment according to the invention is the compound according to formula Ia wherein
  $R^{12}$ is $(C_3)$-alkenyloxy.

Another particular embodiment according to the invention is the compound according to formula Ia wherein
  $R^{12}$ is phenyl.

Another particular embodiment according to the invention is the compound according to formula Ia wherein
  $R^{13}$ is halogen, or $(C_1)$-alkyl.

Another particular embodiment according to the invention is the compound according to formula Ia wherein
  $R^{13}$ is $(C_1)$-alkyl wherein the alkyl is optionally substituted by 1-3 fluorine atoms, or more particularly trifluoromethyl.

Another particular embodiment according to the invention is the compound according to formula Ia wherein
  $R^{13}$ is $(C_1)$-alkyl (methyl).

Another particular embodiment according to the invention is the compound according to formula Ia wherein
  $R^{13}$ is $(C_1)$-alkyl that is substituted by 2-3 fluorine atoms.

Another particular embodiment according to the invention is the compound according to formula Ia wherein
  $R^{13}$ is halogen.

Another particular embodiment according to the invention is the compound according to formula Ia wherein
  $R^{15}$ is [$(C_2-C_3)$-alkyl or $(C_3)$-alkenyl]$((C_1-C_{10})$-alkyl)amino.

Another particular embodiment according to the invention is the compound according to formula Ia wherein
  $R^{15}$ is $(C_2-C_3)$-alkyl$(C_1)$-alkyl)amino, or more particularly isopropylmethylamino.

Another particular embodiment according to the invention is the compound according to formula Ia wherein
  $R^{21}$ is hydrogen.

Another particular embodiment according to the invention is the compound according to formula Ia wherein $R^{22}$ is hydrogen or halogen, $(C_1)$-alkyl when Y is $C(R^{12})=C(R^{13})$.

Another particular embodiment according to the invention is the compound according to formula Ia wherein
$R^{51}$ is COOH.

Specific embodiments of the present invention are selected from the group consisting of
2-(2-Allyloxy-3-methyl-benzoylamino)-indan-2-carboxylic acid,
2-(2-Isopropoxy-3-methyl-benzoylamino)-indan-2-carboxylic acid,
2-(2-Cyclobutoxy-3-methyl-benzoylamino)-indan-2-carboxylic acid,
2-(2-Cyclopropylmethoxy-3-methyl-benzoylamino)-indan-2-carboxylic acid,
2-(2-sec-Butoxy-3-methyl-benzoylamino)-indan-2-carboxylic acid,
2-(3-Chloro-2-isopropoxy-benzoylamino)-indan-2-carboxylic acid
2-(2-Allyloxy-3-chloro-benzoylamino)-indan-2-carboxylic acid,
2-(3,5-Dichloro-2-cyclobutoxy-benzoylamino)-5-fluoro-indan-2-carboxylic acid,
2-(3,5-Dichloro-2-isopropoxy-benzenesulfonylamino)-indan-2-carboxylic acid,
2-(2-Allyloxy-3,5-dichloro-benzenesulfonylamino)-indan-2-carboxylic acid,
2-[(5,6,7,8-Tetrahydro-naphthalene-1-carbonyl)-amino]-indan-2-carboxylic acid,
1,3-Dimethyl-5-[(5,6,7,8-tetrahydro-naphthalene-1-carbonyl)-amino]-5,6-dihydro-4H-cyclopenta[c]thiophene-5-carboxylic acid,
5-Methoxy-2-[(5,6,7,8-tetrahydro-naphthalene-1-carbonyl)-amino]-indan-2-carboxylic acid,
2-[(5,6,7,8-Tetrahydro-naphthalene-1-carbonyl)-amino]-5-trifluoromethyl-indan-2-carboxylic acid
5-Fluoro-2-[(5,6,7,8-tetrahydro-naphthalene-1-carbonyl)-amino]-indan-2-carboxylic acid,
5-(2-Isopropoxy-3-methyl-benzoylamino)-1,3-dimethyl-5,6-dihydro-4H-cyclopenta[c]thiophene-5-carboxylic acid,
2-(2-Isopropoxy-3-methyl-benzoylamino)-5-methoxy-indan-2-carboxylic acid,
2-(2-Isopropoxy-3-methyl-benzoylamino)-5-trifluoromethyl-indan-2-carboxylic acid,
5-Fluoro-2-(2-isopropoxy-3-methyl-benzoylamino)-indan-2-carboxylic acid,
2-(2-Cyclobutoxy-3-methyl-benzoylamino)-5-trifluoro-indan-2-carboxylic acid,
5-Bromo-2-(2-cyclobutoxy-3-methyl-benzoylamino)-indan-2-carboxylic acid
2-(2-Cyclobutoxy-3-methyl-benzoylamino)-5-fluoro-indan-2-carboxylic acid,
2-(2-Cyclobutoxy-3-methyl-benzoylamino)-5,6-difluoro-indan-2-carboxylic acid,
2-[3-Methyl-2-((Z)-pent-1-enyl)-benzoylamino]-indan-2-carboxylic acid,
2-(3-Methyl-2-pentyl-benzoylamino)-indan-2-carboxylic acid,
2-[2-(-1-Ethyl-but-1-enyl)-3-methyl-benzoylamino]-indan-2-carboxylic acid,
2-[2-(1-Ethyl-butyl)-3-methyl-benzoylamino]-indan-2-carboxylic acid,
2-(2-Cyclopent-1-enyl-3-methyl-benzoylamino)-indan-2-carboxylic acid,
2-(2-Cyclopentyl-3-methyl-benzoylamino)-indan-2-carboxylic acid,
2-[3-Methyl-2-(2-methyl-propenyl)-benzoylamino]-indan-2-carboxylic acid,
2-(2-Isobutyl-3-methyl-benzoylamino)-indan-2-carboxylic acid,
2-[2-(-2-Cyclopropyl-vinyl)-3-methyl-benzoylamino]-indan-2-carboxylic acid,
2-[2-(2-Cyclopropyl-ethyl)-3-methyl-benzoylamino]-indan-2-carboxylic acid,
2-(2-Cyclohex-1-enyl-3-methyl-benzoylamino)-indan-2-carboxylic acid,
2-[3-Methyl-2-(1-propenyl)-benzoylamino]-indan-2-carboxylic acid,
2-(3-Methyl-2-propyl-benzoylamino)-indan-2-carboxylic acid,
2-[3-Methyl-2-((E)-pent-1-enyl)-benzoylamino]-indan-2-carboxylic acid,
5-Fluoro-2-[3-methyl-2-(2-methyl-propenyl)-benzoylamino]-indan-2-carboxylic acid,
5-Fluoro-2-(2-isobutyl-3-methyl-benzoylamino)-indan-2-carboxylic acid,
2-(2-Cyclopent-1-enyl-3-methyl-benzoylamino)-5-fluoro-indan-2-carboxylic acid,
5-Fluoro-2-[3-methyl-2-((E)-propenyl)-benzoylamino]-indan-2-carboxylic acid,
5-Fluoro-2-(2-isobutyl-3-methyl-benzoylamino)-indan-2-carboxylic acid,
5,6-Difluoro-2-[3-methyl-2-(2-methyl-propenyl)-benzoylamino]-indan-2-carboxylic acid,
5,6-Difluoro-2-(2-isobutyl-3-methyl-benzoylamino)-indan-2-carboxylic acid,
5,6-Difluoro-2-(3-methyl-2-propenyl-benzoylamino)-indan-2-carboxylic acid,
5,6-Difluoro-2-(3-methyl-2-propyl-benzoylamino)-indan-2-carboxylic acid,
5-Bromo-2-[3-methyl-2-((E)-propenyl)-benzoylamino]-indan-2-carboxylic acid,
2-[(2-Chloro-6-methyl-benzoyl)-amino]-indane-2-carboxylic acid,
2-[(2-methylthio]benzen-1-carbonyl)-amino-indan-2-carboxylic acid,
2-(5-Chloro-2-cyclobutoxy-3-methyl-benzoylamino)-indan-2-carboxylic acid,
2-(2-Isobutyryl-3-methyl-benzoylamino)-indan-2-carboxylic acid,
2-(2,3-Dimethyl-benzoylamino)-indan-2-carboxylic acid,
2-(3-Cyano-2-methyl-benzoylamino)-indan-2-carboxylic acid,
2-[(Biphenyl-2-carbonyl)-amino]-indan-2-carboxylic acid,
2-[2-(1,1-Dimethyl-propyl)-benzoylamino]-indan-2-carboxylic acid,
2-(2-Cyclobutoxy-3-methyl-benzoylamino)-4,5-dichloro-indan-2-carboxylic acid,
2-(2-Cyclobutoxy-3-methyl-benzoylamino)-5-chloro-indan-2-carboxylic acid,
2-(2-Cyclobutoxy-3-methyl-benzoylamino)-4-fluoro-indan-2-carboxylic acid,
2-(2-cyclobutyloxy-3-methylbenzoylamino)indan-2-acetic acid,
2-(3-bromo-2-methylbenzoylamino)indan-2-carboxylic acid,
2-(5-Bromo-2-cyclobutoxy-3-methyl-benzoylamino)-indan-2-carboxylic acid,
2-(2-Isopropylsulfanyl-benzoylamino)-indan-2-carboxylic acid,
2-(5-Chloro-2-cyclobutoxy-3-methyl-benzoylamino)-5-fluoro-indan-2-carboxylic acid, 2-{[2-(Ethyl-methyl-amino)-pyridine-3-carbonyl]-amino}-indan-2-carboxylic acid,
2-{[2-(Allyl-methyl-amino)-pyridine-3-carbonyl]-amino}-indan-2-carboxylic acid,
2-{[2-(Isopropyl-methyl-amino)-pyridine-3-carbonyl]-amino}-indan-2-carboxylic acid,
2-{[5-Chloro-2-(isopropyl-methyl-amino)-pyridine-3-carbonyl)-amino]-indan-2-carboxylic acid,
4,5-Difluoro-2-[3-methyl-2-(2-methyl-propenyl)-benzoylamino]-indan-2-carboxylic acid,
4,5-Difluoro-2-(2-isobutyl-3-methyl-benzoylamino)-indan-2-carboxylic acid
4,7-Difluoro-2-[3-methyl-2-(2-methyl-propenyl)-benzoylamino]-indan-2-carboxylic acid,
4,7-Difluoro-2-(2-isobutyl-3-methyl-benzoylamino)-indan-2-carboxylic acid,
5-Chloro-2-(2-isobutyl-3-methyl-benzoylamino)-indan-2-carboxylic acid
5-Chloro-2-[3-methyl-2-(2-methyl-propenyl)-benzoylamino]-indan-2-carboxylic acid
2-(5,6,7,8-Tetrahydro-naphthalen-1-ylcarbamoyl)-indan-2-carboxylic acid,
2-Cyclobutoxy-N-(2-methanesulfonylaminocarbonyl-indan-2-yl)-3-methyl-benzamide,
2-Cyclobutoxy-3-methyl-N-(2-trifluoromethanesulfonylaminocarbonyl-indan-2-yl)-benzamide,
2-Cyclopent-1-enyl-3-methyl-N-(2-trifluoromethanesulfonylaminocarbonyl-indan-2-yl)-benzamide,
2-Cyclobutoxy-3-methyl-N-[2-(1H-tetrazol-5-yl)-indan-2-yl]-benzamide, and
2-[2-(2-Methyl-propenyl)-3-trifluoromethyl-benzoylamino]-indan-2-carboxylic acid, or
a stereoisomeric form thereof, mixture of stereoisomeric forms thereof in any ratio, or a physiologically acceptable salt thereof.

Another particular embodiment according to the invention is the compound of the following structure

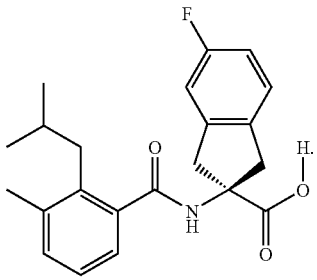

Another particular embodiment according to the invention is the compound of the following structure

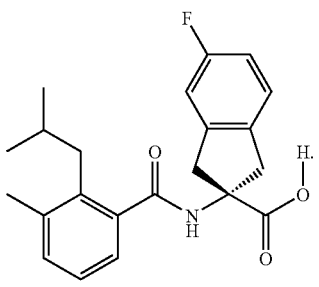

Another particular embodiment according to the invention is a compound selected from Example 232, 150, 231, 149, 136, 158, 152, 159, 144, 397, 135, 161, 155, 132, 139, 125, 329, 262, 154, 143, 160, 163, 21, 87, 212, 103, 352, 395, 392, or 388.

Another particular embodiment according to the invention is a pharmaceutical composition comprising a pharmaceutically acceptable amount of a compound according to formula Ia wherein and at least one of a pharmaceutically acceptable excipient and pharmaceutically acceptable carrier.

Another particular embodiment according to the invention is a method for the treatment of a patient suffering from, or subject to, a physiological condition that can be ameliorated by the administration of a pharmaceutically effective amount of an inhibitor of a CXCR5 receptor to the patient comprising administering the compound according to formula Ia to said patient.

Another particular embodiment according to the invention is the method of treatment wherein the physiological condition is an inflammatory disease.

Another particular embodiment according to the invention is the method of treatment the physiological condition is rheumatoid arthritis.

Another particular embodiment according to the invention is the method of treatment the physiological condition is asthma.

Another particular embodiment according to the invention is the method of treatment with the administering of the compound of claim 1 and another therapeutic agent is administered at the same time or sequentially.

Another particular embodiment according to the invention is a process for producing a compound according to formula Ia as described herein.

The present invention is also directed to a pharmaceutical composition comprising a compound of formula I, and method for using the compound of formula I or formula Ia for preventing and or treating inflammatory diseases, such as rheumatoid arthritis, multiple sclerosis, lupus, Crohn's Disease, associated with the modulation of the human CXCR5 receptor in a patient.

The invention is also directed to a process for preparing a compound that is an intermediate useful in preparing a compound of formula I or formula Ia.

Another aspect of the invention are methods of treating or preventing a physiological condition or a disease state a patient in need thereof, comprising administering to said patient a pharmaceutically effective amount of one or more compounds of formula I or formula Ia.

The amount of the compounds of formula I or formula Ia or other compounds capable of physiological condition or a disease state in any of the foregoing applications can be a pharmaceutically effective amount, a subclinical effective amount, or combinations thereof, so long as the final combination physiological condition or a disease state comprises a pharmaceutically effective amount of compounds that is effective in preventing and or treating inflammatory diseases, such as rheumatoid arthritis, multiple sclerosis, lupus, Crohn's Disease, associated with the modulation of the human CXCR5 receptor in a patient.

List of Abbreviations

As used throughout the description of the invention, the following abbreviations, unless otherwise indicated, shall be understood to have the following meanings:
ACN acetonitrile
AIBN 2,2'-azobisisobutyronitrile BOC or Boc tent-butyl carbamate
BOP benzotriazol-1-yl-oxytris(dimethylamino)phosphonium
n-Bu₃SnH tri-n-butyltin hydride
t-Bu tert-butyl
Cbz benzyl carbamate
CsCO₃ cesium carbonate
DAST (diethylamino)sulfur trifluoride (Et₂NSF₃)
DCC dicyclohexylcarbodiimide
DCM dichloromethane (CH₂Cl₂) or methylenechloride
DIC 1,3-diisopropylcarbodiimide
DIPEA diisopropylethylamine
DMAP 4-(N,N-dimethylamino)pyridine
DMP reagent Dess-Martin Periodinane reagent
DMF dimethylformamide
DMSO dimethylsulfoxide
EDCI 1-ethyl-3-(3-dimethylaminopropyl)carbodiimide HCl
eq equivalent(s)
Et ethyl
Et₂O diethyl ether
EtOH ethanol
EtOAc ethyl acetate
FMOC 9-fluorenylmethoxycarbonyl
HATU O-(7-Azabenzotriazol-1-yl)-N,N,N',N'-tetramethyluronium PF₆
HOAt 1-hydroxy-7-azabensotriazole
HOBT 1-hydroxybenzotriazole
HOSu N-hydroxysuccinamide
HBTU O-Benzotriazole-N,N,N',N'-tetramethyl-uronium-hexafluoro-phosphate
HPLC high performance liquid chromatography
LAH lithium aluminum anhydride
MgSO₄ magnesium sulfate
Me methyl
MeI methyliodide
MeOH methanol
MeOC(O) methyl chloroformate
MOMCI methoxymethylchloride
MOM methoxymethyl
MS mass spectroscopy
NaBH₄ sodium borohydride
NaHCO₃ sodium bicarbonate
Na₂C₄H₄O₆ sodium tartrate
NMR nuclear magnetic resonance
PTC phase transfer catalyst
iPrOH iso-propanol
P Polymer bond
KMnO₄ potassium permanganate
K₂SO₄ potassium carbonate
PyBOP benzotriazole-1-yl-oxytris-pyrrolidino-phosphonium hexafluorophosphate
Na₂SO₄ Sodium sulfate
TBD 1,5,7-triazabicyclo[4.4.0]-dec-5-ene
RP-HPLC reverse phase-high pressure liquid chromatography
RT room temperature
TBSCI tert-butyldimethylsilyl chloride
TCA trichloroacetic acid
TFA trifluoroacetic acid
Tf₂O triflate anhydride
THF tetrahydrofuran
THP tetrahydropyran
TLC thin layer chromatography

Definitions

As used above, and throughout the description of the invention, the following terms, unless otherwise indicated, shall be understood to have the following meanings:—

"Acid bioisostere" means a group which has chemical and physical similarities producing broadly similar biological properties to a carboxy group (see Lipinski, Annual Reports in Medicinal Chemistry, "Bioisosterism In Drug Design" 21, 283 (1986); Yun, Hwahak Sekye, "Application of Bioisosterism To New Drug Design" 33, 576-579, (1933); Zhao, Huaxue Tongbao, "Bioisosteric Replacement And Development Of Lead Compounds In Drug Design" 34-38, (1995); Graham, Theochem, "Theoretical Studies Applied To Drug Design ab initio Electronic Distributions In Bioisosteres" 343, 105-109, (1995)). Exemplary acid bioisosteres include —C(O)—NHOH, —C(O)—CH₂OH, —C(O)—CH₂SH, —C(O)—NH—CN, sulfo, phosphono, alkylsulfonylcarbamoyl, tetrazolyl, arylsulfonylcarbamoyl, N-methoxycarbamoyl, heteroarylsulfonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydroxy-1-methylpyrazolyl and the like.

"Acidic functional group" means a moiety bearing an acidic hydrogen. Exemplary acid functional groups include carboxyl (—C(O)OH), —C(O)—NHOH, —C(O)—CH₂OH, —C(O)—CH₂SH, —C(O)—NH—CN, sulfo, phosphono, alkylsulfonylcarbamoyl tetrazolyl, arylsulfonylcarbamoyl, N-methoxycarbamoyl, heteroarylsulfonylcarbamoyl or 3-hydroxy-3 cyclobutene-1,2-dione, imidazolyl mercapto, and the like, and an appropriate hydroxy such as an aromatic hydroxy, e.g., hydroxyphenyl, hydroxyheteroaryl such as 3,5-dioxo-1,2,4-oxadiazolidinyl 3-hydroxisoxazolyl or 3-hydroxy-1-methylpyrazolyl.

"Acid protecting group" means an easily removable group that is known in the art to protect an acidic hydrogen of a carboxyl group against undesirable reaction during synthetic procedures, e.g., to block or protect the acid functionality while the reactions involving other functional sites of the compound are carried out, and to be selectively removable. Such acid protecting groups are well known to those skilled in the art, having been extensively used in the protection of carboxyl groups, as described in U.S. Pat. Nos. 3,840,556 and 3,719,66, the disclosures of which are hereby incorporated herein by reference. For suitable acid protecting groups, see T. W. Green and P. G. M. Wuts in "Protective Groups in Organic Chemistry" John Wiley and sons, 1991. Acid protecting group also includes hydrogenation labile acid protecting group as defined herein. Exemplary acid protecting groups include esters such as substituted and unsubstituted $C_{1-8}$ lower alkyl, e.g., methyl, ethyl, t-butyl, methoxymethyl, methylthiomethyl, 2,2,2-trichloroethyl and the like, tetrahydropyranyl, substituted and unsubstituted phenylalkyl such as benzyl and substituted derivatives thereof such as alkoxybenzyl or nitrobenzyl groups and the like, cinnamyl, dialkylaminoalkyl, e.g., dimethylaminoethyl and the like, trimethylsilyl, substituted and unsubstituted amides and hydrazides, e.g., amides and hydrazides on N,N-dimethylamine, 7-nitroindole, hydrazine, N-phenylhydrazine and the like, acyloxyalkyl groups such as pivaloyloxymethyl or propionyloxymethyl and the like, aroyloxyalkyl such as benzoyloxyethyl and the like, alkoxycarbonylalkyl such as methoxycarbonylmethyl, cyclohexyloxycarbonylmethyl and the like, alkoxycarbonyloxyalkyl such as t-butyloxycarbonyloxymethyl and the like, alkoxycarbonylaminoalkyl such as t-butyloxycarbonylaminomethyl and the like, alkylaminocarbonylaminoalkyl, such as methylaminocarbonylaminomethyl and the like, acylaminoalkyl such as acetylaminomethyl and the like, heterocyclylcarbonyloxyalkyl such as 4-methylpiperazinylcarbonyloxymethyl and the like, dialkylaminocarbonylalkyl such as dimethylaminocarbonyl-methyl and the like, (5-(lower alkyl)-2-oxo-1,3-dioxolen-4-yl)alkyl such as (5-t-butyl-2- oxo-1,3-dioxolen-4-yl)methyl and the like, and (5-phenyl-2-oxo-1,3-dioxolen-4-yl)alkyl such as (5-phenyl-2-oxo-1,3-dioxolen-4-yl)methyl and the like.

"Acid labile amine protecting group" means an amine-protecting group as defined herein that is readily removed by treatment with acid while remaining relatively stable to other reagents. A preferred acid labile amine-protecting group is BOC.

"Aliphatic" means alkyl, alkenyl or alkynyl as defined herein.

"Aliphatic group substituent(s)" means substituents attached to an aliphatic group as defined herein inclusive or aryl, heteroaryl, hydroxy, alkoxy, cyclyloxy, aryloxy, heteroaryloxy, acyl or its thioxo analogue, cyclylcarbonyl or its thioxo analogue, aroyl or its thioxo analogue, heteroaroyl or its thioxo analogue, acyloxy, cyclylcarbonyloxy, aroyloxy, heteroaroyloxy, halo, nitro, cyano, carboxy (acid), —C(O)—NHOH, —C(O)—CH$_2$OH, —C(O)—CH$_2$SH, —C(O)—NH—CN-sulfo, phosphono, alkylsulfonylcarbamoyl, tetrazolyl, arylsulfonylcarbamoyl, tetrazolyl, arylsulfonylcarbamoyl, N-methoxycarbamoyl, heteroarylsulfonylcarbamoyl, 3-hydroxy-3-cyclobutene-1,2-dione, hydroxyheteroaryl such as 3-hydroxyisoxazolyl, 3,5-dioxo-1,2,4-oxadiazolidinyl or 3-hydroxy-1-methylpyrazolyl, alkoxycarbonyl, cyclyloxycarbonyl, aryloxycarbonyl, heteroaryloxycarbonyl, alkylsulfonyl, cyclylsulfonyl, arylsulfonyl, heteroarylsulfonyl, alkylsulfinyl, cyclylsulfinyl, arylsulfinyl, heteroarylsulfinyl, alkylthio, cyclylthio, arylthio, heteroarylthio, cyclyl, aryldiazo, heteroaryldiazo, thiol, methylene (H$_2$C=), oxo (O=), thioxo (S=), $Y^1Y^2$N—, $Y^1Y^2$NC(O)—, $Y^1Y^2$NC(O)O—, $Y^1Y^2$NC(O)N$Y^3$—, $Y^1Y^2$NSO$_2$—, or $Y^3$SO$_2$N$Y^1$— wherein $R^2$ is as defined herein, $Y^1$ and $Y^2$ are independently hydrogen, alkyl, aryl or heteroaryl, and $Y^3$ is alkyl, cycloalkyl aryl or heteroaryl, or for where the substituent is $Y^1Y^2$N—, then one of $Y^1$ and $Y^2$ may be acyl, cyclylcarbonyl, aroyl, heteroaroyl, alkoxycarbonyl, cyclyloxycarbonyl, aryloxycarbonyl or heteroaryloxycarbonyl, as defined herein and the other of $Y^1$ and $Y^2$ is as defined previously, or for where the substituent is $Y^1Y^2$NC(O)—, $Y^1Y^2$NC(O)O—, $Y^1Y^2$NC(O)N$Y^3$— or $Y^1Y^2$NSO$_2$—, $Y^1$ and $Y^2$ may also be taken together with the N atom through which $Y^1$ and $Y^2$ are linked to form a 4 to 7 membered azaheterocyclyl or azaheterocyclenyl. Acidic/amide aliphatic group substituents are carboxy (acid), —C(O)—NHOH, —C(O)CH$_2$OH, —C(O)—CH$_2$SH, —C(O)—NH—CN, sulfo?), phosphono?), alkylsulfonylcarbamoyl, tetrazolyl, arylsulfonylcarbamoyl, N-methoxycarbamoyl, heteroarylsulfonylcarbamoyl, 3-hydroxy-3-cyclobutene-1,2-dione, hydroxyheteroaryl such as 3-hydroxyisoxazolyl, 3,5-dioxo-1,2,4-oxadiazolidinyl or 3-hydroxy-1-methylpyrazolyl and $Y^1Y^2$NCO—. Non-acidic polar aliphatic group substituents are hydroxy, oxo (O=), thioxo (S=), acyl or its thioxo analogue, cyclylcarbonyl or its thioxo analogue, aroyl or its thioxo analogue, heteroaroyl or its thioxo analogue, alkoxycarbonyl, cyclyloxycarbonyl, aryloxycarbonyl, heteroaryloxycarbonyl, acyloxy, cyclylcarbonyloxy, aroyloxy, heteroaroyloxy, alkylsulfonyl, cyclylsulfonyl, arylsulfonyl, heteroarylsulfonyl, alkylsulfinyl, cyclylsulfinyl, arylsulfinyl, heteroarylsulfinyl, thiol, $Y^1Y^2$N—, $Y^1Y^2$NC(O)—, $Y^1Y^2$NC(O)O—, $Y^1Y^2$NC(O)N$Y^3$— or $Y^1Y^2$NSO$_2$—. Exemplary aliphatic groups bearing an aliphatic group substituent include methoxymethoxy, methoxyethoxy, ethoxyethoxy, (methoxy-, benzyloxy-, phenoxy-, or ethoxy-) carbonyl(methyl or ethyl), benzyloxycarbonyl, pyridylmethyloxy-carbonylmethyl, methoxyethyl, ethoxymethyl, n-butoxymethyl, cyclopentylmethyloxyethyl, phenoxypropyl, phenoxyallyl, trifluoromethyl, cyclopropyl-methyl, cyclopentylmethyl, carboxy(methyl or ethyl), 2-phenethenyl, benzyloxy, 1- or 2-naphthyl-methoxy, 4-pyridyl-methyloxy, benzyloxyethyl, 3-benzyloxyallyl, 4-pyridylmethyl-oxyethyl, 4-pyridylmethyloxyallyl, benzyl, 2-phenethyl, naphthylmethyl, styryl, 4-phenyl-1,3-pentadienyl, phenyl-propynyl, 3-phenylbut-2-ynyl, pyrid-3-ylacetylenyl and quinolin-3-ylacetylenyl, 4-pyridyl-ethynyl, 4-pyridylvinyl, thienylethenyl, pyridylethenyl, imidazolyl-ethenyl, pyrazinylethenyl, pyridylpentenyl, pyridylhexenyl and pyridylheptenyl, thienyl-methyl, pyridylmethyl, imidazolylmethyl, pyrazinylmethyl, tetrahydropyranylmethyl, tetrahydropyranyl-methoxymethyl, and the like.

"Acyl" means an H—CO— or (aliphatic or cyclyl)-CO— group wherein the aliphatic group is as herein described. Preferred acyls contain a lower alkyl. Exemplary acyl groups include formyl, acetyl, propanoyl, 2-methylpropanoyl, butanoyl, palmitoyl, acryloyl, propynoyl, cyclohexylcarbonyl, and the like.

"Alkenoyl" means an alkenyl-CO— group wherein alkenyl is as defined herein.

"Alkenyl" means an aliphatic hydrocarbon group containing a carbon-carbon double bond and which may be straight or branched having about 2 to about 15 carbon atoms in the chain. Preferred alkenyl groups have 2 to about 12 carbon atoms in the chain; and more preferably about 2 to about 4 carbon atoms in the chain. Branched means that one or more lower alkyl groups such as methyl, ethyl or propyl are attached to a linear alkenyl chain. "Lower alkenyl" means about 2 to about 4 carbon atoms in the chain that may be straight or branched. Exemplary alkenyl groups include ethenyl, propenyl, n-butenyl, i-butenyl, 3-methylbut-2-enyl, n-pentenyl, heptenyl, octenyl, cyclohexylbutenyl, decenyl, and the like. "Substituted alkenyl" means an alkenyl group as defined above which is substituted with one or more "aliphatic group substituents" (preferably 1 to 3) which may be the same or different and are as defined herein. Exemplary alkenyl aliphatic group substituents include halo or cycloalkyl groups.

"Alkenyloxy" means an alkenyl-O— group wherein the alkenyl group is as herein described. Exemplary alkenyloxy groups include allyloxy, 3-butenyloxy, and the like.

"Alkoxy" means an alkyl-O— group wherein the alkyl group is as herein described. Exemplary alkoxy groups include methoxy, ethoxy, n-propoxy, i-propoxy, n-butoxy, heptoxy, and the like.

"Alkoxycarbonyl" means an alkyl-O—CO— group, wherein the alkyl group is as herein defined. Exemplary alkoxycarbonyl groups include methoxycarbonyl, ethoxycarbonyl, t-butyloxycarbonyl, and the like.

"Alkyl" means an aliphatic hydrocarbon group which may be straight or branched having about 1 to about 20 carbon atoms in the chain. Preferred alkyl groups have 1 to about 12 carbon atoms in the chain, more preferred is lower alkyl as defined herein. Branched means that one or more lower alkyl groups such as methyl, ethyl or propyl are attached to a linear alkyl chain. "Lower alkyl" means about 1 to about 4 carbon atoms in the chain that may be straight or branched. "Substituted alkyl" means an alkyl group as defined above which is substituted with one or more "aliphatic group substituents" (preferably 1 to 3) which may be the same or different, and are as defined herein.

"Alkylsulfinyl" means an alkyl-SO— group wherein the alkyl group is as defined above. Preferred groups are those wherein the alkyl group is lower alkyl.

"Alkylsulfonyl" means an alkyl-SO$_2$— group wherein the alkyl group is as defined above. Preferred groups are those wherein the alkyl groups is lower alkyl.

"Alkylsulfonylcarbamoyl" means an alkyl-SO$_2$—NH—C(=O)— group wherein the alkyl group is as herein described. Preferred alkysulfonylcarbamoyl groups are those wherein the alkyl group is lower alkyl.

"Alkylthio" means an alkyl-S— group wherein the alkyl group is as herein described. Exemplary alkylthio groups include methylthio ethylthio i-propylthio and heptylthio.

"Alkynyl" means an aliphatic hydrocarbon group containing a carbon-carbon triple bond and which may be straight or branched having about 2 to about 15 carbon atoms in the chain. Preferred alkynyl groups have 2 to about 12 carbon atoms in the chain; and more preferably about 2 to about r carbon atoms in the chain. Branched means that one or more lower alkyl groups such as methyl, ethyl or propyl are attached to a linear alkynyl chain. "Lower alkynyl" means about 2 to about 4 carbon atoms in the chain that may be straight or branched. The alkynyl group may be substituted by one or more halo. Exemplary alkynyl groups include ethynyl, propynyl, n-butynyl, 2-butynyl, 3-methylbutynyl, n-pentynyl, heptynyl, octynyl, decynyl, and the like. "Substituted alkynyl" means alkynyl as defined above which is substituted with one or more "aliphatic group substituents" (preferably 1 to 3) which may be the same or different, and are as defined herein.

"Amine protecting group" means an easily removable group that is known in the art to protect a nitrogen moiety of an amino group against undesirable reaction during synthetic procedures and to be selectively removable. The use of amine protecting groups is well known in the art for protecting groups against undesirable reactions during a synthetic procedure and many such protecting groups are known, for example, T. W. Greene and P. G. M. Wuts, Protective groups in Organic synthesis, 2nd edition, John Wiley & Sons, New York (1991), incorporated herein by reference. Amine protecting group also includes "acid labile amine protecting group" and "hydrogenation labile amine protecting group". Exemplary amine protecting groups are acyl, including formyl, acetyl, chloroacetyl, trichloroacetyl, o-nitrophenylacetyl, o-nitrophenoxy-acetyl, trifluoroacetyl, acetoacetyl, 4-chlorobutyryl, isobutyryl, o-nitrocinnamoyl, picolinoyl, acylisothiocyanate, aminocaproyl, benzoyl and the like, and acyloxy including methoxy-carbonyl, 9-fluorenylmethoxycarbonyl, 2,2,2-trifluoroethoxycarbonyl, 2-trimethylsilylethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, and the like.

"Amide protecting group" means an easily removable group that is known in the art to protect a nitrogen moiety of an amide group against undesirable reaction during synthetic procedures and to be selectively removable after its conversion to the amide. The use of amide protecting groups is well known in the art for protecting groups against undesirable reactions during a synthetic procedure and many such protecting groups are known for example, T. W. Greene and P. G. M. Wuts, Protective Groups in Organic Synthesis, 2nd edition, John Wiley & Sons, New York (1991), incorporated herein by reference. Amide protecting group also includes "acid labile amide protecting group" and "hydrogenation labile amide protecting group". Exemplary amide protecting groups are o-nitrocinnamoyl, picolinoyl, aminocaproyl, benzoyl and the like, and acyloxy including methoxy-carbonyl, 9-fluorenylmethoxycarbonyl, 2,2,2-trifluoroethoxycaronyl, 2-trimethylsilyethoxy-carbonyl, vinyloxycarbonyl, allyloxycarbonyl, t-butyloxycarbonyl (BOC), 1,1-dimethyl-propynyloxycarbonyl, benzyloxycarbonyl (CBZ), p-nitrobenzyloxycarbonyl, 2,4-dichloro-benzyloxycarbonyl, and the like.

"Amino acid" as defined herein is selected from the group consisting of natural and unnatural amino acids. Amino acid is also meant to include amino acids having L or D stereochemistry at the α-carbon. Preferred amino acids are those possessing an α-amino group. The amino acids may be neutral, positive or negative depending on the substituents in the side chain. "Neutral amino acid" means an amino acid containing uncharged side chain substituents. Exemplary neutral amino acids include alanine, valine, leucine, isoleucine, proline, phenylalanine, tryptophan, methionine, glycine, serine, threonine and cysteine. "Positive amino acid" means an amino acid in which the side chain substituents are positively charged at physiological pH. Exemplary positive amino acids include lysine, arginine, and histidine "Negative amino acid" means an amino acid in which the side chain substituents bear a net negative charge at physiological pH. Exemplary negative amino acids include aspartic acid and glutamic acid. Exemplary natural amino acids are isoleucine, proline, phenylalanine, tryptophan, methionine, glycine, serine, threonine, cysteine, tyrosine, asparagine, glutamine, lysine, arginine histidine, aspartic acid and glutamic acid. "Unnatural amino acid" means an amino acid for which there is no nucleic acid codon. Exemplary unnatural amino acids include, for example, the D-isomers of the natural α-amino acids as indicated above; Aib (aminobutyric acid), βAib (3-amino-isobutyric acid) Nva (norvaline), β-Ala, Aad (2-aminoadiphic acid), βAad (3-aminoadipic acid), Abu (2-aminobutyric acid), Gaba (γ-aminobutyric acid), Acp (6-aminocaproic acid), Dbu (2,4-diaminopropionic acid), α-aminopimelic acid, TMSA (trimethylsilyl-Ala), alle (alloisoleucine), Nle (norleucine), teri-Leu, Cit (citrulline), Orn, Dpm (2,2'-diaminopimelic acid), α- or β-Nal, Cha (cyclohexyl-Ala), hydroxyproline, Sar (sarcosine), and the like; cyclic amino acids; N$^a$-alkylated amino acids such as MeGly. (N$^a$-methylglycine), EtGly (N$^a$-ethylglycine) and EtAsn (Na-ethylasparagine); and amino acids in which the α-carbon bears two side-chain substituents. The names of natural and unnatural amino acids and residues thereof used herein follow the naming conventions suggested by the IUPAC Commission on the Nomenclature of Organic chemistry and the IUPAC-IUB Commission on Biochemical Nomenclature as set out in "Nomenclature of α-Amino Acids (Recommendations, 1974)" Biochemistry, 14(2), (1975). To the extent that the names and abbreviations of amino acids and residues thereof employed in this specification and appended claims differ from those noted, differing names and abbreviations will be made clear.

"Amino acid protecting group" mean a group that protects an acid or amine moiety of the amino acid or other reactive moiety on the side chain of an amino acid, e.g., hydroxy or thiol. For examples of "corresponding protected derivatives" of amino acid side chains, see T. W. Green and P. G. M. Wuts in "Protective Groups in Organic Chemistry" John Wiley and Sons, 1991. Protecting groups for an acid group in an amino acid are described herein, for example in the sections "acidic functional group" and "hydrogenation labile acid protecting group". Protecting groups for an amine group in an amino acid are described herein, for example in the sections "amine protecting group", "acid labile amine protecting group" and "hydrogenation labile amine protecting group".

"Amino acid residue" means the individual amino acid units incorporated into the compound of the invention.

"Amino acid side chain" means the substituent found on the carbon between the amino and carboxy groups in α-amino acids. Exemplary amino acid side chains include isopropyl, methyl, and carboxymethyl for valine, alanine, and aspartic acid, respectively.

"Amino acid equivalent" means an amino acid that may be substituted for another amino acid in the peptides according to the invention without any appreciable loss of function. In making such changes, substitutions of like amino acids are made on the basis of relative similarity of side chain substituents, for example regarding size, charge, hydrophilicity, hydropathicity and hydrophobicity as described herein.

"Aromatic group" means aryl or heteroaryl as defined herein. Exemplary aromatic groups include phenyl, halo substituted phenyl, azaheteroaryl, and the like.

"Aroyl" means an aryl-CO-group wherein the aryl group is as herein described. Exemplary aroyl groups include benzoyl, 1- and 2-naphthoyl, and the like.

"Aryl" means an aromatic monocyclic or multicyclic ring system of about 6 to about 14 carbon atoms, preferably of about 6 to 10 carbon atoms. Encompassed by aryl are fused cycloalkenylaryl, fused cycloalkylaryl, fused heterocyclenylaryl and fused heterocyclylaryl as defined herein when bonded through the aryl moiety thereof. The aryl is optionally substituted with one or more "ring group substituents" (preferably 1 to 3 substituents which may be the same or different, and are as defined herein. A "Substituted aryl" means an aryl group which is substituted as defined above. Exemplary aryl groups include phenyl or naphthyl, or substituted phenyl or substituted naphthyl.

"Aryldiazo" means an aryl-diazo-group wherein the aryl and diazo groups are as defined herein.

"Arylene" means an optionally substituted 1,2-, 1,3-, 1,4-, bivalent aryl group, wherein the aryl group is as defined herein. "Substituted arylene" means an arylene group as defined above which is substituted with one or more "ring group substituents" (preferably 1 to 3) which may be the same or different and are as defined herein. Exemplary arylene groups include optionally substituted phenylene, naphthylene and indanylene. A particular arylene is optionally substituted phenylene.

"Aryloxy" means an aryl-O— group wherein the aryl group is as defined herein. Exemplary aryloxy groups include phenoxy and 2-naphtyloxy.

"Aryloxycarbonyl" means an aryl-O—CO— group wherein the aryl group is as defined herein. Exemplary aryloxycarbonyl groups include phenoxycarbonyl and naphthoxycarbonyl.

"Arylsulfonyl" means an aryl-$SO_2$— group wherein the aryl group is defined herein.

"Arylsulfonylcarbamoyl" means an aryl-$SO_2$—NH—C(=O)-group wherein the aryl group is herein described. An exemplary arylsulfonylcarbamoyl group is phenylsulfonylcarbamoyl.

"Arylsulfinyl" means an aryl-SO— group wherein the aryl group is as defined herein.

"Arylthio" means an aryl-S— group wherein the aryl group is as herein described. Exemplary arylthio groups include phenylthio and naphthylthio.

"Basic nitrogen atom" means a $sp^2$ or $sp^3$ hybridized nitrogen atom having a non-bonded pair of electrons which is capable of being protonated. Exemplary basic nitrogen atoms include optionally substituted imino, optionally substituted amino and optionally substituted amidino groups.

"Carboxy" means an HO(O)C— (carboxylic acid) group.

"Coupling agent" means a compound that reacts with the hydroxyl moiety of a carboxy moiety thereby rendering it susceptible to nucleophilic attack. Exemplary coupling agents include DIC, EDCI, DCC, and the like.

"Cycloalkenyl" means an optionally substituted non aromatic mono- or multicyclic ring system of about 3 to about 10 carbon atoms, preferably of about 5 to about 10 carbon atoms, and which contains at least one carbon-carbon double bond and which can be optionally fused by an aromatic group as defined herein. "Fused (aromatic) "cycloalkenyl" means fused arylcycloalkenyl and fused heteroarylcycloalkenyl as defined herein bonded through the cycloalkenyl moiety thereof. Preferred sizes or the rings of the ring system are about 5 to about 6 ring atoms; and such preferred ring sizes are also referred to as "lower". "Substituted cycloalkenyl" means an cycloalkenyl group as defined above which is substituted with one or more "ring group substituents" (preferably 1 to 3) which may be the same or different and are defined herein. Exemplary monocyclic cycloalkenyl include cyclopentenyl, cyclohexenyl, cycloheptenyl, and the like. An exemplary multicyclic cycloalkenyl is norbornylenyl.

"Cycloalkyl" means a non-aromatic mono- or multicyclic ring system of about 3 to about 10 carbon atoms, preferably of about 5 to about 10 carbon atoms, and which can be optionally fused by an aromatic group as defined herein. Preferred sizes of the rings of the ring system include about 5 to about 6 ring atoms; and such preferred ring sizes are also referred to as "lower". "Fused (aromatic) cycloalkyl" means fused arylcycloalkyl and fused heteroarylcycloalkyl as defined herein bonded through the cycloalkyl moiety thereof. "Substituted cycloalkyl" means a cycloalkyl group as defined above which is substituted with one or more "ring group substituents" (preferably 1 to 3) which may be the same or different and are as defined herein. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl, and the like.

"Cycloalkylene" means a bivalent cycloalkyl group as defined herein having about 4 to about 8 carbon atoms. Preferred ring sizes of the cycloalkylene include about 5 to about 6 ring atoms; and such preferred ring sizes are also referred to as "lower". The points of binding on the cycloalkylene group include 1,1-, 1,2-, 1,3-, or 1,4-binding patterns, and where applicable the stereochemical relationship of the points of binding is either cis or trans. Exemplary monocyclic cycloalkylene groups include (1,1-, 1,2-, or 1,3-)cyclohexylene and (1,1- or 1,2-) cyclopentylene. "Substituted cycloalkylene" means an cycloalkylene group as defined above which is substituted with one or more "ring group substitutes" (preferably 1 to 3) which may be the same or different and are as defined herein.

"Cyclic" or "Cyclyl" means cycloalkyl, cycloalkenyl, heterocyclyl or heterocyclenyl as defined herein. The term "lower" as used in connection with the term cyclic is the same as noted herein regarding the cycloalkyl, cycloalkenyl, heterocyclyl or heterocyclenyl.

"Cyclyloxy" means a cyclyl-O— group wherein the cyclyl group is as herein described. Exemplary cycloalkoxy groups include cyclopentyloxy, cyclohexyloxy, quinuclidyloxy, pentamethylenesulfidoxy, tetrahydropyranyloxy, tetrahydrothiophenyloxy, pyrrolidinyloxy, tetrahydrofuranyloxy, or 7-oxabicyclo[2.2.1]heptanyloxy, hydroxytetrahydropyranyloxy, hydroxy-7-oxabicyclo[2.2.1]heptanyloxy, and the like.

"Cyclylsulfinyl" means a cyclyl-S(O)— group wherein the cyclyl group is as herein described.

"Cyclylsulfonyl" means a cyclyl-$S(O)_2$— group wherein the cyclyl group is as herein described.

"Cyclylthio" means a cyclyl-S— group wherein the cyclyl group is as herein described.

"Diazo" means a bivalent —N=N— radical.

"Displaceable moiety" means a group that where associated with L as defined herein is subject to being displaced by nucleophilic attack by a mono- or di-substituted amine moiety with or without the presence of an agent that facilitates said attack, e.g., coupling agent. Exemplary displaceable moieties include hydroxy, aliphatic oxy, halo, N-oxysuccinimide, acyloxy, and the like.

"Effective amount" is means an amount of a compound/composition according to the present invention effective in producing the desired therapeutic effect.

"Fused arylcycloalkenyl" means a fused aryl and cycloalkenyl as defined herein. Preferred fused arylcycloalkenyls are those wherein the aryl thereof is phenyl and the cycloalkenyl consists of about 5 to about 6 ring atoms. A fused arylcycloalkenyl as a variable may be bonded through any atom of the ring system thereof capable of such. "Substituted fused arylcycloalkenyl" means a fused arylcycloalkenyl group as defined above which is substituted with one or more "ring group substituents" (preferably 1 to 3) which may be the same or different and are as defined herein. Exemplary fused arylcycloalkenyl include 1,2-dihydronaphthylene, indene, and the like.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. "Substituted fused arylcycloalkyl" means a fused arylcycloalkyl group as defined above which is substituted with one or more "ring group substituents" (preferably 1 to 3) which may be the same or different and are as defined herein. Exemplary fused arylcycloalkyl includes 1,2,3,4-tetrahydro-naphthylene, and the like.

"Fused arylheterocyclenyl" means a fused aryl and heterocyclenyl as defined herein. Preferred fused arylheterocyclenyls are those wherein the aryl thereof is phenyl and the heterocyclenyl consists of about 5 to about 6 ring atoms. A fused arylheterocyclenyl as a variable may be bonded through any atom of the ring system thereof capable of such. The designation of the aza, oxa or thia as a prefix before heterocyclenyl portion of the fused arylheterocyclenyl define that at least a nitrogen, oxygen or sulfur atom is present, respectively, as a ring atom. "Substituted fused arylheterocyclenyl" means a fused arylheterocyclenyl group as defined above which is substituted with one or more "ring group substituents" (preferably 1 to 3) which may be the same or different and are as defined herein. The nitrogen atom of a fused arylheterocyclenyl may be a basic nitrogen atom. The nitrogen or sulfur atom of the heterocyclenyl portion of the fused arylheterocyclenyl may also be optionally oxidized to the corresponding N-oxide, S-oxide or S,S-dioxide. Exemplary fused arylheterocyclenyl include 3H-indolinyl, 1H-2-oxoquinolyl, 2H-1-oxoisoquinolyl, 1,2-di-hydroquinolinyl, 3,4-dihydroquinolinyl, 1,2-dihydroisoquinolinyl, 3,4-dihydroisoquinolinyl, and the like.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or ilia as a prefix before heterocyclyl portion of the fused arylheterocyclyl define that at least a nitrogen, oxygen or sulfur atom is present, respectively, as a ring atom. "Substituted fused arylheterocyclyl" means a fused arylheterocyclyl group as defined above which is substituted with one or more "ring group substituents" (preferably 1 to 3) which may be the same or different and are as defined herein. The nitrogen atom of a fused arylheterocyclyl may be a basic nitrogen atom. The nitrogen or sulfur atom of the heterocyclyl portion of the fused arylheterocyclyl may also be optionally oxidized to the corresponding N-oxide, S-oxide or S,S-dioxide. Exemplary fused arylheterocyclyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]-isoquinolin-2-yl, and the like.

"Fused heteroarylcycloalkenyl" means a fused heteroaryl and cycloalkenyl as defined herein. Preferred fused heteroarylcycloalkenyls are those wherein the heteroaryl thereof is phenyl and the cycloalkenyl consists of about 5 to about 6 ring atoms. A fused heteroaryl-cycloalkenyl as a variable may be bonded through any atom of the ring system thereof capable of such. The designation of the aza, oxa or thia as a prefix before heteroaryl portion of the fused heteroarylcycloalkenyl define that at least a nitrogen, oxygen or sulfur atom is present, respectively, as a ring atom. "Substituted fused heteroarylcycloalkenyl" means a fused heteroarylcycloalkenyl group as defined above which is substituted with one or more "ring group substituents" (preferably 1 to 30 which may be the same or different and are as defined herein. The nitrogen atom of a fused heteroarylcycloalkenyl may be a basic nitrogen atom.

The nitrogen atom of the heteroaryl portion of the fused heteroarylcycloalkenyl may also be optionally oxidized to the corresponding N-oxide. Exemplary fused heteroarylcycloalkenyls include 5,6-dihydroquinolyl, 5,6-dihydroisoquinolyl, 5,6-dihydroquinoxalinyl, 5,6-dihydroquinazolinyl, 4,5-dihydro-1H-benzimidazolyl, 4,5-di-hydrobenzoxazolyl, and the like.

"Fused heteroarylcycloalkyl" means a fused heteroaryl and cycloalkyl as defined herein. Preferred fused heteroarylcycloalkyls are those wherein the heteroaryl thereof consists of about 5 to about 6 ring atoms and the cycloalkyl consists of about 5 to about. 6 ring atoms. A fused heteroarylcycloalkyl as a variable may be bonded through any atom of the ring system thereof capable of such. The designation of the aza, oxa or ilia as a prefix before heteroaryl portion of the fused heteroarylcycloalkyl define that at least a nitrogen, oxygen or sulfur atom is present, respectively, as a ring atom. "Substituted fused heteroarylcycloalkyl" means a fused heteroarylcycloalkyl group as defined above which is substituted with one or more "ring group substituents" (preferably 1 to 3) which may be the same or different and are as defined herein. The nitrogen atom of a fused heteroarylcycloalkyl may be a basic nitrogen atom. The nitrogen atom of the heteroaryl portion of the fused heteroarylcycloalkyl may also be optionally oxidized to the corresponding N-oxide. Exemplary fused heteroarylcycloalkyl include 5,6,7,8-tetrahydroquinolinyl, 5,6,7,8-tetra-hydroisoquinolyl, 5,6,7,8-tetrahydroquinoxalinyl, 5,6,7,8-tetrahydroquinazolyl, 4,5,6,7-tetrahydro-1H-benzimidazolyl, 4,5,6,7-tetrahydrobenzoxazolyl, 1H-4-oxa-1,5-diazanaphthalen-2-onyl, 1,3-dihydroimidizole-[4,5]-pyridin-2-onyl, and the like.

"Fused heteroarylheterocyclenyl" means a fused heteroaryl and heterocyclenyl as defined herein. Preferred fused heteroarylheterocyclenyls are those wherein the heteroaryl thereof consists of about 5 to about 6 ring atoms and the heterocyclenyl consists of about 5 to about 6 ring atoms. A fused heteroarylheterocyclenyl as a variable may be bonded through any atom of the ring system thereof capable of such. The designation of the aza, oxa or thia as a prefix before the heteroaryl or heterocyclenyl portion of the fused heteroarylheterocyclenyl define that at least a nitrogen, oxygen or sulfur atom is present, respectively, as a ring atom "Substituted fused heteroarylheterocyclenyl" means a fused heteroarylheterocyclenyl group as defined above which is substituted with one or more "ring group substituents" (preferably 1 to 3) which may be the same or different and are as defined herein.

The nitrogen atom of a fused heteroarylazaheterocyclenyl may be a basic nitrogen atom. The nitrogen or sulfur atom of the heteroaryl portion of the fused heteroarylheterocyclyl may also be optionally oxidized to the corresponding N-oxide. The nitrogen or sulfur atom of the heteroaryl or heterocyclyl portion of the fused heteroarylheterocyclyl may also be optionally oxidized to the corresponding N-oxide, S-oxide or S,S-dioxide. Exemplary fused heteroarylheterocyclenyl include 7,8-dihydro[1,7]naphthyridinyl, 1,2-dihydro[2,7]-naphthyridinyl, 6,7-dihydro-3H-imidazo[4,5-c]pyridyl, 1,2-dihydro-1,5-naphthyridinyl, 1,2-dihydro-1,6-naphthyridinyl, 1,2-dihydro-1,7-naphthyridinyl, 1,2-dihydro-1,8-naphthyridinyl. 1,2-dihydro-2,6-naphthyridinyl, and the like.

"Halo or halogen" means fluoro, chloro, bromo, or iodo. Preferred are fluoro, chloro or bromo, and more preferred are fluoro or chloro.

"Heteroaroyl" means an heteroaryl-CO— group wherein the heteroaryl group is as herein described. Exemplary heteroaroyl groups include thiophenoyl, nicotinoyl, pyrrol-2-ylcarbonyl, 1- and 2-naphthoyl, pyridinoyl, and the like.

"Heteroaryl" means an aromatic monocyclic or multicyclic ring system of about 5 to about 14 carbon atoms, preferably about 5 to about 10 carbon atoms, in which one or more of the carbon atoms in the ring system is/are hetero element(s) other than carbon, for example nitrogen, oxygen or sulfur. Preferably the ring system includes 1 to 3 heteroatoms. Preferred ring sizes of rings of the ring system include about 5 to about 6 ring atoms. Encompassed by heteroaryl are fused heteroarylcycloalkenyl, fused heteroarylcycloalkyl, fused heteroarylheterocyclenyl and fused heteroarylheterocyclyl as defined herein when bonded through the heteroaryl moiety thereof "Substituted heteroaryl" means a heteroaryl group as defined above which is substituted with one or more "ring group substituents" (preferably 1 to 3) which may be the same or different and are as defined herein. The designation of the aza, oxa or thia as a prefix before heteroaryl define that at least a nitrogen, oxygen or sulfur atom is present, respectively, as a ring atom. A nitrogen atom of an heteroaryl may be a basic nitrogen atom and may also be optionally oxidized to the corresponding N-oxide. Exemplary heteroaryl and substituted heteroaryl groups include pyrazinyl, thienyl, isothiazolyl, oxazolyl, pyrazolyl, furazanyl, pyrrolyl, 1,2,4-thiadiazolyl, pyridazinyl, quinoxalinyl, phthalazinyl, imidazo[1,2-a]pyridine, imidazo[2,1-b]thiazolyl, benzofurazanyl, azaindolyl, benzimidazolyl, benzothienyl, thienopyridyl, thienopyrimidyl, pyrrolopyridyl, imidazopyridyl, benzoazaindolyl, 1,2,4-triazinyl, benzthiazolyl, furanyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl, triazolyl, and the like. A preferred heteroaryl group is pyrazinyl.

"Heteroaryldiyl" means a bivalent radical derived from a heteroaryl, wherein the heteroaryl is as described herein. An exemplary heteroaryldiyl radical is optionally substituted pyridinediyl.

"Heteroarylsulfonylcarbamoyl" means a heteroaryl-SO$_2$—NH—C(=O)— group wherein the heteroaryl group is as herein described.

"Heterocyclenyl" means a non-aromatic monocyclic or multicyclic hydrocarbon ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur atoms, and which contains at least one carbon-carbon double bond or carbon-nitrogen double bond. Preferably, the ring includes 1 to 3 heteroatoms. Preferred ring sizes of rings of the ring system include about 5 to about 6 ring atoms; and such preferred ring sizes are also referred to as "lower". Encompassed by heterocyclenyl are fused arylheterocyclenyl and fused heteroarylheterocyclenyl as defined herein when bonded through the heterocyclenyl moiety thereof. The designation of the aza, oxa or thia as a prefix before heterocyclenyl define that at least a nitrogen, oxygen or sulfur atom is present, respectively, as a ring atom. "Substituted heterocyclenyl" means a heterocyclenyl group as defined above which is substituted with one or more "ring group substituents" (preferably 1 to 3) which may be the same or different and are as defined herein. The nitrogen atom of an heterocyclenyl may be a basic nitrogen atom. The nitrogen or sulfur atom of the heterocyclenyl may also be optionally oxidized to the corresponding N-oxide, S-oxide or S,S-dioxide. Exemplary monocyclic azaheterocyclenyl groups include 1,2,3,4-tetrahydrohydropyridine, 1,2-dihydropyridyl, 1,4-dihydropyridyl, 1,2,3,6-tetra-hydropyridine, 1,4,5,6-tetrahydro-pyrimidine, 2-pyrrolinyl, 3-pyrrolinyl, 2-imidazolinyl, 2-pyrazolinyl, and the like. Exemplary oxaheterocyclenyl groups include 3,4-dihydro-2H-pyran, dihydrofuranyl, and fluorodihydro-furanyl. An exemplary multicyclic oxaheterocyclenyl group is 7-oxabicyclo[2.2.1]heptenyl.

Exemplary monocyclic thiaheterocyclenyl rings include dihydrothiophenyl and dihydrothiopyranyl.

"Heterocyclyl" means a non-aromatic saturated monocyclic or multicyclic ring system of about 3 to about 10 carbon atoms, preferably about 5 to about 10 carbon atoms, in which one or more of the carbon atoms in the ring system is/are hetero element(s) other than carbon, for example nitrogen, oxygen or sulfur. Preferably, the ring system contains from 1 to 3 heteroatoms. Preferred ring sizes of rings of the ring system include about 5 to about 6 ring atoms; and such preferred ring sizes are also referred to as "lower". Encompassed by heterocyclyl are fused arylheterocyclyl and fused heteroarylheterocyclyl as defined herein when bonded through the heterocyclyl moiety thereof. The designation of the aza, oxa or thia as a prefix before heterocyclyl define that at least a nitrogen, oxygen or sulfur atom is present respectively as a ring atom. "Substituted heterocyclyl" means a heterocyclyl group as defined above which is substituted with one or more "ring group substituents" (preferably 1 to 3) which may be the same or different and are as defined herein The nitrogen atom of an heterocyclyl may be a basic nitrogen atom. The nitrogen or sulfur atom of the heterocyclyl may also be optionally oxidized to 20 the corresponding N-oxide, S-oxide or S,S-dioxide. Exemplary monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclene" means a bivalent heterocyclyl group as defined herein having about 4 to about 8 carbon atoms. Preferred ring sizes of the heterocyclylene include about 5 to about 6 ring atoms; and such preferred ring sizes are also referred to as "lower". The points of binding on the cycloalkylene group include 1,1-, 1,2-, 1,3-, or 1,4-binding patterns, and where applicable the stereochemical relationship of the points of binding is either cis or trans. Exemplary heterocyclylene groups include (1,1-, 1,2- or 1,3-)piperidinylene and (1,1- or 1,2-)tetrahydrofuranylene. "Substituted heterocyclylene" means a heterocyclylene group as defined above which is substituted with one or more "ring group substituents" (preferably 1 to 3) which may be the same or different and are as defined herein.

"Hydrate" means a solvate wherein the solvent molecule{s) is/are H₂O.

"N-oxide" means a moiety of the following structure.

"Patient" includes both human and other mammals.

"Pharmaceutically acceptable ester" refers to esters that hydrolyze in vivo and include those that break down readily in the human body to leave the parent compound or a salt thereof, Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Exemplary esters include formates, acetates, propionates, butyrates, acrylates, ethylsuccinates, and the like.

"Pharmaceutically acceptable prodrugs" as used herein refers to those prodrugs of the compounds of the present invention which are, within the scope of sound medical judgment, suitable for use in contact with the tissues of patients with undue toxicity, irritation, allergic response, and the like, commensurate with a reasonable benefit/risk ratio, and effective for their intended use of the compounds of the invention. The term "prodrug" refers to compounds that are rapidly transformed in vivo to yield the parent compound of the above formula, for example by hydrolysis in blood. Functional groups that may be rapidly transformed, by metabolic cleavage, in vivo form a class of groups reactive with the carboxyl group of the compounds of this invention. They include, but are not limited to such groups as alkanoyl (such as acetyl, propanoyl, butanoyl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds of this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion is provided in Design of Prodrugs, H. Bundgaard, ed., Elsevier (1985); Methods in Enzymology; K. Widder et al, Ed., Academic Press, 42, 309-396 (1985); A Textbook of Drug Design and Development, Krogsgaard-Larsen and H. Bandaged, ed., Chapter 5; "Design and Applications of Prodrugs" 113-191 (1991); Advanced Drug Delivery Reviews, H. Bundgard, 8, 1-38, (1992); J. Pharm. Sci., 77.,285 (1988); Chem. Pharm. Bull., N. Nakeya et al, 32, 692 (1984); Pro-drugs as Novel Delivery Systems, T. Higuchi and V. Stella, 14 A.C.S. Symposium Series, and Bioreversible Carriers in Drug Design, E. B. Roche, ed., American Pharmaceutical Association and Pergamon Press, 1987, which are incorporated herein by reference.

"Pharmaceutically acceptable salts" refers to the relatively non-toxic, inorganic and organic acid addition salts, and base addition salts, of compounds of the present invention. These: salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-β-hydroxynaphthoates, gentisates, isethionates, di-p-toluoyltartrates, methanesulfonates, ethanesulfonates, benzenesulfonates, p-toluenesulfonates, cyclohexylsulfonates and laurylsulfonate salts, and the like. See, for example S. M. Berge, et al., "Pharmaceutical Salts," *J. Pharm. Sci.,* 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use. ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

"Ring group substituents" mean substituents attached to aromatic or non-aromatic ring systems inclusive of aryl, heteroaryl, hydroxy, alkoxy, cyclyloxy, aryloxy, heteroaryloxy, acyl or its thioxo analogue, cyclylcarbonyl or its thioxo analogue, aroyl or its thioxo analogue heteroaroyl or its thioxo analogue, acyloxy, cyclylcarbonyloxy, aroyloxy, heteroaroyloxy, halo, nitro, cyano, carboxy (acid), —C(O)—NHOH—C(O)—CH₂OH, —C(O)—CH₂SH—C(O)—NH—CN, sulfo, phosphono, alkylsulfonylcarbamoyl, tetrazolyl, arylsulfonylcarbamoyl, N-methoxycarbamoyl, heteroarylsulfonylcarbamoyl, 3-hydroxy-3-cyclobutene-1,2-dione, 3,5-di-oxo-1,2,4-oxadiazolidinyl or hydroxyheteroaryl such as 3-hydroxyisoxazolyl, 3-hydroxy-1-methylpyrazoly, alkoxycarbonyl, cyclyloxycarbonyl, aryloxycarbonyl, heteroaryloxycarbonyl, alkylsulfonyl, cyclylsulfonyl, arylsulfonyl, heteroarylsulfonyl, alkylsulfinyl, cyclylsulfinyl, arylsulfinyl, heteroarylsulfinyl, alkylthio, cyclylthio, arylthio, heteroarylthio, cyclyl, aryldiazo, heteroaryldiazo, thiol, $Y^1Y^2N$—, $Y^1Y^2NC(O)$—, $Y^1Y^2NC(O)O$—, $Y^1Y^2NC(O)NY^3$— or $Y^1Y^2NSO_2$—, wherein $Y^1$, $Y^2$ and $Y^3$ are independently hydrogen, alkyl, aryl or heteroaryl, or for where the substituent is $Y^1Y^2N$—, then one of $Y^1$ and $Y^2$ may be acyl, cyclylcarbonyl, aroyl, heteroaroyl, alkoxycarbonyl, cyclyloxycarbonyl, aryloxycarbonyl or heteroaryloxycarbonyl, as defined herein and the other of $Y^1$ and $Y^2$ is as defined previously, or for where the substituent is $Y^1Y^2NC(O)$—, $Y^1Y^2NC(O)O$—, $Y^1Y^2NC(O)NY^3$— or $Y^1Y^2NSO_2$—, $Y^1$ and $Y^2$ may also be taken together with the N atom through which $Y^1$ and $Y^2$ are linked to form a 4 to 7 membered azaheterocyclyl or azaheterocyclenyl. When a ring system is saturated or partially saturated, the "ring group substituents" further include, methylene ($H_2C=$), oxo ($O=$) and thioxo ($S=$). Acidic/amide ring group substituents are carboxy (acid). —C(O)—NHOH, —C(O)—CH₂OH, —C(O)—CH₂SH, —C(O)—

NH—CN, sulfo, phosphono, alkylsulfonylcarbamoyl, tetrazolyl, arylsulfonylcarbamoyl, N-methoxycarbamoyl, heteroarylsulfonylcarbamoyl, 3-hydroxy-3-cyclobutene-1,2-dione, 3,5-dioxo-1,2,4-oxadiazolidinyl or hydroxyheteroaryl such as 3-hydroxyisoxazolyl, 3-hydroxy-1-methylpyrazoly and $Y^1Y^2NCO$—. Non-acidic polar ring group substituents are hydroxy, oxo (O=), thioxo (S=), acyl or its thioxo analogue, cyclylcarbonyl or its thioxo analogue, aroyl or its thioxo analogue, heteroaroyl or its thioxo analogue, alkoxycarbonyl, cyclyloxycarbonyl, aryloxycarbonyl, heteroaryloxycarbonyl, acyloxy, cyclylcarbonyloxy, aroyloxy, heteroaroyloxy, alkylsulfonyl, cyclylsulfonyl, arylsulfonyl, heteroarylsulfonyl, alkylsulfinyl, cyclylsulfinyl, arylsulfinyl, heteroarylsulfinyl, thiol, $Y^1Y^2N$—, $Y^1Y^2NC(O)$—, $Y^1Y^2NC(O)O$—, $Y^1Y^2NC(O)NY^3$— or $Y^1Y^2NSO_2$.

"Solvate" means a physical association of a compound of this invention with one or more solvent molecules. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, and the like.

Pharmacology

Experimental Methods and or Assays Used for Determining Activity

FLIPR Assay—Human CXCR5:

Changes in the intracellular $Ca^{2+}$ are measured in RBL cell line stably transfected with human CXCR5 DNA. 9,000 cells/well are plated and incubated at 37° C., 5% $CO_2$ 20 h prior to the assay. On the following day, cells are washed once with assay buffer containing Hank's (Invitrogen, 14025-092) plus 20 mM HEPES, pH 7.4 and loaded with dye by incubating for 30 min at 37° C. with 2 µM fluo-4/AM (Molecular Probes, F14202) in assay buffer plus 2.5 mM probenecid. Cells are washed 3 times with assay buffer, then compounds in assay buffer plus 0.1% BSA are added into cells. Cells are washed 3 additional times with assay buffer, then stimulated with 10 nM human CXCL13 (R&D, 801-CX/CF). Changes of intracellular $Ca^{2+}$ are recorded using the 384-B FLIPR (Molecular Devices).

FLIPR Assay—Murine CXCR5

Changes in the intracellular $Ca^{2+}$ are measured in RBL cell line stably transfected with murine CXCR5 DNA. 9,000 cells/well are plated and incubated at 37° C., 5% $CO_2$ 20 h prior to the assay. On the following day, cells are washed once with assay buffer containing Hank's (Invitrogen, 14025-092) plus 20 mM HEPES, pH 7.4 and loaded with dye by incubating for 30 min at 37° C. with 2 µM fluo-4/AM (Molecular Probes, F14202) in assay buffer plus 2.5 mM probenecid. Cells are washed 3 times with assay buffer, then compounds in assay buffer plus 0.1% BSA are added into cells. Cells are washed 3 additional times with assay buffer, then stimulated with 6 nM murine CXCL13 (R&D, 470-BC). Changes of intracellular $Ca^{2+}$ are recorded using the 384-B FLIPR (Molecular Devices).

GTPγS Assay:

The [$^{35}$S]-GTPγS binding assay for CXCR5 is performed using membranes prepared from RBL cell line stably transfected with human CXCR5 DNA. 2.5 µM GDP, test compound at the desired concentration (or DMSO in the controls), 10 µM un-labeled GTPγS (or buffer in controls) and 7.5 µg cell membrane/well are mixed together (plate shaker) for 15 min at RT. 750 nM human CXCL13 and 400 µM [$^{35}$S]-GTPγS are added and the plate shaken for 5 min at RT. 1.134 mg/well spa beads are then added and the plate shaken for 45 min at RT. The reaction is stopped by centrifugation at 230 g for 10 minutes and radioactivity measured on a Wallac Microbeta Trilux beta counter.

Chemotaxis Assay:

Wells in the assay plate are pre-coated with 150 µl RPMI (no phenol red) containing 1% BSA for 2 h at room temperature. Pre-coating buffer is discarded and wells washed twice with CTX assay buffer (see below). CXCR5$^+$ HS Sultan cells (ATCC cat#CRL 1484) are added to the upper chamber of the transwell plate (Millipore Cat#MAMI C5S 10) at 0.6×10$^5$ cells/well and incubated with test compound for 15 min at RT. CXCL13 ligand at 100 nM (R&D, cat#801-cx/cf) or CTX-buffer (RPMI no phenol red supplemented with 0.02% BSA, 1 mM Na pyruvate) is added to the lower chamber. The two chambers are assembled and incubated at 37° C. for 2 h. The upper chamber is subsequently removed and cells in lower chamber are counted after adding colorimetric reagent (Promega Cat#G3581) and reading $OD_{490}$. CXCR5 specific migration=total migrated cell-spontaneous migrated cells (wells containing CTX buffer without ligand).

Experimental data below is a representation of inhibitory activity as indicated by $IC_{50}$ values for the Examples herein. The particular embodiments below are exemplary and do not limit the equivalents pertaining thereto.

TABLE I

| EXAMPLE | IC50 |
|---|---|
| 5 | 2.4 |
|  | 0.493 |
| 18 | 3.65 |
| 7 | 0.844 |
|  | 0.425 |
|  | 0.105 |
| 38 | 0.675 |
| 9 | 0.47 |
| 11 | 2.93 |
| 13 | 1.08 |
| 24 | ND |
| 26 | ND |
| 44 | ~13 |
| 42 | 5.45 |
| 52 | >30 |
| 46 | 19.6 |
| 119 | >30 |
| 36 | >30 |
| 56 | >30 |
| 58 | >30 |
| 48 | >30 |
| 121 | ND |
| 29 | ~24 |
| 75 | 2.85 |
| 79 | ND |
| 87 | 0.298 |
| 81 | ~9.5 |
| 54 | >30 |
| 77 | ND |
| 93 | 18.2 |
| 91 | ~27 |
| 89 | 17.35 |
| 97 | 0.537 |
| 103 | 0.38 |
| 99 | ~7.8 |
| 85 | 6.1 |
| 95 | 14.75 |
| 112 | >30 |
| 111 | ~20.5 |
| 108 | >30 |
| 109 | >30 |
| 107 | ~30 |
| 116 | >30 |

TABLE I-continued

| EXAMPLE | IC50 |
|---|---|
| 115 | ~10.15 |
| 113 | >30 |
| 117 | >30 |
| 123 | 19.3 |
| 125 | 0.099 |
| 127 | 2.3 |
| 129 | 15.25 |
| 132 | 0.056 |
| 21 | 0.268 |
| 135 | 0.033 |
| 130 | 3.87 |
| 133 | 0.533 |
| 32 | ~16 |
| 34 | ~13 |
| 138 | 8.2 |
| 143 | 0.232 |
| 146 | 0.446 |
| 144 | 0.023 |
| 141 | 1.05 |
| 139 | 0.097 |
| 60 | >30 |
| 149 | 0.011 |
| 62 | ~30 |
| 152 | 0.013 |
| 64 | >30 |
| 154 | 0.2 |
| 152 | 0.013 |
| 397 | 0.026 |
| 136 | 0.014 |
| 232 | 0.007 |
| 161 | 0.045 |
| 155 | 0.047 |
| 132 | 0.056 |
| 150 | 0.015 |
| 231 | 0.030 |
| 158 | 0.015 |
| 395 | 0.009 |
| 388 | 0.005 |
| 392 | 0.038 |
| 159 | 0.017 |

Preparation of Compounds of the Invention

The starting materials and intermediates of compounds of the invention may be prepared by the application or adaptation of known methods described below, their obvious chemical equivalents, or, for example, as described in literature by R. C. Larock in Comprehensive Organic Transformations, VCH publishers (1989).

Purification by HPLC refers to preparative high performance liquid chromatography using the following conditions: [C18 column, 10 micron particle size, gradient elution: 20-100% CH$_3$CN (0.1% TFA) in H$_2$O (0.1% TFA)].

EXAMPLES

Example 1

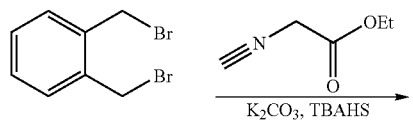

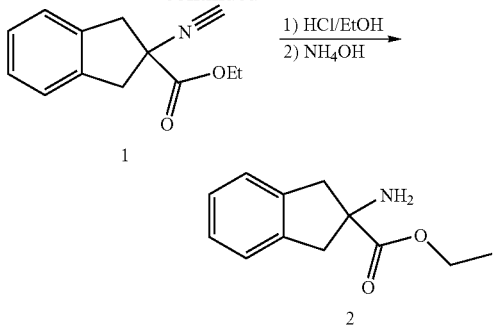

Isocyano-indan-2-carboxylic acid ethyl ester (1)

To a solution of ethyl isocyanoacetate (4.29 g, 37.9 mmol) in anhydrous ACN (400 mL) is added anhydrous K$_2$CO$_3$ (K$_2$SO$_4$, 31.4 g, 227 mmol), TBAHS (tetrabutyl ammonium hydrogen sulfate, 2.57 g, 7.58 mmol), and 1,2-bis-bromomethyl-benzene (10.0 g, 37.9 mmol). The resulting heterogeneous mixture is stirred at 75° C. overnight. The reaction mixture is cooled down to RT and filtered to remove the unwanted salts. The filter cake is washed with ACN (20 mL) and the filtrate is concentrated in vacuo. The residue is dissolved in ethyl ether (150 mL) and washed with water (1×10 mL) and brine (3×10 mL). The organic layer is dried over Na$_2$SO$_4$ and concentrated in vacuo. The residue is purified by flash column chromatography (400 g silica gel; gradient elution: 20-100% EtOAc in heptane) to give a pure product as white solid (8.0 g, 49%).

$^1$H NMR (CDCl$_3$, 300 MHz): δ 1.35 (t, 3H), 3.47 (d, 2H), 3.71 (d, 2H), 4.32 (q, 2H), 7.25 (s, 4H)

LC/MS (ES+) m/z=449.25

Example 2

2-Amino-indan-2-carboxylic acid ethyl ester (2)

To a solution of 2-isocyano-indan-2-carboxylic acid ethyl ester (1) (8.0 g, 37.2 mmol) in absolute EtOH (200 mL) is added concentrated HCl (5 mL) dropwise. The resulting solution is stirred at RT for 5 h. After the removal of the EtOH in vacuo, the remaining hydrochloride salt is dissolved in water (100 mL) and extracted with of ethyl ether (3×5 mL) to remove unwanted organic impurities. The aqueous layer is brought to pH=10 by addition of NH$_4$OH solution and then extracted with EtOAc (3×50 mL). The combined EtOAc layer is washed with water (1×10 mL) and brine (2×10 mL). The organic layer is dried over Na$_2$SO$_4$ and concentrated in vacuo to give a pure product as white solid (4.7 g, 62%).

$^1$H NMR (CDCl$_3$, 300 MHz): δ 1.29 (t, 3H), 2.88 (d, 2H), 3.57 (d, 2H), 4.23 (q, 2H), 7.16-7.23 (m, 4H)

LC/MS (EZ+) m/z=206.08

Example 3

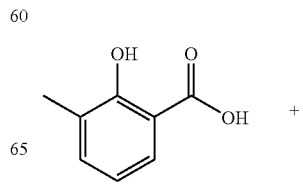

-continued

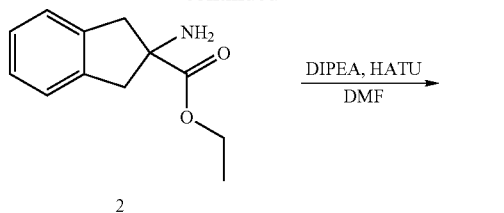

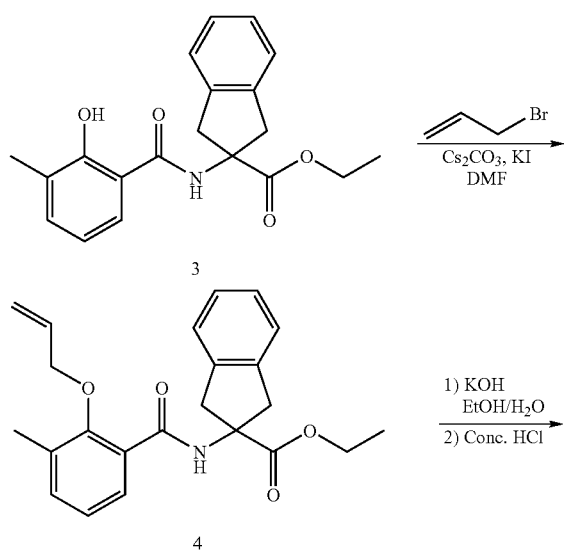

2-(2-Hydroxy-3-methyl-benzoylamino)-indan-2-carboxylic acid ethyl ester (3)

To a solution of 2-hydroxy-3-methyl-benzoic acid (3.65 g, 24 mmol), 2-amino-indan-2-carboxylic acid ethyl ester (5.00 g, 24 mmol), HATU [O-(7-azabenzotriazol-1-yl)-N,N,N',N'-tetramethyluronium PF₆] (11.0 g, 29 mmol) in anhydrous DMF (30 mL) is added DIPEA (8.30 mL, 50 mmol). The resulting solution is stirred at RT overnight. After the removal of DMF in vacuo, the residue is dissolved in EtOAc (150 mL) and washed with water (1×10 mL) and brine (2×10 mL). The organic layer is dried over anhydrous Na₂SO₄ and concentrated in vacuo. The residue is purified by flash column chromatography (400 g silica gel, gradient elution: 10-80% EtOAc in heptane) to give a pure product (3) as white solid (5.5 g, 67%).

¹H NMR (CDCl₃, 300 MHz): δ 1.24 (t, 3H), 2.23 (s, 3H), 3.40 (d, 2H), 3.74 (d, 2H), 4.25 (q, 2H), 6.70 (t, 1H), 6.84 (s, 1H), 7.15-7.25 (m, 6H), 12.21 (s, 1H)

LC/MS (ES+) m/z=340.15

Example 4

2-(2-Allyloxy-3-methyl-benzoylamino)-indan-2-carboxylic acid ethyl ester (4)

To a suspension of 2-(2-hydroxy-3-methyl-benzoylamino)-indan-2-carboxylic acid ethyl ester (3) (300 mg, 0.88 mmol), anhydrous Cs₂CO₃ (573 mg, 1.76 mmol), and KI (30 mg, 0.18 mmol) in DMF (8 mL) is added 3-bromo-propene (90 µL, 1.06 mmol). The resulting reaction suspension is stirred at RT overnight. After the removal of DMF in vacuo, the residue is dissolved in EtOAc (30 mL) and washed with water (1×5 mL) and brine (2×5 mL). The organic layer is dried over anhydrous Na₂SO₄ and concentrated in vacuo. The residue is purified by flash column chromatography (120 g silica gel, gradient elution: 10-30% EtOAc in heptane) to give a pure product (4) as white solid (303 mg, 91%).

¹H NMR (CDCl₃, 300 MHz): δ 1.25 (t, 3H), 2.26 (s, 3H), 3.33 (d, 2H), 3.75 (d, 2H), 4.25 (q, 2H), 5.21 (d, 1H), 5.33 (d, 1H), 5.86 (m, 1H), 7.09 (t, 1H), 7.19 (br s 4H), 7.27 (d, 1H), 7.88 (d, 1H), 8.43 (s, 1H)

LC/MS (ES+) m/z=380.20

Example 5

2-(2-Allyloxy-3-methyl-benzoylamino)-indan-2-carboxylic acid (5)

The mixture of 2-(2-allyloxy-3-methyl-benzoylamino)-indan-2-carboxylic acid ethyl ester (4) (168 mg, 0.44 mmol) and KOH (500 mg, 8.9 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (5) as white solid (150 mg, 97%).

¹H NMR (CDCl₃+drops of CD₃OD, 300 MHz): δ 2.26 (s, 3H), 3.34 (d, 2H), 3.77 (d, 2H), 4.23 (d, 2H), 5.20 (d, 1H), 5.32 (d, 1H), 5.84 (m, 1H), 7.10 (t, 1H), 7.16-7.23 (m, 4H), 7.29 (d, 1H), 7.83 (dd, 1H), 8.57 (s, 1H)

LC/MS (ES+) m/z=352.15

Example 6

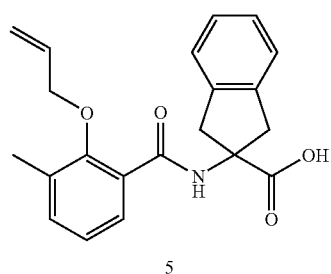

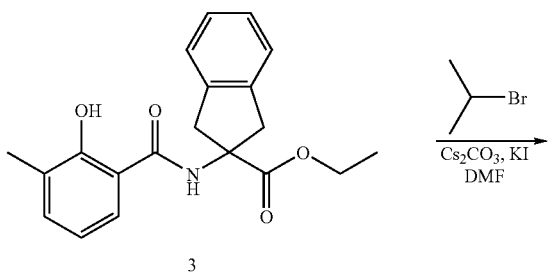

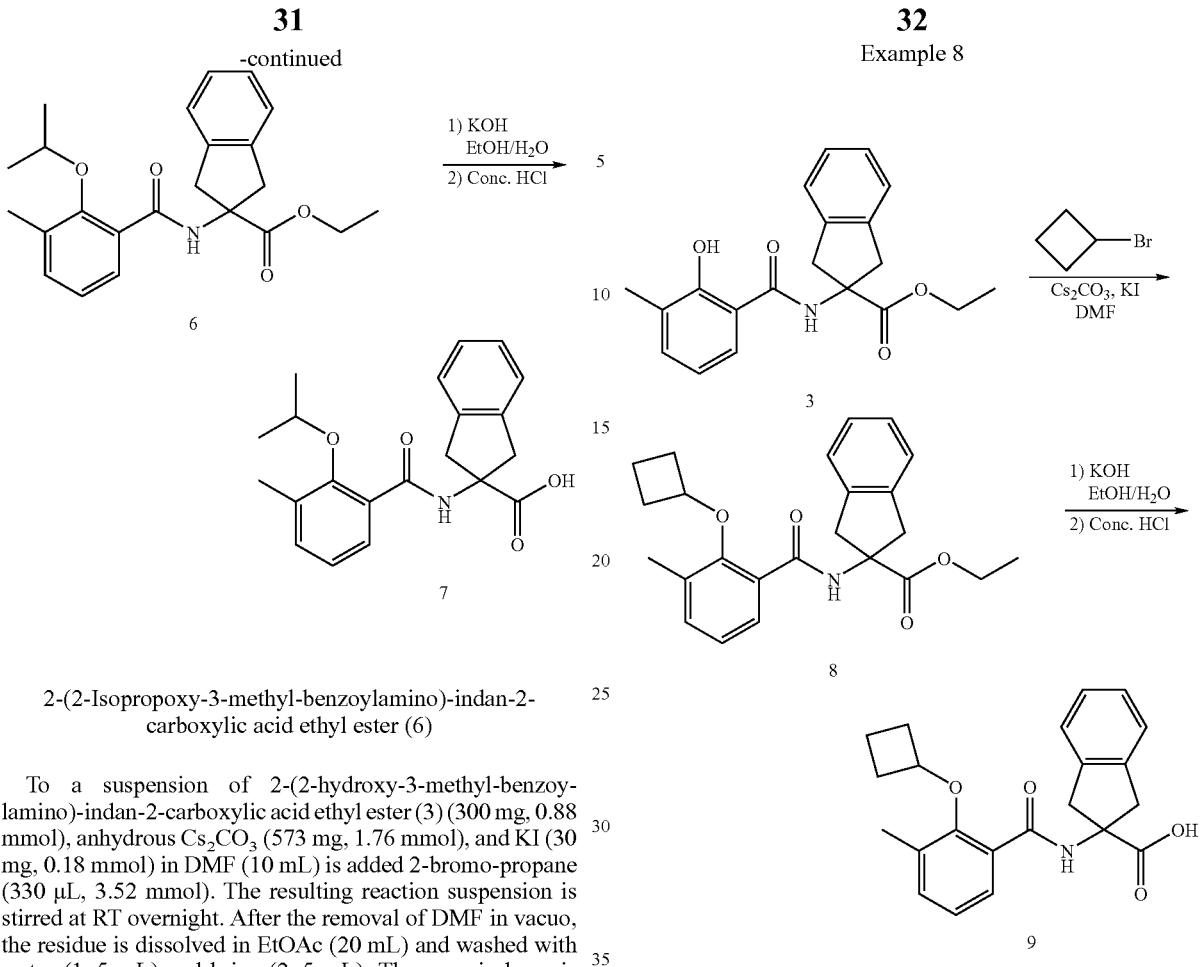

2-(2-Isopropoxy-3-methyl-benzoylamino)-indan-2-carboxylic acid ethyl ester (6)

To a suspension of 2-(2-hydroxy-3-methyl-benzoylamino)-indan-2-carboxylic acid ethyl ester (3) (300 mg, 0.88 mmol), anhydrous $Cs_2CO_3$ (573 mg, 1.76 mmol), and KI (30 mg, 0.18 mmol) in DMF (10 mL) is added 2-bromo-propane (330 μL, 3.52 mmol). The resulting reaction suspension is stirred at RT overnight. After the removal of DMF in vacuo, the residue is dissolved in EtOAc (20 mL) and washed with water (1×5 mL) and brine (2×5 mL). The organic layer is dried over anhydrous $Na_2SO_4$ and concentrated in vacuo. The residue is purified by flash column chromatography (120 g silica gel, gradient elution: 10-40% EtOAc in heptane) to give a pure product (6) as white solid (174 mg, 52%).

$^1$H NMR (CDCl$_3$, 300 MHz): δ 1.03 (d, 6H), 1.24 (t, 3H), 2.25 (s, 3H), 3.34 (d, 2H), 3.77 (d, 2H), 4.21 (m, 1H), 4.25 (q, 2H), 7.07 (t, 1H), 7.17-7.26 (m, 5H), 7.85 (dd, 1H), 8.31 (s, 1H)

LC/MS (ES+) m/z=382.18

Example 7

2-(2-Isopropoxy-3-methyl-benzoylamino)-indan-2-carboxylic acid (7)

The mixture of 2-(2-isopropoxy-3-methyl-benzoylamino)-indan-2-carboxylic acid ethyl ester (6) (265 mg, 0.69 mmol) and KOH (500 mg, 8.9 mmol) is dissolved in EtOH (6 mL) and water (1 mL) under a water bath. The water bath is removed when KOH is completely dissolved and the resulting reaction solution is stirred at RT for 8 h. After concentration in vacuo, the residue is dissolved in water (20 mL) and the solution acidified with conc. HCl until no more white precipitate came out of the water. The precipitate is filtered to give a pure product (7) as white solid (244 mg, 100%).

$^1$H NMR (CDCl$_3$, 300 MHz): δ 0.98 (d, 6H), 2.24 (s, 3H), 3.41 (d, 2H), 3.85 (d, 2H), 4.14 (m, 1H), 7.08 (t, 1H), 7.18-7.30 (m, 5H), 7.88 (d, 1H), 8.52 (s, 1H)

LC/MS (ES+) m/z=354.16

Example 8

2-(2-Cyclobutoxy-3-methyl-benzoylamino)-indan-2-carboxylic acid ethyl ester (8)

To a suspension of 2-(2-hydroxy-3-methyl-benzoylamino)-indan-2-carboxylic acid ethyl ester (3) (400 mg, 1.18 mmol), anhydrous $Cs_2CO_3$ (769 mg, 2.36 mmol), and KI (40 mg, 0.24 mmol) in DMF (10 mL) is added bromo-cyclobutane (130 μL, 1.42 mmol). The resulting reaction suspension is stirred at RT overnight. After the removal of DMF in vacuo, the residue is dissolved in EtOAc (20 mL) and washed with water (1×5 mL) and brine (2×5 mL). The organic layer is dried over anhydrous $Na_2SO_4$ and concentrated in vacuo. The residue is purified by flash column chromatography (120 g silica gel, gradient elution: 10-40% EtOAc in heptane) to give a pure product (8) as white solid (320 mg, 69%).

$^1$H NMR (CDCl$_3$, 300 MHz): δ 1.25 (t, 3H), 1.18-1.34 (m, 1H), 1.41-1.52 (m, 1H), 1.87-2.07 (m, 4H), 2.26 (s, 3H), 3.36 (d, 2H), 3.78 (d, 2H), 4.22-4.29 (m, 1H), 4.24 (q, 2H), 7.07 (t, 1H), 7.17-7.27 (m, 5H), 7.86 (dd, 1H), 8.33 (s, 1H)

LC/MS (ES+) m/z=394.19

Example 9

2-(2-Cyclobutoxy-3-methyl-benzoylamino)-indan-2-carboxylic acid (9)

The mixture of 2-(2-cyclobutoxy-3-methyl-benzoylamino)-indan-2-carboxylic acid ethyl ester (8) (250 mg, 0.64 mmol) and KOH (600 mg, 10.7 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and the solution acidified with conc. HCl until pH~3 to yield a precipitate. The precipitate is filtered to give a pure product (9) as white solid (190 mg, 81%).

$^1$H NMR (CDCl$_3$+drops of CD$_3$OD, 300 MHz): δ 1.24 (m, 1H), 1.45 (m, 1H), 1.87-2.01 (m, 4H), 2.26 (s, 3H), 3.40 (d, 2H), 3.81 (d, 2H), 4.26 (m, 1H), 7.08 (t, 1H), 7.18-7.29 (m, 5H), 7.82 (dd, 1H), 8.48 (s, 1H)

LC/MS (ES+) m/z=366.16

Example 10

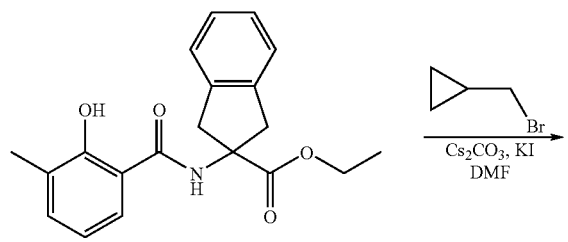

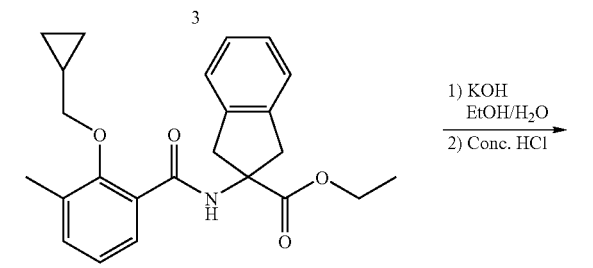

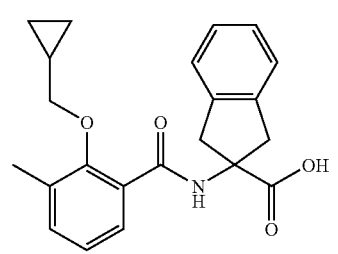

2-(2-Cyclopropylmethoxy-3-methyl-benzoylamino)-indan-2-carboxylic acid ethyl ester (10)

To a suspension of 2-(2-hydroxy-3-methyl-benzoylamino)-indan-2-carboxylic acid ethyl ester (3) (400 mg, 1.18 mmol), anhydrous Cs$_2$CO$_3$ (769 mg, 2.36 mmol), and KI (40 mg, 0.24 mmol) in DMF (10 mL) is added bromomethylcyclopropane (229 μL, 2.36 mmol). The resulting reaction suspension is stirred at RT overnight. After the removal of DMF in vacuo, the residue is dissolved in EtOAc (30 mL) and washed with water (1×5 mL) and brine (2×5 mL). The organic layer is dried over anhydrous Na$_2$SO$_4$ and concentrated in vacuo. The residue is purified by flash column chromatography (120 g silica gel, gradient elution: 10-40% EtOAc in heptane) to give a pure product (10) as white solid (330 mg, 71%).

$^1$H NMR (CDCl$_3$, 300 MHz): δ 0.17 (m, 2H), 0.50 (m, 2H), 0.91 (m, 1H), 1.24 (t, 3H), 2.26 (s, 3H), 3.36 (d, 2H), 3.54 (d, 2H), 3.79 (d, 2H), 4.24 (q, 2H), 7.08 (t, 1H), 7.15-7.27 (m, 5H), 7.86 (dd, 1H), 8.44 (s, 1H)

LC/MS (ES+) m/z=394.18

Example 11

2-(2-Cyclopropylmethoxy-3-methyl-benzoylamino)-indan-2-carboxylic acid (11)

The mixture of 2-(2-cyclopropylmethoxy-3-methyl-benzoylamino)-indan-2-carboxylic acid ethyl ester (10) (240 mg, 0.61 mmol) and KOH (500 mg, 8.93 mmol) is dissolved in EtOH (6 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (11) as white solid (223 mg, 100%).

$^1$H NMR (CDCl$_3$, 300 MHz): δ 0.11 (m, 2H), 0.51 (m, 2H), 0.84 (m, 1H), 2.26 (s, 3H), 3.46 (dd, 4H), 3.88 (d, 2H), 7.11 (t, 1H), 7.17-7.32 (m, 5H), 7.89 (d, 1H), 8.74 (s, 1H)

LC/MS (ES+) m/z=366.17

Example 12

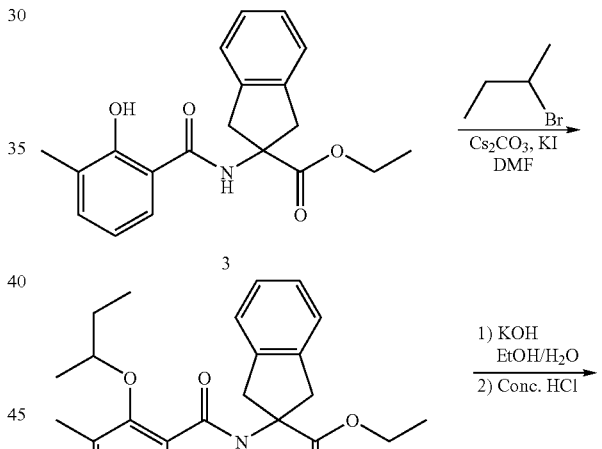

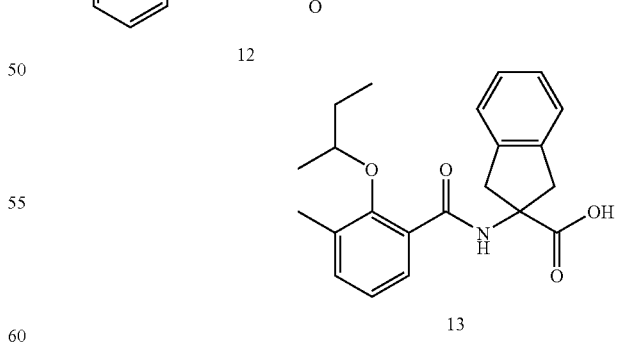

2-(2-sec-Butoxy-3-methyl-benzoylamino)-indan-2-carboxylic acid ethyl ester (12)

To a suspension of 2-(2-hydroxy-3-methyl-benzoylamino)-indan-2-carboxylic acid ethyl ester (3) (400 mg, 1.18 mmol), anhydrous $Cs_2CO_3$ (574 mg, 2.36 mmol), and KI (40 mg, 0.24 mmol) in DMF (10 mL) is added 2-bromobutane (508 μL, 4.72 mmol). The resulting reaction suspension is stirred at RT overnight. After the removal of DMF in vacuo, the residue is dissolved in EtOAc (30 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 10-40% EtOAc in heptane) to give a pure product (12) as white solid (395 mg, 85%).

$^1$H NMR ($CDCl_3$, 300 MHz): δ 0.80 (t, 3H), 0.93 (d, 3H), 1.22-1.30 (m, 4H), 1.48 (m, 1H), 2.25 (s, 3H), 3.33 (dd, 2H), 3.76 (dd, 2H), 3.97 (m, 1H), 4.25 (q, 2H), 7.01 (t, 1H), 7.17-7.26 (m, 5H), 7.87 (dd, 1H), 8.35 (s, 1H)

LC/MS (ES+) m/z=396.19

Example 13

2-(2-sec-Butoxy-3-methyl-benzoylamino)-indan-2-carboxylic acid (13)

The mixture of 2-(2-sec-butoxy-3-methyl-benzoylamino)-indan-2-carboxylic acid ethyl ester (12) (176 mg, 0.44 mmol) and KOH (500 mg, 8.93 mmol) is dissolved in EtOH (6 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (13) as white solid (162 mg, 100%).

$^1$H NMR ($CDCl_3$, 300 MHz): δ 0.79 (t, 3H), 0.86 (d, 3H), 1.18 (m, 1H), 1.49 (m, 1H), 2.25 (s, 3H), 3.42 (t, 2H), 3.86 (dd, 2H), 3.91 (m, 1H), 7.09 (t, 1H), 7.19-7.31 (m, 5H), 7.90 (d, 1H), 8.59 (s, 1H)

LC/MS (ES+) m/z=368.17

Example 14

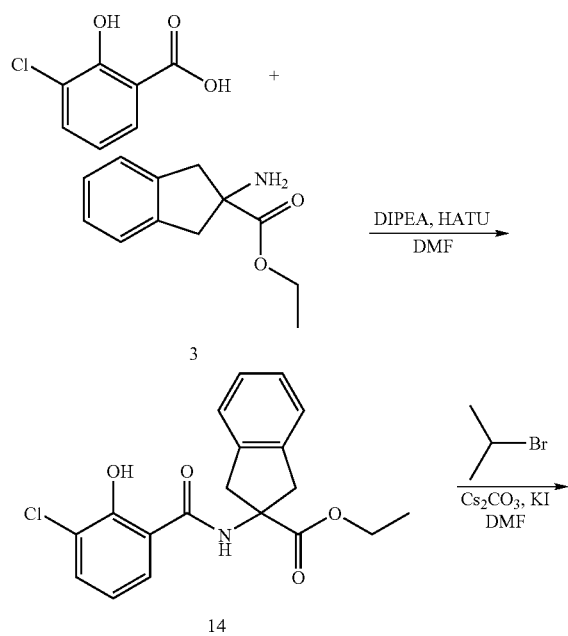

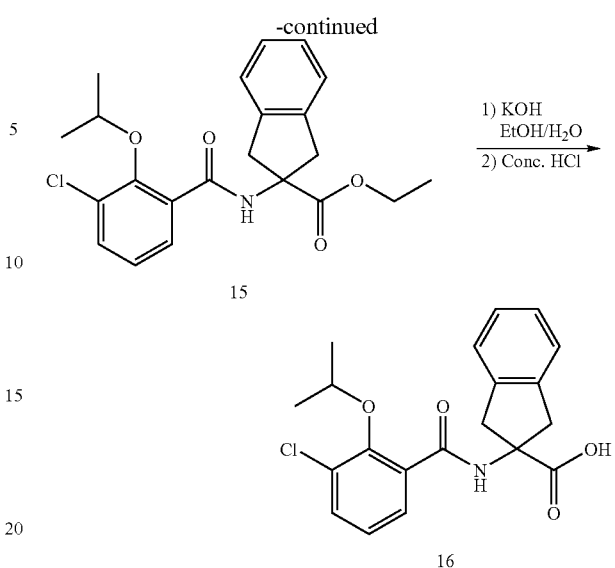

2-(3-Chloro-2-hydroxy-benzoylamino)-indan-2-carboxylic acid ethyl ester (14)

To a solution of 3-chloro-2-hydroxy-benzoic acid (413 mg, 2.4 mmol), 2-Amino-indan-2-carboxylic acid ethyl ester (500 mg, 2.4 mmol), HATU (1.1 g, 2.9 mmol) in anhydrous DMF (10 mL) is added DIPEA (0.88 ml, 5.3 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 10%-80% EtOAc in heptane) to give a pure product (14) as white solid (420 mg, 49%).

$^1$H NMR ($CDCl_3$, 300 MHz): δ 1.24 (t, 3H), 3.42 (d, 2H), 3.73 (d, 2H), 4.25 (q, 2H), 6.76 (t, 1H), 6.97 (s, 1H), 7.23-7.29 (m, 5H), 7.47 (dd, 1H), 12.5 (s, 1H)

LC/MS (ES+) m/z=360.07, 362.08

Example 15

2-(3-Chloro-2-isopropoxy-benzoylamino)-indan-2-carboxylic acid ethyl ester (15)

To a suspension of 2-(3-chloro-2-hydroxy-benzoylamino)-indan-2-carboxylic acid ethyl ester (14) (150 mg, 0.42 mmol), anhydrous $Cs_2CO_3$ (274 mg, 0.84 mmol), and KI (13 mg, 0.08 mmol) in DMF (7 mL) is added 3-bromo-propene (237 μL, 2.52 mmol). The resulting reaction suspension is stirred at RT overnight. After the removal of DMF in vacuo, the residue is dissolved in EtOAc (20 mL) and washed with water (1×5 mL) and brine (2×5 mL). The organic layer is dried over anhydrous $Na_2SO_4$ and concentrated in vacuo. The residue is purified by flash column chromatography (80 g silica gel, gradient elution: 10-40% EtOAc in heptane) to give a pure product (15) as white solid (137 mg, 81%).

$^1$H NMR ($CDCl_3$, 300 MHz): δ 1.05 (d, 6H), 1.24 (t, 3H), 3.33 (d, 2H), 3.76 (d, 2H), 4.25 (q, 2H), 4.56 (m, 1H), 7.11 (t, 1H), 7.19-7.26 (m, 4H), 7.46 (dd, 1H), 7.95 (dd, 1H), 8.28 (s, 1H)

LC/MS (ES+) m/z=402.13, 404.14

Example 16

2-(3-Chloro-2-isopropoxy-benzoylamino)-indan-2-carboxylic acid (16)

The mixture of 2-(3-chloro-2-isopropoxy-benzoylamino)-indan-2-carboxylic acid ethyl ester (15) (122 mg, 0.30 mmol) and KOH (500 mg, 8.9 mmol) is dissolved in EtOH (5 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (16) as white solid (119 mg, 100%).

$^1$H NMR (CDCl$_3$, 300 MHz): δ 1.01 (d, 6H), 3.40 (d, 2H), 3.84 (d, 2H), 4.55 (m, 1H), 7.13 (t, 1H), 7.19-7.26 (m, 4H), 7.48 (dd, 1H), 7.98 (dd, 1H), 8.43 (s, 1H)

LC/MS (ES+) m/z=374.11, 376.13

Example 17

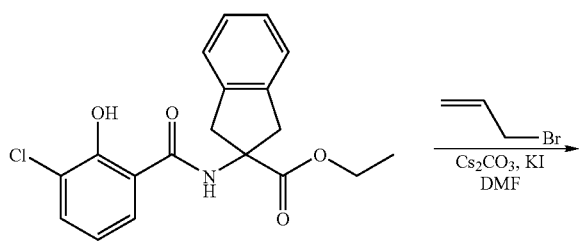

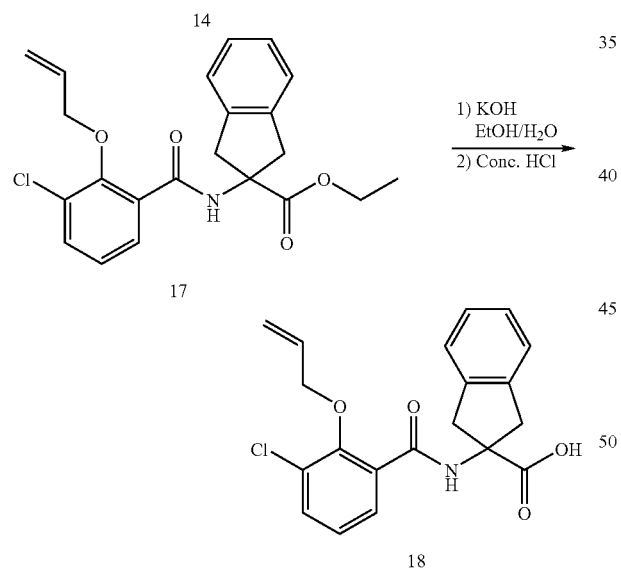

2-(2-Allyloxy-3-chloro-benzoylamino)-indan-2-carboxylic acid ethyl ester (17)

To a suspension of 2-(3-chloro-2-hydroxy-benzoylamino)-indan-2-carboxylic acid ethyl ester (14) (250 mg, 0.69 mmol), anhydrous Cs$_2$CO$_3$ (453 mg, 1.39 mmol), and KI (23 mg, 0.14 mmol) in DMF (10 mL) is added 3-bromo-propene (70 μL, 0.83 mmol). The resulting reaction suspension is stirred at RT overnight. After the removal of DMF in vacuo, the residue is dissolved in EtOAc (20 mL) and washed with water (1×5 mL) and brine (2×5 mL). The organic layer is dried over anhydrous Na$_2$SO$_4$ and concentrated in vacuo. The residue is purified by flash column chromatography (80 g silica gel, gradient elution: 10-40% EtOAc in heptane) to give a pure product (17) as white solid (160 mg, 58%).

$^1$H NMR (CDCl$_3$, 300 MHz): δ 1.25 (t, 3H), 3.32 (d, 2H), 3.75 (d, 2H), 4.25 (q, 2H), 4.41 (d, 2H), 5.20-5.34 (m, 2H), 5.88 (m, 1H), 7.13-7.26 (m, 5H), 7.49 (dd, 1H), 7.97 (dd, 1H), 8.36 (s, 1H)

LC/MS (ES+) m/z=402.13, 404.14

Example 18

2-(2-Allyloxy-3-chloro-benzoylamino)-indan-2-carboxylic acid (18)

The mixture of 2-(2-allyloxy-3-chloro-benzoylamino)-indan-2-carboxylic acid ethyl ester (17) (140 mg, 0.35 mmol) and KOH (500 mg, 8.9 mmol) is dissolved in EtOH (5 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH~3. After filtration, the solid is purified by HPLC to give a pure product (18) as white solid (88 mg, 68%).

$^1$H NMR (CDCl$_3$+drops of CD$_3$OD, 300 MHz): δ 3.35 (d, 2H), 3.78 (d, 2H), 4.41 (d, 2H), 5.21-5.34 (m, 2H), 5.87 (m, 1H), 7.13-7.30 (m, 5H), 7.50 (dd, 1H), 7.93 (dd, 1H), 8.49 (s, 1H)

LC/MS (ES+) m/z=372.09, 374.10

Example 19

2-Amino-5-fluoroindane-2-carboxylic acid ethyl ester

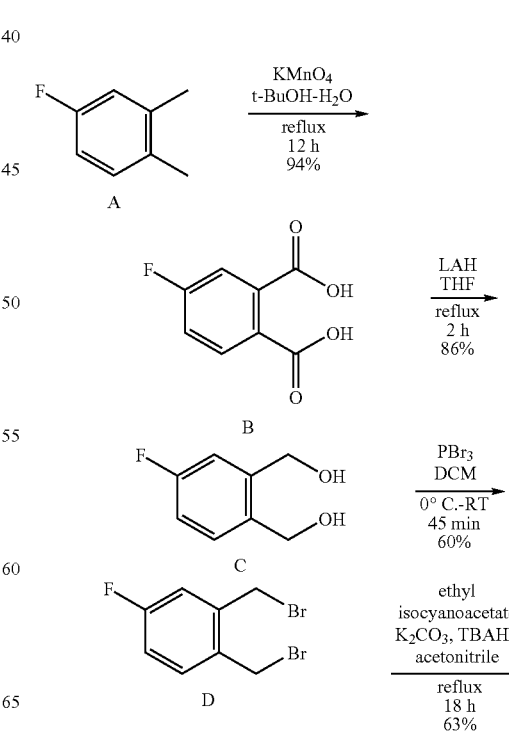

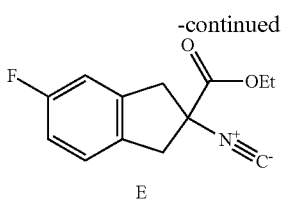

E

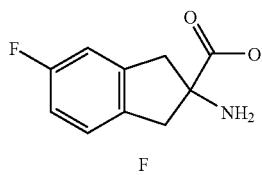

F

Preparation of B:

4-Fluoro-1,2-dimethyl benzene A (50.0 g, 402.7 mmol) and a large excess of KMnO$_4$ (400 g, 2.54 mol) are dissolved in 1500 mL of a water/t-butanol (70/30%, v/v) mixture. The reaction mixture is refluxed overnight. EtOH (900 mL) is added to destroy unreacted KMnO$_4$ and the alcohols are distilled off. The resulting brown suspension is filtered through a celite pad. The colorless solution is concentrated and acidified with conc. HCl to pH 1. The product is filtered and the aqueous phase is extracted with EtOAc and dried over Na$_2$SO$_4$. 70.0 g (94%) of white solid B is obtained after evaporation under reduced pressure.

$^1$H-NMR (400 MHz, DMSO-d6): δ 7.39 (m, 1H), 7.63 (br s, 1H), 7.99 (br s, 1H).

Preparation of C:

LAH (37.5 g, 989 mmol) is added to THF (850 mL). The mixture is cooled in an ice bath and 4-fluorophthalic acid B (70.0 g, 380 mmol) in THF (420 mL) is added dropwise. After addition, the reaction mixture is refluxed for 2 h. The mixture is cooled in an ice bath and water (35 mL), aqueous 15% NaOH (35 mL) and water (70 mL) are added dropwise. The solid material is removed by filtration and washed with DCM, and the combined organic solutions are dried over Na$_2$SO$_4$ and evaporated under reduced pressure to give 51.2 g (86%) of C.

$^1$H-NMR (400 MHz, CDCl$_3$): 4.71 (t, J=4.5 Hz, 4H), 6.98 (m, 1H), 7.08 (m, 1H), 7.29 (m, 1H).

Preparation of D:

To a solution of 2-hydroxy-methyl-5-fluoro-phenyl-methanol C (51.2 g, 327.8 mmol) in 520 mL of DCM is added phosphorous tribromide (37.3 mL, 393.5 mmol) in DCM (520 mL) dropwise at 0° C. under a N$_2$ atmosphere and stirred for 45 min. The reaction mixture is quenched with water (70 mL) added slowly and extracted with EtOAc, washed with water, satd. Na$_2$SO$_4$ solution and brine. The organic layer is evaporated under reduced pressure to give crude product, which is purified by silica gel 100-200 mesh column eluting with hexane to give 55.8 g (60%) of D.

$^1$H-NMR (400 MHz, CDCl$_3$): 4.61 (m, 4H), 6.99 (m, 1H), 7.07 (m, 1H), 7.33 (m, 1H).

Preparation of E:

A solution of 5-fluoro-1,2-bisbromomethylbenzene (20.4 g, 72.3 mmol), ethyl isocyanoacetate (5.7 mL, 51 mmol), tetrabutylammonium hydrogen sulfate (6.7 g, 19.7 mmol) and dry K$_2$SO$_4$ (41.8 g, 303 mmol) in ACN (1500 mL) is refluxed for 18 h. After completion of reaction, the mixture is cooled and filtered. The filtrate is concentrated under reduced pressure and dissolved with EtOAc. The organic layer is washed with water and brine, dried over Na$_2$SO$_4$ and concentrated under reduced pressure. The crude mass obtained is purified by silica gel 100-200 mesh column eluting with 5% EtOAc-hexane to give 10.8 g (63%) of E.

$^1$H-NMR (400 MHz, CDCl$_3$): 1.32 (m, 3H), 3.43 (m, 2H), 3.66 (m, 2H), 4.32 (m, 2H), 6.94 (m, 2H), 7.17 (m, 1H).

Preparation of F:

A methanolic solution of conc. HCl (35%) (9.3 mL in 110 mL of MeOH) is added dropwise to a methanolic solution of 5-fluoro-2-isocyano-indan-2-carboxylic acid ethyl ester E (17.6 g, 75.4 mmol) at RT and the mixture is stirred for 2 h. The mixture is then neutralized by saturated NaHCO$_3$ solution and extracted with DCM (500 mL). The organic layer is washed with water, brine, dried over Na$_2$SO$_4$, and concentrated under reduced pressure to obtain 16.0 g (94%) of F as yellowish semi solid.

$^1$H-NMR (400 MHz, CDCl$_3$): 1.26 (q, 3H), 1.62 (br s, 2H), 2.84 (m, 2H), 3.50 (q, 2H), 4.20 (m, 2H), 6.88 (m, 2H), 7.12 (t, J=7.6 Hz, 1H). $^1$H-NMR (400 MHz, D$_2$O exchange, CDCl$_3$): 1.26 (q, 3H), 2.83 (m, 2H), 3.49 (q, 2H), 4.20 (m, 2H), 6.88 (m, 2H), 7.12 (t, J=7 Hz, 1H).

$^{13}$C-NMR (100 MHz, CDCl$_3$): 13.98, 45.14, 45.83, 61.21, 65.28, 111.82, 113.59, 125.54, 135.70, 142.44, 163.35, 176.05. IR (Neat): 1728 cm$^{-1}$. FIA-MS: 234 [M+H]$^+$. Qualitative GC-FID showed purity of 19 is 96.32% (% by area normalization).

Example 20

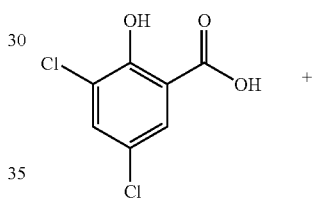

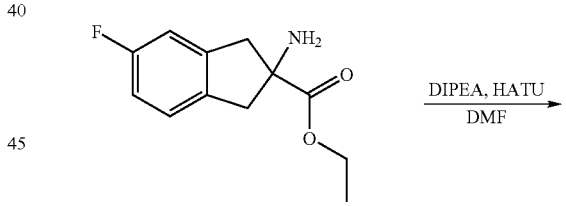

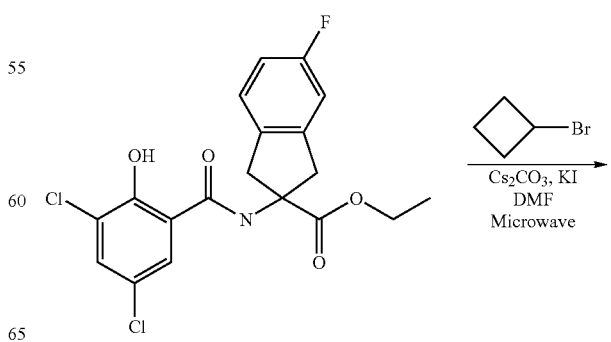

19

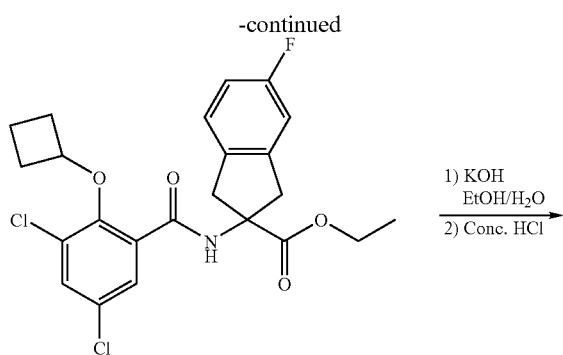

20

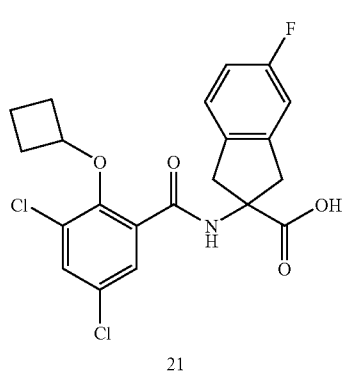

21

2-(3,5-Dichloro-2-hydroxy-benzoylamino)-5-fluoro-indan-2-carboxylic acid ethyl ester (19)

To a solution of 3,5-dichloro-2-hydroxy-benzoic acid (500 mg, 2.42 mmol), 2-amino-5-fluoro-indan-2-carboxylic acid ethyl ester F (1.08 g, 4.84 mmol), HATU (1.10 g, 2.89 mmol) in anhydrous DMF (15 mL) is added DIPEA (599 µl, 3.63 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 10%-80% EtOAc in heptane) to give a pure product (A) as white solid (779 mg, 78%).

$^1$H NMR (CDCl$_3$+drops of CD$_3$OD, 300 MHz): δ 1.24 (t, 3H), 3.39 (dd, 2H), 3.68 (dd, 2H), 4.24 (q, 2H), 6.91-6.94 (m, 2H), 7.14-7.18 (m, 1H), 7.46 (d, 1H), 7.52 (d, 1H), 7.92 (s, 1H), LC/MS (ES+) m/z=412.06, 414.06

Example 20

2-(3,5-Dichloro-2-cyclobutoxy-benzoylamino)-5-fluoro-indan-2-carboxylic acid ethyl ester (20)

To a suspension 2-(3,5-dichloro-2-hydroxy-benzoylamino)-5-fluoro-indan-2-carboxylic acid ethyl ester (19) (624 mg, 1.51 mmol), anhydrous $Cs_2CO_3$ (984 mg, 3.02 mmol), and KI (50 mg, 0.30 mmol) in DMF (20 mL) is added bromocyclobutane (711 µL, 7.55 mmol). The resulting reaction suspension is covered with argon and ran in a microwave reaction: 110° C., 2 h. After the removal of DMF in vacuo, the residue is dissolved in EtOAc (50 mL) and washed with water (1×5 mL) and brine (2×5 mL). The organic layer is dried over anhydrous $Na_2SO_4$ and concentrated in vacuo. The residue is purified by flash column chromatography (120 g silica gel, gradient elution: 10%-50% EtOAc in heptane) to give a pure product (20) as white solid (365 mg, 52%).

$^1$H NMR (CDCl$_3$+drops of CD$_3$OD, 300 MHz): δ 1.23-1.38 (m, 4H), 1.51-1.55 (m, 1H), 1.94-2.07 (m, 4H), 3.32 (t, 2H), 3.73 (dd, 2H), 4.26 (q, 2H), 4.58 (m, 1H), 6.88-6.96 (m, 2H), 7.18 (br s, 1H), 7.47 (s, 1H), 7.93 (s, 1H), 8.27 (s, 1H), LC/MS (ES+) m/z=466.12, 468.12

Example 21

2-(3,5-Dichloro-2-cyclobutoxy-benzoylamino)-5-fluoro-indan-2-carboxylic acid (21)

The mixture of 2-(3,5-dichloro-2-cyclobutoxy-benzoylamino)-5-fluoro-indan-2-carboxylic acid ethyl ester (20) (300 mg, 0.64 mmol) and KOH (500 mg, 8.9 mmol) is dissolved in EtOH (5 mL) and water (1 mL) under a water bath. The water bath is removed when KOH is completely dissolved and the resulting reaction solution is stirred at RT for 6 h. After concentration in vacuo, the residue is dissolved in water (20 mL) and acidified with conc. HCl until pH~3. The precipitate is filtered to give a pure product (21) as white solid (200 mg, 71%).

$^1$H NMR (CDCl$_3$+drops of CD$_3$OD, 300 MHz): δ 1.32 (m, 1H), 1.50 (m, 1H), 1.92-2.09 (m, 4H), 3.36 (t, 2H), 3.75 (dd, 2H), 4.56 (m, 1H), 6.91-6.96 (m, 2H), 7.16-7.20 (m, 1H), 7.48 (dd, 1H), 7.90 (dd, 1H), 8.37 (s, 1H), LC/MS (ES+) m/z=438.09, 440.08

Example 22

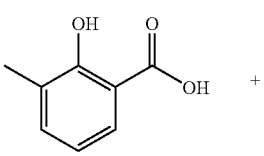

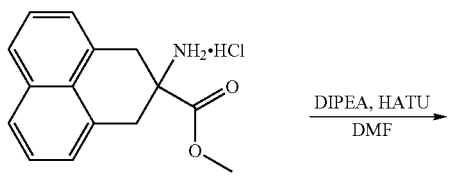

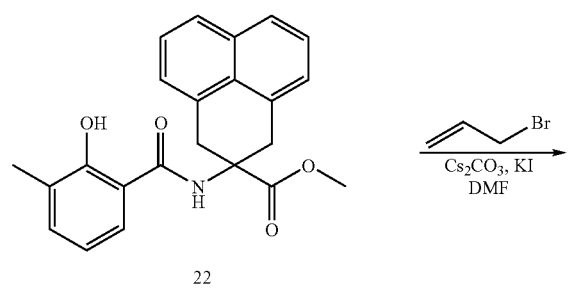

22

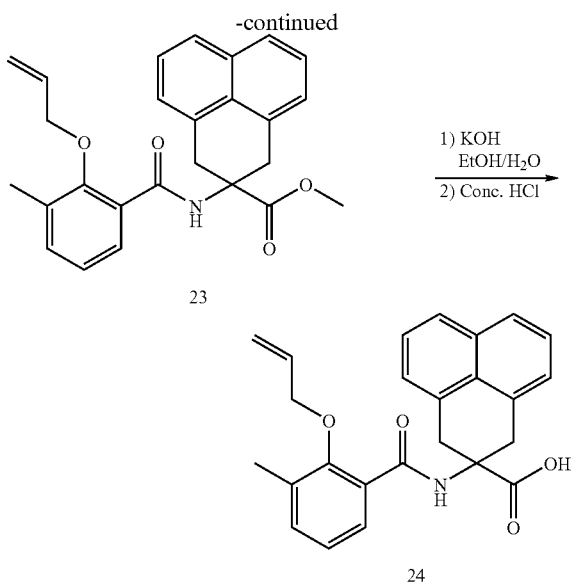

Example 24

2-(2-Allyloxy-3-methyl-benzoylamino)-2,3-dihydro-1H-phenalene-2-carboxylic acid (24)

The mixture of 2-(2-allyloxy-3-methyl-benzoylamino)-2,3-dihydro-1H-phenalene-2-carboxylic acid ethyl ester (23) (107 mg, 0.26 mmol) and KOH (500 mg, 8.9 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out from the water. The precipitate is filtered to give a pure product (24) as white solid (98 mg, 94%).

$^1$H NMR (CDCl$_3$+drops of CD$_3$OD, 300 MHz): δ 2.09 (s, 3H), 3.71-3.74 (m, 6H), 5.06-5.11 (m, 2H), 5.28-5.41 (m, 1H), 7.01 (t, 1H), 7.18 (dd, 1H), 7.30 (dd, 1H), 7.41 (t, 2H), 7.70 (d, 2H), 7.75 (dd, 1H), 8.20 (s, 1H)

LC/MS (ES+) m/z=402.16

2-(2-Hydroxy-3-methyl-benzoylamino)-2,3-dihydro-1H-phenalene-2-carboxylic acid methyl ester (22)

To a solution of 2-hydroxy-3-methyl-benzoic acid (1.12 g, 7.4 mmol), 2-amino-2,3-dihydro-1H-phenalene-2-carboxylic acid methyl ester (2.05 g, 7.4 mmol), HATU (3.38 g, 8.9 mmol) in anhydrous DMF (28 mL) is added DIPEA (4.89 mL, 29.6 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous Na$_2$SO$_4$ and concentrated in vacuo. The residue is purified by flash column chromatography (300 g silica gel, gradient elution: 10%-80% EtOAc in heptane) to give the pure product (22) as white solid (353 mg, 13%).

$^1$H NMR (CDCl$_3$, 300 MHz): δ 2.18 (s, 1H), 3.70 (s, 4H), 3.85 (s, 3H), 6.30 (s, 1H), 6.48 (t, 1H), 6.58 (d, 1H), 7.13 (d, 1H), 7.33 (d, 2H), 7.44 (t, 2H), 7.75 (d, 2H), 12.08 (s, 1H)

LC/MS (ES+) m/z=376.14

Example 23

2-(2-Allyloxy-3-methyl-benzoylamino)-2,3-dihydro-1H-phenalene-2-carboxylic acid ethyl ester (23)

To a suspension of 2-(2-hydroxy-3-methyl-benzoylamino)-2,3-dihydro-1H-phenalene-2-carboxylic acid methyl ester (22) (175 mg, 0.47 mmol), anhydrous Cs$_2$CO$_3$ (306 mg, 0.94 mmol), and KI (15.6 mg, 0.09 mmol) in DMF (8 mL) is added 3-bromo-propene (199 μL, 2.35 mmol). The resulting reaction suspension is stirred at RT overnight. After the removal of DMF in vacuo, the residue is dissolved in EtOAc (20 mL) and washed with water (1×5 mL) and brine (2×5 mL). The organic layer is dried over anhydrous Na$_2$SO$_4$ and concentrated in vacuo. The residue is purified by flash column chromatography (115 g silica gel, gradient elution: 5%-40% EtOAc in heptane) to give a pure product (23) as white solid (107 mg, 55%).

$^1$H NMR (CDCl$_3$, 300 MHz): δ 2.08 (s, 3H), 3.68-3.73 (m, 6H), 3.84 (s, 3H), 5.02-5.11 (m, 2H), 5.28-5.40 (m, 1H), 6.70 (t, 1H), 7.16 (dd, 1H), 7.28 (dd, 1H), 7.39 (t, 2H), 7.69 (d, 2H), 7.79 (dd, 1H), 8.10 (s, 1H)

LC/MS (ES+) m/z=416.23

Example 25

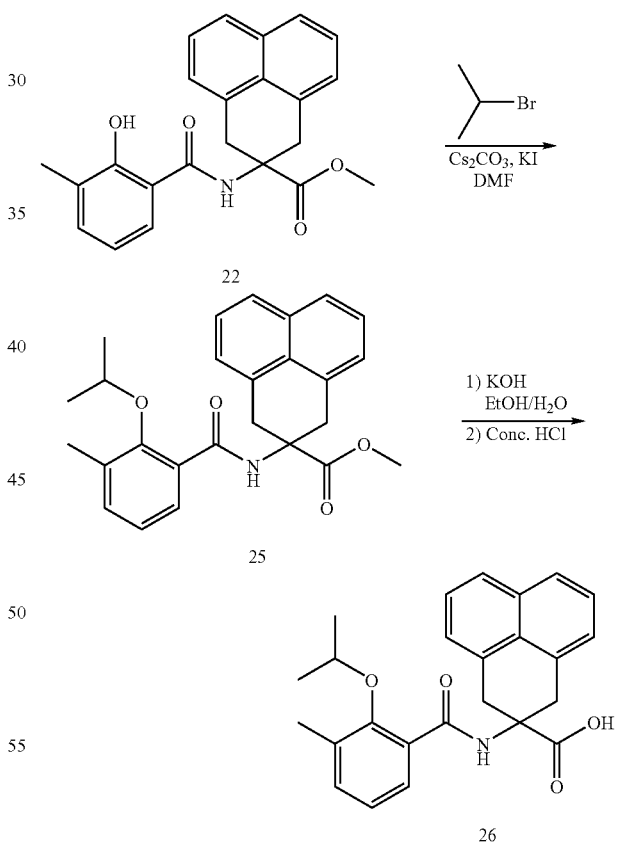

2-(2-Isopropoxy-3-methyl-benzoylamino)-2,3-dihydro-1H-phenalene-2-carboxylic acid methyl ester (25)

To a suspension of 2-(2-hydroxy-3-methyl-benzoylamino)-2,3-dihydro-1H-phenalene-2-carboxylic acid methyl ester (22) (175 mg, 0.47 mmol), anhydrous Cs₂CO₃ (306 mg, 0.94 mmol), and KI (16 mg, 0.09 mmol) in DMF (8 mL) is added 2-bromo-propane (220 μL, 2.35 mmol). The resulting reaction suspension is stirred at RT overnight. After the removal of DMF in vacuo, the residue is dissolved in EtOAc (20 mL) and washed with water (1×5 mL) and brine (2×5 mL). The organic layer is dried over anhydrous Na₂SO₄ and concentrated in vacuo. The residue is purified by flash column chromatography (115 g silica gel, gradient elution: 5%-40% EtOAc in heptane) to give the pure product (25) as white solid (143 mg, 73%).

¹H NMR (CDCl₃, 300 MHz): δ 0.51 (d, 6H), 2.10 (s, 3H), 3.71 (s, 4H), 3.81 (s, 3H), 3.81-3.89 (m, 1H), 6.98 (t, 1H), 7.16 (dd, 1H), 7.31 (d, 2H), 7.41 (t, 2H), 7.71 (d, 2H), 7.82 (dd, 1H), 8.04 (s, 1H)

LC/MS (ES+) m/z=418.23

Example 26

2-(2-Allyloxy-3-methyl-benzoylamino)-2,3-dihydro-1H-phenalene-2-carboxylic acid (26)

The mixture of 2-(2-isopropoxy-3-methyl-benzoylamino)-2,3-dihydro-1H-phenalene-2-carboxylic acid methyl ester (25) (143 mg, 0.34 mmol) and KOH (500 mg, 8.9 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (26) as white solid (127 mg, 93%).

¹H NMR (CDCl₃+drops of CD₃OD, 300 MHz): δ 0.49 (d, 6H), 2.10 (s, 3H), 3.71 (s, 4H), 3.81 (m, 1H), 6.99 (t, 1H), 7.16 (d, 1H), 7.33 (d, 2H), 7.42 (t, 2H), 7.72 (d, 2H), 7.79 (dd, 1H), 8.12 (s, 1H)

LC/MS (ES+) m/z=404.17

Example 27

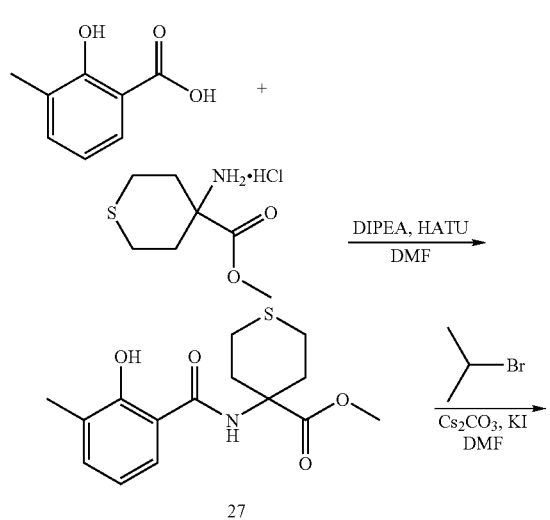

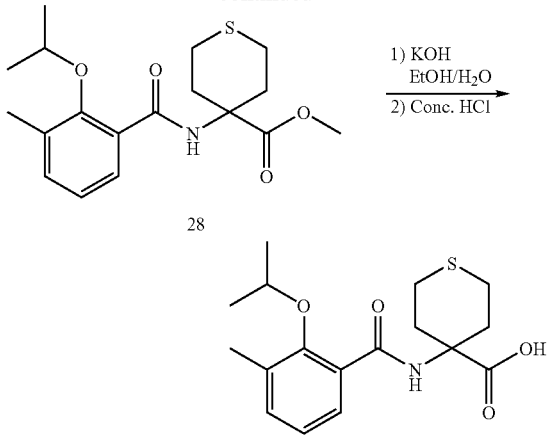

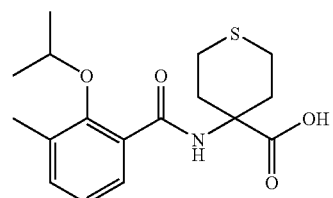

4-(2-hydroxy-3-methyl-benzoylamino)-tetrahydro-thiopyran-4-carboxylic acid methyl ester (27)

To a solution of HCl salt of 4-amino-tetrahydro-thiopyran-4-carboxylic acid methyl ester (529 mg, 2.5 mmol), 2-hydroxy-3-methyl-benzoic acid (380 mg, 2.5 mmol), HATU (1.14 g, 3.0 mmol) in anhydrous DMF (20 mL) is added DIPEA (1.66 mL, 10 mmol). The resulting solution is stirred at RT overnight. After the removal of DMF in vacuo, the residue is dissolved in EtOAc (30 mL) and washed with water (1×10 mL) and brine (2×10 mL). The organic layer is dried over anhydrous Na₂SO₄ and concentrated in vacuo. The residue is purified by flash column chromatography (115 g silica gel, gradient elution: 10-80% EtOAc in heptane) to give a pure product (27) as white solid (102 mg, 13%).

¹H NMR (CDCl₃, 300 MHz): δ 2.41 (m, 4H), 2.72-2.80 (m, 4H), 3.74 (s, 3H), 6.36 (s, 1H), 6.78 (t, 1H), 7.25-7.30 (m, 2H), 12.00 (s, 1H)

LC/MS (ES+) m/z=310.17

Example 28

4-(2-Isopropoxy-3-methyl-benzoylamino)-tetrahydro-thiopyran-4-carboxylic acid methyl ester (28)

To a suspension of 4-(2-hydroxy-3-methyl-benzoylamino)-tetrahydro-thiopyran-4-carboxylic acid methyl ester (27) (98 mg, 0.32 mmol), anhydrous Cs₂CO₃ (208 mg, 0.64 mmol), and KI (11 mg, 0.06 mmol) in DMF (5 mL) is added 2-bromopropane (150 μL, 1.6 mmol). The resulting reaction suspension is stirred at RT overnight. After the removal of DMF in vacuo, the residue is dissolved in EtOAc (20 mL) and washed with water (1×5 mL) and brine (2×5 mL). The organic layer is dried over anhydrous Na₂SO₄ and concentrated in vacuo. The residue is purified by flash column chromatography (80 g silica gel, gradient elution: 5-40% EtOAc in heptane) to give a pure product (28) as white solid (92 mg, 81%).

¹H NMR (CDCl₃, 300 MHz): δ 1.35 (d, 6H), 2.33 (s, 3H), 2.33-2.40 (m, 4H), 2.63-2.69 (m, 2H), 2.76-2.81 (m, 2H), 3.76 (s, 3H), 4.39 (m, 1H), 7.10 (t, 1H), 7.31 (d, 1H), 7.84 (dd, 1H), 8.28 (s, 1H)

LC/MS (ES+) m/z=352.13

Example 29

4-(2-Isopropoxy-3-methyl-benzoylamino)-tetrahydro-thiopyran-4-carboxylic acid (29)

The mixture of 4-(2-isopropoxy-3-methyl-benzoylamino)-tetrahydro-thiopyran-4-carboxylic acid methyl ester (28) (75 mg, 0.21 mmol) and KOH (500 mg, 8.9 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate came out of the water. The precipitate is filtered to give a pure product (29) as a pale yellow solid (68 mg, 94%).

$^1$H NMR (CDCl$_3$, 300 MHz): δ 1.32 (d, 6H), 2.33 (s, 3H), 2.41-2.43 (m, 4H), 2.64-2.74 (m, 4H), 4.37 (m, 1H), 7.11 (t, 1H), 7.33 (d, 1H), 7.86 (dd, 1H), 8.42 (s, 1H), 9.07 (br s, 1H)

LC/MS (ES+) m/z=338.11

Example 30

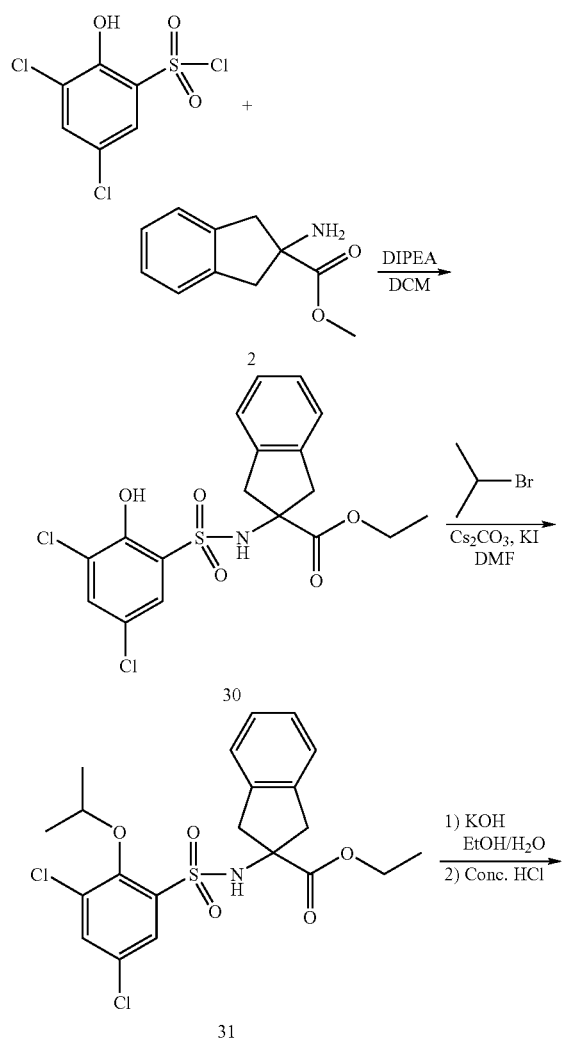

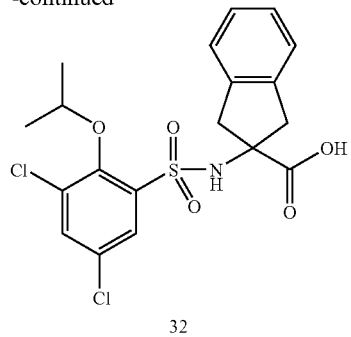

2-(3,5-Dichloro-2-hydroxy-benzenesulfonylamino)-indan-2-carboxylic acid ethyl ester (30)

To a solution of 2-amino-indan-2-carboxylic acid ethyl ester (3.14 g, 15.3 mmol) and 3,5-dichloro-2-hydroxy-benzenesulfonyl chloride (1 g, 3.82 mmol) in anhydrous DCM (dichloromethane, 20 mL) is added DIPEA (631 μL, 3.82 mmol). The resulting solution is stirred at RT for 1 hour. The reaction solution is diluted in DCM (50 mL) and washed with water (1×5 mL) and brine (2×5 mL). The organic layer is dried over anhydrous Na$_2$SO$_4$ and concentrated in vacuo. The residue is purified by HPLC to give a pure product (30) as white solid (450 mg, 27%).

$^1$H NMR (CDCl$_3$, 300 MHz): δ 1.26 (t, 3H), 3.25 (d, 2H), 3.57 (d, 2H), 4.18 (q, 2H), 5.60 (s, 1H), 7.04-7.07 (m, 2H), 7.14-7.17 (m, 2H), 7.43 (d, 1H), 7.49 (d, 1H), 8.30 (br s, 1H)

LC/MS (ES+) m/z=447.04, 449.04, 430.01

Example 31

2-(3,5-Dichloro-2-isopropoxy-benzenesulfonylamino)-indan-2-carboxylic acid ethyl ester (31)

To a suspension of 2-(3,5-dichloro-2-hydroxy-benzenesulfonylamino)-indan-2-carboxylic acid ethyl ester (30) (226 mg, 0.53 mmol), anhydrous Cs$_2$CO$_3$ (300 mg, 0.92 mmol), and KI (15 mg, 0.09 mmol) in DMF (15 mL) is added 2-bromopropane (432, 4.60 mmol). The resulting reaction suspension is filled with argon and run in a microwave reaction: 110° C., 2.5 h. After the removal of DMF in vacuo, the residue is dissolved in EtOAc (30 mL) and washed with water (1×5 mL) and brine (2×5 mL). The organic layer is dried over anhydrous Na$_2$SO$_4$ and concentrated in vacuo. The residue is purified by flash column chromatography (120 g silica gel, gradient elution: 10%-60% EtOAc in heptane) to give a pure product (31) as a white semi-solid (248 mg, 100%).

$^1$H NMR (CDCl$_3$, 300 MHz): δ 1.23 (t, 3H), 1.27 (d, 6H), 3.19 (d, 2H), 3.50 (d, 2H), 4.10 (q, 2H), 5.12 (m, 1H), 5.75 (s, 1H), 6.98-7.01 (m, 2H), 7.12-7.15 (m, 2H), 7.47 (dd, 1H), 7.58 (dd, 1H),

LC/MS (ES+) m/z=494.0

Example 32

2-(3,5-Dichloro-2-isopropoxy-benzenesulfonylamino)-indan-2-carboxylic acid (32)

The mixture of 2-(3,5-dichloro-2-isopropoxy-benzenesulfonylamino)-indan-2-carboxylic acid ethyl ester (31) (248 mg, 0.52 mmol) and KOH (500 mg, 8.9 mmol) is dissolved in EtOH (10 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (32) as white solid (230 mg, 100%).

$^1$H NMR (CDOD, 300 MHz): δ 1.27 (d, 6H), 3.23 (d, 2H), 3.48 (d, 2H), 5.05 (m, 1H), 6.98-7.01 (m, 2H), 7.08-7.12 (m, 2H), 7.44 (d, 1H), 7.60 (d, 1H)

LC/MS (ES−) m/z=442.08, 444.08

Example 33

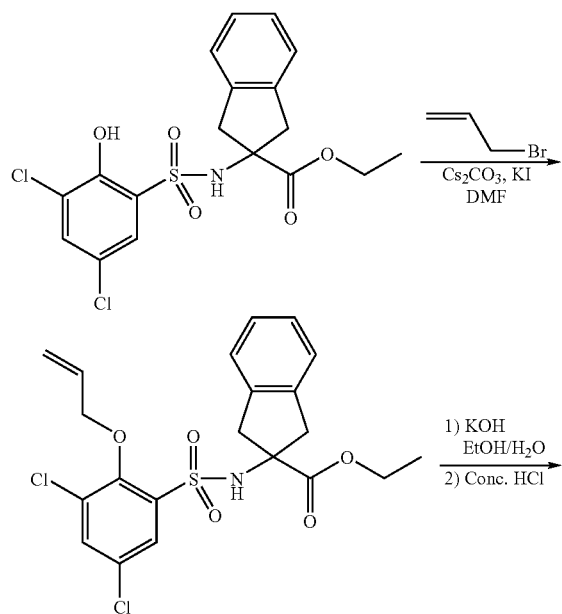

33

2-(2-Allyloxy-3,5-dichloro-benzenesulfonylamino)-indan-2-carboxylic acid ethyl ester (33)

To a suspension of 2-(3,5-dichloro-2-hydroxy-benzoylamino)-indan-2-carboxylic acid ethyl ester (10) (200 mg, 0.46 mmol), anhydrous Cs$_2$CO$_3$ (300 mg, 0.92 mmol), and KI (15 mg, 0.09 mmol) in DMF (15 mL) is added 3-bromopropene (390 μL, 4.6 mmol). The resulting reaction suspension is filled in argon and run in a microwave reaction: 110° C., 2 h. After the removal of DMF in vacuo, the residue is dissolved in EtOAc (20 mL) and washed with water (1×5 mL) and brine (2×5 mL). The organic layer is dried over anhydrous Na$_2$SO$_4$ and concentrated in vacuo. The residue is purified by flash column chromatography (120 g silica gel, gradient elution: 10%-60% EtOAc in heptane) to give a pure product (33) as white solid (162 mg, 75%).

$^1$H NMR (CDCl$_3$, 300 MHz): δ 1.22 (t, 3H), 3.21 (d, 2H), 3.52 (d, 2H), 4.09 (q, 2H), 4.55 (d, 2H), 5.36 (dd, 2H), 5.68 (s, 1H), 6.05 (m, 1H), 6.99-7.02 (m, 2H), 7.12-7.14 (m, 2H), 7.52 (d, 1H), 7.58 (d, 1H)

LC/MS (ES−) m/z=468.10, 470.10

Example 34

2-(2-Allyloxy-3,5-dichloro-benzenesulfonylamino)-indan-2-carboxylic acid (34)

The mixture of 2-(2-allyloxy-3,5-dichloro-benzenesulfonylamino)-indan-2-carboxylic acid ethyl ester (33) (143 mg, 0.30 mmol) and KOH (500 mg, 8.9 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH~3. After filtration, the solid is purified by HPLC to give a pure product (34) as white solid (91 mg, 69%).

$^1$H NMR (CDCl$_3$, 300 MHz): δ 3.24 (d, 2H), 3.58 (d, 2H), 4.53 (d, 2H), 5.36 (dd, 2H), 5.72 (s, 1H), 6.03 (m, 1H), 7.02-7.04 (m, 2H), 7.13-7.17 (m, 2H), 7.34 (d, 1H), 7.60 (d, 1H)

LC/MS (ES+) m/z=459.03, 461.02, 442.00

Example 35

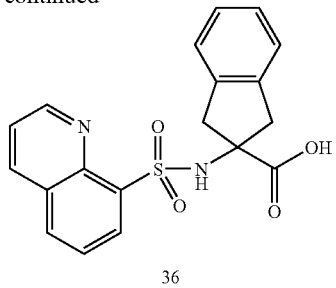

36

2-(Quinoline-8-sulfonylamino)-indan-2-carboxylic acid ethyl ester (35)

To a solution of quinoline-8-sulfonyl chloride (400 mg, 1.76 mmol), 2-amino-indan-2-carboxylic acid ethyl ester (361 mg, 1.76 mmol) in anhydrous DCM (8 mL) is added DIPEA (291 μL, 1.76 mmol). The resulting solution is stirred at RT overnight. The reaction solution is diluted with DCM (40 mL), washed with water (1×5 mL) and brine (2×5 mL). The organic layer is dried over anhydrous $Na_2SO_4$ and concentrated in vacuo. The residue is purified by flash column chromatography (115 g silica gel, gradient elution: 5-50% EtOAc in heptane) to give a pure product (35) as white solid (245 mg, 35%).

$^1$H NMR ($CDCl_3$, 300 MHz): δ 1.08 (t, 3H), 3.20 (d, 2H), 3.46 (d, 2H), 3.94 (q, 2H), 6.74-6.78 (m, 2H), 6.86-6.90 (m, 2H), 7.32 (s, 1H), 7.39 (dd, 1H), 7.64 (t, 1H), 8.01 (dd, 1H), 8.18 (dd, 1H), 8.34 (dd, 1H), 8.67 (dd, 1H),

LC/MS (ES+) m/z=397.11

Example 36

2-(Quinoline-8-sulfonylamino)-indan-2-carboxylic acid (36)

The mixture of 2-(quinoline-8-sulfonylamino)-indan-2-carboxylic acid ethyl ester (35) (210 mg, 0.53 mmol) and KOH (600 mg, 10.7 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (36) as white solid (195 mg, 100%).

$^1$H NMR ($CDCl_3$+drops of $CD_3OD$, 300 MHz): δ 3.18 (d, 2H), 3.46 (d, 2H), 6.66-6.69 (m, 2H), 6.81-6.84 (m, 2H), 7.40 (dd, 1H), 7.65 (t, 1H), 8.02 (d, 1H), 8.18 (dd, 1H), 8.34 (dd, 1H), 8.64 (dd, 1H)

LC/MS (ES+) m/z=369.10

Example 37

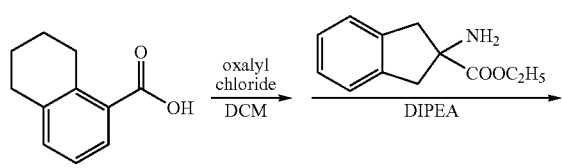

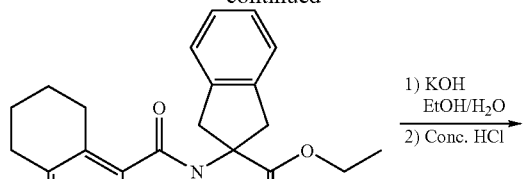

37

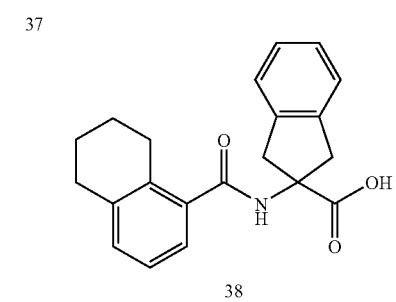

38

2-[(5,6,7,8-Tetrahydro-naphthalene-1-carbonyl)-amino]-indan-2-carboxylic acid ethyl ester (37)

To a solution of 5,6,7,8-tetrahydro-naphthalene-1-carboxylic acid (500 mg, 2.84 mmol) in DCM (10 mL) is added oxalyl chloride (0.50 mL, 5.68 mmol) dropwise. The resulting solution is stirred at RT for 2 h. After the removal of DCM and excess oxalyl chloride, the residue, 2-amino-indan-2-carboxylic acid ethyl ester (583 mg, 2.84 mmol) and DIPEA (1.88 mL, 11.3 mmol) are dissolved in DCM (20 mL). The resulting solution is stirred overnight. The reaction solution is diluted with DCM (30 mL) and washed with water (1×5 mL) and brine (2×5 mL). The organic layer is dried over anhydrous $Na_2SO_4$ and concentrated in vacuo. The residue is purified by flash column chromatography (120 g silica gel, gradient elution: 0%-20% EtOAc in heptane) to give the pure product (37) as white solid (610 mg, 59%).

$^1$H NMR ($CDCl_3$, 300 MHz): δ 1.29 (t, 3H), 1.74 (m, 4H), 2.76 (m, 2H), 2.84 (m, 2H), 3.34 (d, 2H), 3.75d, 2H), 4.72 (q, 2H), 6.20 (s, 1H), 7.02-7.12 (m, 3H), 7.18-7.25 (m, 4H)

LC/MS (ES+) m/z=364.18

Example 38

2-[(5,6,7,8-Tetrahydro-naphthalene-1-carbonyl)-amino]-indan-2-carboxylic acid (38)

The mixture of 2-[(5,6,7,8-Tetrahydro-naphthalene-1-carbonyl)-amino]-indan-2-carboxylic acid ethyl ester (37) (400 mg, 1.1 mmol) and KOH (1 g, 17.8 mmol) is dissolved in EtOH (10 mL) and water (2 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more white precipitate came out of the water. The precipitate is filtered to give a pure product (38) as white solid (300 mg, 82%).

$^1$H NMR (CD$_3$OD, 300 MHz): δ 1.74 (m, 4H), 2.76 (m, 2H), 3.38 (d, 2H), 3.68 (d, 2H), 4.85 (s, 1H), 7.02-7.08 (m, 3H), 7.14-7.23 (m, 4H)
LC/MS (ES+) m/z=336.15

Example 39

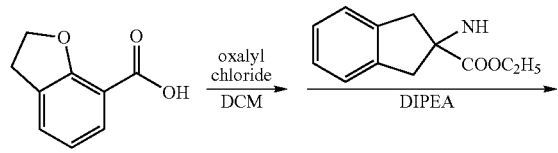

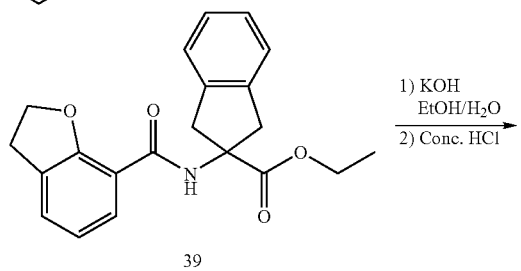

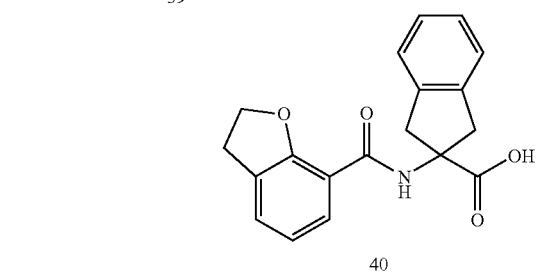

2-[(2,3-Dihydro-benzofuran-7-carbonyl)-amino]-indan-2-carboxylic acid ethyl ester (39)

To a solution of 2,3-dihydro-benzofuran-7-carboxylic acid (394 mg, 2.4 mmol) in DCM (10 mL) is added oxalyl chloride (0.85 mL, 9.6 mmol). The resulting solution is stirred at RT for 2 h. After the removal of DCM and excess oxalyl chloride, the residue, 2-amino-indan-2-carboxylic acid ethyl ester (500 mg, 2.4 mmol) and DIPEA (3.17 mL, 19.2 mmol) are dissolved in DCM (20 mL). The resulting solution is stirred at RT overnight. The reaction solution is diluted with DCM (40 mL) and washed with water (1×5 mL) and brine (2×5 mL). The organic layer is dried over anhydrous Na$_2$SO$_4$ and concentrated in vacuo. The residue is purified by flash column chromatography (120 g silica gel, gradient elution: 0%-20% EtOAc in heptane) to give a pure product (39) as white solid (635 mg, 75%).

$^1$H NMR (CDCl$_3$, 300 MHz): δ 1.23 (t, 3H), 3.22 (t, 2H), 3.40 (d, 2H), 3.77 (d, 2H), 4.26 (q, 2H), 4.67 (t, 2H), 6.93 (t, 1H), 7.17-7.30 (m, 6H), 7.87 (d, 1H), 8.18 (s, H)
LC/MS (ES+) m/z=352.12

Example 40

2-[(2,3-Dihydro-benzofuran-7-carbonyl)-amino]-indan-2-carboxylic acid (40)

The mixture of 2-[(2,3-Dihydro-benzofuran-7-carbonyl)-amino]-indan-2-carboxylic acid ethyl ester (39) (250 mg, 0.71 mmol) and KOH (600 mg, 10.7 mmol) is dissolved in EtOH (5 mL) and water (1 mL) under a water bath. The water bath is removed when KOH is completely dissolved and the resulting reaction solution is stirred at RT overnight. After concentration in vacuo, the residue is dissolved in water (30 mL) and acidified with conc. HCl until no more white precipitate came out of the water. The precipitate is filtered to give a pure product (40) as white solid (200 mg, 87%).

$^1$H NMR (CDCl$_3$+drops of CD$_3$OD, 300 MHz): δ 3.22 (t, 2H), 3.40 (d, 2H), 3.82 (d, 2H), 4.68 (t, 2H), 6.94 (t, 1H), 7.17-7.25 (m, 4H), 7.30 (d, 1H), 7.83 (d, 1H), 8.28 (s, 1H)
LC/MS (ES+) m/z=324.11

Example 41

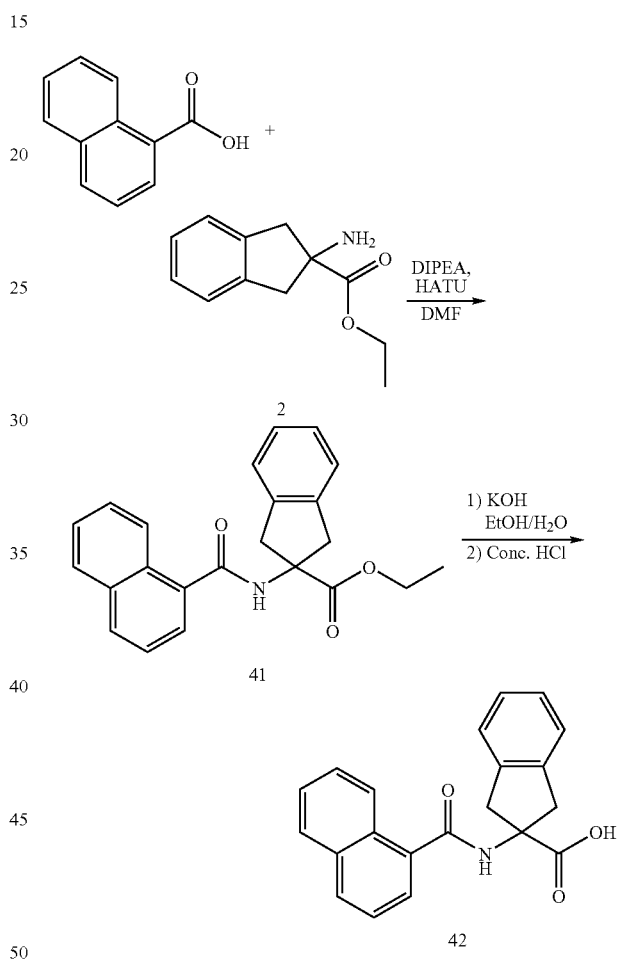

2-[(Naphthalene-1-carbonyl)-amino]-indan-2-carboxylic acid ethyl ester (41)

To a solution of naphthalene-1-carboxylic acid (300 mg, 1.74 mmol), 2-amino-indan-2-carboxylic acid ethyl ester (357 mg, 1.74 mmol), HATU (992 mg, 2.61 mmol) in anhydrous DMF (8 mL) is added DIPEA (431 μL, 2.61 mmol). The resulting solution is stirred at RT overnight. After the removal of DMF in vacuo, the residue is dissolved in EtOAc (40 mL) and washed with water (1×5 mL) and brine (2×5 mL). The organic layer is dried over anhydrous Na$_2$SO$_4$ and concentrated in vacuo. The residue is purified by flash column chromatography (115 g silica gel, gradient elution: 5-50% EtOAc in heptane) to give a pure product (41) as white solid (383 mg, 61%).

¹H NMR (CDCl₃, 300 MHz): δ 1.30 (t, 3H), 3.40 (d, 2H), 3.77 (d, 2H), 4.29 (q, 2H), 6.59 (s, 1H), 7.20-7.24 (m, 4H), 7.34 (t, 1H), 7.46-7.52 (m, 3H), 7.79-7.85 (m, 2H), 8.28-8.31 (m, 1H)

LC/MS (ES+) m/z=360.19

Example 42

2-[(Naphthalene-1-carbonyl)-amino]-indan-2-carboxylic acid (42)

The mixture of 2-[(naphthalene-1-carbonyl)-amino]-indan-2-carboxylic acid ethyl ester (41) (220 mg, 0.61 mmol) and KOH (600 mg, 10.7 mmol) is dissolved in EtOH (10 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. The precipitate is filtered to give a pure product (42) as white solid (196 mg, 97%).

¹H NMR (CDCl₃+drops of CD₃OD, 300 MHz): δ 3.47 (d, 2H), 3.82 (d, 2H), 6.93 (m, 1H), 7.19-7.28 (m, 4H), 7.37-7.50 (m, 4H), 7.81-7.89 (m, 2H), 8.23-8.27 (m, 1H)

LC/MS (ES+) m/z=332.11

Example 43

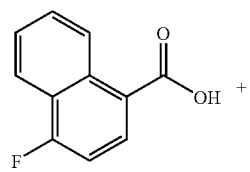

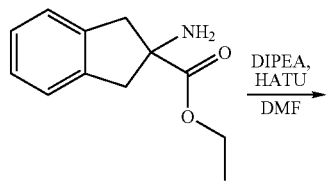

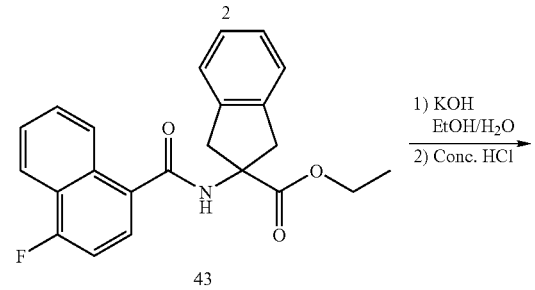

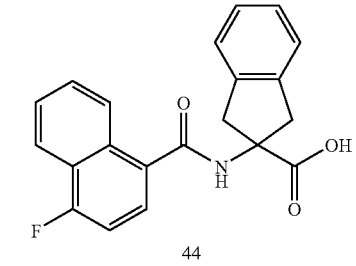

2-[(4-Fluoro-naphthalene-1-carbonyl)-amino]-indan-2-carboxylic acid ethyl ester (43)

To a solution of 4-fluoro-naphthalene-1-carboxylic acid (232 mg, 1.22 mmol), 2-amino-indan-2-carboxylic acid ethyl ester (250 mg, 1.22 mmol), HATU (696 mg, 1.83 mmol) in anhydrous DMF (8 mL) is added DIPEA (302 μL, 1.83 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous Na₂SO₄ and concentrated in vacuo. The residue is purified by flash column chromatography (115 g silica gel, gradient elution: 5-50% EtOAc in heptane) to give a pure product (43) as white solid (340 mg, 74%).

¹H NMR (CDCl₃, 300 MHz): δ 1.31 (t, 3H), 3.42 (d, 2H), 3.80 (d, 2H), 4.31 (q, 2H), 6.53 (s, 1H), 7.03 (dd, 1H), 7.19-7.26 (m, 4H), 7.47-7.82 (m, 3H), 8.07-8.10 (m, 1H), 8.31-8.35 (m, 1H)

LC/MS (ES+) m/z=378.12

Example 44

2-[(4-Fluoro-naphthalene-1-carbonyl)-amino]-indan-2-carboxylic acid (44)

The mixture of 2-[(4-fluoro-naphthalene-1-carbonyl)-amino]-indan-2-carboxylic acid ethyl ester (43) (180 mg, 0.48 mmol) and KOH (600 mg, 10.7 mmol) is dissolved in EtOH (10 mL) and water (1 mL) under a water bath. The water bath is removed when KOH is completely dissolved and the resulting reaction solution is stirred at RT for 6 h. After concentration in vacuo, the residue is dissolved in water (20 mL) and acidified with conc. HCl until no more white precipitate formed. The precipitate is filtered to give a pure product (44) as white solid (174 mg, 100%).

¹H NMR (CDCl₃+drops of CD₃OD, 300 MHz): δ 3.46 (d, 2H), 3.81 (d, 2H), 6.99-7.06 (m, 2H), 7.19-7.26 (m, 4H), 7.48-7.54 (m, 3H), 8.06-8.09 (m, 1H), 8.24-8.28 (m, 1H)

LC/MS (ES+) m/z=350.09

Example 45

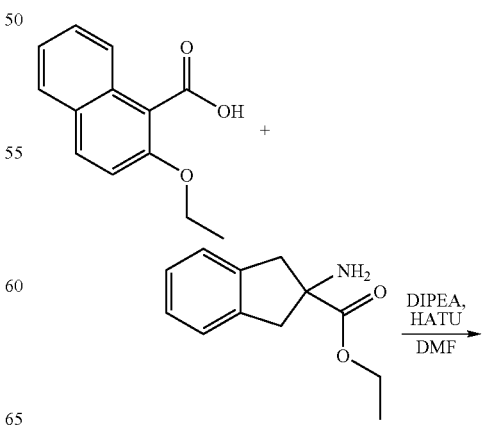

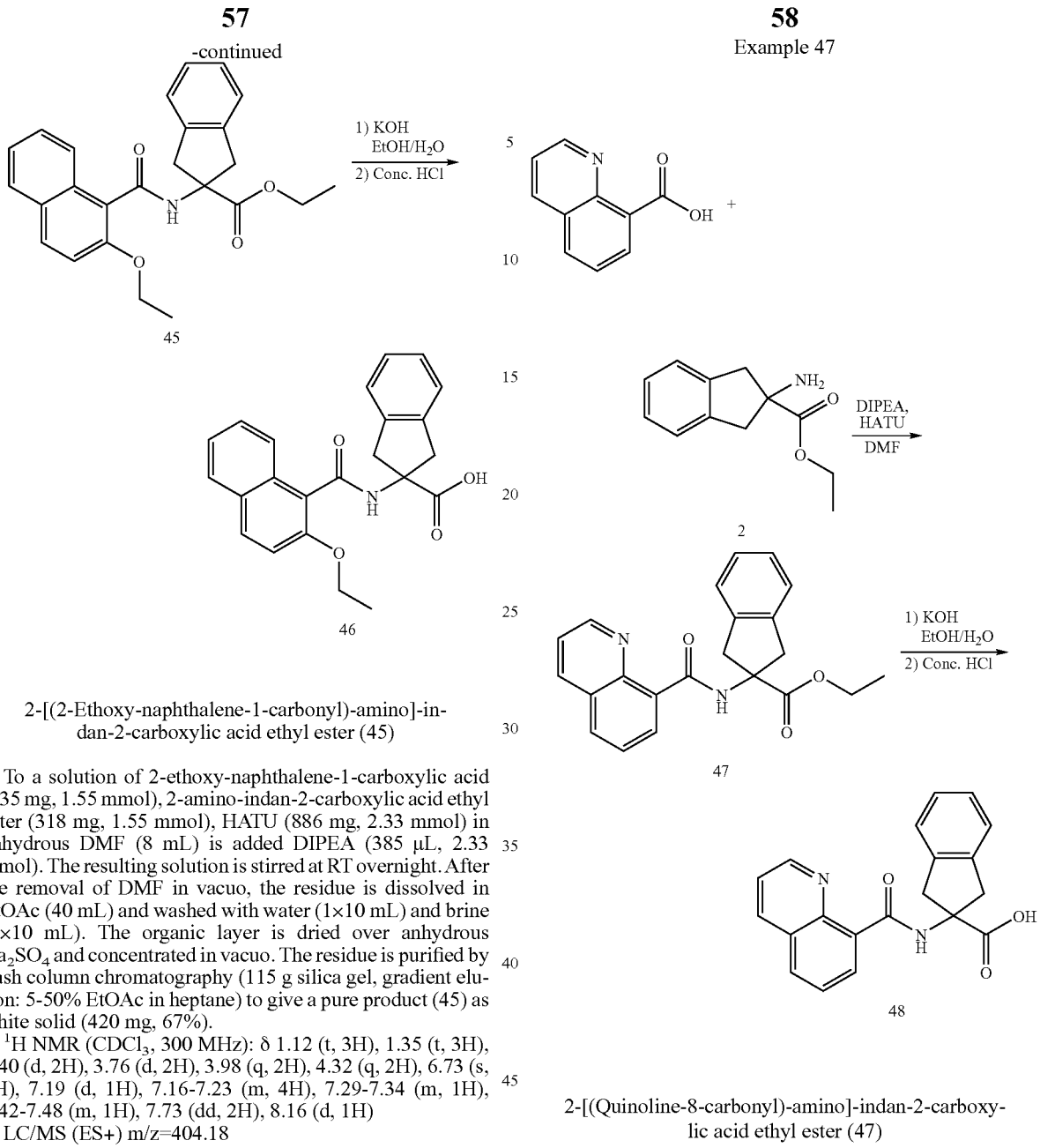

2-[(2-Ethoxy-naphthalene-1-carbonyl)-amino]-indan-2-carboxylic acid ethyl ester (45)

To a solution of 2-ethoxy-naphthalene-1-carboxylic acid (335 mg, 1.55 mmol), 2-amino-indan-2-carboxylic acid ethyl ester (318 mg, 1.55 mmol), HATU (886 mg, 2.33 mmol) in anhydrous DMF (8 mL) is added DIPEA (385 µL, 2.33 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5-50% EtOAc in heptane) to give a pure product (45) as white solid (420 mg, 67%).

$^1$H NMR ($CDCl_3$, 300 MHz): δ 1.12 (t, 3H), 1.35 (t, 3H), 3.40 (d, 2H), 3.76 (d, 2H), 3.98 (q, 2H), 4.32 (q, 2H), 6.73 (s, 1H), 7.19 (d, 1H), 7.16-7.23 (m, 4H), 7.29-7.34 (m, 1H), 7.42-7.48 (m, 1H), 7.73 (dd, 2H), 8.16 (d, 1H)

LC/MS (ES+) m/z=404.18

Example 46

2-[(2-Ethoxy-naphthalene-1-carbonyl)-amino]-indan-2-carboxylic acid (46)

The mixture of 2-[(2-ethoxy-naphthalene-1-carbonyl)-amino]-indan-2-carboxylic acid ethyl ester (45) (270 mg, 0.67 mmol) and KOH (600 mg, 10.7 mmol) is dissolved in EtOH (10 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH ~4. The precipitate is filtered to give a pure product (46) as white solid (170 mg, 68%).

$^1$H NMR ($CDCl_3$+drops of $CD_3OD$, 300 MHz): δ 1.18 (t, 3H), 3.47 (d, 2H), 3.82 (d, 2H), 4.04 (q, 2H), 7.09 (s, 1H), 7.15-7.37 (m, 7H), 7.47 (t, 1H), 7.78 (dd, 2H), 8.07 (d, 1H)

LC/MS (ES+) m/z=376.19

Example 47

2-[(Quinoline-8-carbonyl)-amino]-indan-2-carboxylic acid ethyl ester (47)

To a solution of quinoline-8-carboxylic acid (421 mg, 2.43 mmol), 2-amino-indan-2-carboxylic acid ethyl ester (500 mg, 2.43 mmol), HATU (1.39 g, 3.65 mmol) in anhydrous DMF (15 mL) is added DIPEA (603 µL, 3.65 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5-50% EtOAc in heptane) to give a pure product (47) as white solid (281 mg, 32%).

$^1$H NMR ($CDCl_3$, 300 MHz): δ 1.24 (t, 3H), 3.54 (d, 2H), 3.86 (d, 2H), 4.27 (q, 2H), 7.17-7.27 (m, 4H), 7.44 (dd, 1H), 7.65 (t, 1H), 7.94 (dd, 1H), 8.24 (dd, 1H), 8.80-8.84 (m, 2H), 12.00 (s, 1H)

LC/MS (ES+) m/z=361.13

Example 48

2-[(Quinoline-8-carbonyl)-amino]-indan-2-carboxylic acid (48)

The mixture of 2-[(quinoline-8-carbonyl)-amino]-indan-2-carboxylic acid ethyl ester (47) (190 mg, 0.53 mmol) and KOH (500 mg, 8.9 mmol) is dissolved in EtOH (5 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. The precipitate is filtered to give the pure product (48) as white solid (152 mg, 86%).

$^1$H NMR (CDCl$_3$+drops of CD$_3$OD, 300 MHz): δ 3.50 (d, 2H), 3.83 (d, 2H), 7.17-7.24 (m, 4H), 7.44-7.49 (m, 1H), 7.64 (t, 1H), 7.98 (d, 1H), 8.28 (dd, 1H), 8.69 (d, 1H), 8.83 (s, 1H)

LC/MS (ES+) m/z=333.08

Example 49

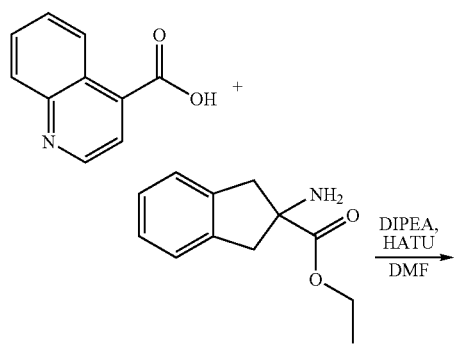

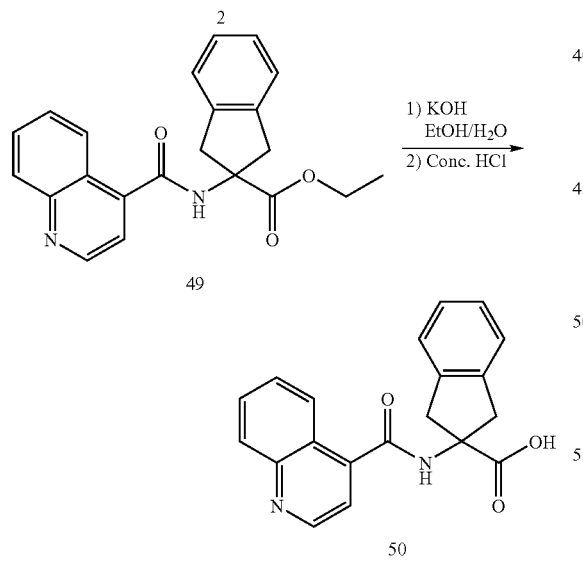

2-[(Quinoline-4-carbonyl)-amino]-indan-2-carboxylic acid ethyl ester (49)

To a solution of quinoline-4-carboxylic acid (301 mg, 1.74 mmol), 2-amino-indan-2-carboxylic acid ethyl ester (357 mg, 1.74 mmol), HATU (992 mg, 2.61 mmol) in anhydrous DMF (8 mL) is added DIPEA (431 μL, 2.61 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous Na$_2$SO$_4$ and concentrated in vacuo. The residue is purified by flash column chromatography (120 g silica gel, gradient elution: 5-70% EtOAc in heptane) to give a pure product (49) as a pale yellow solid (370 mg, 59%).

$^1$H NMR (CDCl$_3$, 300 MHz): δ 1.34 (t, 3H), 3.48 (d, 2H), 3.82 (d, 2H), 4.34 (q, 2H), 6.86 (s, 1H), 7.21-7.29 (m, 5H), 7.51-7.56 (m, 1H), 7.65-7.71 (m, 1H), 7.98 (d, 1H), 8.18 (d, 1H), 8.73 (d, 1H)

LC/MS (ES+) m/z=361.14

Example 50

2-[(Quinoline-4-carbonyl)-amino]-indan-2-carboxylic acid (50)

The mixture of 2-[(quinoline-4-carbonyl)-amino]-indan-2-carboxylic acid ethyl ester (49) (220 mg, 0.61 mmol) and KOH (600 mg, 10.7 mmol) is dissolved in EtOH (10 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH~4. The precipitate is filtered to give a pure product (50) as a pale yellow solid (98 mg, 48%).

$^1$H NMR (CDCl$_3$+drops of CD$_3$OD, 300 MHz): δ 3.49 (d, 2H), 3.83 (d, 2H), 7.20-7.28 (m, 4H), 7.50 (d, 1H), 7.61 (t, 1H), 7.79 (t, 1H), 8.13 (d, 1H), 8.24 (d, 1H), 8.86 (d, 1H)

LC/MS (ES+) m/z=333.13

Example 51

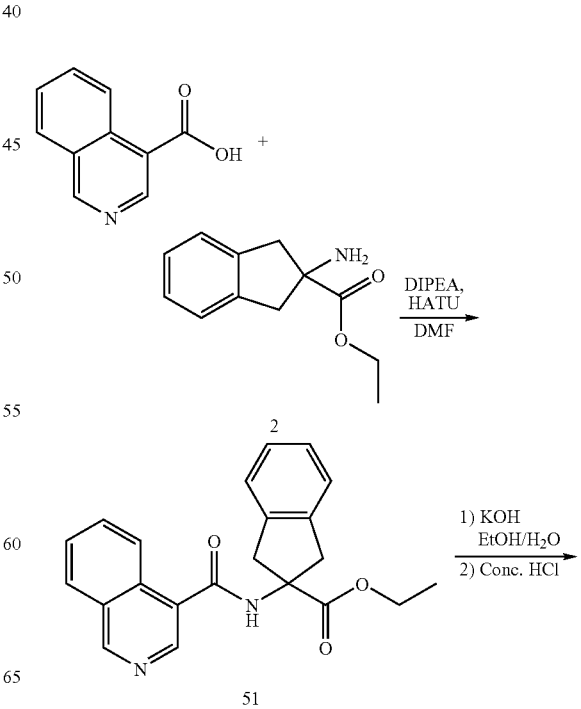

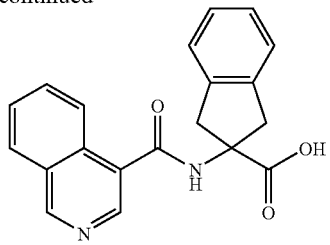

2-[(Isoquinoline-4-carbonyl)-amino]-indan-2-carboxylic acid ethyl ester (51)

To a solution of isoquinoline-4-carboxylic acid (211 mg, 1.22 mmol), 2-amino-indan-2-carboxylic acid ethyl ester (250 mg, 1.22 mmol), HATU (696 mg, 1.83 mmol) in anhydrous DMF (8 mL) is added DIPEA (302 μL, 1.83 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5-50% EtOAc in heptane) to give a pure product (51) as white solid (359 mg, 82%).

$^1$H NMR (CDCl$_3$, 300 MHz): δ 1.26 (t, 3H), 3.49 (d, 2H), 3.79 (d, 2H), 4.28 (q, 2H), 6.96 (s, 1H), 7.20-7.27 (m, 4H), 7.57-7.62 (m, 1H), 7.76-7.82 (m, 1H), 7.86 (d, 1H), 8.12 (d, 1H), 8.54 (d, 1H), 9.22 (d, 1H)

LC/MS (ES+) m/z=361.15

Example 52

2-[(Isoquinoline-4-carbonyl)-amino]-indan-2-carboxylic acid (52)

The mixture of 2-[(isoquinoline-4-carbonyl)-amino]-indan-2-carboxylic acid ethyl ester (51) (200 mg, 0.55 mmol) and KOH (600 mg, 10.7 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. The precipitate is filtered to give a pure product (52) as white solid (170 mg, 93%).

$^1$H NMR (CDCl$_3$+CD$_3$OD, 300 MHz): δ 3.38 (d, 2H), 3.53 (d, 2H), 7.19-7.27 (m, 4H), 7.64 (t, 1H), 7.83 (t, 1H), 7.94 (d, 1H), 8.09 (d, 1H), 8.40 (s, 1H), 8.71 (d, 1H), 9.22 (d, 1H)

LC/MS (ES+) m/z=333.06

Example 53

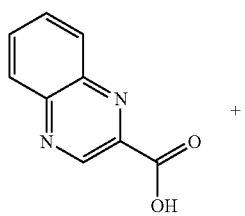

+

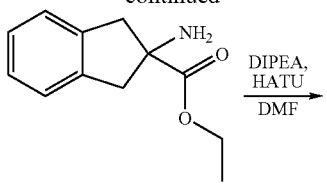

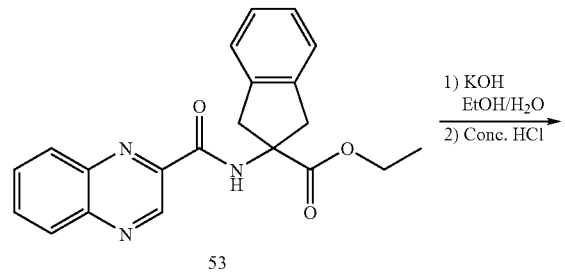

2-[(Quinoxaline-2-carbonyl)-amino]-indan-2-carboxylic acid ethyl ester (53)

To a solution of quinoxaline-5-carboxylic acid (400 mg, 2.3 mmol), 2-amino-indan-2-carboxylic acid ethyl ester (471 mg, 2.3 mmol), HATU (1.3 g, 3.45 mmol) in anhydrous DMF (15 mL) is added DIPEA (570 μL, 3.45 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5-40% EtOAc in heptane) to give a pure product (56) as an orange solid (605 mg, 73%).

$^1$H NMR (CDCl$_3$, 300 MHz): δ 1.26 (t, 3H), 3.55 (d, 2H), 3.84 (d, 2H), 4.28 (q, 2H), 7.21-7.29 (m, 4H), 7.79-7.89 (m, 2H), 8.08-8.18 (m, 2H), 8.46 (s, 1H), 9.64 (s, 1H)

LC/MS (ES+) m/z=361.12

Example 54

2-[(Quinoxaline-2-carbonyl)-amino]-indan-2-carboxylic acid (54)

The mixture of 2-[(quinoxaline-5-carbonyl)-amino]-indan-2-carboxylic acid ethyl ester (56) (480 mg, 1.33 mmol) and KOH (1 g, 18 mmol) is dissolved in EtOH (13 mL) and water (1 mL) under a water bath. The water bath is removed when KOH is completely dissolved and the resulting reaction solution is stirred at RT for 8 h. After concentration in vacuo, the residue is dissolved in water (40 mL) and acidified with conc. HCl dropwise until no more precipitate formed. The precipitate is filtered to give a pure product (54) as a brown solid (444 mg, 100%).

¹H NMR (CDCl₃+CD₃OD, 300 MHz): δ 3.58 (d, 2H), 3.86 (d, 2H), 7.21-7.30 (m, 4H), 7.81-7.90 (m, 2H), 8.10-8.18 (m, 2H), 8.58 (s, 1H), 9.61 (s, 1H)

LC/MS (ES+) m/z=361.12

Example 55

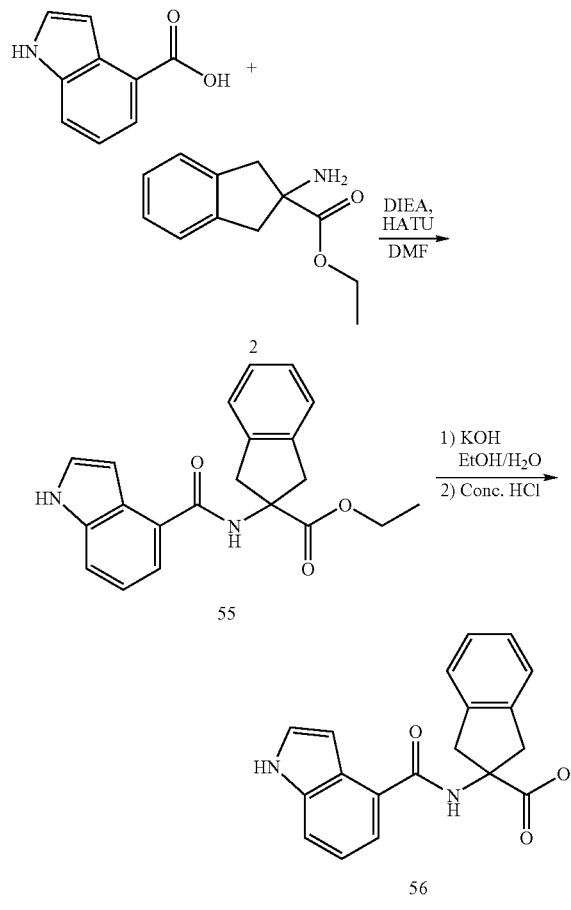

2-[(1H-Indole-4-carbonyl)-amino]-indan-2-carboxylic acid ethyl ester (55)

To a solution of 1H-indole-4-carboxylic acid (250 mg, 1.55 mmol), 2-amino-indan-2-carboxylic acid ethyl ester (318 mg, 1.55 mmol), HATU (886 mg, 2.33 mmol) in anhydrous DMF (8 mL) is added DIPEA (385 μL, 2.33 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous Na₂SO₄ and concentrated in vacuo. The residue is purified by flash column chromatography (115 g silica gel, gradient elution: 5-60% EtOAc in heptane) to give a pure product (55) as white solid (278 mg, 52%).

¹H NMR (CDCl₃, 300 MHz): δ 1.24 (t, 3H), 3.46 (d, 2H), 3.78 (d, 2H), 4.26 (q, 2H), 6.78 (m, 1H), 7.14-7.25 (m, 6H), 7.46-7.49 (m, 2H), 8.65 (s, 1H)

LC/MS (ES+) m/z=349.14

Example 56

2-[(1H-Indole-4-carbonyl)-amino]-indan-2-carboxylic acid (56)

The mixture of 2-[(1H-indole-4-carbonyl)-amino]-indan-2-carboxylic acid ethyl ester (55) (200 mg, 0.57 mmol) and KOH (600 mg, 10.7 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. The precipitate is filtered to give a pure product (56) as white solid (162 mg, 89%).

¹H NMR (CDCl₃=CD₃OD, 300 MHz): δ 3.50 (d, 2H), 3.80 (d, 2H), 6.68 (m, 1H), 7.15-7.29 (m, 6H), 7.46 (d, 1H), 7.53 (dd, 1H), 9.79 (s, 1H)

LC/MS (ES+) m/z=321.15

Example 57

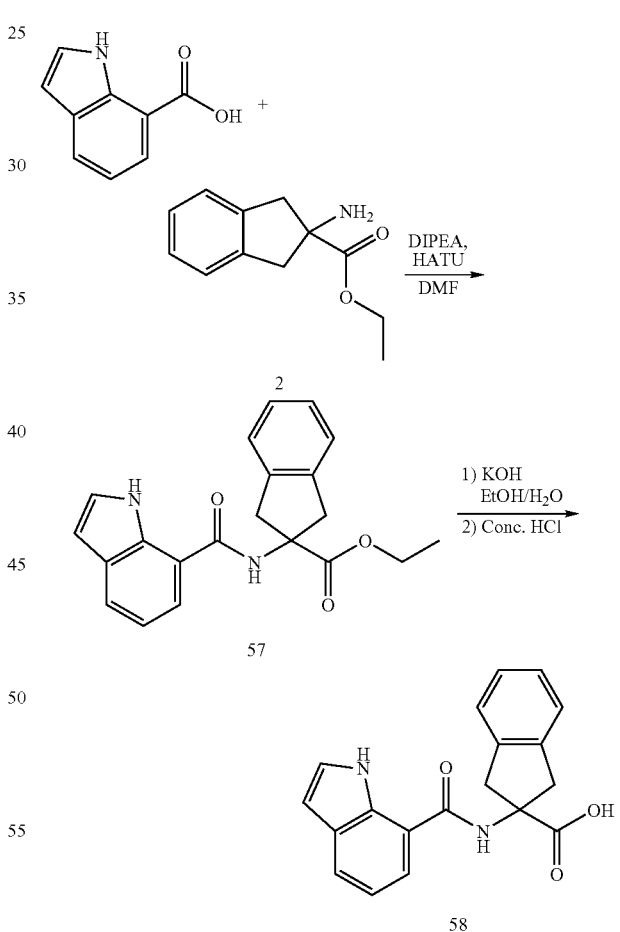

2-[(1H-Indole-7-carbonyl)-amino]-indan-2-carboxylic acid ethyl ester (57)

To a solution of 1H-indole-7-carboxylic acid (250 mg, 1.55 mmol), 2-Amino-indan-2-carboxylic acid ethyl ester (318 mg, 1.55 mmol), HATU (886 mg, 2.33 mmol) in anhydrous DMF (8 mL) is added DIPEA (385 μL, 2.33 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5-60% EtOAc in heptane) to give a pure product (57) as white solid (378 mg, 70%).

$^1$H NMR ($CDCl_3$, 300 MHz): δ 1.22 (t, 3H), 3.44 (d, 2H), 3.78 (d, 2H), 4.25 (q, 2H), 6.53 (t, 1H), 6.93 (s, 1H), 7.03 (t, 1H), 7.18-7.27 (m, 5H), 7.32 (d, 1H), 7.77 (d, 1H), 10.25 (s, 1H)

LC/MS (ES+) m/z=349.21

Example 58

2-[(1H-Indole-7-carbonyl)-amino]-indan-2-carboxylic acid (58)

The mixture of 2-[(1H-indole-7-carbonyl)-amino]-indan-2-carboxylic acid ethyl ester (57) (220 mg, 0.63 mmol) and KOH (600 mg, 10.7 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. The precipitate is filtered to give a pure product (58) as an off white solid (186 mg, 92%).

$^1$H NMR ($CDCl_3$+drops of $CD_3OD$, 300 MHz): δ 3.50 (d, 2H), 3.79 (d, 2H), 6.54 (m, 2H), 7.06 (t, 1H), 7.19-7.31 (m, 5H), 7.42 (d, 1H), 7.78 (d, 1H), 10.25 (s, 1H)

LC/MS (ES+) m/z=325.15

Example 59

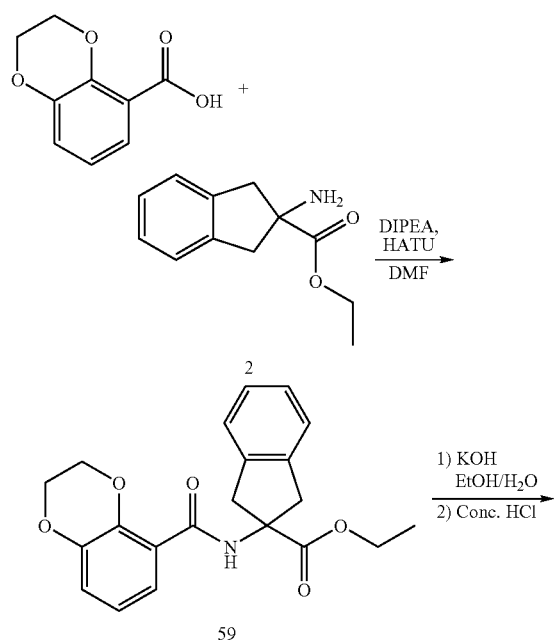

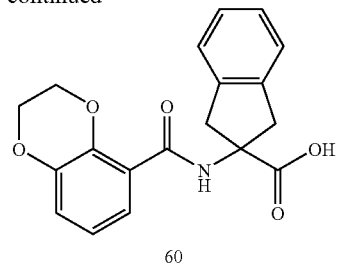

2-[(2,3-Dihydro-benzo[1,4]dioxine-5-carbonyl)-amino]-indan-2-carboxylic acid ethyl ester (59)

To a solution of 2,3-dihydro-benzo[1,4]dioxine-5-carboxylic acid (351 mg, 1.95 mmol), 2-amino-indan-2-carboxylic acid ethyl ester (400 mg, 1.95 mmol), HATU (1.11 g, 2.93 mmol) in anhydrous DMF (8 mL) is added DIPEA (484 μL, 2.93 mmol). The resulting solution is stirred at RT overnight. After the removal of DMF in vacuo, the residue is dissolved in EtOAc (70 mL) and washed with water (1×10 mL) and brine (2×10 mL). The organic layer is dried over anhydrous $Na_2SO_4$ and concentrated in vacuo. The residue is purified by HPLC to give a pure product (59) as white solid (650 mg, 91%).

$^1$H NMR ($CDCl_3$, 300 MHz): δ 1.24 (t, 3H), 3.39 (d, 2H), 3.74 (d, 2H), 4.21-4.33 (m, 6H), 6.90 (t, 1H), 6.98 (dd, 1H), 7.17-7.24 (m, 4H), 7.69 (dd, 1H), 8.25 (s, 1H)

LC/MS (ES+) m/z=368.15

Example 60

2-[(2,3-Dihydro-benzo[1,4]dioxine-5-carbonyl)-amino]-indan-2-carboxylic acid (60)

The mixture of 2-[(2,3-Dihydro-benzo[1,4]dioxine-5-carbonyl)-amino]-indan-2-carboxylic acid ethyl ester (59) (495 mg, 1.35 mmol) and KOH (1 g, 17.9 mmol) is dissolved in EtOH (10 mL) and water (1 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more white precipitate came out of the water. The precipitate is filtered to give a pure product (60) as white solid (440 mg, 96%).

$^1$H NMR ($CDCl_3$+drops of $CD_3OD$, 300 MHz): δ 3.40 (d, 2H), 3.78 (d, 2H), 4.26-4.33 (m, 4H), 6.91 (t, 1H), 7.49 (dd, 1H), 7.18-7.25 (m, 4H), 7.65 (dd, 1H), 8.39 (s, 1H)

LC/MS (ES+) m/z=340.11

Example 61

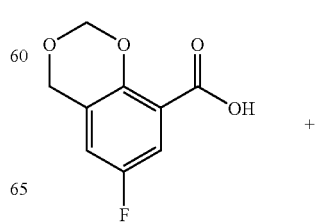

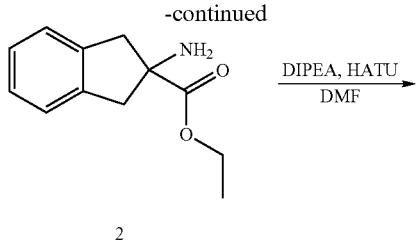

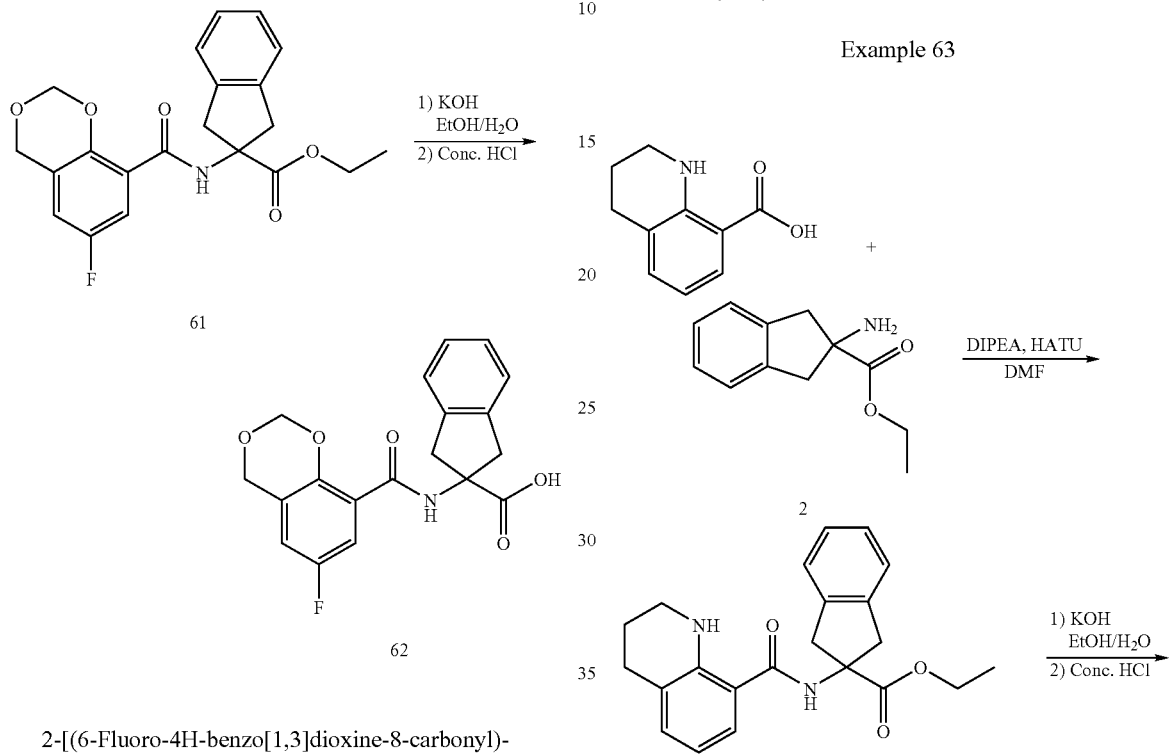

After concentration in vacuo, the residue is dissolved in water (30 mL) and acidified with conc. HCl until no more precipitate came out of the water. After the filtration, the solid is purified by HPLC to give a pure product (62) as white solid (520 mg, 100%).

$^1$H NMR (CDCl$_3$+CD$_3$OD, 300 MHz): δ 3.39 (d, 2H), 3.75 (d, 2H), 4.92 (s, 2H), 5.30 (s, 2H), 6.85 (dd, 1H), 7.18-7.25 (m, 4H), 7.64 (dd, 1H), 8.49 (s, 1H)

LC/MS (ES−) m/z=356.10

Example 63

2-[(1,2,3,4-Tetrahydro-quinoline-8-carbonyl)-amino]-indan-2-carboxylic acid ethyl ester (63)

To a solution of 1,2,3,4-tetrahydro-quinoline-8-carboxylic acid (173 mg, 0.97 mmol), 2-amino-indan-2-carboxylic acid ethyl ester (200 mg, 0.97 mmol), HATU (553 mg, 1.46 mmol) in anhydrous DMF (20 mL) is added DIPEA (241 μL, 1.46 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous Na$_2$SO$_4$ and concentrated in vacuo. The residue is purified by HPLC to give a pure product (63) as white solid (300 mg, 85%).

2-[(6-Fluoro-4H-benzo[1,3]dioxine-8-carbonyl)-amino]-indan-2-carboxylic acid ethyl ester (61)

To a solution of 6-fluoro-4H-benzo[1,3]dioxine-8-carboxylic acid (386 mg, 1.95 mmol), 2-amino-indan-2-carboxylic acid ethyl ester (400 mg, 1.95 mmol), HATU (1.11 g, 2.93 mmol) in anhydrous DMF (8 mL) is added DIPEA (484 μL, 2.93 mmol). The resulting solution is stirred at RT overnight. After the removal of DMF in vacuo, the residue is dissolved in EtOAc (70 mL) and washed with water (1×10 mL) and brine (2×10 mL). The organic layer is dried over anhydrous Na$_2$SO$_4$ and concentrated in vacuo. The residue is purified by flash column chromatography (120 g silica gel, gradient elution: 5-50% EtOAc in heptane) to give a pure product (61) as white solid (720 mg, 6%).

$^1$H NMR (CDCl$_3$, 300 MHz): δ 1.24 (t, 3H), 3.38 (d, 2H), 3.74 (d, 2H), 4.24 (q, 2H), 4.90 (s, 2H), 5.27 (s, 2H), 6.79 (dd, 1H), 7.17-7.24 (m, 4H), 7.74 (dd, 1H), 8.25 (s, 1H)

LC/MS (ES+) m/z=386.11

Example 62

2-[(6-Fluoro-4H-benzo[1,3]dioxine-8-carbonyl)-amino]-indan-2-carboxylic acid (62)

The mixture of 2-[(6-fluoro-4H-benzo[1,3]dioxine-8-carbonyl)-amino]-indan-2-carboxylic acid ethyl ester (61) (560 mg, 1.45 mmol) and KOH (1 g, 17.9 mmol) is dissolved in EtOH (10 mL) and water (1 mL) under a water bath. The water bath is removed when KOH is completely dissolved and the resulting reaction solution is stirred at RT for 8 h.

¹H NMR (CDCl₃, 300 MHz): δ 1.24 (t, 3H), 1.87 (m, 2H), 2.74 (t, 2H), 3.31-3.36 (m, 4H), 3.73 (d, 2H), 4.24 (q, 2H), 6.38 (t, 2H), 6.50 (s, 1H), 6.95 (d, 1H), 7.09 (d, 1H), 7.17-7.24 (m, 4H), 7.67 (br s, 1H)

LC/MS (ES+) m/z=365.18

Example 64

2-[(1,2,3,4-Tetrahydro-quinoline-8-carbonyl)-amino]-indan-2-carboxylic acid (64)

The mixture of 2-[(1,2,3,4-tetrahydro-quinoline-8-carbonyl)-amino]-indan-2-carboxylic acid ethyl ester (63) (259 mg, 0.71 mmol) and KOH (1 g, 17.9 mmol) is dissolved in EtOH (15 mL) and water (1 mL) under a water bath. The water bath is removed when KOH is completely dissolved and the resulting reaction solution is stirred at RT for 8 h. After concentration in vacuo, the residue is dissolved in water (30 mL) and acidified with conc. HCl dropwise until precipitate falls out of the water. After the filtration, the solid is washed by water and collected. The filtrate is acidified with conc. HCl carefully again to see if more precipitate comes out or not. The combined solid is dried in vacuo to give a pure product (64) as a yellow solid (205 mg, 86%).

¹H NMR (CDCl₃, 300 MHz): δ 1.87 (m, 2H), 2.74 (t, 2H), 3.40-3.45 (m, 4H), 3.81 (d, 2H), 6.36 (t, 1H), 6.48 (s, 1H), 6.98 (t, 2H), 7.18-7.26 (m, 4H)

LC/MS (ES+) m/z=337.17

Example 65

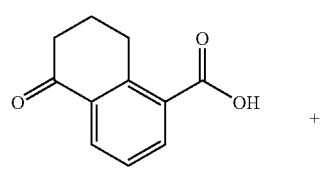

+

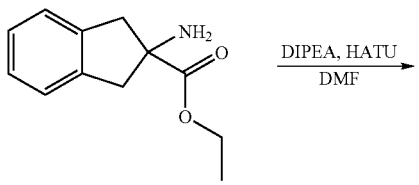

$\xrightarrow{\text{DIPEA, HATU}}{\text{DMF}}$

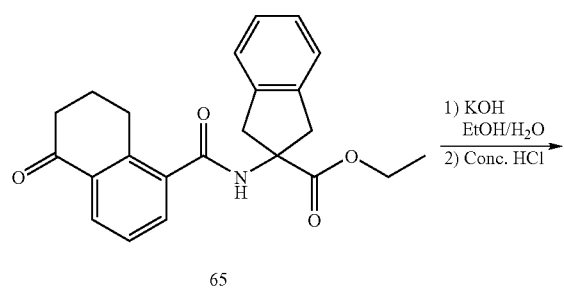

65

$\xrightarrow[\text{2) Conc. HCl}]{\text{1) KOH EtOH/H}_2\text{O}}$

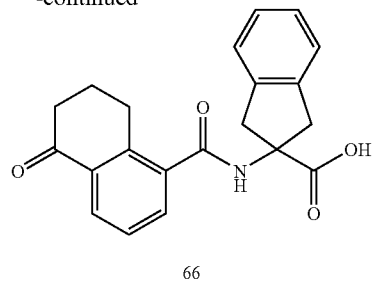

66

2-[(5-oxo-5,6,7,8-tetrahydro-naphthalene-1-carbonyl)-amino]-indan-2-carboxylic acid ethyl ester (65)

To a solution of 5-oxo-5,6,7,8-tetrahydro-naphthalene-1-carboxylic acid (430 mg, 2.26 mmol), 2-amino-indan-2-carboxylic acid ethyl ester (464 mg, 2.26 mmol), HATU (1 g, 2.70 mmol) in anhydrous DMF (20 mL) is added DIPEA (446 μL, 2.70 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous Na₂SO₄ and concentrated in vacuo. The residue is purified by flash column chromatography (120 g silica gel, gradient elution: 5-50% EtOAc in heptane) to give a pure product (65) as white solid (828 mg, 97%).

¹H NMR (CDCl₃, 300 MHz): δ 1.30 (t, 3H), 2.09 (m, 2H), 2.63 (t, 2H), 3.07 (t, 2H), 3.38 (d, 2H), 3.77 (d, 2H), 4.29 (q, 2H), 6.31 (t, 2H), 7.20-7.26 (m, 4H), 7.30 (d, 1H), 7.50 (dd, 1H), 8.05 (dd, 1H)

LC/MS (ES+) m/z=378.13

Example 66

2-[(5-oxo-5,6,7,8-tetrahydro-naphthalene-1-carbonyl)-amino]-indan-2-carboxylic acid (66)

The mixture of 2-[(5-oxo-5,6,7,8-tetrahydro-naphthalene-1-carbonyl)-amino]-indan-2-carboxylic acid ethyl ester (65) (250 mg, 0.66 mmol) and KOH (500 mg, 8.9 mmol) is dissolved in EtOH (10 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. After the filtration, the solid is purified by HPLC to give a pure product (66) as white solid (150 mg, 65%).

¹H NMR (CDCl₃+CD₃OD, 300 MHz): δ 1.98 (m, 2H), 2.60 (t, 2H), 2.97 (t, 2H), 3.34 (d, 2H), 3.58 (d, 2H), 7.15-7.25 (m, 4H), 7.38 (d, 1H), 7.48 (t, 1H), 7.94 (dd, 1H), 9.02 (s, 1H)

LC/MS (ES+) m/z=350.16

Example 67

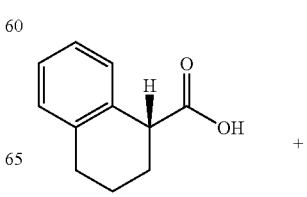

+

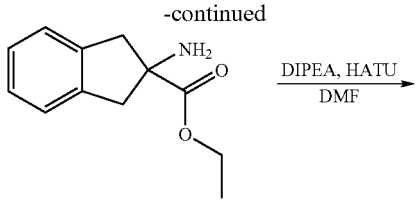
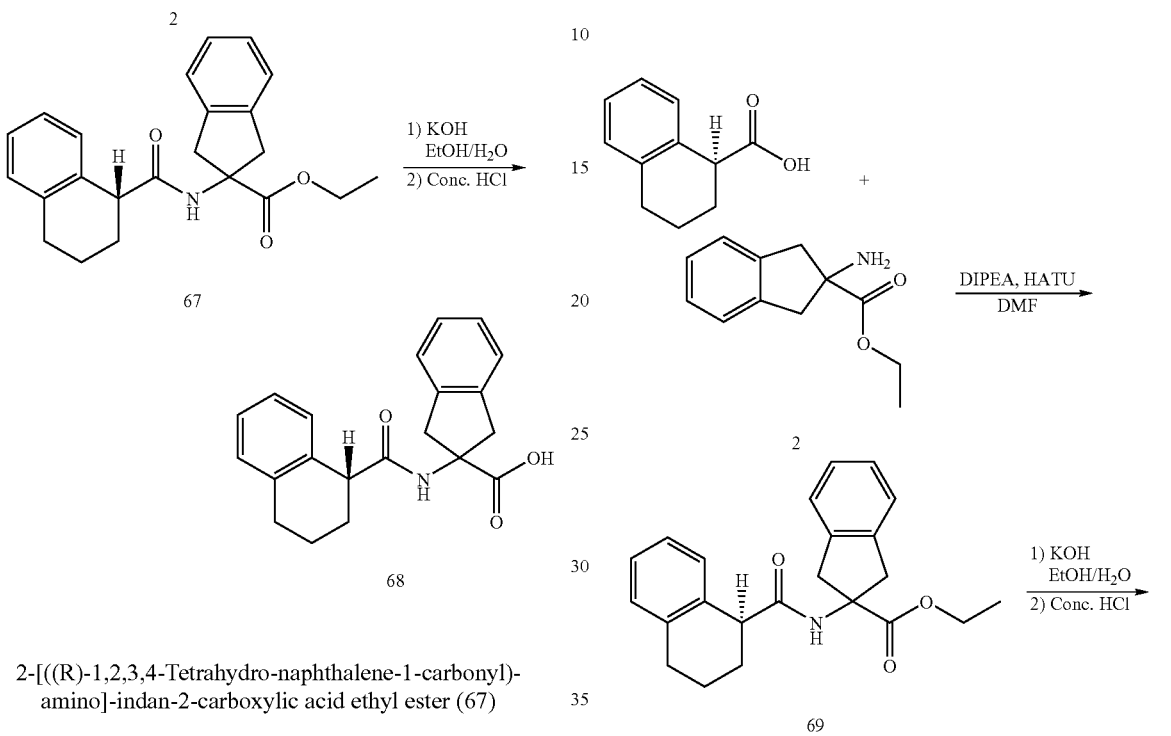

2-[((R)-1,2,3,4-Tetrahydro-naphthalene-1-carbonyl)-amino]-indan-2-carboxylic acid ethyl ester (67)

To a solution of (R)-1,2,3,4-tetrahydro-naphthalene-1-carboxylic acid (300 mg, 1.7 mmol), 2-amino-indan-2-carboxylic acid ethyl ester (349 mg, 1.7 mmol), HATU (760 mg, 2.0 mmol) in anhydrous DMF (10 mL) is added DIPEA (330 μL, 2 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 5%-50% EtOAc in heptane) to give a pure product (67) as white solid (615 mg, 100%).

$^1$H NMR (CDCl$_3$, 300 MHz): δ 1.24 (t, 3H), 1.57-2.00 (m, 3H), 2.17-2.26 (m, 1H), 2.76 (m, 2H), 3.10 (dd, 2H), 3.57-3.68 (m, 3H), 4.19 (q, 2H), 5.87 (s, 1H), 7.03-7.18 (m, 8H)

LC/MS (ES+) m/z=364.16

Example 68

2-[((R)-1,2,3,4-Tetrahydro-naphthalene-1-carbonyl)-amino]-indan-2-carboxylic acid (68)

The mixture of 2-[((R)-1,2,3,4-tetrahydro-naphthalene-1-carbonyl)-amino]-indan-2-carboxylic acid ethyl ester (67) (440 mg, 1.21 mmol) and KOH (500 mg, 8.9 mmol) is dissolved in EtOH (10 mL) and water (0.5 mL) under a water bath. The water bath is removed when KOH is completely dissolved and the resulting reaction solution is stirred at RT for 3 h. After concentration in vacuo, the residue is dissolved in water (30 mL) and acidified with conc. HCl until no more precipitate came out of the water. The precipitate is filtered to give a pure product (68) as white solid (391 mg, 96%).

$^1$H NMR (CDCl$_3$, 300 MHz): δ 1.65-1.73 (m, 2H), 1.93-1.96 (m, 1H), 2.17-2.27 (m, 1H), 2.69 (t, 2H), 3.12 (t, 2H), 3.63-3.70 (m, 3H), 5.84 (s, 1H), 6.86 (d, 1H), 7.00 (t, 1H), 7.07 (d, 1H), 7.13-7.20 (m, 5H)

LC/MS (ES−) m/z=334.14

Example 69

2-[((S)-1,2,3,4-Tetrahydro-naphthalene-1-carbonyl)-amino]-indan-2-carboxylic acid ethyl ester (69)

To a solution of (S)-1,2,3,4-tetrahydro-naphthalene-1-carboxylic acid (300 mg, 1.7 mmol), 2-amino-indan-2-carboxylic acid ethyl ester (349 mg, 1.7 mmol), HATU (760 mg, 2 mmol) in anhydrous DMF (8 mL) is added DIPEA (330 μL, 2 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 5%-50% EtOAc in heptane) to give a pure product (69) as white solid (615 mg, 100%).

$^1$H NMR (CDCl$_3$, 300 MHz): δ 1.24 (t, 3H), 1.58-2.00 (m, 3H), 2.17-2.26 (m, 1H), 2.76 (m, 2H), 3.10 (dd, 2H), 3.57-3.68 (m, 3H), 4.19 (q, 2H), 5.87 (s, 1H), 7.05-7.26 (m, 8H)

LC/MS (ES+) m/z=364.19

Example 70

2-[((S)-1,2,3,4-Tetrahydro-naphthalene-1-carbonyl)-amino]-indan-2-carboxylic acid (70)

The mixture of 2-[((S)-1,2,3,4-tetrahydro-naphthalene-1-carbonyl)-amino]-indan-2-carboxylic acid ethyl ester (69) (440 mg, 1.21 mmol) and KOH (800 mg, 14.2 mmol) is dissolved in EtOH (10 mL) and water (0.5 mL) under a water bath. The water bath is removed when KOH is completely dissolved and the resulting reaction solution is stirred at RT for 4 h. After concentration in vacuo, the residue is dissolved in water (30 mL) and acidified with conc. HCl until no more precipitate came out of the water. The precipitate is filtered to give a pure product (70) as white solid (405 mg, 100%).

$^1$H NMR (CDCl$_3$, 300 MHz): δ 1.66-1.73 (m, 2H), 1.93-1.96 (m, 1H), 2.20-2.22 (m, 1H), 2.69 (t, 2H), 3.12 (t, 2H), 3.17-3.71 (m, 3H), 5.82 (s, 1H), 6.87 (d, 1H), 7.01 (t, 1H), 7.07 (d, 1H), 7.13-7.21 (m, 5H)

LC/MS (ES+) m/z=336.13

Example 71

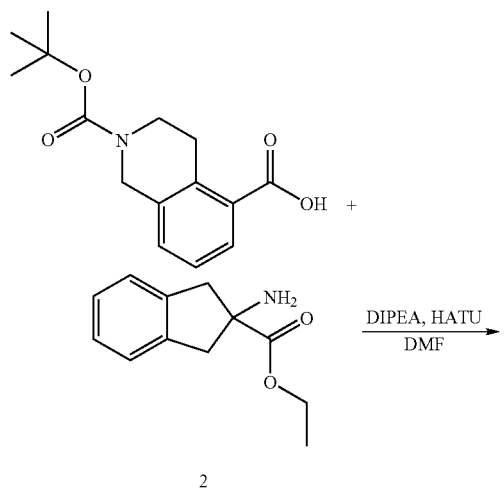

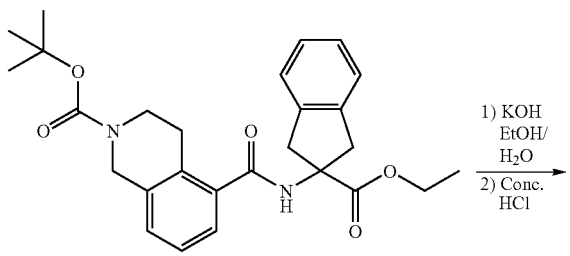

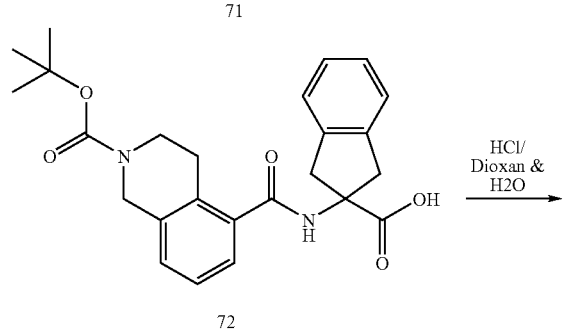

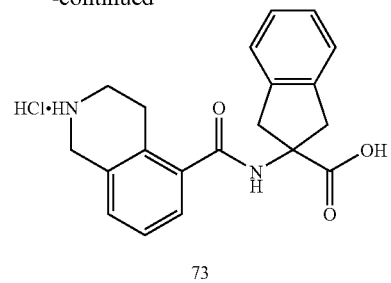

73

5-(2-Ethoxycarbonyl-indan-2-ylcarbamoyl)-3,4-dihydro-1H-isoquinoline-2-carboxylic acid tert-butyl ester (71)

To a solution of 3,4-dihydro-1H-isoquinoline-2,5-dicarboxylic acid 2-tert-butyl ester (2 g, 7.2 mmol), 2-amino-indan-2-carboxylic acid ethyl ester (1.5 g, 7.2 mmol), HATU (3.27 g, 8.6 mmol) in anhydrous DMF (20 mL) is added DIPEA (1.42 mL, 8.6 mmol). The resulting solution is stirred at RT overnight. After the removal of DMF in vacuo, the residue is dissolved in EtOAc (150 mL) and washed with water (1×20 mL) and brine (2×20 mL). The organic layer is dried over anhydrous Na$_2$SO$_4$ and concentrated in vacuo. The residue is purified by HPLC to give a pure product (71) as white solid (1.02 g, 30%).

$^1$H NMR (CDCl$_3$, 300 MHz): δ 1.29 (t, 3H), 1.48 (s, 9H), 2.95 (t, 2H), 3.35 (d, 2H), 3.57 (t, 2H), 3.75 (d, 2H), 4.27 (q, 2H), 4.55 (s, 2H), 6.26 (s, 1H), 7.14-7.26 (m, 7H)

LC/MS (ES+) m/z=465.26

Example 72

5-(2-Carboxy-indan-2-ylcarbamoyl)-3,4-dihydro-1H-isoquinoline-2-carboxylic acid tert-butyl ester (72)

The mixture of 5-(2-ethoxycarbonyl-indan-2-ylcarbamoyl)-3,4-dihydro-1H-isoquinoline-2-carboxylic acid tert-butyl ester (71) (882 mg, 1.78 mmol) and KOH (1 g, 17.9 mmol) is dissolved in EtOH (15 mL) and water (1 mL) under a water bath. The water bath is removed when KOH is completely dissolved and the resulting reaction solution is stirred at RT for 3 h. After concentration in vacuo, the residue is dissolved in water (50 mL) and acidified with conc. HCl until no more white precipitate came out of the water. After the filtration, the solid is purified by HPLC to give a pure product (72) as white solid (680 mg, 88%).

$^1$H NMR (CDCl$_3$, 300 MHz): δ 1.46 (s, 9H), 2.84 (t, 2H), 3.36 (d, 2H), 3.48 (t, 2H), 3.74 (d, 2H), 4.49 (s, 2H), 6.57 (br s, 1H), 7.10-7.19 (m, 7H)

LC/MS (ES+) m/z=381.17, 437.23

Example 73

2-[(1,2,3,4-Tetrahydro-isoquinoline-5-carbonyl)-amino]-indan-2-carboxylic acid hydrochloride salt (73)

5-(2-Carboxy-indan-2-ylcarbamoyl)-3,4-dihydro-1H-isoquinoline-2-carboxylic acid tert-butyl ester (72) (650 mg, 1.49 mmol) is dissolved in 30% solution of TFA in DCM (10 mL) and the resulting solution is stirred at RT for 2 h. The solution is concentrated to give a TFA salt of 2-[(1,2,3,4-tetrahydro-isoquinoline-5-carbonyl)-amino]-indan-2-carboxylic acid (670 mg, 100%). This TFA salt (250 mg, 0.56 mmol) is dissolved in 6N aqueous solution of HCl (20 mL). The resulting suspension is stirred overnight and turned into a clear solution. The solution is concentrated to give a pure product (73) as white solid (130 mg, 62%).

$^1$H NMR (DMSO-d6, 300 MHz): δ 3.05 (t, 2H), 3.32-3.37 (m, 4H), 3.57 (d, 2H), 4.27 (s, 2H), 7.15-7.29 (m, 7H), 8.98 (s, 1H), 9.42 (s, 2H), 12.51 (br s, 1H)

LC/MS (ES+) m/z=337.17

Example 74

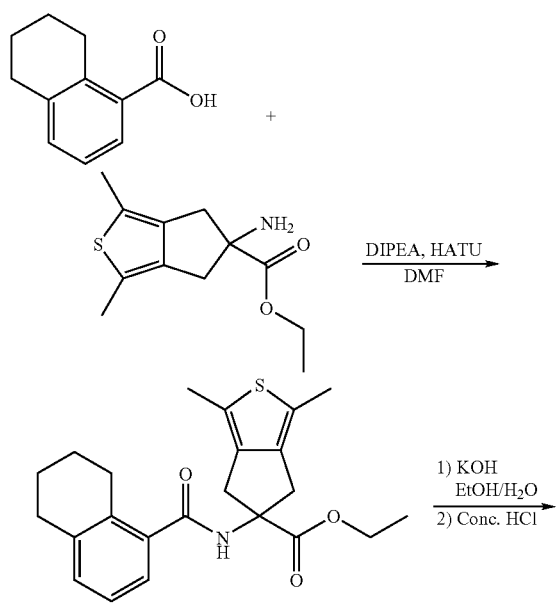

1,3-Dimethyl-5-[(5,6,7,8-tetrahydro-naphthalene-1-carbonyl)-amino]-5,6-dihydro-4H-cyclopenta[c]thiophene-5-carboxylic acid ethyl ester (74)

To a solution of 5,6,7,8-tetrahydro-naphthalene-1-carboxylic acid (500 mg, 2.84 mmol), 5-amino-1,3-dimethyl-5, 6-dihydro-4H-cyclopenta[c]thiophene-5-carboxylic acid ethyl ester (816 mg, 3.41 mmol), HATU (1.62 g, 4.26 mmol) in anhydrous DMF (15 mL) is added DIPEA (704 µL, 4.26 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous Na$_2$SO$_4$ and concentrated in vacuo. The residue is purified by flash column chromatography (115 g silica gel, gradient elution: 5-50% EtOAc in heptane) to give a pure product (74) as white solid (1.10 g, 97%).

$^1$H NMR (CDCl$_3$, 300 MHz): δ 1.29 (t, 3H), 1.76 (m, 4H), 2.25 (s, 6H), 2.80 (m, 4H), 2.97 (d, 2H), 3.31 (d, 2H), 4.26 (q, 2H), 6.22 (s, 1H), 7.15-7.15 (m, 3H)

LC/MS (ES+) m/z=398.16

Example 75

1,3-Dimethyl-5-[(5,6,7,8-tetrahydro-naphthalene-1-carbonyl)-amino]-5,6-dihydro-4H-cyclopenta[c]thiophene-5-carboxylic acid (75)

The mixture of 1,3-dimethyl-5-[(5,6,7,8-tetrahydro-naphthalene-1-carbonyl)-amino]-5,6-dihydro-4H-cyclopenta[c]thiophene-5-carboxylic acid ethyl ester (74) (942 mg, 2.37 mmol) and KOH (3 g, 23 mmol) is dissolved in EtOH (20 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate formed. The precipitate is filtered to give a pure product (75) as a pale brown solid (832 mg, 95%).

$^1$H NMR (CDCl$_3$, 300 MHz): δ 1.75 (m, 4H), 2.25 (s, 6H), 2.75 (m, 4H), 3.03 (d, 2H), 3.36 (d, 2H), 6.26 (s, 1H), 7.08-7.16 (m, 3H)

LC/MS (ES+) m/z=370.12

Example 76

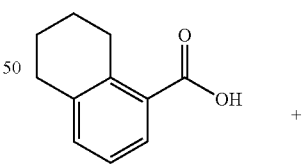

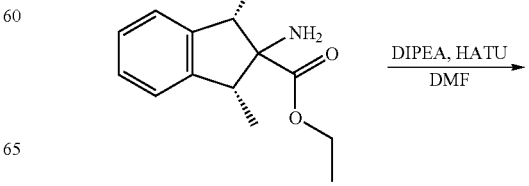

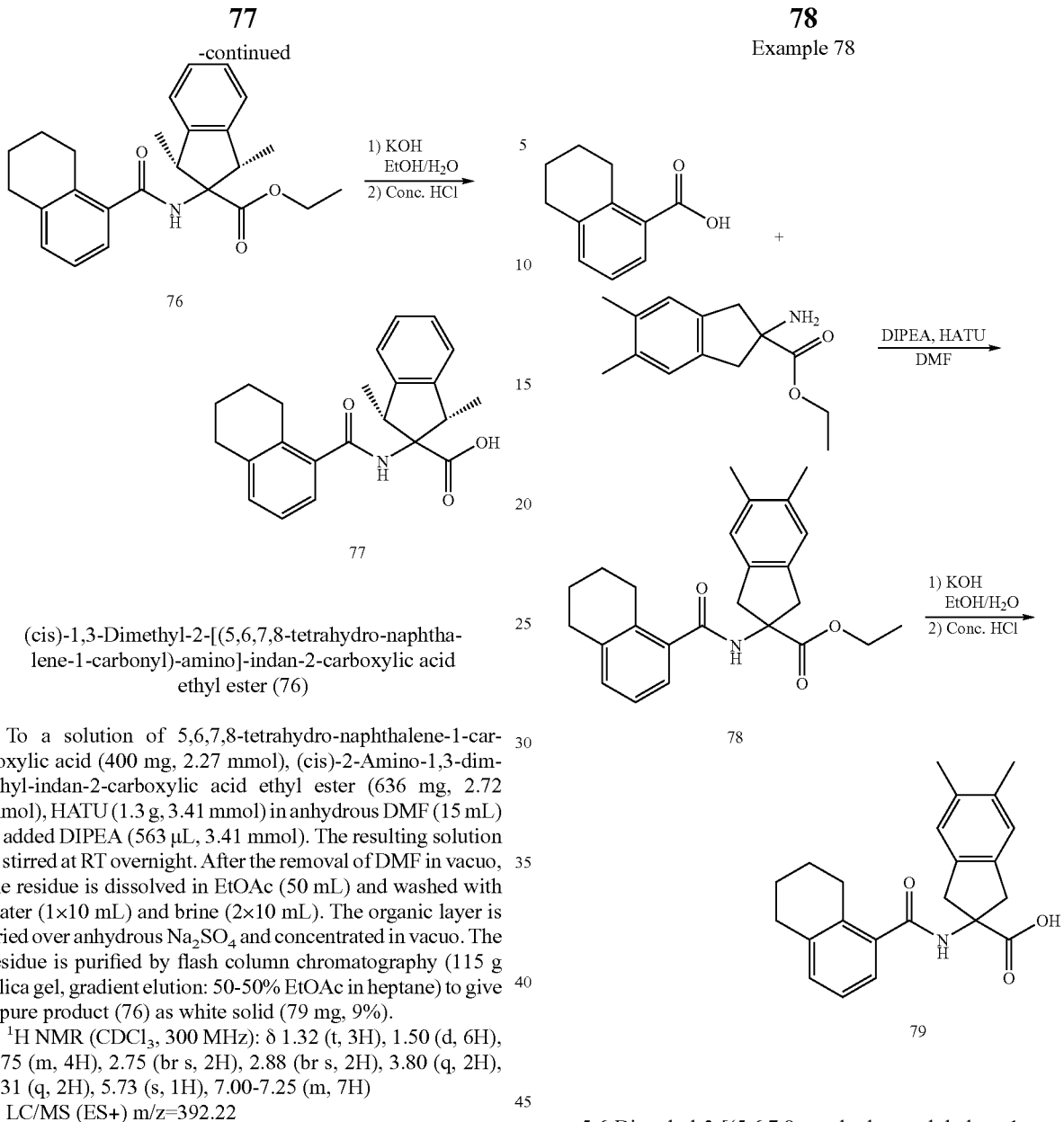

(cis)-1,3-Dimethyl-2-[(5,6,7,8-tetrahydro-naphthalene-1-carbonyl)-amino]-indan-2-carboxylic acid ethyl ester (76)

To a solution of 5,6,7,8-tetrahydro-naphthalene-1-carboxylic acid (400 mg, 2.27 mmol), (cis)-2-Amino-1,3-dimethyl-indan-2-carboxylic acid ethyl ester (636 mg, 2.72 mmol), HATU (1.3 g, 3.41 mmol) in anhydrous DMF (15 mL) is added DIPEA (563 µL, 3.41 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 50-50% EtOAc in heptane) to give a pure product (76) as white solid (79 mg, 9%).

$^1$H NMR ($CDCl_3$, 300 MHz): δ 1.32 (t, 3H), 1.50 (d, 6H), 1.75 (m, 4H), 2.75 (br s, 2H), 2.88 (br s, 2H), 3.80 (q, 2H), 4.31 (q, 2H), 5.73 (s, 1H), 7.00-7.25 (m, 7H)

LC/MS (ES+) m/z=392.22

Example 77

(cis)-1,3-Dimethyl-2-[(5,6,7,8-tetrahydro-naphthalene-1-carbonyl)-amino]-indan-2-carboxylic acid (77)

The mixture of (cis)-1,3-dimethyl-2-[(5,6,7,8-tetrahydro-naphthalene-1-carbonyl)-amino]-indan-2-carboxylic acid ethyl ester (76) (62 mg, 1.2 mmol) and KOH (300 mg, 5.4 mmol) is dissolved in EtOH (3 mL) and water (0.3 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH~4. The precipitate is filtered to give a pure product (77) as white solid (44 mg, 75%).

$^1$H NMR ($CDCl_3$, 300 MHz): δ 1.51 (d, 6H), 1.74 (m, 4H), 2.75 (br s, 2H), 2.86 (br s, 2H), 3.88 (q, 2H), 5.81 (s, 1H), 7.01-7.26 (m, 7H)

LC/MS (ES+) m/z=364.23

Example 78

5,6-Dimethyl-2-[(5,6,7,8-tetrahydro-naphthalene-1-carbonyl)-amino]-indan-2-carboxylic acid ethyl ester (78)

To a solution of 5,6,7,8-tetrahydro-naphthalene-1-carboxylic acid (400 mg, 2.27 mmol), 2-amino-5,6-dimethyl-indan-2-carboxylic acid ethyl ester (636 mg, 2.72 mmol), HATU (1.30 g, 3.41 mmol) in anhydrous DMF (15 mL) is added DIPEA (563 µL, 3.41 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5-50% EtOAc in heptane) to give a pure product (78) as white solid (817 mg, 92%).

$^1$H NMR ($CDCl_3$, 300 MHz): δ 1.29 (t, 3H), 1.74 (m, 4H), 2.23 (s, 6H), 2.75 (br s, 2H), 2.84 (br s, 2H), 3.25 (d, 2H), 3.69 (d, 2H), 4.26 (q, 2H), 6.20 (s, 1H), 6.99-7.11 (m, 5H)

LC/MS (ES+) m/z=392.20

Example 79

5,6-Dimethyl-2-[(5,6,7,8-tetrahydro-naphthalene-1-carbonyl)-amino]-indan-2-carboxylic acid (79)

The mixture of 5,6-dimethyl-2-[(5,6,7,8-tetrahydro-naphthalene-1-carbonyl)-amino]-indan-2-carboxylic acid ethyl ester (78) (438 mg, 1.11 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate formed. The precipitate is filtered to give a pure product (79) as a pale brown solid (390 mg, 97%).

$^1$H NMR (CDCl$_3$+drops CD$_3$OD, 300 MHz): δ 1.73 (m, 4H), 2.23 (s, 6H), 2.74-2.80 (m, 4H), 3.29 (d, 2H), 3.69 (d, 2H), 6.60 (s, 1H), 6.99-7.08 (m, 5H)

LC/MS (ES+) m/z=364.23

Example 80

5-Methoxy-2-[(5,6,7,8-tetrahydro-naphthalene-1-carbonyl)-amino]-indan-2-carboxylic acid ethyl ester (80)

To a solution of 5,6,7,8-tetrahydro-naphthalene-1-carboxylic acid (400 mg, 2.27 mmol), 2-amino-5-methoxy-indan-2-carboxylic acid ethyl ester (639 mg, 2.72 mmol), HATU (1.3 g, 3.41 mmol) in anhydrous DMF (15 mL) is added DIPEA (563 μL, 3.41 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous Na$_2$SO$_4$ and concentrated in vacuo. The residue is purified by flash column chromatography (115 g silica gel, gradient elution: 5%-40% EtOAc in heptane) to give a pure product (52) as white solid (622 mg, 70%).

$^1$H NMR (CDCl$_3$, 300 MHz): δ 1.28 (t, 3H), 1.74 (m, 4H), 2.75 (br s, 2H), 2.84 (br s, 2H), 3.27 (dd, 2H), 3.69 (dd, 2H), 3.78 (s, 3H), 4.25 (q, 2H), 6.26 (s, 1H), 6.72-6.76 (m, 2H), 7.01-7.11 (m, 4H),

LC/MS (ES+) m/z=394.21

Example 81

5-Methoxy-2-[(5,6,7,8-tetrahydro-naphthalene-1-carbonyl)-amino]-indan-2-carboxylic acid (81)

The mixture of 5-methoxy-2-[(5,6,7,8-tetrahydro-naphthalene-1-carbonyl)-amino]-indan-2-carboxylic acid ethyl ester (80) (458 mg, 1.2 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate formed. The precipitate is filtered to give a pure product (81) as a pale brown solid (448 mg, 100%).

$^1$H NMR (CDCl$_3$+drops of CD$_3$OD, 300 MHz): δ 1.72 (m, 4H), 2.75-2.78 (m, 4H), 3.32 (dd, 2H), 3.78 (dd, 2H), 3.78 (s, 3H), 6.45 (s, 1H), 6.73-6.77 (m, 2H), 7.03-7.11 (m, 4H), LC/MS (ES+) m/z=366.20

Example 82

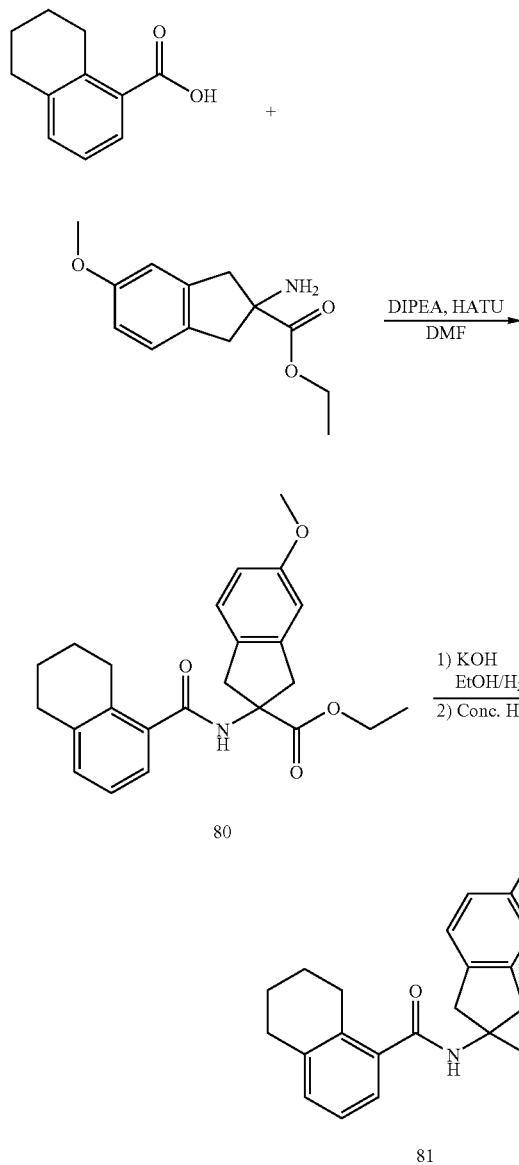

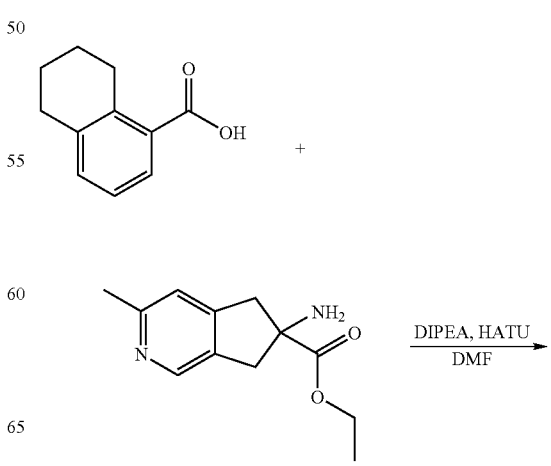

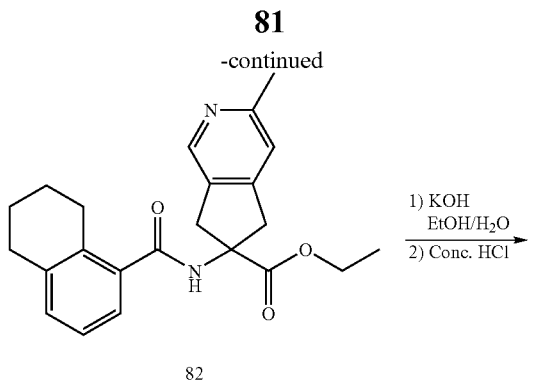

82

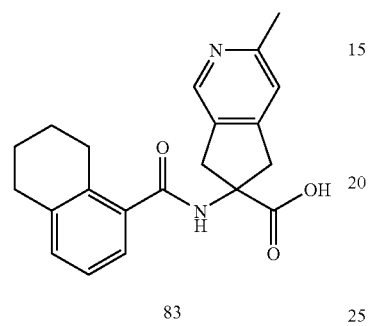

83

3-Methyl-6-[(5,6,7,8-tetrahydro-naphthalene-1-carbonyl)-amino]-6,7-dihydro-5H-[2]pyrindine-6-carboxylic acid ethyl ester (82)

To a solution of 1,2,3,4-tetrahydro-quinoline-8-carboxylic acid (240 mg, 1.36 mmol), 6-amino-3-methyl-6,7-dihydro-5H-[2]pyrindine-6-carboxylic acid ethyl ester (not pure, 300 mg, 1.36 mmol), HATU (608 mg, 1.60 mmol) in anhydrous DMF (10 mL) is added DIPEA (264 μL, 1.60 mmol). The resulting solution is stirred at RT overnight. After the removal of DMF in vacuo, the residue is dissolved in EtOAc (40 mL) and washed with water (1×10 mL) and brine (2×10 mL). The organic layer is dried over anhydrous Na$_2$SO$_4$ and concentrated in vacuo. The residue is purified by HPLC to give a product (82) as a colorless oil (100 mg, 19%).

$^1$H NMR (CDCl$_3$, 300 MHz): δ 1.26 (t, 3H), 1.75 (br s, 4H), 2.76 (br s, 2H), 3.68 (s, 2H), 3.86 (q, 2H), 4.26 (q, 2H), 7.02-7.12 (m, 3H), 7.32 (s, 1H), 7.52 (s, 1H), 8.51 (s, 1H)
LC/MS (ES+) m/z=379.22

Example 83

3-Methyl-6-[(5,6,7,8-tetrahydro-naphthalene-1-carbonyl)-amino]-6,7-dihydro-5H-[2]pyrindine-6-carboxylic acid (83)

The mixture of 3-methyl-6-[(5,6,7,8-tetrahydro-naphthalene-1-carbonyl)-amino]-6,7-dihydro-5H-[2]pyrindine-6-carboxylic acid ethyl ester (82) and KOH (1 g, 17.9 mmol) in EtOH (5 mL) and water (0.3 mL) under a water bath. The water bath is removed when KOH is completely dissolved and the resulting reaction solution is stirred at RT for 3 h. After concentration in vacuo, the residue is dissolved in water (20 mL) and acidified with conc. HCl dropwise until no more precipitate came out of the water. After the filtration, the solid is purified by HPLC to give a pure product (83) as colorless oil (20 mg, 22%).

$^1$H NMR (CDCl$_3$+drops of CD$_3$OD, 300 MHz): δ 1.77 (br s, 4H), 2.79 (br s, 2H), 3.69 (m, 2H), 3.88 (q, 2H), 7.06-7.15 (m, 3H), 7.53 (s, 1H), 8.56 (s, 1H)
LC/MS (ES+) m/z=351.11

Example 84

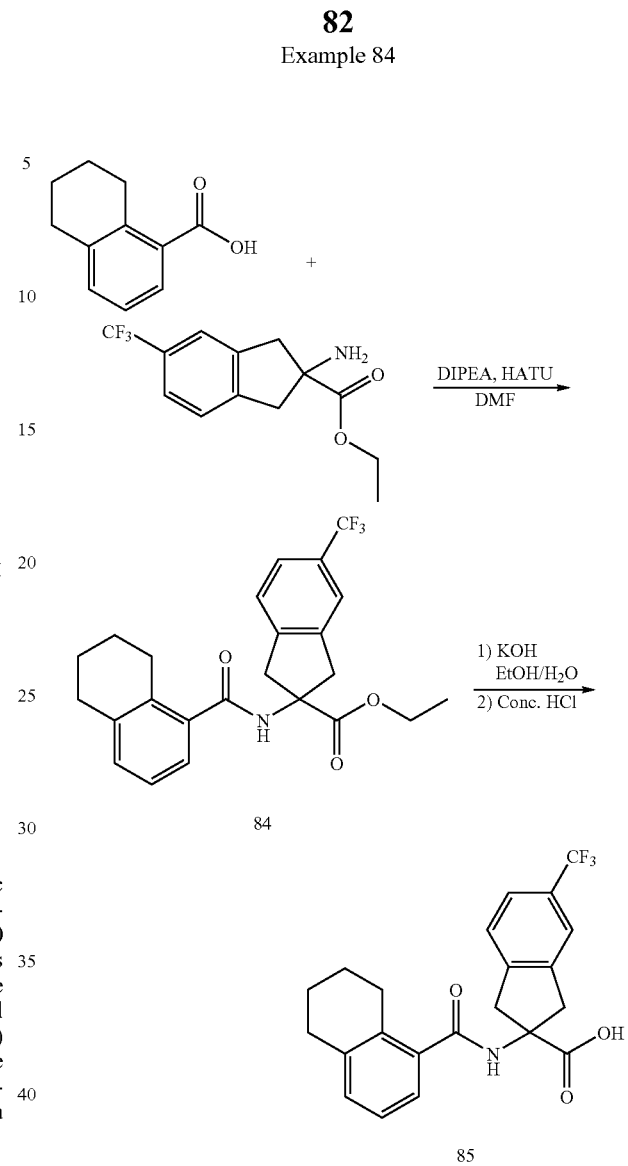

2-[(5,6,7,8-Tetrahydro-naphthalene-1-carbonyl)-amino]-5-trifluoromethyl-indan-2-carboxylic acid ethyl ester (84)

To a solution of 5,6,7,8-tetrahydro-naphthalene-1-carboxylic acid (306 mg, 1.74 mmol), 2-amino-5-trifluoro-indan-2-carboxylic acid ethyl ester (583 mg, 2.13 mmol), HATU (992 mg, 2.61 mmol) in anhydrous DMF (15 mL) is added DIPEA (431 μL, 2.61 mmol). The resulting solution is stirred at RT overnight. After the removal of DMF in vacuo, the residue is dissolved in EtOAc (80 mL) and washed with water (1×10 mL) and brine (2×10 mL). The organic layer is dried over anhydrous Na$_2$SO$_4$ and concentrated in vacuo. The residue is purified by flash column chromatography (120 g silica gel, gradient elution: 5%-70% EtOAc in heptane) to give a pure product (84) as white solid (589 mg, 78%).

$^1$H NMR (CDCl$_3$, 300 MHz): δ 1.27 (t, 3H), 1.75 (m, 4H), 2.76 (br s, 2H), 2.83 (br s, 2H), 3.44 (dd, 2H), 3.74 (dd, 2H), 4.26 (q, 2H), 6.35 (s, 1H), 7.02-7.12 (m, 3H), 7.32 (d, 1H), 7.46 (br s, 2H) LC/MS (ES+) m/z=432.17

Example 85

2-[(5,6,7,8-Tetrahydro-naphthalene-1-carbonyl)-amino]-5-trifluoromethyl-indan-2-carboxylic acid (85)

The mixture of 2-[(5,6,7,8-tetrahydro-naphthalene-1-carbonyl)-amino]-5-trifluoromethyl-indan-2-carboxylic acid ethyl ester (84) (437 mg, 1.0 mmol) and KOH (1 g, 18 mmol) is dissolved in EtOH (8 mL) and water (1 mL) under a water bath. The water bath is removed when KOH is completely dissolved and the resulting reaction solution is stirred at RT for 3 h. After concentration in vacuo, the residue is dissolved in water (50 mL) and acidified with conc. HCl until no more white precipitate formed. The precipitate is filtered to give a pure product (85) as white solid (408 mg, 100%).

$^1$H NMR (CDCl$_3$+drops of CD$_3$OD, 300 MHz): δ 1.74 (m, 4H), 2.78 (m, 4H), 3.49 (dd, 2H), 3.76 (dd, 2H), 6.69 (s, 1H), 7.03-7.13 (m, 3H), 7.32 (d, 1H), 7.47 (dd, 2H)

LC/MS (ES+) m/z=404.15

Example 86

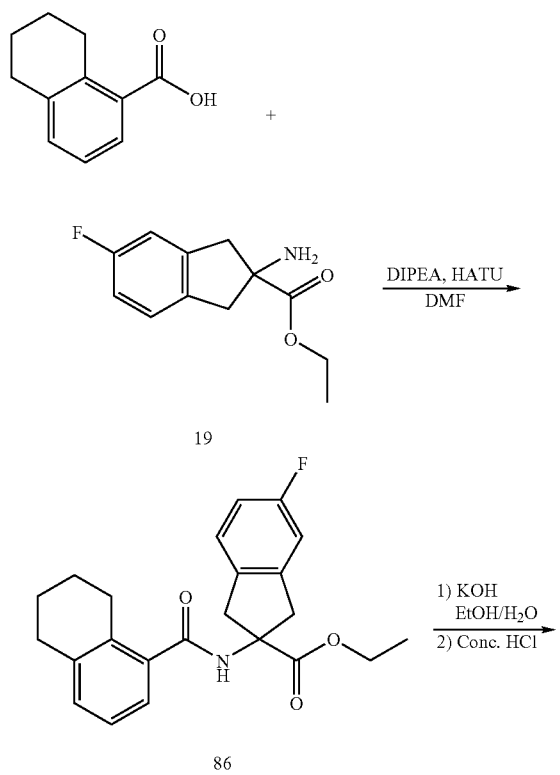

Example 86 (continued)

5-Fluoro-2-[(5,6,7,8-tetrahydro-naphthalene-1-carbonyl)-amino]-indan-2-carboxylic acid ethyl ester (86)

To a solution of 5,6,7,8-tetrahydro-naphthalene-1-carboxylic acid (400 mg, 2.27 mmol), 2-amino-5-fluoro-indan-2-carboxylic acid ethyl ester (610 mg, 2.72 mmol), HATU (1.30 g, 3.41 mmol) in anhydrous DMF (15 mL) is added DIPEA (563 μL, 3.41 mmol). The resulting solution is stirred at RT overnight. After the removal of DMF in vacuo, the residue is dissolved in EtOAc (70 mL) and washed with water (1×10 mL) and brine (2×10 mL). The organic layer is dried over anhydrous Na$_2$SO$_4$ and concentrated in vacuo. The residue is purified by flash column chromatography (115 g silica gel, gradient elution: 5%-40% EtOAc in heptane) to give a pure product (86) as white solid (345 mg, 40%).

$^1$H NMR (CDCl$_3$, 300 MHz): δ 1.28 (t, 3H), 1.75 (m, 4H), 2.76 (br s, 2H), 2.83 (br s, 2H), 3.33 (dd, 2H), 3.69 (dd, 2H), 4.25 (q, 2H), 6.29 (s, 1H), 6.85-6.93 (m, 2H), 7.02-7.16 (m, 4H)

LC/MS (ES+) m/z=382.16

Example 87

5-Fluoro-2-[(5,6,7,8-tetrahydro-naphthalene-1-carbonyl)-amino]-indan-2-carboxylic acid (87)

The mixture of 5-fluoro-2-[(5,6,7,8-tetrahydro-naphthalene-1-carbonyl)-amino]-indan-2-carboxylic acid ethyl ester (86) (190 mg, 0.50 mmol) and KOH (500 mg, 8.9 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate formed. The precipitate is filtered to give a pure product (87) as a pale brown solid (178 mg, 100%).

$^1$H NMR (CDCl$_3$+drops of CD$_3$OD, 300 MHz): δ 1.75 (m, 4H), 2.76-2.81 (m, 4H), 3.40 (dd, 2H), 3.72 (dd, 2H), 6.65 (s, 1H), 6.86-6.94 (m, 2H), 7.03-7.18 (m, 4H)

LC/MS (ES+) m/z=382.16

Example 88

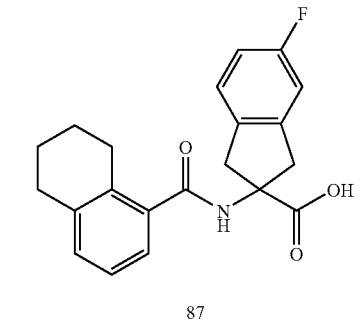

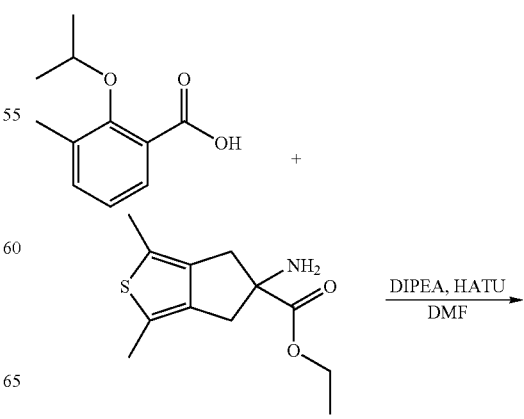

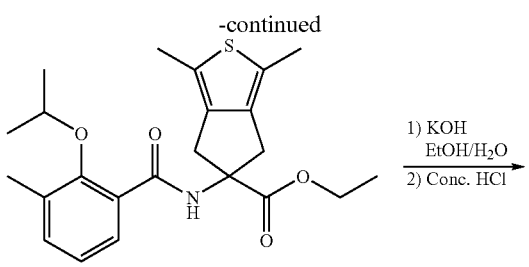

88

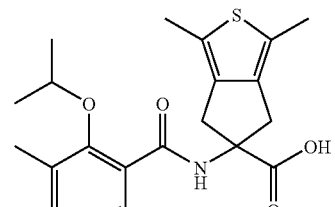

89

5-(2-Isopropoxy-3-methyl-benzoylamino)-1,3-dimethyl-5,6-dihydro-4H-cyclopenta[c]thiophene-5-carboxylic acid ethyl ester (88)

To a solution of 2-isopropoxy-3-methyl-benzoic acid (300 mg, 1.54 mmol), 5-amino-1,3-dimethyl-5,6-dihydro-4H-cyclopenta[c]thiophene-5-carboxylic acid ethyl ester (443 mg, 1.85 mmol), HATU (878 g, 2.31 mmol) in anhydrous DMF (10 mL) is added DIPEA (382 µL, 2.31 mmol). The resulting solution is stirred at RT overnight. After the removal of DMF in vacuo, the residue is dissolved in EtOAc (70 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5%-50% EtOAc in heptane) to give a pure product (88) as a pale yellow solid (599 mg, 95%).

$^1$H NMR (CDCl$_3$, 300 MHz): δ 1.09 (d, 6H), 1.23 (t, 3H), 2.25 (s, 6H), 2.28 (s, 3H), 2.98 (d, 2H), 3.33 (d, 2H), 4.20-4.24 (m, 3H), 7.08 (t, 1H), 7.28 (d, 1H), 7.87 (d, 1H), 8.37 (s, 1H)

LC/MS (ES+) m/z=416.17

Example 89

5-(2-Isopropoxy-3-methyl-benzoylamino)-1,3-dimethyl-5,6-dihydro-4H-cyclopenta[c]thiophene-5-carboxylic acid (89)

The mixture of 5-(2-isopropoxy-3-methyl-benzoylamino)-1,3-dimethyl-5,6-dihydro-4H-cyclopenta[c]thiophene-5-carboxylic acid ethyl ester (88) (448 mg, 1.08 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate formed. The precipitate is filtered to give a pure product (89) as a brown solid (360 mg, 86%).

$^1$H NMR (CDCl$_3$, 300 MHz): δ 1.06 (d, 6H), 2.26 (s, 6H), 2.28 (s, 3H), 3.09 (d, 2H), 3.43 (d, 2H), 4.17 (m, 1H), 7.12 (t, 1H), 7.32 (d, 1H), 7.91 (d, 1H), 8.61 (s, 1H)

LC/MS (ES+) m/z=388.14

Example 90

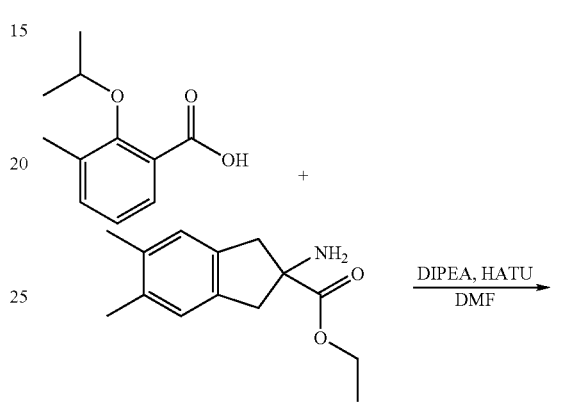

90

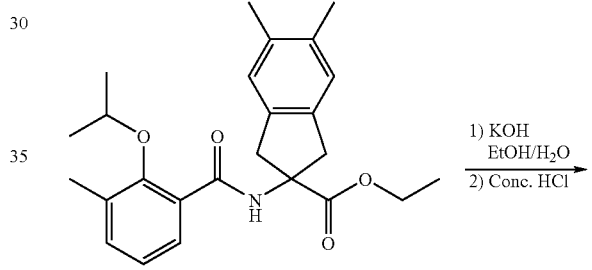

2-(2-Isopropoxy-3-methyl-benzoylamino)-5,6-dimethyl-indan-2-carboxylic acid ethyl ester (90)

To a solution of 2-isopropoxy-3-methyl-benzoic acid (300 mg, 1.54 mmol), 2-amino-5,6-dimethyl-indan-2-carboxylic acid ethyl ester (432 mg, 1.85 mmol), HATU 878 g, 2.31 mmol) in anhydrous DMF (10 mL) is added DIPEA (382 µL, 2.31 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous $Na_2SO_4$ and concentrated in vacuo. The residue is purified by

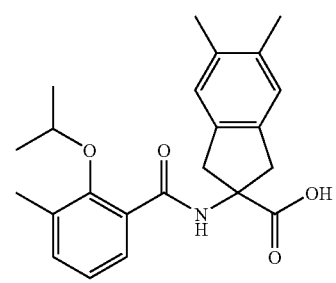

91 flash column chromatography (115 g silica gel, gradient elution: 5-40% EtOAc in heptane) to give a pure product (90) as white solid (591 mg, 94%).

¹H NMR (CDCl₃, 300 MHz): δ 1.08 (d, 6H), 1.24 (t, 3H), 2.22 (s, 6H), 2.24 (s, 3H), 3.25 (d, 2H), 3.70 (d, 2H), 4.20-4.28 (m, 3H), 7.00-7.08 (m, 3H), 7.24 (d, 1H), 7.83 (d, 1H), 8.27 (s, 1H)

LC/MS (ES+) m/z=410.21

Example 91

2-(2-Isopropoxy-3-methyl-benzoylamino)-5,6-dimethyl-indan-2-carboxylic acid (91)

The mixture of 2-(2-isopropoxy-3-methyl-benzoylamino)-5,6-dimethyl-indan-2-carboxylic acid ethyl ester (90) (440 mg, 1.07 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more precipitate formed. The precipitate is filtered to give the pure product (91) as a pale brown solid (374 mg, 92%).

¹H NMR (CDCl₃, 300 MHz): δ 1.02 (d, 6H), 2.22 (s, 6H), 2.25 (s, 3H), 3.34 (d, 2H), 3.80 (d, 2H), 4.14 (m, 1H), 7.01 (s, 2H), 7.09 (t, 1H), 7.29 (d, 1H), 7.87 (dd, 1H), 8.52 (s, 1H)

LC/MS (ES+) m/z=382.19

Example 92

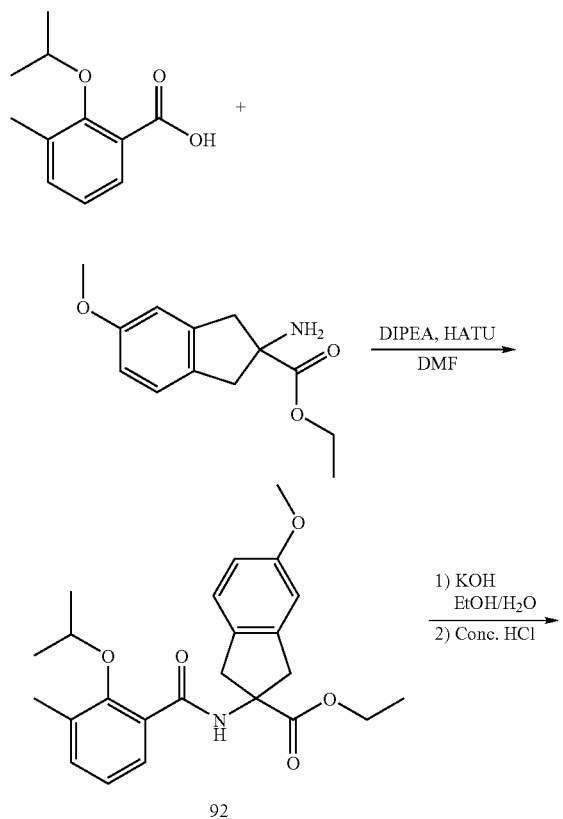

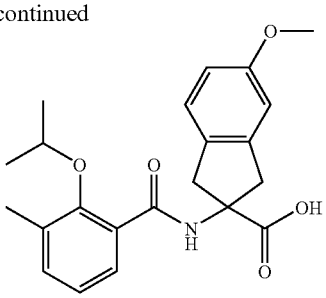

2-(2-Isopropoxy-3-methyl-benzoylamino)-5-methoxy-indan-2-carboxylic acid ethyl ester (92)

To a solution of 2-isopropoxy-3-methyl-benzoic acid (300 mg, 1.54 mmol), 2-amino-5-methoxy-indan-2-carboxylic acid ethyl ester (435 mg, 1.85 mmol), HATU (878 g, 2.31 mmol) in anhydrous DMF (10 mL) is added DIPEA (382 μL, 2.31 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous Na₂SO₄ and concentrated in vacuo. The residue is purified by flash column chromatography (115 g silica gel, gradient elution: 5%-40% EtOAc in heptane) to give a pure product (92) as a pale yellow oil (569 mg, 90%).

¹H NMR (CDCl₃, 300 MHz): δ 1.07 (d, 6H), 1.24 (t, 3H), 2.25 (s, 3H), 3.28 (d, 2H), 3.72 (dd, 2H), 3.78 (s, 3H), 4.21-4.25 (m, 3H), 6.73-6.78 (m, 2H), 7.04-7.13 (m, 2H), 7.26 (d, 1H), 7.85 (d, 1H), 8.32 (s, 1H)

LC/MS (ES+) m/z=412.18

Example 93

2-(2-Isopropoxy-3-methyl-benzoylamino)-5-methoxy-indan-2-carboxylic acid (93)

The mixture of 2-(2-isopropoxy-3-methyl-benzoylamino)-5-methoxy-indan-2-carboxylic acid ethyl ester (92) (410 mg, 1 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. The precipitate is filtered to give a pure product (93) as white solid (400 mg, 100%).

¹H NMR (CDCl₃, 300 MHz): δ 1.02 (m, 6H), 2.25 (s, 3H), 3.34 (d, 2H), 3.78 (s, 3H), 3.80 (dd, 2H), 4.16 (m, 1H), 6.73-6.78 (m, 2H), 7.05-7.14 (m, 2H), 7.27-7.30 (m, 1H), 7.88 (dd, 1H), 8.51 (s, 1H)

LC/MS (ES+) m/z=384.17

Example 94

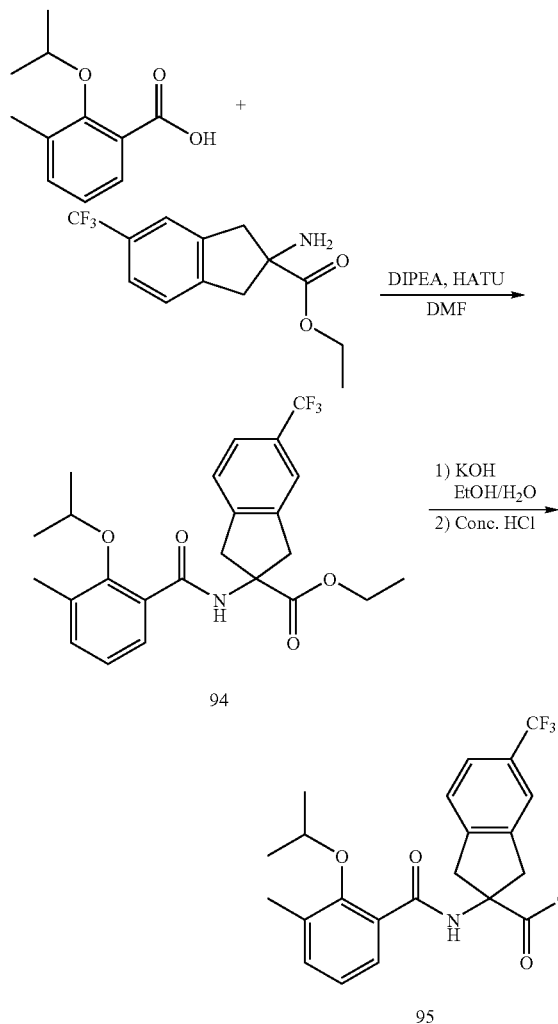

2-(2-Isopropoxy-3-methyl-benzoylamino)-5-trifluoromethyl-indan-2-carboxylic acid ethyl ester (94)

To a solution of 2-isopropoxy-3-methyl-benzoic acid (377 mg, 1.94 mmol), 2-amino-5-trifluoro-indan-2-carboxylic acid ethyl ester (650 mg, 2.38 mmol), HATU (1.11 g, 2.91 mmol) in anhydrous DMF (15 mL) is added DIPEA (480 μL, 2.91 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 5%-70% EtOAc in heptane) to give a pure product (94) as white solid (842 mg, 97%).

$^1$H NMR (CDCl$_3$, 300 MHz): δ 1.06 (d, 6H), 1.24 (t, 3H), 2.26 (s, 3H), 3.43 (d, 2H), 3.78 (dd, 2H), 4.16-4.29 (m, 1H), 4.25 (q, 2H), 7.08 (t, 1H), 7.26-7.35 (m, 2H), 7.47 (d, 2H), 7.85 (dd, 1H), 8.39 (s, 1H)

LC/MS (ES+) m/z=450.18

Example 95

2-(2-Isopropoxy-3-methyl-benzoylamino)-5-trifluoromethyl-indan-2-carboxylic acid (95)

The mixture of 2-(2-isopropoxy-3-methyl-benzoylamino)-5-trifluoromethyl-indan-2-carboxylic acid ethyl ester (94) (690 mg, 1.5 mmol) and KOH (1.5 g, 18 mmol) is dissolved in EtOH (8 mL) and water (1 mL) under a water bath. The water bath is removed when KOH is completely dissolved. The resulting reaction solution is stirred at RT for 8 h. After concentration in vacuo, the residue is dissolved in water (30 mL) and acidified with conc. HCl until pH~4. The precipitate is filtered to give a pure product (95) as a pale brown solid (495 mg, 78%).

$^1$H NMR (CDCl$_3$, 300 MHz): δ 0.99 (d, 6H), 2.25 (s, 3H), 3.48 (d, 2H), 3.89 (d, 2H), 4.15 (m, 1H), 7.10 (t, 1H), 7.29-7.37 (m, 2H), 7.49 (d, 2H), 7.88 (dd, 1H), 8.57 (s, 1H)

LC/MS (ES+) m/z=422.15

Example 96

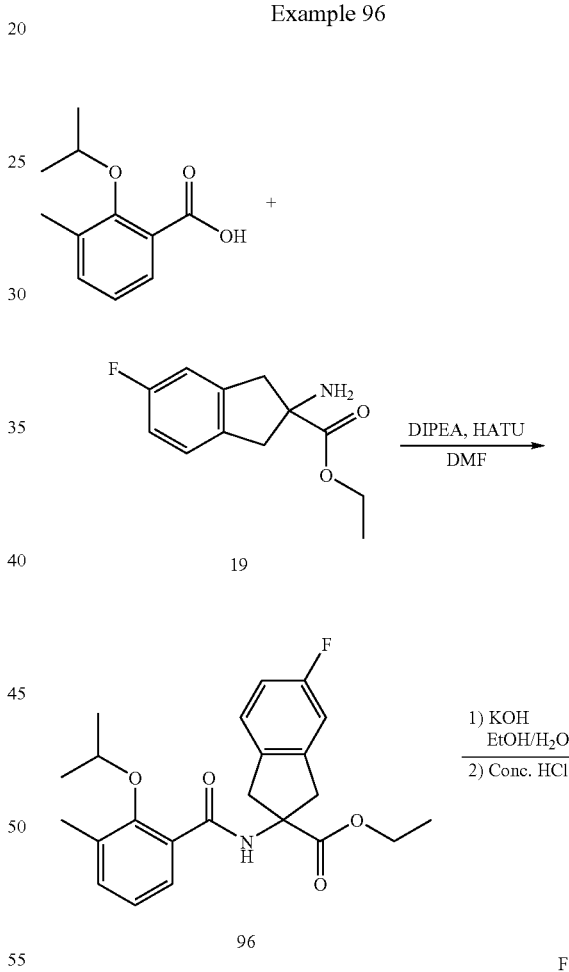

5-Fluoro-2-(2-isopropoxy-3-methyl-benzoylamino)-indan-2-carboxylic acid ethyl ester (96)

To a solution of 2-isopropoxy-3-methyl-benzoic acid (400 mg, 2.06 mmol), 2-amino-5-fluoro-indan-2-carboxylic acid ethyl ester (554 mg, 2.47 mmol), HATU 1.17 g, 3.09 mmol) in anhydrous DMF (10 mL) is added DIPEA (511 µL, 3.09 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 5%-50% EtOAc in heptane) to give a pure product (96) as white solid (709 mg, 86%).

$^1$H NMR (CDCl$_3$, 300 MHz): δ 1.07 (m, 6H), 1.24 (t, 3H), 2.26 (s, 3H), 3.32 (t, 2H), 3.72 (dd, 2H), 4.23 (m, 3H), 6.85-6.94 (m, 2H), 7.05-7.28 ((m, 3H), 7.85 (dd, 1H), 8.36 (s, 1H)
LC/MS (ES+) m/z=400.18

Example 97

5-Fluoro-2-(2-isopropoxy-3-methyl-benzoylamino)-indan-2-carboxylic acid (97)

The mixture of 5-fluoro-2-(2-isopropoxy-3-methyl-benzoylamino)-indan-2-carboxylic acid ethyl ester (96) (544 mg, 1.36 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more white precipitate formed. The precipitate is filtered to give a pure product (97) as white solid (460 mg, 91%).

$^1$H NMR (CDCl$_3$, 300 MHz): δ 1.02 (m, 6H), 2.26 (s, 3H), 3.38 (dd, 2H), 3.82 (dd, 2H), 4.16 (m, 1H), 6.87-6.95 (m, 2H), 7.07-7.31 ((m, 3H), 7.88 (dd, 1H), 8.56 (s, 1H)
LC/MS (ES+) m/z=372.16

Example 98

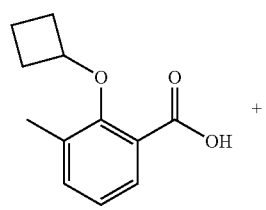

+

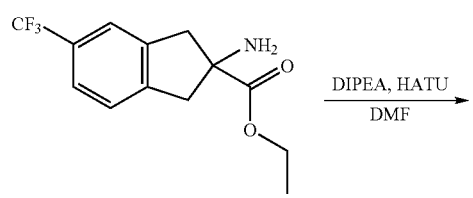

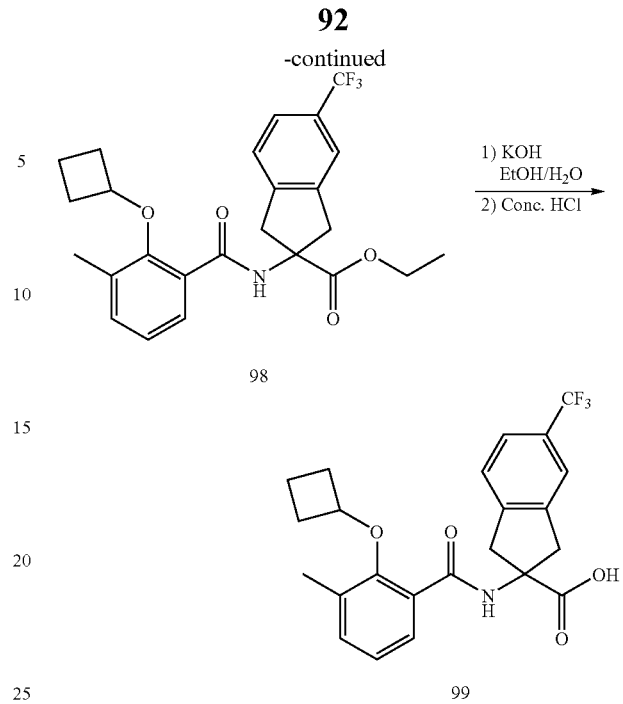

2-(2-Cyclobutoxy-3-methyl-benzoylamino)-5-trifluoro-indan-2-carboxylic acid ethyl ester (98)

To a solution of 2-cyclobutoxy-3-methyl-benzoic acid (400 mg, 1.94 mmol), 2-amino-5-trifluoro-indan-2-carboxylic acid ethyl ester (650 mg, 2.38 mmol), HATU (1.11 g, 2.91 mmol) in anhydrous DMF (15 mL) is added DIPEA (480 µL, 2.91 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 5%-60% EtOAc in heptane) to give a pure product (98) as white solid (800 mg, 89%).

$^1$H NMR (CDCl$_3$, 300 MHz): δ 1.25 (t, 3H), 1.26-1.38 (m, 1H), 1.45-1.55 (m, 1H), 1.89-2.17 (S, 3H), 2.27 (s, 3H), 3.44 (dd, 2H), 3.80 (dd, 2H), 4.22-4.35 (m, 3H), 7.08 (t, 1H), 7.27 (d, 1H), 7.34 (d, 1H), 7.47 (d, 2H), 7.85 (d, 1H), 8.41 (s, 1H)
LC/MS (ES+) m/z=462.18

Example 99

2-(2-Cyclobutoxy-3-methyl-benzoylamino)-5-trifluoro-indan-2-carboxylic acid (99)

The mixture of 2-(2-cyclobutoxy-3-methyl-benzoylamino)-5-trifluoro-indan-2-carboxylic acid ethyl ester (98) (648 mg, 1.4 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more precipitate formed. The precipitate is filtered to give a pure product (99) as a pale brown solid (595 mg, 98%).

$^1$H NMR (CDCl$_3$, 300 MHz): δ 1.21-1.32 (m, 1H), 1.41-1.51 (m, 1H), 1.85-2.08 (S, 3H), 2.25 (s, 3H), 3.48 (dd, 2H), 3.89 (dd, 2H), 4.26 (m, 1H), 7.09 (t, 1H), 7.26-7.36 (m, 2H), 7.49 (d, 2H), 7.87 (dd, 1H), 8.55 (s, 1H)

LC/MS (ES+) m/z=434.16

Example 100

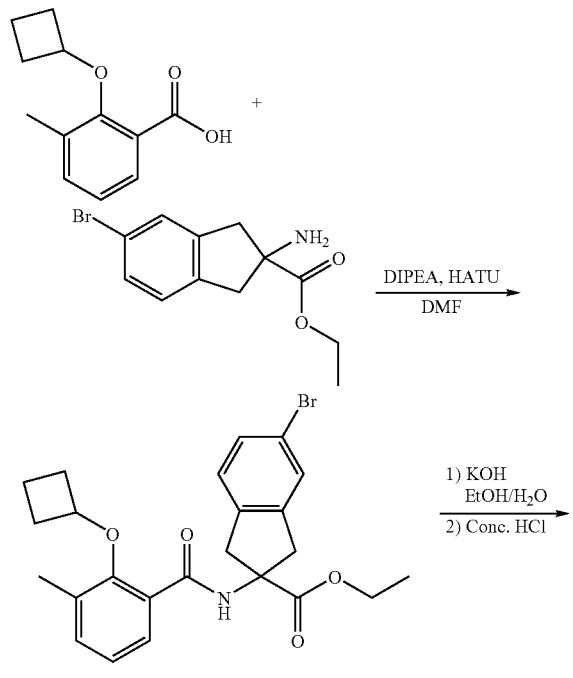

100

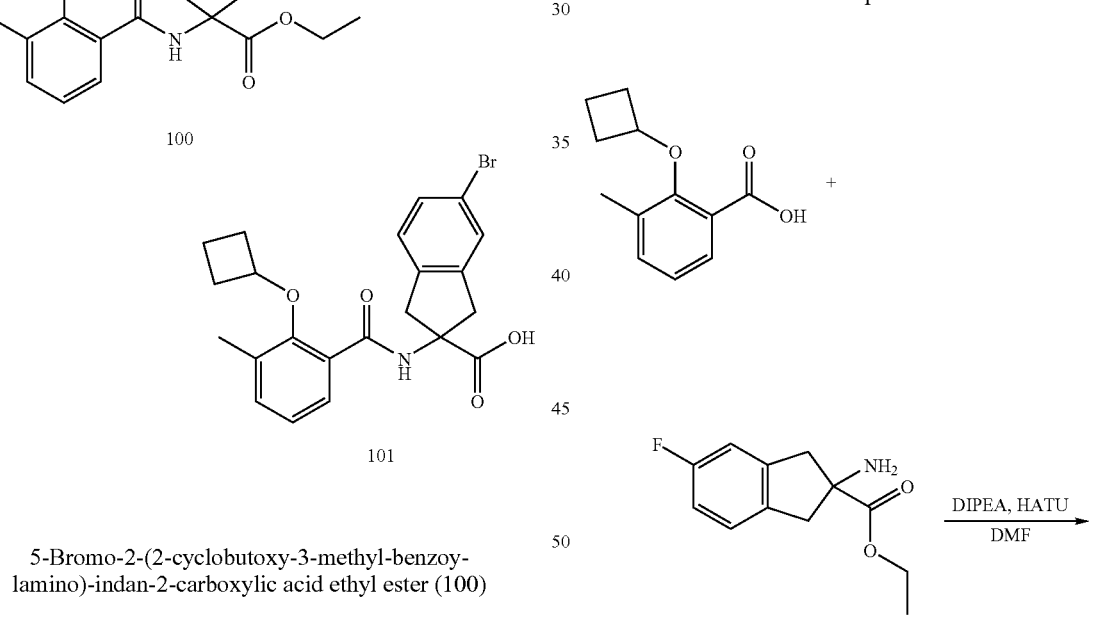

101

5-Bromo-2-(2-cyclobutoxy-3-methyl-benzoylamino)-indan-2-carboxylic acid ethyl ester (100)

To a solution of 2-cyclobutoxy-3-methyl-benzoic acid (250 mg, 1.21 mmol), 2-amino-5-bromo-indan-2-carboxylic acid ethyl ester (344 mg, 1.21 mmol), HATU (551 mg, 1.45 mmol) in anhydrous DMF (10 mL) is added DIPEA (240 μL, 1.45 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 5%-70% EtOAc in heptane) to give a pure product (100) as a colorless oil (520 mg, 91%).

$^1$H NMR (CDCl$_3$, 300 MHz): δ 1.22-1.40 (m, 4H), 1.48-1.63 (m, 1H), 1.90-2.12 (m, 4H), 2.27 (s, 3H), 3.44 (dd, 2H), 3.72 (dd, 2H), 4.21-4.35 (m, 3H), 7.05-7.12 (m, 2H), 7.26-7.27 (m, 3H), 7.85 (dd, 1H), 8.38 (s, 1H)

LC/MS (ES+) m/z=472.14, 474.13

Example 101

5-Bromo-2-(2-cyclobutoxy-3-methyl-benzoylamino)-indan-2-carboxylic acid (101)

The mixture 5-bromo-2-(2-cyclobutoxy-3-methyl-benzoylamino)-indan-2-carboxylic acid ethyl ester (100) (442 mg, 0.94 mmol) and KOH (700 mg, 12 mmol) is dissolved in EtOH (10 mL) and water (1 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more white precipitate formed. The precipitate is filtered to give a pure product (101) as white solid (390 mg, 93%).

$^1$H NMR (CDCl$_3$, 300 MHz): δ 1.29 (m, 1H), 1.49 (m, 1H), 1.83-2.00 (m, 4H), 2.22 (s, 3H), 3.31-3.61 (m, 4H), 4.33 (m, 1H), 7.04 (t, 1H), 7.21 (d, 1H), 7.28-7.37 (m, 3H), 7.46 (s, 1H), 8.67 (s, 1H), 12.65 (s, 1H)

LC/MS (ES+) m/z=444.07, 446.06

Example 102

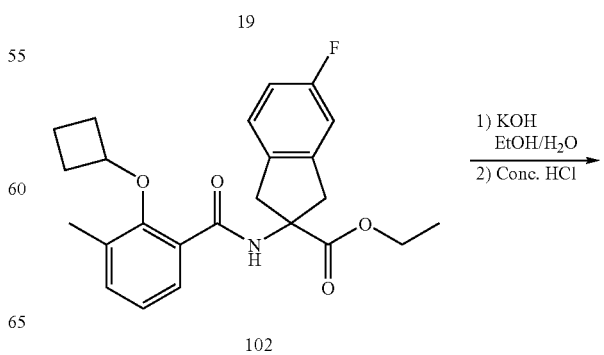

19

102

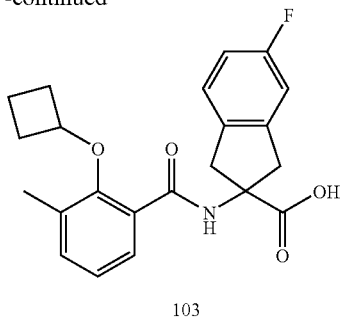

103

2-(2-Cyclobutoxy-3-methyl-benzoylamino)-5-fluoro-indan-2-carboxylic acid ethyl ester (102)

To a solution of 2-cyclobutoxy-3-methyl-benzoic acid (400 mg, 1.94 mmol), 2-amino-5-fluoro-indan-2-carboxylic acid ethyl ester (523 mg, 2.33 mmol), HATU (1.11 g, 2.91 mmol) in anhydrous DMF (18 mL) is added DIPEA (480 µL, 2.91 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous $Na_2SO_4$ and concentrated in vacuo. The residue is purified by flash column chromatography (115 g silica gel, gradient elution: 5%-40% EtOAc in heptane) to give a pure product (102) as white solid (681 mg, 85%).

$^1$H NMR (CDCl$_3$, 300 MHz): δ 1.21-1.36 (m, 4H), 1.50-1.56 (m, 1H), 1.96-2.09 (m, 4H), 2.27 (s, 3H), 3.44 (t, 2H), 3.73 (dd, 2H), 4.21-4.33 (m, 3H), 6.85-6.94 (m, 2H), 7.08 (t, 1H), 7.14-7.19 (m, 1H), 7.27 (d, 1H), 7.85 (dd, 1H), 8.37 (s, 1H)

LC/MS (ES+) m/z=412.19

Example 103

2-(2-Cyclobutoxy-3-methyl-benzoylamino)-5-fluoro-indan-2-carboxylic acid (103)

The mixture of 2-(2-cyclobutoxy-3-methyl-benzoylamino)-5-fluoro-indan-2-carboxylic acid ethyl ester (102) (510 mg, 1.24 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate formed. The precipitate is filtered to give a pure product (103) as white solid (469 mg, 99%).

$^1$H NMR (CDCl$_3$+drops of CD$_3$OD, 300 MHz): δ 1.21-1.36 (m, 1H), 1.50 (m, 1H), 1.92-2.14 (m, 4H), 2.26 (s, 3H), 3.38 (t, 2H), 3.73 (dd, 2H), 4.29 (m, 1H), 6.86-6.95 (m, 2H), 7.11 (t, 1H), 7.15-7.20 (m, 1H), 7.29 (d, 1H), 7.83 (dd, 1H), 8.51 (s, 1H)

LC/MS (ES+) m/z=384.15

Example 104

2-(2-Cyclobutoxy-3-methyl-benzoylamino)-5,6-difluoro-indan-2-carboxylic acid ethyl (104)

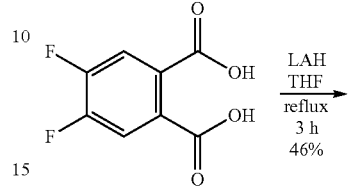

A2

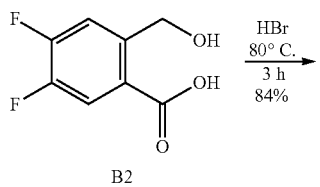

B2

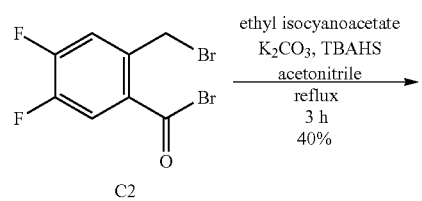

C2

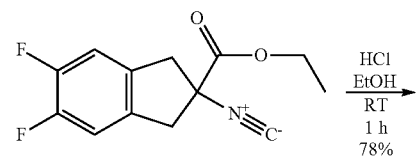

D2

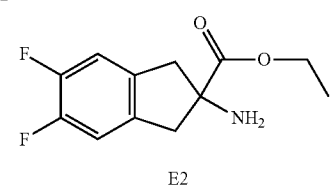

E2

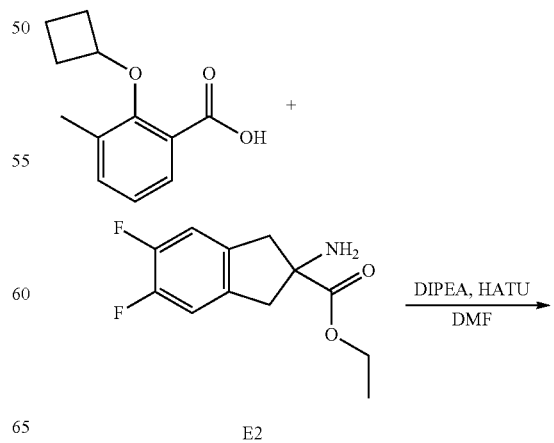

E2

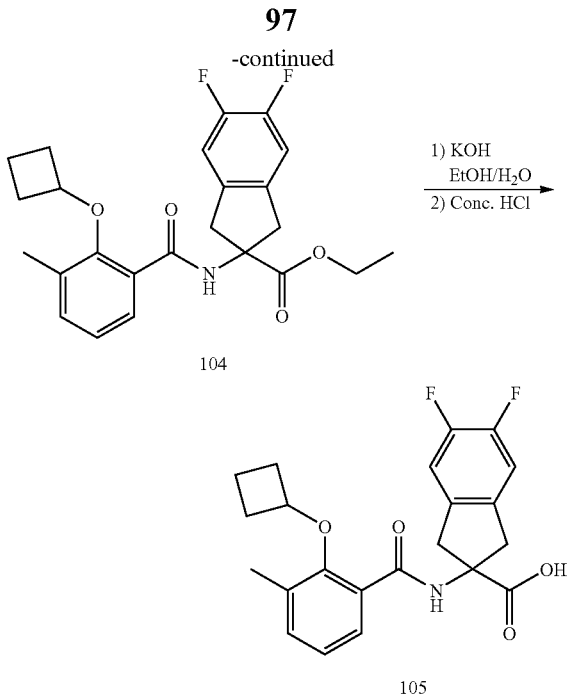

Preparation of B2

To a suspension of LAH (375 mg, 9.9 mmol) in THF (5 mL) is added a solution of 4,5-difluorophthalic acid A2 (1 g, 4.95 mmol) in THF (15 mL), dropwise at 0° C. The resulting mixture is refluxed for 3 hr following which it is cooled to 0° C. and quenched by slow addition of EtOAc. The reaction mass is filtered through a pad of celite and the filter bed is washed with methanol. The combined filtrate is concentrated to yield crude product that is purified over silica eluting with 5% MeOH in DCM to yield B2 (400 mg, 46%).

$^1$H-NMR (400 MHz, CDCl$_3$): 4.69 (s, 4H), 7.19 (t, J=9.2 and 2 Hz, 2H); FIA-MS: m/z 173 (M+H).

Preparation of C2

A stirred suspension of B2 (1 g, 5.74 mmol) in aq. HBr (47%, 10 mL) is stirred at 80° C. for 3 h. The progress of the reaction is monitored by tlc. After complete consumption of starting material, the reaction mixture is cooled to RT and extracted with DCM. The combined organics is washed with brine, dried and concentrated to give C2 (1.4 g, 84%). The dibromide is rather unstable and is immediately utilized for the next step.

$^1$H-NMR (400 MHz, CDCl$_3$): 4.59 (s, 4H), 7.19 (t, J=9 and 2 Hz, 2H); FIA-MS: m/z 201 (M+H).

Preparation of D2

A mixture of dibromide C2 (5.5 g, 18.33 mmol), ethylcyanoacetate (2.07 g, 18.33 mmol), K$_2$CO$_3$ (14 g, 106.3 mmol) and tetrabutylammonium hydrogensulfate (1.8 g, 5.33 mmol) in CH$_3$CN (150 mL) is refluxed for 3 h. The reaction mixture is cooled to RT, filtered and concentrated. The residue is dissolved in ether, washed with water, brine, dried, concentrated to get a sticky mass that is purified over silica eluting with 10% EtOAc in hexanes to yield D2 (1.8 g, 40%).

$^1$H-NMR (400 MHz, CDCl$_3$): 1.32 (t, J=7.2 and 3 Hz, 3H), 3.40 (d, J=16.3 Hz, 2H), 3.60 (d, J=16.3 Hz, 2H), 4.30 (q, J=7.2 and 2 Hz, 2H), 7.04 (t, J=8.6 and 2 Hz, 2H).

Preparation of E2

To a stirred solution of D2 (2 g, 7.96 mmol) in EtOH (50 mL) is added conc HCl (1 mL) and reaction mixture is stirred at RT for 1 h. The reaction mixture is concentrated, diluted with water and extracted with ether. The organic layer is discarded and the aqueous layer is brought to pH 9-10 by using aq. ammonia solution maintaining internal temperature below 10° C. The resulting solution is extracted with EtOAc (3×50 mL). The combined organics is washed with water, brine, dried, and concentrated to get a sticky mass that is purified over silica eluting with 10% EtOAc in hexanes to yield E2 (1.5 g, 78%) as off-white solid of mp 69-71° C.

$^1$H-NMR (400 MHz, CDCl$_3$): 1.26 (t, J=7.1 and 3 Hz, 3H), 2.80 (d, J=15.9 Hz, 2H), 4.22 (q, J=7.1 Hz, 2H), 6.99 (t, J=8.8 and 2 Hz, 2H). $^{13}$C-NMR (100 MHz, CDCl$_3$): 175.7, 150.7, 150.5, 148.2, 148.1, 136.3, 136.26, 136.22, 113.24, 113.17, 113.11, 113.05, 65.2, 61.2, 45.2, 13.8; FIA-MS: m/z 242 (M+H); HPLC purity: 94.28% (qualitative).

Preparation of 104

To a solution of 2-cyclobutoxy-3-methyl-benzoic acid (250 mg, 1.21 mmol), 2-amino-5,6-difluoro-indan-2-carboxylic acid ethyl ester E2 (292 mg, 1.21 mmol), HATU (551 mg, 1.45 mmol) in anhydrous DMF (10 mL) is added DIPEA (240 μL, 1.45 mmol). The resulting solution is stirred at RT overnight. After the removal of DMF in vacuo, the residue is dissolved in EtOAc (50 mL) and washed with water (1×10 mL) and brine (2×10 mL). The organic layer is dried over anhydrous Na$_2$SO$_4$ and concentrated in vacuo. The residue is purified by flash column chromatography (120 g silica gel, gradient elution: 10%-70% EtOAc in heptane) to give a pure product (104A) as white solid (420 mg, 81%).

$^1$H NMR (CDCl$_3$, 300 MHz): δ 1.25 (t, 3H), 1.30-1.41 (m, 1H), 1.52-1.62 (m, 1H), 1.96-2.16 (m, 4H), 2.28 (s, 3H), 3.34 (d, 2H), 3.70 (d, 2H), 4.21-4.39 (m, 3H), 6.99-7.11 (m, 3H), 7.28 (d, 1H), 7.85 (dd, 1H), 8.43 (s, 1H)

LC/MS (ES+) m/z=430.22

Example 105

2-(2-Cyclobutoxy-3-methyl-benzoylamino)-5,6-difluoro-indan-2-carboxylic acid (105)

The mixture 2-(2-cyclobutoxy-3-methyl-benzoylamino)-5,6-difluoro-indan-2-carboxylic acid ethyl ester (104) (367 mg, 0.85 mmol) and KOH (600 mg, 10.7 mmol) is dissolved in EtOH (10 mL) and water (1 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more white precipitate formed. After the filtration, the solid is purified by HPLC to give a pure product (105) as white solid (300 mg, 88%).

$^1$H NMR (DMSO-d6, 300 MHz): δ 1.28 (m, 1H), 1.48 (m, 1H), 1.85-2.00 (m, 4H), 2.21 (s, 3H), 3.34 (d, 2H), 3.51 (d, 2H), 4.33 (m, 1H), 7.02 (t, 1H), 7.28-7.34 (m, 4H), 8.69 (s, 1H)

LC/MS (ES+) m/z=430.22

Example 106

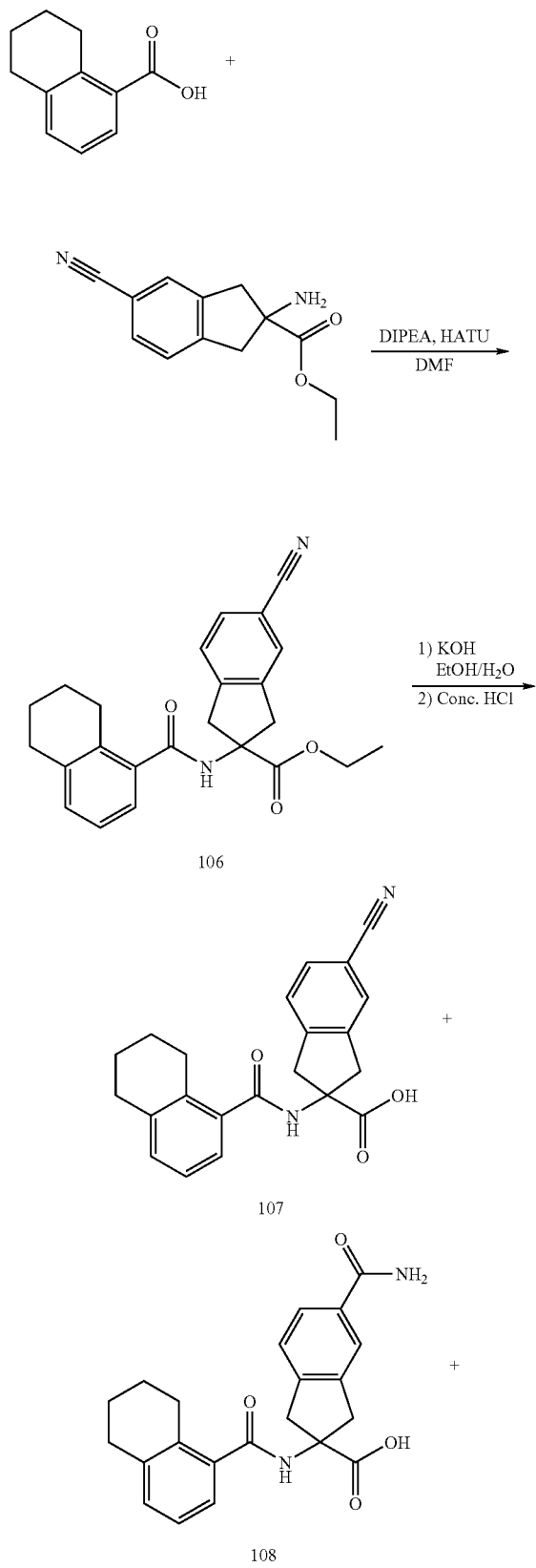

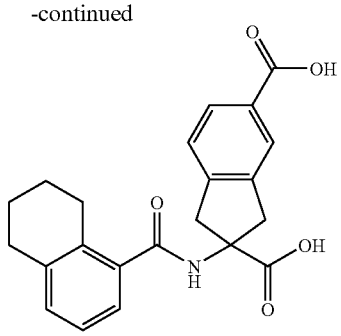

5-Cyano-2-[(5,6,7,8-tetrahydro-naphthalene-1-carbonyl)-amino]-indan-2-carboxylic acid ethyl ester (106)

To a solution of 5,6,7,8-tetrahydro-naphthalene-1-carboxylic acid (306 mg, 1.74 mmol), 2-amino-5-cyano-indan-2-carboxylic acid ethyl ester (601 mg, 2.61 mmol), HATU (992 mg, 2.61 mmol) in anhydrous DMF (15 mL) is added DIPEA (431 µL, 2.61 mmol). The resulting solution is stirred at RT overnight. After the removal of DMF in vacuo, the residue is dissolved in EtOAc (70 mL) and washed with water (1×10 mL) and brine (2×10 mL). The organic layer is dried over anhydrous $Na_2SO_4$ and concentrated in vacuo. The residue is purified by flash column chromatography (120 g silica gel, gradient elution: 5%-80% EtOAc in heptane) to give a pure product (106) as white solid (473 mg, 70%).

$^1$H NMR (CDCl$_3$, 300 MHz): δ 1.26 (t, 3H), 1.74 (m, 4H), 2.76 (br s, 2H), 2.82 (br s, 2H), 3.47 (dd, 2H), 3.72 (t, 2H), 4.25 (q, 2H), 6.47 (s, 1H), 7.03-7.12 (m, 3H), 7.31 (d, 1H), 7.49 (d, 2H)

LC/MS (ES+) m/z=389.18

Examples 107, 108, 109

5-Cyano-2-[(5,6,7,8-tetrahydro-naphthalene-1-carbonyl)-amino]-indan-2-carboxylic acid (107)

5-Carbamoyl-2-[(5,6,7,8-tetrahydro-naphthalene-1-carbonyl)-amino]-indan-2-carboxylic acid (108)

and 2-[(5,6,7,8-Tetrahydro-naphthalene-1-carbonyl)-amino]-indan-2,5-dicarboxylic acid (109)

The mixture of 5-cyano-2-[(5,6,7,8-tetrahydro-naphthalene-1-carbonyl)-amino]-indan-2-carboxylic acid ethyl ester (106) (320 mg, 0.82 mmol) and KOH (1 g, 18 mmol) is dissolved in EtOH (8 mL) and water (1 mL) under a water bath. The water bath is removed when KOH is completely dissolved. The resulting reaction solution is heated up to 50° C. and stirred at this temperature overnight. After concentration in vacuo, the residue is dissolved in water (30 mL) and acidified with conc. HCl until pH~2. After filtration, the solid is purified by HPLC to give 3 pure products: (107) as white solid (44 mg, 15%), (108) as white solid (154 mg, 50%) and (109) as white solid (28 mg, 9%).

(107): $^1$H NMR (CD$_3$OD, 300 MHz): δ 1.75 (m, 4H), 2.77 (br s, 4H), 3.49 (dd, 2H), 3.75 (t, 2H), 7.04-7.12 (m, 3H), 7.41 (d, 1H), 7.54-7.59 (m, 2H), 8.87 (s, ⅓H)

LC/MS (ES+) m/z=361.15

(108): ¹H NMR (CD₃OD, 300 MHz): δ 1.74 (m, 4H), 2.76 (m, 4H), 3.44 (d, 2H), 3.73 (dd, 2H), 7.04-7.11 (m, 3H), 7.32 (d, 1H), 7.72 (d, 2H), 8.87 (s, ½H)

LC/MS (ES+) m/z=379.17

(109): ¹H NMR (CD₃OD, 300 MHz): δ 1.74 (m, 4H), 2.77 (m, 4H), 3.45 (dd, 2H), 3.74 (t, 2H), 7.04-7.09 (m, 3H), 7.33 (d, 1H), 7.88 (d, 2H), 8.88 (s, ½H)

LC/MS (ES+) m/z=380.16

Example 110

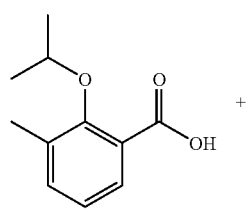

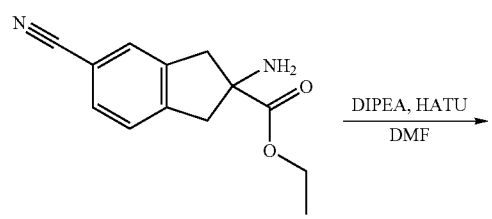

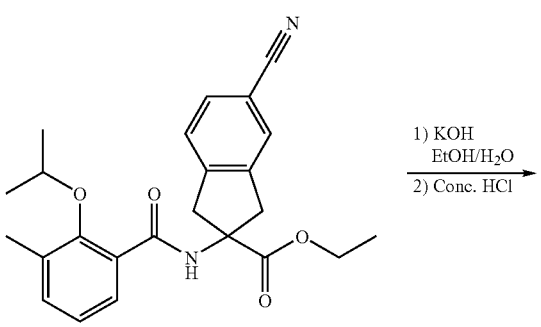

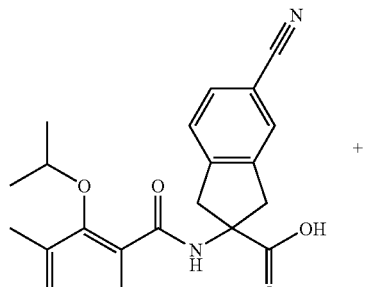

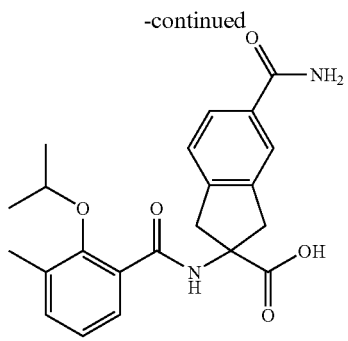

112

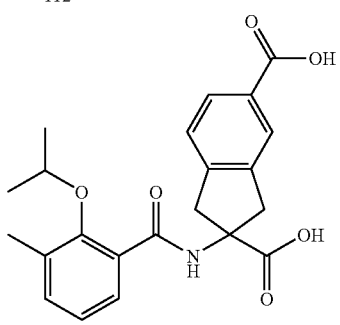

113

5-Cyano-2-(2-isopropoxy-3-methyl-benzoylamino)-indan-2-carboxylic acid ethyl ester (110)

To a solution of 2-isopropoxy-3-methyl-benzoic acid (377 mg, 1.94 mmol), 2-amino-5-cyano-indan-2-carboxylic acid ethyl ester (670 mg, 2.91 mmol), HATU (1.11 g, 2.91 mmol) in anhydrous DMF (15 mL) is added DIPEA (480 µL, 2.91 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous Na₂SO₄ and concentrated in vacuo. The residue is purified by flash column chromatography (120 g silica gel, gradient elution: 5%-70% EtOAc in heptane) to give a pure product (110) as a white semisolid (680 mg, 86%).

¹H NMR (CDCl₃, 300 MHz): δ 1.12 (m, 6H), 1.23 (t, 3H), 2.27 (s, 3H), 3.47 (dd, 2H), 3.77 (t, 2H), 4.21-4.26 (m, 3H), 7.08 (t, 1H), 7.28-7.35 (m, 2H), 7.51 (d, 2H), 7.84 (d, 1H), 8.47 (s, 1H)

LC/MS (ES+) m/z=407.19

Example 111, 112, 113

5-Cyano-2-(2-isopropoxy-3-methyl-benzoylamino)-indan-2-carboxylic acid (111)

5-Carbamoyl-2-(2-isopropoxy-3-methyl-benzoylamino)-indan-2-carboxylic acid (112)

2-(2-Isopropoxy-3-methyl-benzoylamino)-indan-2,5-dicarboxylic acid (113)

The mixture of 5-cyano-2-(2-isopropoxy-3-methyl-benzoylamino)-indan-2-carboxylic acid ethyl ester (110) (527 mg, 1.3 mmol) and KOH (1.3 g, 23 mmol) is dissolved in EtOH (8 mL) and water (1 mL) under a water bath. The water bath is removed when KOH is completely dissolved. The resulting reaction solution is heated up to 50° C. and stirred at this temperature overnight. After concentration in vacuo, the residue is dissolved in water (30 mL) and acidified with conc. HCl until pH~2. After filtration, the solid is purified by HPLC to give 3 pure products: (111) as white solid (37 mg, 8%), (112) as white solid (295 mg, 57%) and (113) as white solid (62 mg, 12%).

(111): $^1$H NMR (CDCl$_3$, 300 MHz): δ 1.06 (m, 6H), 2.27 (s, 3H), 3.49 (dd, 2H), 3.90 (dd, 2H), 4.19 (m, 1H), 7.11 (t, 1H), 7.34 (t, 2H), 7.53 (d, 2H), 7.88 (dd, 1H), 8.65 (s, 1H)

LC/MS (ES+) m/z=379.16

(112): $^1$H NMR (CDCl$_3$+drops of D30D, 300 MHz): δ 1.08 (dd, 6H), 2.26 (s, 3H), 3.43 (dd, 2H), 3.80 (dd, 2H), 4.20 (m, 1H), 7.08 (t, 1H), 7.28-7.32 (m, 2H), 7.67-7.77 (m, 2H), 7.79 (dd, 1H), 8.58 (s, ¼H)

LC/MS (ES+) m/z=397.18

(113): $^1$H NMR (CDCl$_3$+drops of CD$_3$OD, 300 MHz): δ 1.04 (m, 6H), 2.26 (s, 3H), 3.45 (dd, 2H), 3.81 (t, 2H), 4.18 (m, 1H), 7.08 (t, 1H), 7.27-7.32 (m, 2H), 7.80 (d, 1H), 7.92 (dd, 2H), 8.53 (s, 1H)

LC/MS (ES+) m/z=398.16

Example 114

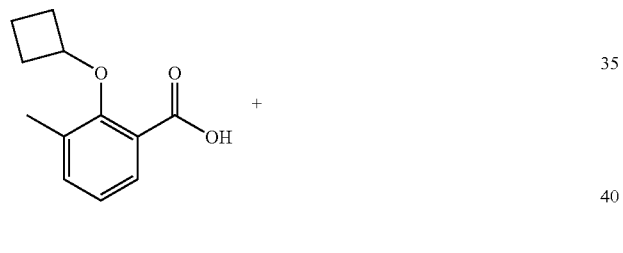

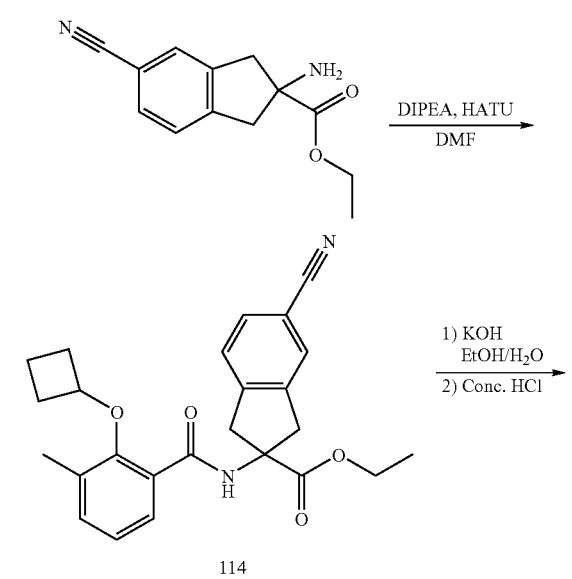

114

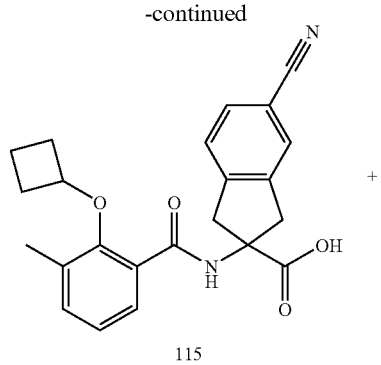

115

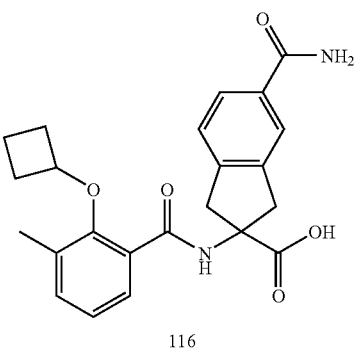

116

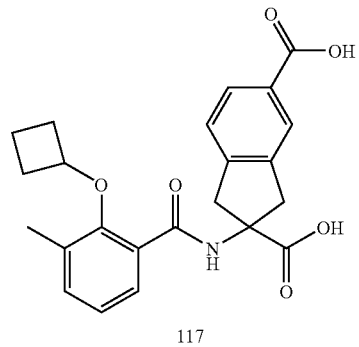

117

5-Cyano-2-(2-cyclobutoxy-3-methyl-benzoylamino)-indan-2-carboxylic acid ethyl ester (114)

To a solution of 2-cyclobutoxy-3-methyl-benzoic acid (400 mg, 1.94 mmol), 2-amino-5-cyano-indan-2-carboxylic acid ethyl ester (670 mg, 2.91 mmol), HATU (1.11 g, 2.91 mmol) in anhydrous DMF (15 mL) is added DIPEA (480 μL, 2.91 mmol). The resulting solution is stirred at RT overnight. After the removal of DMF in vacuo, the residue is dissolved in EtOAc (100 mL) and washed with water (1×10 mL) and brine (2×10 mL). The organic layer is dried over anhydrous Na$_2$SO$_4$ and concentrated in vacuo. The residue is purified by flash column chromatography (120 g silica gel, gradient elution: 5%-60% EtOAc in heptane) to give a pure product (114) as a white semisolid (682 mg, 84%).

$^1$H NMR (CDCl$_3$, 300 MHz): δ 1.27 (t, 3H), 1.30-1.43 (m, 1H), 1.51-1.65 (m, 1H), 1.98-2.12 (m, 4H), 2.28 (s, 3H), 3.47 (dd, 2H), 3.78 (t, 2H), 4.22-4.33 (m, 3H), 7.08 (t, 1H), 7.27-7.35 (m, 2H), 7.51 (d, 2H), 7.85 (d, 1H), 8.47 (s, 1H)

LC/MS (ES+) m/z=419.19

Examples 115, 116, 117

5-Cyano-2-(2-cyclobutoxy-3-methyl-benzoylamino)-indan-2-carboxylic acid (115)

5-Carbamoyl-2-(2-cyclobutoxy-3-methyl-benzoylamino)-indan-2-carboxylic acid (116)

2-(2-Cyclobutoxy-3-methyl-benzoylamino)-indan-2,5-dicarboxylic acid (117)

The mixture of 5-cyano-2-(2-cyclobutoxy-3-methyl-benzoylamino)-indan-2-carboxylic acid ethyl ester (114) (530 mg, 1.3 mmol) and KOH (1.3 g, 23 mmol) is dissolved in EtOH (8 mL) and water (1 mL) under a water bath. The water bath is removed when KOH is completely dissolved. The resulting reaction solution is heated up to 50° C. and stirred at this temperature overnight. After concentration in vacuo, the residue is dissolved in water (30 mL) and acidified with conc. HCl until pH~2. After filtration, the obtained solid is purified by HPLC to give three pure products: (115) as white solid (167 mg, 33%), (116) as white solid (239 mg, 45%) and (117) as white solid (21 mg, 4%).

(115): $^1$H NMR (CDCl$_3$, 300 MHz): δ 1.24-1.39 (m, 1H), 1.46-1.56 (m, 1H), 1.89-2.13 (m, 4H), 2.10 (s, 3H), 3.47 (dd, 2H), 3.89 (dd, 2H), 4.29 (m, 1H), 7.09 (t, 1H), 7.26-7.36 (m, 2H), 7.52 (d, 2H), 7.85 (d, 2H), 8.60 (s, 1H)

LC/MS (ES+) m/z=391.13

(116): $^1$H NMR (CDCl$_3$+drops of CD$_3$OD, 300 MHz): δ 1.22-1.38 (m, 1H), 1.46-1.56 (m, 1H), 1.92-2.09 (m, 4H), 2.26 (s, 3H), 3.47 (dd, 2H), 3.82 (dd, 2H), 4.30 (m, 1H), 7.08 (t, 1H), 7.27-7.32 (m, 2H), 7.66-7.72 (m, 2H), 7.81 (d, 1H), 8.57 (s, 1H)

LC/MS (ES+) m/z=409.14

(117): $^1$H NMR (CDCl$_3$+drops of CD$_3$OD, 300 MHz): δ 1.22-1.35 (m, 1H), 1.42-1.52 (m, 1H), 1.87-2.06 (m, 4H), 2.26 (s, 3H), 3.47 (dd, 2H), 3.83 (dd, 2H), 4.28 (m, 1H), 7.08 (t, 1H), 7.27-7.33 (m, 2H), 7.82 (d, 1H), 7.93 (d, 2H), 8.53 (s, 1H)

LC/MS (ES+) m/z=410.17

Example 118

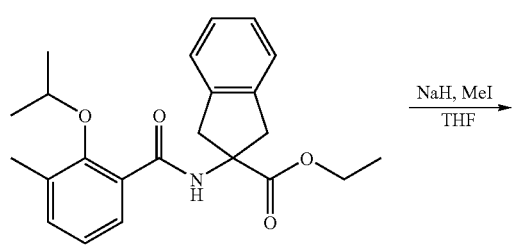

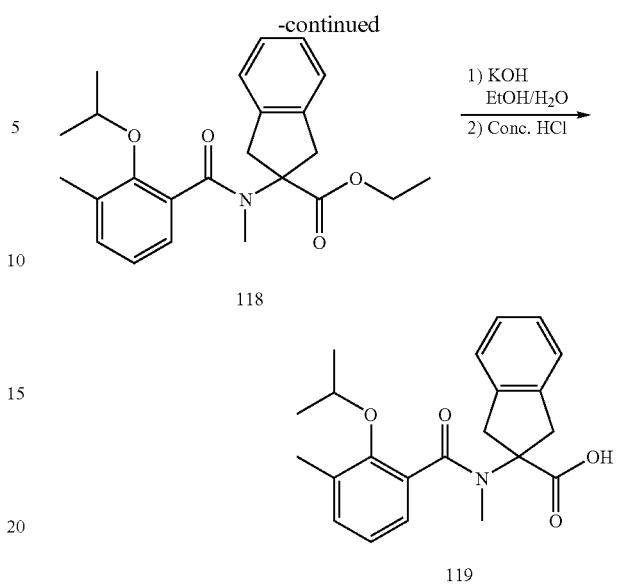

2-[(2-Isopropoxy-3-methyl-benzoyl)-methyl-amino]-indan-2-carboxylic acid ethyl ester (118)

To a solution of NaH (sodium hydride, 60% dispersion, 86.0 mg, 2.15 mmol)) in anhydrous THF (20 mL) is added dropwise the solution of 2-(2-isopropoxy-3-methyl-benzoylamino)-indan-2-carboxylic acid ethyl ester (6) (410 mg, 1.07 mmol) in THF (5 mL) at 0° C. After stirring for 20 min, methyl iodide (452 μL, 7.26 mmol) is added dropwise and the resulting suspension is warmed up to RT and continued stirring overnight. After being quenched by saturated aqueous solution of ammonium chloride (5 mL), the reaction mixture is diluted in EtOAc (50 mL). The organic layer is separated, washed with water (1×5 mL) and brine (2×5 mL), dried over anhydrous Na$_2$SO$_4$ and concentrated in in vacuo. The residue is purified by flash column chromatography (115 g silica gel, gradient elution: 0%-30% EtOAc in heptane) to give the pure product (118) as a colorless oil (240 mg, 57%).

$^1$H NMR (CDCl$_3$, 300 MHz): δ 1.18 (br d, 6H), 1.28 (t, 3H), 2.24 (s, 3H), 2.85 (s, 3H), 3.44 (d, 2H), 3.62 (br d, 1H), 4.02 (br d, 1H), 4.18-4.36 (m, 3H), 7.00 (t, 1H), 7.09 (d, 1H), 7.18-7.20 (m, 5H)

LC/MS (ES+) m/z=396.21

Example 119

2-[(2-Isopropoxy-3-methyl-benzoyl)-methyl-amino]-indan-2-carboxylic acid (119)

The mixture of 2-[(2-isopropoxy-3-methyl-benzoyl)-methyl-amino]-indan-2-carboxylic acid ethyl ester (118') (200 mg, 0.51 mmol) and KOH (600 mg, 10.7 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate formed. The precipitate is filtered to give a pure product (119) as a pale orange solid (170 mg, 91%).

$^1$H NMR (CDCl$_3$, 300 MHz): δ 1.15 (br d, 6H), 2.24 (s, 3H), 2.86 (s, 3H), 3.46 (d, 2H), 3.74 (br d, 1H), 4.02 (br d, 1H), 4.26 (m, 1H), 6.99 (t, 1H), 7.15-7.26 (m, 6H), 8.79 (br s, 1H)

LC/MS (ES+) m/z=368.20

Example 120

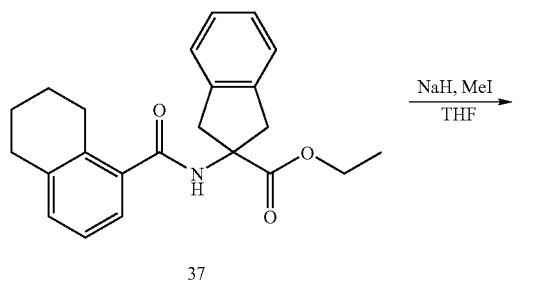

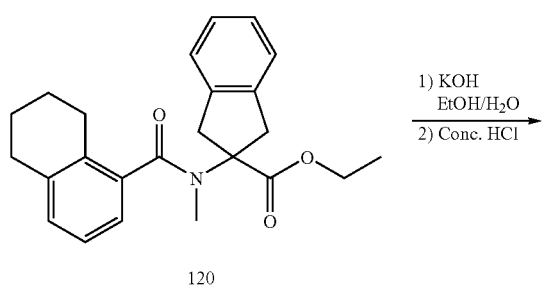

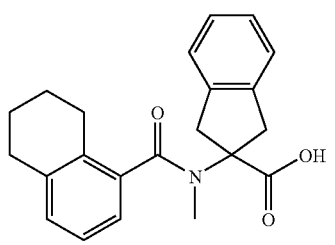

2-[Methyl-(5,6,7,8-tetrahydro-naphthalene-1-carbonyl)-amino]-indan-2-carboxylic acid ethyl ester (120)

To a solution of NaH (sodium hydride, 60% dispersion, 124 mg, 3.08 mmol) in anhydrous THF (20 mL) is added dropwise the solution of 2-[(5,6,7,8-tetrahydro-naphthalene-1-carbonyl)-amino]-indan-2-carboxylic acid ethyl ester (37) (280 mg, 0.77 mmol) in THF (5 mL) at 0° C. After stirring for 20 min, methyl iodide (377 µL, 6.05 mmol) is added dropwise and the resulting suspension is warmed up to RT and continued stirring overnight. After being quenched by saturated ammonium chloride aqueous solution (5 mL), the reaction mixture is diluted in EtOAc (50 mL). The organic layer is separated, washed with water (1×5 mL) and brine (2×5 mL), dried over anhydrous Na$_2$SO$_4$ and concentrated in in vacuo. The residue is purified by flash column chromatography (115 g silica gel, gradient elution: 0%-30% EtOAc in heptane) to give a pure product (120) as a colorless semisolid (250 mg, 86%).

$^1$H NMR (CDCl$_3$, 300 MHz): δ 1.29 (t, 3H), 1.76 (br s, 4H), 2.47 (br s, 1H), 2.76 (br s, 2H), 2.82 (s, 3H), 2.82 (br s, 1H), 3.45 (d, 2H), 3.83 (d, 2H), 4.24 (m, 2H), 6.92 (d, 1H), 7.05-7.08 (m, 2H), 7.17-7.23 (m, 4H)

LC/MS (ES+) m/z=378.22

Example 121

2-[Methyl-(5,6,7,8-tetrahydro-naphthalene-1-carbonyl)-amino]-indan-2-carboxylic acid (121)

The mixture of 2-[methyl-(5,6,7,8-tetrahydro-naphthalene-1-carbonyl)-amino]-indan-2-carboxylic acid ethyl ester (120) (226 mg, 0.60 mmol) and KOH (600 mg, 10.7 mmol) is dissolved in EtOH (5 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH~3. The precipitate is filtered to give a pure product (121) as a pale orange solid (150 mg, 72%).

$^1$H NMR (CDCl$_3$, 300 MHz): δ 1.74 (br s, 4H), 2.45 (br s, 1H), 2.76-2.84 (m, 3H), 2.85 (s, 3H), 3.48 (d, 2H), 3.90 (d, 2H), 4.24 (m, 2H), 6.96-7.26 (m, 7H)

LC/MS (ES+) m/z=350.16

Example 122

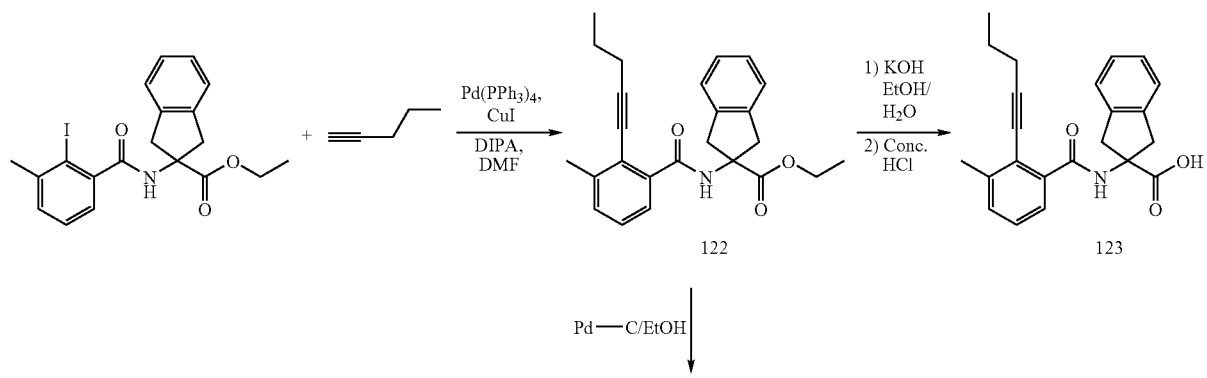

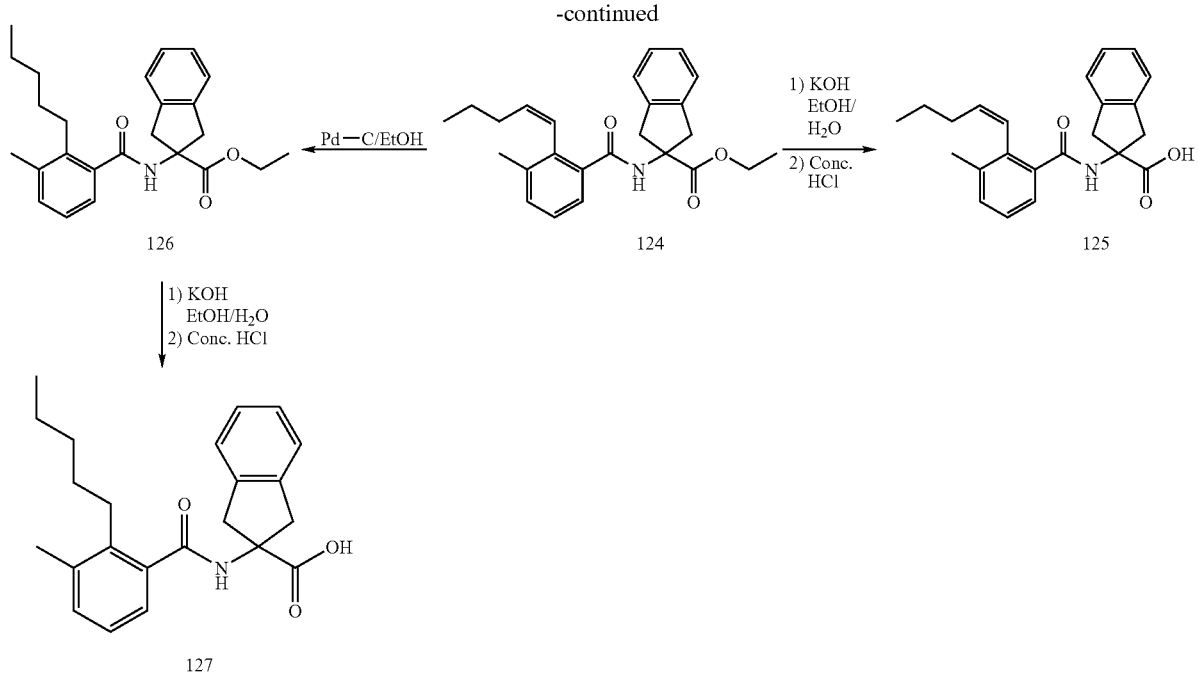

2-(3-Methyl-2-pent-1-ynyl-benzoylamino)-indan-2-carboxylic acid ethyl ester (122)

To a solution of 2-(2-iodo-3-methyl-benzoylamino)-indan-2-carboxylic acid ethyl ester (693 mg, 1.54 mmol) in anhydrous DMF (5 mL) and DIPA (diisopropylamine, 10 mL) is added Pd(PPh$_3$)$_4$ (89 mg, 7.7% mmol), CuI (29 mg, 0.154 mmol) and pent-1-yne (1.5 mL, 15.4 mmol). The resulting solution is covered in argon and run in a microwave reaction: 110° C., 35 minutes. After the removal of DMF and DIPA in vacuo, the residue is dissolved in EtOAc (100 mL) and washed with water (1×10 mL) and brine (2×10 mL). The organic layer is dried over anhydrous Na$_2$SO$_4$ and concentrated in vacuo. The residue is purified by flash column chromatography (120 g silica gel, gradient elution: 0%-40% EtOAc in heptane) to give a pure product (122) as a pale yellow solid (144 mg, 24%).

$^1$H NMR (CDCl$_3$, 300 MHz): δ 0.99 (t, 3H), 1.25 (t, 3H), 1.51 (m, 2H), 2.14 (t, 1H), 2.39 (s, 3H), 3.35 (d, 2H), 3.77 (d, 2H), 4.25 (q, 2H), 7.17-7.30 (m, 6H), 7.84 (d, 1H), 8.21 (s, 1H)

LC/MS (ES+) m/z=390.18

Example 123

2-(3-Methyl-2-pent-1-ynyl-benzoylamino)-indan-2-carboxylic acid (123)

The mixture of 2-(3-methyl-2-pent-1-ynyl-benzoylamino)-indan-2-carboxylic acid ethyl ester (122) (180 mg, 0.46 mmol) and KOH (1 g, 18 mmol) is dissolved in EtOH (8 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH~4. After filtration, the solid is purified by HPLC to give a pure product (123) as white solid (114 mg, 69%).

$^1$H NMR (CDCl$_3$+drops of CD$_3$OD, 300 MHz): δ 0.99 (t, 3H), 1.53 (m, 2H), 2.14 (t, 1H), 2.40 (s, 3H), 3.39 (d, 2H), 3.82 (d, 2H), 7.18-7.32 (m, 6H), 7.83 (d, 1H), 8.39 (s, 1H)

LC/MS (ES+) m/z=362.17

Example 124

2-[3-Methyl-2-((Z)-pent-1-enyl)-benzoylamino]-indan-2-carboxylic acid ethyl ester (124)

To a solution of 2-(3-methyl-2-pent-1-ynyl-benzoylamino)-indan-2-carboxylic acid ethyl ester (122) (300 mg, 0.77 mmol) in absolute EtOH (18 mL) is added the catalyst, Pd—C (50% wetted powder, 10% Pd, 30 mg, 1.4% mmol) under argon. The resulting reaction mixture is moved to the Paar apparatus to run hydrogenation: 50 psi, room temperature, overnight. The catalyst is removed by the filtration through a pre-column (10 g silica gel) and washed by EtOH. The combined EtOH solution is concentrated in vacuo. The residue is purified by HPLC to give a pure product as white solid (168 mg, 56%).

$^1$H NMR (CDCl$_3$, 300 MHz): δ 0.72 (t, 3H), 1.13-1.30 (m, 5H), 1.64 (m, 2H), 2.16 (s, 3H), 3.29 (d, 2H), 3.69 (d, 2H), 4.25 (q, 2H), 5.56 (dt, 1H), 6.29 (d, 1H), 6.78 (s, 1H), 7.17-7.26 (m, 6H), 7.57 (d, 1H)

LC/MS (ES+) m/z=392.12

Example 125

2-[3-Methyl-2-((Z)-pent-1-enyl)-benzoylamino]-indan-2-carboxylic acid (125)

The mixture of 2-[3-methyl-2-((Z)-pent-1-enyl)-benzoylamino]-indan-2-carboxylic acid ethyl ester (124) (69 mg, 0.18 mmol) and KOH (500 mg, 8.9 mmol) is dissolved in EtOH (8 mL) and water (0.5 mL) under a water bath. The water bath is removed when KOH is completely dissolved and the resulting reaction solution is stirred at RT for 5 h.

After concentration in vacuo, the residue is dissolved in water (20 mL) and acidified with conc. HCl until pH~4. The precipitate is filtered to give a pure product (125) as white solid (42 mg, 64%).

$^1$H NMR (CDCl$_3$+drops of CD$_3$OD, 300 MHz): δ 0.73 (t, 3H), 1.11-1.25 (m, 2H), 1.62 (q, 2H), 2.16 (s, 3H), 3.33 (d, 2H), 3.72 (d, 2H), 5.54 (dt, 1H), 6.25 (d, 1H), 7.01 (s, 1H), 7.18-7.28 (m, 6H), 7.57 (d, 1H)

LC/MS (ES+) m/z=364.18

Example 126

2-(3-Methyl-2-pentyl-benzoylamino)-indan-2-carboxylic acid ethyl ester (126)

To a solution of 2-[3-methyl-2-((Z)-pent-1)-enyl-benzoylamino]-indan-2-carboxylic acid ethyl ester (124) (92 mg, 0.23 mmol) in absolute EtOH (10 mL) is added the catalyst, Pd—C (50% wetted powder, 10% Pd, 30 mg, 1.4% mmol) under argon. The resulting reaction mixture is moved to the Paar apparatus to run hydrogenation: 50 psi, room temperature, overnight. The catalyst is removed by the filtration through a pre-column (10 g silica gel) and washed by EtOH. The combined EtOH solution is concentrated in vacuo. The residue is purified by HPLC to give a pure product (126) as white solid (80 mg, 89%).

$^1$H NMR (CDCl$_3$, 300 MHz): δ 0.88 (t, 3H), 1.26-1.33 (m, 7H), 1.42-1.47 (m, 2H), 2.29 (s, 3H), 2.64-2.69 (m, 2H), 3.34 (d, 2H), 3.74 (d, 2H), 4.28 (q, 2H), 6.18 (s, 1H), 7.02-7.26 (m, 7H)

LC/MS (ES+) m/z=394.23

Example 127

2-(3-Methyl-2-pentyl-benzoylamino)-indan-2-carboxylic acid (127)

The mixture of 2-(3-methyl-2-pentyl-benzoylamino)-indan-2-carboxylic acid ethyl ester (126) (68 mg, 0.17 mmol) and KOH (500 mg, 8.9 mmol) is dissolved in EtOH (8 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more white precipitate came out of the water. The precipitate is filtered to give a pure product (127) as a pale brown solid (63 mg, 100%).

$^1$H NMR (CDCl$_3$, 300 MHz): δ 0.88 (t, 3H), 1.26-1.30 (m, 4H), 1.41-1.43 (m, 2H), 2.30 (s, 3H), 2.62-2.67 (m, 2H), 3.40 (d, 2H), 3.83 (d, 2H), 6.22 (s, 1H), 7.01-7.07 (m, 2H), 7.17-7.26 (m, 5H)

LC/MS (ES+) m/z=366.20

Example 128

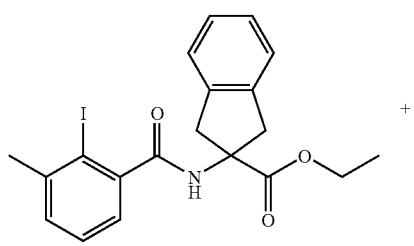

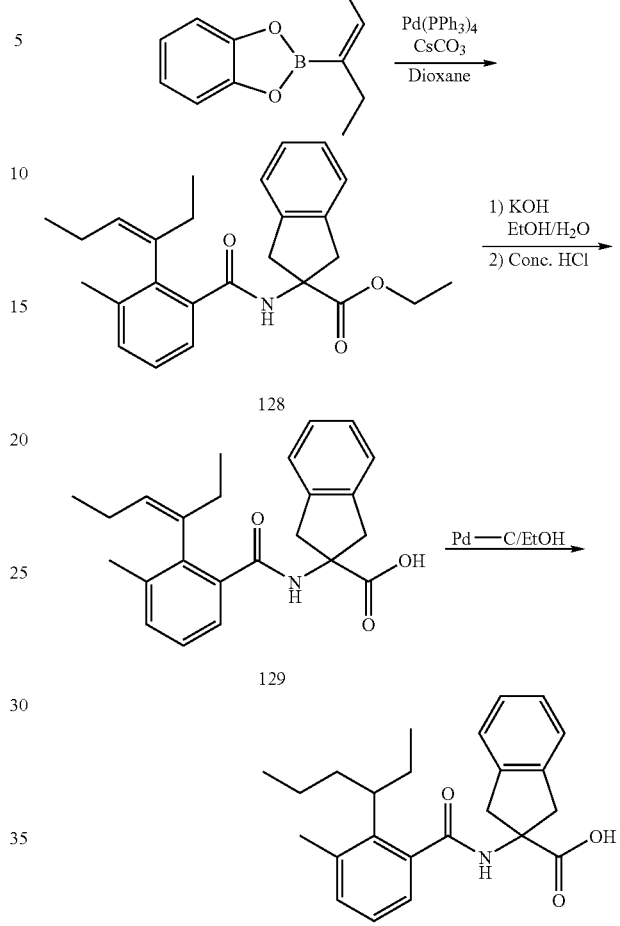

2-[2-(-1-Ethyl-but-1-enyl)-3-methyl-benzoylamino]-indan-2-carboxylic acid ethyl ester (128)

To a solution of 2-(2-iodo-3-methyl-benzoylamino)-indan-2-carboxylic acid ethyl ester (400 mg, 0.89 mmol) and 2-(1-Ethyl-but-1-enyl)-benzo[1,3,2]dioxaborole (709 μL, 3.56 mmol) in dioxane (15 mL) is added Pd(PPh$_3$)$_4$ (103 mg, 8.9% mmol) and 2M aqueous solution of CsCO$_3$ (1.34 mL, 2.67 mmol). The resulting reaction mixture is covered with argon and run in a microwave reaction: 110° C., 2 h. After concentration in vacuo, the residue is purified by flash column chromatography (120 g silica gel, gradient elution: 5%-50% EtOAc in heptane) to give a pure product (128) as a brown semi-solid (530 mg, 73%).

$^1$H NMR (CDCl$_3$, 300 MHz): δ 0.71 (t, 3H), 0.99 (t, 3H), 1.27 (t, 3H), 1.75-2.05 (m, 3H), 2.11-2.25 (m, 1H), 2.21 (s, 3H), 3.11 (d, 1H), 3.33 (d, 1H), 3.37 (dd, 2H), 4.25 (q, 2H), 5.54 (t, 1H), 7.16-7.27 (m, 6H), 7.66 (d, 1H)

LC/MS (ES+) m/z=406.25

Example 129

2-[2-(-1-Ethyl-but-1-enyl)-3-methyl-benzoylamino]-indan-2-carboxylic acid (129)

The mixture of 2-[2-(-1-ethyl-but-1-enyl)-3-methyl-benzoylamino]-indan-2-carboxylic acid ethyl ester (128) (503 mg, 1.24 mmol) and KOH (1 g, 17.9 mmol) is dissolved in EtOH (10 mL) and water (1 mL) under a water bath. The water bath is removed when KOH is completely dissolved and the resulting reaction solution is stirred at RT for 8 h. After concentration in vacuo, the residue is dissolved in water (40 mL) and acidified with conc. HCl until pH~3. The precipitate is filtered to give a pure product (129) as a brown solid (452 mg, 97%).

$^1$H NMR (CDCl$_3$+drops of CD$_3$OD, 300 MHz): δ 0.68 (t, 3H), 0.99 (t, 3H), 1.83 (m, 2H), 1.95-2.18 (m, 2H), 2.20 (s, 3H), 3.11 (d, 1H), 3.39 (d, 1H), 3.72 (dd, 2H), 5.54 (t, 1H), 7.16-7.35 (m, 6H), 7.63 (d, 1H)

LC/MS (ES+) m/z=378.21

Example 130

2-[2-(1-Ethyl-butyl)-3-methyl-benzoylamino]-indan-2-carboxylic acid (130)

To a solution of 2-[2-(-1-ethyl-but-1-enyl)-3-methyl-benzoylamino]-indan-2-carboxylic acid ethyl ester (129) (270 mg, 0.72 mmol) in absolute EtOH (15 mL) is added the catalyst, Pd—C (50% wetted powder, 10% Pd, 46 mg, 2.2% mmol) under argon. The resulting reaction mixture is moved to the Paar apparatus to run hydrogenation: 50 psi, 70° C., overnight. The catalyst is removed by the filtration through a pre-column (10 g silica gel) and washed by EtOH. The combined EtOH solution is concentrated in vacuo. The residue is purified by HPLC to give a pure product (130) as white solid (75 mg, 28%).

$^1$H NMR (CDCl$_3$, 300 MHz): δ 0.66-0.75 (m, 6H), 0.83-1.26 (m, 2H), 1.56-1.69 (m, 4H), 2.34 (s, 3H), 2.87 (m, 1H), 3.34-3.43 (m, 2H), 3.72 (d, 2H), 6.15 (s, 1H), 7.00-7.25 (m, 7H), 8.83 (br s, 1H)

LC/MS (ES+) m/z=380.22

Example 131

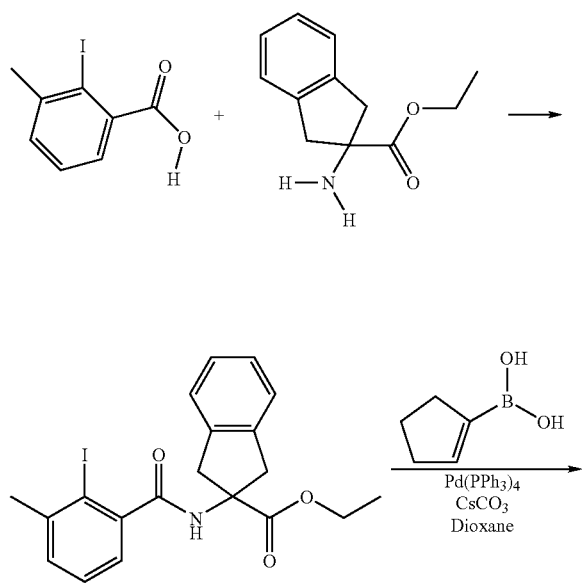

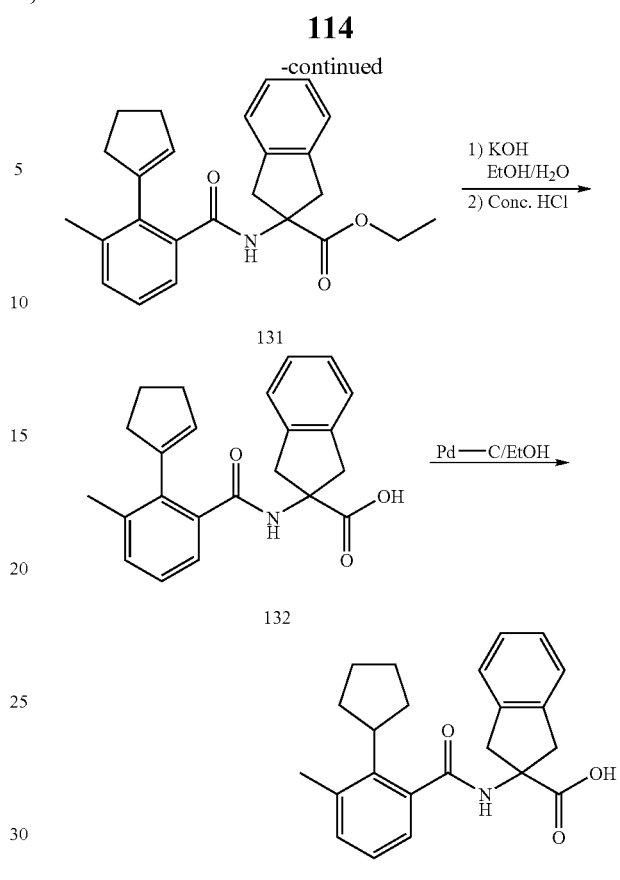

2-(2-Iodo-3-methyl-benzoylamino)-indan-2-carboxylic Acid Ethyl Ester

A 100 mL round bottom flask is charged with 2-Iodo-3-methylbenzoic Acid (1.92 g, 7.3 μmol) and dry DCM (25 mL). A stirring bar is added and stirring initiated. After 5 min, HTBU (2.37 g, 7.3 μmol) is added. After 5 min, the 2-amino-indane-2-carboxylic Acid Ethyl Ester (1.50 g, 7.31 mmoles) is added followed by DIPEA (3.2 mL, 18.37 mmol). The reaction is allowed to stir for 118 hours. Analysis by tlc of the reaction mixture (silica, 15% iPrOH/Dischloromethane) indicates complete consumption of the starting amine. The contents of the reaction flask are transferred to a separatory funnel and diluted with EtOAc (70 mL). This is washed with dilute aqueous HCl (3%, 2×30 mL), saturated aqueous NaHCO$_3$ (2×30 mL) and brine (30 mL), dried over MgSO4, filtered and evaporated in vacuo to provide 2.04 g of white solid. This material is dissolved in DCM (15 mL). This material is purified utilizing an ISCO Companion with a 40 g cartridge of silica. The gradient is 10% EtOAC in heptanes over 4 column volumes followed by a linear gradient to 50% EtOAc over 10 column volumes. 27 mL fractions of UV active elutant were collected. Fractions 10 through 15 are combined and evaporated in vacuo to constant weight to give 2-(2-iodo-3-methyl-benzoylamino)-indan-2-carboxylic acid ethyl ester 1.04 g of white solid.

2-(2-Cyclopent-1-enyl-3-methyl-benzoylamino)-indan-2-carboxylic acid ethyl ester (131)

To a solution of 2-(2-iodo-3-methyl-benzoylamino)-indan-2-carboxylic acid ethyl ester (800 mg, 1.78 mmol) and cyclopenten-1-ylboronic acid (796 mg, 7.11 mmol) in dioxane (20 mL) is added Pd(PPh$_3$)$_4$ (412 mg, 0.36 mmol) and 2M aqueous solution of CsCO$_3$ (5.34 mL, 10.7 mmol). The resulting reaction mixture is covered with argon and run in a microwave reaction: 110° C., 2.7 h. After concentration in vacuo, the residue is purified by flash column chromatography (120 g silica gel, gradient elution: 5-40% EtOAc in heptane) to give a pure product (131) as a brown solid (589 mg, 85%).

$^1$H NMR (CDCl$_3$, 300 MHz): δ 1.27 (t, 3H), 1.72 (m, 2H), 2.19 (s, 3H), 2.33-2.43 (m, 4H), 3.23 (d, 2H), 3.70 (dd, 2H), 4.25 (q, 2H), 5.57 (m, 1H), 6.99 (s, 1H), 7.16-7.26 (m, 6H), 7.58 (d, 1H)

LC/MS (ES+) m/z=390.22

Example 132

2-(2-Cyclopent-1-enyl-3-methyl-benzoylamino)-indan-2-carboxylic acid (132)

The mixture of 2-(2-cyclopent-1-enyl-3-methyl-benzoylamino)-indan-2-carboxylic acid ethyl ester (131) (560 mg, 1.43 mmol) and KOH (1 g, 17.9 mmol) is dissolved in EtOH (8 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until pH~3. The precipitate is filtered to give a pure product (132) as a pale yellow solid (518 mg, 100%).

$^1$H NMR (CDCl$_3$+drops of CD$_3$OD, 300 MHz): δ 1.73 (m, 2H), 2.19 (s, 3H), 2.36-2.39 (m, 4H), 3.27 (d, 2H), 3.73 (dd, 2H), 5.57 (m, 1H), 7.16-7.29 (m, 6H), 7.53 (d, 1H)

LC/MS (ES+) m/z=362.17

Example 133

2-(2-Cyclopentyl-3-methyl-benzoylamino)-indan-2-carboxylic acid (133)

To a solution of 2-(2-cyclopent-1-enyl-3-methyl-benzoylamino)-indan-2-carboxylic acid (132) (365 mg, 1.01 mmol) in absolute EtOH (15 mL) is added the catalyst, Pd—C (50% wetted powder, 10% Pd, 192 mg, 9% mmol) under argon. The resulting reaction mixture is moved to the Paar apparatus to run hydrogenation: 50 psi, 50° C., overnight. The catalyst is removed by the filtration through a pre-column (10 g silica gel) and washed by EtOH. The combined EtOH solution is concentrated in vacuo. The residue is purified by HPLC to give a pure product (133) as white solid (184 mg, 50%).

$^1$H NMR (CDCl$_3$, 300 MHz): δ 1.55-1.77 (m, 8H), 2.33 (s, 3H), 3.22 (m, 1H), 3.27 (d, 2H), 3.77 (dd, 2H), 6.22 (m, 1H), 7.101-7.26 (m, 7H)

LC/MS (ES+) m/z=364.22

Example 134

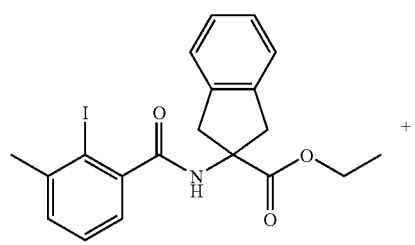

2-[3-Methyl-2-(2-methyl-propenyl)-benzoylamino]-indan-2-carboxylic acid ethyl ester (134)

To a solution of 2-(2-iodo-3-methyl-benzoylamino)-indan-2-carboxylic acid ethyl ester (400 mg, 0.89 mmol) and 2,2-dimethyethylenelboronic acid (133 mg, 1.34 mmol) in dioxane (15 mL) is added PdCl$_2$(dppf) ([1,1'-bis(diphenylphosphine)ferrocene]-dichloropalladium(II), 73 mg, 8.9% mmol) and 2M aqueous solution of CsCO$_3$ (1.34 mL, 2.67 mmol). The resulting reaction mixture is covered with argon and run in a microwave reaction: 110° C., 2 h. After concentration in vacuo, the residue is purified by flash column chromatography (120 g silica gel, gradient elution: 5-50% EtOAc in heptane) to give a pure product (134) as a pale yellow solid (523 mg, 78%).

$^1$H NMR (CDCl$_3$, 300 MHz): δ 1.27 (t, 3H), 1.30 (s, 3H), 1.65 (s, 3H), 2.14 (s, 3H), 3.24 (br d, 2H), 3.70 (br d, 2H), 4.25 (q, 2H), 6.10 (s, 1H), 7.02 (s, 1H), 7.17-7.26 (m, 6H), 7.69 (d, 1H)

LC/MS (ES+) m/z=378.22

Example 135

2-[3-Methyl-2-(2-methyl-propenyl)-benzoylamino]-indan-2-carboxylic acid (135)

The mixture 2-[3-methyl-2-(2-methyl-propenyl)-benzoylamino]-indan-2-carboxylic acid ethyl ester (134) (283 mg,

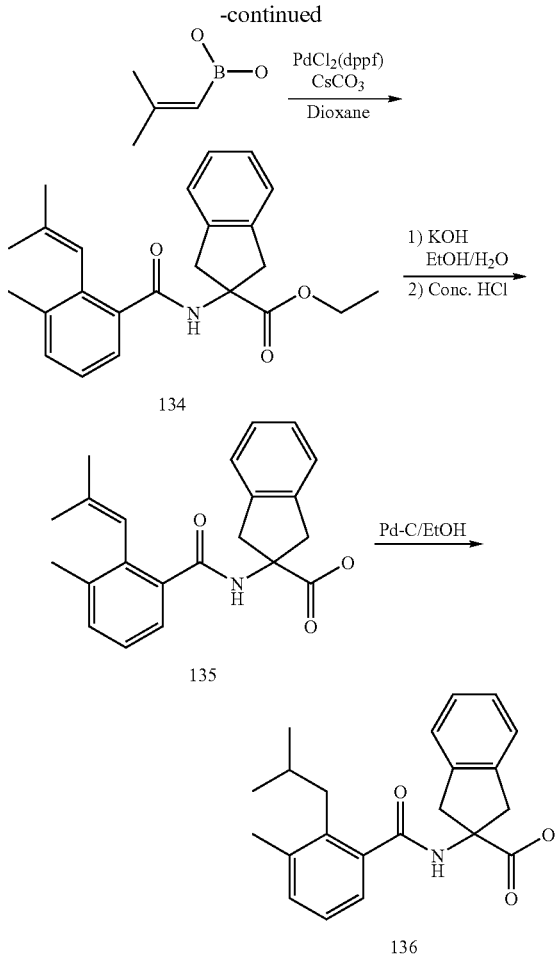

0.75 mmol) and KOH (600 mg, 10.7 mmol) is dissolved in EtOH (8 mL) and water (1 mL) under a water bath. The water bath is removed when KOH is completely dissolved and the resulting reaction solution is stirred at RT for 3 h. After concentration in vacuo, the residue is dissolved in water (20 mL) and acidified with conc. HCl until no more white precipitate formed. The precipitate is filtered to give a pure product (135) as white solid (250 mg, 95%).

$^1$H NMR (CDCl$_3$+drops of CD$_3$OD, 300 MHz): δ 1.28 (t, 3H), 1.68 (s, 3H), 2.14 (s, 3H), 3.28 (d, 2H), 3.74 (d, 2H), 6.09 (s, 1H), 7.17-7.29 (m, 6H), 7.66 (d, 1H)

LC/MS (ES+) m/z=350.19

Example 136

2-(2-Isobutyl-3-methyl-benzoylamino)-indan-2-carboxylic acid (136)

To a solution of 2-[3-methyl-2-(2-methyl-propenyl)-benzoylamino]-indan-2-carboxylic acid (135) (120 mg, 0.34 mmol) in acetic acid (15 mL) is added the catalyst, Pd—C (5 wt. % Pd, 72 mg, 3.4% mmol) under argon. The resulting reaction mixture is moved to the Paar apparatus to run hydrogenation: 50 psi, 95° C., overnight. The catalyst is removed by filtration through a pre-column (10 g silica gel) and washed by EtOH. The combined organic solution is concentrated in vacuo. The residue is purified by HPLC to give a pure product (136) as white solid (65 mg, 54%).

$^1$H NMR (CDCl$_3$+drops of CD$_3$OD, 300 MHz): δ 0.80 (d, 6H), 1.75-1.78 (m, 1H), 2.30 (s, 3H), 2.68 (d, 2H), 3.38 (d, 2H), 3.76 (d, 2H), 6.53 (s, 1H), 7.03-7.25 (m, 7H)

LC/MS (ES+) m/z=352.15

Example 137

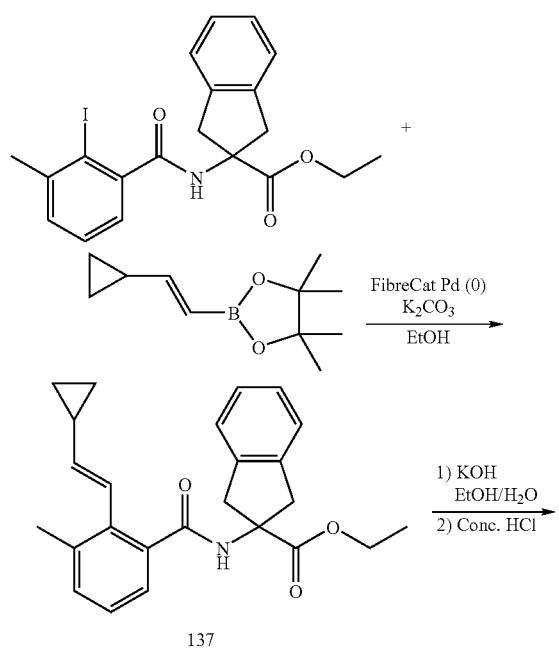

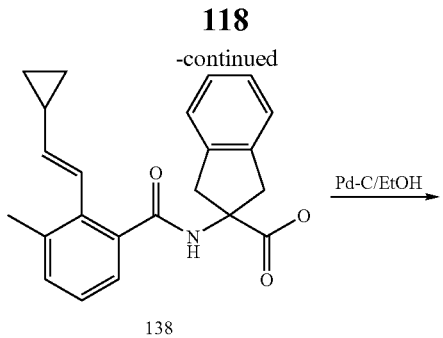

138

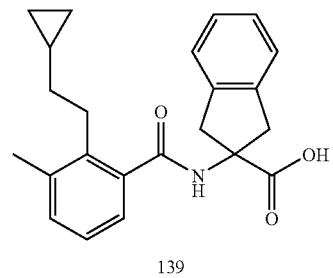

139

2-[2-(-2-Cyclopropyl-vinyl)-3-methyl-benzoylamino]-indan-2-carboxylic acid ethyl ester (137)

To a solution of 2-(2-iodo-3-methyl-benzoylamino)-indan-2-carboxylic acid ethyl ester (600 mg, 1.34 mmol) and 2-(2-cyclopropyl-vinyl)-4,4,5,5-tetramethyl-[1,3,2]dioxaborolane (1.11 mL, 5.36 mmol) in EtOH (10 mL) and dioxane (10 mL) is added palladium anchored homogeneous catalyst, FibreCatPd(0), (4.84% Pd, 285 mg, 0.13 mmol) and 2M aqueous solution of K$_2$SO$_4$ (2.68 mL, 5.36 mmol). The resulting reaction mixture is covered with argon and run in a microwave reaction: 110° C., 8 h. After concentration in vacuo, the residue is purified by HPLC to give a pure product (137) as white solid (250 mg, 49%).

$^1$H NMR (CDCl$_3$, 300 MHz): δ 0.47-0.50 (m, 2H), 0.76-0.82 (m, 2H), 1.29 (t, 3H), 1.45 (m, 1H), 2.27 (s, 3H), 3.32 (d, 2H), 3.72 (d, 2H), 4.27 (q, 2H), 5.30 (dd, 1H), 6.45 (dd, 1H), 6.52 (s, 1H), 7.09-7.23 (m, 6H), 7.39 (d, 1H)

LC/MS (ES+) m/z=390.20

Example 138

2-[2-(-2-Cyclopropyl-vinyl)-3-methyl-benzoylamino]-indan-2-carboxylic acid (138)

The mixture 2-[2-(-2-cyclopropyl-vinyl)-3-methyl-benzoylamino]-indan-2-carboxylic acid ethyl ester (137) (220 mg, 0.56 mmol) and KOH (600 mg, 10.7 mmol) is dissolved in EtOH (8 mL) and water (0.5 mL) under a water bath. The water bath is removed when KOH is completely dissolved and the resulting reaction solution is stirred at RT for 8 h.

After concentration in vacuo, the residue is dissolved in water (20 mL) and acidified with conc. HCl until no more precipitate came out of the water. The precipitate is filtered to give a pure product (138) as white solid (209 mg, 100%).

$^1$H NMR (CDCl$_3$, 300 MHz): δ 0.47-0.50 (m, 2H), 0.78-0.84 (m, 2H), 1.43 (m, 1H), 2.26 (s, 3H), 3.38 (d, 2H), 3.83 (d, 2H), 5.24 (dd, 1H), 6.34 (d, 1H), 6.68 (s, 1H), 7.11-7.26 (m, 6H), 7.41 (d, 1H)

LC/MS (ES+) m/z=362.17

Example 139

2-[2-(2-Cyclopropyl-ethyl)-3-methyl-benzoylamino]-indan-2-carboxylic acid (139)

To a solution of 2-[2-((E)-2-cyclopropyl-vinyl)-3-methyl-benzoylamino]-indan-2-carboxylic acid (138) (120 mg, 0.33 mmol) in absolute EtOH (10 mL) is added the catalyst, Pd—C (5 wt. % Pd, 28 mg, 1.3% mmol) under argon. The resulting reaction mixture is moved to the Paar apparatus to run hydrogenation: 50 psi, room temperature, overnight. The catalyst is removed by the filtration through a pre-column (10 g silica gel) and washed by EtOH. The combined solution is concentrated in vacuo. The residue is purified by HPLC to give a pure product (139) as white solid (30 mg, 25%).

$^1$H NMR (CDCl$_3$, 300 MHz): δ 0.00 (m, 2H), 0.35-0.41 (m, 2H), 0.66 (m, 1H), 1.32-1.39 (m, 2H), 2.30 (s, 3H), 2.76-2.82 (m, 2H), 3.40 (d, 2H), 3.82 (d, 2H), 6.23 (s, 1H), 7.03-7.04 (m, 2H), 7.16-7.26 (m, 4H)

LC/MS (ES+) m/z=364.13

Example 140

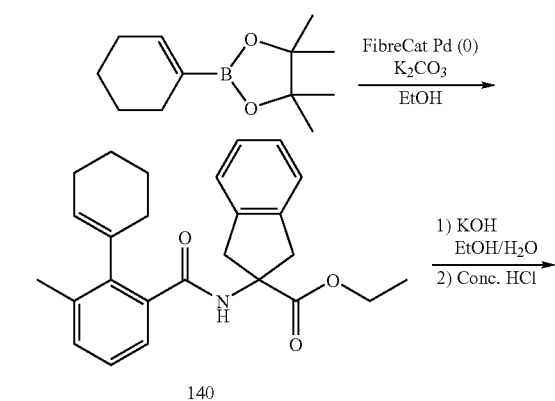

2-(2-Cyclohex-1-enyl-3-methyl-benzoylamino)-indan-2-carboxylic acid ethyl ester (140)

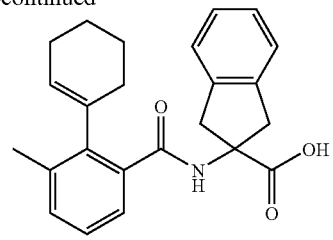

To a solution of 2-(2-iodo-3-methyl-benzoylamino)-indan-2-carboxylic acid ethyl ester (491 mg, 1.09 mmol) and 2-cyclohex-1-enyl-4,4,5,5-tetramethyl-[1,3,2]dioxaborolane (937 μL, 4.36 mmol) in EtOH (10 mL) and dioxane (10 mL) is added palladium anchored homogeneous catalyst, FibreCatPd(0) (4.84% Pd, 240 mg, 0.11 mmol) and 2M aqueous solution of K$_2$SO$_4$ (2.18 mL, 4.36 mmol). The resulting reaction mixture is covered with argon and run in a microwave reaction: 110° C., 8 h. After concentration in vacuo, the residue is purified by HPLC to give a pure product (140) as white solid (95 mg, 22%).

$^1$H NMR (CDCl$_3$, 300 MHz): δ 1.26 (t, 3H), 1.55 (br t, 4H), 2.01-2.34 (m, 4H), 2.21 (s, 3H), 3.27 (br t, 2H), 3.74 (br d, 2H), 4.22-4.27 (m, 2H), 5.56 (s, 1H), 7.16-7.29 (m, 7H), 7.63 (d, 1H)

LC/MS (ES+) m/z=404.22

Example 141

2-(2-Cyclohex-1-enyl-3-methyl-benzoylamino)-indan-2-carboxylic acid (141)

The mixture 2-(2-cyclohex-1-enyl-3-methyl-benzoylamino)-indan-2-carboxylic acid ethyl ester (141) (80 mg, 0.20 mmol) and KOH (300 mg, 5.36 mmol) is dissolved in EtOH (8 mL) and water (0.5 mL) under a water bath. The water bath is removed when KOH is completely dissolved and the resulting reaction solution is stirred at RT for 3 h. After concentration in vacuo, the residue is dissolved in water (20 mL) and acidified with conc. HCl until no more white precipitate came out of the water. The precipitate is filtered to give a pure product (141) as white solid (71 mg, 95%).

$^1$H NMR (CDCl$_3$, 300 MHz): δ 1.41-1.56 (m, 4H), 2.03-2.24 (m, 4H), 2.21 (s, 3H), 3.32 (m, 2H), 3.83 (d, 2H), 5.56 (s, 1H), 7.16-7.34 (m, 6H), 7.61 (d, 1H)

LC/MS (ES+) m/z=376.22

Example 142

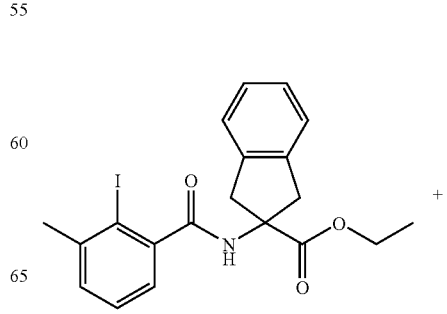

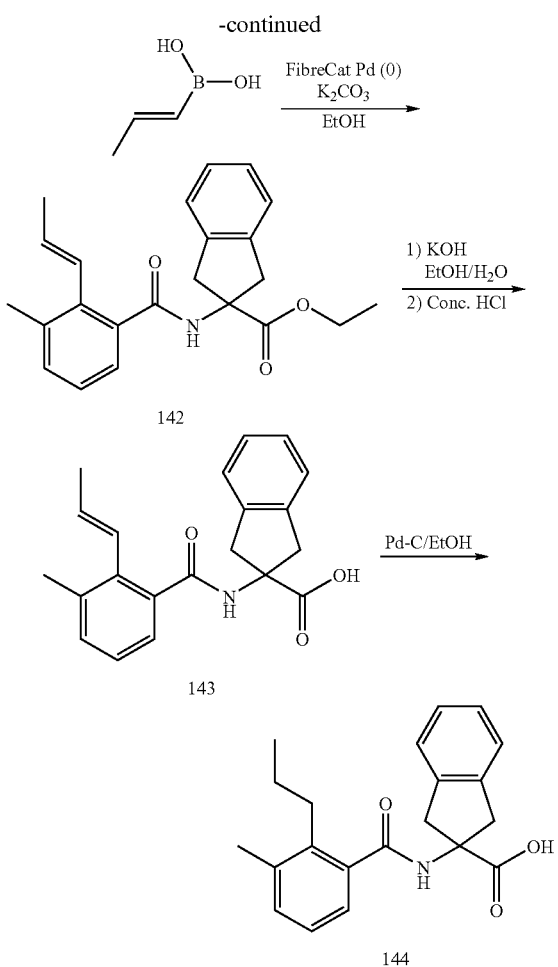

142

143

144

2-[3-Methyl-2-(1-propenyl)-benzoylamino]-indan-2-carboxylic acid ethyl ester (142)

To a solution of 2-(2-iodo-3-methyl-benzoylamino)-indan-2-carboxylic acid ethyl ester (600 mg, 1.34 mmol) and trans-1-propen-1-ylboronic acid (460 mg, 5.36 mmol) in EtOH (10 mL) and dioxane (10 mL) is added palladium anchored homogeneous catalyst, FibreCatPd(0), (4.84% Pd, 285 mg, 0.13 mmol) and 2M aqueous solution of $K_2SO_4$ (2.68 mL, 5.36 mmol). The resulting reaction mixture is covered with argon and run in a microwave reaction: 110° C., 8 h. After concentration in vacuo, the residue is purified by HPLC and gave the pure product (142) as white solid (300 mg, 63%).

$^1$H NMR (CDCl$_3$, 300 MHz): δ 1.29 (t, 3H), 1.74 (dd, 3H), 2.25 (s, 3H), 3.28 (d, 2H), 3.71 (d, 2H), 4.27 (q, 2H), 5.75 (dq, 1H), 6.37 (d, 1H), 7.10-7.26 (m, 6H), 7.36 (d, 1H)

LC/MS (ES+) m/z=364.18

Example 143

2-[3-Methyl-2-(1-propenyl)-benzoylamino]-indan-2-carboxylic acid (143)

The mixture 2-[3-methyl-2-(1-propenyl)-benzoylamino]-indan-2-carboxylic acid ethyl ester (142) (340 mg, 0.94 mmol) and KOH (700 mg, 12.5 mmol) is dissolved in EtOH (8 mL) and water (0.5 mL) under a water bath. The water bath is removed when KOH is completely dissolved and the resulting reaction solution is stirred at RT for 8 h. After concentration in vacuo, the residue is dissolved in water (30 mL) and acidified with conc. HCl until no more precipitate came out of the water. The precipitate is filtered to give a pure product (143) as white solid (315 mg, 100%).

$^1$H NMR (CDCl$_3$+drops of CD$_3$OD, 300 MHz): δ 1.75 (dd, 3H), 2.25 (s, 3H), 3.32 (d, 2H), 3.73 (d, 2H), 5.75 (dq, 1H), 6.36 (dd, 1H), 6.76 (s, 1H), 7.10-7.24 (m, 6H), 7.31 (d, 1H)

LC/MS (ES+) m/z=336.16

Example 144

2-(3-Methyl-2-propyl-benzoylamino)-indan-2-carboxylic acid (144)

To a solution of 2-[3-methyl-2-(1-propenyl)-benzoylamino]-indan-2-carboxylic acid (143) (220 mg, 0.65 mmol) in absolute EtOH (10 mL) is added the catalyst, Pd—C (5 wt. % Pd, 55 mg, 2.6% mmol) under argon. The resulting reaction mixture is moved to the Paar apparatus to run hydrogenation: 50 psi, room temperature, overnight. The catalyst is removed by the filtration through a pre-column (10 g silica gel) and washed with EtOH. The combined solution is concentrated in vacuo. The residue is purified by HPLC to give a pure product (144) as white solid (128 mg, 58%).

$^1$H NMR (CDCl$_3$+drops of CD$_3$OD, 300 MHz): δ 0.91 (t, 3H), 1.45 (m, 2H), 2.45 (s, 3H), 2.61-2.66 (d, 2H), 3.40 (d, 2H), 3.82 (d, 2H), 6.22 (s, 1H), 7.04 (d, 2H), 7.17-7.26 (m, 5H)

LC/MS (ES+) m/z=338.17

Examples 145-146

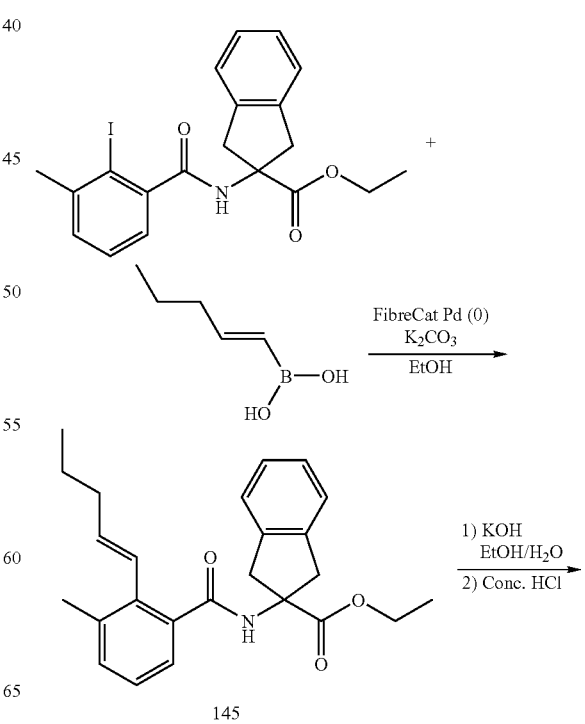

145

Examples 147-150

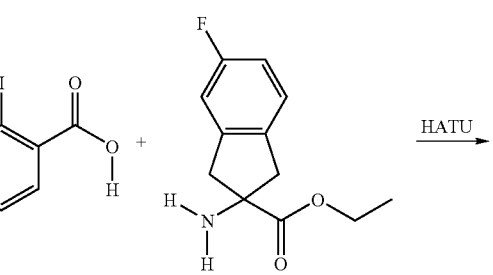

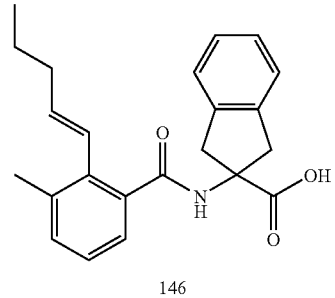

146

2-[3-Methyl-2-((E)-pent-1-enyl)-benzoylamino]-
indan-2-carboxylic acid ethyl ester (145)

To a solution of 2-(2-iodo-3-methyl-benzoylamino)-indan-2-carboxylic acid ethyl ester (200 mg, 0.45 mmol) and trans-1-penten-1-ylboronic acid (205 mg, 1.80 mmol) in EtOH (10 mL) and dioxane (10 mL) is added palladium anchored homogeneous catalyst, FibreCatPd(0) (4.84% Pd, 96 mg, 0.045 mmol) and 2M aqueous solution of $K_2SO_4$ (0.90 mL, 1.80 mmol). The resulting reaction mixture is covered with argon and run in a microwave reaction: 110° C., 8 h. After concentration in vacuo, the residue is purified by HPLC to give a pure product (145) as white solid (107 mg, 60%).

$^1$H NMR (CDCl$_3$, 300 MHz): δ 0.93 (t, 3H), 1.28 (t, 3H), 1.42 (m, 2H), 2.03 (q, 3H), 2.26 (s, 3H), 3.29 (d, 2H), 3.70 (d, 2H), 4.25 (q, 2H), 5.75 (dt, 1H), 6.37 (d, 1H), 6.43 (s, 1H), 7.09-7.25 (m, 6H), 7.37 (d, 1H)

LC/MS (ES+) m/z=392.0

Example 146

2-[3-Methyl-2-((E)-pent-1-enyl)-benzoylamino]-
indan-2-carboxylic acid (146)

The mixture 2-[3-methyl-2-((E)-pent-1-enyl)-benzoylamino]-indan-2-carboxylic acid ethyl ester (145) (170 mg, 0.43 mmol) and KOH (60 mg, 10.7 mmol) is dissolved in EtOH (8 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate came out of the water. The precipitate is filtered to give a pure product (146) as white solid (160 mg, 100%).

$^1$H NMR (CDCl$_3$, 300 MHz): δ 0.93 (t, 3H), 1.42 (m, 2H), 2.05 (q, 3H), 2.26 (s, 3H), 3.33 (d, 2H), 3.74 (d, 2H), 4.25 (q, 2H), 5.73 (dt, 1H), 6.35 (d, 1H), 6.68 (s, 1H), 7.11-7.21 (m, 6H), 7.34 (d, 1H)

LC/MS (ES+) m/z=364.18

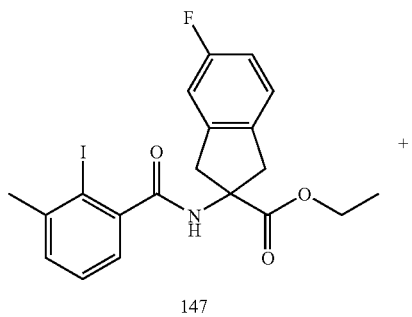

147

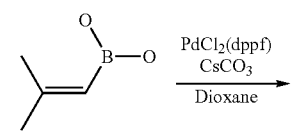

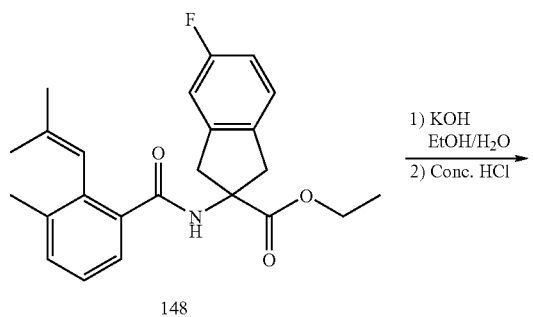

148

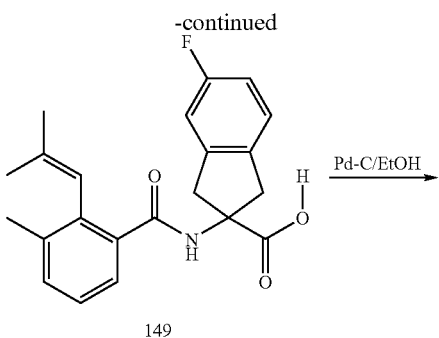

149

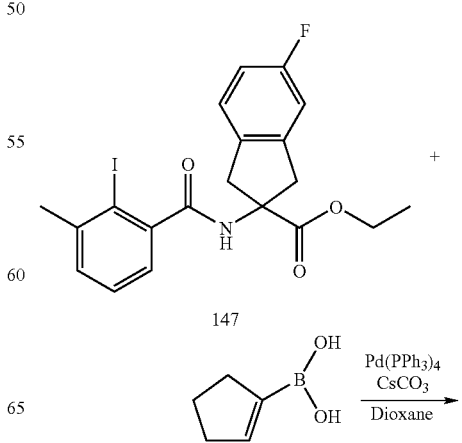

150

Example 147

5-Fluoro-2-(2-iodo-3-methyl-benzoylamino)-indan-2-carboxylic acid ethyl ester (147)

To a solution of 2-iodo-3-methyl-benzoic acid (3.85 g, 14.7 mmol), 2-amino-5-fluoro-indan-2-carboxylic acid ethyl ester (3.00 g, 13.4 mmol), HATU (6.10 g, 16.1 mmol) in anhydrous DMF (6 mL) is added DIPEA (3.30 mL, 20.1 mmol). The resulting solution is stirred at RT overnight. After the removal of DMF in vacuo, the residue is recrystallized from EtOAc to give a pure product (147) as white solid (3.90 g, 62%).

$^1$H NMR (CDCl$_3$, 300 MHz): δ 1.29 (t, 3H), 2.44 (s, 3H), 3.45-3.67 (m, 4H), 4.28 (q, 2H), 6.32 (s, 1H), 6.85-6.94 (m, 2H), 7.12-7.26 (m, 4H)

LC/MS (ES+) m/z=468.03

Example 148

5-Fluoro-2-[3-methyl-2-(2-methyl-propenyl)-benzoylamino]-indan-2-carboxylic acid ethyl ester (148)

To a solution of 5-fluoro-2-(2-iodo-3-methyl-benzoylamino)-indan-2-carboxylic acid ethyl ester (400 mg, 0.85 mmol) and 2,2-dimethyethylenelboronic acid (342 mg, 3.42 mmol) in EtOH (10 mL) and dioxane (5 mL) is added palladium anchored homogeneous catalyst, FibreCatPd(0) (4.84% Pd, 186 mg, 8.5% mmol) and 2M aqueous solution of K$_2$SO$_4$ (1.71 mL, 3.42 mmol). The resulting reaction mixture is covered with argon and run in a microwave reaction: 120° C., 7 h. After concentration in vacuo, the residue is purified by HPLC to give a pure product (148) as a colorless oil (245 mg, 73%).

$^1$H NMR (CDCl$_3$, 300 MHz): δ 1.26 (t, 3H), 1.34 (d, 3H), 1.71 (dd, 3H), 2.15 (s, 3H), 3.25 (br dd, 2H), 3.65 (br dd, 2H), 4.24 (q, 2H), 6.12 (s, 1H), 6.86-6.92 (m, 2H), 7.19-7.26 (m, 4H), 7.65 (d, 1H)

LC/MS (ES+) m/z=396.18

Example 149

5-Fluoro-2-[3-methyl-2-(2-methyl-propenyl)-benzoylamino]-indan-2-carboxylic acid (149)

The mixture 5-fluoro-2-[3-methyl-2-(2-methyl-propenyl)-benzoylamino]-indan-2-carboxylic acid ethyl ester (148) (245 mg, 0.62 mmol) and KOH (600 mg, 10.7 mmol) is dissolved in EtOH (10 mL) and water (0.5 mL) under a water bath. The water bath is removed when KOH is completely dissolved and the resulting reaction solution is stirred at RT for 3 h. After concentration in vacuo, the residue is dissolved in water (30 mL) and acidified with conc. HCl until no more precipitate came out of the water. The precipitate is filtered to give a pure product (149) as white solid (230 mg, 100%).

$^1$H NMR (CDCl$_3$+drops of CD$_3$OD, 300 MHz): δ 1.32 (s, 3H), 1.73 (s, 3H), 2.15 (s, 3H), 3.27 (t, 2H), 3.68 (dd, 2H), 6.12 (s, 1H), 6.86-6.93 (m, 2H), 7.13-7.30 (m, 4H), 7.61 (d, 1H)

LC/MS (ES+) m/z=368.10

Example 150

5-Fluoro-2-(2-isobutyl-3-methyl-benzoylamino)-indan-2-carboxylic acid (150)

To a solution of 2-[3-methyl-2-(2-methyl-propenyl)-benzoylamino]-indan-2-carboxylic acid (149) (230 mg, 0.63 mmol) in acetic acid (10 mL) is added the catalyst, Pd—C (5 wt. % Pd, 134 mg, 6.3% mmol) under argon. The resulting reaction mixture is moved to the Paar apparatus to run hydrogenation: 55 psi, 95° C., overnight. The catalyst is removed by filtration through a pre-column (10 g silica gel) and washed with EtOH. The combined organic solution is concentrated in vacuo. The residue is purified by HPLC to give a pure product (150) as white solid (200 mg, 86%).

$^1$H NMR (CDCl$_3$+drops of CD$_3$OD, 300 MHz): δ 0.81 (dd, 6H), 1.78 (m, 1H), 2.30 (s, 3H), 2.68 (d, 2H), 3.37 (t, 2H), 3.69 (dd, 2H), 6.88-6.93 (m, 3H), 7.13-7.30 (m, 4H), 7.32 (s, 1H)

LC/MS (ES+) m/z=370.19

Example 151-152

-continued

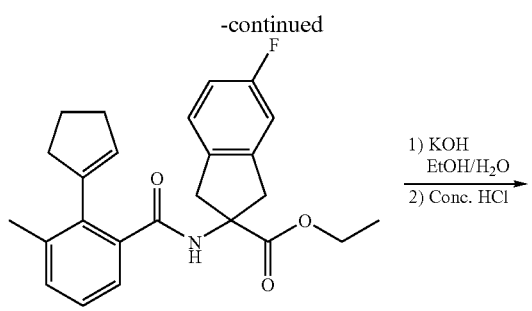

151

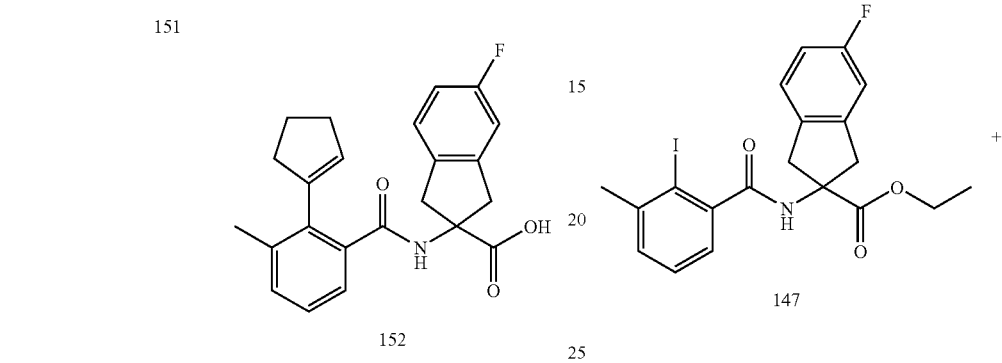

152

2-(2-Cyclopent-1-enyl-3-methyl-benzoylamino)-5-fluoro-indan-2-carboxylic acid ethyl ester (151)

To a solution of 5-fluoro-2-(2-iodo-3-methyl-benzoylamino)-indan-2-carboxylic acid ethyl ester (400 mg, 0.85 mmol) and cyclopenten-1-ylboronic acid (383 mg, 3.42 mmol) in EtOH (10 mL) and dioxane (5 mL) is added palladium anchored homogeneous catalyst, FibreCatPd(0) (4.84% Pd, 186 mg, 8.5% mmol) and 2M aqueous solution of $K_2SO_4$ (1.71 mL, 3.42 mmol). The resulting reaction mixture is covered with argon and run in a microwave reaction: 110° C., 8 h. After concentration in vacuo, the residue is purified HPLC to give a pure product (151) as white solid (240 mg, 69%).

$^1$H NMR (CDCl$_3$, 300 MHz): δ 1.27 (t, 3H), 1.76 (m, 2H), 2.20 (s, 3H), 2.38-2.41 (m, 4H), 3.25 (dd, 2H), 3.66 (dd, 2H), 4.25 (q, 2H), 5.62 (t, 1H), 6.87-6.93 (m, 2H), 7.12-7.30 (m, 4H), 7.53 (d, 1H), 8.39 (br s, 1H)

LC/MS (ES+) m/z=408.22

Example 152

2-(2-Cyclopent-1-enyl-3-methyl-benzoylamino)-5-fluoro-indan-2-carboxylic acid (152)

The mixture of 2-(2-cyclopent-1-enyl-3-methyl-benzoylamino)-5-fluoro-indan-2-carboxylic acid ethyl ester (151) (190 mg, 0.47 mmol) and KOH (600 mg, 10.7 mmol) is dissolved in EtOH (10 mL) and water (0.5 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate formed. The precipitate is filtered to give a pure product (152) as white solid (182 mg, 100%).

$^1$H NMR (CDCl$_3$, 300 MHz): δ 1.72 (m, 2H), 2.18 (s, 3H), 2.34 (t, 4H), 3.20 (t, 2H), 3.66 (dd, 2H), 5.55 (s, 1H), 6.84-6.89 (m, 2H), 7.07-7.26 (m, 4H), 7.56 (d, 1H)

LC/MS (ES+) m/z=380.19

Example 153

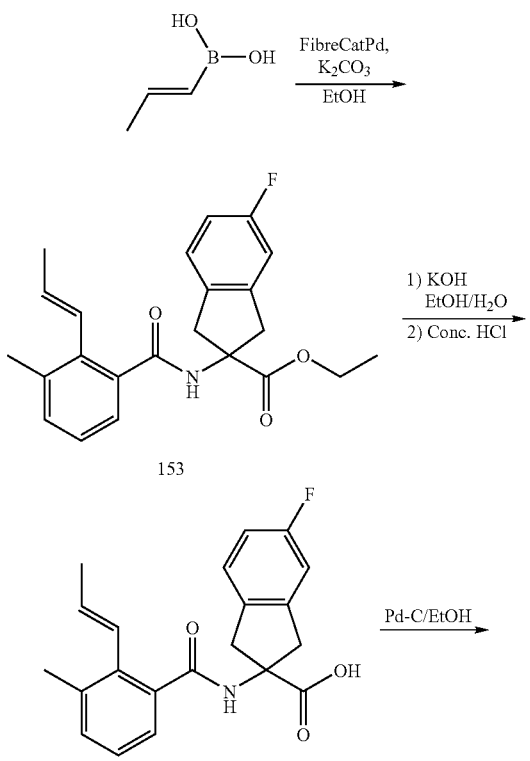

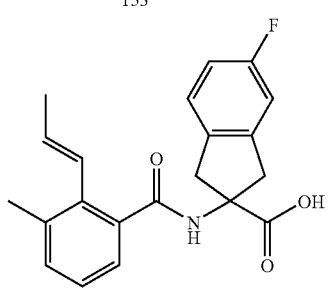

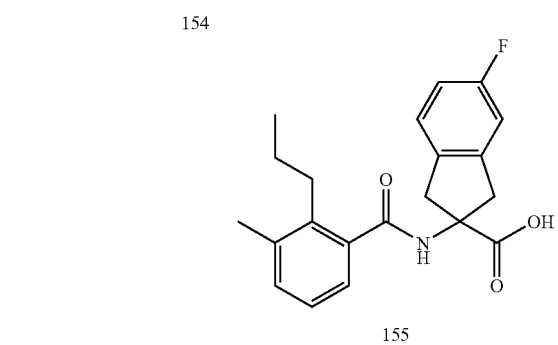

5-Fluoro-2-[3-methyl-2-((E)-propenyl)-benzoylamino]-indan-2-carboxylic acid ethyl ester (153)

To a solution of 5-fluoro-2-(2-iodo-3-methyl-benzoylamino)-indan-2-carboxylic acid ethyl ester (400 mg, 0.85mmol) and trans-1-propen-1-ylboronic acid (294 mg, 3.42 mmol) in EtOH (10 mL) and dioxane (5 mL) is added palladium anchored homogeneous catalyst, FibreCatPd(0) (4.84% Pd, 186 mg, 8.5% mmol) and 2M aqueous solution of $K_2SO_4$ (1.71 mL, 3.42 mmol). The resulting reaction mixture is covered with argon and run in a microwave reaction: 110° C., 7 h. After concentration in vacuo, the residue is purified by HPLC to give a pure product (153) as white solid (165 mg, 51%).

$^1$H NMR ($CDCl_3$, 300 MHz): δ 1.28 (t, 3H), 1.75 (m, 3H), 2.26 (s, 3H), 3.27 (dd, 2H), 3.62 (dd, 2H), 4.26 (q, 2H), 5.76 (dq, 1H), 6.38 (d, 1H), 6.44 (s, 1H), 6.85-6.91 (m, 2H), 7.11-7.22 (m, 3H), 7.35 (d, 1H)

LC/MS (ES+) m/z=382.21

Example 154

5-Fluoro-2-[3-methyl-2-((E)-propenyl)-benzoylamino]-indan-2-carboxylic acid (154)

The mixture 5-fluoro-2-[3-methyl-2-((E)-propenyl)-benzoylamino]-indan-2-carboxylic acid ethyl ester (153) (260 mg, 0.68 mmol) and KOH (600 mg, 10.7 mmol) is dissolved in EtOH (8 mL) and water (0.2 mL) under a water bath. The water bath is removed when KOH is completely dissolved and the resulting reaction solution is stirred at RT for 2.5 h. After concentration in vacuo, the residue is dissolved in water (30 mL) and acidified with conc. HCl until no more precipitate came out of the water. The filtered compound is purified by HPLC to give a pure product (154) as white solid (267 mg, 100%).

$^1$H NMR ($CDCl_3$+drops of $CD_3OD$, 300 MHz): δ 1.76 (m, 3H), 2.26 (s, 3H), 3.31 (t, 2H), 3.65 (dd, 2H), 5.76 (dq, 1H), 6.38 (d, 1H), 6.80 (s, 1H), 6.85-6.93 (m, 2H), 7.10-7.22 (m, 3H), 7.31 (d, 1H)

LC/MS (ES+) m/z=354.18

Example 155

5-Fluoro-2-(2-isobutyl-3-methyl-benzoylamino)-indan-2-carboxylic acid (155)

5-Fluoro-2-[3-methyl-2-((E)-propenyl)-benzoylamino]-indan-2-carboxylic acid (154) (270 mg, 0.76 mmol) is dissolved in absolute EtOH (15 mL) by heating. The resulting solution is cooled down to RT under argon and then is added the catalyst, Pd—C (5 wt. % Pd, 125 mg, 5.9% mmol). The resulting reaction mixture is moved to the Paar apparatus to run hydrogenation: 50 psi, 50° C., overnight. The catalyst is removed by filtration through a pre-column (10 g silica gel) and washed with EtOH. The combined organic solution is concentrated in vacuo. The residue is purified by HPLC to give a pure product (155) as white solid (210 mg, 78%).

$^1$H NMR ($CDCl_3$+drops of $CD_3OD$, 300 MHz): δ 0.92 (t, 3H), 1.46 (m, 2H), 2.30 (s, 3H), 2.65-2.68 (m, 2H), 3.36 (t, 2H), 3.71 (dd, 2H), 6.85-6.93 (m, 2H), 7.03-7.18 (m, 4H)

LC/MS (ES+) m/z=356.14

Example 156

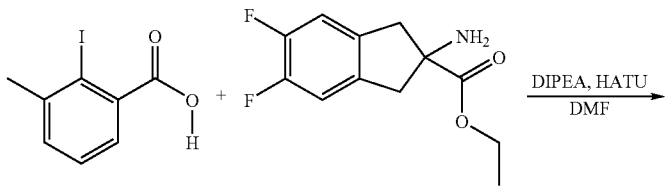

104

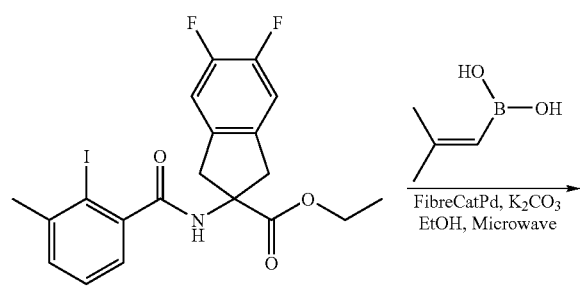

156

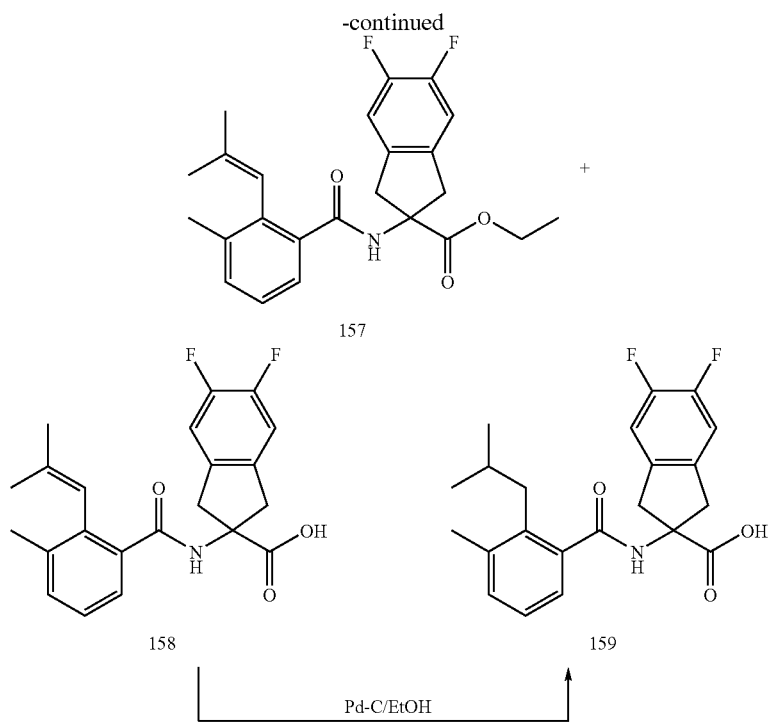

5,6-Difluoro-2-(2-iodo-3-methyl-benzoylamino)-indan-2-carboxylic acid ethyl ester (156)

To a solution of 2-iodo-3-methyl-benzoic acid (1.50 g, 5.75 mmol), 2-amino-5,6-difluoro-indan-2-carboxylic acid ethyl ester (1.39 g, 5.75 mmol), HATU (2.63 g, 6.90 mmol) in anhydrous DMF (6 mL) is added DIPEA (1.14 mL, 6.90 mmol). The resulting solution is stirred at RT overnight. After the removal of DMF in vacuo, the residue is dissolved in EtOAc (200 mL) and washed with water (1×20 mL) and brine (2×20 mL). The organic layer is dried over anhydrous $Na_2SO_4$ and concentrated in vacuo. The residue is purified by flash column chromatography (400 g silica gel, gradient elution: 10%-80% EtOAc in heptane) to give a pure product (156) as white solid (2.32 g, 83%).

$^1$H NMR ($CDCl_3$, 300 MHz): δ 1.29 (t, 3H), 2.45 (s, 3H), 3.48 (d, 2H), 3.63 (d, 2H), 4.27 (q, 2H), 6.38 (s, 1H), 7.04 (t, 2H), 7.10-7.13 (m, 1H), 7.24-7.27 (m, 2H)

LC/MS (ES+) m/z=486.02

Examples 157 and 158

5,6-Difluoro-2-[3-methyl-2-(2-methyl-propenyl)-benzoylamino]-indan-2-carboxylic acid ethyl ester (157) and 5,6-Difluoro-2-[3-methyl-2-(2-methyl-propenyl)-benzoylamino]-indan-2-carboxylic acid (158)

To a solution of 5,6-difluoro-2-(2-iodo-3-methyl-benzoylamino)-indan-2-carboxylic acid ethyl ester (400 mg, 0.82 mmol) and 2,2-dimethyethylenelboronic acid (328 mg, 3.28 mmol) in EtOH (10 mL) and dioxane (5 mL) is added palladium anchored homogeneous catalyst, FibreCatPd(0) (4.84% Pd, 180 mg, 8.2% mmol) and 2M aqueous solution of $K_2SO_4$ (1.64 mL, 3.28 mmol). The resulting reaction mixture is covered with argon and run in a microwave reaction: 120° C., 6 h. After concentration in vacuo, the residue is purified by HPLC to give two pure products: (157) as white solid (100 mg, 29%) and (158) as white solid as well (120 mg, 38%).

(157): $^1$H NMR ($CDCl_3$, 300 MHz): δ 1.26 (t, 3H), 1.38 (d, 3H), 1.76 (s, 3H), 2.15 (s, 3H), 3.27 (d, 2H), 3.59 (d, 2H), 4.24 (q, 2H), 6.14 (s, 1H), 6.98-7.31 (m, 5H), 7.61 (d, 1H)

LC/MS (ES+) m/z=414.20

(158): $^1$H NMR ($CDCl_3$, 300 MHz): δ 1.34 (d, 3H), 1.79 (s, 3H), 2.15 (s, 3H), 3.26 (d, 2H), 3.75 (d, 2H), 6.09 (s, 1H), 7.02 (t, 2H), 7.21-7.34 (m, 3H), 7.77 (d, 1H)

LC/MS (ES+) m/z=386.19

Example 159

5,6-Difluoro-2-(2-isobutyl-3-methyl-benzoylamino)-indan-2-carboxylic acid (159)

5,6-Difluoro-2-[3-methyl-2-(2-methyl-propenyl)-benzoylamino]-indan-2-carboxylic acid (158) (200 mg, 0.63 mmol) is dissolved in acetic acid (15 mL) by heating. The resulting solution is cooled down to RT and then the catalyst, Pd—C (5 wt. % Pd, 134 mg, 6.3% mmol) is added under argon. The resulting reaction mixture is moved to the Paar apparatus to run hydrogenation: 55 psi, 95° C., overnight. The catalyst is removed by filtration through a pre-column (10 g silica gel) and washed with EtOH. The combined organic solution is concentrated in vacuo. The residue is purified by HPLC to give a pure product (159) as white solid (170 mg, 84%).

(159): $^1$H NMR ($CDCl_3$+drops of $CD_3OD$, 300 MHz): δ 0.83 (d, 6H), 1.80 (m, 1H), 2.32 (s, 3H), 2.68 (d, 2H), 3.39 (d, 2H), 7.00-7.20 (m, 5H), 7.44 (s, 1H)

LC/MS (ES+) m/z=388.17

Examples 160-161

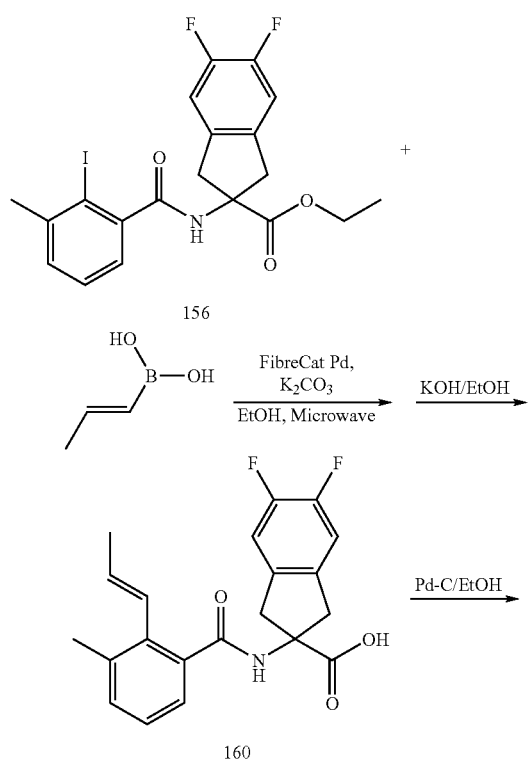

5,6-Difluoro-2-(3-methyl-2-propenyl-benzoy-lamino)-indan-2-carboxylic acid (160)

To a solution of 5,6-difluoro-2-(2-iodo-3-methyl-benzoylamino)-indan-2-carboxylic acid ethyl ester (400 mg, 0.82 mmol) and trans-1-propen-1-ylboronic acid (282 mg, 3.28 mmol) in EtOH (10 mL) and dioxane (5 mL) is added palladium anchored homogeneous catalyst, FibreCatPd(0) (4.84% Pd, 180 mg, 8.2% mmol) and 2M aqueous solution of $K_2SO_4$ (1.64 mL, 3.28 mmol). The resulting reaction mixture is covered with argon and run in a microwave reaction: 120° C., 5 h. After concentration in vacuo, the residue is purified by HPLC to give a white solid (160 mg), which is dissolved in EtOH (5 mL) and water (0.2 mL) together with KOH (600 mg, 10.7 mmol) under a water bath. The water bath is removed when KOH is completely dissolved and the resulting reaction solution is stirred at RT for 3 h. After concentration in vacuo, the residue is dissolved in water (20 mL) and acidified with conc. HCl until no more white precipitate came out of the water. The filtration is purified by HPLC to give a pure product (160) as white solid (127 mg, 42% overall yield).

$^1$H NMR (CDCl$_3$+drops of CD$_3$OD, 300 MHz): δ 1.80 (dd, 3H), 2.27 (s, 3H), 3.36 (d, 2H), 3.63 (d, 2H), 5.77 (dq, 1H), 6.40 (d, 1H), 7.01 (t, 2H), 7.10-7.29 (m, 4H)

LC/MS (ES+) m/z=372.15

Example 161

5,6-Difluoro-2-(3-methyl-2-propyl-benzoylamino)-indan-2-carboxylic acid (161)

5,6-Difluoro-2-[3-methyl-2-(-propenyl)-benzoylamino]-indan-2-carboxylic acid (160) (110 mg, 0.30 mmol) is dissolved in absolute EtOH (15 mL) by heating. The resulting solution is cooled to RT and catalyst, Pd—C (5 wt. % Pd, 64 mg, 3.0% mmol) is added under argon. The resulting reaction mixture is moved to the Paar apparatus to run hydrogenation: 55 psi, 50° C., overnight. The catalyst is removed by filtration through a pre-column (10 g silica gel) and washed with EtOH. The combined EtOH solution is concentrated in vacuo. The residue is purified by HPLC to give a pure product (161) as white solid (80 mg, 71%).

$^1$H NMR (DMSO-d6, 300 MHz): δ 0.86 (q, 3H), 1.40 (m, 2H), 2.27 (s, 3H), 2.58 (m, 2H), 3.29 (d, 2H), 3.52 (d, 2H), 7.00 (d, 1H), 7.08 (t, 1H), 7.18 (d, 1H), 7.29 (t, 2H), 8.87 (s, 1H), 12.58 (s, 1H)

LC/MS (ES+) m/z=374.14

Example 162

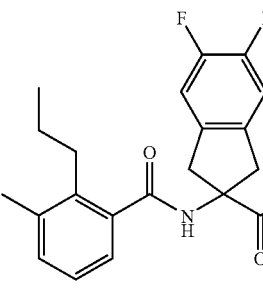

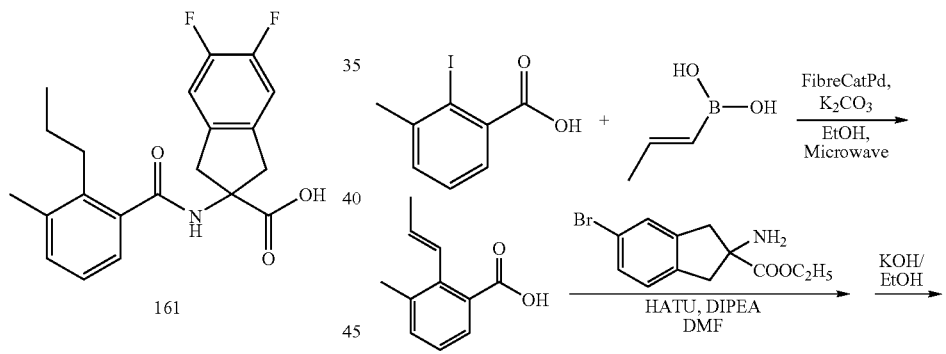

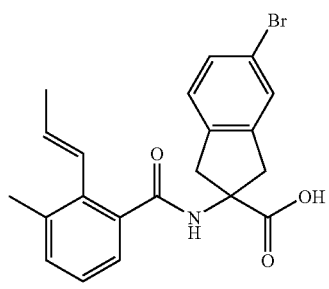

3-Methyl-2-((E)-propenyl)-benzoic acid (162)

To a solution of 2-iodo-3-methyl-benzoic acid (708 mg, 2.70 mmol) and trans-1-propen-1-ylboronic acid (526 mg, 6.12 mmol) in EtOH (10 mL) is added palladium anchored homogeneous catalyst, FibreCatPd(0) (4.84% Pd, 235 mg, 0.15 mmol) and 2M aqueous solution of $K_2SO_4$ (3.06 mL, 6.12 mmol). The resulting reaction mixture is covered with argon and run in a microwave reaction: 110° C., 7 h. After concentration in vacuo, the residue is purified by HPLC to give a pure product (162) as a pale yellow solid (500 mg, 93%).

$^1$H NMR (CDCl$_3$, 300 MHz): δ 1.90 (dd, 3H), 2.34 (s, 3H), 5.68 (dq, 1H), 6.67 (d, 1H), 7.20 (t, 1H), 7.35 (d, 1H), 7.70 (d, 1H)

LC/MS (ES+) m/z=177.10, 218.13

Example 163

5-Bromo-2-[3-methyl-2-((E)-propenyl)-benzoylamino]-indan-2-carboxylic acid (163)

To a solution of 3-methyl-2-((E)-propenyl)-benzoic acid (162) (470 mg, 2.67 mmol), 2-amino-5-bromo-indan-2-carboxylic acid ethyl ester (835 mg, 2.94 mmol) and HATU (1.22 mg, 3.20 mmol) in anhydrous DMF (12 mL) is added DIPEA (529 µL, 3.20 mmol). The resulting solution is stirred at RT overnight. After the removal of DMF in vacuo, the residue is dissolved in EtOAc (150 mL) and washed with water (1×10 mL) and brine (2×10 mL). The organic layer is dried over anhydrous $Na_2SO_4$ and concentrated in vacuo. The residue is purified by flash column chromatography (300 g silica gel, gradient elution: 5-60% EtOAc in heptane) to give a white solid (1.12 g), which is dissolved in EtOH (15 mL) and water (1 mL) together with KOH (1.20 g, 21 mmol) under a water bath. The water bath is removed when KOH is completely dissolved and the resulting reaction solution is stirred at RT for 4 h. After concentration in vacuo, the residue is dissolved in water (100 mL) and acidified with conc. HCl until no more precipitate came out of the water. The filtered compound is purified by HPLC to give a pure product (163) as white solid (1.03 g, 93% overall yield).

$^1$H NMR (CDCl$_3$, 300 MHz): δ 1.74 (dd, 3H), 2.25 (s, 3H), 3.30 (dd, 2H), 3.74 (dd, 2H), 5.73 (dq, 1H), 6.32 (d, 1H), 6.51 (s, 1H), 7.08-7.38 (m, 6H)

LC/MS (ES+) m/z=414.09, 416.09

Example 164

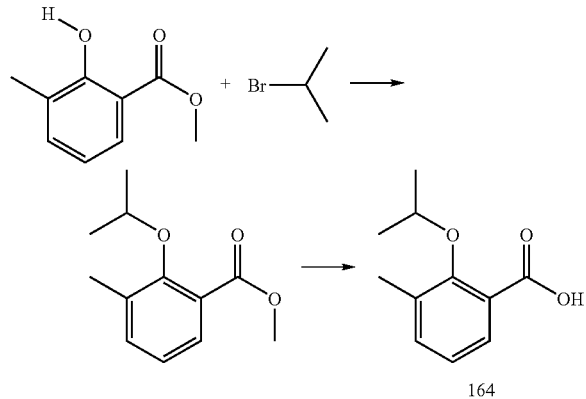

2-Isopropoxy-3-methyl-benzoic acid (164)

A 250 mL round bottom flask is charged with methyl 2-hydroxy-3-methylbenzoate (10 g, 60.18 mmol) and dry N,N-dimethylformamide (DMF, 120 mL). A stirring bar is added and stirring is initiated. After 2 minutes 2-Bromopropane (8.1 mL, 86.65 mmol) is added via syringe. KI (20 mg, cat.) and $CsCO_3$ (44.42 g, 136.32 mmol) are added in order. The reaction is capped. The reaction flask is fitted with a heating mantle that is warmed to 43° C. After 4 days, tlc analysis (silica, 1:3 EtOAc:heptanes) indicates that the starting phenol is consumed and converted to a single spot as visualized by UV analysis. The heating source is removed from the reaction flask. After stirring for an additional 2 h at ambient temperature, the contents of the reaction flask are filtered through a pad of Celite. The Celite pad is washed with EtOAc:heptanes (1:1, 200 mL). The filtrate is transferred to a reparatory funnel and washed with brine (100 mL), water (100 mL), saturated aqueous $NaHCO_3$ (100 mL). This washing sequence is repeated (1 time) followed by a final washing with brine (50 mL). The organic layer is dried over $MgSO_4$, filtered and evaporated in vacuo. Pumping to constant weight provided 11.88 g of pale yellow oil. The 250 mL flask containing the above material is charged with 1,4-dioxane (50 mL) and MeOH (100 mL). A stirring bar is added and stirring is initiated. After dissolution, water (50 mL) is added followed by the LiOH hydrate (5.7 g, 135.8 mmol). After 18 h, tlc analysis (silica, 10% MeOH/DCM) indicates that the starting material is completely consumed. The pH of the reaction mixture is carefully adjusted to pH 2 by slowly adding dilute aqueous HCl (3%, 55 mL). The contents of the flask are transferred to a separatory funnel containing EtOAc (100 mL). The layers are separated. The aqueous layer is extracted with EtOAc (50 mL). The combined organic extracts are washed with water (50 mL) and brine (50 mL), dried over $MgSO_4$, filtered and concentrated under reduced pressure. Pumping to constant weight gives 10.19 g (52.46 mmol, 87.18%) of off-white solid.

$^1$H NMR (300 MHz, DMSO-d6): δ 1.18 (d, 6H), 2.22, (s, 3H), 4.19 (m, 1H), 7.03 (dd, 1H), 7.38, (dd, 1H), 7.48 (dd, 1H).

LC/MS m/z=195.

Example 165

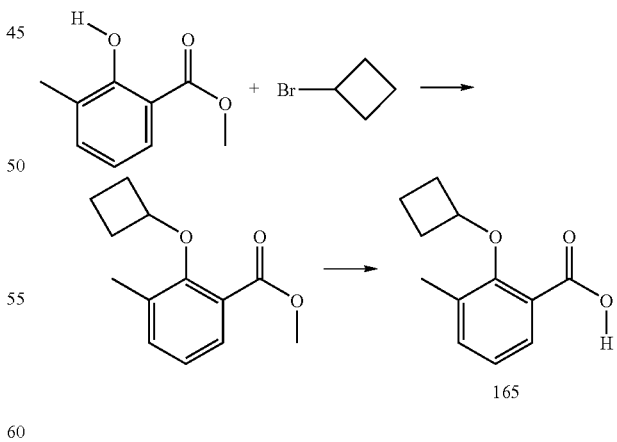

2-Cyclobutoxy-3-methyl-benzoic acid (165)

A 100 mL round bottom flask is charged with methyl 2-hydroxy-3-methylbenzoate (5 g, 30.09 mmol) and dry N,N-dimethylformamide (DMF, 60 mL). A stirring bar is added and stirring is initiated. After 2 min bromocyclobutane (5 g, 37.04 mmoles) is added via syringe. Potassium iodide (10 mg, cat.) and CsCO₃ (22.21 g, 68.16 mmol) are added in order. The reaction is capped. The reaction flask is fitted with a heating mantle that is warmed to 43° C. After 4 days, tlc analysis (silica, 1:3 EtOAc:heptanes) indicates that the starting phenol had been consumed and converted to a single spot as visualized by UV analysis. The heating source is removed from the reaction flask. After stirring for an additional 16 h at ambient temperature, the contents of the reaction flask are filtered through a pad of Celite. The Celite pad is washed with EtOAc:heptanes (1:1, 200 mL). The filtrate is transferred to a separatory funnel and washed with brine (50 mL), water (50 mL), saturated aqueous NaHCO₃ (50 mL). This washing sequence is repeated (1×) followed by a final washing with brine (50 mL). The organic layer is dried over MgSO₄, filtered and evaporated in vacuo. Pumping to constant weight gives 5.94 g of pale yellow oil. The 100 mL flask containing the above material is charged with 1,4-dioxane (30 mL) and MeOH (30 mL). A stirring bar is added and stirring is initiated. After dissolution, water (10 mL) is added followed by the LiOH hydrate (2.80 g, 66.78 mmol). After 18 h, tlc analysis (silica, 10% MeOH/DCM) indicates that the starting material is completely consumed. The pH of the reaction mixture is carefully adjusted to pH 2 by slowly adding dilute aqueous HCl (3%, 30 mL). The contents of the flask are transferred to a reparatory funnel that contains EtOAc (80 mL). The layers are separated. The aqueous layer is extracted with EtOAc (40 mL). The combined organic extracts are washed with water (50 mL) and brine (50 mL), dried over MgSO₄, filtered and concentrated under reduced pressure. Pumping to constant weight gives 5.3 g (25.70 mmol, 85.40%) of a white solid.

$^1$H NMR (300 MHz, DMSO-d6): δ 1.37 (m, 1H), 1.42 (m, 1H), 2.02-2.26, (m, 4H), 2.22 (s, 3H) 4.35 (m, 1H), 7.03 (dd, 1H), 7.36, (dd, 1H), 7.47 (dd, 1H).

LC/MS m/z=207.

Example 166

2-[(2,2-Dimethyl-2,3-dihydro-benzofuran-7-carbonyl)-amino]-indan-2-carboxylic acid ethyl ester (166)

A test tube (25×150 mm) containing a stirring bar and 2-amino-indane-2-carboxylic acid ethyl ester (0.5 g, 2.436 mmol) is charged with dry DCM (3 mL). Stirring is initiated. After dissolution, the DIPEA (1.50 mL, 8.6 mmol) and 4-dimethylaminopyridine (2 mg, 17 μmol) are added. A solution of 2,2-dimethyl-2,3-dihydro-1-benzofuran-7-carbonyl chloride (0.73 g, 3.47 mmol) in dry DCM (4 mL) is added to the reaction tube. After stirring for 18 h, tlc analysis (silica, 10% CH₃OH in DCM) indicates complete consumption of the starting amine. The reaction mixture is diluted with DCM (10 mL) and washed with 5% aqueous HCl (2×5 mL) and brine (5 mL), dried over MgSO₄ filtered and evaporated by pumping to constant weight gives 0.72 g of a light brown gum. This material is purified by chromatography (silica, 0% to 20% EtOAc in DCM) on the ISCO Companion using a 40 g cartridge (silica). Fractions 17-22 are combined, evaporated and pumped to a constant weight to provide 0.62 g (67%) of a glassy solid.

$^1$H NMR (300 MHz, DMSO-d6): δ 1.14 (t, 3H), 1.37 (s, 6H) 3.03, (s, 2H), 3.43 (dd, 4H), 4.12 (q, 2H), 6.91 (dd, 1H), 7.16-7.27 (m, 4H), 7.35 (dd, 1H), 7.56 (d, 1H), 8.32 (s, 1H).

LC/MS m/z=380.

Example 167

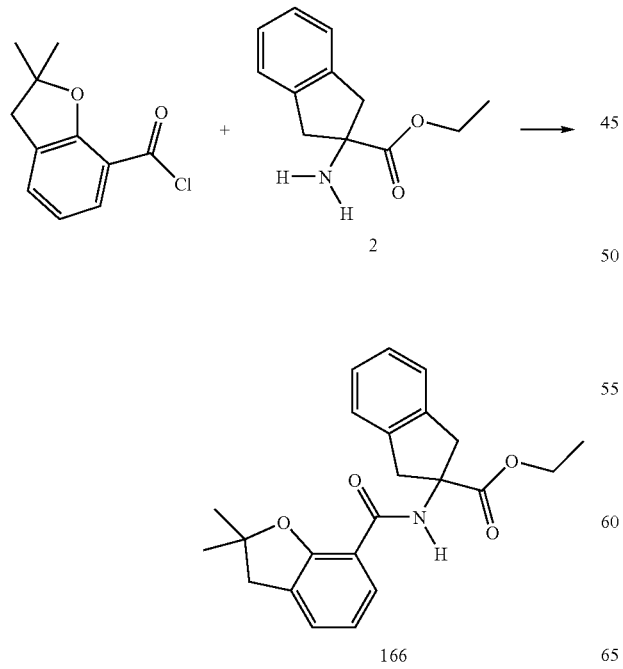

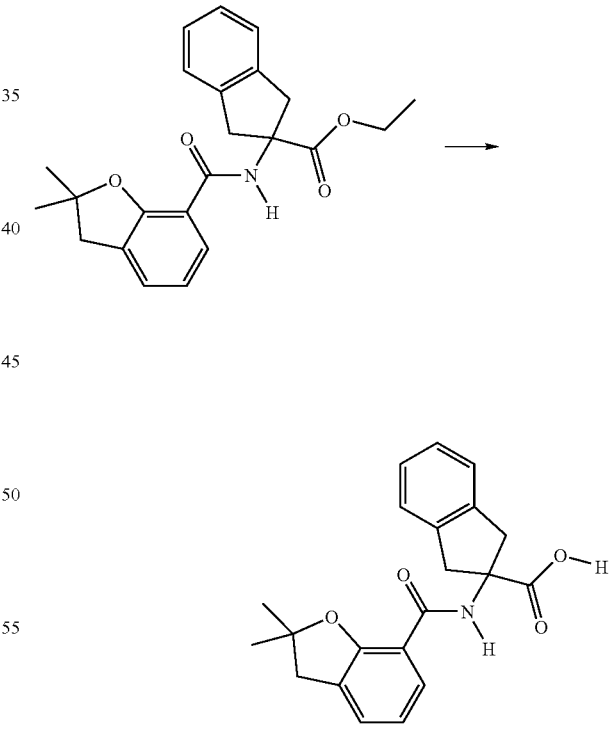

2-[(2,2-Dimethyl-2,3-dihydro-benzofuran-7-carbonyl)-amino]-indan-2-carboxylic acid (167)

A 50 mL round bottom flask containing the 2-[(2,2-dimethyl-2,3-dihydro-benzofuran-7-carbonyl)-amino]-indan-2- carboxylic acid ethyl ester (0.45 g, 1.179 mmol) is charged with MeOH (25 mL) and a stirring bar is added. Stirring is initiated. After dissolution, water (8 mL) and the LiOH (108 mg, 2.58 mmol) are added. After 56 h, tlc analysis (silica, 5% i-PrOH/DCM) indicates that the starting material is completely consumed. The pH of the reaction mixture is carefully adjusted to pH 3 by slowly adding dilute aqueous HCl (3%, ~20 mL). The contents of the flask are poured into a reparatory funnel containing EtOAc (30 mL). The layers are separated. The aqueous layer is extracted with EtOAc (20 mL). The combined organic extracts are washed with water (30 mL) and brine (20 mL), dried over MgSO$_4$, filtered and concentrated. Pumping to constant weight gives 460 mg of material. The sample is purified by column chromatography (silica, 2% to 15% CH$_3$OH in DCM) using an ISCO Companion and a 12 g cartridge. Fraction 3 is collected and evaporated. After pumping to constant weight, 375 mg (90%) of a dry white powder is obtained.

$^1$H NMR (300 MHz, DMSO-d6): δ 1.36 (s, 6H) 2.99, (s, 2H), 3.40 (dd, 4H), 6.88 (dd, 1H), 7.11-7.20 (m, 4H), 7.30 (dd, 1H), 7.57 (d, 1H), 8.34 (s, 1H).

LC/MS m/z=352.

Example 168

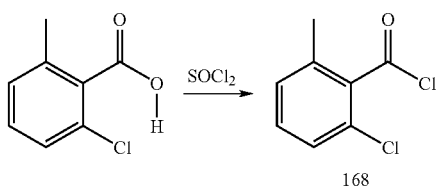

2-Chloro-6-methylbenzoyl chloride (168)

A round bottom flask containing the 2-chloro-6-methylbenzoic acid (1.5 g, 8.79 mmol) and a stirring bar is charged with dry DCM (10 mL). Stirring is initiated. After several min, a solution of thionyl chloride (in DCM (2M), 6.6 mL, 13.2 mmol) is added via syringe. 2 drops of DMF are then added. The reaction immediately began to bubble gently. After 2 h bubbling ceases. After 3 h, the solvent is removed from the reaction mixture in vacuo. The oily residue is redissolved in DCM (6 mL) and the solvent once again removed in vacuo. The residue is dissolved in dry DCM (6 mL) and used without further purification in the next reaction sequence.

Example 169

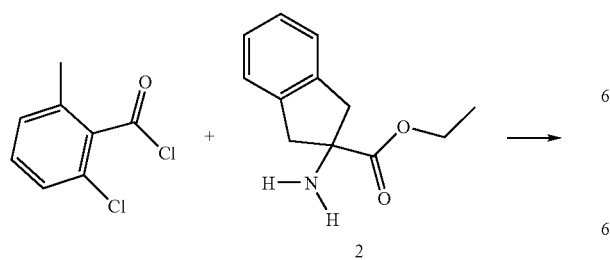

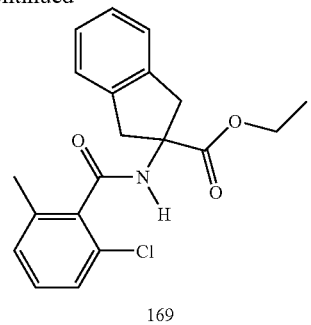

2-[(2-Chloro-6-methyl-benzoyl)-amino]-indane-2-carboxylic acid ethyl ester (169)

A test tube (25×150 mm) containing a stirring bar and 2-amino-indan-2-carboxylic acid ethyl ester (0.53 g, 2.58 mmol) is charged with dry DCM (3 mL). Stirring is initiated. After dissolution, the DIPEA (1.50 mL, 8.6 mmol) and 4-dimethylaminopyridine (2 mg, 17 µmol) are added. A solution of 2-chloro-6-methylbenzoyl chloride (5.8 mmol) in dry DCM (4 mL), as prepared above, is added to the reaction tube. After stirring for 18 h, tlc analysis (silica, 10% CH$_3$OH in DCM) indicates complete consumption of the amine. The reaction mixture is diluted with DCM (10 mL) and washed with 5% aqueous HCl (2×5 mL) and brine (5 mL), dried over MgSO4 filtered and evaporated by pumping to constant weight gives 1.07 g of light brown solid. This material is purified by chromatography (silica, 2% to 20% EtOAc in DCM) on the ISCO Companion using a 40 g cartridge. Fractions 6-10 are combined, evaporated and pumped to yield a constant weight 550 mg of white amorphous solid.

$^1$H NMR (300 MHz, DMSO-d6): δ 1.19 (t, 3H) 3.33, (s, 3H), 3.45 (dd, 4H), 4.13 (q, 2H), 6.88 (dd, 1H), 7.12-7.47 (m, 7H), 9.11 (s, 1H).

LC/MS m/z=358.

Example 170

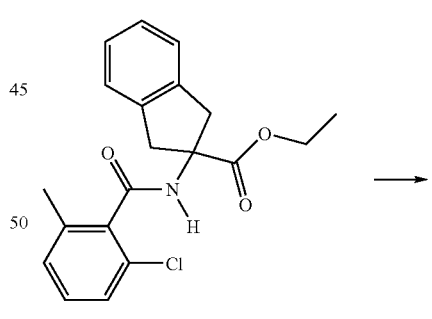

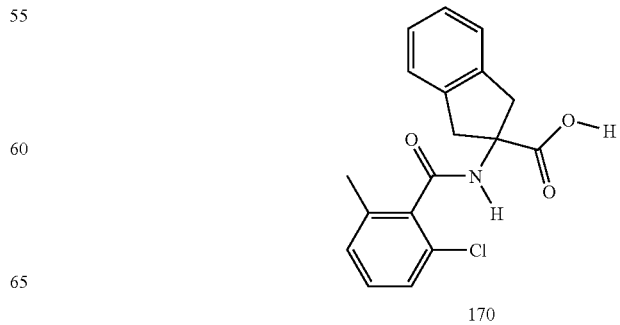

2-[(2-Chloro-6-methyl-benzoyl)-amino]-indane-2-carboxylic acid (170)

A 100 mL round bottom flask containing the 2-(2-chloro-6-methyl-benzoylamino)-indane-2-carboxylic acid ethyl ester (0.255 g, 0.712 mmol) is charged with MeOH (15 mL) and a stirring bar is added. Stirring is initiated. After dissolution, water (5 mL) is added and starting material begins to precipitate out. Tetrahydrofuran is added to re-solubilize the starting material. LiOH (90 mg, 2.14 mmol) is added. After 16 h, tlc analysis (silica, 5% i-PrOH/DCM) indicates that the starting material is completely consumed. The pH of the reaction mixture is carefully adjusted to pH 3 by slowly adding dilute aqueous HCl (3%, ~20 mL). The contents of the flask are poured into an addition funnel containing DCM (30 mL). The layers are separated. The aqueous layer is extracted with DCM (20 mL). The combined organic extracts are washed with water (30 mL) and brine (20 mL), dried over MgSO4, filtered and concentrated to yield 280 mg of material. The material is purified by column chromatography (silica, 2% to 15% CH$_3$OH in DCM) using an ISCO Companion and a 12 g cartridge. Fraction 2 is collected and evaporated. After pumping to constant weight, 130 mg of dry white powder is obtained.

$^1$H NMR (300 MHz, DMSO-d6): δ 2.27, (s, 3H), 3.45 (dd, 4H), 7.14-7.39 (m, 7H), 8.96 (s, 1H). LC/MS m/z=330.

Example 171

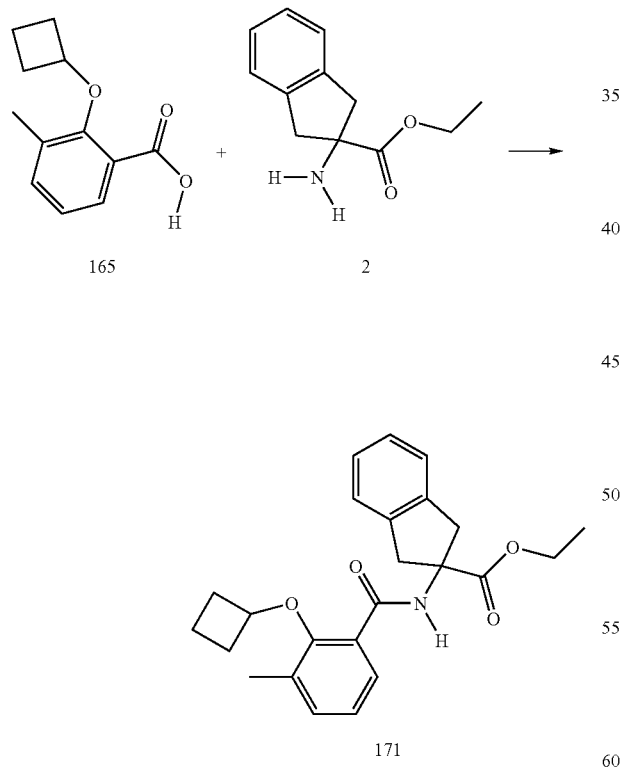

2-(2-Cyclobutoxy-3-methyl-benzoylamino)-indan-2-carboxylic acid ethyl ester (171)

A 25 mL vial containing a stirring bar is charged with 2-cyclobutoxy-3-methyl-benzoic acid (1.01 g, 4.87 mmol) and dry DCM (14 mL). Stirring is initiated. HBTU (1.84 g, 4.86 mmol) is added. After 5 min, the 2-aminoindane-2-carboxylic acid ethyl ester (1 g, 4.87 mmol) is added followed by the DIPEA (1.9 mL, 10.92 mmol). The reaction is allowed to stir for 12 days. Analysis by tlc of the reaction mixture (silica, 10% MeOH/DCM) indicates complete consumption of the starting amine. The contents of the reaction flask are diluted with EtOAc (70 mL) and transferred to a separatory funnel. This is washed consecutively with dilute aqueous HCl (3%, 35 mL), saturated aqueous NaHCO$_3$ (35 mL) and brine (35 mL), dried over MgSO$_4$, filtered and evaporated in vacuo to provide 2.56 g of an off-white solid. This material is dissolved in 15 mL of DCM. This is purified utilizing an ISCO Companion with a 40 g cartridge of silica. The gradient is 10% EtOAc in heptanes for 3 column volumes followed by a linear gradient to 50% over 10 column volumes and then 100% EtOAc for 2 column volumes with a ramp of 1 column volume. 25 mL fractions are collected. Fractions 7 through 22 are combined and evaporated in vacuo. Pumping to a constant weight gives amorphous white solid 1.73 g.

Example 172

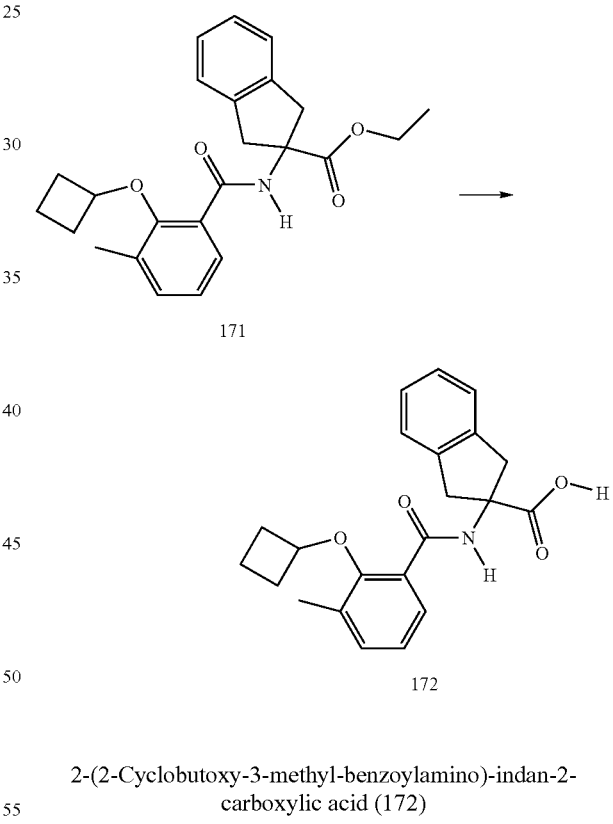

2-(2-Cyclobutoxy-3-methyl-benzoylamino)-indan-2-carboxylic acid (172)

A 50 mL flask containing the 2-[(2-cyclobutoxy-3-methyl-benzoyl)-amino]-indan-2-carboxylic acid ethyl ester (1.72 g, 4.37 mmol) is charged with 1,4-dioxane (16 mL) and MeOH (16 mL). A stirring bar is added and stirring is initiated. After dissolution, water (8 mL) is added followed by the LiOH (458 mg, 10.91 mmol). After 20 h, tlc analysis (silica, 5% i-PrOH/DCM) indicates that the starting material is completely consumed. The pH of the reaction mixture is carefully adjusted to pH 2 by slowly adding dilute aqueous HCl (3%, ~25 mL). The contents of the flask are poured into a separatory funnel containing EtOAc (60 mL). The layers are separated. The aqueous layer is extracted with EtOAc (30 mL). The combined organic extracts are washed with water (35 mL) and brine (35 mL), dried over MgSO4, filtered and concentrated. Pumping to constant weight gives 1.58 g of a white solid.

¹H NMR (300 MHz, DMSO-d6): δ 1.16-1.27 (m, 1H), 1.38-1.53 (m, 1H), 1.78-2.03 (m, 4H), 2.23, (s, 3H), 3.44 (dd, 4H), 4.34 (m, 1H), 7.03 (dd, 1H), 7.17-7.37 (m, 6H), 8.64 (s, 1H), 12.59 (bs, 1H).

LC/MS m/z=364.

Example 173

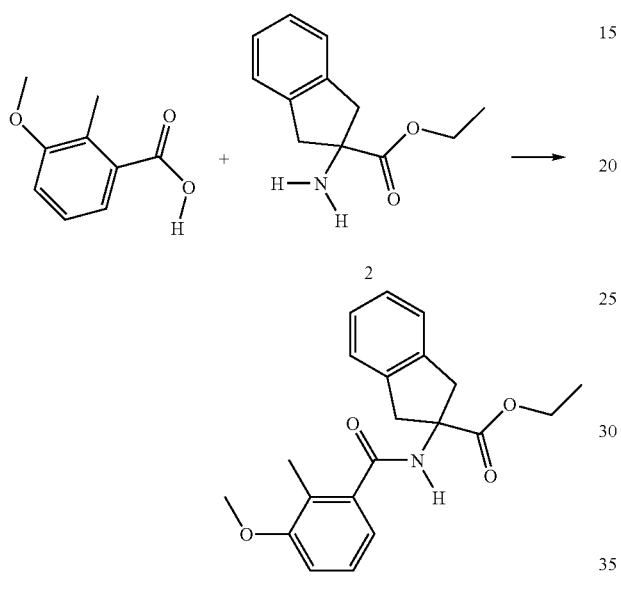

173

2-(3-Methoxy-2-methyl-benzoylamino)-indane-2-carboxylic acid ethyl ester (173)

A 100 mL round bottom flask is charged with 2-amino-indane-2-carboxylic acid ethyl ester (750 mg, 3.65 mmol) and dry DCM (10 mL). A stirring bar is added and stirring is initiated. The HBTU (1.38 g, 3.65 mmol) is added. After 2 min, the 2-methyl-3-methoxy-benzoic acid (0.61 g, 3.65 mmol) and DIPEA (1.5 mL, 8.6 mmol) are added. The reaction is allowed to stir for 36 h. Analysis by tlc of the reaction mixture (silica, 50% EtOAc/heptanes) indicates complete consumption of the starting amine. The contents of the reaction flask are diluted with EtOAc (50 mL) and transferred to a separatory funnel. This is washed consecutively with dilute aqueous NaHCO3 (25 mL) and brine (25 mL), dried over MgSO4, filtered and evaporated in vacuo to provide 1.1 g of thick brownish gum. This material is purified utilizing an ISCO Companion with a 40 g cartridge of silica. The gradient is 15% EtOAc in heptanes over 2 column volumes followed by a step gradient to 30% EtOAc then 50% and then 70% EtOAc for 3 column volumes each with ramp of 1 column volume. 35 mL fractions are collected. Fractions 15 through 21 are combined and evaporated in vacuo. Pumping to a constant weight gives a white solid (1.15 g).

¹H NMR (300 MHz, DMSO-d6): δ 1.19 (t, 3H), 2.12 (s, 3H), 3.54 (dd, 4H), 3.78 (s, 3H), 4.12 (q, 2H), 6.79 (d, 1H), 6.99 (d, 1H), 7.14-7.24 (m, 6H), 8.97 (s, 1H).

LC/MS m/z=354.

Example 174

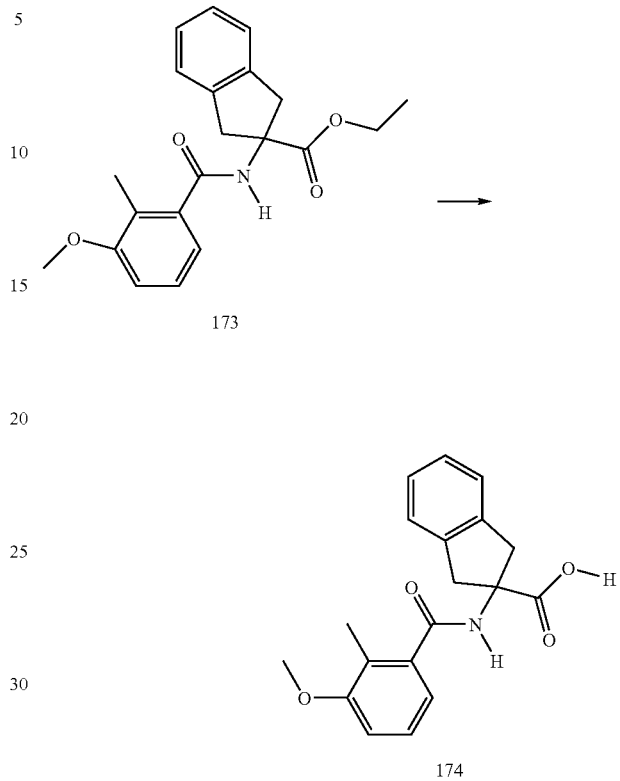

2-(3-Methoxy-2-methyl-benzoylamino)-indane-2-carboxylic acid (174)

A 40 mL vial containing the 2-(3-methoxy-2-methyl-benzoylamino)-indane-2-carboxylic acid ethyl ester (0.65 g, 1.84 mmol) is charged with THF (10 mL) MeOH (10 mL) and a stirring bar is added. Stirring is initiated. After dissolution, water (5 mL) is added followed by the LiOH (267 mg, 6.36 mmol). After 36 h, tlc analysis (silica, 5% i-PrOH/DCM) indicates that the starting material is completely consumed. The pH of the reaction mixture is carefully adjusted to pH 2 by slowly adding dilute aqueous HCl (3%, ~10 mL). The contents of the flask are poured into an addition funnel containing EtOAc (30 mL). The layers are separated. The aqueous layer is extracted with EtOAc (20 mL). The combined organic extracts are washed with water (20 mL) and brine (20 mL), dried over MgSO4, filtered and concentrated to yield 620 mg of amorphous white solid. The sample is purified by column chromatography (silica, 2% to 15% CH3OH in DCM) using an ISCO Companion and a 40 g cartridge. Fractions 14-16 are collected and evaporated by pumping to constant weight gives 380 mg of dry white powder.

¹H NMR (300 MHz, DMSO-d6): δ 2.11, (s, 3H), 3.44 (dd, 4H), 3.77, (s, 3H), 6.79 (d, 1H), 6.97 (d, 1H), 7.13-7.23 (m, 5H), 8.82 (s, 1H), 12.49 (s, 1H).

LC/MS m/z=326.

Example 175

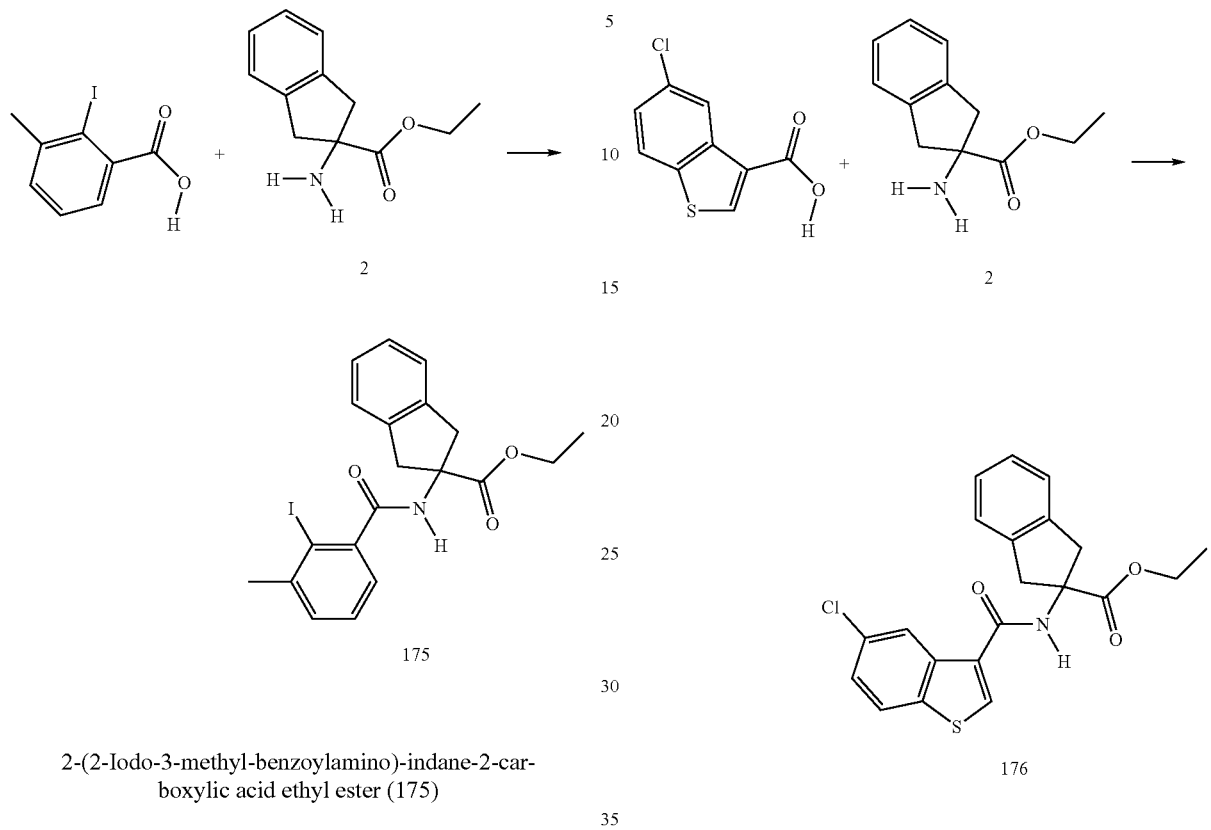

2-(2-Iodo-3-methyl-benzoylamino)-indane-2-carboxylic acid ethyl ester (175)

A 100 mL round bottom flask is charged with 2-iodo-3-methylbenzoic acid (1.92 g, 7.31 mmol) and dry DCM (25 mL). A stirring bar is added and stirring is initiated. After 5 min, the HBTU (2.37 g, 7.31 mmol) is added. After 5 min, the 2-amino-indane-2-carboxylic acid ethyl ester (1.5 g, 7.31 mmol) is added followed by N,N-diisopropylethyl-amine (3.2 mL, 18.37 mmol). The reaction is allowed to stir for 118 h. Analysis by tlc of the reaction mixture (silica, 15% iPrOH/DCM) indicates complete consumption of the starting amine. The contents of the reaction flask are transferred to a separatory funnel and diluted with EtOAc (70 mL). This is washed dilute aqueous HCl (3%, 2×30 mL), saturated aqueous NaHCO$_3$ (2×30 mL) and brine (30 mL), dried over MgSO$_4$, filtered and evaporated in vacuo to provide 2.04 g of a white solid. This material is dissolved in 15 mL of DCM. This material is purified utilizing an ISCO Companion with a 40 g cartridge of silica. The gradient is 10% EtOAc in heptanes over 4 column volumes followed by a linear gradient to 50% EtOAc over 10 column volumes. 27 mL fractions of UV active eluent are collected. Fractions 10 through 15 are combined and evaporated in vacuo. Pumping to constant weight gives 1.04 g a white solid material.

$^1$H NMR (300 MHz, DMSO-d6): δ 1.20 (t, 3H), 2.39 (s, 3H), 3.52 (dd, 4H), 4.15 (q, 2H), 6.79 (d, 1H), 6.97 (d, 1H), 7.16-7.24 (m, 4H), 7.28-7.38 (m, 2H), 9.15 (s, 1H).

LC/MS m/z=450.

Example 176

2-[(5-Chloro-benzo[b]thiophene-3-carbonyl)-amino]-indane-2-carboxylic acid ethyl ester (176)

To a 40 mL vial containing a stirring bar, 5-chloro-benzo[b]thiophene-3-carboxylic acid (518 g, 2.44 mmol) is charged with dry DCM (7 mL). Stirring is initiated. HBTU (922 mg, 2.43 mmol) and DIPEA (0.95 mL, 8.0 mmol) are added. Then 2-aminoindane-2-carboxylic acid ethyl ester (500 mg, 2.44 mmol) is added. The reaction is allowed to stir for 20 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous NaHCO$_3$ (25 mL) and brine (25 mL), dried over MgSO$_4$, filtered and evaporated in vacuo to provide 1.64 g of off white solid. This material is purified utilizing an ISCO Companion with a 40 g cartridge of silica. The gradient is 20% EtOAc in heptanes over 3 column volumes followed by a linear gradient to 50% over 8 column volumes and then 90% EtOAc for 2 column volumes with a ramp of 1 column volume. 25 mL fractions are collected.

Fractions 7 through 31 are combined and evaporated in vacuo. Pumping to a constant weight gives amorphous white solid 0.94 g.

Example 177

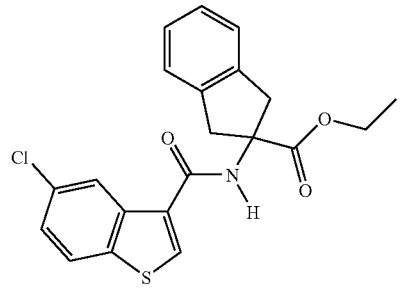

2-[(5-Chloro-benzo[b]thiophene-3-carbonyl)-amino]-indane-2-carboxylic acid (177)

A 50 mL flask containing the 2-[(5-chloro-3-benzo[b]thiophene-3-carbonyl)-amino]-indane-2-carboxylic acid ethyl ester (0.66 g, 1.65 mmol) is charged with 1,4-dioxane (10 mL) and MeOH 10 mL). A stirring bar is added and stirring is initiated. After dissolution, water (5 mL) is added followed by the LiOH (173 mg, 4.13 mmol). After 15 h, tlc analysis (silica, 5% i-PrOH/DCM) indicates that the starting material is completely consumed. The pH of the reaction mixture is carefully adjusted to pH 2 by slowly adding dilute aqueous HCl (3%, ~10 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over MgSO4, filtered and concentrated. Pumping to constant weight gives 590 mg of dry white powder.

$^1$H NMR (300 MHz, DMSO-d6): δ 3.52 (dd, 4H), 7.15-7.27 (m, 4H), 7.46 (dd, 1H), 8.09 (d, 1H), 8.44 (d, 1H), 8.52 (s, 1H), 8.99 (s, 1H), 12.55 (bs, 1H).

LC/MS m/z=372.

Example 178

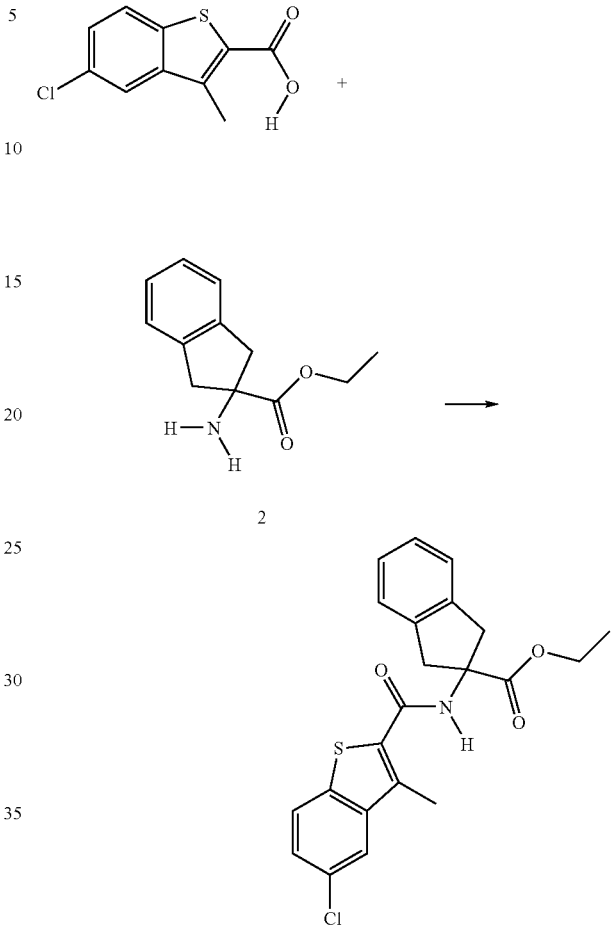

2-[(5-Chloro-3-methyl-benzo[b]thiophene-2-carbonyl)-amino]-indane-2-carboxylic acid ethyl ester (178)

To a 40 mL vial containing a stirring bar, 5-chloro3-methyl-benzo[b]thiophene-2-carboxylic acid ([50451-84-8], 0.81 g, 3.53 mmol) is charged with dry DCM (10 mL). Stirring is initiated. HBTU (1.34 g, 3.54 mmol) and the DIPEA (1.4 mL, 8.0 mmol) are added. The 2-aminoindane-2-carboxylic acid ethyl ester (0.725 g, 3.53 mmol) is added. The reaction is allowed to stir for 240 h. Analysis by tlc of the reaction mixture (silica, 10% MeOH/DCM) indicates complete consumption of the starting amine. The contents of the reaction flask are diluted with EtOAc (80 mL) and transferred to a reparatory funnel. This is washed consecutively with dilute aqueous NaHCO₃ (25 mL) and brine (25 mL), dried over MgSO₄, filtered and evaporated in vacuo to provide 1.26 g of a off white solid. This material is purified utilizing an ISCO Companion with a 40 g cartridge of silica. The gradient is 20% EtOAc in heptanes over 3 column volumes followed by a step gradient to 30% and then 50% and then 70% EtOAc for 2 column volumes each with a ramp of 1 column volume.

25 mL fractions are collected. Fractions 22 through 60 are combined and evaporated in vacuo. Pumping to a constant weight gives amorphous white solid 0.78 g.

Example 179

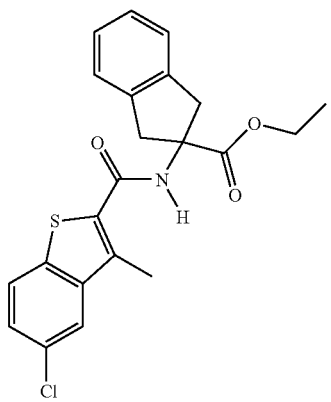

178

2-[(5-Chloro-3-methyl-benzo[b]thiophene-2-carbonyl)-amino]-indane-2-carboxylic acid (179)

40 mL vial containing the 2-[(5-chloro-3-methyl-benzo[b] thiophene-2-carbonyl)-amino]-indane-2-carboxylic acid ethyl ester (0.53 g, 1.28 mmol) is charged with MeOH (7.5 mL) and a stirring bar is added. Stirring is initiated. After dissolution, water (3.8 mL) is added followed by the LiOH (134 mg, 3.20 mmol). After 36 h, tlc analysis (silica, 5% i-PrOH/DCM) indicates that the starting material is completely consumed. The pH of the reaction mixture is carefully adjusted to pH 2 by slowly adding dilute aqueous HCl (3%, ~10 mL). The contents of the flask are poured into a reparatory funnel containing EtOAc (30 mL). The layers are separated. The aqueous layer is extracted with EtOAc (20 mL). The combined organic extracts are washed with water (20 mL) and brine (20 mL), dried over MgSO$_4$, filtered and concentrated to yield 360 mg of amorphous white solid.

$^1$H NMR (300 MHz, DMSO-d6): δ 2.45 (s, 3H) 3.49 (dd, 4H), 7.15-7.29 (m, 4H), 7.48 (dd, 1H), 7.92 (d, 1H), 8.02 (d, 1H), 8.96 (s, 1H).

LC/MS m/z=386.

Example 180

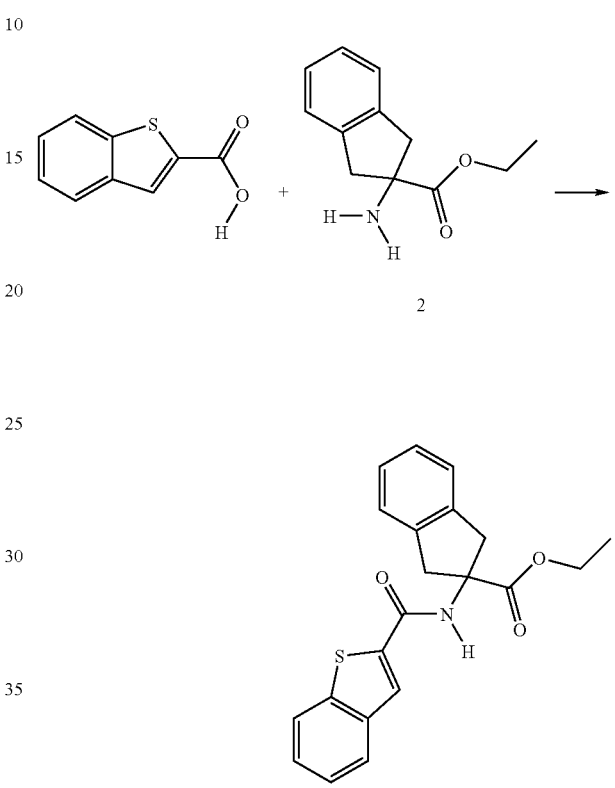

180

2-[(Benzo[b]thiophene-2-carbonyl)-amino]-indane-2-carboxylic acid ethyl ester (180)

To a 40 mL vial containing a stirring bar, benzo[b] thiophene-2-carboxylic acid (518 g, 2.44 mmol) is charged with dry DCM (7 mL). Stirring is initiated. HBTU (922 mg, 2.43 mmol) and the DIPEA (0.95 mL, 8.0 mmol) are added. The 2-aminoindane-2-carboxylic acid ethyl ester (500 mg, 2.44 mmol) is added. The reaction is allowed to stir for 110 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous NaHCO$_3$ (25 mL) and brine (25 mL), dried over MgSO4, filtered and evaporated in vacuo to provide 1.54 g of an off white solid. This material is purified utilizing an ISCO Companion with a 40 g cartridge of silica. The gradient is 20% EtOAc in heptanes over 3 column volumes followed by a linear gradient to 50% over 10 column volumes and then 90% EtOAc for 2 column volumes with a ramp of 1 column volume. 25 mL fractions are collected.

Fractions 13 through 27 are combined and evaporated in vacuo. Pumping to a constant weight gives amorphous white solid 0.62 g.

Example 181

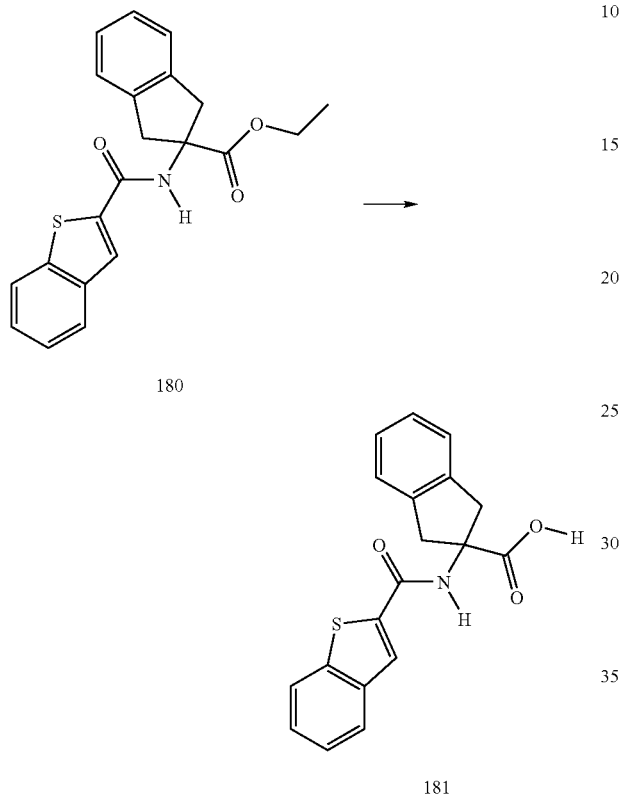

2-[(Benzo[b]thiophene-2-carbonyl)-amino]-indane-2-carboxylic acid (181)

A 50 mL flask containing the 2-[(Benzo[b]thiophene-2-carbonyl)-amino]-indan-2-carboxylic acid ethyl ester (0.37 g, 1.01 mmol) is charged with 1,4-dioxane (6 mL) and MeOH (6 mL). A stirring bar is added and stirring is initiated. After dissolution, water (3.0 mL) is added followed by the LiOH (106 mg, 2.53 mmol). After 18 h, tlc analysis (silica, 5% i-PrOH/DCM) indicates that the starting material is completely consumed. The pH of the reaction mixture is carefully adjusted to pH 2 by slowly adding dilute aqueous HCl (3%, ~10 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over MgSO$_4$, filtered and concentrated. Pumping to constant weight gives 290 mg (89%) of dry white powder.

$^1$H NMR (300 MHz, DMSO-d6): δ 3.57 (dd, 4H), 7.15-7.32 (m, 4H), 7.45-7.48 (m, 2H) 7.91 (dd, 1H), 8.01 (dd, 1H), 8.18 (s, 1H), 9.11 (s, 1H), 12.58 (bs, 1H).

LC/MS m/z=338.

Example 182

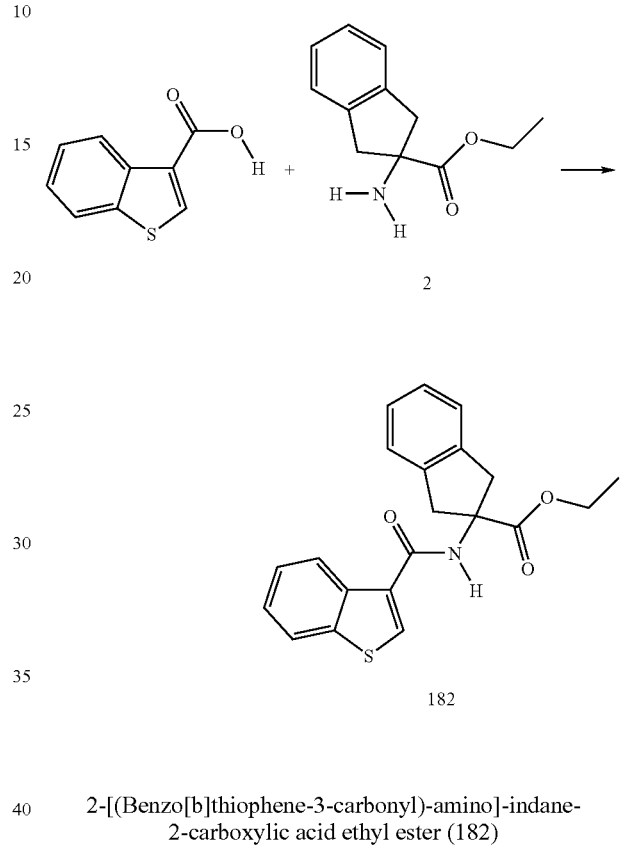

2-[(Benzo[b]thiophene-3-carbonyl)-amino]-indane-2-carboxylic acid ethyl ester (182)

To a 40 mL vial containing a stirring bar, benzo[b]thiophene-3-carboxylic acid ([5381-25-9], 434 g, 2.44 mmol) is charged with dry DCM (7 mL). Stirring is initiated. HBTU (922 mg, 2.43 mmol) and DIPEA (0.95 mL, 8.0 mmol) are added. The 2-aminoindane-2-carboxylic acid ethyl ester (500 mg, 2.44 mmol) is added. The reaction is allowed to stir for 20 h. Analysis by tlc of the reaction mixture (silica, 10% MeOH/DCM) indicates complete consumption of the starting amine. The contents of the reaction flask are diluted with EtOAc (50 mL) and transferred to a reparatory funnel. This is washed consecutively with dilute aqueous NaHCO$_3$ (25 mL) and brine (25 mL), dried over MgSO$_4$, filtered and evaporated in vacuo to provide 1.64 g of off white solid. This material is purified utilizing an ISCO Companion with a 40 g cartridge of silica. The gradient is 20% EtOAc in heptanes over 3 column volumes followed by a linear gradient to 50% over 8 column volumes and then 90% EtOAc for 2 column volumes with a ramp of 1 column volume. 25 mL fractions are collected.

Fractions 4 through 16 are combined and evaporated in vacuo. Pumping to a constant weight gives amorphous white solid 0.69 g.

Example 183

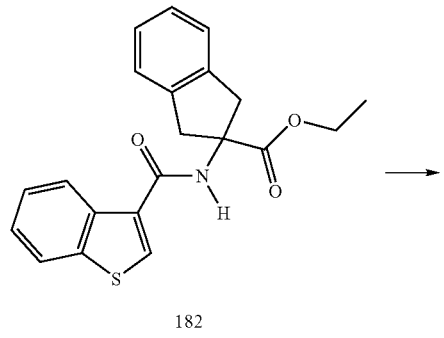

182

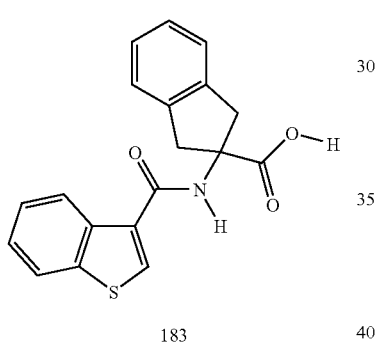

183

2-[(Benzo[b]thiophene-3-carbonyl)-amino]-indane-2-carboxylic acid (183)

A 50 mL flask containing the 2-[(benzo[b]thiophene-3-carbonyl)-amino]-indan-2-carboxylic acid ethyl ester (182, 0.40 g, 1.10 mmol) is charged with 1,4-dioxane (10 mL) and MeOH 10 mL). A stirring bar is added and stirring is initiated. After dissolution, water (5.0 mL) is added followed by the LiOH (115 mg, 2.74 mmol). After 18 h, tlc analysis (silica, 50% EtOAc/heptanes) indicates that the starting material is completely consumed. Dilute aqueous HCl (3%, ~15 mL) and EtOAc (25 mL) are added to the reaction flask. After stirring for 10 min, the contents of the flask are poured into a reparatory funnel. The layers are separated. The aqueous layer is extracted with EtOAc (30 mL). The combined organic extracts are washed with water (20 mL) and brine (20 mL), dried over MgSO$_4$, filtered and concentrated. Pumping to constant weight gives 450 mg of a dry white powder.

$^1$H NMR (300 MHz, DMSO-d6): δ 3.52 (dd, 4H), 7.18-7.28 (m, 4H), 7.38-7.43 (m, 2H) 8.03X (dd, 1H), 8.37-8.41 (m, 2H), 8.92 (s, 1H), 13.53 (bs, 1H).

LC/MS m/z=338.

Example 184

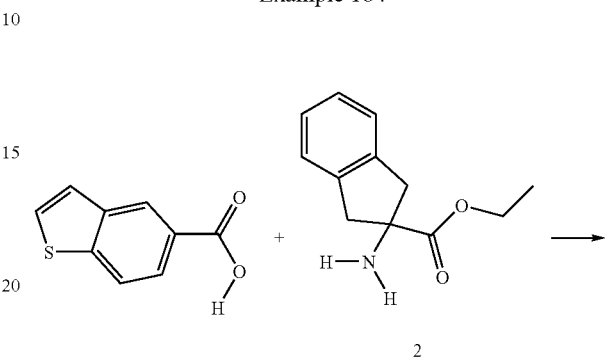

2

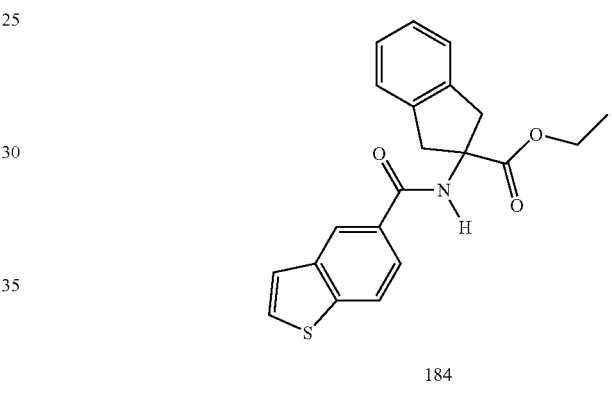

184

2-[(Benzo[b]thiophene-5-carbonyl)-amino]-indane-2-carboxylic acid ethyl ester (184)

To a 40 mL vial containing a stirring bar, benzo[b]thiophene-5-carboxylic acid (434 g, 2.44 mmol) is charged with dry DCM (7 mL). Stirring is initiated. HBTU (922 mg, 2.43 mmol) and DIPEA (0.95 mL, 8 mmol) are added. The 2-aminoindane-2-carboxylic acid ethyl ester (500 mg, 2.44 mmol) is added. The reaction is allowed to stir for 64 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous NaHCO$_3$ (25 mL) and brine (25 mL), dried over MgSO4, filtered and evaporated in vacuo to provide 1.4 g of an off white solid. This material is purified utilizing an ISCO Companion with a 40 g cartridge of silica. The gradient is 10% EtOAc in heptanes over 3 column volumes followed by a linear gradient to 50% over 8 column volumes and then 90% EtOAc for 2 column volumes with a ramp of 1 column volume. 25 mL fractions are collected.

Fractions 4 through 16 are combined and evaporated in vacuo. Pumping to a constant weight gives amorphous white solid 0.79 g.

$^1$H NMR (300 MHz, DMSO-d6): δ 3.57 (dd, 4H), 7.18-7.28 (m, 5H), 7.59 (d, 1H), 7.78-7.93 (m, 2H), 8.08 (d, 1H), 8.41 (s, 1H), 8.91 (s, 1H).

LC/MS m/z=338.

Example 185

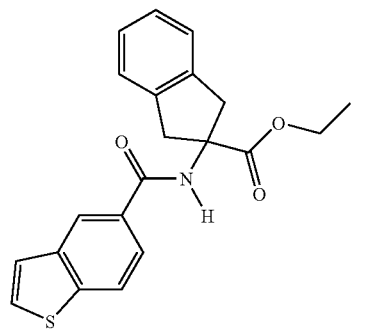

184

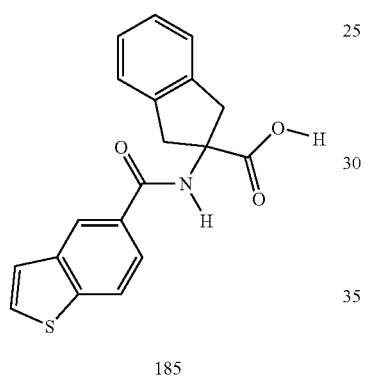

185

2-[(Benzo[b]thiophene-5-carbonyl)-amino]-indane-2-carboxylic acid (185)

A 50 mL flask containing the 2-[(benzo[b]thiophene-5-carbonyl)-amino]-indane-2-carboxylic acid ethyl ester (184, 0.45 g, 1.25 mmol) is charged with 1,4-dioxane (8 mL) and MeOH (8 mL). A stirring bar is added and stirring is initiated. After dissolution, water (4.0 mL) is added followed by the LiOH (131 mg, 3.11 mmol). After 114 h, tlc analysis (silica, 5% i-PrOH/DCM) indicates that the starting material is completely consumed. The pH of the reaction mixture is carefully adjusted to pH 2 by slowly adding dilute aqueous HCl (3%, ~12 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over MgSO$_4$, filtered and concentrated. Pumping to constant weight gives 0.42 g of off-white solid.

Example 186

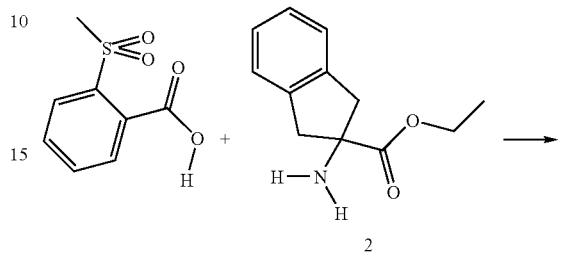

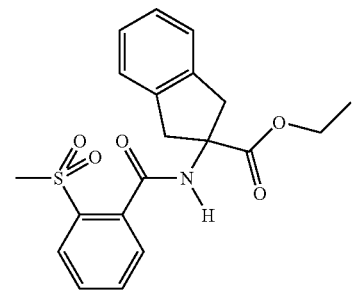

186

2-[(2-methylsulfonylbenzen-1-carbonyl)-amino]-indan-2-carboxylic acid ethyl ester (186)

To a 40 mL vial containing a stirring bar, 2-(methylsulfonyl)benzoic acid (0.4 g, 2.88 mmol) is charged with dry DCM (7 mL). Stirring is initiated. HBTU (922 mg, 2.43 mmol). The 2-aminoindane-2-carboxylic acid ethyl ester (500 mg, 2.44 mmol) is added followed by the DIPEA (0.95 mL, 8 mmol). The reaction is allowed to stir for 36 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous NaHCO$_3$ (25 mL) and brine (25 mL), dried over MgSO4, filtered and evaporated in vacuo to provide 1.32 g of white solid. This material is dissolved in 10 mL of DCM and purified utilizing an ISCO Companion with a 40 g cartridge of silica. The gradient is 15% EtOAc in heptanes for 3 column volumes followed by a linear gradient to 50% over 8 column volumes and then 90% EtOAc for 2 column volumes with a ramp of 1 column volume. 25 mL fractions are col- Example 187

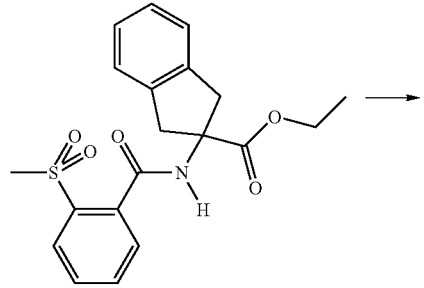

186

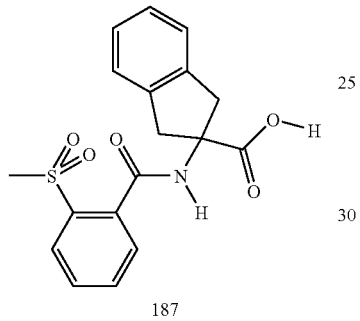

187

2-[(2-methylsulfonylbenzen-1-carbonyl)-amino]-
indan-2-carboxylic acid (187)

lected. Fractions 5 through 8 are combined and evaporated in vacuo. Pumping to a constant weight gives amorphous white solid 0.71 g.

A 50 mL flask containing 2-[(2-methylsulfonylbenzene-1-carbonyl)-amino]-indan-2-carboxylic acid ethyl ester (186, 0.50 g, 1.27 mmol) is charged with 1,4-dioxane (5 mL) and MeOH (5 mL). A stirring bar is added and stirring is initiated. After dissolution, water (2.5 mL) is added followed by the LiOH (133 mg, 3.17 mmol). After 69 h, tlc analysis (silica, 5% i-PrOH/DCM) indicates that the starting material is completely consumed. The pH of the reaction mixture is carefully adjusted to pH 2 by slowly adding dilute aqueous HCl (3%, ~12 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over MgSO$_4$, filtered and concentrated. Pumping to constant weight gives 0.46 g of white solid.

$^1$H NMR (300 MHz, DMSO-d6): δ 3.37-3.61 (m, 7H), 7.16-7.23 (m, 4H), 7.54 (d, 1H), 7.69 (dd, 1H), 7.79 (dd, 1H), 7.93 (d, 1H), 9.25 (s, 1H), 12.55 (s, 1H).

LC/MS m/z=360.

Example 188

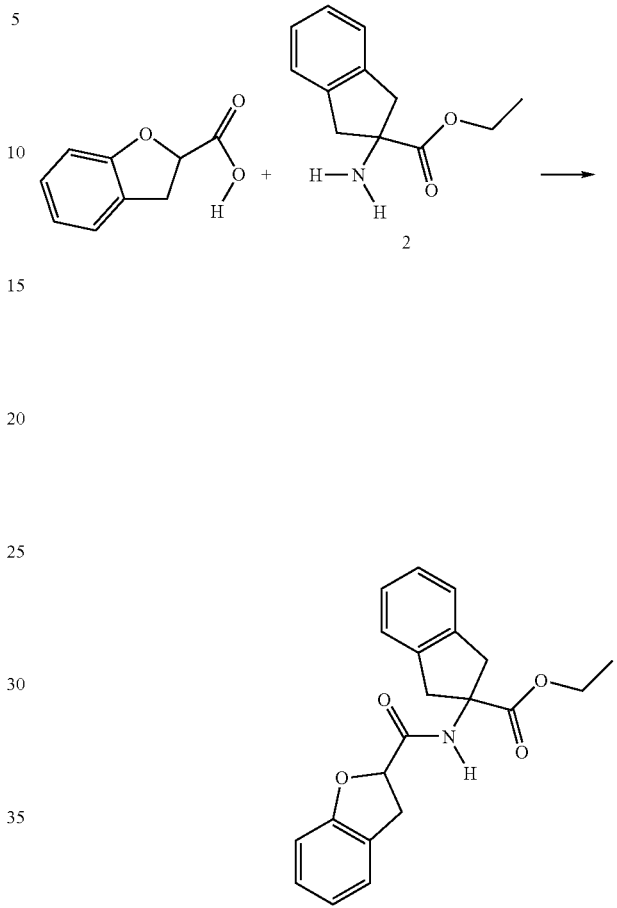

2-[(2,3-Dihydrobenzofuran-2-carbonyl)-amino]-
indan-2-carboxylic acid ethyl ester (188)

To a 40 mL vial containing a stirring bar, 2,3-dihydro-1-benzofuran-2-carboxylic acid (0.4 g, 2.44 mmol) is charged with dry DCM (7 mL). Stirring is initiated. HBTU (922 mg, 2.43 mmol) and the DIPEA (0.95 mL, 8.0 mmol) are added. The 2-aminoindane-2-carboxylic acid ethyl ester (500 mg, 2.44 mmol) is added. The reaction is allowed to stir for 16 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous NaHCO$_3$ (25 mL) and brine (25 mL), dried over MgSO$_4$, filtered and evaporated in vacuo to provide 1.47 g of viscous yellow oil. This material is dissolved in 10 mL of DCM and purified utilizing an ISCO Companion with a 40 g cartridge of silica. The gradient is 15% EtOAc in heptanes for 3 column volumes followed by a linear gradient to 50% over 8 column volumes and then 90% EtOAc for 2 column volumes with a ramp of 1 column volume. 25 mL fractions are collected. Fractions 3 through 6 are combined and evaporated in vacuo. Pumping to a constant weight gives amorphous white solid 0.68 g.

Example 189

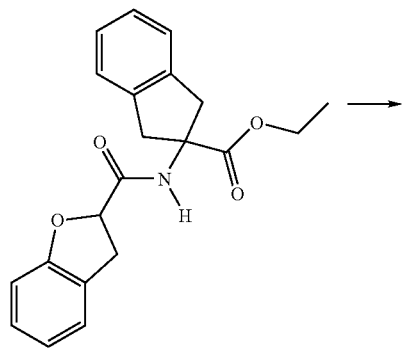

188

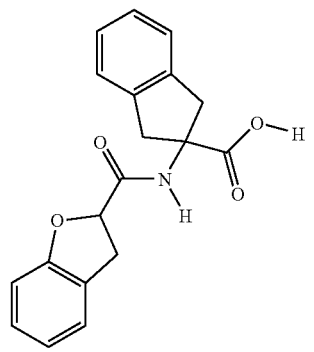

189

2-[(2,3-Dihydrobenzofuran-2-carbonyl)-amino]-indan-2-carboxylic acid (189)

A 50 mL flask containing the 2-[(2,3-dihydrobenzofuran-2-carbonyl)-amino]-indan-2-carboxylic acid ethyl ester (0.447 g, 1.39 mmol) is charged with 1,4-dioxane (5 mL) and MeOH (5 mL). A stirring bar is added and stirring is initiated. After dissolution, water (2.5 mL) is added followed by the LiOH hydrate (133 mg, 3.17 mmol). After 19 h, tlc analysis (silica, 5% i-PrOH/DCM) indicates that the starting material is completely consumed. The pH of the reaction mixture is carefully adjusted to pH 2 by slowly adding dilute aqueous HCl (3%, ~12 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over MgSO₄, filtered and concentrated. Pumping to constant weight gives 0.43 g of white solid.

¹H NMR (300 MHz, DMSO-d6): δ 3.17 (dd, 1H), 3.21-3.58 (m, 5H), 5.13 (dd, 1H), 6.79 (dd, 1H), 6.84 (dd, 1H), 7.03-7.28 (m, 6H) 8.64 (s, 1H), 12.55 (bs, 1H).

LC/MS m/z=324.

Example 190

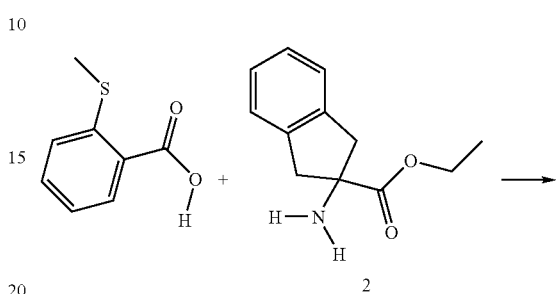

190

2-[(2-methylthiolbenzen-1-carbonyl)-amino]-indan-2-carboxylic acid ethyl ester (190)

To a 40 mL vial containing a stirring bar, 2-(methylthiol)benzoic acid ([3724-10-5], 0.0410 g, 2.44 mmol) is charged with dry DCM (7 mL). Stirring is initiated. HBTU (922 mg, 2.43 mmol) is added. After 2 min, the 2-aminoindane-2-carboxylic acid ethyl ester (500 mg, 2.44 mmol) is added followed by DIPEA (0.95 mL, 8.0 mmol). The reaction is allowed to stir for 38 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous HCl (3%, 25 mL), saturated aqueous NaHCO₃ (25 mL) and brine (25 mL), dried over MgSO₄, filtered and evaporated in vacuo to provide 1.49 g of viscous yellow oil. This material is dissolved in 10 mL of DCM and purified utilizing an ISCO Companion with a 40 g cartridge of silica. The gradient is 15% EtOAc in heptanes for 3 column volumes followed by a linear gradient to 50% over 8 column volumes and then 90% EtOAc for 2 column volumes with a ramp of 1 column volume. 25 mL fractions are collected. Fractions 8 through 15 are Example 191

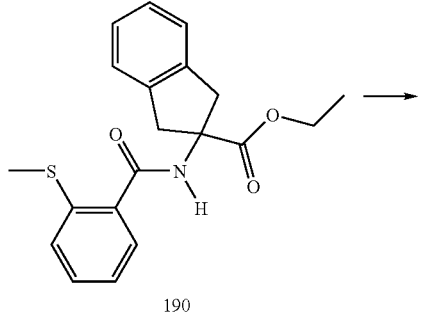

190

Example 192

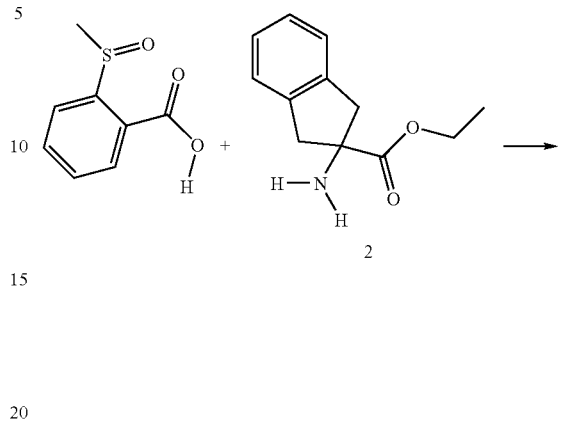

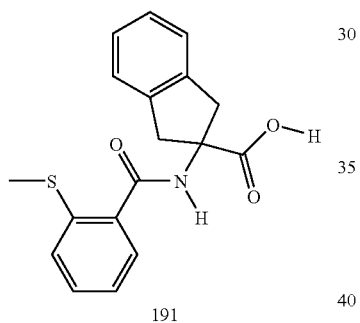

191

2-[(2-methylthiolbenzen-1-carbonyl)-amino]-indan-2-carboxylic acid (191)

A 50 mL flask containing the 2-[(2-methylthiobenzene-2-carbonyl)-amino]-indan-2-carboxylic acid ethyl ester (0.510 g, 1.44 mmol) is charged with 1,4-dioxane (5 mL) and MeOH (5 mL). A stirring bar is added and stirring is initiated. After dissolution, water (2.5 mL) is added followed by the LiOH hydrate (150 mg, 3.58 mmol). After 96 h, tlc analysis (silica, 5% i-PrOH/DCM) indicates that the starting material is completely consumed. The pH of the reaction mixture is carefully adjusted to pH 2 by slowly adding dilute aqueous HCl (3%, ~12 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over MgSO4, filtered and concentrated. Pumping to constant weight gives 0.34 g of white solid.

$^1$H NMR (300 MHz, DMSO-d6): δ 2.37 (s, 3H), 3.47 (dd, 4H), 7.14-7.21 (m, 5H), 7.22-7.44 (m, 3H), 8.88 (s, 1H), 12.46 (s, 1H).

LC/MS m/z=328.

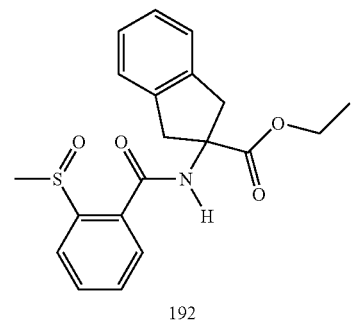

192

2-[(2-methylsulfinylbenzoyl)-amino]-indan-2-carboxylic acid ethyl ester (192)

To a 40 mL vial containing a stirring bar, 2-(methylsulfinyl)benzoic acid (0.449 g, 2.44 mmol) is charged with dry DCM (7 mL). Stirring is initiated. HBTU (922 mg, 2.43 mmol) is added. The 2-aminoindane-2-carboxylic acid ethyl ester ([500 mg, 2.44 mmol) is added followed by DIPEA (0.95 mL, 8.0 mmol). The reaction is allowed to stir for 94 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous NaHCO$_3$ (25 mL) and brine (25 mL), dried over MgSO$_4$, filtered and evaporated in vacuo to provide 1.2 g of yellow foam. This material is dissolved in 10 mL of DCM and purified utilizing an ISCO Companion with a 40 g cartridge of silica. The gradient is 10% EtOAc in heptanes for 3 column volumes followed by a linear gradient to 100% EtOAc over 8 column volumes and then hold for 5 column volumes. 25 mL fractions are col-

Example 193

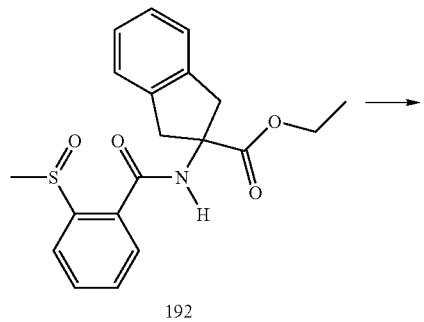

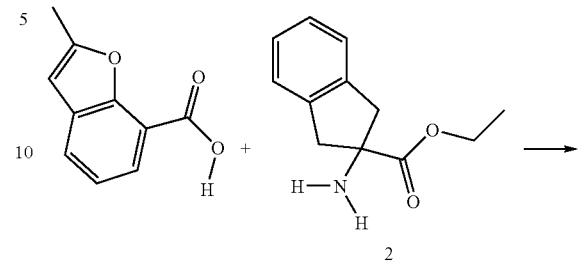

Example 194

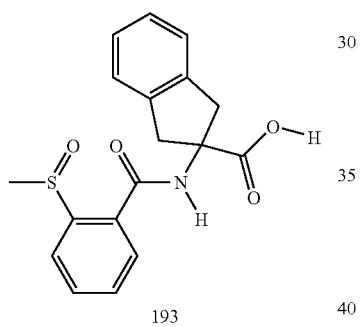

2-[(2-methylsulfinylbenzoyl)-amino]-indan-2-carboxylic acid (193)

A 50 mL flask containing the 2-(2-methylsulfinylbenzoyl-amino)-indan-2-carboxylic acid ethyl ester (0.50 g, 1.34 mmol) is charged with 1,4-dioxane (5 mL) and MeOH (5 mL). A stirring bar is added and stirring is initiated. After dissolution, water (2.5 mL) is added followed by the LiOH (141 mg, 3.36 mmol). After 39 h, tlc analysis (silica, 5% i-PrOH/DCM) indicates that the starting material is completely consumed. The pH of the reaction mixture is carefully adjusted to pH 2 by slowly adding dilute aqueous HCl (3%, ~12 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over $MgSO_4$, filtered and concentrated by vacuum to constant weight of 0.39 g of white solid.

$^1$H NMR (300 MHz, DMSO-d6): δ 3.35 (s, 3H), 3.48 (dd, 4H), 7.16-7.27 (m, 4H), 7.60 (dd, 1H), 7.67-7.84, (m, 2H), 8.07 (d, 1H), 9.22 (s, 1H), 12.63 (bs, 1H).

LC/MS m/z=344.

2-[(2-Methylbenzofuran-7-carbonyl)-amino]-indan-2-carboxylic acid ethyl ester (194)

To a 25 mL vial containing a stirring bar, 2-methylbenzofuran-7-carboxylic acid (0.343 g, 1.95 mmol) is charged with dry DCM (6 mL). Stirring is initiated. HBTU (738 mg, 1.95 mmol) is added. The 2-aminoindane-2-carboxylic acid ethyl ester (400 mg, 1.95 mmol) is added followed by DIPEA (0.75 mL, 4.31 mmol). The reaction is allowed to stir for 16 h. Analysis by tlc of the reaction mixture (silica, 10% EtOH/dichloromethane) indicates complete consumption of the starting amine. The contents of the reaction flask are diluted with EtOAc (50 mL) and transferred to a separatory funnel. This is washed consecutively with dilute aqueous HCl (3%, 25 mL), saturated aqueous $NaHCO_3$ (25 mL) and brine (25 mL), dried over $MgSO_4$, filtered and evaporated in vacuo to provide 0.97 g of yellow oil. This material is dissolved in 10 mL of DCM. This is purified utilizing an ISCO Companion with a 40 g cartridge of silica. The gradient is 15% EtOAc in heptanes for 3 column volumes followed by a linear gradient to 90% over 15 column volumes and then 100% EtOAc for 2 column volumes with a ramp of 1 column volume. 25 mL fractions are collected. Fractions 2 through 7 are combined and evaporated in vacuo to a constant weight to give 0.63 g of amorphous white solid.

Example 195

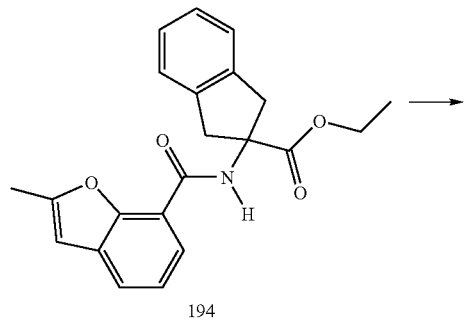

194

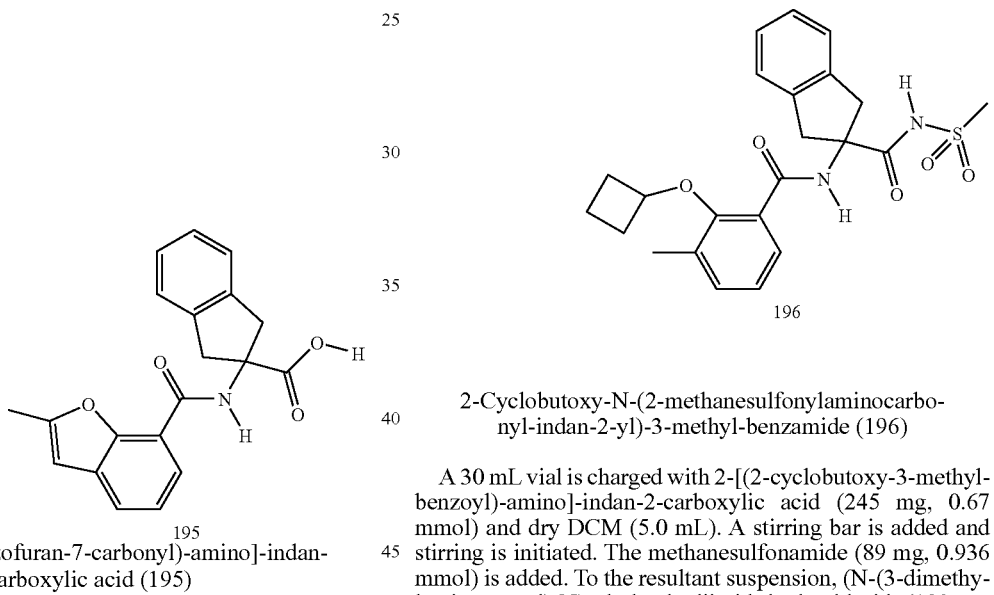

195
2-[(2-Methylbenzofuran-7-carbonyl)-amino]-indan-2-carboxylic acid (195)

A 50 mL flask containing the 2-[(2-methylbenzofuran-7-carbonyl)-amino]-indan-2-carboxylic acid ethyl ester (0.40 g, 1.10 mmol) is charged with 1,4-dioxane (4 mL) and MeOH (4 mL). A stirring bar is added and stirring is initiated. After dissolution, water (2 mL) is added followed by the LiOH (115 mg, 2.75 mmol). After 18 h, tlc analysis (silica, 5% i-PrOH/DCM) indicates that the starting material is completely consumed. The pH of the reaction mixture is carefully adjusted to pH 2 by slowly adding dilute aqueous HCl (3%, ~12 mL). The contents of the flask are poured into a reparatory funnel containing EtOAc (30 mL). The layers are separated. The aqueous layer is extracted with EtOAc (20 mL). The combined organic extracts are washed with water (20 mL) and brine (20 mL), dried over MgSO₄, filtered and concentrated by vacuum to constant weight to give 0.37 g of white solid.

$^1$H NMR (300 MHz, DMSO-d6): δ 2.42, (s, 3H), 3.47 (dd, 4H), 6.68, (s, 1H), 7.17-7.27 (m, 5H) 7.57 (dd, 1H), 7.67 (dd, 1H), 8.68 (s, 1H), 12.63 (s, 1H).

LC/MS m/z=336.

Example 196

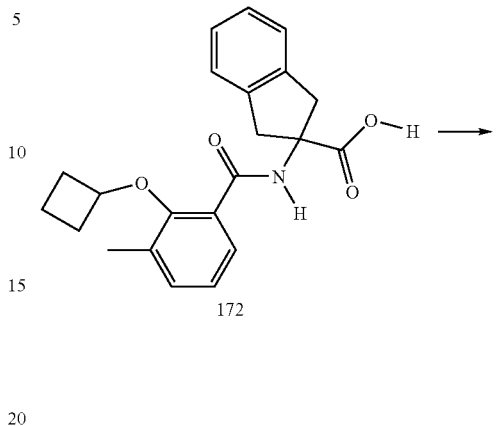

172

2-Cyclobutoxy-N-(2-methanesulfonylaminocarbo-nyl-indan-2-yl)-3-methyl-benzamide (196)

A 30 mL vial is charged with 2-[(2-cyclobutoxy-3-methyl-benzoyl)-amino]-indan-2-carboxylic acid (245 mg, 0.67 mmol) and dry DCM (5.0 mL). A stirring bar is added and stirring is initiated. The methanesulfonamide (89 mg, 0.936 mmol) is added. To the resultant suspension, (N-(3-dimethy-laminopropyl)-N'-ethylcarbodiimide hydrochloride (120 mg, 0.624 mmol) and 4-dimethylaminopyridine (76 mg, 0.62 mmol) are added. After 6 days, tlc analysis (silica, 10% MeOH in DCM) indicates that the starting acid is consumed. The reaction mixture is diluted with EtOAc (50 mL), transferred to a separatory funnel and washed with dilute aqueous HCl (3 N, 3×20 mL) and brine, dried over MgSO₄, filtered and evaporated by pumping to constant weight gives 0.26 g of amorphous white foam. This material is dissolved in DCM (5 mL) and applied to a 12 g column (silica) on an ISCO Companion. The column is eluted with 1% iPrOH in DCM for 3 column volumes followed by a linear gradient to 30% iPrOH in DCM over 15 column volumes. 12 mL fractions of UV active eluent are collected. Fractions 4 through 9 are combined and evaporated to a constant weight to give 0.2 g of white solid.

$^1$H NMR (300 MHz, DMSO-d6): δ 1.01-1.31 (m, 2H), 1.45-1.68 (m, 2H), 1.72-1.83 (m, 2H), 2.21 (s, 3H), 3.18 (s, 3H), 3.42 (m, 4H), 4.18 (m, 1H), 7.16 (t, 1H), 7.19-7.22 (m, 2H), 7.27-7.36 (m, 2H), 7.38 (d, 1H), 7.62 (d, 1H), 8.43 (s, 1H), 11.59 (s, 1H).

LC/MS m-/z=441.

Example 197

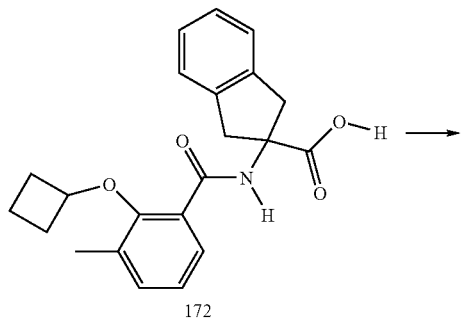

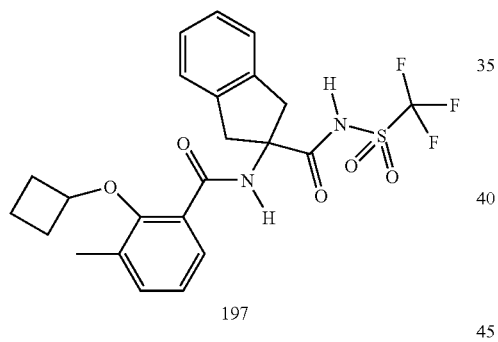

2-Cyclobutoxy-3-methyl-N-(2-trifluoromethane-sulfonylaminocarbonyl-indan-2-yl)-benzamide (197)

A 30 mL vial is charged with 2-[(2-cyclobutoxy-3-methyl-benzoyl)-amino]-indan-2-carboxylic acid (323 mg, 0.884 mmol) and dry DCM (7.0 mL). A stirring bar is added and stirring is initiated, and then trifluoromethanesulfonamide (198 mg, 1.33 mmol) is added. To the resultant suspension, N-(3-dimethylaminopropyl)-N'-ethylcarbodiimide hydrochloride (170 mg, 0.88 mmol) and 4-dimethylaminopyridine (108 mg, 0.88 mmol) are added. After 8 days, tlc analysis (silica, 10% MeOH in DCM) indicates that the starting acid had been consumed. The reaction mixture is diluted with EtOAc (50 mL), transferred to a separatory funnel and washed with dilute aqueous HCl (3 N, 2×20 mL) and brine, dried over MgSO$_4$, filtered and evaporated to constant weight to give 0.51 g of white solid.

$^1$H NMR (300 MHz, DMSO-d6): δ 1.21-1.38 (m, 1H), 1.41-1.56 (m, 1H), 1.91-2.04 (m, 4H), 2.23 (s, 3H), 3.42 (m, 4H), 4.37 (m, 1H), 7.04 (t, 1H), 7.14-7.21 (m, 4H), 7.31 (d, 1H), 7.51 (d, 1H), 8.66 (s, 1H), 8.95 (s, 1H).

LC/MS m/z=497.

Example 198

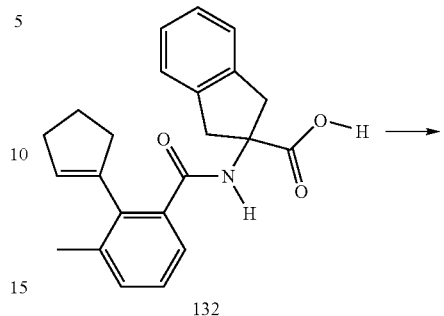

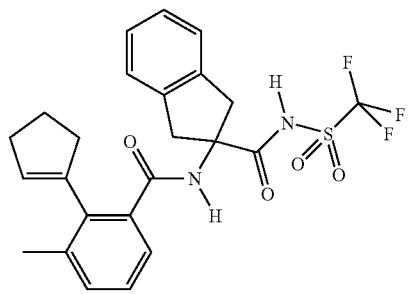

2-Cyclopent-1-enyl-3-methyl-N-(2-trifluoromethanesulfonylaminocarbonyl-indan-2-yl)-benzamide (198)

A 50 mL flask is charged with 2-(2-cyclopent-1-enyl-3-methyl-benzoyllamino)-indan-2-carboxylic acid (323 mg, 0.884 mmol) and dry DCM (7.0 mL). A stirring bar is added and stirring is initiated. Trifluoromethanesulfonamide (198 mg, 1.33 mmol) is added. To the resultant suspension, N-(3-dimethylaminopropyl)-N'-ethylcarbodiimide hydrochloride 170 mg, 0.88 mmol) and 4-dimethylaminopyridine ([MFCD00006418], 108 mg, 0.88 mmol) are added. After 80 h, tlc analysis (silica, 10% MeOH in DCM) indicates that the starting acid had been consumed. The reaction mixture is diluted with EtOAc (50 mL), transferred to a separatory funnel and washed with dilute aqueous HCl (3 N, 2×20 mL) and brine, dried over MgSO$_4$, filtered and evaporated to constant weight to give 0.50 g of white solid.

$^1$H NMR (300 MHz, DMSO-d6): δ 1.76 (m, 2H), 2.17 (s, 3H), 2.22-2.42 (m, 4H), 3.38 (dd, 4H), 5.39, (s, 1H), 7.04-7.29 (m, 7H), 8.02 (s, 1H), 8.94 (s, 1H).

LC/MS m/z=493.

Example 199

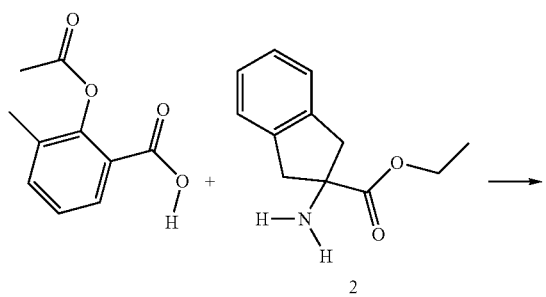

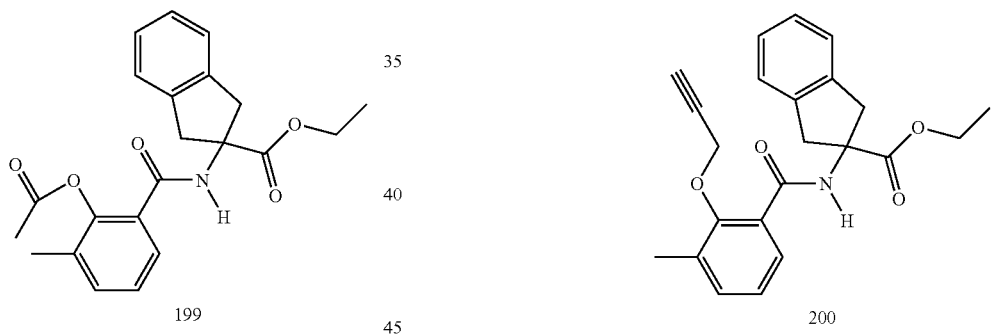

2-(2-Acetoxy-3-methyl-benzoyl-amino)-indane-2-carboxylic acid ethyl ester (199)

A 40 mL vial containing a stirring bar is charged with 2-acetoxyl-3-methyl-benzoic acid (1 g, 4.87 mmol) and dry DCM (14 mL), and stirring is initiated. After dissolution is complete, HBTU (1.85 g, 4.87 mmoles) is added. After 5 min, 2-amino-indane-2-carboxylic acid ethyl ester (1 g, 4.87 mmol) is added followed by DIPEA (2.1 mL, 12.18 mmol). The reaction is allowed to stir for 110 h. Analysis by tlc of the reaction mixture (silica, 5% iPrOH/DCM) indicates complete consumption of the starting amine. The contents of the reaction flask are transferred to a reparatory funnel and diluted with EtOAc (100 mL). This is washed consecutively with dilute aqueous HCl (3%, 40 mL), saturated aqueous NaHCO₃ (50 mL) and brine (50 mL), dried over MgSO₄, filtered and evaporated in vacuo to provide 3 g of a light orange solid. This material is dissolved in 15 mL of DCM. This material is purified utilizing an ISCO Companion with an 80 g cartridge of silica. The gradient is 10% EtOAc in heptanes over 3 column volumes followed by a linear gradient to 50% EtOAc over 12 column volumes. Fractions 19 through 27 are combined and evaporated in vacuo to give 1.38 g of white solid.

Example 200

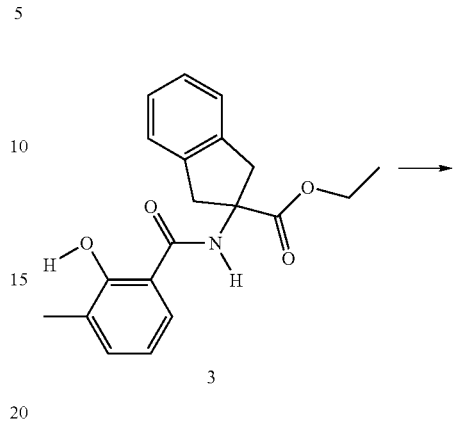

2-(3-Methyl-2-prop-2-ynyloxy-benzoylamino)-indan-2-carboxylic acid ethyl ester (200)

A 100 mL round bottom flask containing the 2-(hydroxy-3-methyl-benzoyl)-indan-2-carboxylic acid ethyl ester (3) (0.29 g 0.855 mmol) is charged with DMF (4 mL) and a stirring bar is added. After dissolution of the starting material, $K_2SO_4$ (0.3 g, 2.17 mmol) is added followed by a solution of propargyl bromide in toluene (11.59 M, 240 µL, 2.78 mmol). After stirring for 62 h tlc analysis (silica, 1:1 EtOAc/heptanes) indicates that the starting material had been consumed. The material is cleanly converted to a UV positive spot with a slightly lower Rf. The reaction is diluted with EtOAc (80 mL) and filtered through a pad of Celite. The filtrate is transferred to a reparatory funnel. This is washed repeatedly with a saturated aqueous solution of NaHCO₃ (2×50 mL) and brine (50 mL), dried over Na₂SO₄, filtered and evaporated in vacuo to yield 2.09 g of a light brown oil. This is purified (silica, 40 g ISCO column 10% EtOAc in heptanes for 3 column volumes followed by a linear gradient to 50% EtOAc in heptanes for 10 column volumes). 17 mL fractions of UV positive eluent are collected. Fractions 4 through 10 are combined, evaporated in vacuo and pumped to constant weight to give 0.21 g of white solid.

Example 201

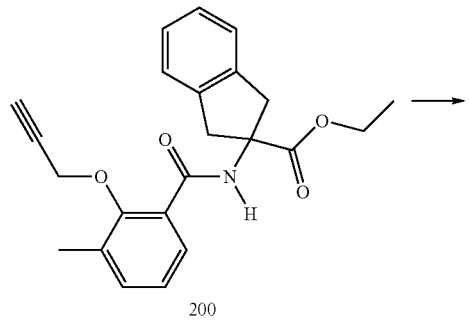

200

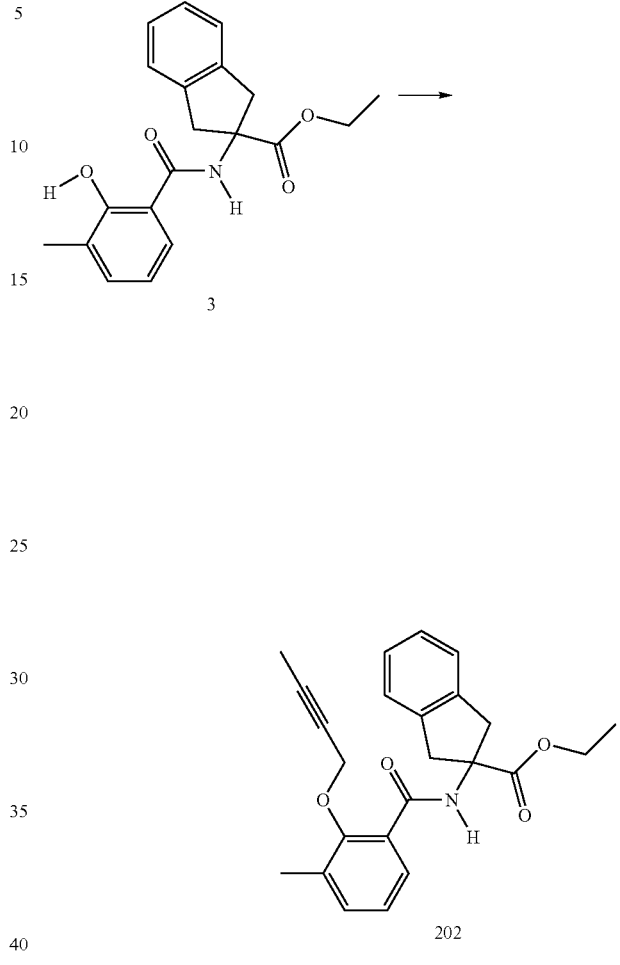

201

2-(3-Methyl-2-prop-2-ynyloxy-benzoylamino)-indan-2-carboxylic acid (201)

A 50 mL flask containing the 2-(3-methyl-2-prop-2-ynyloxy-benzoylamino)-indan-2-carboxylic acid ethyl ester (0.20 g, 0.53 mmol) is charged with 1,4-dioxane (3 mL) and MeOH (3 mL). A stirring bar is added and stirring is initiated. After dissolution, water (1.5 mL) is added followed by the LiOH (56 mg, 1.35 mmol). After 108 h, tlc analysis (silica, 10% MeOH/DCM) indicates that the starting material is completely consumed. The pH of the reaction mixture is carefully adjusted to pH 2 by slowly adding dilute aqueous HCl (3%, ~10 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over $MgSO_4$, filtered and concentrated to constant weight to give 0.2 g of off-white solid.

$^1$H NMR (300 MHz, DMSO-d6): δ 2.26 (s, 3H), 3.43 (dd, 4H), 4.52 (s, 2H), 7.08 (dd, 1H), 7.12-7.38 (m, 6H), 8.79 (s, 1H), 12.53 (bs, 1H).

LC/MS m/z=350.

Example 202

3

202

2-(3-Methyl-2-but-2-ynyloxy-benzoylamino)-indan-2-carboxylic acid ethyl ester (202)

A 100 mL round bottom flask containing the 2-(hydroxy-3-methyl-benzoyl)-indan-2-carboxylic acid ethyl ester (0.62 g, 1.87 mmol) is charged with DMF (3 mL) and a stirring bar is added. After dissolution of the starting material, the $K_2SO_4$ (0.791 g, 5.95 mmol) is added followed by a solution of 1-bromo-2-butyne (537 µL, 5.95 mmol). After stirring for 110 h tlc analysis (silica, 1:1 EtOAc/heptanes) indicates that the starting material is consumed. The material is cleanly converted to a UV positive spot with a slightly lower Rf. The reaction is diluted with EtOAc (80 mL) and filtered through a pad of Celite. The filtrate is transferred to a separatory funnel. This is washed repeatedly with a saturated aqueous solution of $NaHCO_3$ (2×50 mL) and brine (50 mL), dried over $MgSO_4$, filtered and evaporated in vacuo to yield 0.75 g of a light brown oil. This is purified (silica, 40 g ISCO column 10% EtOAc in heptanes for 3 column volumes followed by a linear gradient to 50% EtOAc in heptanes for 10 column volumes).

Example 203

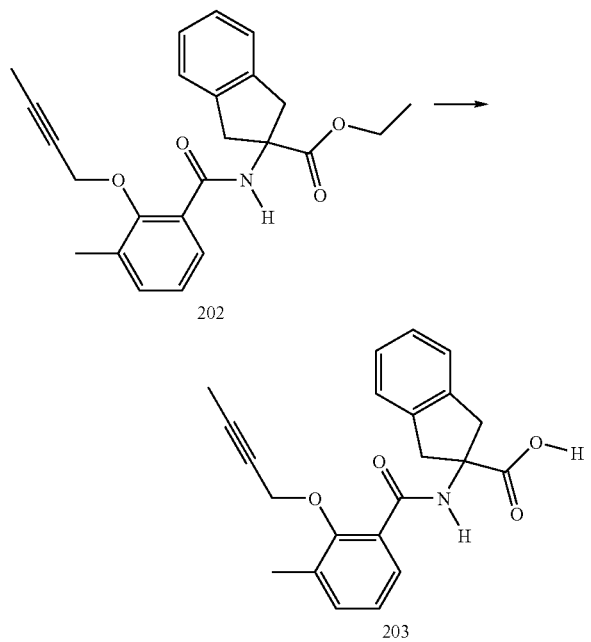

2-(3-Methyl-2-but-2-ynyloxy-benzoylamino)-indan-2-carboxylic acid (203)

A 100 mL flask containing 2-(3-methyl-2-but-2-ynyloxy-benzoylamino)-indan-2-carboxylic acid (0.30 g, 0.77 mmol) is charged with 1,4-dioxane (4 mL) and MeOH (4 mL). A stirring bar is added and stirring is initiated. After dissolution, water (2 mL) is added followed by the LiOH (81 mg, 1.93 mmol). After 14 h, tlc analysis (silica, 10% MeOH/DCM) indicates that the starting material is completely consumed. The pH of the reaction mixture is carefully adjusted to pH 2 by slowly adding dilute aqueous HCl (3%, ~6 mL). The contents of the flask are poured into a reparatory funnel containing EtOAc (30 mL). The layers are separated. The aqueous layer is extracted with EtOAc (20 mL). The combined organic extracts are washed with water (20 mL) and brine (20 mL), dried over MgSO$_4$, filtered and concentrated by pumping to constant weight to give 0.25 g of off-white solid.

$^1$H NMR (300 MHz, DMSO-d6): δ 1.77 (s, 3H), 2.24 (s, 3H), 3.44 (dd, 4H), 4.42 (s, 2H), 7.08 (dd, 1H), 7.14-7.23 (m, 4H), 7.31 (d, 2H), 8.75 (s, 1H), 12.52 (bs, 1H).

LC/MS m/z=364.

Example 204

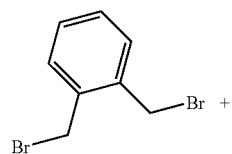

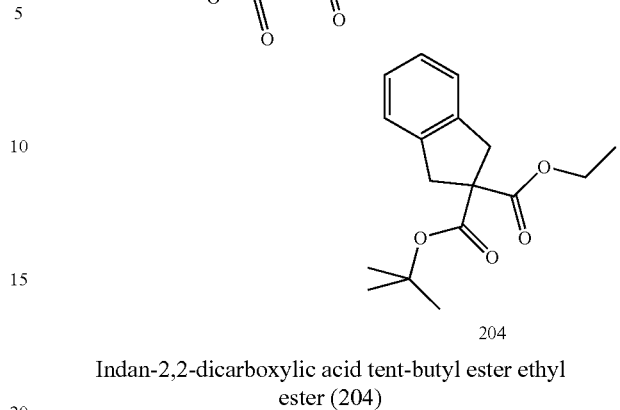

Indan-2,2-dicarboxylic acid tent-butyl ester ethyl ester (204)

A 3-neck flask containing a stirring bar is fitted with an addition funnel and flushed with nitrogen. The flask is charged with NaH (60% dispersion in oil, 3.38 g, 84.48 mmol) and dry THF (50 mL), and then stirring is initiated, t-Butyl ethyl malonate (8 mL, 42.24 mmol) is added dropwise via syringe over a period of 5 minutes. After ½ hour the addition funnel is charged with a solution of o-xylenedibromide (11.15 g, 42.24 mmol) in dry tetrahydrofuran (THF, 50 mL). The solution is added to the reaction mixture over a period of 30 minutes. At the end of this time the addition funnel is washed with dry THF (10 mL). This is also added to the reaction mixture. The reaction mixture is allowed to stir for 6 days. The reaction mixture is then transferred to a round-bottom flask and the solvent removed under reduced pressure. The resultant white semi-solid is dissolved in a mixture of EtOAc (200 mL) and water (150 mL) this is transferred to a reparatory funnel. The layers are separated. The aqueous phase is extracted with EtOAc (150 mL). The organic extracts are combined, washed with brine (150 mL), dried over MgSO$_4$, filtered and evaporated to constant weight to give 12.44 g of viscous oil. This material is diluted with heptanes (30 mL) and applied to a silica gel column (300 g). The material is eluted with EtOAc/heptanes (5% over 5 column volumes) with a gradient to 75% EtOAc in heptanes over 7 column volumes. 43 mL fractions of UV positive eluent are collected. Fractions 11-20 are combined and evaporated by pumping to a constant weight to give 9.82 g of clear viscous oil.

Example 205

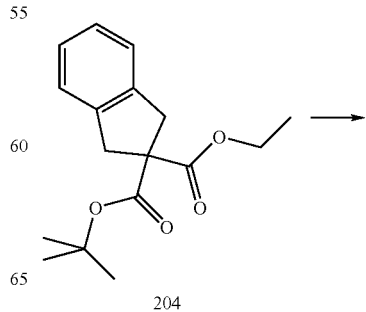

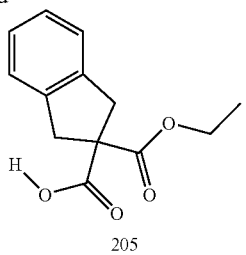

Indan-2,2-dicarboxylic acid ethyl ester (205)

A 200 mL round bottom flask is charged with indan-2,2-dicarboxylic acid tent-butyl ester ethyl ester (8.69 g, 29.93 mmol). DCM (40 mL) and a stirring bar are added. Stirring is initiated. Trifluoroacetic acid (20.0 mL, 269 mmol) is added. After 20 h, tlc analysis (silica, 1:1 ethyl actetate:heptanes), indicates complete consumption of starting material. The reaction mixture is diluted with DCM (50 mL) and evaporated under reduced pressure. The resultant oil is diluted with DCM (55 mL) and evaporated under reduced pressure. The resultant oil is diluted with toluene (50 mL) and evaporated under reduced pressure by pumping to constant weight to give 6.78 g of white solid material.

Example 206

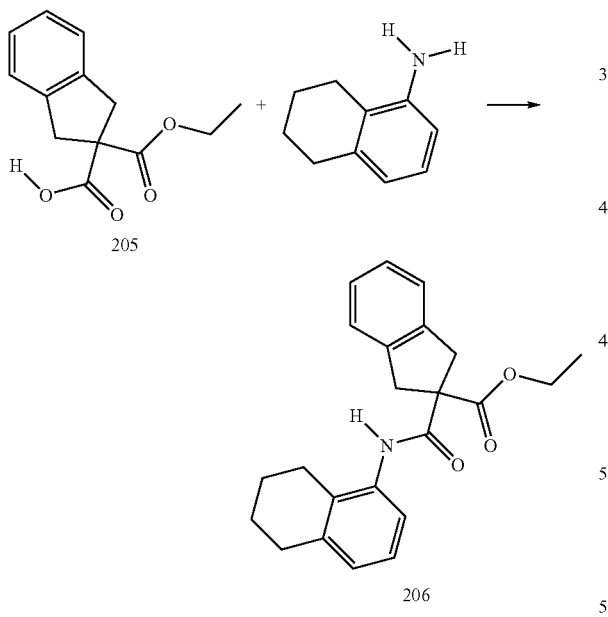

2-(5,6,7,8-Tetrahydro-naphthalen-1-ylcarbamoyl)-indan-2-carboxylic acid ethyl ester (206)

A 25 mL reaction vial containing a stirring bar is charged with indane-2-carboxylic acid ethyl ester (0.48 g, 1.79 mmol) and dry DCM (7 mL). Stirring is initiated. After dissolution is complete, HBTU (0.68 g, 1.79 mmol) is added. After 5 min, the 5,6,7,8-tetrahydrol-naphthylamine (0.26 mL, 1.79 mmol is added followed by DIPEA (0.72 mL, 4.12 mmol). The reaction is allowed to stir for 68 h. Analysis by tlc of the reaction mixture (silica, 10% MeOH/DCM) indicates complete consumption of the starting acid. The contents of the reaction flask are transferred to a reparatory funnel and diluted with EtOAc (40 mL). This is washed consecutively with dilute aqueous HCl (3%, 20 mL), saturated aqueous NaHCO$_3$ (20 mL) and brine (20 mL), dried over MgSO$_4$, filtered and evaporated in vacuo to provide 0.50 g of a light purple solid. This material is dissolved in 10 mL of DCM. This material is purified utilizing an ISCO Companion with a 40 g cartridge of silica. The gradient is 10% EtOAc in heptanes over 4 column volumes followed by a linear gradient to 50% EtOAc over 12 column volumes. 17 mL fractions of eluent are collected. Fractions 11 through 16 are combined and evaporated in vacuo by pumping to constant weight to give 0.41 of white solid material.

Example 207

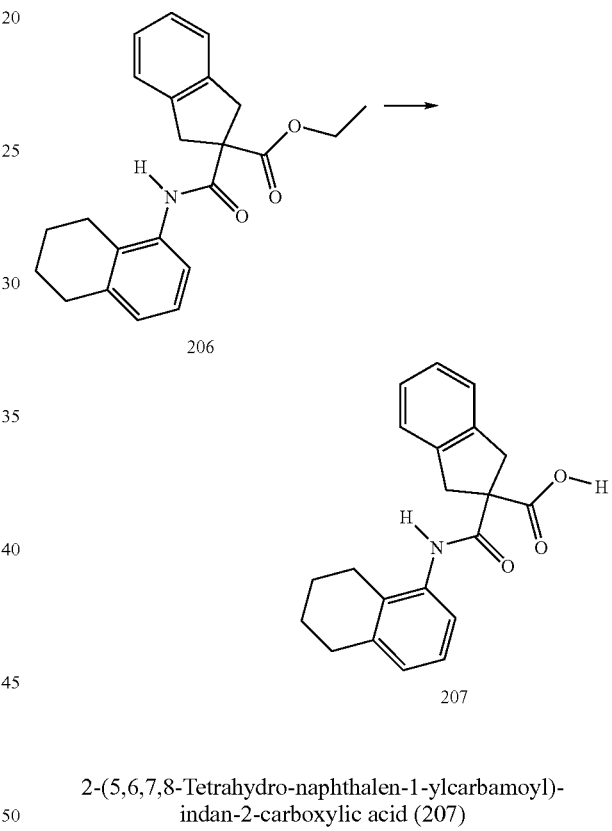

2-(5,6,7,8-Tetrahydro-naphthalen-1-ylcarbamoyl)-indan-2-carboxylic acid (207)

A 100 mL flask containing 2-(5,6,7,8-tetrahydro-napthalene-1-yl-carbamoyl)-indan-2-carboxylic acid ethyl ester (0.23 g, 0.63 mmol) is charged with 1,4-dioxane (4 mL) and MeOH (4 mL). A stirring bar is added and stirring is initiated. After dissolution, water (2 mL) is added followed by the LiOH (67 mg, 1.58 mmol). After 14 h, tlc analysis (silica, 10% MeOH/DCM) indicates that the starting material is completely consumed. The pH of the reaction mixture is carefully adjusted to pH 2 by slowly adding dilute aqueous HCl (3%, ~6 mL). The contents of the flask are poured into a reparatory funnel containing EtOAc (30 mL). The layers are separated. The aqueous layer is extracted with EtOAc (20 mL). The combined organic extracts are washed with water (20 mL) and brine (20 mL), dried over MgSO$_4$, filtered and concentrated by pumping to constant weight to give 0.18 g of white solid.

¹H NMR (300 MHz, DMSO-d6): δ 1.58-1.78 (m, 4H), 2.43-2.58 (m, 2H), 2.63-2.78 (m, 2H), 3.57 (dd, 4H), 6.96 (dd, 1H), 6.98-7.08 (m, 2H), 7.09-7.19 (m, 2H), 7.20-7.28 (m, 2H), 9.15 (s, 1H), 12.82 (bs, 1H).
LC/MS m/z=336.

Example 208

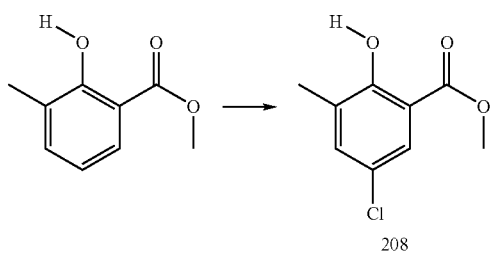

208

2-Hydroxy-3-methyl-5-chlorobenzoic acid methyl ester (208)

A 250 mL 3-neck round bottom flask is charged with 2-hydroxy-3-methyl-5-benzoic acid methyl ester (5 g, 30.1 mmol) and dry DCM (50 mL). A stirring bar is added and the flask is immersed in an ice/water bath. After 10 minutes, sulfuryl chloride (2.9 mL, 36.1 mmol) is added via syringe over a period of 5 minutes. After 0.5 h, the ice-water bath is removed. After 2 additional h, tlc Analysis (silica, 40% EtOAc-heptanes) indicates no reaction.

After 27 days, tlc analysis (silica, 40% EtOAc-heptanes) still indicated no reaction. MeOH (50 mL) is added to the reaction mixture. A white crystalline solid began to precipitate. The precipitate is collected by suction filtration to give 2.1 g of white solid. A 2$^{nd}$ crop of 1.25 g of additional white solid is collected from the filtrate.

Example 209

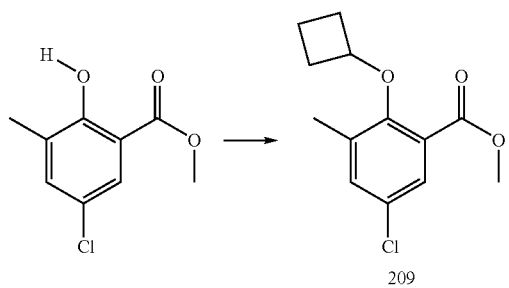

209

5-Chloro-2-cyclobutoxy-3-methyl-benzoic acid methyl ester (209)

A 100 mL round bottom flask is charged with 5-chloro-2-hydroxy-3-methyl-benzoic acid methyl ester (0.92 g, 4.59 mmol). Dry N,N-dimethylformamide (DMF, 15 mL) and a stirring bar are added. Stirring is initiated. After dissolution, $K_2SO_4$ (1.90 g, 13.76 mmol) and bromocyclobutane (0.65 mL, 6.88 mmol) are added. After 12 days, tlc analysis (silica, 25% EtOAc/heptanes) indicated a slight consumption of starting material and the appearance of a UV positive spot with a slightly higher $R_f$ value. The reaction is fitted with a heating mantle and warmed to 37° C. After 3 more days, tlc analysis (silica, 25% EtOAc/heptanes) indicates a slight consumption of starting material and complete conversion to a UV positive spot with a slightly higher $R_f$ value. The reaction mixture is filtered through a pad of Celite. The filtrate is diluted with EtOAc and (100 mL) and transferred to a separatory funnel. The EtOAc solution is washed with saturated $NaHCO_3$ (2×25 mL) and brine (25 mL), dried over $MgSO_4$, filtered and evaporated by pumping to constant weight to give 0.79 g of semi-solid material.

Example 210

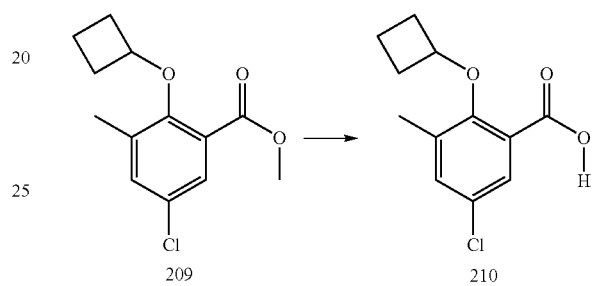

209 210

5-Chloro-2-cyclobutoxy-3-methyl-benzoic acid (210)

A 100 mL flask containing 5-chloro-2-cyclobutoxy-3-methyl-benzoic acid methyl ester (0.57 g, 2.23 mmol) is charged with 1,4-dioxane (4 mL) and MeOH (4 mL). A stirring bar is added and stirring is initiated. After dissolution, water (2 mL) is added followed by the LiOH (237 mg, 5.65 mmol). After 39 h, tlc analysis (silica, 10% MeOH/DCM) indicates that the starting material is completely consumed. The pH of the reaction mixture is carefully adjusted to pH 2 by slowly adding dilute aqueous HCl (3%, ~6 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over $MgSO_4$, filtered and concentrated by pumping to constant weight to give 0.53 g of white solid.

Example 211

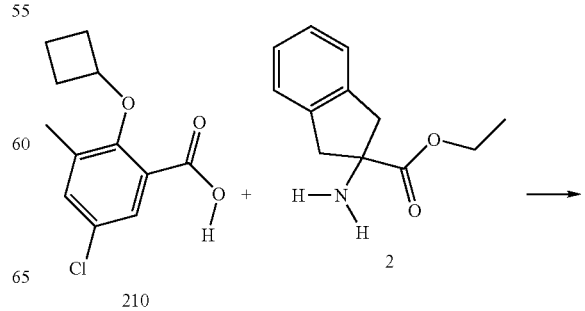

210

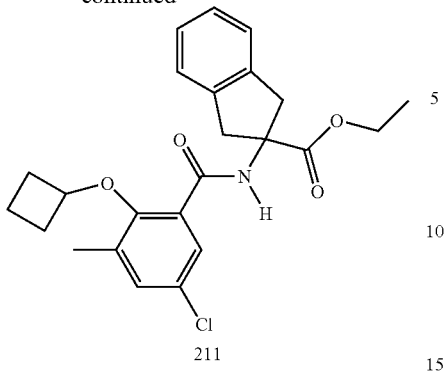

211

2-(5-Chloro-2-cyclobutoxy-3-methyl-benzoylamino)-indan-2-carboxylic acid ethyl ester (211)

A 100 mL round bottom flask containing a stirring bar is charged with 2-cyclobutoxyl-3-methyl-5-chloro-benzoic acid (0.36 g, 1.5 mmol) and dry DCM (7 mL). Stirring is initiated. After dissolution is complete, HBTU (567 mg, 1.5 mmol) is added. After 5 min, the 2-amino-indane-2-carboxylic acid ethyl ester (307 mg, 1.50 mmol) is added followed by DIPEA (0.74 mL, 3.74 mmol). The reaction is allowed to stir for 39 h. Analysis by tlc of the reaction mixture (silica, 5% iPrOH/DCM) indicates complete consumption of the starting amine. The contents of the reaction flask are transferred to a separatory funnel and diluted with EtOAc (100 mL). This is washed consecutively with dilute aqueous HCl (3%, 40 mL), saturated aqueous NaHCO$_3$ (50 mL) and brine (50 mL), dried over MgSO$_4$, filtered and evaporated in vacuo to provide 0.8 g of a light orange solid. This material is dissolved in 10 mL of DCM. This material is purified utilizing an ISCO Companion with a 40 g cartridge of silica. The gradient is 10% EtOAc in heptanes over 4 column volumes followed by a linear gradient to 70% EtOAc in heptanes over 10 column volumes. 17 mL fractions of UV active eluent are collected. Fractions 8 through 11 are combined and evaporated in vacuo by pumping to a constant weight to give 0.48 g white solid.

Example 212

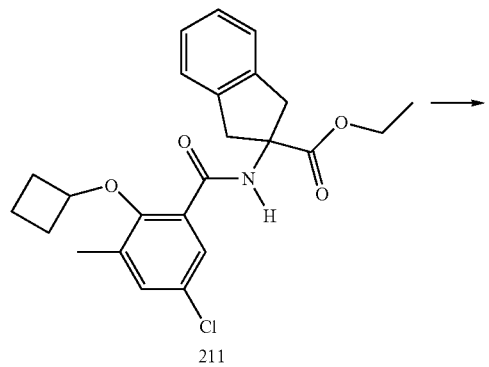

211

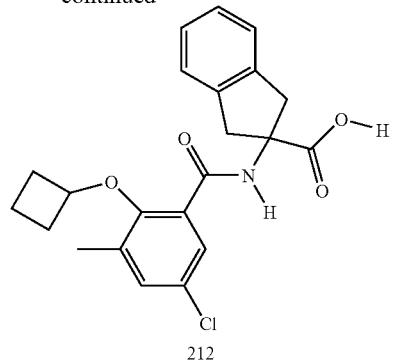

212

2-(5-Chloro-2-cyclobutoxy-3-methyl-benzoylamino)-indan-2-carboxylic acid (212)

A 100 mL flask containing 2-(5-chloro-2-cyclobutoxy-3-methyl-benzoylamino)-indan-2-carboxylic acid ethyl ester (0.3 g, 0.7 mmol) is charged with 1,4-dioxane (4 mL) and MeOH (4 mL). A stirring bar is added and stirring is initiated. After dissolution, water (2 mL) is added followed by the LiOH (74 mg, 1.77 mmol). After 20 h, tlc analysis (silica, 10% MeOH/DCM) indicates that the starting material is completely consumed. The pH of the reaction mixture is carefully adjusted to pH 2 by slowly adding dilute aqueous HCl (3%, ~6 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), dried over MgSO$_4$, filtered and concentrated. Pumping to constant weight gives 0.21 g of a white solid.

$^1$H NMR (300 MHz, DMSO-d6): δ 1.17-1.28 (m, 1H), 1.49 (m, 1H), 1.78-1.95 (m, 2H), 1.96-2.04 (m, 2H), 3.46 (dd, 4H), 4.28 (m, 1H), 7.15-7.26 (m, 5H), 7.39 (d, 1H), 8.78 (s, 1H), 12.62 (bs, 1H).

LC/MS m/z=400.

Example 213

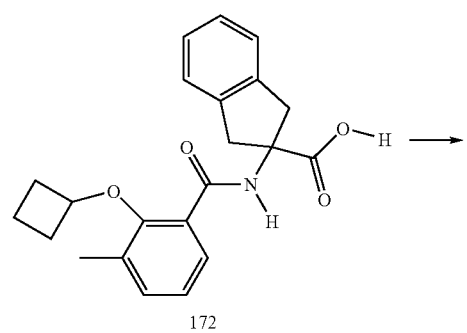

172

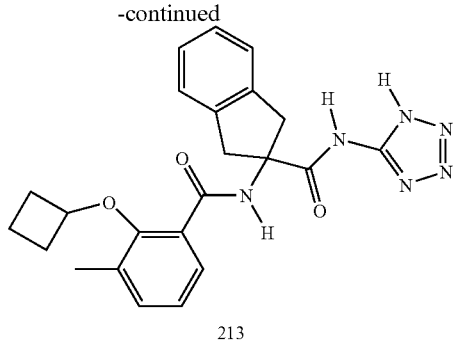

213

2-(2-Cyclobutoxy-3-methyl-benzoylamino)-indan-2-carboxylic acid (1H-tetrazol-5-yl)-amide (213)

A 40 mL tube is charged with 2-[(2-cyclobutoxy-3-methyl-benzoyl)-amino]-indan-2-carboxylic acid (323 mg, 0.884 mmol) and dry DCM (7 mL). A stirring bar is added and stirring is initiated. 5-Amino-1H-tetrazole (113 mg, 1.33 mmol) is added. To the resultant suspension, N-(3-Dimethylaminopropyl)-N'-ethylcarbodiimide hydrochloride (170 mg, 0.88 mmol) and 4-dimethylaminopyridine (108 mg, 0.88 mmol) is added. After 11½ days, tlc analysis (silica, 10% MeOH in DCM) indicates that the starting acid had been consumed. The reaction mixture is diluted with EtOAc (50 mL), transferred to an Erlenmeyer flask containing saturated aqueous ammonium chloride (50 mL). This mixture is allowed to stir. After 16 h of stirring, this mixture contained a white solid that is collected by suction filtration and washed with water (2×25 mL). Air drying gives 0.26 g of white powder.

$^1$H NMR (300 MHz, DMSO-d6): δ 1.01-1.31 (m, 2H), 1.62 (m, 2H), 1.73-1.93 (m, 2H), 2.22 (s, 3H), 3.39 (dd, 4H), 4.19 (m, 1H), 7.08 (t, 1H), 7.19-7.51 (m, 5H), 7.57 (dd, 1H), 8.61 (s, 1H), 12.01 (bs, 1H).
LC/MS m/z=433.

Example 214

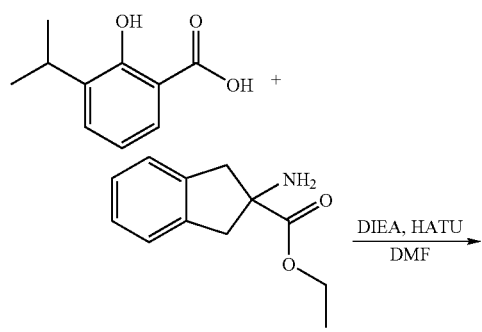

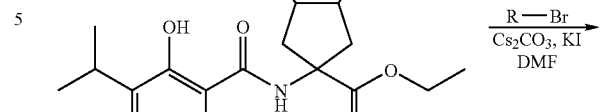

214

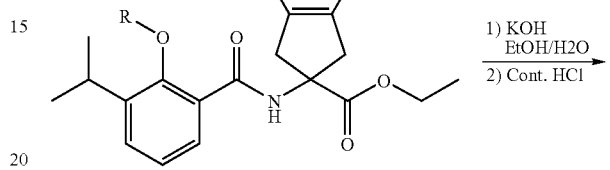

215

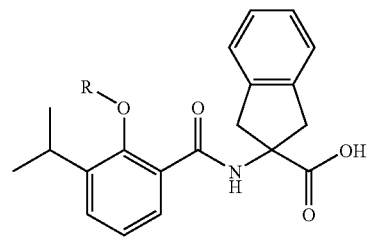

216

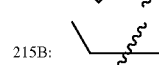 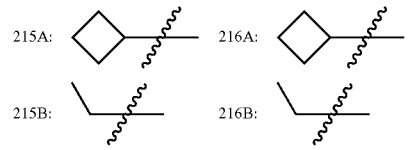

2-(2-Hydroxy-3-isopropyl-benzoylamino)-indan-2-carboxylic acid ethyl ester (214)

To a solution of 2-hydroxy-3-isopropyl-benzoic acid (539 mg, 2.99 mmol), 2-amino-indan-2-carboxylic acid ethyl ester (737 mg, 3.59 mmol), HATU (1.36 g, 3.59 mmol) in anhydrous DMF (30 mL) is added DIPEA (0.59 mL, 3.59 mmol). The resulting solution is stirred at RT overnight. After the removal of DMF in vacuo, the residue is dissolved in EtOAc (150 mL) and washed with water (1×10 mL) and brine (2×10 mL). The organic layer is dried over anhydrous Na$_2$SO$_4$ and concentrated in vacuo. The residue is purified by HPLC to give a pure product (222) as white solid (920 mg, 84%).
$^1$H NMR (CDCl$_3$, 300 MHz): δ 1.21 (d, 6H), 1.24 (t, 3H), 3.32-3.44 (m, 1H), 3.41 (d, 2H), 3.74 (d, 2H), 4.25 (q, 2H), 6.74-6.81 (m, 2H), 7.16 (d, 1H), 7.18-7.25 (m, 3H), 7.32 (d, 1H), 12.26 (s, 1H)
LC/MS (ES+) m/z=368.17

Examples 215A and 215B

2-(2-Cyclobutoxy-3-isopropyl-benzoylamino)-indan-2-carboxylic acid ethyl ester (215A) and 2-(2-Ethoxy-3-isopropyl-benzoylamino)-indan-2-carboxylic acid ethyl ester (215B)

To a suspension of 2-(2-hydroxy-3-isopropyl-benzoylamino)-indan-2-carboxylic acid ethyl ester (214) (1 eq., 0.82 mmol), anhydrous Cs₂CO₃ (2 eq., 1.64 mmol), and KI (0.2 eq., 0.16 mmol) in DMF (15 mL) is added RBr (4 eq., 3.28 mmol). The resulting reaction suspension is heated in a microwave vessel (215A: 130° C., 2 hr; 215B: 50° C., 30 min). After the removal of DMF in vacuo, the residue is dissolved in EtOAc (30 mL) and washed with water (1×5 mL) and brine (2×5 mL). The organic layer is dried over anhydrous Na₂SO₄ and concentrated in vacuo. The residue is purified by flash column chromatography (120 g silica gel, gradient elution: 10-50% EtOAc in heptane) to give a pure product (215) as white solid (215A: 340 mg, 98%; 215B: 300 mg, 93%).

215A: ¹HNMR (CDCl₃, 300 MHz): δ 1.19 (d, 6H), 1.26 (t, 3H), 1.16-1.57 (m, 2H), 1.87-2.07 (m, 4H), 3.24-3.38 (m, 1H), 3.36 (d, 2H), 3.78 (d, 2H), 4.26 (q, 2H), 4.15-4.30 (m, 1H), 7.12-7.26 (m, 5H), 7.35 (dd, 1H), 7.83 (dd, 1H), 8.20 (s, 1H).

LC/MS (ES+) m/z=422.24

215B: ¹HNMR (CDCl₃, 300 MHz): δ 1.13 (t, 3H), 1.20 (d, 6H), 1.26 (t, 3H), 3.24 (m, 1H), 3.35 (d, 2H), 3.72 (q, 2H), 3.78 (d, 2H), 4.26 (q, 2H), 7.14-7.26 (m, 5H), 7.36 (dd, 1H), 7.82 (dd, 1H), 8.36 (s, 1H)

LC/MS (ES+) m/z=396.22

Examples 216A and 216B 2-(2-Cyclobutoxy-3-isopropyl-benzoylamino)-indan-2-carboxylic acid (216A) and 2-(2-Ethoxy-3-isopropyl-benzoylamino)-indan-2-carboxylic acid (216B)

The mixture of (215) (1 eq., 0.69 mmol) and KOH (13 eq., 8.9 mmol) is dissolved in EtOH (10 mL) and water (0.5 mL) under a water bath. The water bath is removed when KOH is completely dissolved and the resulting reaction solution is stirred at RT for 4 h. After concentration in vacuo, the residue is dissolved in water (20 mL) and acidified with conc. HCl until no more white precipitate came out of the water. The precipitate is filtered to give a pure product (216) as white solid (216A: 190 mg, 70%; 216B: 220 mg, 91%).

216A: ¹HNMR (CDCl₃, 300 MHz): δ 1.17 (d, 6H), 1.13-1.30 (m, 1H), 1.41 (m, 1H), 1.78-2.02 (m, 4H), 3.27 (m, 1H), 3.38 (d, 2H), 3.81 (d, 2H), 4.13 (m, 1H), 7.09 (t, 1H), 7.13-7.23 (m, 4H), 7.34 (dd, 1H), 7.81 (dd, 1H), 8.37 (s, 1H).

LC/MS (ES+) m/z=394.19

216B: ¹HNMR (CDCl₃, 300 MHz): δ 1.08 (t, 3H), 1.19 (d, 6H), 3.20 (m, 1H), 3.46 (d, 2H), 3.55 (q, 2H), 3.88 (d, 2H), 7.18-7.27 (m, 5H), 7.42 (dd, 1H), 7.89 (dd, 1H), 8.63 (s, 1H)

LC/MS (ES+) m/z=368.19

Example 217

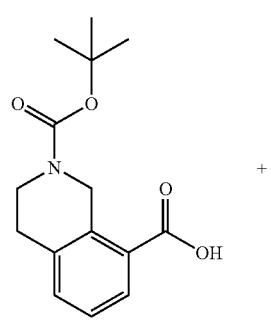

+

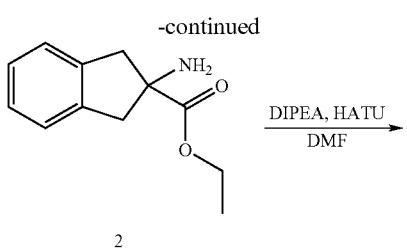

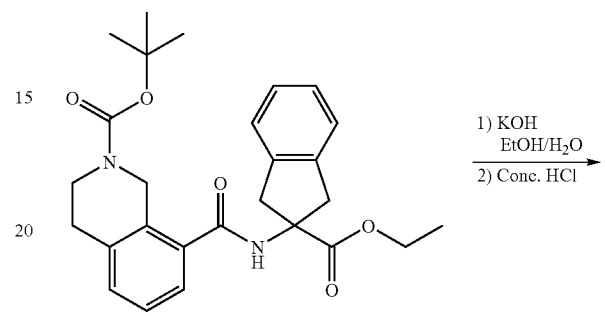

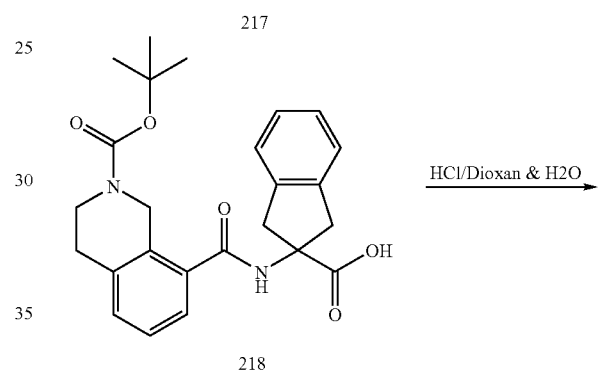

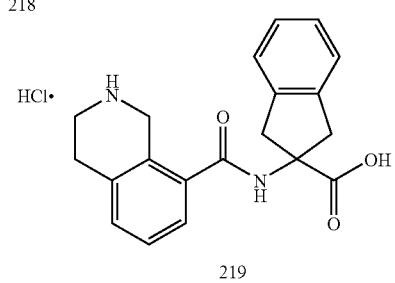

8-(2-Ethoxycarbonyl-indan-2-ylcarbamoyl)-3,4-dihydro-1H-isoquinoline-2-carboxylic acid tert-butyl ester (217)

To a solution of 3,4-dihydro-1H-isoquinoline-2,8-dicarboxylic acid 2-tert-butyl ester (2.0 g, 7.2 mmol), 2-amino-indan-2-carboxylic acid ethyl ester (1.5 g, 7.2 mmol), HATU (3.3 g, 8.6 mmol) in anhydrous DMF (70 mL) is added DIPEA (1.4 mL, 8.6 mmol). The resulting solution is stirred at RT overnight. After the removal of DMF in vacuo, the residue is dissolved in EtOAc (150 mL) and washed with water (1×10 mL) and brine (2×10 mL). The organic layer is dried over anhydrous Na₂SO₄ and concentrated in vacuo. The residue is purified by flash column chromatography (200 g silica gel, gradient elution: 5-50% EtOAc in heptane) to give a pure product (217) as white solid (3.3 g, 99%).

Example 218

8-(2-Carboxy-indan-2-ylcarbamoyl)-3,4-dihydro-1H-isoquinoline-2-carboxylic acid tert-butyl ester (218)

The product (217) (2.46 g, 5.3 mmol) and KOH (2.5 g, 45 mmol) is dissolved in EtOH (20 mL) and water (1 mL) under a water bath. The water bath is removed when the KOH is completely dissolved and the resulting reaction solution is stirred at RT for 3 h. After concentration in vacuo, the residue is dissolved in water (50 mL) and acidified with conc. HCl until no more white precipitate came out of the water. The precipitate is filtered to give a pure product (218) as white solid (1.4 g, 61%).

$^1$H NMR (DMSO-d6, 300 MHz): δ 1.40 (s, 9H), 2.79 (t, 2H), 3.34 (d, 2H), 3.52 (t, 2H), 3.57 (d, 2H), 4.59 (s, 2H), 7.10-7.31 (m, 7H), 8.88 (s, 1H), 11.56-12.92 (br s, 1H)

LC/MS (ES+) m/z=437.26

Example 219

2-[(1,2,3,4-Tetrahydro-isoquinoline-8-carbonyl)-amino]-indan-2-carboxylic acid (219)

To a solution of 8-(2-carboxy-indan-2-ylcarbamoyl)-3,4-dihydro-1H-isoquinoline-2-carboxylic acid tert-butyl ester (226) (128 mg, 0.29 mmol) in 6 ml dioxane is added dropwise 4N solution of HCl in dioxane/water (0.72 mL) and the resulting solution is stirred at RT for 4 h. The concentration gave an HCl salt of (219) as white solid (246 mg, 100%).

$^1$H NMR (DMSO-d6, 300 MHz): δ 3.04 (t, 3H), 3.28-3.41 (m, 4H), 3.58 (d, 2H), 4.31 (s, 2H), 7.13-7.27 (m, 4H), 7.32 (s, 3H), 9.05 (s, 1H), 9.30-9.57 (br s, 1H), 12.46-12.77 (br s, 1H)

LC/MS (ES+) m/z=337.18

Example 220

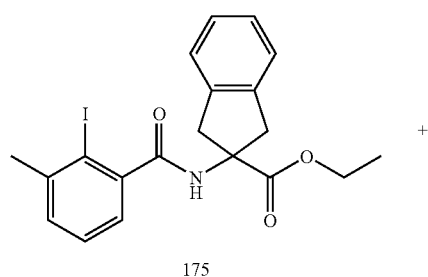

175

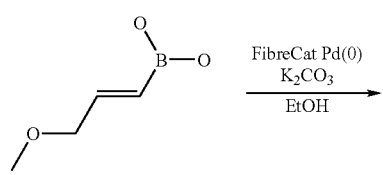

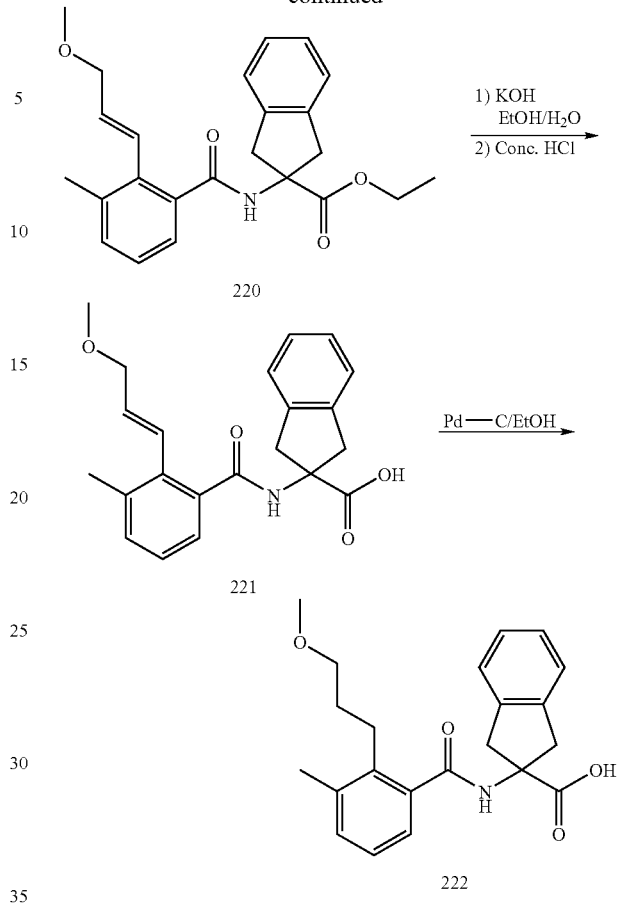

2-[2-(3-Methoxy-propenyl)-3-methyl-benzoylamino]-indan-2-carboxylic acid ethyl ester (220)

To a solution of 2-(2-Iodo-3-methyl-benzoylamino)-indan-2-carboxylic acid ethyl ester (400 mg, 0.89 mmol) and 3-methoxy-1-propenylboronic acid (206 mg, 1.78 mmol) in 10 mL EtOH/10 mL dioxane is added palladium anchored homogeneous catalyst, FibreCatPd(0), (4.84% Pd, 195 mg, 0.089 mmol) and 2M aqueous solution of K$_2$SO$_4$ (1.78 mL, 3.56 mmol). The resulting reaction mixture is covered with argon and run in a microwave reaction: 110° C., 4 h. After concentration in vacuo, the residue is purified by HPLC to give the product (220) as pale yellow oil.

Example 221

2-[2-(3-Methoxy-propenyl)-3-methyl-benzoylamino]-indan-2-carboxylic acid (221)

The product (220) and KOH (1.0 g, 18 mmol) is dissolved in EtOH (8 mL) and water (1 mL) under a water bath. The water bath is removed when KOH is completely dissolved and the resulting reaction solution is stirred at RT for 3 h. After concentration in vacuo, the residue is dissolved in water (20 mL) and acidified with conc. HCl until no more white precipitate formed. After the filtration, the obtained brown solid is purified by HPLC to give pure product (221) as white solid (200 mg, 62%).

$^1$H NMR (CDCl$_3$, 300 MHz): δ 2.28 (s, 3H), 3.31 (s, 1H), 3.37 (s, 4H), 3.78 (d, 2H), 3.93 (dd, 2H), 5.83 (dt, 1H), 6.44 (s, 1H), 6.64 (d, 1H), 7.10-7.35 (m, 7H)

LC/MS (ES+) m/z=366.15

Example 222

2-[2-(3-Methoxy-propyl)-3-methyl-benzoylamino]-indan-2-carboxylic acid (222)

To a solution of 2-[2-(3-methoxy-propenyl)-3-methyl-benzoylamino]-indan-2-carboxylic acid (229) (120 mg, 0.34 mmol) in absolute EtOH (15 mL) is added the catalyst, Pd—C (5 wt. % Pd, 93 mg, 4.4% mmol) under argon. The resulting reaction mixture is moved to the Paar apparatus to run hydrogenation: 55 psi, 50° C., overnight. The catalyst is removed by the filtration through a pre-column (10 g silica gel) and washed with EtOH. The combined organic solution is concentrated in vacuo. The residue is purified by HPLC to give a pure product (222) as white solid (80 mg, 49%).

$^1$H NMR (DMSO-d6, 300 MHz): δ 1.64 (m, 2H), 2.27 (s, 3H), 2.59-2.69 (m, 2H), 3.16-3.40 (m, 7H), 3.56 (d, 2H), 6.97-7.24 (m, 7H), 8.84 (s, 1H), 12.48 (s, 1H)

LC/MS (ES+) m/z=368.18

Example 223

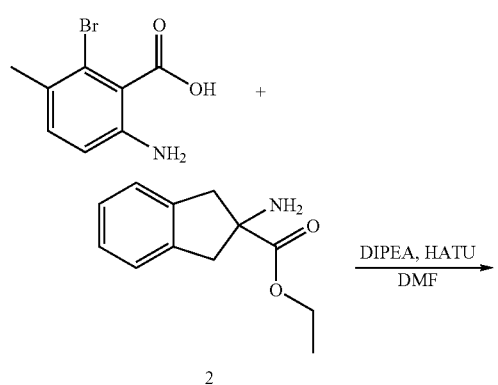

2

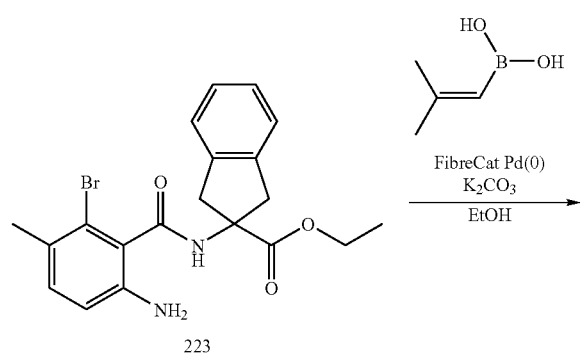

223

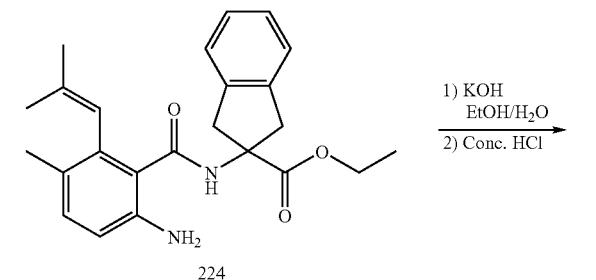

224

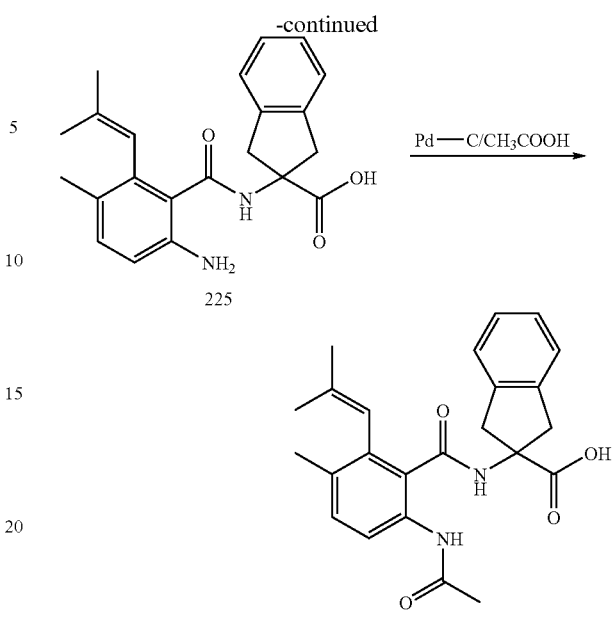

225

226

2-[6-Acetylamino-3-methyl-2-(2-methyl-propenyl)-benzoylamino]-indan-2-carboxylic acid (223)

To a solution of 6-amino-2-bromo-3-methyl-benzoic acid (688 mg, 2.99 mmol), 2-amino-indan-2-carboxylic acid ethyl ester (737 mg, 3.59 mmol), HATU (1.36 g, 3.59 mmol) in anhydrous DMF (30 mL) is added DIPEA (0.59 mL, 3.59 mmol). The resulting solution is stirred at RT overnight. After the removal of DMF in vacuo, the residue is dissolved in EtOAc (150 mL) and washed with water (1×10 mL) and brine (2×10 mL). The organic layer is dried over anhydrous Na$_2$SO$_4$ and concentrated in vacuo. The residue is purified by HPLC to give 278 mg brown oil (223).

Example 224

2-[6-Amino-3-methyl-2-(2-methyl-propenyl)-benzoylamino]-indan-2-carboxylic acid ethyl ester (224)

To a solution of (223) (278 mg, 0.67 mmol) and 2,2-dimethylethyleneboronic acid (134 mg, 1.34 mmol) in 10 ml EtOH is added palladium anchored homogeneous catalyst, FibreCatPd(0), (4.84% Pd, 195 mg, 0.089 mmol) and 2M aqueous solution of K$_2$SO$_4$ (1.78 mL, 3.56 mmol). The resulting reaction mixture is covered with argon and run in a microwave reaction: 110° C., 5 h. After concentration in vacuo, the residue is purified by HPLC to give 380 mg brown semi-solid (224).

Example 225

2-[6-Amino-3-methyl-2-(2-methyl-propenyl)-benzoylamino]-indan-2-carboxylic acid (225)

The mixture (224) and KOH (500 mg, 8.9 mmol) is dissolved in EtOH (8 mL) and water (1 mL) under a water bath. The water bath is removed when KOH is completely dissolved and the resulting reaction solution is stirred at RT for 4 h. After concentration in vacuo, the residue is dissolved in water (20 mL) and acidified with conc. HCl until no more white precipitate formed. After the filtration, the crude solid is purified by HPLC to give 48 mg brown solid (225).

Example 226

2-[6-Acetylamino-3-methyl-2-(2-methyl-propenyl)-benzoylamino]-indan-2-carboxylic acid (226)

To a solution of (225) (48 mg, 0.1 mmol) in acetic acid (10 mL) is added the catalyst, Pd—C (5 wt. % Pd, 21 mg, 1% mmol) under argon. The resulting reaction mixture is moved to the Paar apparatus to run hydrogenation: 55 psi, 90° C., overnight. The catalyst is removed by filtration through a pre-column (10 g silica gel) and washed with EtOH. The combined organic solution is concentrated in vacuo. The residue is purified by HPLC to give a pure product (226) as white solid (35 mg, 86%).

$^1$HNMR (CDCl$_3$+drops of CD$_3$OD, 300 MHz): δ 1.17 (s, 3H), 1.70 (s, 3H), 2.08 (d, 3H), 2.16 (d, 3H), 3.26 (d, 2H), 3.72 (d, 2H), 5.89 (s, 1H), 7.12-7.25 (m, 5H), 7.48 (s, 1H), 7.74 (d, 1H)

LC/MS (ES+) m/z=407.18

Example 227

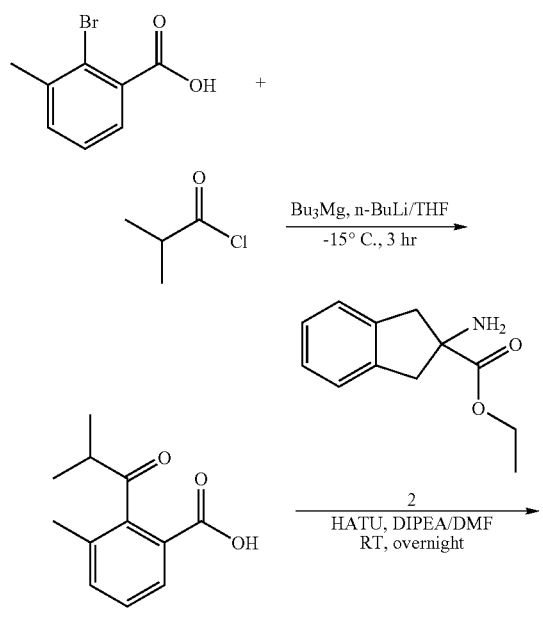

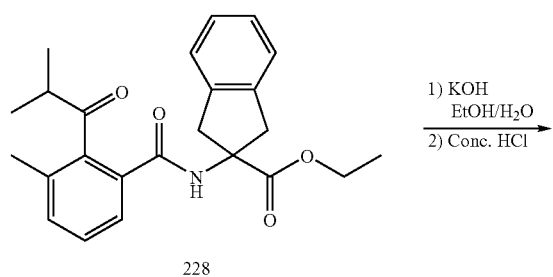

228

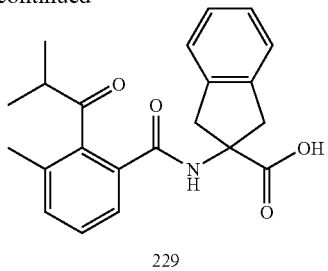

229

2-Isobutyryl-3-methyl-benzoic acid (227)

The solution of 2-bromo-3-methyl-benzoic acid (1.5 g, 6.98 mmol) in 10 mL THF is treated with 1M Bu$_2$Mg/heptane at −15° C. under argon. After stirring for 30 min, 1.6M n-BuLi/hexane is added dropwise at −15° C. and the mixture is left for 1 hr. Then isobutyryl chloride (2.95 ml, 27.9 mmol) is added dropwise. After another 30 min stirring, the reaction is quenched with 2N HCl aqueous solution (2 ml). After concentration, the residue is purified by HPLC to give a pure product (227) as white solid (840 mg, 58%).

$^1$HNMR (CDCl$_3$+drops of CD$_3$OD, 300 MHz): δ 0.62 (d, 3H), 1.31 (d, 3H), 2.51 (s, 3H), 2.61 (s, 1H), 7.42-7.50 (m, 2H), 7.68 (m, 1H)

LC/MS (ES−) m/z=205.06

Example 228

2-(2-Isobutyryl-3-methyl-benzoylamino)-indan-2-carboxylic acid ethyl ester (228)

To a solution of 2-isobutyryl-3-methyl-benzoic acid (227) (200 mg, 0.97 mmol), 2-amino-indan-2-carboxylic acid ethyl ester (220 mg, 1.07 mmol), HATU (441 mg, 1.16 mmol) in anhydrous DMF (10 mL) is added DIPEA (192 μL, 1.16 mmol). The resulting solution is stirred at RT overnight. After the removal of DMF in vacuo, the residue is dissolved in DCM (50 mL) and washed with water (1×5 mL) and brine (1×5 mL). The organic layer is dried over anhydrous Na$_2$SO$_4$ and concentrated in vacuo. The residue is purified by HPLC to give a pure product (228) as a pale yellow solid (340 mg, 89%).

$^1$HNMR (CDCl$_3$, 300 MHz): δ 1.06 (d, 6H), 1.25 (t, 3H), 2.24 (s, 3H), 2.86 (m, 1H), 3.30 (d, 2H), 3.72 (d, 2H), 4.23 (q, 2H), 6.47 (s, 1H), 7.14-7.43 (m, 7H)

LC/MS (ES+) m/z=394.23

Example 229

2-(2-Isobutyryl-3-methyl-benzoylamino)-indan-2-carboxylic acid (229)

The mixture of 2-(2-isobutyryl-3-methyl-benzoylamino)-indan-2-carboxylic acid ethyl ester (228) (170 mg, 0.43 mmol) and KOH (500 mg, 8.9 mmol) is dissolved in EtOH (20 mL) and water (1 mL) under a water bath. The water bath is removed when KOH is completely dissolved and the resulting reaction solution is stirred at RT for 8 h. After concentration in vacuo, the residue is dissolved in water (20 mL) and acidified with conc. HCl until no more precipitate came out of the water. The precipitate is filtered to give a pure product (229) as white solid (140 mg, 89%).

¹HNMR (CDCl₃, 300 MHz): δ 1.07 (d, 6H), 2.25 (s, 3H), 2.87 (m, 1H), 3.35 (d, 2H), 3.74 (d, 2H), 7.16-7.42 (m, 7H)
LC/MS (ES+) m/z=366.16

Example 230

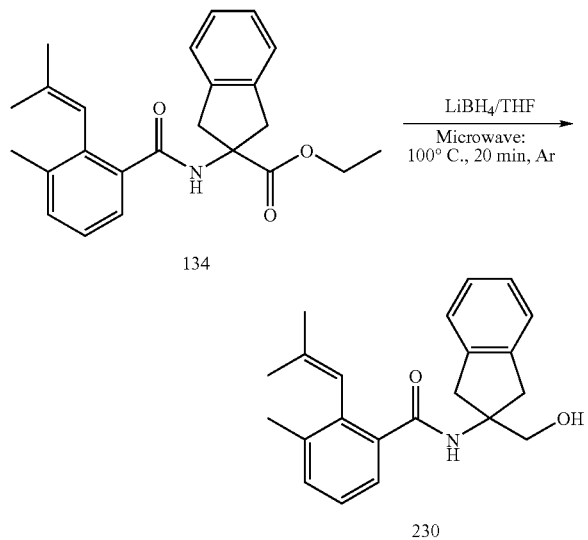

N-(2-Hydroxymethyl-indan-2-yl)-3-methyl-2-(2-methyl-propenyl)-benzamide (230)

To a solution of 2-[3-methyl-2-(2-methyl-propenyl)-benzoylamino]-indan-2-carboxylic acid ethyl ester (80 mg, 0.21 mmol) in anhydrous THF (1 mL) is added dropwise 2M LiBH₄/THF (0.84 mL, 1.68 mmol) at RT under argon. The resulting solution is heated for 20 min at 100° C. on microwave. After cooling to room temperature, the reaction solution is poured into ice-water and aq. NH₄Cl saturated solution to reach pH 7. The solution is extracted with EtOAc (50 mL×3). The combined EtOAc phase is washed with brine (10 ml×2), dried over Na₂SO₄ and concentrated. The residue is purified by HPLC to give a pure product (230) as white solid (58 mg, 82%).

¹HNMR (CDCl₃, 300 MHz): δ 1.38 (s, 3H), 1.80 (s, 1H), 2.16 (s, 1H), 3.11 (d, 2H), 3.33 (d, 2H), 3.88 (s, 2H), 6.11 (s, 1H), 6.71 (br s, 1H), 7.13-7.33 (m, 6H), 7.60 (d, 1H)
LC/MS (ES+) m/z=336.21

Examples 231 and 232

Chiral Separation of Example 150 into Examples 231 and 232

1. Experimental Conditions:
   Instrument: Americhrom Global Technologies VERSAPrep 100 (Detector module, Fraction Collection and Recycle and Injection Valves Module, Pump Module, Sample Injection Pump Module)
   Software: Chiralpak AD, 20 mmID×250 mm, 10 micron
   Eluent: EtOH/Heptane (20/80) with 0.1 TFA (Pre-mixed)
   Flow rate: 15 mL/min
   Detection: UV214 nm
   Column temperature: RT
   Injection volume: 1 mL
   Concentration: ~10 mg/mL 2. Results:

|  | Enantiomer 1 | Enantiomer 2 |
|---|---|---|
| Sample | RT (min)<br>iMax Time 6.78<br>47.7 mg, white solid | RT (min)<br>iMax Time 10.02<br>45.1 mg, white solid |

Fraction 1(−) (231):
¹H NMR (DMSO-d6, 300 MHz): δ 0.76 (d, 6H), 1.74 (m, 1H), 2.27 (s, 3H), 2.62 (d, 2H), 3.24-3.38 (m, 2H), 3.43-3.62 (m, 2H), 6.90-7.28 (m, 6H), 8.83 (s, 1H), 12.51 (s, 1H)
LC/MS (ES+) m/z=370.18

Fraction 2(+) (232):
¹H NMR (DMSO-d6, 300 MHz): δ 0.76 (d, 6H), 1.74 (m, 1H), 2.27 (s, 3H), 2.62 (d, 2H), 3.24-3.38 (m, 2H), 3.43-3.62 (m, 2H), 6.90-7.28 (m, 6H), 8.83 (s, 1H), 12.51 (s, 1H)
LC/MS (ES+) m/z=370.18

The structures for the enantiomers are as follows:

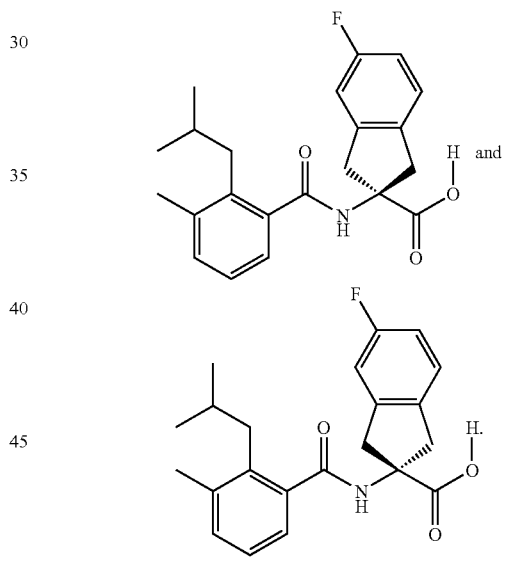

However, the structures are not assigned to either of the particular eluting fraction.

Example 233

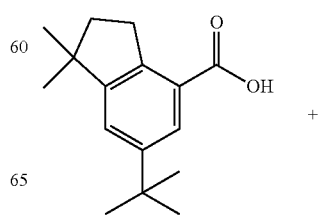

+

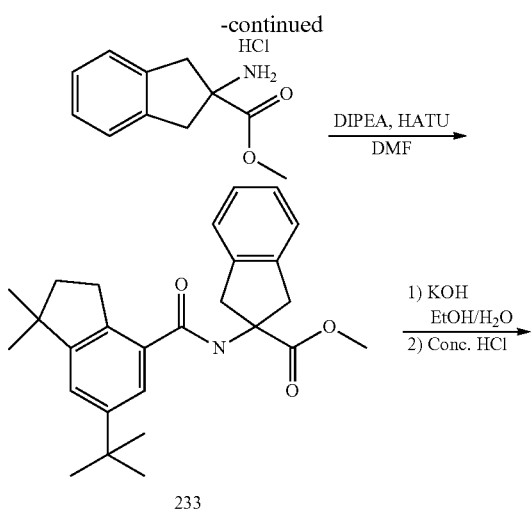

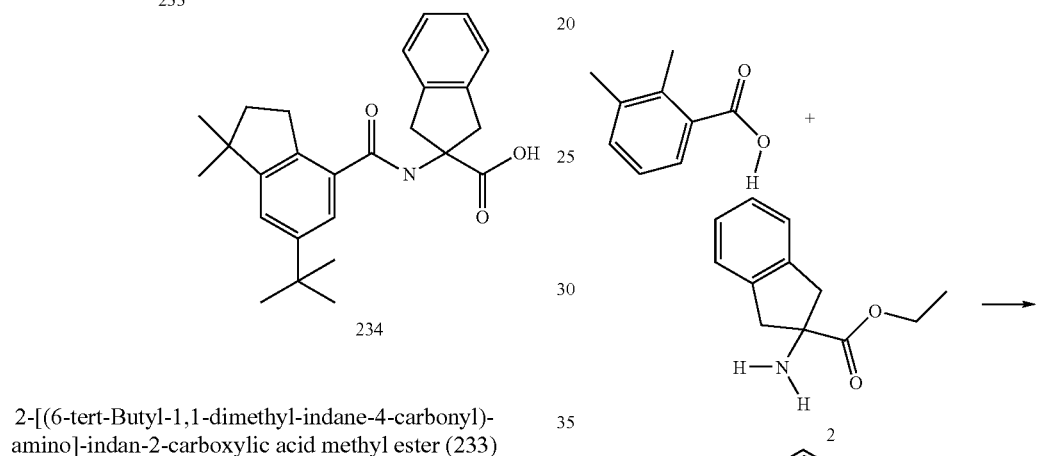

2-[(6-tert-Butyl-1,1-dimethyl-indane-4-carbonyl)-amino]-indan-2-carboxylic acid methyl ester (233)

To a solution of 6-tent-butyl-1,1-dimethyl-indan-4-carboxylic acid (1 g, 4.1 mmol), HCl salt of 2-amino-indan-2-carboxylic acid methyl ester (924 mg, 4.1 mmol), HATU (1.85 g, 4.9 mmol) in anhydrous DMF (15 mL) is added DIPEA (2.5 mL, 14.4 mmol). The resulting solution is stirred at RT overnight. After the removal of DMF in vacuo, the residue is dissolved in EtOAc (100 mL) and washed with water (1×100 mL), 1N HCl (1×100 mL) and brine (1×100 mL). The organic layer is dried over anhydrous MgSO$_4$ and concentrated in vacuo. The residue is purified by flash column chromatography (60 g silica gel, gradient elution: 10-60% EtOAc in heptane) to give pure product as white solid (660 mg, 39%).

$^1$H NMR (DMSO-d6, 300 MHz): δ 1.20 (s, 6H), 1.27 (s, 9H), 1.80 (t, 2H), 2.87 (t, 2H), 3.37 (s, 2H), 3.57 (s, 2H), 3.63 (s, 1H), 3.64 (s, 3H), 7.15-7.29 (m, 6H), 8.78 (s, 1H)
LC/MS (ES+) m/z=420.24

Example 234

2-[(6-tert-Butyl-1,1-dimethyl-indane-4-carbonyl)-amino]-indan-2-carboxylic acid (234)

A mixture of 2-[(6-tert-butyl-1,1-dimethyl-indane-4-carbonyl)-amino]-indan-2-carboxylic acid methyl ester (600 mg, 1.4 mmol) and KOH (1.8 g, 30.8 mmol) is dissolved in EtOH (25 mL) and water (2 mL) under water bath. The water bath is removed when KOH is completely dissolved and the resulting reaction solution is stirred at RT for 8 h. After concentration in vacuo, the residue is neutralized with 1N HCl and extracted with EtOAc (3×150 mL), the organic washes are combined and concentrated in vacuo. The residue is purified by preparative HPLC (C18 column 10 micron, gradient elution: 20-100% ACN 0.1% TFA in H$_2$O 0.1% TFA). Product crystallizes out of the collected fractions on standing. Filtration and drying gave pure product as white solid (454 mg, 78%).

$^1$H NMR (DMSO-d6, 300 MHz): δ 1.20 (s, 6H), 1.27 (s, 9H), 1.79 (t, 2H), 2.87 (t, 2H), 3.37 (s, 2H), 3.55 (s, 2H), 3.61 (s, 1H), 7.12-7.29 (m, 6H), 8.62 (s, 1H)
LC/MS (ES+) m/z=406.22

Example 235

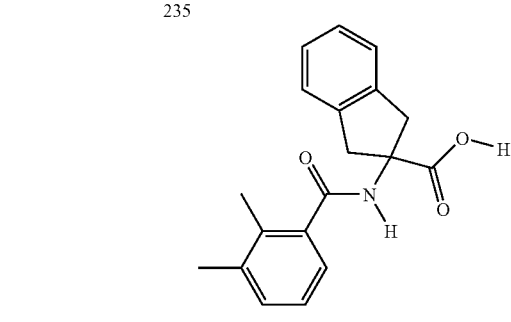

2-(2,3-Dimethyl-benzoylamino)-indan-2-carboxylic acid ethyl ester (235)

2-Amino-indane-2-carboxylic acid ethyl ester (250 mg, 1.2 mmol), 2,3-dimethyl-benzoic acid (183 mg, 1.2 mmol)

and HATU (555 mg, 1.46 mmol) are taken in a vial, evacuated and refilled with nitrogen. Anhydrous DMF (2 mL) is added and stirring is initiated. After a few min, DIPEA (0.302 mL, 1.82 mmol) is added and stirred at RT overnight. Analysis by tlc of the reaction mixture (silica, 50% EtOAc/heptanes) indicates complete consumption of the starting amine. Water (10 mL) is added, extracted with EtOAc (3×5 mL), dried over Na$_2$SO$_4$, concentrated and the crude product is chromatographed on a 25 g silica gel column using 20-50% EtOAc in heptane as a gradient to afford 2-(2,3-dimethyl-benzoylamino)-indan-2-carboxylic acid ethyl ester (350 mg, 87%).

$^1$H NMR (CDCl$_3$, 300 MHz,): δ 1.3 (t, 3H), 2.26 (s, 3H), 2.29 (s, 3H), 3.55 (dd, 4H), 4.28 (q, 2H), 6.19 (s, 1H), 7.04-7.22 (m, 7H).

LC/MS m/z=338.17.

Example 236

2-(2,3-Dimethyl-benzoylamino)-indan-2-carboxylic acid (236)

The mixture of 2-(2,3-dimethyl-benzoylamino)-indan-2-carboxylic acid ethyl ester (235) (290 mg, 0.86 mmol), KOH (50% aqueous solution, 1.92 g, 17.2 mmol), EtOH (10 mL) and water (1 mL) are stirred in a 20 mL vial at 50° C. for 30 min. After concentration in vacuo, the residue is dissolved in water (5 mL) and acidified with conc. HCl until no more white precipitate came out of the water. The filtration gives 2-(2,3-dimethyl-benzoylamino)-indan-2-carboxylic acid (236) as white solid (240 mg, 90%).

$^1$H NMR (CDCl$_3$, 300 MHz): δ 2.22 (s, 3H), 2.25 (s, 3H), 3.61 (dd, 4H), 6.24 (s, 1H), 7.06 (m, 2H), 7.18-7.23 (m, 5H).

LC/MS m/z=310.13.

Example 237

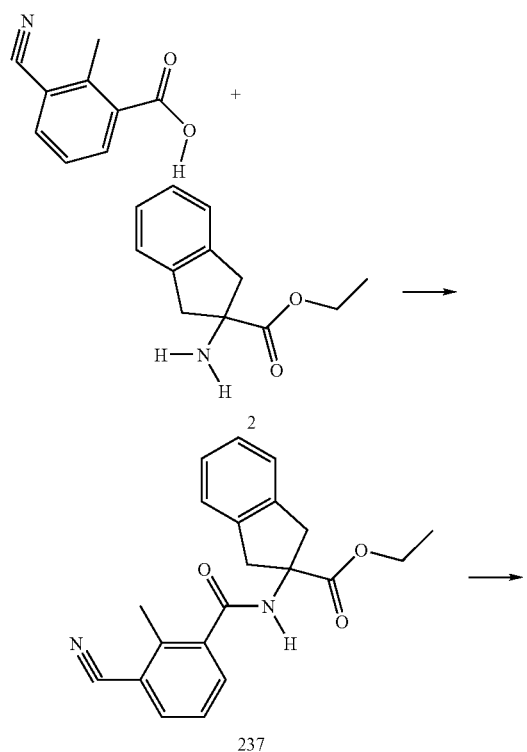

237

2-(3-Cyano-2-methyl-benzoylamino)-indan-2-carboxylic acid ethyl ester (237)

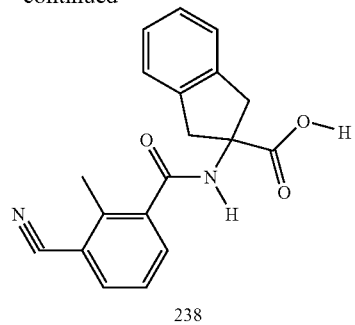

238

2-Amino-indane-2-carboxylic acid ethyl ester (250 mg, 1.2 mmol), 3-cyano-2-methyl-benzoic acid (196 mg, 1.2 mmol) and HATU (555 mg, 1.46 mmol) are taken in a vial, evacuated and refilled with nitrogen. Anhydrous DMF (2 mL) is added and stirring is initiated. After a few min, DIPEA (0.302 mL, 1.82 mmol) is added and stirred at RT overnight. Analysis by tlc of the reaction mixture (silica, 50% EtOAc/heptanes) indicates complete consumption of the starting amine. Water (10 mL) is added, extracted with EtOAc (3×5 mL), dried over Na$_2$SO$_4$, concentrated and the crude product is chromatographed on a 25 g silica gel column using 20-50% EtOAc in heptane as a gradient to afford 2-(3-cyano-2-methyl-benzoylamino)-indan-2-carboxylic acid ethyl ester (373 mg, 89%).

$^1$H NMR (CDCl$_3$, 300 MHz,): δ 1.3 (t, 3H), 2.6 (s, 3H), 3.57 (dd, 4H), 4.29 (q, 2H), 6.23 (s, 1H), 7.23-7.30 (m, 5H), 7.51 (d, 1H), 7.64 (d, 1H).

LC/MS m/z=349.16.

Example 238

2-(3-Cyano-2-methyl-benzoylamino)-indan-2-carboxylic acid (238)

The mixture of 2-(3-cyano-2-methyl-benzoylamino)-indan-2-carboxylic acid ethyl ester (3) (310 mg, 0.89 mmol), KOH (50% aqueous solution, 2 g, 17.8 mmol), EtOH (10 mL) and water (1 mL) are stirred in a 20 mL vial at 50° C. for 30 min. After concentration in vacuo, the residue is dissolved in water (5 mL) and acidified with conc. HCl until no more white precipitate came out of the water. The filtration affords 2-(3-cyano-2-methyl-benzoylamino)-indan-2-carboxylic acid (238) as white solid (270 mg, 95%).

$^1$H NMR (CDCl$_3$, 300 MHz): δ 2.56 (s, 3H), 3.62 (dd, 4H), 6.30 (s, 1H), 7.22-7.31 (m, 5H), 7.51 (d, 1H), 7.65 (d, 1H).

LC/MS m/z=321.12.

Example 239

2-Benzyl-4-bromo-benzoic acid (239)

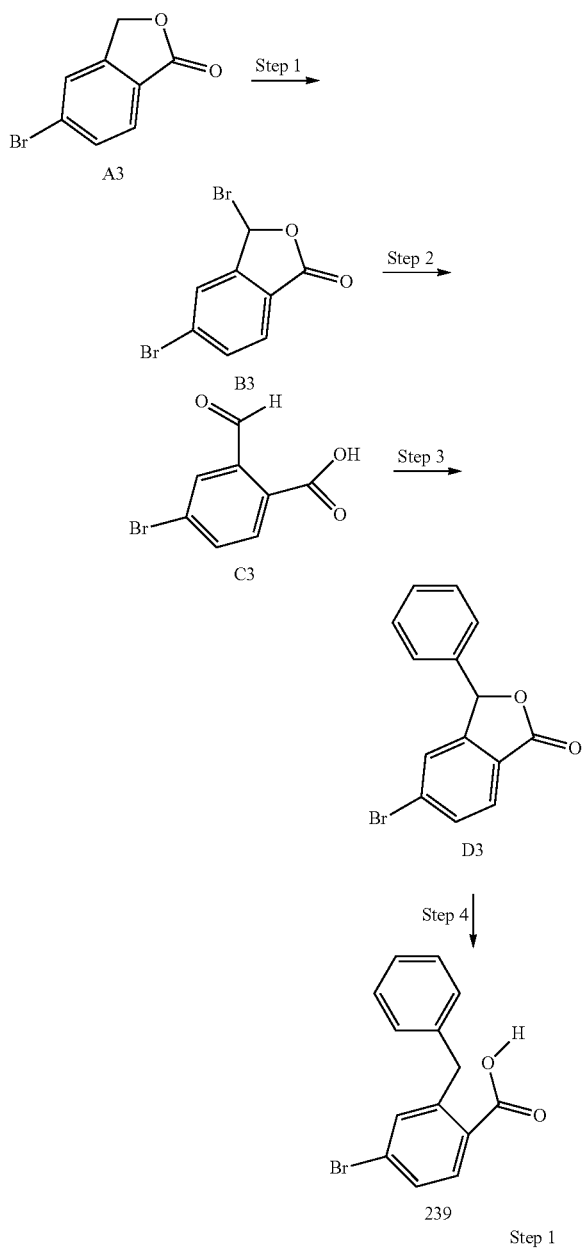

Step 1

3,5-Dibromo-3H-isobenzofuran-1-one (B3)

The mixture of 5-bromo-3H-isobenzofuran-1-one (A3) (51.5 g, 242 mmol) in bromobenzene (100 mL) is heated to 158° C. Bromine (18.8 mL, 363 mmol) is added dropwise to the mixture over 2 h. The mixture is stirred for another 30 min. at 158° C. The bromobenzene is removed by distillation under vacuum. The residue is vacuum dried 1 hour at 120° C. to yield a black crystalline residue. Recrystallization: The residue is dissolved in hot isopropyl ether (300 mL). Activated charcoal (1 g) is added, stirred and filtered while hot. The filtrate is cooled in ice-water bath (0° C.) over night. The solid is filtered and is rinsed with cold isopropyl ether (2×10 mL) and vacuum dry over KOH (KOH) to yield 3,5-dibromo-3H-isobenzofuran-1-one (B3) (38 g, 54%, mp: 100° C.).

Step 2

4-Bromo-2-formyl-benzoic acid (C3)

The mixture of 3,5-dibromo-3H-isobenzofuran-1-one (B3) (38 g, 130 mmol) in a solution of 10N NaOH (28.6 mL, 286 mmol) and water (240 mL) is heated for 2 h at 80° C. Activated charcoal (2 g) is added and the mixture is refluxed for another 1 hour. Mixture is hot filtered and acidified with 2N methanesulfonic acid (100 mL). The resulting mixture is cooled in an ice-water bath for 1 h. The solid is filtered and washed with water (4×25 mL) and vacuum dried under KOH to yield 4-bromo-2-formyl-benzoic acid (C3) (26.5 g, 89%, mp: 202° C.). Recrystallization: Dissolved 4-bromo-2-formyl-benzoic acid (C3) in hot EtOH (220 mL) and cooled the mixture in an ice-water bath for 4 h. The solid is filtered and rinsed with cold EtOH (3×20 mL). The solid is then vacuum dried over KOH to yield 4-bromo-2-formyl-benzoic acid (16.8 g, 63%, mp: 204-205° C.).

Step 3

5-Bromo-3-phenyl-3H-isobenzofuran-1-one (D3)

A tricol of 1 L with a condenser and an addition funnel is purged with N₂ and magnesium turnings (5 g, 206 mmol) in tetrahydrofuran (80 mL) are added. Bromobenzene (32 g, 206 mmol) in tetrahydrofuran (80 mL) is added dropwise over 1¼ hour by maintaining the mixture temperature at 30° C. The resulting mixture is stirred for 45 min. at 30° C. 4-Bromo-2-formyl-benzoic acid (C3) (18.9 g, 83 mmol) in anhydrous tetrahydrofuran (200 mL) is added dropwise over 45 min. The mixture is stirred for 2 h at 30° C. The mixture is cooled in an ice-water bath and water (120 mL) and 5N HCl solution (80 mL) are added. The mixture is stirred overnight. THF is removed in vacuo and extracted with DCM (3×100 mL). The combined organics are washed with water (2×100 mL), dried over Na₂SO₄, filtered and the solvent is removed in vacuo to yield 5-bromo-3-phenyl-3H-isobenzofuran-1-one (22.5 g, 94%). Recrystallization: 5-bromo-3-phenyl-3H-isobenzofuran-1-one is dissolved in hot acetone (250 mL) and the mixture cooled in an ice-water bath over night. The resultant solid is filtered, rinsed with cold ACN (2×15 mL), and then vacuum dried over KOH to yield 5-bromo-3-phenyl-3H-isobenzofuran-1-one (D3) (14.4 g, 61%, mp: 189° C.).

Step 4

2-Benzyl-4-bromo-benzoic acid (239)

The mixture of 5-bromo-3-phenyl-3H-isobenzofuran-1-one (D3) (14.4 g, 50 mmol), iodine (9 g, 70 mmol), amorphous red phosphorous (7.8 g, 250 mmol), acetic acid (125 mL) and distilled water (15 mL) are taken in this order in a 3-neck flask with a mechanical stirrer and condenser. After stirring overnight at 50° C. (90% product and 10% starting material), the reaction is quenched by adding into water (500 mL), added ether (200 mL) and filtered off phosphorous. The aqueous layer is extracted with ether (3×100 mL) and the combined organic layers are washed with sodium bisulfite solution (100 mL) and water (2×100 mL). The organic phase is extracted using 1N NaOH aqueous solution (4×100 mL), washed again with water (4×100 mL), dried over Na₂SO₄ and evaporated to get the neutral fraction (2 g, mp 180° C.). The basic phase is acidified with 5N HCl (150 mL) and extracted with DCM (4×100 mL). The combined extracts are washed with water (3×100 mL), dried over Na₂SO₄ and evaporated to get product (12 g, mp 137° C.). This is further recrystallized from boiling ACN (50 mL) to afford 2-benzyl-4-bromo-benzoic acid (239) (10 g, 83%, mp 145° C.).

Example 240

(2-Benzyl-4-bromo-benzoylamino)-indan-2-carboxylic acid ethyl ester (240)

2-Amino-indane-2-carboxylic acid ethyl ester (2) (250 mg, 1.2 mmol), 2-benzyl-4-bromo-benzoic acid (239) (354 mg, 1.2 mmol) and HATU (555 mg, 1.46 mmol) are taken in a vial, evacuated and refilled with nitrogen. Anhydrous DMF (2 mL) is added and stirring is initiated. After few min, DIPEA (0.302 mL, 1.82 mmol) is added and stirred at RT overnight. Analysis by tlc of the reaction mixture (silica, 50% EtOAc/heptanes) indicates complete consumption of the starting amine. Water (10 mL) is added, extracted with EtOAc (3×5 mL), dried over Na₂SO₄, concentrated and the crude product is chromatographed on a 25 g silica gel column using 20-50% EtOAc in heptane as a gradient to afford 2-(2-benzyl-4-bromo-benzoylamino)-indan-2-carboxylic acid ethyl ester (495 mg, 86%).

¹H NMR (CDCl₃, 300 MHz,): δ 1.26 (t, 3H), 3.35 (dd, 4H), 4.14 (s, 3H), 4.24 (q, 2H), 6.12 (s, 1H), 7.05-7.39 (m, 12H).

LC/MS m/z=478.13.

Example 241

2-(2-Benzyl-4-bromo-benzoylamino)-indan-2-carboxylic acid (241)

The mixture of 2-(2-benzyl-4-bromo-benzoylamino)-indan-2-carboxylic acid ethyl ester (240) (339 mg, 0.71 mmol), KOH (50% aqueous solution, 1.58 g, 14.14 mmol), EtOH (10 mL) and water (1 mL) are stirred in a 20 mL vial at 50° C. for 30 min. After concentration in vacuo, the residue is dissolved in water (5 mL) and acidified with conc. HCl until no more white precipitate came out of the water. The filtration affords 2-(2-benzyl-4-bromo-benzoylamino)-indan-2-carboxylic acid (241) as white solid (310 mg, 97%).

¹H NMR (CDCl₃, 300 MHz): δ 3.37 (dd, 4H), 4.10 (s, 2H), 6.23 (s, 1H), 7.01-7.38 (m, 12H).

LC/MS m/z=450.06.

Example 242

4-Difluoromethoxy-2-methyl-benzoicacid (242)

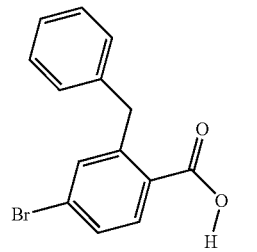

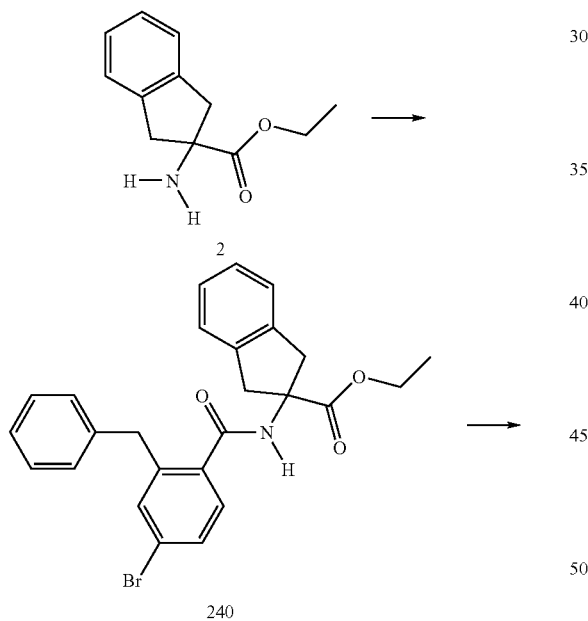

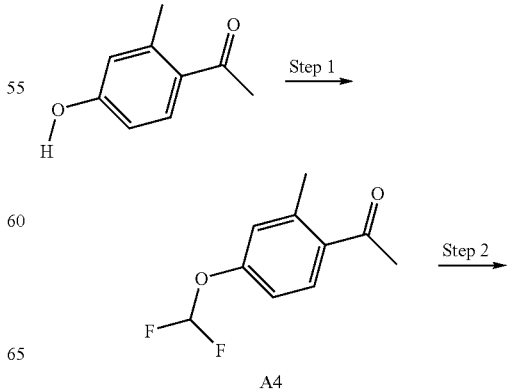

-continued

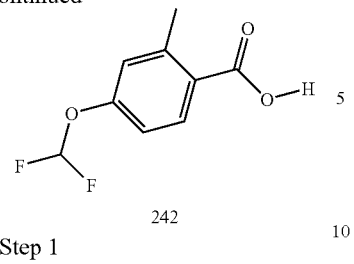

242

Step 1

1-(4-Difluoromethoxy-2-methyl-phenyl)-ethanone (A4)

To a stirred suspension of 1-(4-hydroxy-2-methyl-phenyl)-ethanone (15 g, 100 mmol) in dioxane (30 mL) is added water (25 mL) followed by the addition of NaOH (20 g, 500 mmol). Reaction is heated to 65° C. and passed gaseous chlorodifluoromethane (30 g, 150 mmol) using a glass tube dipped below the solution level for 75 minutes. Stirred for 30 min longer and left at RT over the weekend. Water (100 mL) and ether (40 mL) are added after transferring to a reparatory funnel. A semi-gelatinous material settled at the bottom of the aqueous layer after some time. The bottom aqueous layer is drained off and extracted with ether (2×40 mL). The combined ether layers are washed with water (5×25 mL), dried over solid $K_2SO_4$, evaporated and distilled (0.04 mm Hg, 61-64° C.) to afford 1-(4-difluoromethoxy-2-methyl-phenyl)-ethanone (A4) (16.2 g, 81%). Rf in tlc 0.60 with ether.

Step 2

4-Difluoromethoxy-2-methyl-benzoic acid (242)

A stirred solution of sodium hypochlorite (5.25% Aqueous, 204 mL, 143 mmol) and 2N aqueous KOH (22 mL, 44 mmol) are heated to 50° C. and 1-(4-difluoromethoxy-2-methyl-phenyl)-ethanone (A4) (5.8 g, 29 mmol) is added. After maintaining the temperature at 50-70° C. for 3 h and keeping at RT overnight, the reaction is reheated to 50° C. and sodium metabisulfite (4.5 g) is added in 3 portions. The reaction is then acidified with 12N HCl and stirred well. The precipitated white solid is filtered off, rinsed with a little water and air dried to afford 4-difluoromethoxy-2-methyl-benzoic acid (242) (5.4 g, 92%). The product is recrystallized from 1:1 mixture of ACN and water. mp: 117-119° C. Elemental Analysis: Actual C (53.23), H (3.88), F (18.66) Theoretical C (53.47), H (3.99), F (18.80).

Example 243

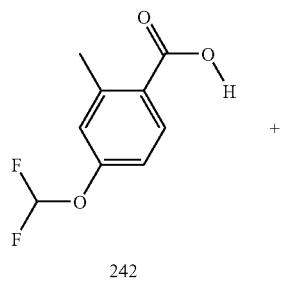

242

+

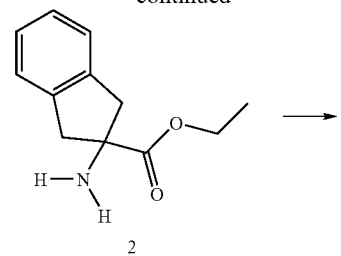

2

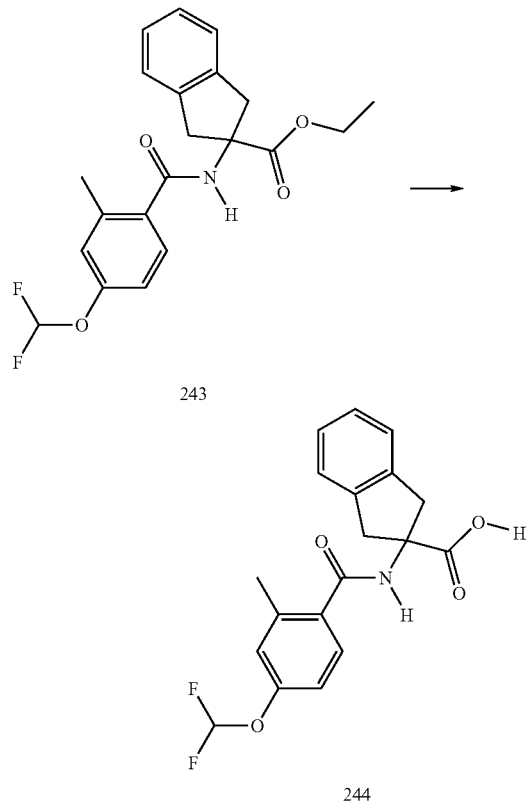

243

244

2-(4-Difluoromethoxy-2-methyl-benzoylamino)-indan-2-carboxylic acid ethyl ester (243)

2-Amino-indane-2-carboxylic acid ethyl ester (2) (250 mg, 1.2 mmol), 4-difluoromethoxy-2-methyl-benzoic acid (242) (246 mg, 1.2 mmol) and HATU (555 mg, 1.46 mmol) are taken in a vial, evacuated and refilled with nitrogen Anhydrous DMF (2 mL) is added and stirring is initiated. After few min, DIPEA (0.302 mL, 1.82 mmol) is added and stirred at RT overnight. Analysis by tlc of the reaction mixture (silica, 50% EtOAc/heptanes) indicates complete consumption of the starting amine. Water (10 mL) is added, extracted with EtOAc (3×5 mL), dried over $Na_2SO_4$, concentrated and the crude product is chromatographed on a 25 g silica gel column using 20-50% EtOAc in heptane as a gradient to afford 2-(4-difluoromethoxy-2-methyl-benzoylamino)-indan-2-carboxylic acid ethyl ester (415 mg, 89%).

$^1$H NMR (CDCl$_3$, 300 MHz,): δ 1.29 (t, 3H), 2.42 (s, 3H), 3.56 (dd, 4H), 4.27 (q, 2H), 6.21 (s, 1H), 6.91 (m, 2H), 7.22 (m, 4H), 7.33 (d, 1H).

LC/MS m/z=390.16.

Example 244

2-(4-Difluoromethoxy-2-methyl-benzoylamino)-indan-2-carboxylic acid (244)

The mixture of 2-(4-difluoromethoxy-2-methyl-benzoylamino)-indan-2-carboxylic acid ethyl ester (243) (301 mg, 0.77 mmol), KOH (50% aqueous solution, 1.73 g, 15.5 mmol), EtOH (10 mL) and water (1 mL) are stirred in a 20 mL vial at 50° C. for 30 min. After concentration in vacuo, the residue is dissolved in water (10 mL) and acidified with conc. HCl until no more white precipitate came out of the water. The filtration affords 2-(4-difluoromethoxy-2-methyl-benzoylamino)-indan-2-carboxylic acid (244) as white solid (245 mg, 88%).

$^1$H NMR (CDCl$_3$, 300 MHz): δ 2.37 (s, 3H), 3.62 (dd, 4H), 6.23 (s, 1H), 6.92 (m, 2H), 7.24 (m, 5H).

LC/MS m/z=362.10.

Example 245

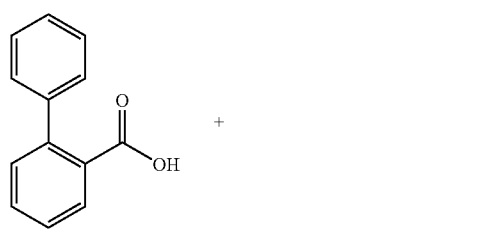

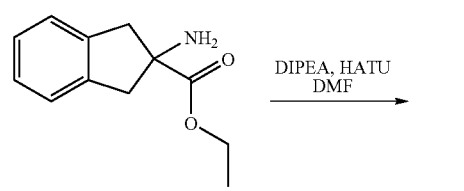

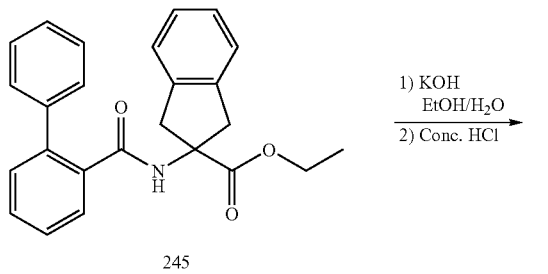

245

2-[((Biphenyl-2-carbonyl)-amino]-indan-2-carboxylic acid ethyl ester (245)

To a solution of biphenyl-2-carboxylic acid (289 mg, 1.46 mmol), 2-amino-indan-2-carboxylic acid ethyl ester (300 mg, 1.46 mmol), HATU (666 mg, 1.75 mmol) in anhydrous DMF (1.8 mL) is added DIPEA (3814, 2.19 mmol). The resulting solution is stirred at RT overnight. Poured reaction into water (10 mL) and extracted with EtOAc (3×5 mL). The combined organic layers are concentrated in vacuo and the residue purified by flash column chromatography (12 g silica gel, gradient elution: 0-30% EtOAc in heptane) to give product (245) as off-white solid (525 mg, 93%).

Example 246

2-[(Biphenyl-2-carbonyl)-amino]-indan-2-carboxylic acid (246)

2-[(Biphenyl-2-carbonyl)-amino]-indan-2-carboxylic acid ethyl ester (525 mg, 1.36 mmol) is dissolved in EtOH (15 mL), and solid KOH (1.42 g, 24.7 mmol) and water (1.5 mL) are added. The mixture is stirred at RT for 30 minutes then concentrated in vacuo. The residue is dissolved in water (10 mL) and acidified with concentrated HCl until no more white solid precipitated. The solid is collected by vacuum filtration to give product (246) as white solid (453 mg, 93%).

$^1$H NMR (CDCl$_3$, 300 MHz): δ 2.92 (d, 2H), 3.63 (d, 2H), 5.84 (s, 1H), 7.08-7.12 (m, 2H), 7.15-7.19 (m, 2H), 7.24 (s, 4H), 7.30 (dd, 2H), 7.40-7.54 (m, 2H), 7.85 (dd, 1H)

LC/MS (ES+) m/z=358.14

Example 247

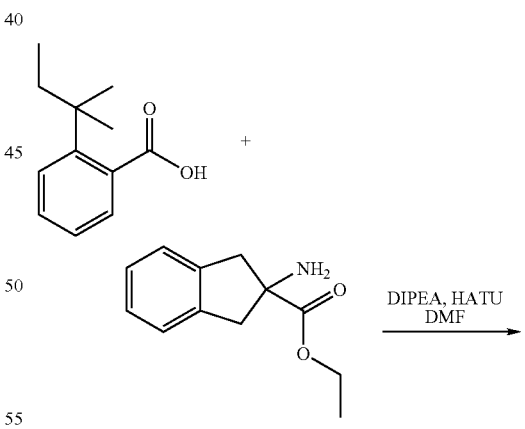

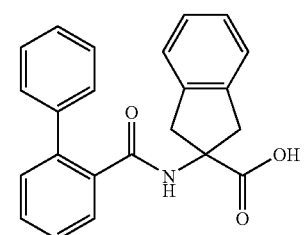

246

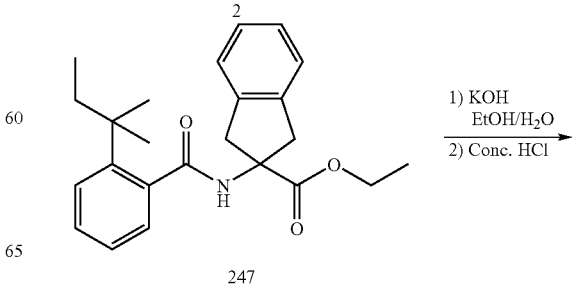

247

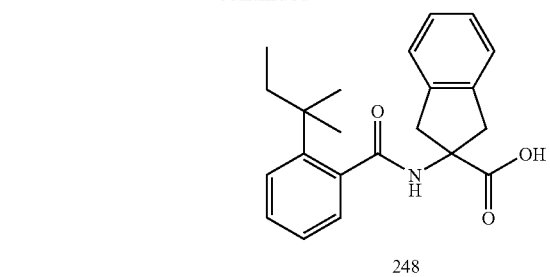

248

2-[2-(1,1-Dimethyl-propyl)-benzoylamino]-indan-2-carboxylic acid ethyl ester (247)

To a solution of 2-(1,1-dimethyl-propyl)-benzoic acid (140 mg, 0.73 mmol), 2-amino-indan-2-carboxylic acid ethyl ester (150 mg, 0.73 mmol), HATU (333 mg, 0.87 mmol) in anhydrous DMF (1 mL) is added DIPEA (1904, 1.1 mmol). The resulting solution is stirred at RT overnight. Water (10 mL) is then poured into the reaction mixture, and then the reaction mixture is extracted with EtOAc (3×5 mL). The combined organic layers are concentrated in vacuo. The residue is purified by flash column chromatography (12 g silica gel, gradient elution: 0-30% EtOAc in heptane) to give product (247) as yellow oil (220 mg, 89%).

Example 248

2-[2-(1,1-Dimethyl-propyl)-benzoylamino]-indan-2-carboxylic acid (248)

2-[2-(1,1-Dimethyl-propyl)-benzoylamino]-indan-2-carboxylic acid ethyl ester (220 mg, 0.58 mmol) is dissolved in EtOH (8 mL), and solid KOH (600 mg, 10 mmol) and water (0.8 mL) are added. The mixture is stirred at RT for 30 minutes then concentrated in vacuo. The residue is dissolved in water (10 mL) and acidified with concentrated HCl until no more white solid precipitated. The solid is collected by vacuum filtration to give product (248) as white solid (158 mg, 78%).

$^1$H NMR (CDCl$_3$, 300 MHz): δ 0.53 (t, 3H), 1.29 (s, 6H), 1.66-1.73 (q, 2H), 3.44 (d, 2H), 3.80 (d, 2H), 6.14 (s, 1H), 7.13-7.14 (m, 1H), 7.15 (d, 1H), 7.22 (d, 4H), 7.32 (d, 1H), 7.34 (t, 1H), 7.37 (dd, 1H)

LC/MS (ES+) m/z=352.17

Example 249

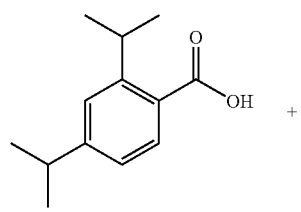

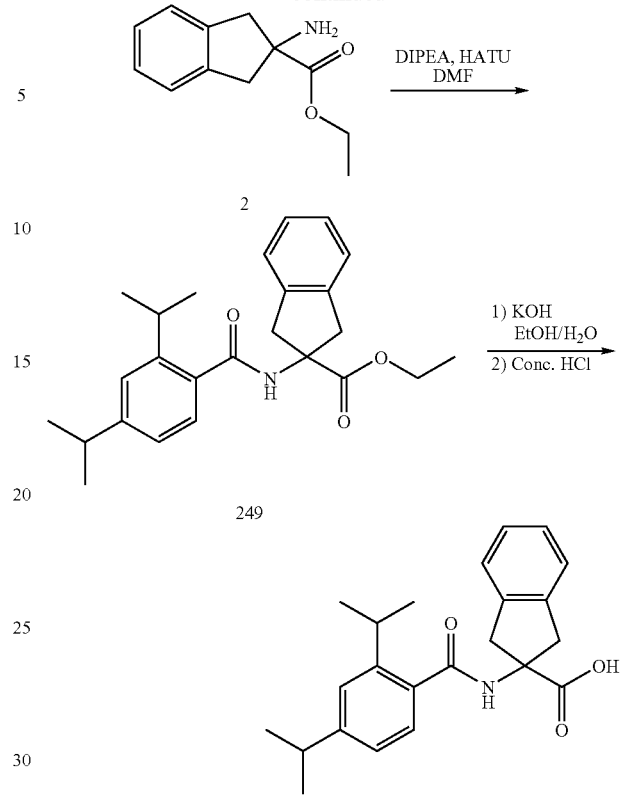

2-(2,4-Diisopropyl-benzoylamino)-indan-2-carboxylic acid ether ester (249)

To a solution of 2,4-diisopropyl-benzoic acid (150 mg, 0.73 mmol), 2-amino-indan-2-carboxylic acid ethyl ester (150 mg, 0.73 mmol), HATU (333 mg, 0.87 mmol) in anhydrous DMF (1 mL) is added DIPEA (1904, 1.10 mmol). The resulting solution is stirred at RT overnight. Poured reaction into water (10 mL) and extracted with EtOAc (3×5 mL). The combined organic layers and concentrated in vacuo. The residue is purified by flash column chromatography (12 g silica gel, gradient elution: 0-30% EtOAc in heptane) to give product (249) as off-white solid (211 mg, 73%).

Example 250

2-(2,4-Diisopropyl-benzoylamino)-indan-2-carboxylic acid (250)

2-(2,4-diisopropyl-benzoylamino)-indan-2-carboxylic acid ethyl ester (211 mg, 0.54 mmol) is dissolved in EtOH (8 mL), and solid KOH (823 mg, 14 mmol) and water (0.8 mL) are added. The mixture is stirred at RT for 30 min then concentrated in vacuo. The residue is dissolved in water (10 mL) and acidified with concentrated HCl until no more white solid precipitated. The solid is collected by vacuum filtration to give product (250) as white solid (188 mg, 95%).

$^1$H NMR (CDCl$_3$, 300 MHz): 1.12 (d, 6H), 1.21 (d, 6H), 2.83-2.92 (m, 1H), 3.10-3.19 (m, 1H), 3.41 (d, 2H), 3.82 (d, 2H), 6.18 (s, 1H), 7.00-7.10 (m, 2H), 7.16 (s, 1H), 7.22-7.31 (m, 4H)

LC/MS (ES+) m/z=366.20

Example 251

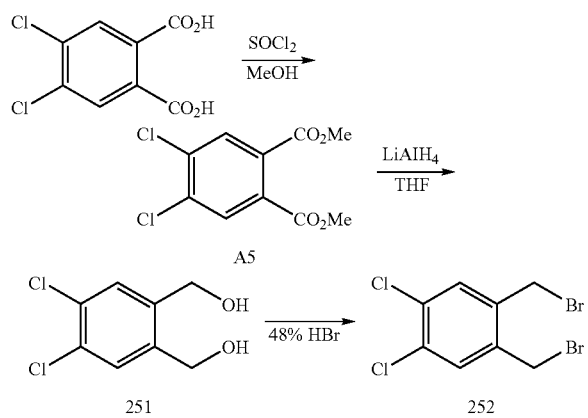

Dimethyl 4,5-Dichlorophthalate (A5)

Thionyl chloride (150 mL, 2.05 mol) is added dropwise over 2 h to a magnetically stirred solution of 4,5-dichlorophthalic acid (110.43 g, 469.8 mmol) in MeOH (1 L) at RT. After stirring overnight, the MeOH is removed in vacuo on a rotary evaporator. The residue is dissolved in EtOAc (750 mL) and extracted with water (1×500 mL) and saturated aqueous NaHCO$_3$ (1×500 mL). The organic layer is separated, dried over MgSO$_4$, filtered and concentrated in vacuo on a rotary evaporator to afford A5 (122.8 g) as a pale yellow liquid. [A. Rosowsky, C. M. Vaidya, h. Bader, J. E. Wright, B. A. Teicher, *J. Med. Chem.* 40, 286-299 (1997); E. J. Hennessy, S. L. Buchwald, *J. Org. Chem.*, 70, 7371-7375 (2005)]

$^1$H NMR (CDCl$_3$, 300 MHz): δ 3.92 (s, 3H), 7.82 (s, 1H)

4,5-Dichloro-1,2-bis(hydroxymethyl)benzene (251)

A solution of dimethyl 4,5-dichlorophthalate A5 (98.86 g, 375.78 mmol) in tetrahydrofuran (150 mL) is added dropwise over 1 h to a mechanically stirred suspension of LAH (20.8 g, 548.1 mmol) in tetrahydrofuran (1.5 L). During the addition, the reaction is cooled in an ice-water bath. When the addition is completed, the reaction is stirred overnight at RT. The excess LAH is decomposed by cautious addition of water (20 mL), 10% aqueous NaOH (40 mL) and water (20 mL). The solids are removed by filtration through a celite pad and washed with tetrahydrofuran. The combined filtrate and wash is concentrated in vacuo on a rotary evaporator to afford crude 251 as white solid that is purified by crystallization from acetone (150 mL)-heptane (150 mL). The crystals are collected by filtration, washed with heptane and dried to give 4,5-dichloro-1,2-bis(hydroxymethyl)benzene (37.2 g). The combined filtrate and wash afforded a second crop of 251 (18.8 g, 24.1%). [L. A. Levy, *Synth. Commun.*, 13, 639-648 (1983); O. Farooq, *Synthesis*, 1035-1036 (1994)]

$^1$H NMR (DMSO-d6, 300 MHz): δ 4.49 (d, 2H), 5.32 (t, 1H), 7.57 (s, 1H)

EI-MS m/z 209,207

Anal. Calcd. for C$_8$H$_8$Cl$_2$O$_2$: C, 46.41; H, 3.89. Found: C, 46.50; H, 3.83.

Example 252

1,2-Bis-(bromomethyl)-4,5-dichlorobenzene (252)

A mixture of 4,5-dichloro-1,2-bis(hydroxymethyl)benzene (251, 32.87 g, 158.75 mmol) and 48% aqueous hydrobromic acid (160 mL) is heated at reflux temperature for 6 h. The reaction is cooled and extracted with diethyl ether (1×450 mL+2×200 mL). The combined organic extracts are backwashed with water (1×200 mL) and with brine (1×200 mL). The organic layer is separated, dried over MgSO$_4$, filtered and concentrated in vacuo on a rotary evaporator to afford a light yellow solid that is dissolved in heptane-0.5% EtOAc by heating and placed atop a column of silica gel (7.2 cm×23 cm) prepared in heptane-0.5% EtOAc and flash chromatographed taking 500 mL fractions and eluting with heptane-0.5% EtOAc (1.6 L), and heptane-1% EtOAc (4 L). The product containing fractions (5-14) are combined and concentrated in vacuo on a rotary evaporator to give 1,2-bis-(bromomethyl)-4,5-dichlorobenzene (252, 50.01 g) as a colorless liquid. [L. A. Levy, *Synth. Commun.*, 13, 639-648 (1983)]

$^1$H NMR (CDCl$_3$, 300 MHz): δ 4.55 (s, 2H), 7.46 (s, 1H)

EI-MS m/z 330, 332, 334, 336

Anal. Calcd. for C$_8$H$_6$Br$_2$Cl$_2$: C, 28.87; H, 1.82. Found: C, 28.84; H, 1.68.

Example 253

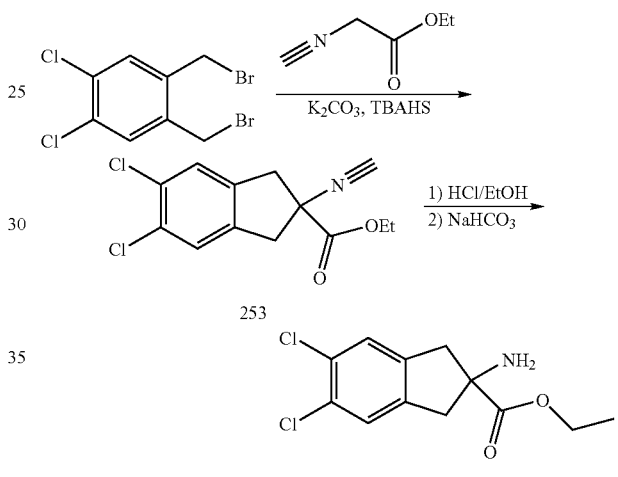

4,5-Dichloro-isocyano-indan-2-carboxylic acid ethyl ester (253)

To a solution of ethyl isocyanoacetate (3.85 mL, 35 mmol) in anhydrous ACN (300 mL) is added finely ground anhydrous K$_2$CO$_3$ (29 g, 210 mmol), TBAHS (tetrabutyl ammonium hydrogen sulfate, 2.34 g, 7 mmol), and 1,2-bis-(bromomethyl)-4,5-dichlorobenzene (11.6 g, 35 mmol). The resulting heterogeneous mixture is stirred at 80° C. overnight. The reaction mixture is cooled down to RT and filtered to remove the unwanted salts. The filtrate is concentrated in vacuo. The residue is purified by flash column chromatography (200 g silica gel; gradient elution: 0-25% EtOAc in heptane) to give a pure product as white powder (6.63 g, 66%).

$^1$H NMR (CDCl$_3$, 300 MHz): δ 1.35 (t, 3H), 3.47 (d, 2H), 3.71 (d, 2H), 4.32 (q, 2H), 7.46 (s, 2H)

LC/MS (ES+) m/z=286.14

Example 254

2-Amino-4,5-dichloro-indan-2-carboxylic acid ethyl ester (254)

To a solution of 4,5-dichloro-isocyano-indan-2-carboxylic acid ethyl ester (253) (6.63 g, 23.2 mmol) in absolute EtOH (200 mL) is added concentrated HCl (10 mL) dropwise. The resulting solution is stirred at RT for 24 h. After the removal of the EtOH in vacuo, the remaining hydrochloride salt is dissolved in water (100 mL) and extracted with ethyl ether (3×50 mL) to remove unwanted organic impurities. The aqueous layer is brought to pH 9 by addition of saturated NaHCO$_3$ solution and then extracted with EtOAc (3×100 mL). The combined EtOAc layer is washed with brine (100 mL). The organic layer is dried over Na$_2$SO$_4$ and concentrated in vacuo to give a pure product as white solid (5.2 g, 82%).

$^1$H NMR (CDCl$_3$, 300 MHz): δ 1.29 (t, 3H), 2.88 (d, 2H), 3.57 (d, 2H), 4.23 (q, 2H), 7.46 (s, 2H)

LC/MS (EZ+) m/z=275.18

Example 255

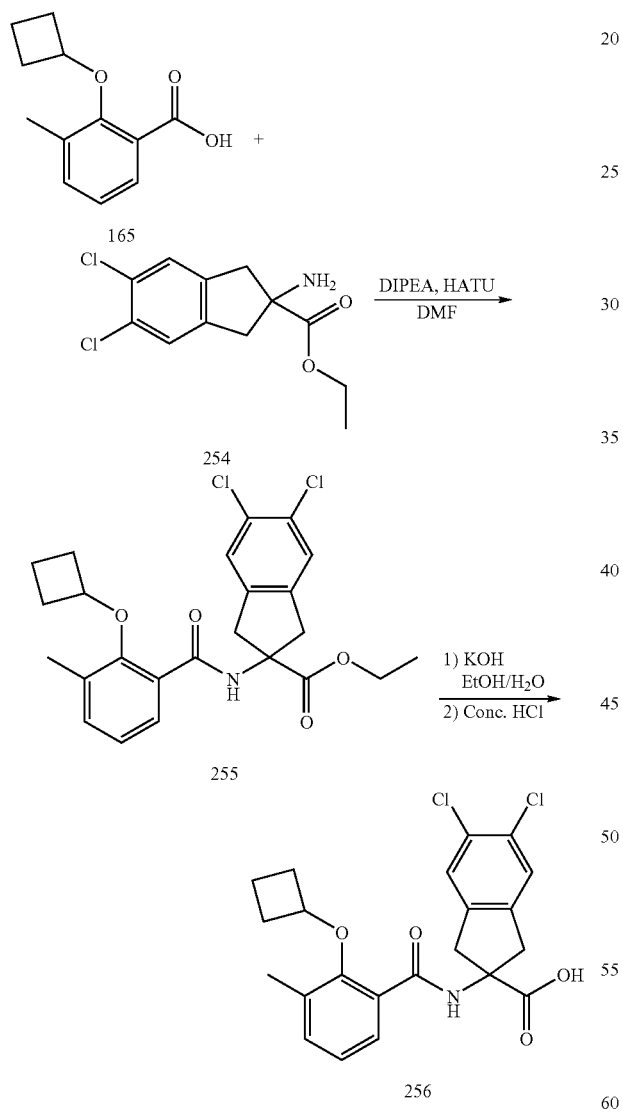

2-(2-Cyclobutoxy-3-methyl-benzoylamino)-4,5-dichloro-indan-2-carboxylic acid ethyl ester (255)

To a solution of 2-cyclobutoxy-3-methyl-benzoic acid (225 mg, 1.1 mmol), 2-amino-4,5-dichloro-indan-2-carboxylic acid ethyl ester (254) (360 mg, 1.3 μmol), HATU 622 mg, 1.64 mmol) in anhydrous DMF (10 mL) is added DIPEA (360 μL, 2.20 mmol). The resulting solution is stirred at RT overnight. After the removal of DMF in vacuo, the residue is suspended in H$_2$O (50 mL) and washed with EtOAc (3×50 mL). Organics are combined and washed successively with NaHCO$_3$ and brine, and then the organic layer is dried over anhydrous Na$_2$SO$_4$ and concentrated in vacuo. The residue is purified by flash column chromatography (12 g silica gel, gradient elution: 0%-20% EtOAc in heptane) to give a pure product (255) as white powder (460 mg, 90%).

$^1$H NMR (CDCl$_3$, 300 MHz): δ 1.21-1.36 (m, 4H), 1.50-1.56 (m, 1H), 1.96-2.09 (m, 4H), 2.27 (s, 3H), 3.44 (t, 2H), 3.73 (dd, 2H), 4.21-4.33 (m, 3H), 6.85-6.94 (m, 2H), 7.08 (t, 1H), 7.14-7.19 (m, 1H), 7.27 (d, 1H), 7.85 (dd, 1H), 8.37 (s, 1H)

LC/MS (ES+) m/z=428.93

Example 256

2-(2-Cyclobutoxy-3-methyl-benzoylamino)-4,5-dichloro-indan-2-carboxylic acid (256)

2-(2-Cyclobutoxy-3-methyl-benzoylamino)-4,5-dichloro-indan-2-carboxylic acid ethyl ester (255) (460 mg, 0.99 mmol) is dissolved in EtOH (50 mL) and set to stir at RT. To this solution is added 5M KOH (3 ml). The reaction mixture is stirred at RT overnight. After concentration in vacuo, the residue is dissolved in water (20 mL) and acidified with concentrated HCl to pH 2. The resultant mixture is washed with EtOAc (3×100 ml). Organics are combined and washed with brine, then dried over anhydrous Na$_2$SO$_4$ and concentrated in vacuo. The desired product (256) is obtained as white solid (405 mg, 94%).

$^1$H NMR (d-DMSO-d6, 300 MHz): δ 1.21-1.36 (m, 1H), 1.50 (m, 1H), 1.92-2.14 (m, 4H), 2.26 (s, 3H), 3.38 (t, 2H), 3.73 (dd, 2H), 4.29 (m, 1H), 6.86-6.95 (m, 2H), 7.11 (t, 1H), 7.15-7.20 (m, 1H), 7.29 (d, 1H), 7.83 (dd, 1H), 8.51 (s, 1H)

LC/MS (ES+) m/z=434.32

Example 257

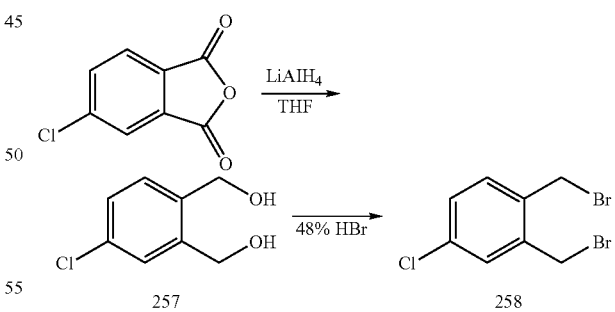

4-Chloro-1,2-bis(hydroxymethyl)benzene (257)

A solution of 4-chlorophthalic anhydride (24.83 g, 136.01 mmol) in tetrahydrofuran (100 mL) is added dropwise to a mechanically stirred suspension of LAH (8.72 g, 229.78 mmol) in tetrahydrofuran (500 mL). After stirring overnight at room temperature, the excess LAH is decomposed by cautious addition of water (8.5 mL), 10% aqueous NaOH (17 mL) and water (8.5 mL). The reaction is diluted with tetrahydrofuran (300 mL) and the solids are removed by filtration through a celite pad and washed with tetrahydrofuran. The combined filtrate and wash is concentrated in vacuo on a rotary evaporator to afford diol 257 as a colorless liquid (22.16 g) that crystallized on standing. Crystallization is effected in benzene. [O. Farooq, *Synthesis,* 1035-1036 (1994); R. F. Bird, E. E. Turner, *J. Chem. Soc.* 5050-5051 (1952); J. Tirouflet, *Compt. rend.,* 238, 2246-2247 (1954)]

$^1$H NMR (DMSO-d6, 300 MHz): δ 4.48 (t, 2H), 4.52 (t, 2H), 5.15 (t, 1H), 5.24 (t, 1H), 7.27 (dd, 1H), 7.38 (s, 1H), 7.41 (t, 1H)

Example 258

1,2-Bis(bromomethyl)-4-chlorobenzene (258)

A mixture of 4-chloro-1,2-bis(hydroxymethyl)benzene (257, 20.57 g, 119.17 mmol) and 48% aqueous hydrobromic acid (140 mL) is heated at 137° C. for 4.5 h. The reaction is cooled to RT then diluted with cold water (250 mL) and extracted with diethyl ether (1×400 mL+2×200 mL). The combined organic extracts are washed with water (1×200 mL), with brine (1×200 mL), dried over MgSO$_4$, filtered and concentrated in vacuo on a rotary evaporator to afford crude dibromide 258 as a yellow liquid. This material is dissolved in heptane-0.5% EtOAc, placed atop a column of silica gel (7.2 cm×22 cm) and flash chromatographed taking 400 mL fractions eluting with heptane-0.5% EtOAc (1.6 L) and heptane-1% EtOAc (3 L). Product containing fractions (5-9) are combined and concentrated in vacuo on a rotary evaporator to afford dibromide 258 as a colorless liquid (34.46 g). [D. R. Lyon, F. G. Mann, G. H. Cookson, *J. Chem. Soc.,* 662-670 (1947)]

$^1$H NMR (CDCl$_3$, 300 MHz): δ 4.58+4.61 (s+s, 4H), 7.28-7.32 (m, 2H), 7.36 (d, 1H)

EI-MS 298, 300

Anal. Calcd. For C$_8$H$_7$Br$_2$Cl: C, 32.20; H, 2.36. Found: C, 32.30; H, 2.22.

Alternate Route:

A magnetically stirred mixture of 4-chloro-ortho-xylene (5 g, 35.56 mmol), N-bromosuccinimide (12.65 g, 71.07 mmol), AIBN (0.55 g) and CCl$_4$ (150 mL) is heated at reflux temperature for 3.5 h, and then cooled to RT. The solids are removed by filtration and washed with CCl$_4$. The combined filtrate and wash is concentrated in vacuo on a rotary evaporator to give crude dibromide 10 as a colorless liquid that is dissolved in heptane-1% EtOAc, placed atop a column of silica gel (7.2 cm×18 cm) prepared in heptane-1% EtOAc and flash chromatographed taking 200 mL fractions eluting with heptane-1% EtOAc. Product containing fractions (7-11) are combined and concentrated in vacuo on a rotary evaporator to afford impure 258 as colorless liquid.

$^1$H NMR (CDCl$_3$, 300 MHz): δ 4.46 (s, 0.3H), 4.51 (s, 0.6H), 4.58+4.61 (pr s, 4H), 7.26-7.29 (m, 2.5H), 7.36 (d, 1.2H).

Example 259

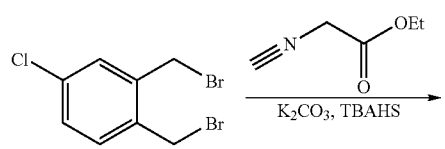

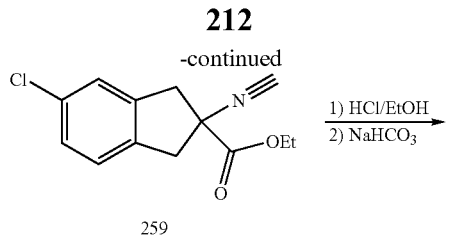

259

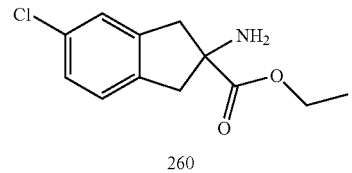

260

4-Chloro-isocyano-indan-2-carboxylic acid ethyl ester (259)

To a solution of ethyl isocyanoacetate (3.85 mL, 35.0 mmol) in anhydrous ACN (300 mL) is added finely ground anhydrous K$_2$CO$_3$ (29 g, 210 mmol), TBAHS (tetrabutyl ammonium hydrogen sulfate, 2.34 g, 7 mmol), and 1,2-bis (bromomethyl)-4-chlorobenzene (10.4 g, 35 mmol). The resulting heterogeneous mixture is stirred at 80° C. overnight. The reaction mixture is cooled to RT and filtered to remove the unwanted salts. The filtrate is concentrated in vacuo. The residue is purified by flash column chromatography (200 g silica gel; gradient elution: 0-25% EtOAc in heptane) to give a pure product as a colorless oil (5.06 g, 58%).

$^1$H NMR (CDCl$_3$, 300 MHz): δ 1.35 (t, 3H), 3.47 (d, 2H), 3.71 (d, 2H), 4.32 (q, 2H), 7.28-7.32 (m, 2H), 7.36 (d, 1H)

LC/MS (ES+) m/z=250.56

Example 260

2-Amino-4-chloro-indan-2-carboxylic acid ethyl ester (260)

To a solution of 4-chloro-isocyano-indan-2-carboxylic acid ethyl ester (259) (5.06 g, 20.2 mmol) in absolute EtOH (200 mL) is added concentrated HCl (10 mL) dropwise. The resulting solution is stirred at RT for 24 h. After the removal of the EtOH in vacuo, the remaining hydrochloride salt is dissolved in water (100 mL) and extracted with of ethyl ether (3×50 mL) to remove unwanted organic impurities. The aqueous layer is brought to pH 9 by addition of saturated NaHCO$_3$ solution and then extracted with EtOAc (3×100 mL). The combined EtOAc layer is washed with brine (100 mL). The organic layer is dried over Na$_2$SO$_4$ and concentrated in vacuo to give a pure product as white solid (4.2 g, 87%).

$^1$H NMR (CDCl$_3$, 300 MHz): δ 1.29 (t, 3H), 2.88 (d, 2H), 3.57 (d, 2H), 4.23 (q, 2H), 7.28-7.32 (m, 2H), 7.36 (d, 1H)

LC/MS (EZ+) m/z=239.58

Example 261

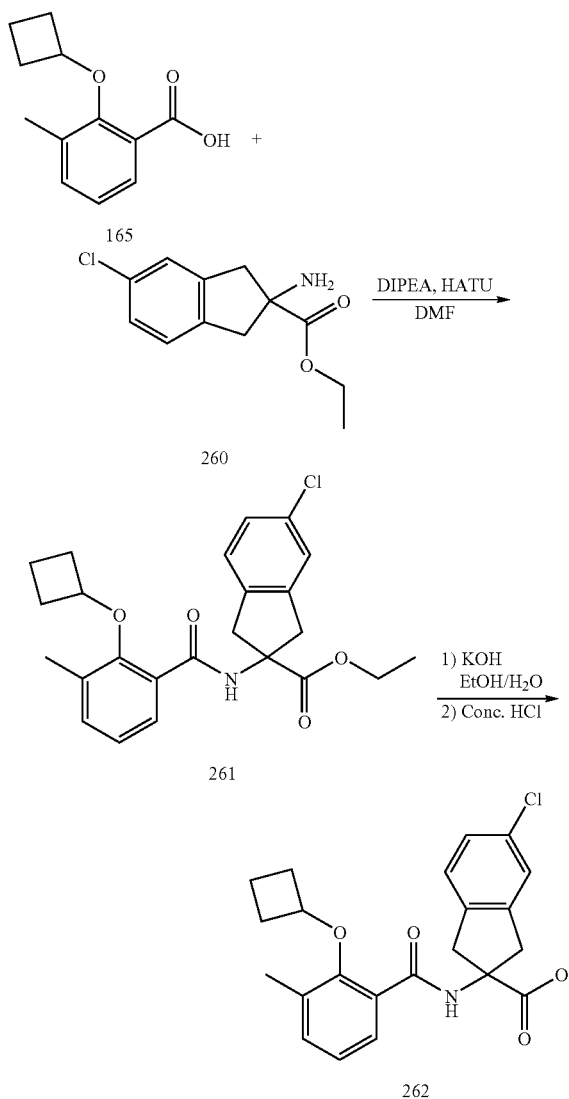

2-(2-Cyclobutoxy-3-methyl-benzoylamino)-5-chloro-indan-2-carboxylic acid ethyl ester (261)

To a solution of 2-cyclobutoxy-3-methyl-benzoic acid (213 mg, 1.04 mmol), 2-amino-4-chloro-indan-2-carboxylic acid ethyl ester (260) (298 mg, 1.24 mmol), HATU (591 mg, 1.55 mmol) in anhydrous DMF (10 mL) is added DIPEA (345 µL, 2.07 mmol). The resulting solution is stirred at RT overnight. After the removal of DMF in vacuo, the residue is suspended in $H_2O$ (50 mL) and washed with EtOAc (3×50 mL). Organics are combined and washed successively with $NaHCO_3$ and brine, and then the organic layer is dried over anhydrous $Na_2SO_4$ and concentrated in vacuo. The residue is purified by flash column chromatography (12 g silica gel, gradient elution: 0%-20% EtOAc in heptane) to give a pure product (261) as white powder (370 mg, 83%).

$^1$H NMR (CDCl$_3$, 300 MHz): δ 1.21-1.36 (m, 4H), 1.50-1.56 (m, 1H), 1.96-2.09 (m, 4H), 2.27 (s, 3H), 3.44 (t, 2H), 3.73 (dd, 2H), 4.21-4.33 (m, 3H), 6.85-6.94 (m, 2H), 7.08 (t, 1H), 7.14-7.19 (m, 1H), 7.27 (d, 1H), 7.85 (dd, 1H), 8.37 (s, 1H)
LC/MS (ES+) m/z=428.93

Example 262

2-(2-Cyclobutoxy-3-methyl-benzoylamino)-5-chloro-indan-2-carboxylic acid (262)

2-(2-Cyclobutoxy-3-methyl-benzoylamino)-5-chloro-indan-2-carboxylic acid ethyl ester (261) (370 mg, 0.86 mmol) is dissolved in EtOH (50 mL) and set to stir at RT. To this solution is added 5M KOH (3 ml). The reaction mixture is stirred at RT overnight. After concentration in vacuo, the residue is dissolved in water (20 mL) and acidified with conc. HCl to pH 2. The resultant mixture is washed with EtOAc (3×100 ml). Organics are combined and washed with brine, then dried over anhydrous $Na_2SO_4$ and concentrated in vacuo. The desired product (262) is obtained as white solid (320 mg, 93%).

$^1$H NMR (d-DMSO-d6, 300 MHz): δ 1.21-1.36 (m, 1H), 1.50 (m, 1H), 1.92-2.14 (m, 4H), 2.26 (s, 3H), 3.38 (t, 2H), 3.73 (dd, 2H), 4.29 (m, 1H), 6.86-6.95 (m, 2H), 7.11 (t, 1H), 7.15-7.20 (m, 1H), 7.29 (d, 1H), 7.83 (dd, 1H), 8.51 (s, 1H)
LC/MS (ES+) m/z=399.93

Example 263

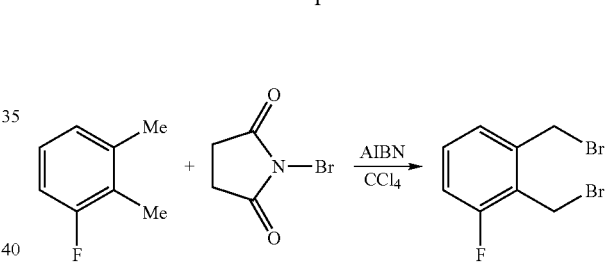

1,2-Bis(bromomethyl)-3-fluorobenzene (263)

A magnetically stirred mixture of 3-fluoro-ortho-xylene (5.05 g, 40.67 mmol), N-bromosuccinimide (15.23 g, 85.56 mmol), AIBN (78 mg) and $CCl_4$ (75 mL) is heated at reflux temperature for 1.75 h, then cooled to RT. The solids are removed by filtration and washed with $CCl_4$. The combined filtrate and wash is concentrated in vacuo on a rotary evaporator to give crude dibromide 263 as a yellow liquid that is dissolved in heptane-0.5% EtOAc, placed atop a column of silica gel (7.2 cm×18 cm) prepared in heptane-0.5% EtOAc and flash chromatographed taking 200 mL fractions eluting with heptane-0.5% EtOAc. Product containing fractions are combined and concentrated in vacuo on a rotary evaporator to afford a colorless liquid. On standing crystals form in the liquid. The liquid is separated using a pipette. The process is repeated once more. The resulting liquid is pure 1,2 bis(bromomethyl)-3-fluorobenzene. [J. E. Rice, A. Czech, N, Hussain, E. J. La Voie, *J. Org. Chem.*, 53, 1775-1779 (1988); R. A. Aitken, P. K. g. Hodgson, M. J. Morrison, A. O. Oyewale, *J. Chem. Soc.* (Perkin I), 402-415 (2002)]

$^1$H NMR (CDCl$_3$, 300 MHz): δ 4.63 (s, 3H), 4.70 (s, 3H), 7.05 (ddd, 1H), 7.17 (d, 1H), 7.29 (ddd, 1H)

F NMR (CDCl$_3$, 300 MHz): δ 115.26 (d)
LC-MS 3.23 (no parent ion)
Anal. Calcd. for C$_8$H$_7$Br$_2$F: C, 34.08; H, 2.50; F, 6.74. Found: C, 34.11; H, 2.28; F, 6.88.

Example 264

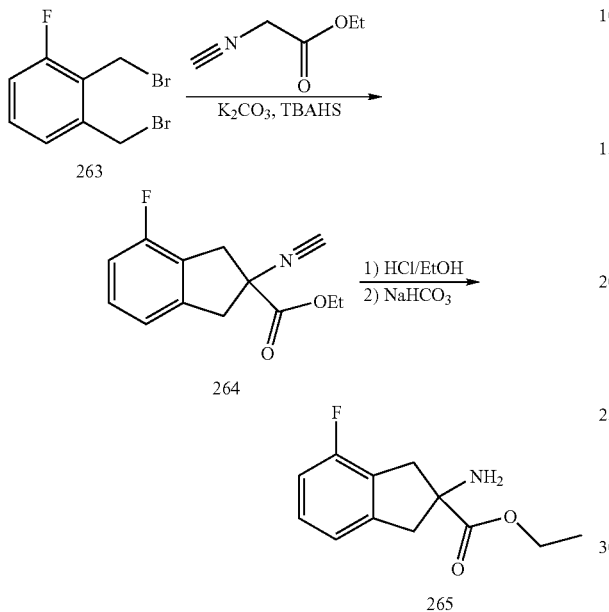

3-Fluoro-isocyano-indan-2-carboxylic acid ethyl ester (264)

To a solution of ethyl isocyanoacetate (3.85 mL, 35.0 mmol) in anhydrous ACN (300 mL) is added finely ground anhydrous K$_2$CO$_3$ (K$_2$SO$_4$, 29.0 g, 210 mmol), TBAHS (tetrabutyl ammonium hydrogen sulfate, 2.34 g, 7.0 mmol), and 1,2-bis(bromomethyl)-3-fluorobenzene (9.87 g, 35 mmol). The resulting heterogeneous mixture is stirred at 80° C. overnight. The reaction mixture is cooled down to RT and filtered to remove the unwanted salts. The filtrate is concentrated in vacuo. The residue is purified by flash column chromatography (200 g silica gel; gradient elution: 0-25% EtOAc in heptane) to give a pure product as colorless oil (4.5 g, 55%).
$^1$H NMR (CDCl$_3$, 300 MHz): δ 1.35 (t, 3H), 3.47 (d, 2H), 3.71 (d, 2H), 4.32 (q, 2H), 7.05 (ddd, 1H), 7.17 (d, 1H), 7.29 (ddd, 1H)
LC/MS (ES+) m/z=234.26

Example 265

2-Amino-3-fluoro-indan-2-carboxylic acid ethyl ester (265)

To a solution of 2-isocyano-indan-2-carboxylic acid ethyl ester (264) (4.5 g, 19.3 mmol) in absolute EtOH (200 mL) is added concentrated HCl (10 mL) dropwise. The resulting solution is stirred at RT for 24 h. After the removal of the EtOH in vacuo, the remaining hydrochloride salt is dissolved in water (100 mL) and extracted with of ethyl ether (3×50 mL) to remove unwanted organic impurities. The aqueous layer is brought to pH 9 by addition of saturated NaHCO$_3$ solution and then extracted with EtOAc 3×100 mL). The combined EtOAc layer is washed with brine (100 mL). The organic layer is dried over Na$_2$SO$_4$ and concentrated in vacuo to give a pure product as white solid (2.3 g, 53%).
$^1$H NMR (CDCl$_3$, 300 MHz): δ 1.29 (t, 3H), 2.88 (d, 2H), 3.57 (d, 2H), 4.23 (q, 2H), 7.05 (ddd, 1H), 7.17 (d, 1H), 7.29 (ddd, 1H)
LC/MS (EZ+) m/z=223.08

Example 266

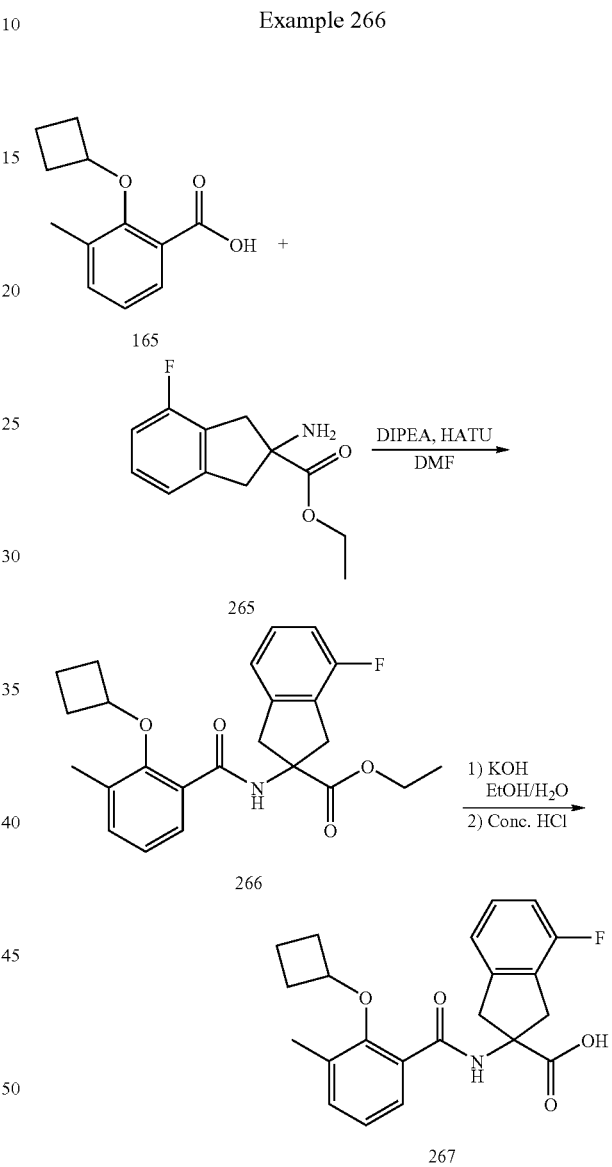

2-(2-Cyclobutoxy-3-methyl-benzoylamino)-4-fluoro-indan-2-carboxylic acid ethyl ester (266)

To a solution of 2-cyclobutoxy-3-methyl-benzoic acid (127 mg, 0.61 mmol), 2-Amino-3-fluoro-indan-2-carboxylic acid ethyl ester (265) (165 mg, 0.74 mmol), HATU 352 mg, 0.93 mmol) in anhydrous DMF (10 mL) is added DIPEA (204 μL, 1.23 mmol). The resulting solution is stirred at RT overnight. After the removal of DMF in vacuo, the residue is suspended in H$_2$O (50 mL) and washed with EtOAc (3×50 mL). Organics are combined and washed successively with NaHCO$_3$ and brine, and then the organic layer is dried over anhydrous Na$_2$SO$_4$ and concentrated in vacuo. The residue is purified by flash column chromatography (12 g silica gel, gradient elution: 0%-20% EtOAc in heptane) to give a pure product (266) as a colorless oil (210 mg, 84%).

$^1$H NMR (CDCl$_3$, 300 MHz): δ 1.21-1.36 (m, 4H), 1.50-1.56 (m, 1H), 1.96-2.09 (m, 4H), 2.27 (s, 3H), 3.44 (t, 2H), 3.73 (dd, 2H), 4.21-4.33 (m, 3H), 6.85-6.94 (m, 2H), 7.08 (t, 1H), 7.14-7.19 (m, 1H), 7.27 (d, 1H), 7.85 (dd, 1H), 8.37 (s, 1H)

LC/MS (ES+) m/z=412.19

Example 267

2-(2-Cyclobutoxy-3-methyl-benzoylamino)-4-fluoro-indan-2-carboxylic acid (267)

2-(2-Cyclobutoxy-3-methyl-benzoylamino)-4-fluoro-indan-2-carboxylic acid ethyl ester (7) (210 mg, 0.51 mmol) is dissolved in EtOH (50 mL) and set to stir at RT. To this solution is added 5M KOH (3 ml). The reaction mixture is stirred at RT overnight. After concentration in vacuo, the residue is dissolved in water (20 mL) and acidified with concentrated HCl to pH 2. The resultant mixture is washed with EtOAc (3×100 ml). Organics are combined and washed with brine, then dried over anhydrous Na$_2$SO$_4$ and concentrated in vacuo. The desired product (267) is obtained as white solid (168 mg, 86%).

$^1$H NMR (d-DMSO-d6, 300 MHz): δ 1.21-1.36 (m, 1H), 1.50 (m, 1H), 1.92-2.14 (m, 4H), 2.26 (s, 3H), 3.38 (t, 2H), 3.73 (dd, 2H), 4.29 (m, 1H), 6.86-6.95 (m, 2H), 7.11 (t, 1H), 7.15-7.20 (m, 1H), 7.29 (d, 1H), 7.83 (dd, 1H), 8.51 (s, 1H)

LC/MS (ES+) m/z=384.15

Example 268

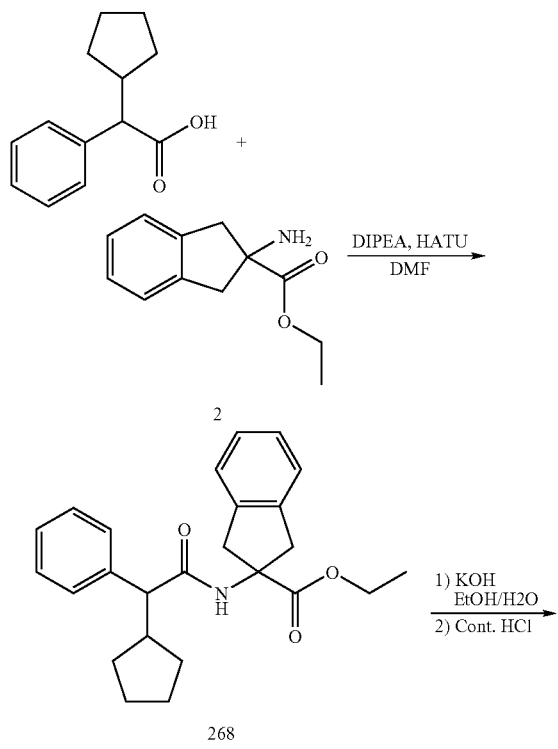

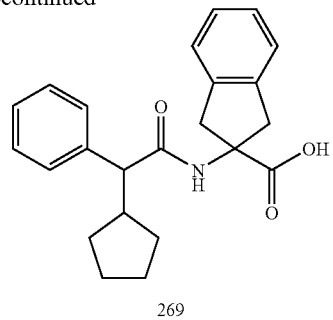

2-(2-Cyclopentyl-2-phenyl-acetylamino)-indan-2-carboxylic acid ethyl ester (268)

To a solution of α-phenylcyclopenteacetic acid (2.04 g, 10 mmol), 2-Amino-indan-2-carboxylic acid ethyl ester (2.05 g, 10 mmol), HATU (7.60 g, 20 mmol) in anhydrous DMF (50 mL) is added DIPEA (3.30 mL, 20 mmol). The resulting solution is stirred at RT overnight. After the removal of DMF in vacuo, the residue is dissolved in EtOAc (100 mL) and washed with saturated NaHCO$_3$ (1×100 mL), water (1×100 mL) and brine (1×100 mL). The organic layer is dried over anhydrous Na$_2$SO$_4$ and concentrated in vacuo. The residue is purified by flash column chromatography (115 g silica gel, gradient elution: 0%-20% EtOAc in heptane) to give a pure product (268) as a solid (3.16 g, 82%).

$^1$H NMR (d-DMSO-d6, 300 MHz): δ 0.91 (m, 1H), 1.23 (m, 2H), 1.29 (t, 3H), 1.35-1.64 (m, 4H), 1.65-1.81 (m, 1H), 2.34-2.49 (m, 1H), 2.78 (d, 2H), 2.89-3.03 (d, 1H), 3.13-3.23 (m, 2H), 3.42-3.52 (m, 2H), 7.1-7.35 (m, 9H)

LC/MS (ES+) m/z=392.19

Example 269

2-(2-Cyclopentyl-2-phenyl-acetylamino)-indan-2-carboxylic acid (269)

2-(2-Cyclopentyl-2-phenyl-acetylamino)-indan-2-carboxylic acid ethyl ester (268) (1 g, 2.56 mmol) is dissolved in EtOH (50 mL) and set to stir at RT. To this solution is added 5M KOH (3 ml). The reaction mixture is stirred at RT overnight. After concentration in vacuo, the residue is dissolved in water (20 mL) and washed with EtOAc (20 ml). The phases are separated and the aqueous phase is acidified with concentrated HCl to pH 2. The solid precipitate is collected via filtration and dried under vacuum. The desired product (269) is obtained as white solid (710 mg, 71%).

$^1$H NMR (d-DMSO-d6, 300 MHz): δ 0.91 (m, 1H), 1.23 (m, 2H), 1.35-1.64 (m, 4H), 1.65-1.81 (m, 1H), 2.34-2.49 (m, 1H), 2.89-3.03 (d, 1H), 3.13-3.23 (m, 2H), 3.42-3.52 (m, 2H), 7.1-7.35 (m, 9H), 8.57 (s, 1H)

LC/MS (ES+) m/z=364.46

Example 270

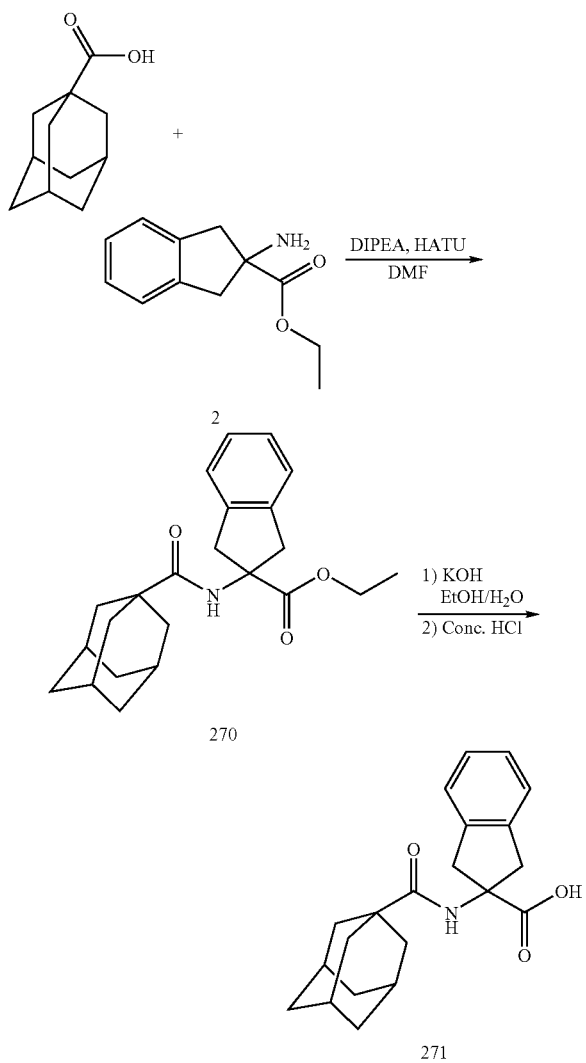

2-[(Adamantane-1-carbonyl)-amino]-indan-2-carboxylic acid ether ester (270)

To a solution of adamantane-1-carboxylic acid (131 mg, 0.73 mmol), 2-amino-indan-2-carboxylic acid ethyl ester (150 mg, 0.73 mmol), HATU (333 mg, 0.87 mmol) in anhydrous DMF (1 mL) is added DIPEA (1904, 1.1 mmol). The resulting solution is stirred at RT overnight. Poured reaction into water (10 mL) and extracted with EtOAc (3×5 mL). The combined organic layers and concentrated in vacuo. The residue is purified by flash column chromatography (12 g silica gel, gradient elution: 0-30% EtOAc in heptane) to give product (270) as white solid (261 mg, 97%).

2-[(Adamantane-1-carbonyl)-amino]-indan-2-carboxylic acid (271)

2-[(Adamantane-1-carbonyl)-amino]-indan-2-carboxylic acid ether ester (261 mg, 0.71 mmol) is dissolved in EtOH (8 mL), and solid KOH (823 mg, 14 mmol) and water (0.8 mL) are added. The mixture is stirred at RT for 30 minutes then concentrated in vacuo. The residue is dissolved in water (10 mL) and acidified with concentrated HCl until no more white solid precipitated. The solid is collected by vacuum filtration to give product (271) as white solid (159 mg, 66%).

$^1$H NMR (CDCl$_3$, 300 MHz): 1.62-1.76 (q, 6H), 1.76 (d, 6H), 2.02 (s, 3H), 3.25 (d, 2H), 3.79 (d, 2H), 6.04 (s, 1H), 7.15 (d, 1H), 7.21 (s, 4H)

LC/MS (ES+) m/z=340.18

Example 272

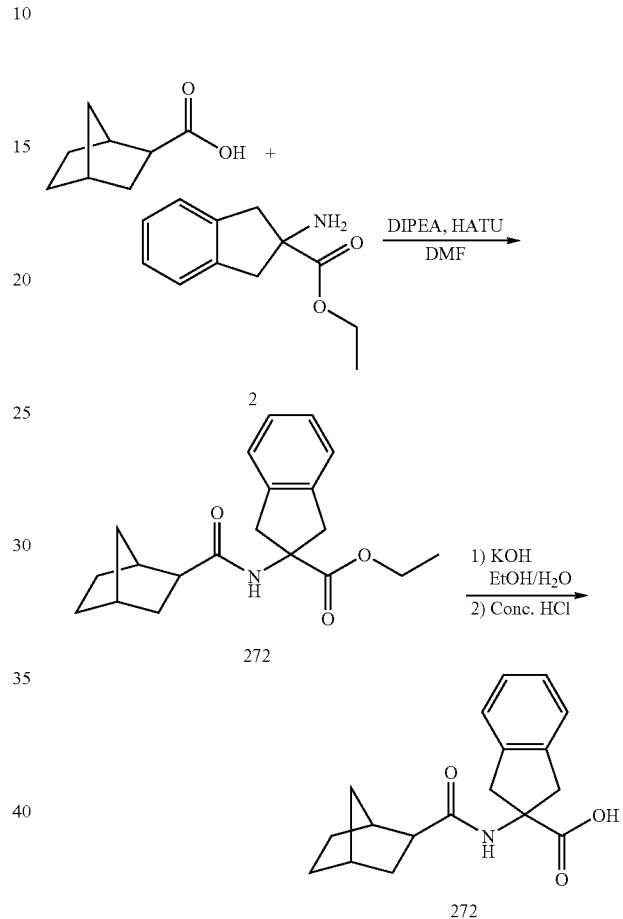

2-[(Bicyclo[2.2.1]heptane-2-carbonyl)-amino]-indan-2-carboxylic acid ethyl ester (272)

To a solution of bicyclo[2.2.1]heptane-2-carboxylic acid (102 mg, 0.73 mmol), 2-amino-indan-2-carboxylic acid ethyl ester (150 mg, 0.73 mmol), HATU (333 mg, 0.87 mmol) in anhydrous DMF (1 mL) is added DIPEA (1904, 1.10 mmol). The resulting solution is stirred at RT overnight. Water (10 mL) is poured into the reaction mixture and then extracted with EtOAc (3×5 mL). The combined organic layers are concentrated in vacuo. The residue is purified by flash column chromatography (12 g silica gel, gradient elution: 0-30% EtOAc in heptane) to give product (272) as yellow oil (148 mg, 62%).

Example 273

2-[(Bicyclo[2.2.1]heptane-2-carbonyl)-amino]-indan-2-carboxylic acid (273)

2-[(Bicyclo[2.2.1]heptane-2-carbonyl)-amino]-indan-2-carboxylic acid ethyl ester (148 mg, 0.45 mmol) is dissolved in EtOH (8 mL), and solid KOH (600 mg, 10 mmol) and water (0.8 mL) are added. The mixture is stirred at RT for 30 min then concentrated in vacuo. The residue is dissolved in water (10 mL) and acidified with concentrated HCl until no more white solid precipitated. The solid is collected by vacuum filtration to give product (273) as white solid (105 mg, 77%).

$^1$H NMR (CDCl$_3$, 300 MHz): 1.14 (d, 1H), 1.26-1.40 (m, 4H), 1.44-1.54 (q, 2H), 1.57-1.67 (m, 1H), 2.27 (d, 2H), 2.58-2.64 (m, 1H) 3.27 (t, 2H), 3.75 (d, 2H), 5.97 (s, 1H), 7.20 (s, 4H)

LC/MS (ES+) m/z=300.13

Example 274

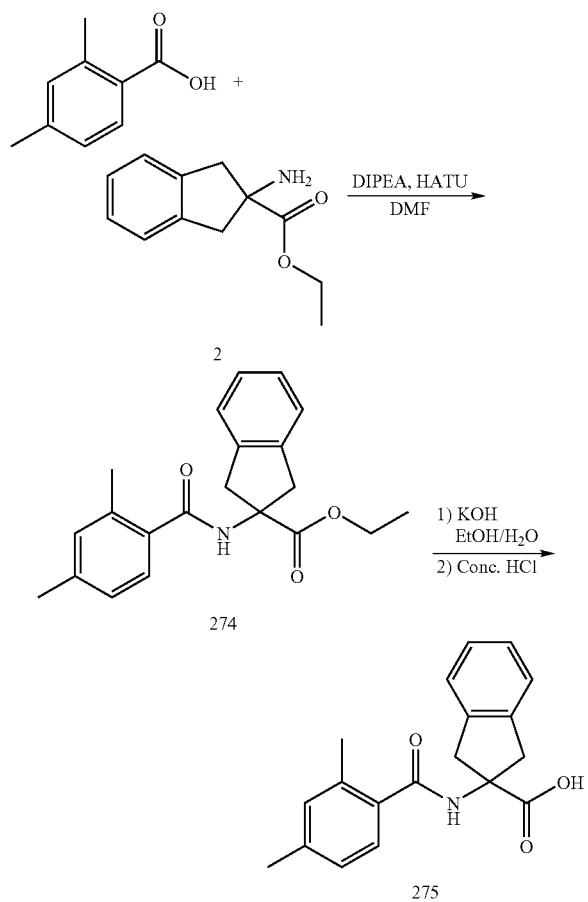

275

2-(2,4-Dimethyl-benzoylamino)-indan-2-carboxylic acid ethyl ester (274)

To a solution of 2,4-dimethyl-benzoic acid (219 mg, 1.46 mmol), 2-amino-indan-2-carboxylic acid ethyl ester (300 mg, 1.46 mmol), HATU (666 mg, 1.75 mmol) in anhydrous DMF (1.8 mL) is added DIPEA (381 μL, 2.19 mmol). The resulting solution is stirred at RT overnight. Water (10 mL) is poured into the reaction mixture, and then extracted with EtOAc (3×5 mL). The combined organic layers and concentrated in vacuo. The residue is purified by flash column chromatography (12 g silica gel, gradient elution: 0-30% EtOAc in heptane) to give product (274) as white solid (414 mg, 84%).

Example 275

2-(2,4-Dimethyl-benzoylamino)-indan-2-carboxylic acid (275)

2-(2,4-Dimethyl-benzoylamino)-indan-2-carboxylic acid ethyl ester (414 mg, 1.23 mmol) is dissolved in EtOH (15 mL), and solid KOH (1.42 g, 24.7 mmol) and water (1.5 mL) are added. The mixture is stirred at RT for 30 min then concentrated in vacuo. The residue is dissolved in water (10 mL) and acidified with concentrated HCl until no more white solid precipitated. The solid is collected by vacuum filtration to give product (275) as white solid (350 mg, 92%).

$^1$H NMR (CDCl$_3$, 300 MHz): 2.30 (s, 6H), 3.41 (d, 2H), 3.84 (d, 2H), 6.20 (s, 1H), 6.96 (d, 1H), 7.00 (s, 1H), 7.13 (d, 1H), 7.24 (d, 4H)

LC/MS (ES+) m/z=310.14

Example 276

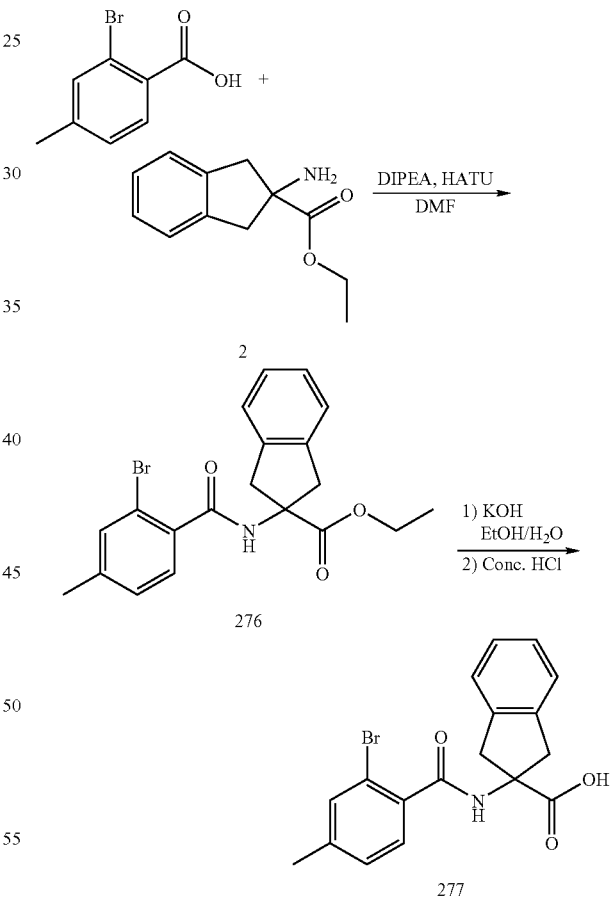

277

2-(2-Bromo-4-methyl-benzoylamino)-indan-2-carboxylic acid ethyl ester (276)

To a solution of 2-bromo-4-methyl-benzoic acid (314 mg, 1.46 mmol), 2-amino-indan-2-carboxylic acid ethyl ester (300 mg, 1.46 mmol), HATU (666 mg, 1.75 mmol) in anhydrous DMF (1.8 mL) is added DIPEA (381 μL, 2.19 mmol).

The resulting solution is stirred at RT overnight. Poured reaction into water (10 mL) and extracted with EtOAc (3×5 mL). The combined organic layers and concentrated in vacuo. The residue is purified by flash column chromatography (12 g silica gel, gradient elution: 0-30% EtOAc in heptane) to give product (276) as off-white solid (445 mg, 76%).

Example 277

2-(2-Bromo-4-methyl-benzoylamino)-indan-2-carboxylic acid (277)

2-(2-bromo-4-methyl-benzoylamino)-indan-2-carboxylic acid ethyl ester (445 mg, 1.11 mmol) is dissolved in EtOH (15 mL), and solid KOH (1.42 g, 24.7 mmol) and water (1.5 mL) are added. The mixture is stirred at RT for 30 min then concentrated in vacuo. The residue is dissolved in water (10 mL) and acidified with conc. HCl until no more white solid precipitated. The solid is collected by vacuum filtration to give product (277) as white solid (415 mg, 100%).

$^1$H NMR (CDCl$_3$, 300 MHz): 2.33 (s, 3H), 3.45 (d, 2H), 3.83 (d, 2H), 6.70 (s, 1H), 7.15 (d, 1H), 7.19-7.25 (m, 4H), 7.35 (s, 1H), 7.51 (d, 1H)

LC/MS (ES+) m/z=374.04, 376.04

Example 278

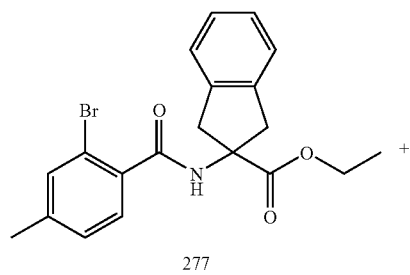

277

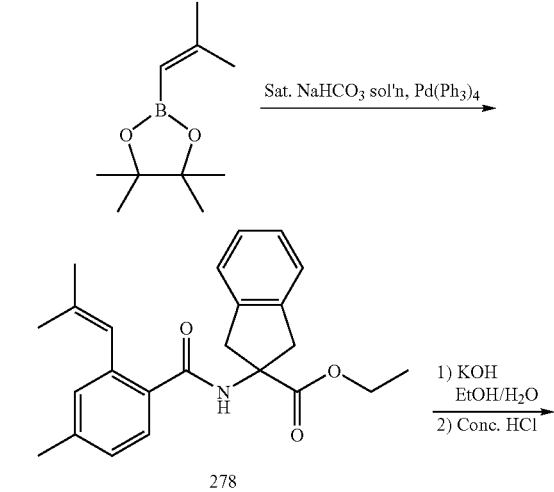

278

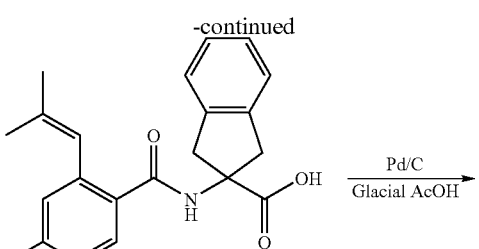

279

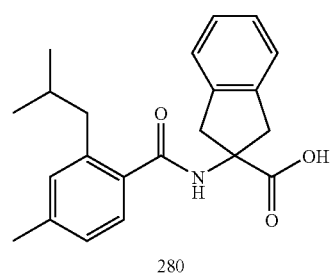

280

2-[4-Methyl-2-(2-methyl-propenyl)-benzoylamino]-indan-2-carboxylic acid ethyl ester (278)

A mixture of 2-(2-bromo-4-methyl-benzoylamino)-indan-2-carboxylic acid ethyl ester (880 mg, 2.2 mmol), 4,4,5,5-tetramethyl-2-(2-methyl-propenyl)-[1,3,2]dioxaborolane (903 μL, 4.4 mmol) and saturated NaHCO$_3$ solution (4.4 mL) in anhydrous DMF (20 mL) is degassed with N$_2$. While under N$_2$ atmosphere, tetrakis(triphenylphosphine)palladium (196 mg, 10 mol %) is added and the reaction is heated in a 110° C. oil bath for 2 h. The reaction is cooled to room temperature, poured into water (40 mL) and extracted with EtOAc (2×30 mL). The combined organic layers are washed with water (15 mL) and brine (20 mL) then concentrated in vacuo. The residue is purified by flash column chromatography (24 g silica gel, gradient elution: 0-50% EtOAc in heptane) to give product (278) as a reddish-brown viscous oil (764 mg, 92%).

Example 279

2-[4-Methyl-2-(2-methyl-propenyl)-benzoylamino]-indan-2-carboxylic acid (279)

2-[4-Methyl-2-(2-methyl-propenyl)-benzoylamino]-indan-2-carboxylic acid ethyl ester (764 mg, 2.02 mmol) is dissolved in EtOH (25 mL), and solid KOH (2.32 g, 40 mmol) and water (2.5 mL) are added. The mixture is stirred at RT for 30 min then concentrated in vacuo. The residue is dissolved in a mixture of water (40 mL) and EtOAc (20 mL) and the organic layer is separated. The aqueous layer is adjusted to approximately pH 7 with conc. HCl then extracted with EtOAc (2×15 mL). The combined organic layers are concentrated in vacuo to yield product (279) as off-white solid (544 mg, 78%).

$^1$H NMR (CDCl$_3$, 300 MHz): 1.49 (s, 3H). 1.70 (s, 3H), 2.34 (s, 3H), 3.34 (d, 2H), 3.82 (d, 2H), 6.01 (s, 1H), 6.87 (s, 1H), 7.14 (d, 1H), 7.22 (s, 4H), 7.31 (d, 1H), 7.91 (d, 1H)

LC/MS (ES+) m/z=350.17

2-(2-Isobutyl-4-methyl-benzoylamino)-indan-2-carboxylic acid (280)

To a solution of 2-[4-methyl-2-(2-methyl-propenyl)-benzoylamino]-indan-2-carboxylic acid (510 mg, 1.45 mmol) in glacial acetic acid (65 mL) under $N_2$ is added Pd/C (10% Pd, 138 mg, 10 mol %). The reaction is hydrogenated at 60 psi $H_2$ and 90° C. overnight. The reaction is cooled to RT and filtered through Celite, washing the filter cake with water (2×15 mL) and MeOH (2×15 mL); the filtrate is concentrated in vacuo. The residue is dissolved in water (75 mL) and extracted with EtOAc (2×30 mL). The combined organic layers are washed with a 5% $NaHCO_3$ solution (3×20 mL), water (20 mL) and brine (20 mL) then dried over anhydrous $Na_2SO_4$. The organic layer is concentrated in vacuo to give product (280) as white solid (350 mg, 69%).

$^1$H NMR (CDCl$_3$, 300 MHz): 0.78 (d, 6H), 1.72-1.81 (m, 1H), 2.30 (s, 3H), 2.55 (d, 2H), 3.38 (d, 2H), 3.77 (d, 2H), 6.30 (s, 1H), 6.94 (d, 1H), 6.95 (s, 1H), 7.16 (d, 1H), 7.20 (s, 4H)

LC/MS (ES+) m/z=352.22

Example 281

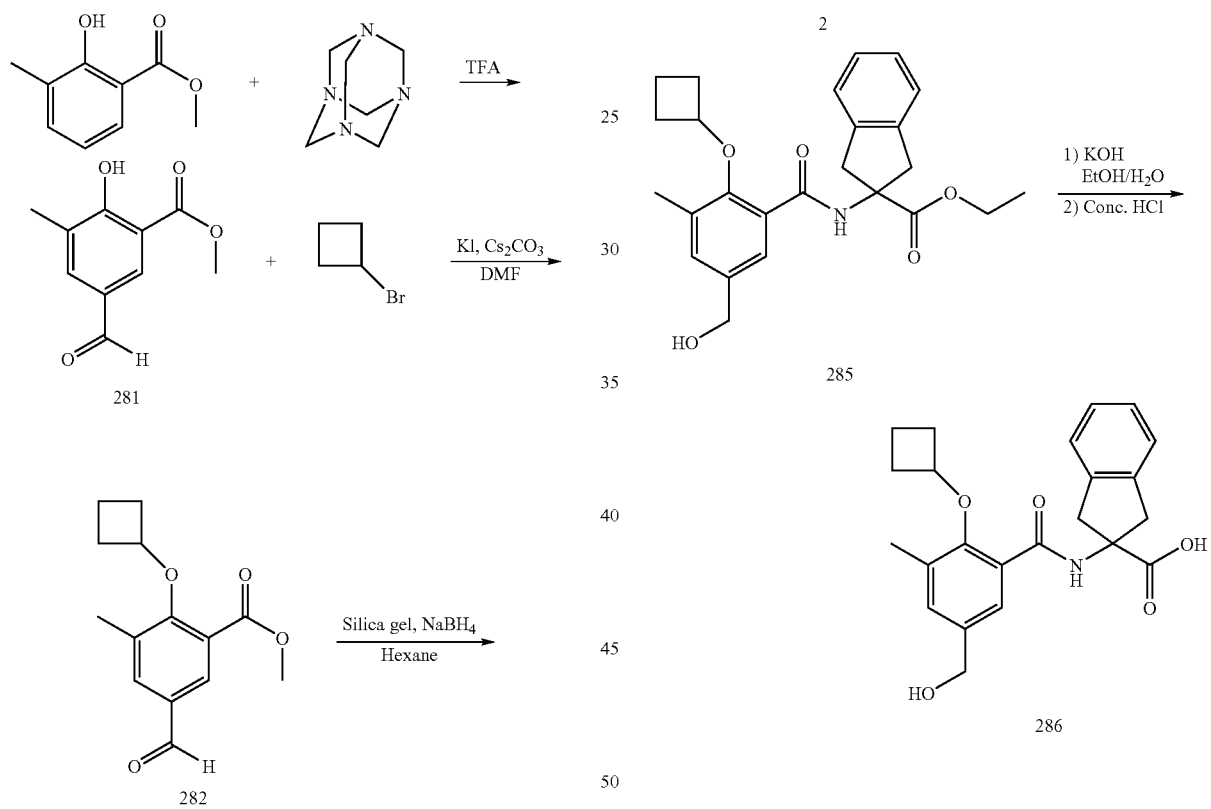

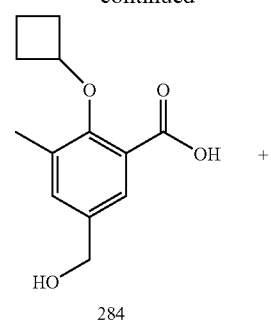
284

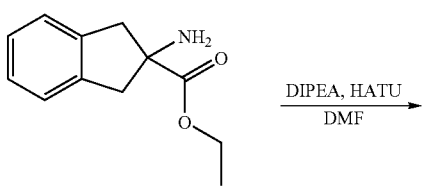

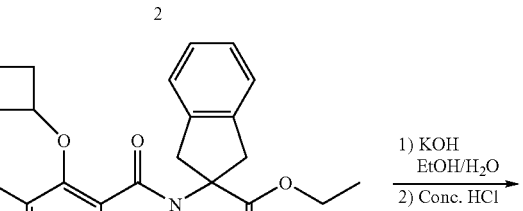

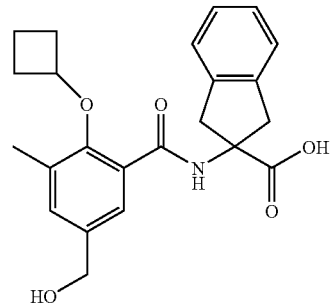

5-Formyl-2-hydroxy-3-methyl-benzoic acid methyl ester (281)

To a solution of HMTA (1,3,5,7-Tetraaza-tricyclo[3.3.1.1$^{3,7}$]decane, 8.43 g, 60.2 mmol) in TFA (100 mL) is added 2-hydroxy-3-methyl-benzoic acid methyl ester (5 g, 30.1 mmol) and the reaction is refluxed (78° C.) overnight. The reaction is cooled to 50° C. and water (400 mL) is added with stirring. The mixture is stirred at 50° C. for 2 h then cooled to RT and extracted with EtOAc (2×200 mL). The combined organic layers are washed with brine (75 mL), dried over anhydrous MgSO$_4$ and concentrated in vacuo. The residue is purified by flash column chromatography (120 silica gel, gradient elution: 0-50% EtOAc in heptane) to give product (281) as off-white solid (5.05 g, 86%).

Example 282

2-Cyclobutoxy-5-formyl-3-methyl-benzoic acid methyl ester (282)

To a mixture of bromocyclobutane (1.39 g, 10.3 mmol), potassium iodide (43 mg, 5 mol %), and CsCO$_3$ (3.84 g, 11.84 mmol) in DMF (18 mL) is added 5-formyl-2-hydroxy-3-methyl-benzoic acid methyl ester (1.0 g, 5.15 mmol). The reaction is placed in the microwave reactor and heated at 110° C. for 6 h. Water (50 mL) is added to the reaction and the solution is extracted with EtOAc (3×40 mL). The combined organic layers are dried over anhydrous MgSO$_4$ and concentrated in vacuo to give product (282) as orange-yellow oil (1.20 g, 94%).

Example 283

2-Cyclobutoxy-5-hydroxymethyl-3-methyl-benzoic acid methyl ester (283)

A mixture of 2-cyclobutoxy-5-formyl-3-methyl-benzoic acid methyl ester (676 mg, 2.7 mmol), silica gel (5.15 g) and NaBH$_4$ (103 mg, 2.7 mmol) in hexane (30 mL) is heated at 40° C. overnight. The mixture is cooled to RT and filtered, washing the solids with EtOAc (15 mL) and diethyl ether (15 mL). The filtrate is concentrated in vacuo to give product (283) as viscous yellow oil (566 mg, 84%).

Example 284

2-Cyclobutoxy-5-hydroxymethyl-3-methyl-benzoic acid (284)

2-Cyclobutoxy-5-hydroxymethyl-3-methyl-benzoic acid methyl ester (410 mg, 1.64 mmol) is dissolved in EtOH (15 mL), and solid KOH (1.90 g, 32.8 mmol) and water (1.5 mL) are added. The mixture is stirred at RT for 1 h then concentrated in vacuo. The residue is dissolved in water (10 mL) and acidified with conc. HCl then extracted with EtOAc (3×10 mL). The combined organic layers are dried over anhydrous MgSO$_4$ and concentrated in vacuo to give product (284) as viscous yellow oil (387 mg, 100%).

Example 285

2-(2-Cyclobutoxy-5-hydroxymethyl-3-methyl-benzoylamino)-indan-2-carboxylic acid ethyl ester (285)

To a solution of 2-cyclobutoxy-5-hydroxymethyl-3-methyl-benzoic acid (410 mg, 1.7 mmol), 2-amino-indan-2-carboxylic acid ethyl ester (425 mg, 1.7 mmol), HATU (760 mg, 2 mmol) in anhydrous DMF (5 mL) is added DIPEA (4354, 2.5 mmol). The resulting solution is stirred at RT overnight. Water (10 mL) is poured into the reaction mixture, and then extracted with EtOAc (3×7 mL). The combined organic layers are concentrated in vacuo. The residue is purified by reverse phase chromatography (gradient elution: 20-100% ACN in water) to give product (285) as colorless oil (70 mg, 10%).

$^1$H NMR (CDCl$_3$, 300 MHz): 1.14-1.24 (m, 1H), 1.34-1.44 (q, 1H), 1.80-1.86 (m, 2H), 1.90-1.99 (m, 2H), 2.20 (s, 3H), 3.37 (d, 2H), 3.81 (d, 2H), 4.13-4.24 (m, 1H), 4.55 (s, 2H) 7.17-7.24 (m, 4H), 7.26 (d, 1H), 7.78 (d, 1H), 8.45 (s, 1H)
LC/MS (ES+) m/z=396.16

Example 286

2-(2-Cyclobutoxy-5-hydroxymethyl-3-methyl-benzoylamino)-indan-2-carboxylic acid (286)

2-(2-Cyclobutoxy-5-hydroxymethyl-3-methyl-benzoylamino)-indan-2-carboxylic acid ethyl ester (70 mg, 0.16 mmol) is dissolved in ethanol (1.5 mL), and solid KOH (191 mg, 3.3 mmol) and water (1504) are added. The mixture is stirred at room temperature for 30 min then concentrated in vacuo. The residue is dissolved in water (1.5 mL) and acidified with conc. HCl until no more white solid precipitated. The mixture is extracted with ethyl acetate (2×8 mL) and the combined organic layers are concentrated in vacuo to give product (286) as white solid (60 mg, 95%).

$^1$H NMR (CDCl$_3$, 300 MHz): δ 1.14-1.24 (m, 1H), 1.34-1.44 (q, 1H), 1.80-1.86 (m, 2H), 1.90-1.99 (m, 2H), 2.20 (s, 3H), 3.37 (d, 2H), 3.81 (d, 2H), 4.13-4.24 (m, 1H), 4.55 (s, 2H) 7.17-7.24 (m, 4H), 7.26 (d, 1H), 7.78 (d, 1H), 8.45 (s, 1H)
LC/MS (ES+) m/z=396.16

Example 287

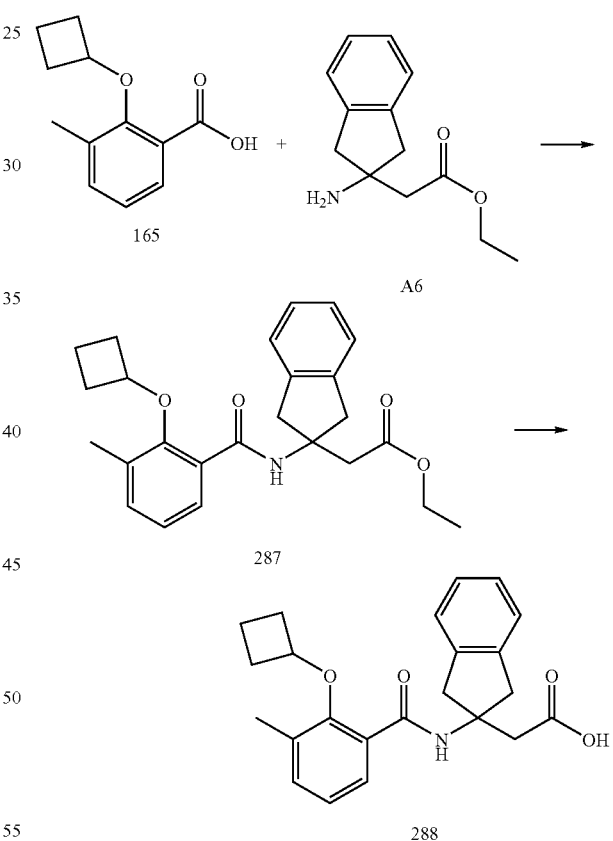

2-aminoindan-2-acetic acid ethyl ester (A6)

This compound is prepared according to the US Patent WDF2006/134111.

2-(2-cyclobutyloxy-3-methylbenzoylamino)indan-2-acetic acid ethyl ester (287)

To a solution of 2-cyclobutyloxy-3-methylbenzoic acid (210 mg-1.02 mmol), 2-aminoindan-2-acetic acid ethyl ester (A6) (260 mg-1.02 mmol) and HATU (470 mg-1.224 mmol-1.2 eq) in dry DMF (10 mL) is added diisopropylethylamine (0.36 mL-2.24 mmol-2.2 eq) and the resulting solution is stirred at RT overnight. After the removal of the DMF in vacuo, the residue is dissolved in EtOAc (60 mL) and washed with water (2×20 mL) and brine (2×20 mL). The organic layer is dried over MgSO$_4$ and concentrated in vacuo. The residue is purified by flash chromatography (120 g silica gel, 15% EtOAc in heptane) to give the pure product as colorless oil (400 mg, 96%).

LC/MS (ES+) m/z 408

Example 288

2-(2-cyclobutyloxy-3-methylbenzoylamino)indan-2-acetic acid (288)

A solution of the 2-(2-cyclobutyloxy-3-methylbenzoy-lamino)indan-2-acetic acid ethyl ester (288) (400 mg-1 mmol) in EtOH (15 mL)/water (1 mL) is treated with NaOH pellets (800 mg-20 mmol) and stirred at RT for 24 h. After concentration in vacuo, the residue is dissolved in water (30 mL) and acidified with HCl to pH 2-3. The product is extracted into EtOAc (3×20 mL) and the combined extracts washed with water (2×10 mL) and brine (2×15 mL). The organic layer is dried over MgSO$_4$ and concentrated in vacuo. The residue is triturated with heptane and the pure product isolated by filtration to give white solid (350 mg, 92%).

LC/MS (ES+) m/z 380

Example 289

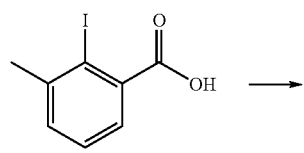

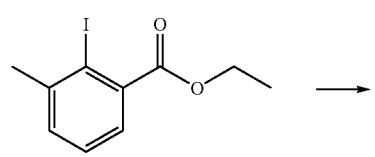

289

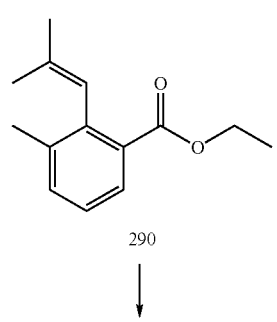

290

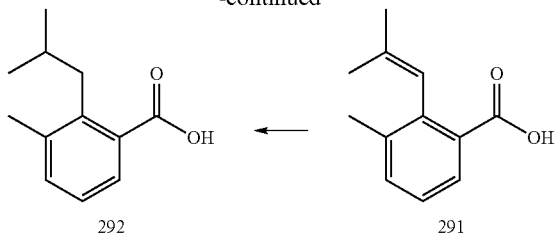

292                                   291

2-iodo-3-methylbenzoic acid ethyl ester (289)

A solution of the 2-iodo-3-methylbenzoic acid (6 g-0.023 mol) in EtOH (150 mL) is treated with concentrated HCl (20 mL) and refluxed for 48 h. After removal of the EtOH in vacuo, the residue is diluted with water (125 mL) and cooled to 0° C. in an ice bath. The pH is adjusted to 10 with solid NaOH pellets and extracted with EtOAc (3×75 mL). The organic extracts are washed with water (2×50 mL) and brine (2×50 mL) and dried over MgSO$_4$. Concentrated in vacuo to give the product as a pale yellow oil. (6 g, 90%).

LC/MS (ES+) m/z 291

Example 290

3-methyl-2-(2-methyl-1-propenyl)benzoic acid ethyl ester (290)

A suspension of the 2-iodo-3-methylbenzoic acid ethyl ester (289) (2.9 g-0.01 mol) and 2-methyl-1-propenylboronic acid pinacol ester (3.64 g-0.02 mol-2 eq) in dry DMF (50 mL) and saturated NaHCO$_3$ (10 mL) is degassed for 10 minutes and then treated with tetrakis(triphenylphosphine)palladium (0) (400 mg). The mixture is stirred at 110° C. overnight. The reaction is cooled and the DMF removed in vacuo and the residue diluted with water (120 mL). The aqueous is filtered through hyflo and extracted with EtOAc (3×75 mL). The organic extracts are washed with water (2×50 mL) and brine (2×50 mL), and dried over MgSO$_4$. The organic extracts are concentrated in vacuo and purified by flash chromatography (400 g silica gel, 5% EtOAc in heptane) to give the product as pale yellow oil (1.85 g, 85%).

LC/MS (ES+) m/z 218

Example 291

3-methyl-2-(2-methyl-1-propenyl)benzoic acid (291)

A solution of the 3-methyl-2-(2-methyl-1-propenyl)ben-zoic acid ethyl ester (290) (3 g-0.014 mol) in MeOH (50 mL) is treated with 2N NaOH (10 mL) and refluxed for 6 h. The solvent is removed in vacuo and the residue diluted with water (75 mL). The aqueous phase is extracted with EtOAc (30 mL) and then separated and acidified to pH 2-3 with concentrated HCl. The solid precipitated is extracted into EtOAc (3×50 mL). The extracts are washed with water (2×30 mL) and brine (2×30 mL), and dried over MgSO$_4$ and concentrated in vacuo to give the product as white solid (2.0 g, 75%).

$^1$H NMR (CDCl$_3$, 300 MHz): 1.43 (s, 3H), 1.91 (s, 3H), 2.24 (s, 3H), 6.35 (s, 1H), 7.2-7.27 (t, 1H), 7.37-7.44 (m, 1H), 7.79-7.81 (d, 1H).

LC/MS (ES+) m/z 191

Example 292
2-isobutyl-3-methylbenzoic acid (292)
A solution of the 3-methyl-2-(2-methyl-1-propenyl)benzoic acid (291) (2 g, 10.5 mmol) in MeOH (40 mL) is hydrogenated using 10% palladium/carbon catalyst at 40 bar/30° C. using the Thales nanotechnology H-cube for 48 h. The MeOH is concentrated in vacuo to give the product as colorless oil (1.85 g, 90%).
$^1$H NMR (CDCl$_3$, 300 MHz): 0.92 (d, 6H), 1.78-1.90 (m, 1H), 2.38 (s, 3H), 7.1-7.2 (t, 1H), 7.35-7.38 (d, 1H), 7.75-7.80 (d, 1H).
LC/MS (E/S+) m/z 193
Example 293
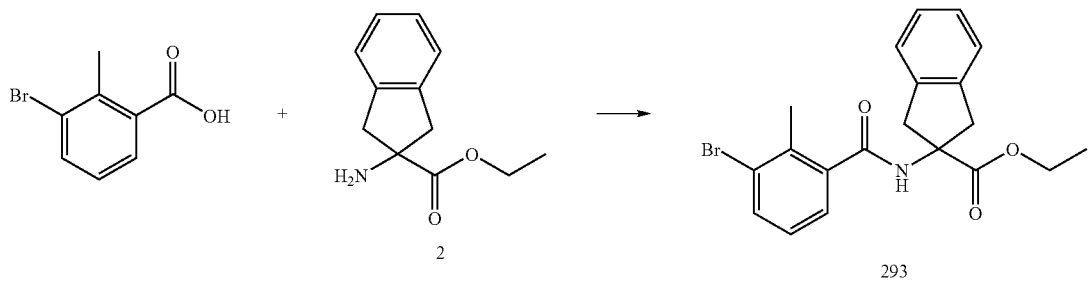
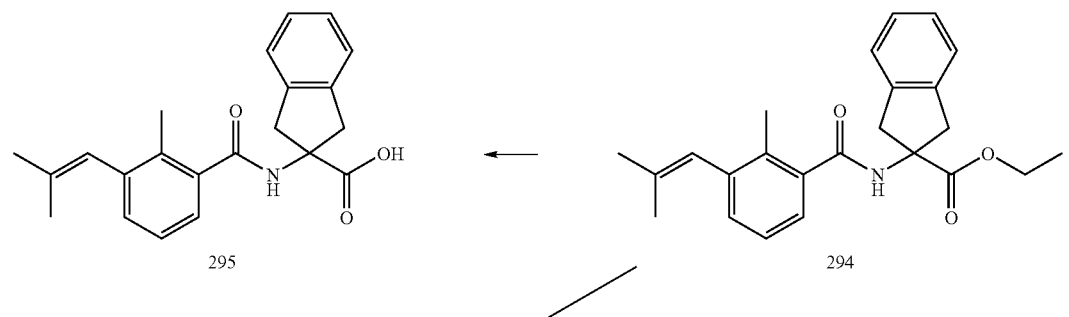
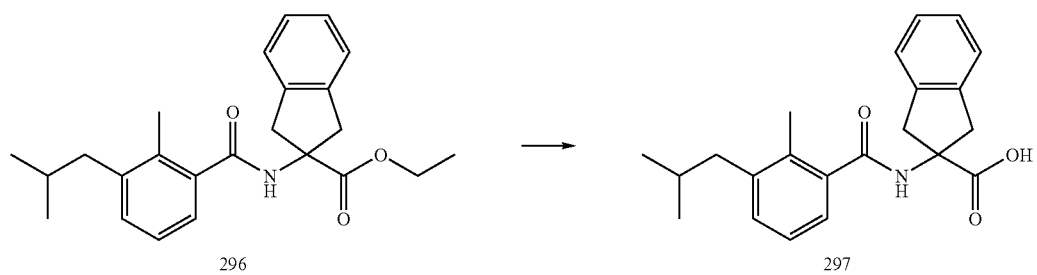

2-(3-bromo-2-methylbenzoylamino)indan-2-carboxylic acid ethyl ester (293)

This compound is prepared in a similar manner to example 287. The crude product obtained is purified by flash chromatography (120 g silica gel, 20% EtOAc in heptane) to give the pure product as white solid (1.9 g, 91%).

$^1$H NMR (CDCl$_3$, 300 MHz): 1.20-1.25 (t, 3H), 3.30-3.40 (d, 2H), 3.40 (s, 3H), 3.70-3.80 (d, 2H), 4.25-4.40 (m, 2H), 6.30-6.40 (s, 1H), 6.95-7.05 (t, 1H), 7.20-7.30 (m, 2H), 7.55-7.60 (d, 1H).

LC/MS (ES+) m/z 403

Example 294

2-[2-methyl-3-(2-methyl-1-propenyl)benzoylamino]indan-2-carboxylic acid ethyl ester (294)

A suspension of 2-(3-bromo-2-methylbenzoylamino)indan-2-carboxylic acid ethyl ester (293) (402 mg-1 mmol) and 2-methyl-1-propenylboronic acid (200 mg, 2 mmol, 2 eq) in dry DMF (20 mL) and saturated NaHCO$_3$ (5 mL) is degassed for 10 min and then treated with tetrakis(triphenylphosphine)palladium(0) (400 mg). The mixture is stirred at 110° C. for 5 h. The reaction is cooled and the DMF removed in vacuo and the residue diluted with water (80 mL). The aqueous is filtered through celite and extracted with EtOAc (3×50 mL). The organic extracts are washed with water (2×30 mL) and brine (2×30 mL), and dried over MgSO$_4$. The organic phase is then concentrated in vacuo and purified by flash chromatography (120 g silica gel, 30% EtOAc in heptane) to give pale yellow oil (350 mg, 92%).

LC/MS (E/S+) m/z 378

Example 295

2-[2-methyl-3-(2-methyl-1-propenyl)benzoylamino]indan-2-carboxylic acid (295)

This compound is prepared in a similar manner to example 288. Purification by flash chromatography (120 g silica gel, 20% EtOAc in heptane) gives white solid. (20 mg, 6%)

LC/MS (E/S+) m/z 350

Example 296

2-(2-methyl-3-isobutylylbenzoylamino)indan-2-carboxylic acid ethyl ester (296)

A solution of 2-[2-methyl-3-(2-methyl-1-propenyl)benzoylamino]indan-2-carboxylic acid ethyl ester (294) (700 mg, 1.86 mmol) in glacial AcOH (125 mL) is treated with the catalyst, Pd—C (10 wt. % Pd, 360 mg) under nitrogen. The resulting reaction mixture is then hydrogenated in a Paar apparatus at 55 psi 75° C. overnight. The catalyst is removed by filtration through a pre-column (10 g silica gel) and washed with EtOH. The combined organic solution is concentrated in vacuo. The residue is dissolved in EtOAc (75 mL) and washed with water (30 mL) and brine (30 mL), and dried over MgSO$_4$ and concentrated in vacuo to leave the product as white solid (660 mg, 94%).

LC/MS (E/S+) m/z 380

Example 297

2-(2-methyl-3-isobutylylbenzoylamino)indan-2-carboxylic acid (297)

This compound is prepared in a similar manner to example 288. Purification by flash chromatography (120 g silica gel, 50% EtOAc in heptane) gives the product as white solid. (130 mg, 21%)

$^1$H NMR (DMSO-d6, 300 MHz): 0.87-0.89 (d, 6H), 1.73-1.82 (m, 1H), 2.21 (s, 3H), 2.40-2.45 (m, 2H), 3.32-3.36 (d, 2H), 3.53-3.59 (d, 2H), 7.00-7.23 (m, 7H), 8.83 (s, 1H), 11.0 (s, 1H).

LC/MS (E/S+) m/z 353

Example 298

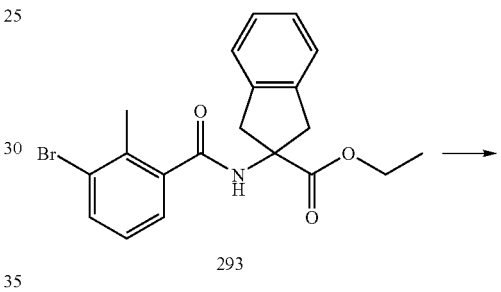

293

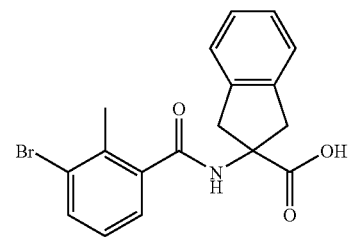

298

2-(3-bromo-2-methylbenzoylamino)indan-2-carboxylic acid (298)

This compound is prepared in a similar manner to example 288. The organic extract is evaporated in vacuo to give the product as white solid (270 mg, 96%)

$^1$H NMR (DMSO-d6, 300 MHz): 2.33 (s, 3H), 2.29-3.35 (d, 2H), 3.54-3.60 (d, 2H), 7.13-7.24 (m, 6H), 7.63-7.66 (d, 1H), 8.99 (s, 1H), 12.55-12.60 (s, 1H).

LC/MS (E/S+) m/z 376

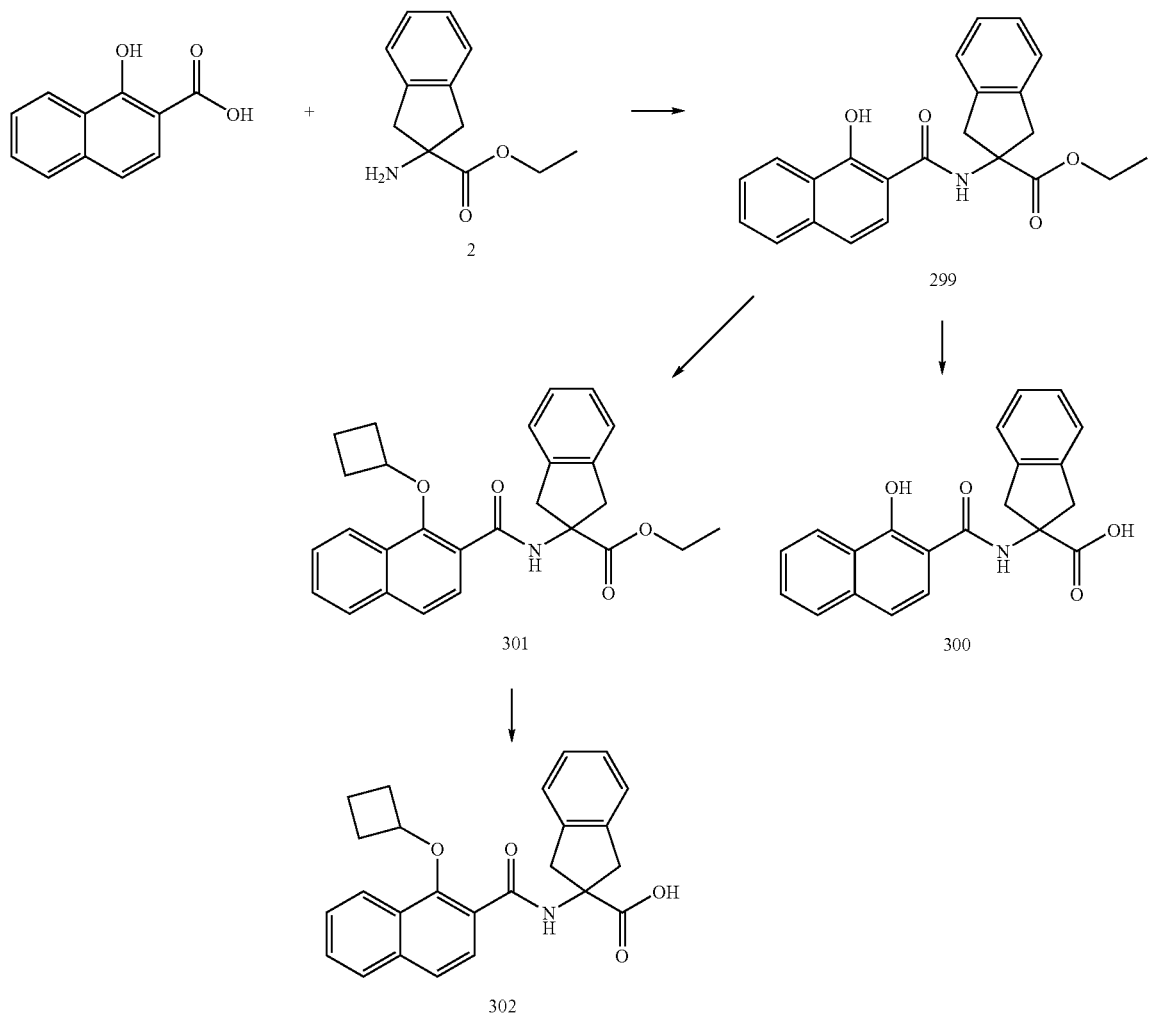

Example 299

2-[(1-hydroxynaphthalene-2-carbonyl)amino]indan-2-carboxylic acid ethyl ester (299)

This compound is prepared in a similar manner to example 287. Purification by flash chromatography (400 g silica gel, 30% EtOAc in heptane) gives orange oil. (1.75 g, 93%)

LC/MS (E/S+) m/z 376

Example 300

2-[(1-hydroxynaphthalene-2-carbonyl)amino]indan-2-carboxylic acid (300)

This compound is prepared in a similar manner to example 288. The organic extract is evaporated in vacuo to give white solid. (280 mg, 99%)

$^1$H NMR (DMSO-d6, 300 MHz): 3.48-3.53 (d, 2H), 3.63-3.69 (d, 2H), 7.17-7.28 (m, 5H), 7.34-7.37 (d, 1H), 7.53-7.66 (m, 2H), 7.85-7.88 (d, 1H), 7.96-7.99 (d, 1 h), 8.26-8.28 (d, 1H), 9.22 (s, 1H).

LC/MS (E/S+) m/z 376

Example 301

2-[(1-cyclobutyloxynaphthalene-2-carbonyl)amino]indan-2-carboxylic acid ethyl ester (301)

A solution of 2-[(1-hydroxynaphthalene-2-carbonyl)amino]indan-2-carboxylic acid ethyl ester (289) (560 mg, 1.5 mmol) in dry DMF is treated with NaH oil dispersion (60%, 100 mg, 2.25 mmol, 1.5 eq) and stirred for 10 min. The cyclobutyl bromide (405 mg, 3 mmol, 2 eq) is added and the reaction heated and stirred in the microwave at 150° C. for 3 hours. After the removal of DMF in vacuo, the residue is dissolved in EtOAc (75 mL) and washed with water (2×30 mL) and brine (30 mL). The organic layer is dried over MgSO$_4$ and concentrated in vacuo. The residue is purified by flash chromatography (200 g silica gel, 10% EtOAc in heptane) to give white solid. (290 mg, 45%)

LC/MS (E/S+) m/z 430

Example 302

2-[(1-cyclobutyloxynaphthalene-2-carbonyl)amino]indan-2-carboxylic acid (302)

This compound is prepared in a similar manner to example 288. Purification by flash chromatography (400 g silica gel, gradient elution: 25-60% EtOAc in heptane) gives the product as white solid. (20 mg, 9%)

LC/MS (E/S+) m/z 402

237
Example 303
238
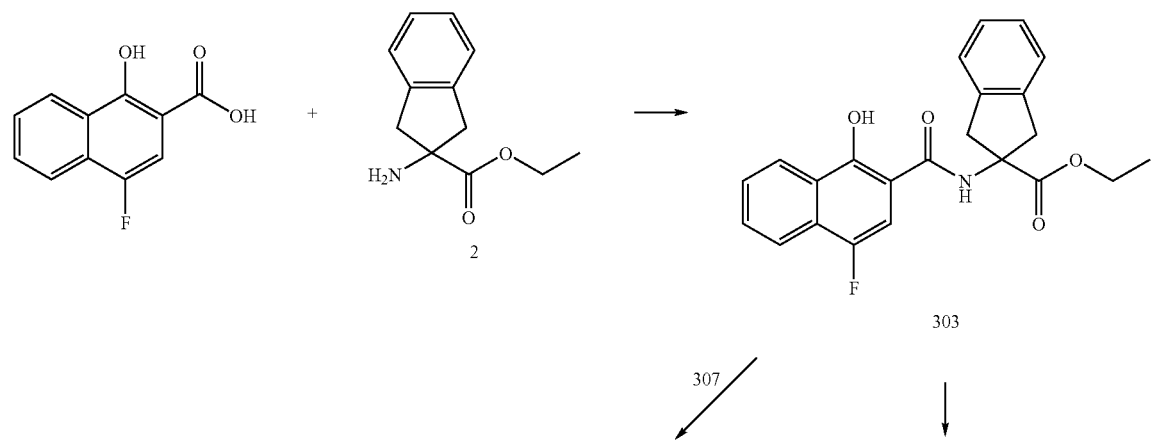
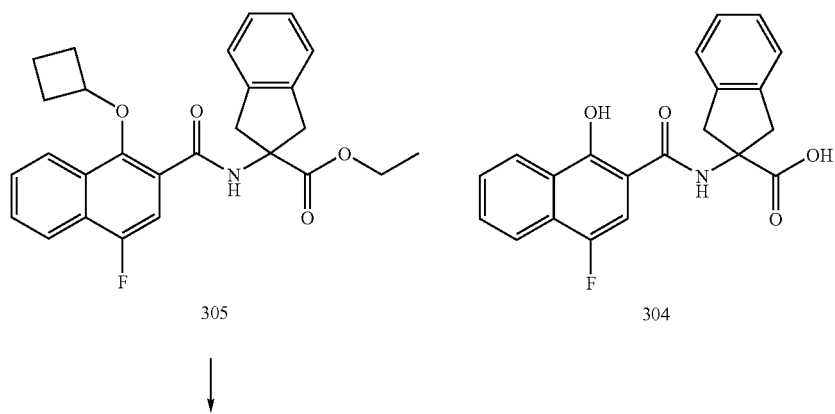
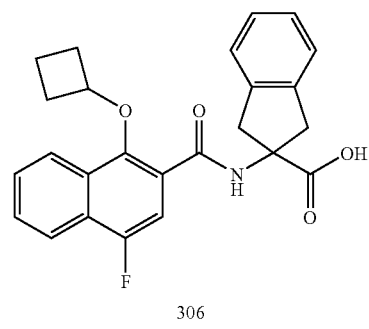

2-[(4-fluoro-1-hydroxynaphthalene-2-carbonyl)amino]indan-2-carboxylic acid ethyl ester (303)

This compound is prepared in a similar manner to example 287. Purification by flash chromatography (400 g silica gel, 30% EtOAc in heptane) gives orange oil. (1.67 g, 85%)

$^1$H NMR (DMSO-d6, 300 MHz): 1.13-1.16 (t, 3H), 3.46-3.52 (d, 2H), 3.64-3.69 (d, 2H), 4.11-4.18 (q, 2H), 7.19-7.29 (m, 4H), 7.69-7.72 (t, 1H), 7.76-7.81 (t, 1H), 7.93-8.01 (m, 2H), 8.31-8.34 (d, 1H), 9.26 (s, 1H), 13.90 (s, 1H).

LC/MS (E/S+) m/z 394

Example 304

2-[(4-fluoro-1-hydroxynaphthalene-2-carbonyl)amino]indan-2-carboxylic acid (304)

This compound is prepared in a similar manner to example 288. The organic extract is evaporated in vacuo to give the product as white solid. (270 mg, 97%)

$^1$H NMR (DMSO-d6, 300 MHz): 3.47-3.58 (d, 2H), 3.64-3.75 (d, 2H), 7.18-7.29 (m, 5H), 7.66-7.75 (m, 1H), 7.77-7.85 (m, 1H), 7.95-8.8.01 (m, 1H), 8.31-8.34 (d, 1H), 9.16 (s, 1H), 12.75 (s, 1H).

LC/MS (E/S−) m/z 364

Example 305

2-[(1-cyclobutyloxy-4-fluoronaphthalene-2-carbonyl)amino]indan-2-carboxylic acid ethyl ester (305)

A solution of 2-[(4-fluoro-1-hydroxynaphthalene-2-carbonyl)amino]indan-2-carboxylic acid ethyl ester (303) (197 mg, 0.5 mmol) and 3,3-dimethyl-1,2,5-thiadiazolidine-5 triphenylphosphine-1,1-dioxide (example 307, 245 mg, 0.6 mmol, 1.2 eq) in DCM (6 mL) is treated with cyclobutanol (44 mg, 0.6 mmol, 1.2 eq) and stirred at RT for 6 days. The crude reaction mixture is purified by flash chromatography (100 g silica gel, 100% DCM) to give colorless oil. (120 mg, 54%)

LC/MS (E/S+) m/z 448

Example 306

2-[(1-cyclobutyloxy-4-fluoronaphthalene-2-carbonyl)amino]indan-2-carboxylic acid (306)

This compound is prepared in a similar manner to example 288. The organic extract is evaporated in vacuo to give white solid. (95 mg, 84%)

$^1$H NMR (DMSO-d6, 300 MHz): 1.20-1.33 (m, 1H), 1.44-1.54 (m, 1H), 3.42-3.47 (d, 2H), 3.58-3.63 (d, 2H), 4.49-4.57 (m, 1H), 7.17-7.36 (m, 6H), 7.69-7.75 (m, 2H), 8.03-8.06 (m, 1H), 8.17-8.19 (m, 1H), 8.88 (s, 1H), 12.70 (s, 1H).

LC/MS (E/S+) m/z 420

Example 307

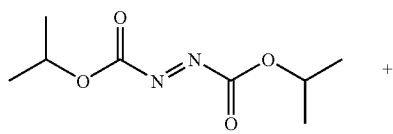

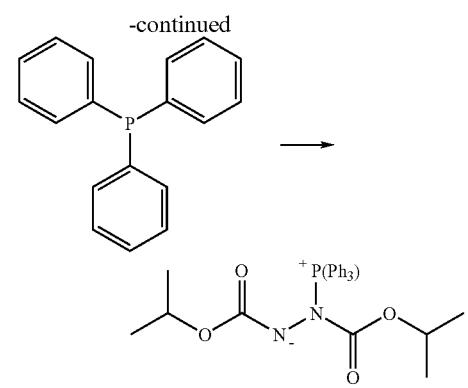

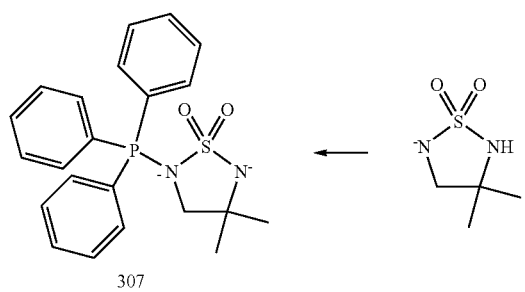

3,3-dimethyl-1,2,5-thiadiazolidine-5 triphenylphosphine-1,1-dioxide (307)

A solution of triphenylphosphine (4.4 g, 0.016 mol) and 3,3-dimethyl-1,2,5-thiadiazoli-dine-1,1-dioxide (2.5 g, 0.016 mol) in dry THF (50 mL) is treated dropwise with diisopro-pyldiazodicarboxylate (3.3 g, 0.016 mol). The white solid precipitated is stirred at RT for a further 4 h. The product is then collected by filtration and washed with diethyl ether (5.7 g, 86%).

Example 308

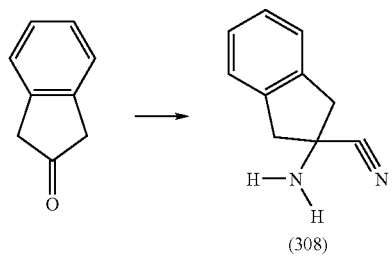 [SMILES: O=C1Cc2ccccc2C1 ; N#CC1(N)Cc2ccccc2C1]

2-Amino-indan-2-carbonitrile (308)

A 250 mL round bottom flask is charged with 2-indanone (2.64 g, 19.98 mmol) and iPrOH (40 mL). A stirring bar is added and stirring is initiated. After dissolution, an aqueous solution of ammonium hydroxide (29%, 8.3 M 16 mL, 132.3 mmol) is added. Ammonium chloride (2.14 g, 39.96 mmol) and NaCN (1.96 g, 39.96 mmol) are added. After 11 days, tlc analysis (silica, 2:1, heptanes:EtOAc) indicates that the starting indone is consumed. The organic solvent is removed in vacuo. The resultant material is transferred to a separatory funnel and partitioned between DCM (200 mL) and water (100 mL). The phases are separated. The aqueous phase is extracted with DCM (100 mL). The organic extracts are combined and washed with brine (100 mL), dried over MgSO$_4$, filtered and evaporated by pumping to constant weight yields 2.6 g of dark brown solid. This material is dissolved in DCM (15 mL). This solution is applied to a column (Silica, 40 g) which is fitted to an ISCO Companion. The gradient is 1% iPrOH in DCM for 4 column volumes followed by a linear gradient to 20% iPrOH in DCM over 10 column volumes. The eluent is collected in 17 mL fractions. Fractions 15 to 32 are combined and evaporated by pumping to constant weight to give light beige solid (0.82 g, 26%).

Example 309

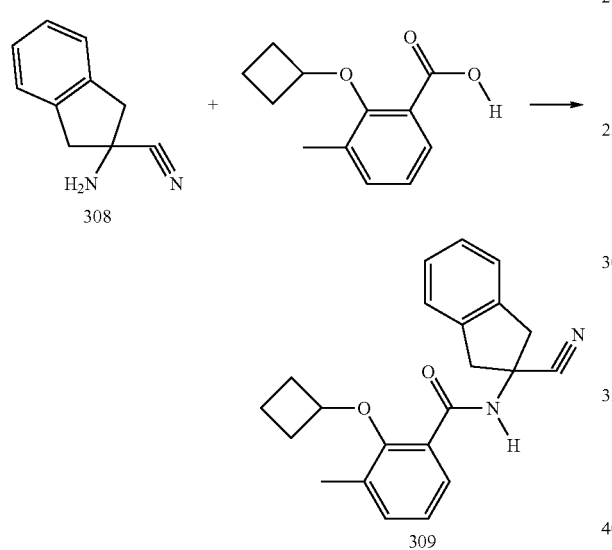

N-(2-Cyano-indan-2-yl)-2-cyclobutoxy-3-methyl-benzamide (309)

A 30 mL vial is charged with 2-cyclobutoxy-3-methyl-benzoic acid (734 mg, 3.56 mmol) and dry DCM (10 mL). A stirring bar is added and stirring is initiated. After 5 min, HTBU (1.35 g, 3.56 mmol) is added. After 5 min, 2-amino-indane-2-carbonitrile. (308, 563 mg, 3.56 mmol) is added followed by DIPEA (1.5 mL, 8.95 mmol). The reaction is allowed to stir for 38 h. Analysis of the reaction mixture by tlc (silica, 15% iPrOH/DCM) indicates complete consumption of the starting amine. The contents of the reaction flask are transferred to a separatory funnel and diluted with EtOAc (60 mL). This is washed saturated aqueous NaHCO$_3$ (2×20 mL) and brine (20 mL), dried over MgSO$_4$, filtered and evaporated in vacuo to provide 1.2 g of thick black oil. This material is dissolved in 10 mL of DCM. This material is purified utilizing an ISCO Companion with a 40 g cartridge of silica. The gradient is 10% EtOAc in heptanes over 4 column volumes followed by a linear gradient to 50% EtOAc over 8 column volumes and then 90% EtOAc in heptanes for 2 column volumes. 17 mL fractions of UV active eluent are collected.

Fractions 27 through 30 are combined and evaporated in vacuo to give white solid (0.51 g, 41%).

Example 310

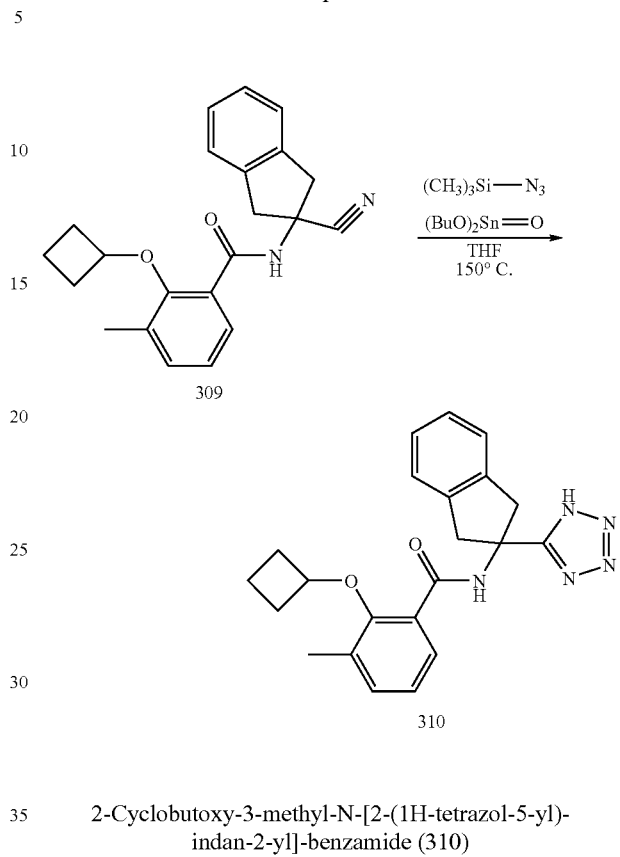

2-Cyclobutoxy-3-methyl-N-[2-(1H-tetrazol-5-yl)-indan-2-yl]-benzamide (310)

A 10 mL microwave reaction vial is charged with N-2-(cyano-indan-2-yl)-2-cylcobutoxy-3-methyl-benzamide (309, 300 mg, 0.87 mmol) and dry tetrahydrofuran (THF, 4 mL). A stirring bar is added and stirring is initiated. After 1 minute, trimethylsislyazide (228 μL, 1.73 mmol) and di-n-butyltinoxide (22 mg, 0.087 mmol) are added to the reaction vial. The reaction vial is capped and inserted into an Emyrs Optimizer microwave apparatus. The reaction vial is prestirred for 10 sec. The temperature is set to hold at 150° C. for 10 min. At the end of this process, additional aliquots of trimethylsislyazide (228 μL, 1.73 mmol) and di-n-butyl tin oxide (22 mg, 0.087 mmol) are added to the reaction vial. The reaction vial is capped and inserted into a Emyrs Optimizer microwave apparatus. The reaction vial is pre-stirred for 10 sec. The temperature is set to hold at 150° C. for 10 min. tlc analysis (silica, 10% MeOH in DCM) indicates that the starting material is completely consumed. The contents of the reaction vial are reconstituted in DCM (8 mL) and iPrOH (4 mL). This solution is stirred for 10 min and filtered through a pad of Celite. The filtrate is evaporated under reduced pressure by pumping to constant weight to give 0.4 g of light yellow foam. The foam is dissolved in DCM (10 mL) and applied to an ISCO Companion (silica, 40 g) Column. The following gradient is applied: 1% iPrOH in DCM for 4 column volumes, followed by a linear gradient to 50% isopropanol in DCM over 10 Column Volumes. 14 mL fractions of UV-active eluent are collected. Fractions 2 to 6 are combined and evaporated by pumping to constant weight to give white solid (0.31 g, 92%).

¹H NMR (DMSO-d6, 300 MHz): δ 1.08-1.25 (m, 2H), 1.38-1.51 (m, 1H), 1.71-1.96 (m, 4H), 2.22 (s, 3H) 3.79-3.93 (m, 4H), 4.35 (m, 1H), 7.03 (dd, 1H), 7.1-7.37 (m, 6H), 8.98 (s, 1H).

LC/MS (ES+) m/z=390.16.

Example 311

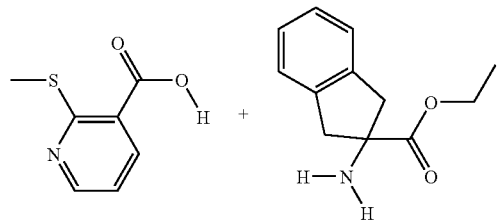

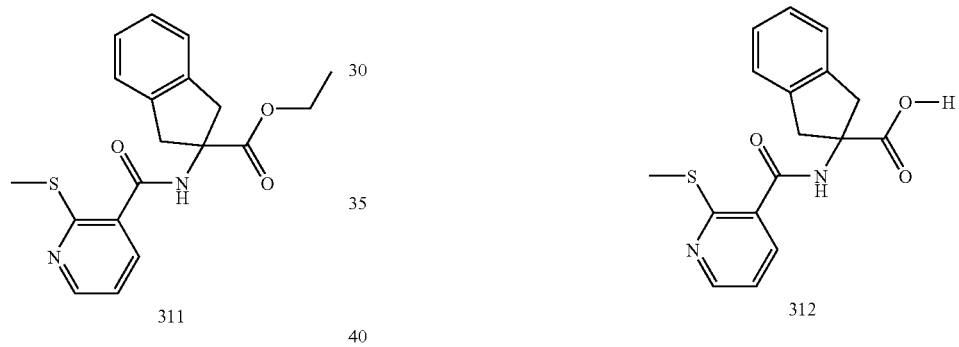

2-[(2-Methylsufamyl-pyridine-3-carbonyl)-amino]-indan-2-carboxylic Acid Ethyl Ester (311)

40 mL vial is charged with 2-(methylthio)-nicotnic acid (0.37 g, 2.19 mmol) and dry DCM (8 mL). A stirring bar is added and stirring is initiated. After dissolution 5 min, HTBU (831 mg, 2.19 mmol) is added. After 5 min, the 2-amino)-indane-2-carboxylic acid ethyl ester. (450 mg, 2.19 mmol) is added followed by DIPEA (0.96 mL, 5.48 mmol). The reaction is allowed to stir for 14 days. Analysis by tlc of the reaction mixture (silica, 15% iPrOH/DCM) indicates complete consumption of the starting amine. The contents of the reaction flask are transferred to a reparatory funnel and diluted with EtOAc (50 mL). The organic phase is washed with brine (20 mL), dried over MgSO₄, filtered and evaporated in vacuo to provide 1.23 g of light yellow foam. The foam is dissolved in 10 mL of DCM. This solution is purified utilizing an ISCO Companion with a 40 g cartridge of silica. The gradient is 10% EtOAc in heptanes over 3 column volumes followed by a linear gradient to 50% EtOAc in heptanes over 10 column volumes. 17 mL fractions of UV active eluent are collected. Fractions 8 through 12 are combined and evaporated in vacuo by pumping to constant weight under reduced pressure gives solid white (0.47 g, 60%).

Example 312

2-[(2-Methylsufamyl-pyridine-3-carbonyl)-amino]-indan-2-carboxylic Acid (312)

To a 100 mL flask containing 2-[(2-methylsufamyl-pyridine-3-carbonyl)-amino]-indan-2-carboxylic acid ethyl ester (311, 490 mg, 1.38 mmol) is added 1,4-dioxane (5 mL) and MeOH (5 mL). A stirring bar is added and stirring is initiated. After dissolution, water (2.5 mL) is added followed by the LiOH (146 mg, 3.5 mmol). After 40 h, tlc analysis (silica, 10% MeOH/DCM) indicates that the starting material is completely consumed. The contents of the flask are diluted with iPrOH (30 mL). Dowex Highly Acidic Ion Exchange Resin (10 g) is added. The reaction flask is capped and allowed to stir at ambient temperature. After 7 days, additional iPrOH (35 mL) is added to the reaction flask. The contents of the reaction flask are filtered through a pad of Celite and concentrated under reduced pressure by pumping to constant weight to give white solid (0.44 g, 97%).

¹H NMR (DMSO-d6, 300 MHz): δ 2.41 (s, 3H), 3.26-3.48 (m, 4H), 7.16-7.25 (m, 5H), 7.71 (dd, 1H), 8.51 (dd, 1H), 9.01 (s, 1H).

LC/MS (ES+) m/z=329.14.

Example 313

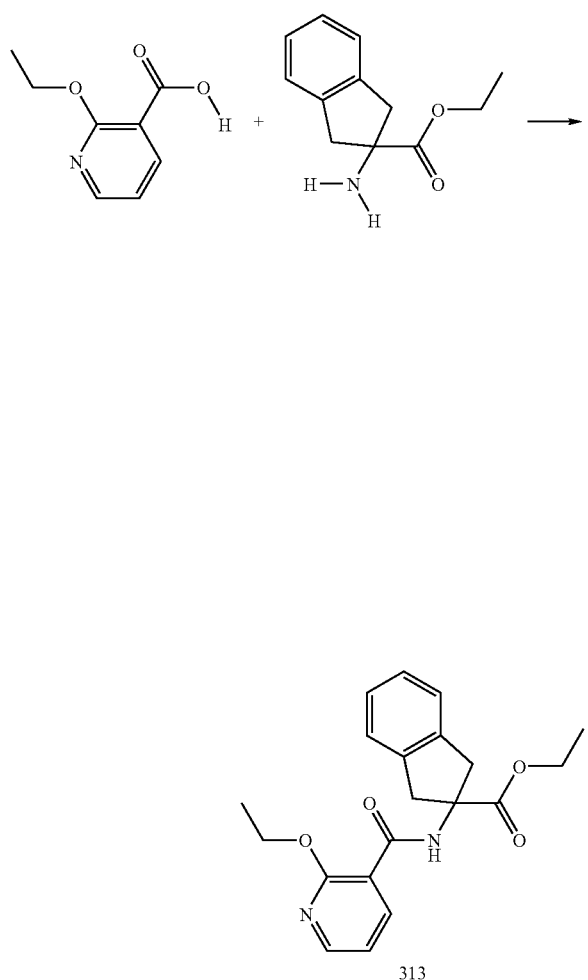

2-[(2-Ethoxy-pyridine-3-carbonyl)-amino]-indan-2-carboxylic Acid Ethyl Ester (313)

A 40 mL vial is charged with 2-ethoxynicotnic acid (366 mg, 2.19 mmol) and dry DCM (7 mL). A stirring bar is added and stirring is initiated. After dissolution 5 min, HTBU (831 mg, 2.19 mmol) is added. After 5 min, the 2-amino-indane-2-carboxylic acid ethyl ester. (450 mg, 2.19 mmol) is added followed by DIPEA (0.96 mL, 5.48 mmol). The reaction is allowed to stir for 17 days. Analysis by tlc of the reaction mixture (silica, 15% iPrOH/DCM) indicates complete consumption of the starting amine. The contents of the reaction flask are transferred to a reparatory funnel and diluted with EtOAc (50 mL). The organic phase is washed with brine (20 mL), dried over $MgSO_4$, filtered and evaporated in vacuo to provide 2.38 g of light yellow syrup. The syrup is dissolved in 10 mL of DCM. This material is purified utilizing an ISCO Companion with a 40 g cartridge of silica. The gradient is 1% iPrOH/DCM over 4 column volumes followed by a linear gradient to 30% iPrOH/DCM over 10 column volumes. 17 mL fractions of UV active eluent are collected. Fractions 5 through 10 are combined and evaporated in vacuo by pumping to constant weight to yield white solid (0.34 g, 44%).

Example 314

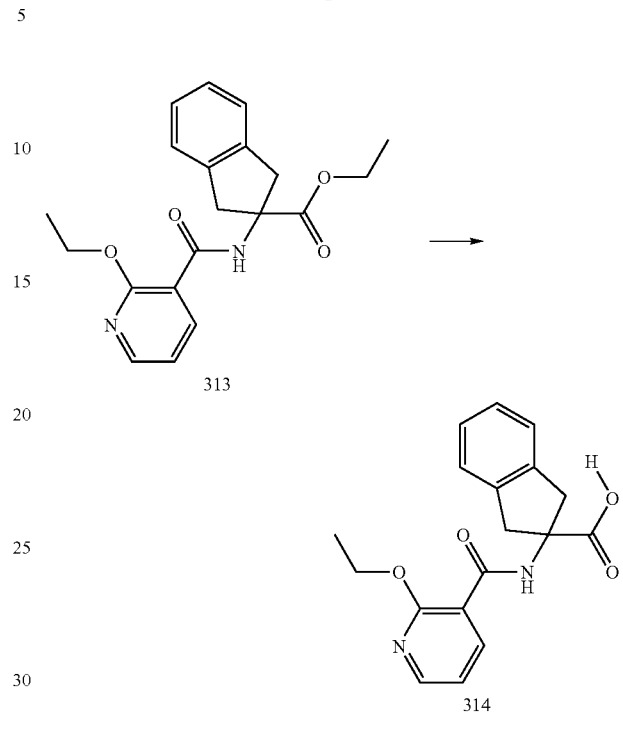

2-[(2-Ethoxy-pyridine-3-carbonyl)-amino]-indan-2-carboxylic Acid (314)

A 100 mL flask containing 2-[(2-ethoxy-pyridine-3-carbonyl)-amino]-indan-2-carboxylic acid ethyl ester ([313], 340 mg, 0.96 mmol) is charged with 1,4-dioxane (4 mL) and MeOH (4 mL). A stirring bar is added and stirring is initiated. After dissolution, water (2 mL) is added followed by the LiOH monohydrate (102 mg, 2.42 mmol). After 13 days, tlc analysis (silica, 10% MeOH/DCM) indicates that the starting material is completely consumed. The contents of the flask are diluted with iPrOH (30 mL). Dowex Highly Acidic Ion Exchange Resin (2 g) is added. The reaction flask is capped and allowed to stir at ambient temperature. After 18 h, additional iPrOH (35 mL) is added to the reaction flask. The contents of the reaction flask are filtered through a pad of Celite and concentrated under reduced pressure by pumping to constant weight to yield 0.44 g of white solid. This material is dissolved in a mixture of DCM (10 mL) and iPrOH (3 mL). Celite (15 g) is added to the flask. The solvent is removed under reduced pressure. The remaining material is transferred to a 40 mL plastic syringe that is fitted with a fritted disk. The syringe is fitted onto an ISCO Companion which had a 40 g column (silica). The following gradient is applied. 1% IPrOH/DCM for 4 column volumes. Then a linear gradient to 50% iPrOH/DCM over 10 column volumes. Hold at 50% iPrOH/DCM for 2 Column Volumes. 14 mL fractions are collected. Fractions 39-41 are combined and evaporated by pumping to constant weight to yield white solid (0.28 g, 89%).

$^1$H NMR (DMSO-d6, 300 MHz): δ 1.22 (t, 3H), 3.26-3.63 (m, 4H), 4.36 (q, 2H), 7.14-7.25 (m, 5H), 8.13 (dd, 1H), 8.28 (dd, 1H), 8.76 (s, 1H).

LC/MS (ES+) m/z=327.11.

Example 315

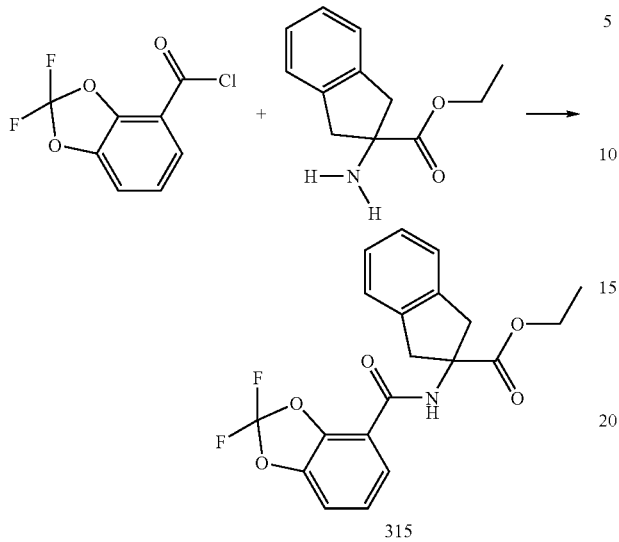

2-[(2,2-Difluoro-benzo[1,3]dioxole-4-carbonyl)-amino]-indan-2-carboxylic acid ethyl ester (315)

A 100 mL round bottom flask is charged with 2-aminoindan-2-carboxylic acid (340 mg, 1.66 mmol) and dry DCM (6 mL). A stirring bar is added and stirring is initiated. DIPEA (0.46 mL, 2.65 mmol) is added. 2-[(2,2-difluoro-benzo[1,3]dioxole-4-carbonyl chloride (438 mg, 1.99 mmol) is added. 4-Dimethylaminopyridine ([MFCD0006418], 2 mg, cat.) is added. The reaction is capped. After 18 days, tlc analysis (silica, 5% iPrOH/DCM) indicates that the starting is completely consumed. The contents of the reaction flask are transferred to a reparatory funnel and diluted with EtOAc (60 mL). This is washed with dilute aqueous HCl (2×25 mL), saturated aqueous NaHCO₃ (2×25 mL), and brine (25 mL), dried over MgSO₄, filtered and evaporated by pumping to constant weight to yield 0.73 g of dark brown foam. This is diluted with DCM and applied to a silica column (40 g) on an ISCO Companion. The column is eluted with 3 column volumes of 10% EtOAc-heptanes followed by a linear gradient to 50% EtOAc/heptanes over 10 Column Volumes. And then 90% EtOAc/heptanes for 2 Column Volumes. 17 mL fractions of UV positive eluent are collected. Fraction 8-10 are combined and evaporated by pumping to constant weight to give light orange solid (0.57 g, 88%).

Example 316

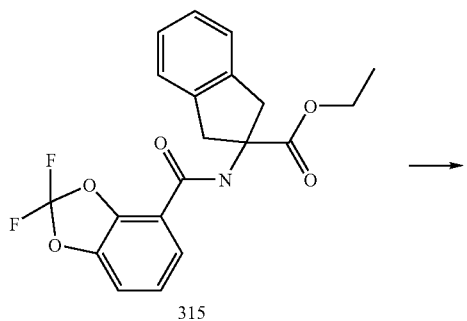

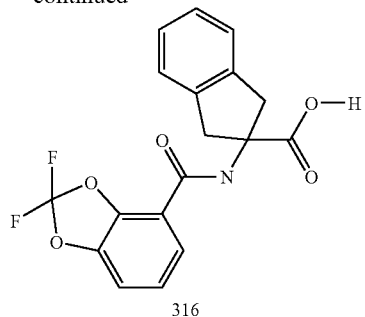

2-[(2,2-Difluoro-benzo[1,3]dioxole-4-carbonyl)-amino]-indan-2-carboxylic acid (316)

A 100 mL flask containing 2-[(2,2-difluoro-1,3-benzodioxole-4-carbonyl)-amino]-indan-2-carboxylic acid ethyl ester (0.38 g, 0.98 mmol) is charged with 1,4-dioxane (6 mL) and MeOH (6 mL). A stirring bar is added and stirring is initiated. After dissolution, water (3 mL) is added followed by the LiOH monohydrate (103 mg, 2.46 mmol). After 70 h, tlc analysis (silica, 10% MeOH/DCM) indicates that the starting material is completely consumed. The pH of the reaction mixture is carefully adjusted to pH 2 by slowly adding dilute aqueous HCl (3%, ~6 mL). The contents of the flask are poured into a separatory funnel which contains EtOAc (30 mL). The layers are separated. The aqueous layer is extracted with EtOAc (20 mL). The combined organic extracts are washed with water (20 mL) and brine (20 mL), dried over MgSO₄, filtered and concentrated by pumping to constant weight to give off white solid (0.33 g, 94%).

¹H NMR (DMSO-d6, 300 MHz): δ 3.26-3.63 (m, 4H), 7.13-7.32 (m, 5H), 7.48 (dd, 1H), 7.55 (dd, 1H), 8.97 (s, 1H), 12.63 (bs, 1H).

LC/MS (ES+) m/z=362.05.

Example 317

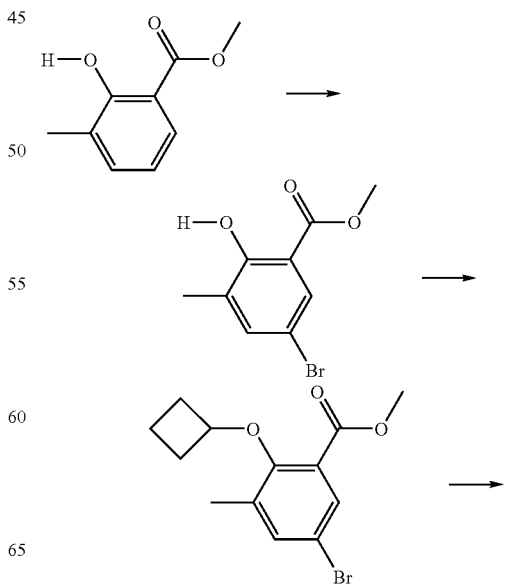

-continued

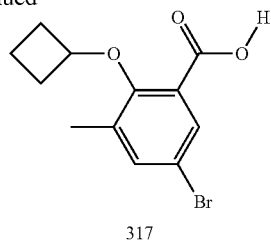

317

5-Bromo-2-cyclobutoxy-3-methyl-benzoic acid (317)

A 250 mL 3-necked round bottom flask which is fitted with an addition funnel, a $N_2$ inlet and a stopper. The flask is charged with bromine (3.6 mL 70.11 mmol) and DCM (40 mL). A stirring bar is added and stirring is initiated. The reaction flask is immersed in an ice-water bath. After stirring for 15 min, the addition funnel is charged with a solution of methyl 2-hydroxy-3-methylbenzoate (10 g, 60.18 mmol) in 1,4-dioxane (40 mL). This solution is added to the stirred reaction mixture dropwise over 30 min. The addition funnel is then washed with 1,4-dioxane (10 mL). This too is added to the reaction mixture. The reaction mixture is then allowed to slowly warm to ambient temperature. After 18 days, the contents of the reaction flask are transferred to a round bottom flask. The solvent is removed under reduced pressure by pumping to constant weight to give 17.66 g of light yellow solid. This solid is triturated with ice-cold MeOH (75 mL). The resultant crystals are collected by suction filtration. Air-drying provides white solid (14.26 g, 97%).

A 100 mL round bottom flask is charged with 5-bromo-2-hydroxy-3-methyl-benzoic acid methyl ester 4.05 g, 16.53 mmol) as prepared above. Dry DMF (20 mL) and a stirring bar are added. Stirring is initiated. After dissolution, $K_2SO_4$ (6.85 g, 49.59 mmol) and bromocyclobutane (2.35 mL, 24.8 mmol) are added. The reaction flask is fitted with a heating mantle. The temperature of the mantle is set to 35 degrees C. After 8 days, tlc analysis (silica, 25% EtOAc/heptanes) indicates a slight consumption of starting material and the appearance of a UV positive spot with a slightly higher $R_f$ value. The reaction is fitted with a heating mantle and warmed to 37° C. After 3 more days, tlc analysis (silica, 25% EtOAc/heptanes) indicates consumption of starting material and complete conversion to a UV positive spot with a slightly higher $R_f$ value. The reaction mixture is filtered through a pad of Celite. The filtrate is diluted with EtOAc and (100 mL) and transferred to a separatory funnel. The EtOAc solution is washed with saturated $NaHCO_3$ (2×25 mL) and brine (25 mL), dried over $MgSO_4$, filtered and evaporated by pumping to constant weight to give semi-solid material (2.09 g, 42%). This material is utilized in the subsequent step.

A 100 mL flask containing 5-bromo-2-cyclobutoxy-3-methyl-benzoic acid methyl ester (2.07 g, 7.25 mmol) as prepared above is charged with 1,4-dioxane (12 mL) and MeOH (12 mL). A stirring bar is added and stirring is initiated. After dissolution, water (6 mL) is added followed by the LiOH (768 mg, 18.3 µmol). After 18 h, tlc analysis (silica, 10% MeOH/DCM) indicates that the starting material is completely consumed. The pH of the reaction mixture is carefully adjusted to pH 2 by slowly adding dilute aqueous HCl (3%, ~11 mL). The contents of the flask are poured into a separatory funnel which contains EtOAc (50 mL). The layers are separated. The aqueous layer is extracted with EtOAc (40 mL). The combined organic phases are washed with water (40 mL) and brine (40 mL), dried over $MgSO_4$, filtered and concentrated by pumping to constant weight to give a white solid (1.82 g, 88%).

$^1$H NMR (DMSO-d6, 300 MHz): δ 1.16-1.25 (m, 2H), 1.38-1.51 (m, 1H), 1.71-2.12 (m, 3H), 2.23 (s, 3H), 4.37 (m, 1H), 7.53-7.62 (m, 2H).

LC/MS (ES+) m/z=390.16.

Example 318

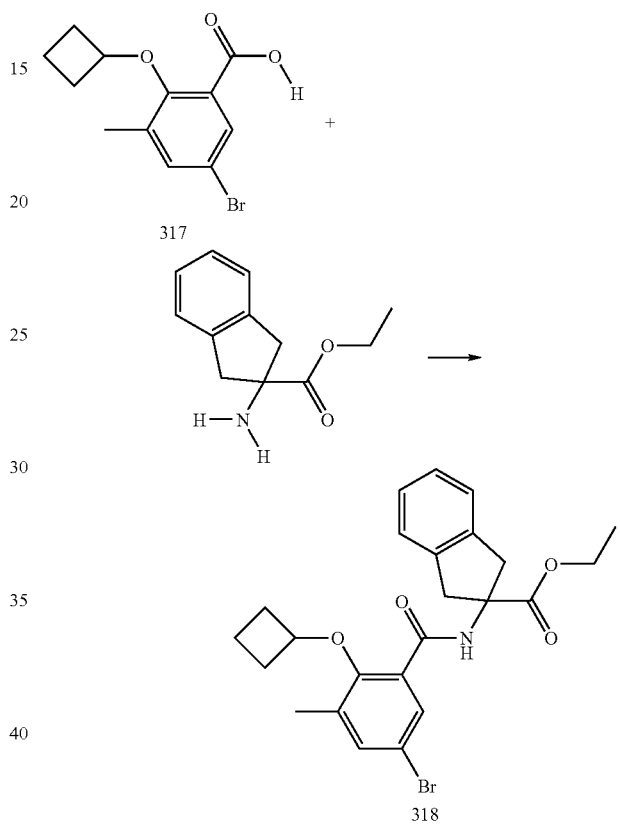

318

2-(5-Bromo-2-cyclobutoxy-3-methyl-benzoylamino)-indan-2-carboxylic acid ethyl ester (318)

A 100 mL round bottom flask which contains a stirring bar is charged with 2-cyclobutoxyl-3-methyl-5-bromo-benzoic acid 317 (695 mg, 2.44 mmol) and dry DCM (8 mL). Stirring is initiated. After dissolution is complete, HTBU (924 mg, 2.44 mmol) is added. After 5 min, 2-amino-indane-2-carboxylic acid ethyl ester (500 mg, 2.44 mmol) is added followed by DIPEA (1.1 mL, 6.1 mmol). The reaction is allowed to stir for 15 days. Analysis by tlc of the reaction mixture (silica, 5% iPrOH/DCM) indicates complete consumption of the starting amine. The contents of the reaction flask are transferred to a separatory funnel and diluted with EtOAc (50 mL). The organic phase is washed consecutively with dilute aqueous HCl (3%, 25 mL), saturated aqueous $NaHCO_3$ (25 mL) and brine (25 mL), and then dried over $MgSO_4$, filtered and evaporated in vacuo to give 1.42 g of light orange solid. This solid is dissolved in 10 mL of DCM. This material is purified utilizing an ISCO Companion with a 40 g cartridge of silica. The gradient is 10% EtOAc in heptanes over 3 column volumes followed by a linear gradient to 60% EtOAc in heptanes over 10 column volumes. 17 mL fractions of UV active eluent are collected. Fractions 4 through 9 are combined and evaporated in vacuo. This yields white solid material (0.8 g, 70%).

Example 319

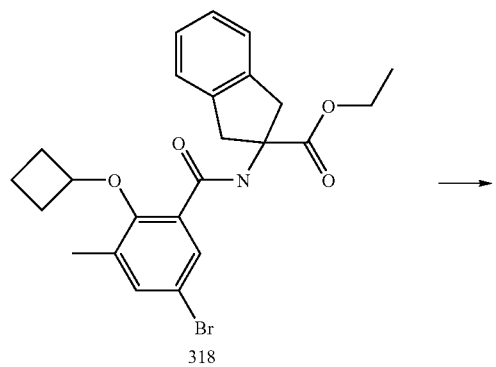

318

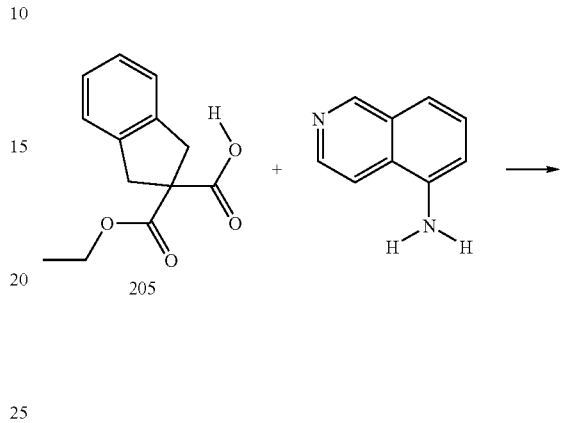

205

Example 320

¹H NMR (DMSO-d6, 300 MHz): δ 1.11-1.27 (m, 2H), 1.43-1.57 (m, 1H), 1.79-1.99 (m, 4H), 2.21 (s, 3H) 3.55-3.84 (m, 4H), 4.37 (m, 1H), 7.18-7.33 (m, 4H), 7.35 (d, 1H), 7.51 (d, 1H), 8.78 (s, 1H) 12.62 (s, 1H).

LC/MS (ES+) m/z=446.11.

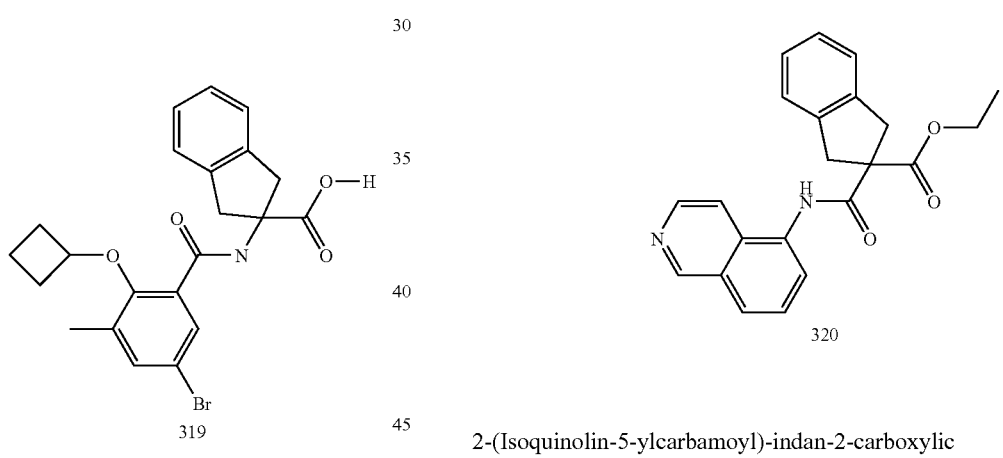

319

320

2-(5-Bromo-2-cyclobutoxy-3-methyl-benzoylamino)-indan-2-carboxylic acid (319)

A 30 mL reaction vial is charged with 2-(5-bromo-2-cyclobutoxy-3-methyl-benzoylamino)-indan-2-carboxylic acid ethyl ester (0.29 g, 0.61 mmoles) is charged with 1,4-dioxane (4 mL) and MeOH (4 mL). A stirring bar is added and stirring is initiated. After dissolution, water (2 mL) is added followed by the LiOH monohydrate (65 mg, 1.55 mmol). After 38 h, tlc analysis (silica, 10% MeOH/DCM) indicates that the starting material is completely consumed. The pH of the reaction mixture is carefully adjusted to pH 2 by slowly adding dilute aqueous HCl (3%, ~6 mL). The contents of the flask are poured into a separatory funnel which contains EtOAc (30 mL). The layers are separated. The aqueous layer is extracted with EtOAc (20 mL). The combined organic phases are washed with water (20 mL) and brine (20 mL), dried over MgSO₄, filtered and concentrated by pumping to constant weight to give off white solid (0.26 g, 95%).

2-(Isoquinolin-5-ylcarbamoyl)-indan-2-carboxylic Acid Ethyl Ester (320)

A 25 mL reaction vial which contains a stirring bar is charged with indane-2-carboxylic acid ethyl ester (205, 1.0 g, 4.27 mmol) and dry DCM (15 mL). Stirring is initiated. After dissolution is complete, the HTBU (1.62 g, 4.27 mmol) is added. After 5 min, the 5,-aminoisoquinoline. (616 mg, 4.27 mmol) is added followed by DIPEA (1.72 mL, 9.8 mmol). The reaction is allowed to stir for 63 h. Analysis by tlc of the reaction mixture (silica, 10% MeOH/DCM) indicates complete consumption of the starting acid. The contents of the reaction flask are transferred to a reparatory funnel and diluted with EtOAc (40 mL). The organic phase is washed consecutively with dilute aqueous HCl (3%, 20 mL), saturated aqueous NaHCO₃ (20 mL) and brine (20 mL), and then dried over MgSO₄, filtered and evaporated in vacuo to provide 3.13 g of light orange solid. This material is dissolved in 15 mL of DCM. This material is purified utilizing an ISCO Companion with a 40 g cartridge of silica. The gradient is 10% EtOAC in heptanes over 4 column volumes followed by a linear gradient to 90% EtOAc over 12 column volumes. 17 mL fractions of eluent are collected. Fractions 17 through 31 are combined and evaporated in vacuo. This gives white solid (1.39 g, 90%).

Example 321

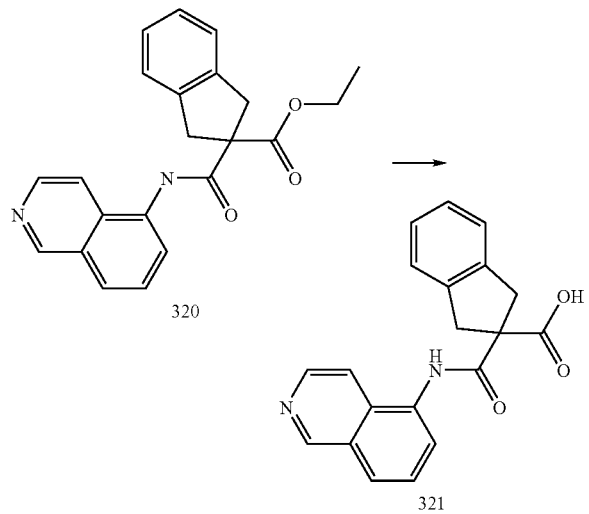

2-(Isoquinolin-5-ylcarbamoyl)-indan-2-carboxylic Acid (321)

A 30 mL reaction vial is charged with 2-(isoquinolin-5-ylcarbamoyl)-indan-2-carboxylic acid ethyl ester (320, 354 mg, 0.98 mmol) is charged with 1,4-dioxane (6 mL) and MeOH (6 mL). A stirring bar is added and stirring is initiated. After dissolution, water (3 mL) is added followed by the LiOH monohydrate (104 mg, 252 mmol). After 20 h, tlc analysis (silica, 10% MeOH/DCM) indicates that the starting material is completely consumed. Amberlyst highly acidic exchange resin (1 g) is added to the reaction vial. The reaction is capped and allowed to stir at ambient temperature. After 64 h, the contents of the flask are filtered through a pad of Celite. The solvent is removed from the filtrate by pumping to constant weight to give 0.29 g of off white solid. This material is triturated with DCM (15 mL). The solids are collected by suction filtration and washed with DCM (20 mL). Suction drying provides off white solid (280 mg, 86%).

$^1$H NMR (DMSO-d6, 300 MHz): δ 3.55-3.76 (m, 4H), 4.37 (m, 1H), 7.02-7.19 (m, 4H), 7.61 (dd, 1H), 7.78 (d, 1H), 8.06 (d, 1H), 8.46 (d, 1H), 8.57 (d, 1H), 9.30 (s, 1H) 13.77 (s, 1H).

LC/MS (ES+) m/z=333.11.

Example 322

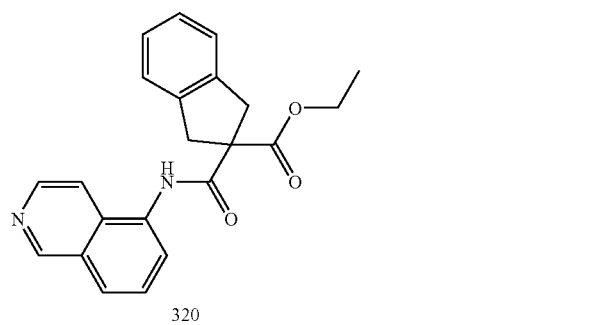

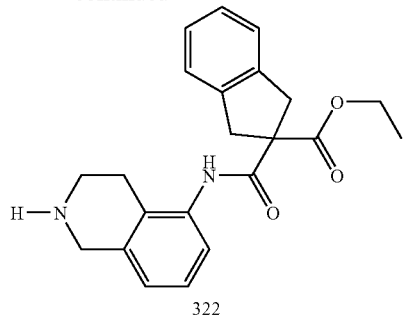

2-(1,2,3,4-Tetrahydro-isoquinolin-5-ylcarbamoyl)-indan-2-carboxylic acid ethyl ester (322)

A 100 mL Parr reaction vessel is charged with 2-(Isoquinolin-5-ylcarbamoyl)-indan-2-carboxylic acid ethyl ester (320, 500 mg, 1.39 mmol) and EtOH (10 mL). The reaction vessel is agitated by swirling until dissolution ° C. curred. Acetic acid (10 mL) and platinum (IV) oxide (117 mg, 0.52 mmol) are added. The vessel is fitted on a Parr hydrogenation apparatus, flushed with $N_2$ and then evacuated. The vessel is charged with hydrogen to 50 psi. The apparatus is set to agitate. After 4 h, agitation is ceased. The reaction vessel is evacuated and flushed with nitrogen. This process is repeated. The contents of the reaction vessel are diluted with iPrOH (50 mL) and filtered through a pad of celite. Solvent is removed from the filtrate under reduced pressure. The resulting residue is reconstituted in iPrOH (15 mL) and toluene (15 mL). The solvent is removed under reduced pressure. This process is repeated. Pumping to constant weight yields light beige solid (0.5 g, 99%).

Example 323

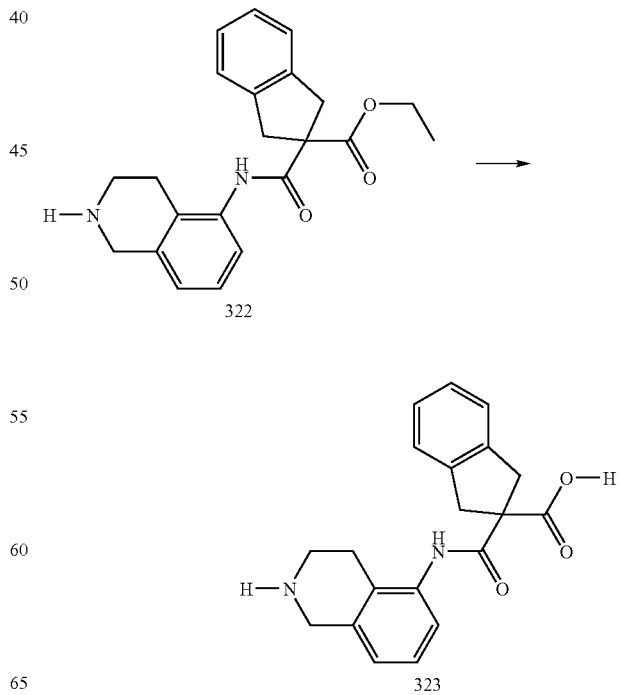

2-(1,2,3,4-Tetrahydro-isoquinolin-5-ylcarbamoyl)-indan-2-carboxylic Acid (323)

A 250 mL round bottom flask containing 2-(1,2,3,4-tetrahydro-isoquinolin-5-ylcarbamoyl)-indan-2-carboxylic acid ethyl ester (322, 440 mg, 1.21 mmoles) is charged with 1,4-dioxane (7 mL) and MeOH (7 mL). A stirring bar is added and stirring is initiated. After dissolution, water (3.5 mL) is added followed by the LiOH monohydrate (128 mg, 3.05 mmol). After 18 h, tlc analysis (silica, 10% MeOH/DCM) indicates that the starting material is completely consumed. Amberlyst highly acidic exchange resin (1 g) is added to the reaction flask. The reaction is capped and allowed to stir at ambient temperature. After 24 h, the contents of the flask are filtered through a pad of Celite. The solvent is removed from the filtrate. The resultant residue is reconstituted with iPrOH/toluene (1:1, 25 mL). The solvent is removed in vacuo. This process is repeated twice. Pumping to constant weight provides an off-white solid (400 mg, 99%).

$^1$H NMR (DMSO-d6, 300 MHz): δ 2.58 (m, 1H), 2.99 (m, 1H), 3.43-3.71 (m, 4H), 3.81 (m, 1H), 6.72 (d, 1H), 7.01 (dd, 1H), 7.04-7.18 (m, 4H), 7.84 (d, 1H), 11.82 (s, 1H).

LC/MS (ES+) m/z=337.15.

Example 324

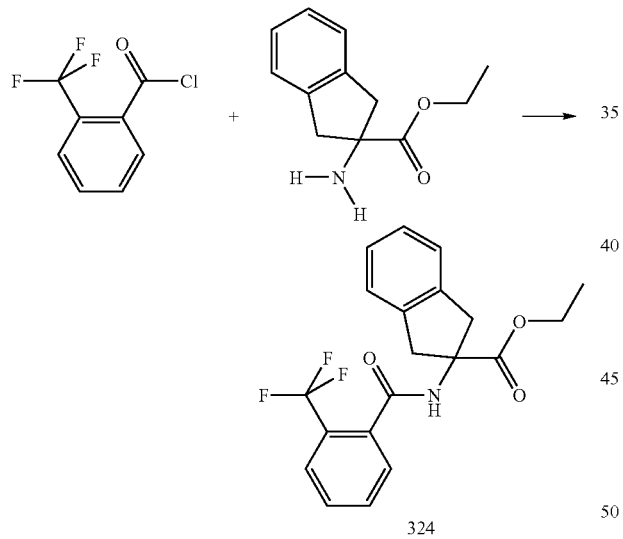

2-(2-Trifluoromethyl-benzoylamino)-indan-2-carboxylic acid ethyl ester (324)

A 30 mL vial is charged with 2-aminoindan-2-carboxylic acid (450 mg, 2.19 mmol) and dry DCM (5 mL). A stirring bar is added and stirring is initiated. DIPEA (0.61 mL, 3.51 mmol) is added. 2-(trifluoromethyl)-benzoyl chloride (388 µL, 2.63 mmol) and DMAP (3 mg, cat.) are added. The reaction is capped. After 38 days, tlc analysis (silica, 10% iPrOH/DCM) indicates that the starting is completely consumed. The contents of the reaction flask are transferred to a reparatory funnel and diluted with EtOAc (60 mL). The organic phase is washed with dilute aqueous HCl (2×25 mL), saturated aqueous NaHCO$_3$ (2×25 mL), and brine (25 mL), dried over MgSO$_4$, filtered and evaporated by pumping to constant weight yields 0.84 g of light orange solid. This is diluted with DCM and applied to a silica column ((24 g) on an ISCO Companion. 14 mL fractions of UV positive eluent are collected. Fraction 4-10 are combined and evaporated by pumping to constant weight to give light yellow solid (0.76 g, 92%).

Example 325

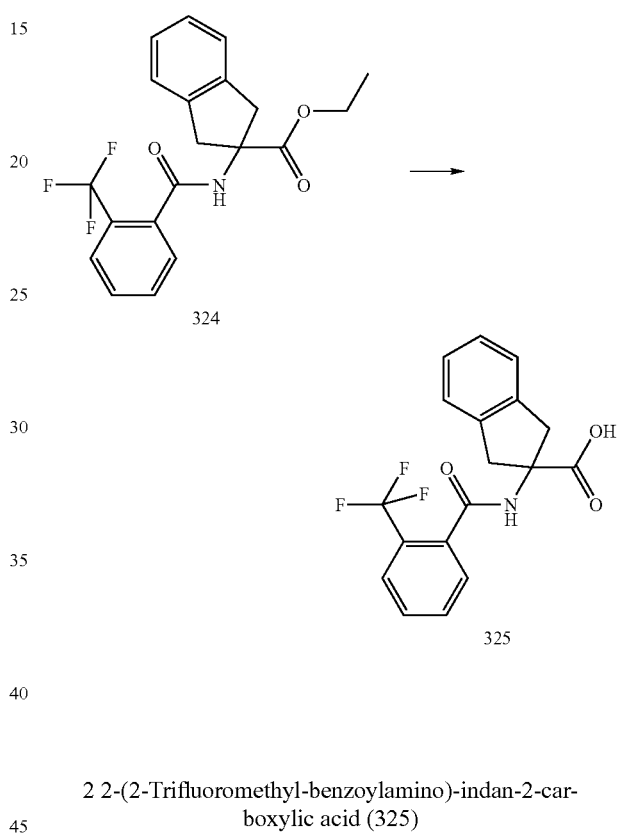

2 2-(2-Trifluoromethyl-benzoylamino)-indan-2-carboxylic acid (325)

A 100 mL flask containing 2-(2-trifluoromethyl-benzoylamino)-indan-2-carboxylic acid ethyl ester (324, 0.57 g, 1.5 µmol) is charged with 1,4-dioxane (9 mL) and MeOH (9 mL). A stirring bar is added and stirring is initiated. After dissolution, water (4.5 mL) is added followed by the LiOH monohydrate (160 mg, 3.81 mmol). After 110 h, tlc analysis (silica, 10% MeOH/DCM) indicates that the starting material is completely consumed. The pH of the reaction mixture is carefully adjusted to pH 2 by slowly adding dilute aqueous HCl (3%, ~9 mL). The contents of the flask are poured into a separatory funnel which contains EtOAc (40 mL). The layers are separated. The aqueous layer is extracted with EtOAc (20 mL). The combined organic phases are washed with water (20 mL) and brine (20 mL), and then dried over MgSO4, filtered and concentrated by pumping to constant weight yields off white solid (0.51 g, 97%).

$^1$H NMR (DMSO-d6, 300 MHz): δ 3.23-3.63 (m, 4H), 7.11-7.23 (m, 4H), 7.47 (d, 1H), 7.60-7.76 (m, 3H), 9.12 (s, 1H), 12.55 (s, 1H).

LC/MS (ES+) m/z=350.11.

Example 326

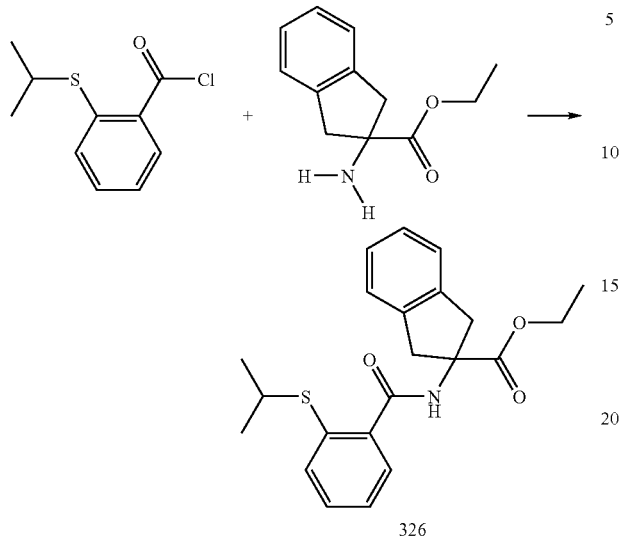

2-(2-Isopropylsulfanyl-benzoylamino)-indan-2-carboxylic acid ethyl ester (326)

A 30 mL reaction vial is charged with 2-isopropylsulfanyl-benzoic acid (430 mg, 2.19 mmol) and dry DCM (7 mL). A stirring bar is added. Stirring is initiated. After dissolution is complete, the HTBU (831 mg, 2.19 mmol) is added. After 5 min, 2-amino-indane-2-carboxylic acid ethyl ester. (450 mg, 2.19 mmol) is added followed by DIPEA (0.96 mL, 5.48 mmol). The reaction is allowed to stir for 3 days. Analysis by tlc of the reaction mixture (silica, 5% iPrOH/DCM) indicates complete consumption of the starting amine. The contents of the reaction flask are transferred to a separatory funnel and diluted with EtOAc (50 mL). This is washed consecutively with dilute aqueous HCl (3%, 25 mL), saturated aqueous NaHCO₃ (25 mL) and brine (25 mL), and then dried over MgSO₄, filtered and evaporated in vacuo to provide 0.87 g of light yellow solid. This material is dissolved in 10 mL of DCM. This material is purified utilizing an ISCO Companion with a 40 g cartridge of silica. The gradient is 10% EtOAc in heptanes over 3 column volumes followed by a linear gradient to 50% EtOAc in heptanes over 10 column volumes. 17 mL fractions of eluent are collected. Fractions 32 through 40 are combined and evaporated in vacuo. This provides white solid material (0.69 g, 82%).

Example 327

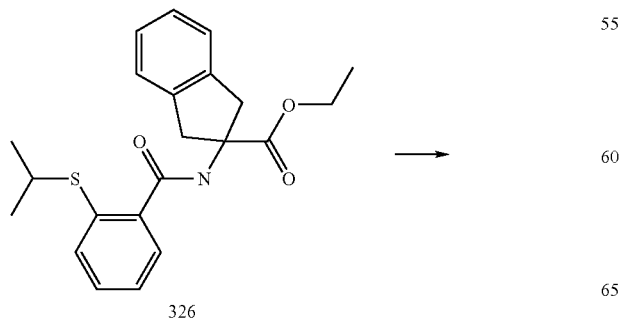

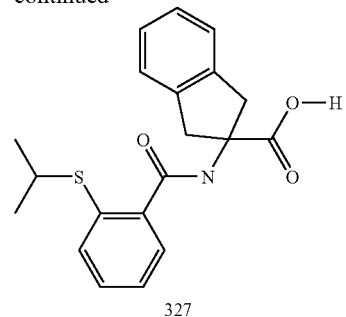

2-(2-Isopropylsulfanyl-benzoylamino)-indan-2-carboxylic acid (327)

A 100 mL flask containing 2-(2-isopropylsulfanyl-benzoylamino)-indan-2-carboxylic acid ethyl ester (326, 0.52 g, 1.45 mmol) is charged with 1,4-dioxane (8 mL) and MeOH (8 mL). A stirring bar is added and stirring is initiated. After dissolution, water (4 mL) is added followed by the LiOH monohydrate (145 mg, 3.46 mmol). After 20 days, tlc analysis (silica, 10% iPrOH/DCM) indicates that the starting material is completely consumed. The pH of the reaction mixture is carefully adjusted to pH 2 by slowly adding dilute aqueous HCl (3%, ~9 mL). The contents of the flask are poured into a separatory funnel which contains EtOAc (40 mL). The layers are separated. The aqueous layer is extracted with EtOAc (20 mL). The combined organic phases are washed with water (20 mL) and brine (20 mL), and then dried over MgSO₄, filtered and concentrated by pumping to constant weight to give off white solid (0.45 g, 93%).

¹H NMR (DMSO-d6, 300 MHz): δ 1.14 (d, 6H), 3.24-3.623 (m, 5H), 7.12-7.44 (m, 8H), 8.85 (s, 1H), 12.92 (s, 1H).

LC/MS (ES+) m/z=356.15.

Example 328

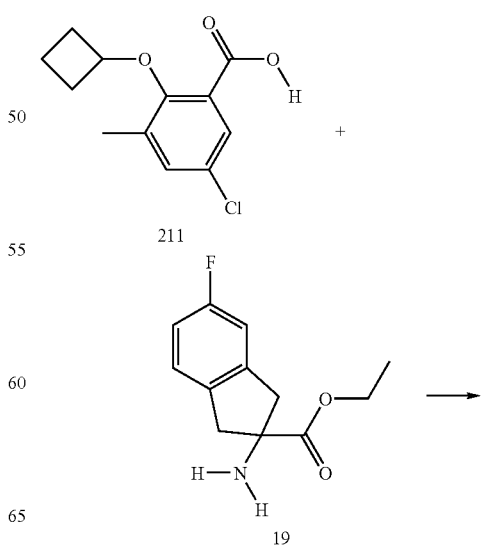

-continued

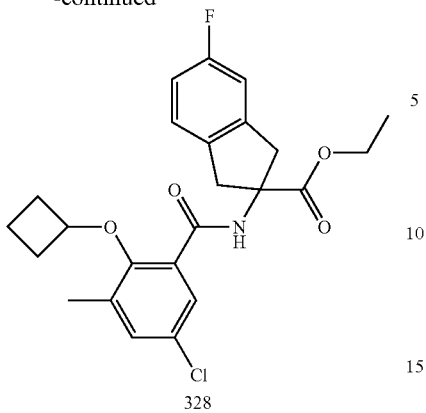

2-(5-Chloro-2-cyclobutoxy-3-methyl-benzoylamino)-5-fluoro-indan-2-carboxylic acid ethyl ester (328)

A 40 mL reaction vial is charged with 2-cyclobutoxyl-3-methyl-5-chloro-benzoic acid (221, 0.40 g, 1.62 mmol) and dry DCM (5 mL). A stirring bar is added. Stirring is initiated. After dissolution is complete, the HBTU (630 mg, 1.66 mmol) is added. After 5 min, the 2-amino-5-fluoro-indane-2-carboxylic acid ethyl ester. (19, 371 mg, 1.66 mmol is added followed by DIPEA (0.74 mL, 4.16 mmol). The reaction is allowed to stir for 5 days. Analysis by tlc of the reaction mixture (silica, 5% iPrOH/DCM) indicates complete consumption of the starting amine. The contents of the reaction flask are transferred to a separatory funnel and diluted with EtOAc (50 mL). This is washed consecutively with dilute aqueous HCl (3%, 20 mL), saturated aqueous NaHCO$_3$ (20 mL) and brine (20 mL), and then dried over MgSO$_4$, filtered and evaporated in vacuo to provide 1 g of light yellow oil. This material is dissolved in 10 mL of DCM. This material is purified utilizing an ISCO Companion with a 24 g cartridge of silica. The gradient is 10% EtOAc in heptanes over 4 column volumes followed by a linear gradient to 70% EtOAc in heptanes over 10 column volumes. 17 mL fractions are collected. Fractions 22 through 28 are combined and evaporated in vacuo by pumping to a constant weight to give white solid (0.65 g, 88%).

Example 329

-continued

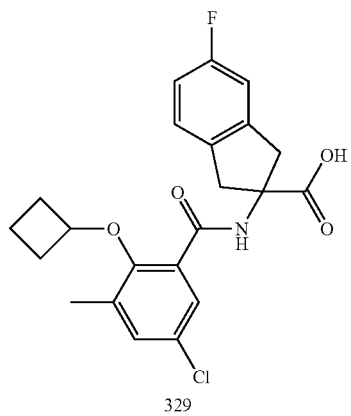

2-(5-Chloro-2-cyclobutoxy-3-methyl-benzoylamino)-5-fluoro-indan-2-carboxylic acid (329)

A 100 mL flask containing 2-(5-chloro-2-cyclobutoxy-3-methyl-benzoylamino)-5-fluoro-indan-2-carboxylic acid ethyl ester (328, 0.49 g, 1.09 mmol) is charged with 1,4-dioxane (3 mL) and MeOH (3 mL). A stirring bar is added and stirring is initiated. After dissolution, water (1.5 mL) is added followed by the LiOH (117 mg, 2.78 mmol). After 1 day, tlc analysis (silica, 10% MeOH/DCM) indicates that the starting material is completely consumed. The pH of the reaction mixture is carefully adjusted to pH 2 by slowly adding dilute aqueous HCl (3%, ~8 mL). The contents of the flask are poured into a separatory funnel which contains EtOAc (25 mL). The layers are separated. The aqueous layer is extracted with EtOAc (20 mL). The combined organic phases are washed with water (20 mL) and brine (20 mL), and then dried over MgSO$_4$, filtered and concentrated by pumping to constant weight to give white solid (0.45 g, 98%).

$^1$H NMR (DMSO-d6, 300 MHz): δ 1.22-1.37 (m, 1H), 1.43-1.57 (m, 1H), 1.78-1.95 (m, 4H), 2.03 (s, 3H) 3.285-3.63 (m, 5H), 4.37 (m, 1H), 6.98 (m, 1H), 7.06-7.11 (m, 1H), 7.20-7.27 (m, 2H), 7.385 (d, 1H), 8.82 (s, 1H) 12.67 (s, 1H).

LC/MS (ES+) m/z=418.18

Example 330

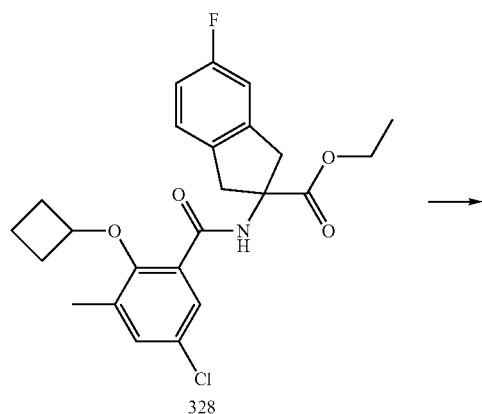

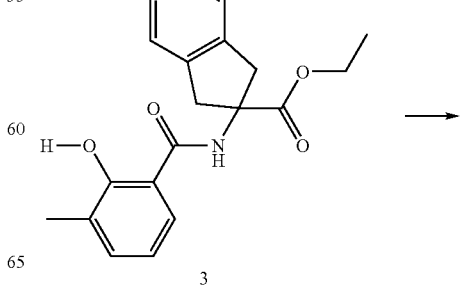

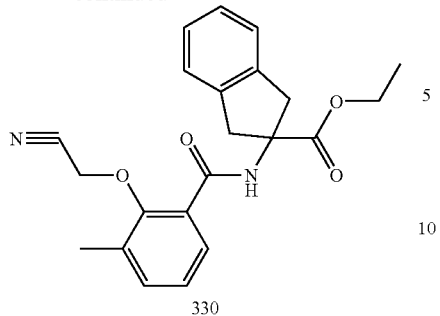

330

2-(2-Cyanomethoxy-3-methyl-benzoylamino)-indan-
2-carboxylic acid ethyl ester (330)

A 30 mL reaction vial is charged with 2-(2-hydroxy-3-methyl-benzoylamino)-indan-2-carboxylic acid ethyl ester (3, 400 mg, 1.18 mmol) and dry DMF (5 mL). A stirring bar is added and stirring is initiated. After dissolution, K$_2$SO$_4$ (326 mg, 2.36 mmol) and bromoacetonitrile (164 µL, 2.36 mmol) are added in turn. The reaction vial is capped and placed in a heating block which is set atop of an orbital shaker. The heating block is set at 55° C. After 16 h, tlc analysis (silica, 1:1 EtOAc in heptanes) indicates that the starting material is completely consumed. Heating is terminated. After sitting at ambient temperature for 1 day, the contents of the flask are filtered through a pad of Celite. The filtrate is transferred to a reparatory funnel which contains EtOAc (40 mL). The layers are separated. The organic phase is washed with water (20 mL), saturated aqueous NaHCO$_3$ and brine (20 mL), and then dried over MgSO$_4$, filtered and concentrated by pumping to constant weight to give dark brown solid (0.42 g). This material is dissolved in 10 mL of DCM. This material is purified utilizing an ISCO Companion with a 25 g cartridge of silica. The gradient is 10% EtOAc in heptanes over 3 column volumes followed by a linear gradient to 50% EtOAc in heptanes over 10 column volumes. 17 mL fractions of eluent are collected. Fractions 4 through 6 are combined and evaporated in vacuo. This provides white solid (0.26 g, 58%).

Example 331

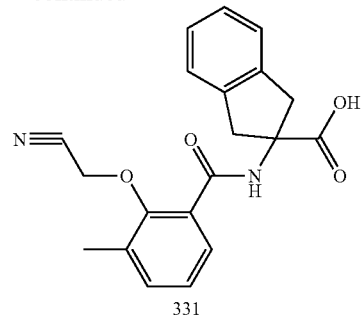

331

2-(2-Cyanomethoxy-3-methyl-benzoylamino)-indan-
2-carboxylic acid (331)

A 100 mL flask containing 2-(2-cyanomethoxy-3-methyl-benzoylamino)-indan-2-carboxylic acid ethyl ester (330, 0.25 g, 0.66 mmol) is charged with 1,4-dioxane (2 mL) and MeOH (2 mL). A stirring bar is added and stirring is initiated. After dissolution, water (1 mL) is added followed by the LiOH monohydrate (71 mg, 1.67 mmol). After 18 h, tlc analysis (silica, 5% MeOH/DCM) indicates that the starting material is completely consumed. The pH of the reaction mixture is carefully adjusted to pH 2 by slowly adding dilute aqueous HCl (3%, ~8 mL). The contents of the flask are poured into a separatory funnel which contains EtOAc (25 mL). The layers are separated. The aqueous layer is extracted with EtOAc (20 mL). The combined organic extracts are washed with water (20 mL) and brine (20 mL), and then dried over MgSO$_4$, filtered and concentrated by pumping to constant weight to give white solid (0.23 g, 99%).

$^1$H NMR (DMSO-d6, 300 MHz): δ 3.26-3.63 (m, 4H), 3.43 (s, 3H), 4.56 (s, 2H), 7.07 (dd, 1H), 7.14-7.23 (m, 5H), 7.29 (dd, 1H), 8.81 (s, 1H), 12.55 (bs, 1H).

LC/MS (ES+) m/z=351.14.

Example 332

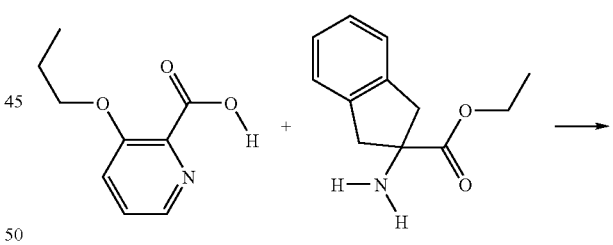

330 → 332

2-[(3-Propoxy-pyridine-2-carbonyl)-amino]-indan-2-carboxylic acid ethyl ester (332)

A 40 mL reaction vial which contains a stirring bar is charged with 3-n-propoxypicolinic acid (397 mg, 2.19 mmol) and dry DCM (6 mL). Stirring is initiated. After 2 min, the HTBU (831 mg, 2.195 mmol) is added. After 5 min, the 2-amino)-indane-2-carboxylic acid ethyl ester (450 mg, 2.19 mmol is added followed by DIPEA (0.96 mL, 5.48 mmol). The reaction is allowed to stir at ambient temperature. After 20 days, analysis by tlc of the reaction mixture (silica, 5% iPrOH/DCM) indicates complete consumption of the starting amine. The contents of the reaction flask are transferred to a separatory funnel and diluted with EtOAc (50 mL). This is washed consecutively with dilute aqueous HCl (3%, 25 mL), saturated aqueous NaHCO₃ (25 mL) and brine (25 mL), and dried over MgSO₄, filtered and evaporated in vacuo to give 1.23 g of light orange solid. This material is dissolved in 10 mL of DCM. This material is purified utilizing an ISCO Companion with a 40 g cartridge of silica. The gradient is 10% EtOAc in heptanes over 3 column volumes followed by a linear gradient to 60% EtOAc in heptanes over 10 column volumes. 17 mL fractions eluent are collected. Fractions 57 through 67 are combined and evaporated in vacuo by pumping to constant weight to give white solid (0.8 g, 99%).

Example 333

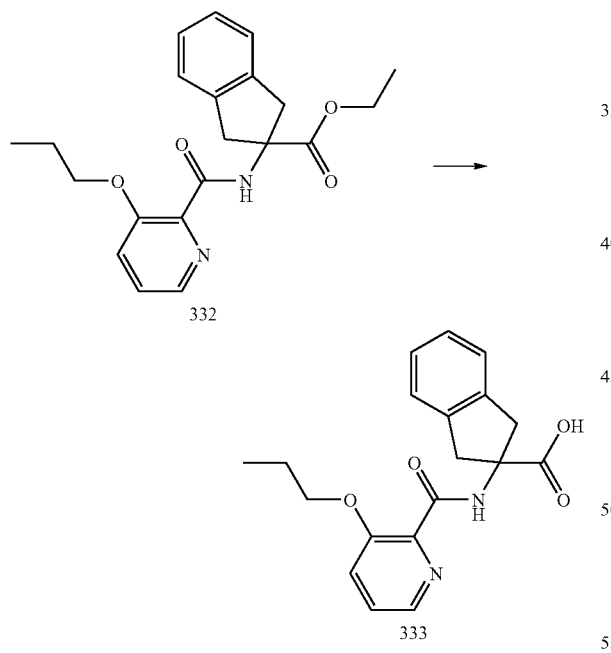

2-[(3-Propoxy-pyridine-2-carbonyl)-amino]-indan-2-carboxylic acid (333)

A 100 mL round bottom flask which contains 2-[(3-propoxy-pyridine-2-carbonyl)-amino]-indan-2-carboxylic acid ethyl ester (332, 620 mg, 1.68 mmol) is charged with 1,4-dioxane (6 mL) and MeOH (6 mL). A stirring bar is added and stirring is initiated. After dissolution, water (3 mL) is added followed by the LiOH monohydrate (178 mg, 4.25 mmol). After 22 h, tlc analysis (silica, 50% EtOAc/heptanes) indicates that the starting material is completely consumed. Amberlyst highly acidic exchange resin (0.5 g) is added to the reaction flask. The reaction is capped and allowed to stir at ambient temperature. After 125 h, the contents of the flask are filtered through a pad of Celite. The solvent is removed from the filtrate. The residue is reconstituted with iPrOH/toluene (20+10 mL) and the solvent is removed. This process is repeated 1 time. Pumping to constant weight provides 0.58 g of white solid.

¹H NMR (DMSO-d6, 300 MHz): δ 0.76 (t, 3H), 1.71 (dt, 2H), 3.17-3.53 (m, 4H), 3.98 (t, 2H), 7.03-7.12 (m, 4H), 7.43 (dd, 1H), 7.55 (dd, 1H), 7.43 (dd, 1H), 8.12 (dd, 1H), 8.86 (s, 1H).

LC/MS (ES+) m/z=341.14

Example 334

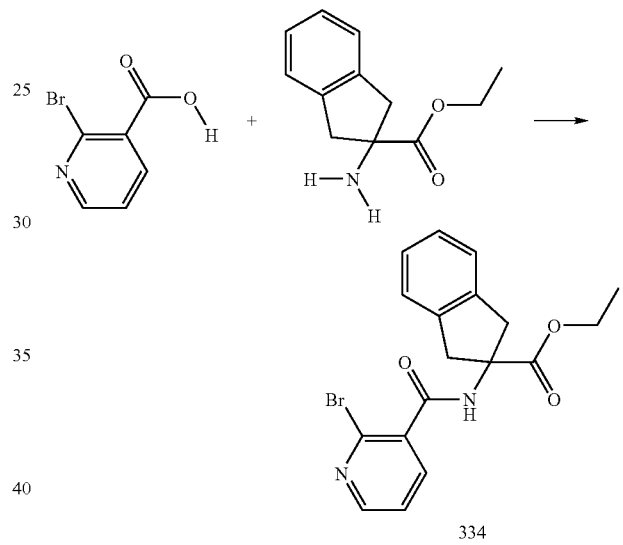

2-[(2-Bromo-pyridinyl-3-carbonyl)-amino]-indan-2-carboxylic acid ethyl ester (334)

A 40 mL reaction vial which contains a stirring bar is charged with 2-bromonicotinic acid (1.18 g, 5.85 mmol) and dry DCM (15 mL). Stirring is initiated. After 2 min, the HTBU (2.22 g, 5.85 mmol) is added. After 5 min, 2-Amino-indan-2-carboxylic acid ethyl ester (1.2 g, 5.25 mmol is added followed by DIPEA (2.55 mL, 14.62 mmol). The reaction is allowed to stir for 32 days. Analysis by tlc of the reaction mixture (silica, 5% iPrOH/DCM) indicates complete consumption of the starting amine. The contents of the reaction flask are transferred to a reparatory funnel and diluted with EtOAc (50 mL). This is washed consecutively with water (3%, 25 mL), saturated aqueous NaHCO₃ (2×25 mL) and brine (25 mL), and then dried over MgSO₄, filtered and evaporated in vacuo to provide 3.1 g of light orange solid. This material is dissolved in 15 mL of DCM. This material is purified utilizing an ISCO Companion with a 40 g cartridge of silica. The gradient is 5% EtOAc in heptanes for 4 column volumes followed by a linear gradient to 60% EtOAc in heptanes over 10 column volumes. 17 mL fractions of eluent are collected. Fractions 30 through 43 are combined and evaporated in vacuo to yield white solid, (1.62 g, 72%).

Example 335

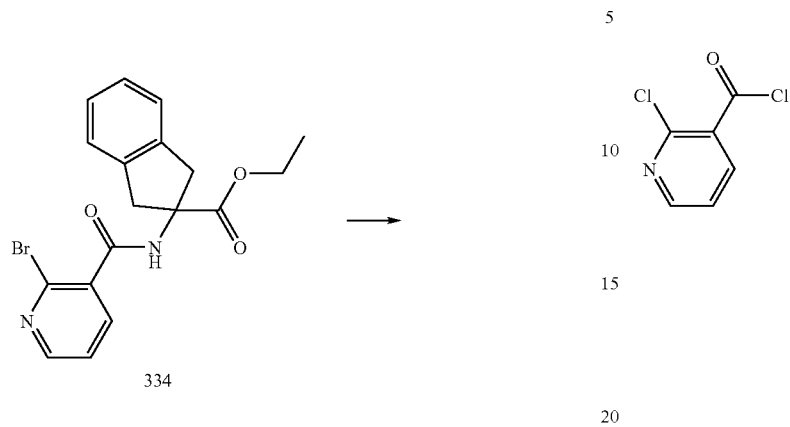

334

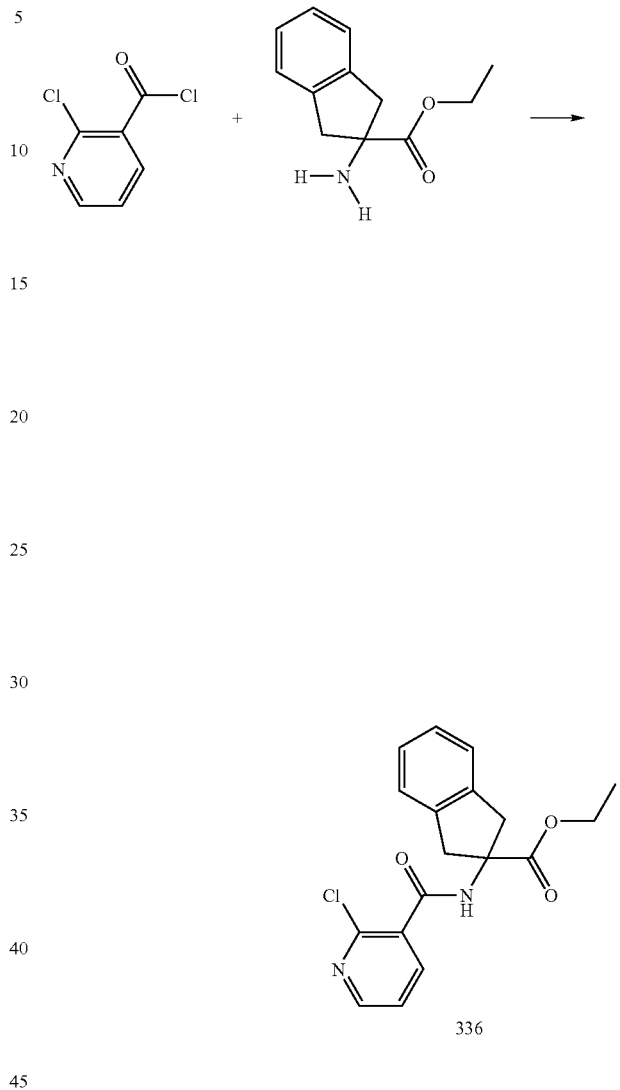

Example 336

336

2-[(2-Bromo-pyridinyl-3-carbonyl)-amino]-indan-2-carboxylic acid (335)

A 50 mL round bottom flask which contains 2-[(2-bromo-pyridine-3-carbonyl)-amino]-indan-2-carboxylic acid ethyl ester (335, 356 mg, 0.92 mmol) is charged with 1,4-dioxane (4 mL) and MeOH (4 mL). A stirring bar is added and stirring is initiated. After dissolution, water (1.5 mL) is added followed by the LiOH (97 mg, 2.3 μmol). After 18 h, tlc analysis (silica, 50% EtOAc/heptanes) indicates that the starting material is completely consumed. Amberlyst highly acidic exchange resin (0.5 g) is added to the reaction vial. The reaction is capped and allowed to stir at ambient temperature. After 6 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides white solid (0.32 g, 97%).

$^1$H NMR (DMSO-d6, 300 MHz): δ 3.23-3.53 (m, 4H), 7.03-7.18 (m, 4H), 7.49 (dd, 1H), 7.86 (dd, 1H), 8.40-8.51 (m, 2H).

LC/MS (ES+) m/z=361.02.

2-[(2-Chloro-pyridine-3-carbonyl)-amino]-indan-2-carboxylic acid ethyl ester (336)

A 100 mL round bottom flask is charged with 2-amino-indan-2-carboxylic acid (1.5 g, 7.31 mmol) and dry DCM (15 mL). A stirring bar is added and stirring is initiated. DIPEA (2 mL, 11.69 mmol) is added. 2-[chloronicotinoyl chloride (1.54 g, 8.77 mmol) and DMAP (8 mg, cat.) are added. The reaction is capped. After 2 days, tlc analysis (silica, 10% iPrOH/DCM) indicates that the starting is completely consumed. The contents of the reaction flask are transferred to a separatory funnel and diluted with EtOAc (60 mL). This is washed with water (2×25 mL), saturated aqueous NaHCO$_3$ (2×25 mL), and brine (25 mL), and then dried over MgSO$_4$, filtered and evaporated by pumping to constant weight to give 2.15 g of off-white solid. This is dissolved with DCM (20 mL) and applied to a silica column ((80 g) on an ISCO Companion. The column is eluted with 10% EtOAc in heptanes for 3 column volumes followed by a linear gradient to 75% EtOAc in heptanes over 12 column volumes. 17 mL fractions of UV

267 positive eluent are collected. Fractions 14-20 are combined and evaporated by pumping to constant weight to give light yellow solid (2 g, 79%).

Example 337

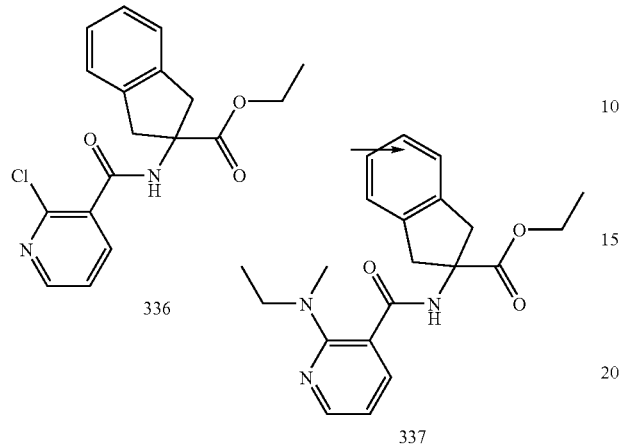

2-{[2-(Ethyl-methyl-amino)-pyridine-3-carbonyl]-amino}-indan-2-carboxylic acid ethyl ester (337)

A 25 mL microwave reaction vessel is charged with 2-[2-(chloro-pyridine-3-carbonyl)-amino]-indan-2-carboxylic acid ethyl ester (336, 400 mg, 1.16 mmol) and dry 1,4-dioxane (4 mL). A stirring bar is added and stirring is initiated. After 30 seconds DIPEA (2.1 mL, 11.6 mmol) and N-methylisopropylamine (1.2 mL, 11.6, mmole) are added. The reaction vessel is sealed with a crimped cap. The reaction vessel is placed in an oil bath that is heated to 80° C. After 6 days, TLC analysis silica, 2:1 EtOAc:heptanes) indicates that the starting material had been consumed as visualized by UV. The contents of the reaction flask are transferred to a round bottom flask and the solvent removed in vacuo by pumping to constant weight to give 0.78 g of viscous yellow oil. The material is dissolved in DCM (10 mL) and applied to an ISCO chromatography column (silica, 40 g). A gradient of 5% EtOAc in heptanes is applied for 3 column volumes followed by a linear ramp to 60% EtOAc in heptanes over 12 column volumes. 14 mL fractions of UV active eluent are collected. Fractions 4 to 13 are combined and evaporated by pumping to constant weight to give off-white solid (0.41 g, 93%).

Example 338

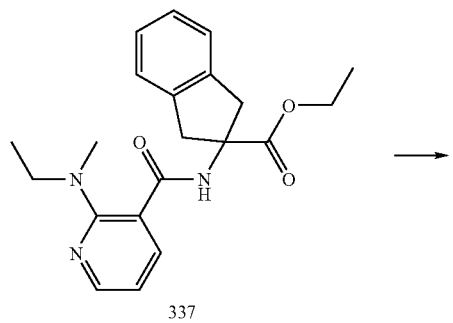

268

-continued

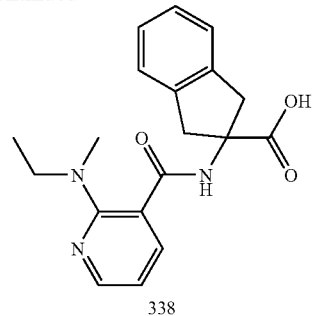

2-{[2-(Ethyl-methyl-amino)-pyridine-3-carbonyl]-amino}-indan-2-carboxylic acid (338)

A 100 mL round bottom flask which contains 2-{[2-(Ethyl-methyl-amino)-pyridine-3-carbonyl]-amino}-indan-2-carboxylic acid ethyl ester (337, 650 mg, 1.77 mmol) is charged with 1,4-dioxane (10 mL) and MeOH (10 mL). A stirring bar is added and stirring is initiated. After dissolution, water (5 mL) is added followed by the LiOH monohydrate (187 mg, 4.46 mmol). After 18 h, tlc analysis (silica, 50% EtOAc/heptanes) indicates that the starting material is completely consumed. Amberlyst highly acidic exchange resin (1 g) is added to the reaction vial. The reaction is capped and allowed to stir at ambient temperature. After 18 h, the contents of the flask are filtered through a pad of celite. The solvent is removed from the filtrate. The residue is reconstituted with iPrOH/toluene (20+20 mL) and the solvent is removed under reduced pressure. This process is repeated 1 time. Pumping to constant weight gives beige solid (0.58 g, 97%).

$^1$H NMR (DMSO-d6, 300 MHz): δ 1.07 (t, 3H), 3.18-3.48 (m, 4H), 3.37 (q, 2H), 6.75 (dd, 1H), 7.03-7.13 (m, 4H), 7.63 (dd, 1H), 8.15 (dd, 1H), 8.77 (s, 1H).

LC/MS (ES+) m/z=340.17.

Example 339

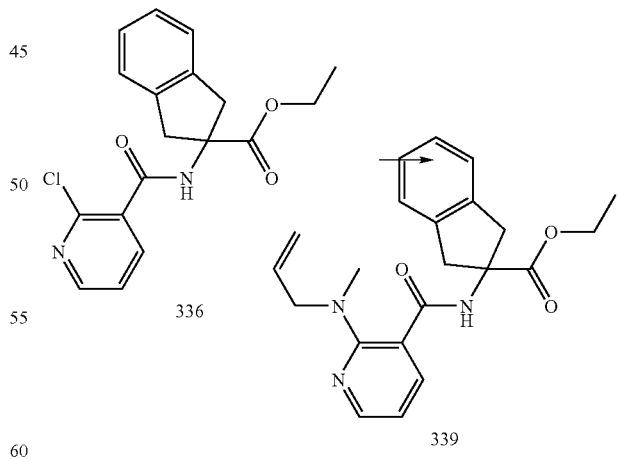

2-{[2-(Allylmethyl-amino)-pyridine-3-carbonyl]-amino}-indan-2-carboxylic acid ethyl ester (339)

A 25 mL microwave reaction vessel is charged with 2-[2-(chloro-pyridine-3-carbonyl)-amino]-indan-2-carboxylic acid ethyl ester (336, 400 mg, 1.16 mmol) and dry 1,4-dioxane (4 mL). A stirring bar is added and stirring is initiated. After 30 seconds DIPEA (2.1 mL, 11.6 mmol) and N-allylmethylamine (1.1 mL, 11.6, mmole) are added. The reaction vessel is sealed with a crimped cap. The reaction vessel is placed in an oil bath that is heated to 80° C. After 21 days, tlc analysis silica, (2:1 EtOAc:heptanes) indicates that the starting material is consumed as visualized by UV. The contents of the reaction flask are transferred to a round bottom flask and the solvent removed in vacuo by pumping to constant weight to give 0.85 mg of dark brown material. The material is dissolved in DCM and applied to an ISCO chromatography column (Silica, 25 g). A gradient of 5% EtOAc in heptanes is applied for 3 column volumes followed by a linear ramp to 60% EtOAc in heptanes over 12 column volumes. 14 mL fractions of UV active eluent are collected. Fractions 2 to 8 are combined and evaporated by pumping to constant weight give off-white solid (0.43 g, 98).

Example 340

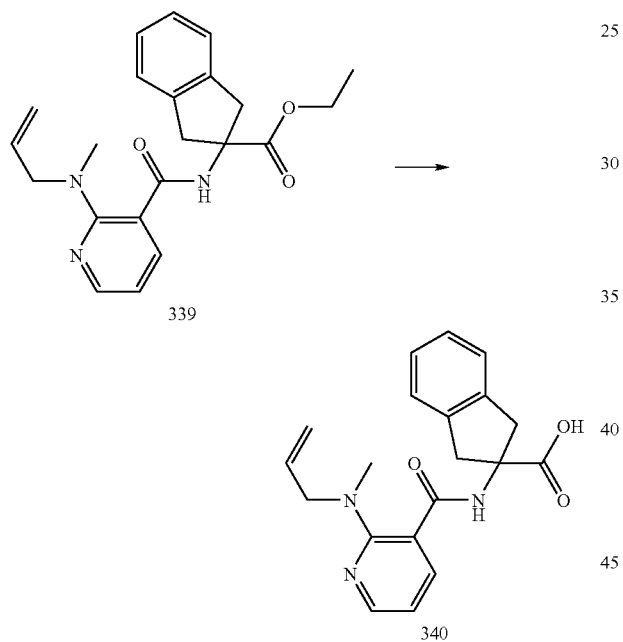

2-{[2-(Allyl-methyl-amino)-pyridine-3-carbonyl]-amino}-indan-2-carboxylic acid (340)

A 100 mL round bottom flask which contains 2-{[2-(allyl-methyl-amino)-pyridine-3-carbonyl]-amino}-indan-2-carboxylic acid ethyl ester (339, 280 mg, 0.74 mmol) is charged with 1,4-dioxane (2 mL) and MeOH (2 mL). A stirring bar is added and stirring is initiated. After dissolution, water (1 mL) is added followed by the LiOH monohydrate (78 mg, 1.86 mmol). After 38 h, tlc analysis (silica, 50% EtOAc/heptanes) indicates that the starting material is completely consumed. Amberlyst highly acidic exchange resin (0.5 g) is added to the reaction vial. The reaction is capped and allowed to stir at ambient temperature. After 15 days, the contents of the flask are filtered through a pad of Celite. The solvent is removed from the filtrate. The residue is reconstituted with iPrOH/ toluene (20+20 mL) and the solvent is removed. This process is repeated 1 time. Pumping to constant weight provides white solid (0.26 g, 100%).

$^1$H NMR (DMSO-d6, 300 MHz): δ 2.82 (s, 3H) 3.18-3.48 (m, 4H), 3.92 (dd, 2H), 5.04-5.22 (m, 2H), 5.86-6.02 (m, 1H), 6.79 (dd, 1H), 7.04-7.11 (m, 4H), 7.67 (dd, 1H), 8.16 (dd, 1H), 8.77 (s, 1H).

LC/MS (ES+) m/z=352.20.

Example 341

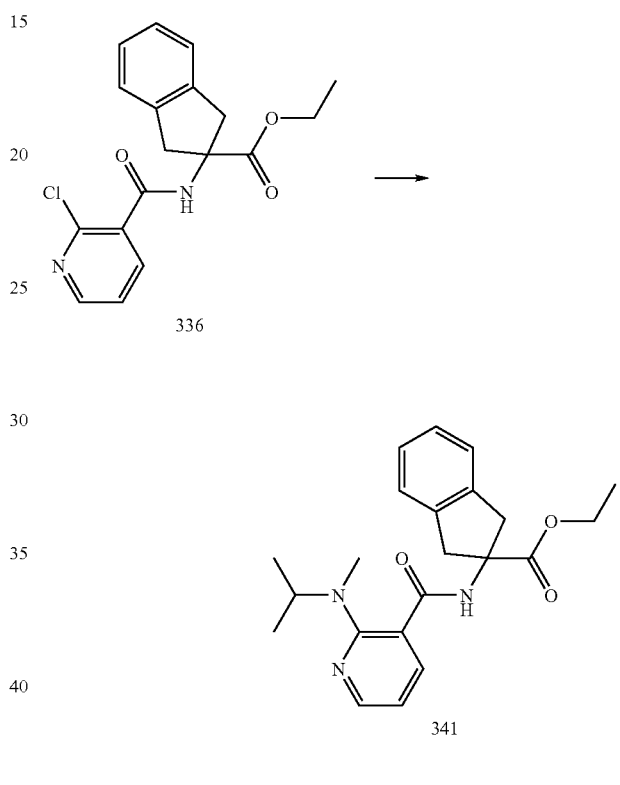

2-{[2-(Isopropyl-methyl-amino)-pyridine-3-carbonyl]-amino}-indan-2-carboxylic acid ethyl ester (341)

A 25 mL microwave reaction vessel is charged with 2-[2-(chloro-pyridine-3-carbonyl]-amino]-indan-2-carboxylic acid ethyl ester (341, 400 mg, 1.16 mmol) and dry 1,4-dioxane (4 mL). A stirring bar is added and stirring is initiated. After 30 sec DIPEA (2.1 mL, 11.6 mmol) and N-methylethylamine (1.2 mL, 11.6, mmole) are added. The reaction vessel is sealed with a crimped cap. The reaction vessel is placed in a oil bath which is heated to 80° C. After 6 days, TLC analysis silica, 2:1 EtOAc:heptanes) indicates that the starting material had been consumed as visualized by UV. The contents of the reaction flask are transferred to a round bottom flask and the solvent removed in vacuo by pumping to constant weight provides 0.78 g of viscous yellow oil. The material is dissolved in DCM and applied to an ISCO chromatography column (Silica, 40 g). A gradient of 5% EtOAc in heptanes is applied for 3 column volumes followed by a linear ramp to 60% EtOAc in heptanes over 12 column volumes. 14 mL fractions of UV active eluent are collected. Fractions 4 to 13

Example 342

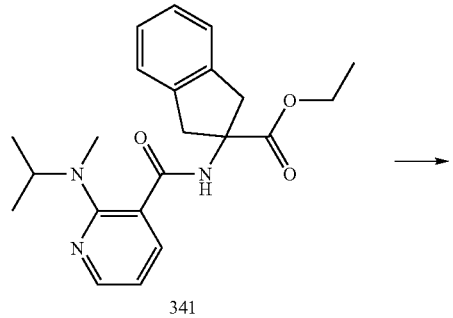

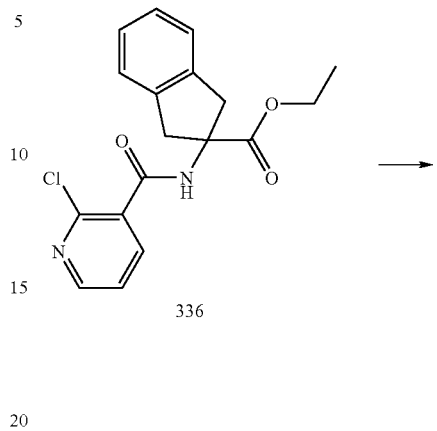

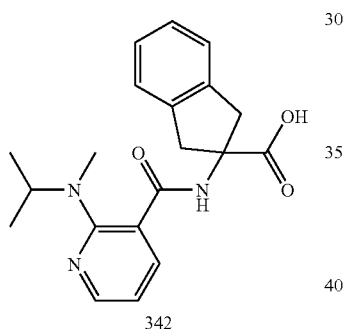

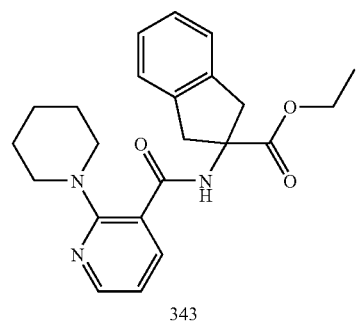

2-{[2-(Isopropyl-methyl-amino)-pyridine-3-carbonyl]-amino}-indan-2-carboxylic acid (342)

A 100 mL round bottom flask which contains 2-{[2-(isopropyl-methyl-amino)-pyridine-3-carbonyl]-amino}-indan-2-carboxylic acid ethyl ester (341, 220 mg, 0.58 mmol) is charged with 1,4-dioxane (2 mL) and MeOH (2 mL). A stirring bar is added and stirring is initiated. After dissolution, water (1 mL) is added followed by the LiOH monohydrate (61 mg, 1.46 mmol). After 16 h, tlc analysis (silica, 50% EtOAc/heptanes) indicates that the starting material is completely consumed. Amberlyst highly acidic exchange resin (0.5 g) is added to the reaction vial. The reaction is capped and allowed to stir at ambient temperature. After 4 days, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides white solid (0.2 g, 98%).
$^1$H NMR (DMSO-d6, 300 MHz): δ 1.15 (d, 6H), 2.48 (s, 3H), 3.18-3.42 (m, 4H), 4.18 (septet, 1H), 6.78 (dd, 1H), 7.05-7.12 (m, 4H), 7.67 (dd, 1H), 8.16 (dd, 1H), 8.81 (s, 1H).
LC/MS (ES+) m/z=354.17 are combined and evaporated by pumping to constant weight yield 0.41 g of off-white solid.

Example 343

2-[(3,4,5,6-Tetrahydro-2H-[1,2']bipyridinyl-3'-carbonyl)-amino]-indan-2-carboxylic acid ethyl ester (343)

25 mL microwave reaction vessel is charged with 2-[2-(chloro-pyridine-3-carbonyl)-amino]-indan-2-carboxylic Acid Ethyl Ester (336, 400 mg, 1.16 mmol) and dry 1,4-dioxane (4 mL). A stirring bar is added and stirring is initiated. After 30 seconds DIPEA (2.1 mL, 11.6 mmol) and N-methylisopropylamine (1.2 mL, 11.6, mmole) are added. The reaction vessel is sealed with a crimped cap. The reaction vessel is placed in an oil bath that is heated to 80° C. After 6 days, TLC analysis silica, 2:1 EtOAc:heptanes) indicates that the starting material is consumed as visualized by UV. The contents of the reaction flask are transferred to a round bottom flask and the solvent removed in vacuo by pumping to constant weight provides 0.78 g of viscous yellow oil. The material is dissolved in DCM and applied to an ISCO chromatography column (Silica, 40 g). A gradient of 5% EtOAc in heptanes is applied for 3 column volumes followed by a linear ramp to 60% EtOAc in heptanes over 12 column volumes. 14 mL fractions of UV active eluent are collected. Fractions 4 to

Example 344

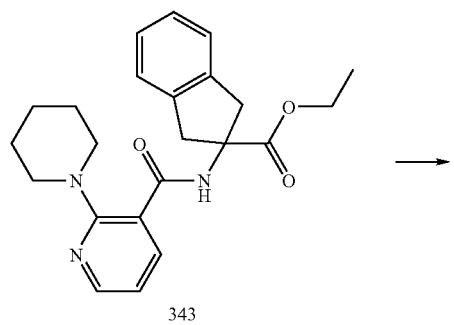

343

↓

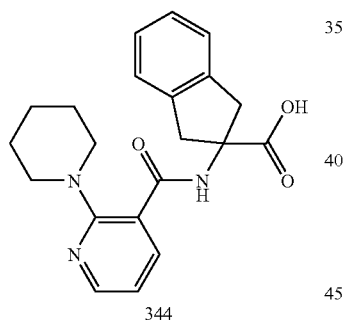

344

2-[(3,4,5,6-Tetrahydro-2H-[1,2']bipyridinyl-3'-carbonyl)-amino]-indan-2-carboxylic acid (344)

A 100 mL round bottom flask which contains 2-[(3,4,5,6-Tetrahydro-2H-[1,2']bipyridinyl-3'-carbonyl)-amino]-indan-2-carboxylic acid ethyl ester (343, 330 mg, 0.84 mmol) is charged with 1,4-dioxane (4 mL) and MeOH (4 mL). A stirring bar is added and stirring is initiated. After dissolution, water (1.5 mL) is added followed by the LiOH monohydrate (89 mg, 2.12 mmol). After 62 h, tlc analysis (silica, 50% EtOAc/heptanes) indicates that the starting material is completely consumed. Amberlyst highly acidic exchange resin (0.5 g) is added to the reaction flask. The reaction is capped and allowed to stir at ambient temperature. After 38 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides 0.3 g of a white solid.

13 are combined and evaporated by pumping to constant weight give off-white solid (0.41 g, 90%).

¹H NMR (DMSO-d6, 300 MHz): δ 1.52 (m, 2H), 1.76 (m, 4H), 3.13 (m, 4H), 3.18-3.43 (m, 4H), 3.92 (dd, 2H), 6.94 (dd, 1H), 7.05-7.12 (m, 4H), 7.81 (dd, 1H), 8.24 (dd, 1H), 9.35 (s, 1H).

LC/MS (ES+) m/z=366.17.

Example 345

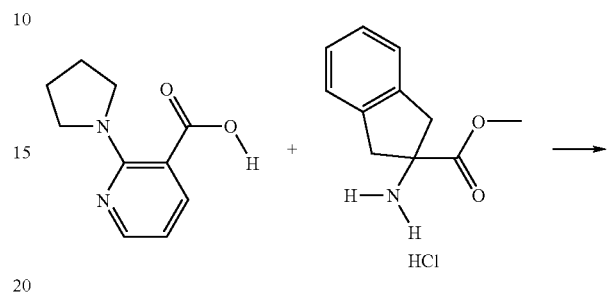

↓

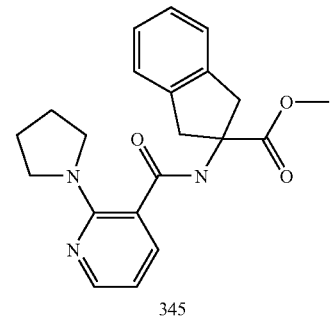

345

2-[(2-Pyrrolidin-1-yl-3-carbonyl)-amino]-indan-2-carboxylic acid methyl ester (345)

A 40 mL reaction vial which contains a stirring bar is charged with 2-(1-pyrrolidinyl)-nicotinic acid (422 mg, 2.2 mmol) and dry DCM (6 mL). Stirring is initiated. After 2 min, the HTBU (833 mg, 2.2 mmol) is added. After 5 min, 2-amino-indan-2-carboxylic acid methyl ester HCl salt. (0.5 g, 2.2 mmol) is added followed by DIPEA (1.17 mL, 6.7 mmol). The reaction vial is capped and allowed to stir at ambient temperature. After 18 h, analysis by tlc of the reaction mixture (silica, 5% iPrOH/DCM) indicates complete consumption of the starting amine. The contents of the reaction flask are transferred to a separatory funnel and diluted with EtOAc (50 mL). This is washed consecutively with water (3%, 25 mL), saturated aqueous NaHCO₃ (2×25 mL) and brine (25 mL), and then dried over MgSO₄, filtered and evaporated in vacuo to provide 1.05 g of light yellow solid. This material is dissolved in 10 mL of DCM. This material is purified utilizing an ISCO Companion with a 24 g cartridge of silica. The gradient is 5% EtOAc in heptanes for 4 column volumes followed by a linear gradient to 60% EtOAc in heptanes over 10 column volumes. 14 mL fractions of UV active eluant are collected. Fractions 6 through 12 are combined and evaporated in vacuo to give white solid (0.73 g, 91%).

Example 346

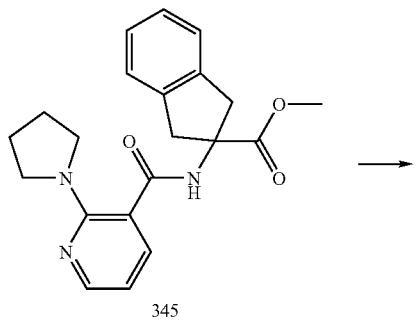

345

2-[(2-Pyrrolidin-1-yl-3-carbonyl)-amino]-indan-2-carboxylic acid methyl ester (345, 440 mg, 1.20 mmol) is charged with 1,4-dioxane (5 mL) and MeOH (5 mL). A stirring bar is added and stirring is initiated. After dissolution, water (2.5 mL) is added followed by the LiOH monohydrate (128 mg, 3.05 mmol). After 30 h, tlc analysis (silica, 50% EtOAc/heptanes) indicates that the starting material is completely consumed. Amberlyst highly acidic exchange resin (0.5 g) is added to the reaction flask. The reaction is capped and allowed to stir at ambient temperature. After 18 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides 0.38 g of white solid.

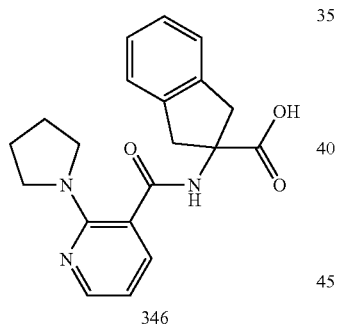

346

2-[(2-Pyrrolidin-1-yl-3-carbonyl)-amino]-indan-2-carboxylic acid (346)

¹H NMR (DMSO-d6, 300 MHz): δ 1.82 (m, 4H), 3.21-3.48 (m, 8H), 3.92 (dd, 2H), 6.59 (dd, 1H), 7.04-7.11 (m, 4H), 7.46 (dd, 1H), 8.08 (dd, 1H), 8.22 (bs, 1H).
LC/MS (ES+) m/z=352.14.

Example 347

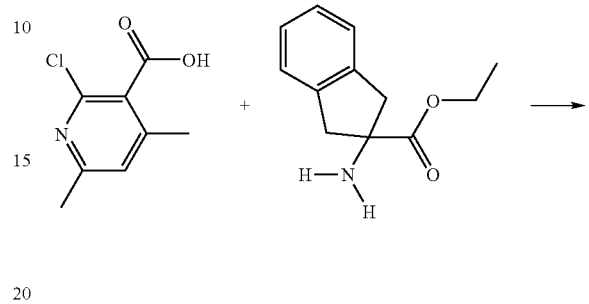

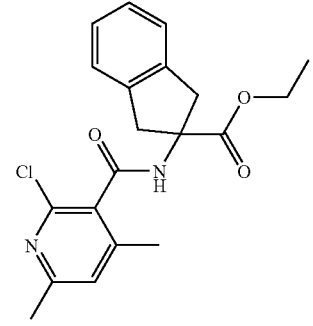

347

2-[(2-Chloro-4,6-dimethyl-pyridine-3-carbonyl)-amino]-indan-2-carboxylic acid ethyl ester (347)

A 40 mL vial is charged with 2-chloro-4,6-dimethylnicotinic acid (497 mg, 2.68 mmol) and dry DCM (9 mL). A stirring bar is added and stirring is initiated. After 2 min, the HTBU (1.02 g, 2.68 mmol) is added. After 5 min, 2-amino-indane-2-carboxylic acid ethyl ester. (550 mg, 2.68 mmol) is added followed by DIPEA (1.2 mL, 6.74 mmol). The reaction is allowed to stir for 14 days. Analysis by tlc of the reaction mixture (silica, 15% iPrOH/DCM) indicates complete consumption of the starting amine. The contents of the reaction flask are transferred to a reparatory funnel and diluted with EtOAc (70 mL). This is washed dilute aqueous HCl (3%, 2×30 mL), saturated aqueous NaHCO₃ (2×30 mL) and brine (30 mL), and then dried over MgSO₄, filtered and evaporated in vacuo to provide 1.6 g of yellow foam. This material is dissolved in 15 mL of DCM. This material is purified utilizing an ISCO Companion with a 40 g cartridge of silica. The gradient is 10% EtOAC in heptanes over 4 column volumes followed by a linear gradient to 50% EtOAc over 10 column volumes. 27 mL fractions of UV active elutant are collected.

Fractions 32 through 40 are combined and evaporated in vacuo to give yellow semi-solid material. (0.67 g, 67%).

Example 348

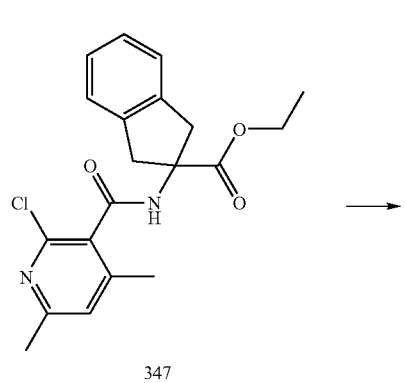

347

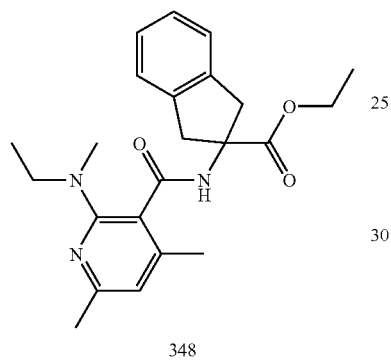

348

2-{[2-(Ethyl-methyl-amino)-4,6-dimethyl-pyridine-3-carbonyl]-amino}-indan-2-carboxylic acid ethyl ester (348)

A 25 mL microwave reaction vessel is charged with 2-[2-(chloro-4,6-dimethyl-pyridine-3-carbonyl]-amino]-indan-2-carboxylic acid ethyl ester (347, 480 mg, 1.29 mmol) and dry 1,4-dioxane (4 mL). A stirring bar is added and stirring is initiated. After 30 seconds, N-ethylmethylamine (2 mL, 23.28 mmole) is added. The reaction vessel is sealed with a crimped cap. The reaction vessel is placed in a Smith Optimizer microwave apparatus. The pre-stir is set at 20 sec followed by heating to 100° C. Hold time is set to 18 min. TLC analysis silica, 2:1 EtOAc:heptanes) indicates that a new Spot appears with a higher $R_f$ value as visualized by UV. Starting material is still present. N-Ethylmethylamine (506 µL, 5.89, mmole) is added. The reaction vessel is sealed with a crimped cap. The reaction vial is immersed in an oil bath that is heated at 80° C. After 5 days, tlc analysis silica, 2:1 EtOAc:heptanes) indicates that the starting material had been converted to a higher moving spot as visualized by UV. The contents of the reaction flask are transferred to a round bottom flask and the solvent removed in vacuo by pumping to constant weight provides 1.3 g of viscous yellow oil. The material is dissolved in DCM (10 mL) and applied to an ISCO Chromatography Column (Silica, 40 g). A gradient of 5% EtOAc in heptanes is applied for 3 column volumes followed by a linear ramp to 60% EtOAc in heptanes over 12 Column Volumes. 14 mL fractions of UV active eluent are collected. Fractions 4 to 9 are combined and evaporated by pumping to constant weight to give white solid (0.41 g, 83%).

Example 349

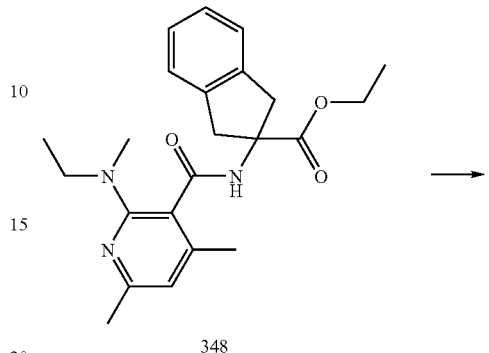

348

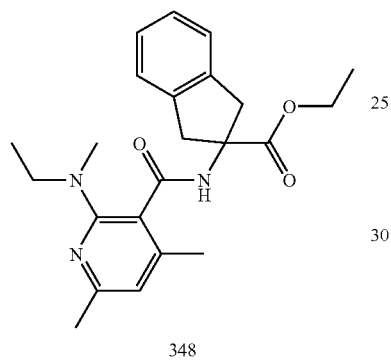

349

2-{[2-(Ethyl-methyl-amino)-4,6-dimethyl-pyridine-3-carbonyl]-amino}-indan-2-carboxylic acid (349)

A 100 mL round bottom flask which contains 2-{[2-(ethyl-methyl-amino)-4,6-dimethyl-pyridine-3-carbonyl]-amino}-indan-2-carboxylic acid ethyl ester (348, 260 mg, 0.66 mmol) is charged with 1,4-dioxane (3 mL) and MeOH (3 mL). A stirring bar is added and stirring is initiated. After dissolution, water (1.5 mL) is added followed by the LiOH monohydrate (70 mg, 1.66 mmol). After 18 h, tlc analysis (silica, 50% EtOAc/heptanes) indicates that the starting material is completely consumed. Amberlyst highly acidic exchange resin (0.5 g) is added to the reaction vial. The reaction is capped and allowed to stir at ambient temperature. After 38 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides white solid (0.18 g, 75%).

$^1$H NMR (DMSO-d6, 300 MHz): δ 1.03 (t, 3H), 3.17-3.53 (m, 6H), 6.41 (s, 1H), 7.05-7.12 (m, 4H), 8.05 (s, 1H).

LC/MS (ES+) m/z=368.25.

Example 350

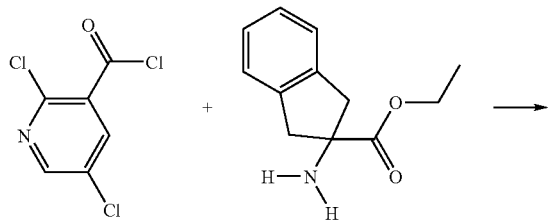

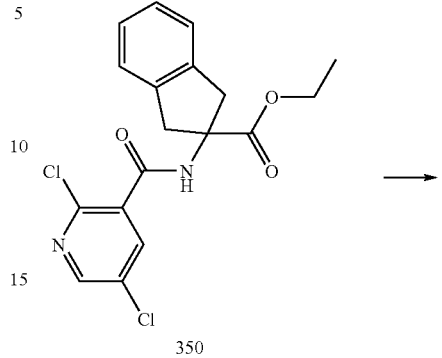

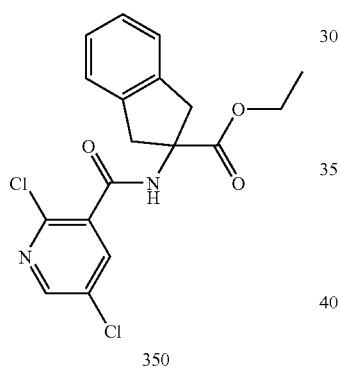

2-[(2,5-Dichloro-pyridine-3-carbonyl)-amino]-indan-2-carboxylic acid ethyl ester (350)

A 30 mL reaction vial is charged with 2-aminoindan-2-carboxylic acid ethyl ester (1 g, 4.87 mmol) and dry DCM (5 mL). A stirring bar is added and stirring is initiated. DIPEA (1.35 mL, 7.8 mmol) is added. 2,5-dichloro-pyridine-3-carbonyl chloride (1.23 g, 5.85 mmol) and DMAP (8 mg, cat.) are added. The reaction is capped. After 57 days, tlc analysis (silica, 10% iPrOH/DCM) indicates that the starting has been completely consumed. The contents of the reaction flask are transferred to a separatory funnel and diluted with EtOAc (60 mL). This is washed with water (2×25 mL), saturated aqueous NaHCO$_3$ (2×25 mL), and brine (25 mL), and then dried over MgSO$_4$, filtered and evaporated by pumping to constant weight yields 1.99 g of off-white solid. This is diluted with DCM (20 mL) and applied to a silica column ((80 g) on an ISCO Companion. The column is eluted with 5% EtOAc in heptanes for 3 column volumes followed by a linear gradient to 75% EtOAc in heptanes over 12 column volumes. 17 mL fractions of UV positive eluent are collected. Fraction 12-16 are combined and evaporated by pumping to constant weight to give light yellow solid (1.39 g, 75%).

Example 351

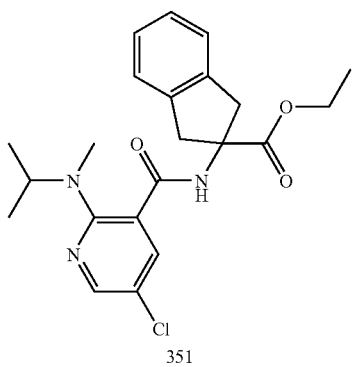

2-{[5-Chloro-2-(isopropyl-methyl-amino)-pyridine-3-carbonyl)-amino]-indan-2-carboxylic acid ethyl ester (351)

A 40 mL reaction vial is charged with 2-[2-(chloro-pyridine-3-carbonyl-amino]-indan-2-carboxylic acid ethyl ester 350, 400 mg, 1.16 mmol) and dry 1,4-dioxane (4 mL). A stirring bar is added and stirring is initiated. After 30 sec DIPEA (2.1 mL, 11.6 mmol) and N-methylisopropylamine (1.2 mL, 11.6, mmole) are added. The reaction vial is tightly sealed with Teflon coated cap. The reaction vessel is placed in an oil bath that is heated to 80° C. After 7 days, TLC analysis silica, 2:1 EtOAc:heptanes) indicates that the starting material had been consumed as visualized by UV. The contents of the reaction flask are transferred to a round bottom flask and the solvent removed in vacuo by pumping to constant weight provides 0.84 g of viscous yellow oil. The material is dissolved in DCM and applied to an ISCO chromatography column (silica, 40 g). A gradient of 5% EtOAc in heptanes is applied for 3 column volumes followed by a linear ramp to 60% EtOAc in heptanes over 12 column volumes. 14 mL fractions of UV active eluent are collected. Fractions 2 to 5

Example 352

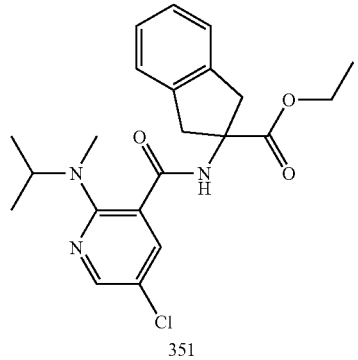

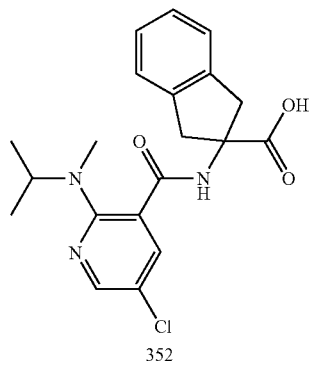

2-{[5-Chloro-2-(isopropyl-methyl-amino)-pyridine-3-carbonyl)-amino]-indan-2-carboxylic acid (352)

A 100 mL round bottom flask which contains 2-{[5-chloro-2-(isopropyl-methyl-amino)-pyridine-3-carbonyl)-amino]-indan-2-carboxylic acid ethyl ester (351, 270 mg, 0.58 mmol) is charged with 1,4-dioxane (3 mL) and MeOH (3 mL). A stirring bar is added and stirring is initiated. After dissolution, water (1.5 mL) is added followed by the LiOH (62 mg, 1.48 mmol). After 18 h, tlc analysis (silica, 50% EtOAc/heptanes) indicates that the starting material is completely consumed. Amberlyst highly acidic exchange resin (0.5 g) is added to the reaction vial. The reaction is capped and allowed to stir at ambient temperature. After 20 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides white solid (0.21 g, 94%).

$^1$H NMR (DMSO-d6, 300 MHz): δ 1.09 (t, 3H), 2.71 (s, 3H), 3.22-3.48 (m, 4H), 4.18 (septet, 1H), 7.04-7.11 (m, 4H), 7.65 (s, 1H), 8.17 (s, 1H), 8.48 (s, 1H), 8.72 (bs, 1H).

LC/MS (ES+) m/z=390.10.

Example 353

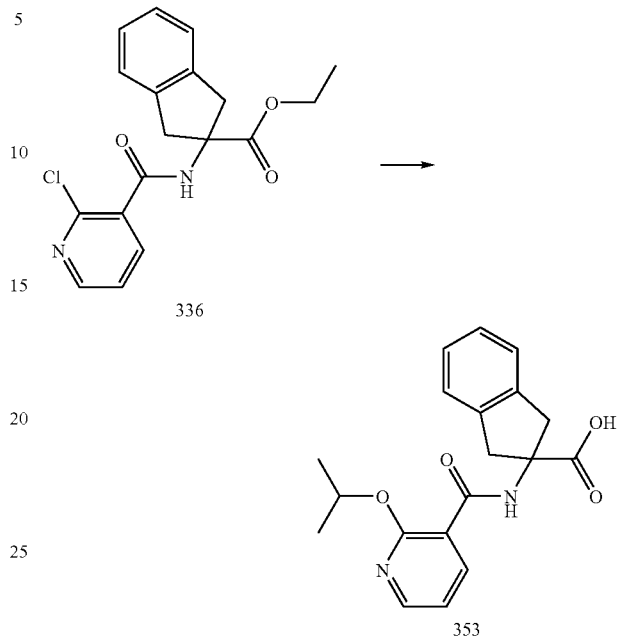

2-[2-(Isopropoxy-pyridine-3-carbonyl)-amino]-indan-2-carboxylic acid (353)

A 10 mL microwave reaction vial is charged with iPrOH (4 mL, 51.9 mmol). A stirring bar is added and stirring is initiated. A suspension of NaH in oil (104 mg, 2.61 mmol) is added. After 2 min, 2-[(2-Chloro-pyridine-3-carbonyl)-amino]-indan-2-carboxylic acid ethyl ester (336, 450 mg, 1.3 μmol) is added. The reaction flask is loosely capped and allowed to stir at ambient temperature. After 7 days, tlc analysis (silica, 2:1, EtOAc/heptanes) indicates that the starting material is consumed. Dowex Highly Acidic Ion Exchange Resin (0.5 g) is added to the reaction flask. The flask is allowed to stir at ambient temperature. After 1 week, the reaction mixture is diluted with iPrOH (20 mL) and filtered through a pad of Celite. The filtrate is transferred to a round bottom flask and evaporated under reduced pressure. The residue is reconstituted with iPrOH (10 mL) and toluene (10 mL). The solvent is removed under reduced pressure. The reconstitution and evaporation steps are repeated. Pumping to constant weight yields amorphous white solid (0.40 g). This material is dissolved in DCM (5 mL). This solution is applied to an ISCO Companion that is fitted with a 12 g column (silica). The column is eluted with 5% ACN/DCM for 5 column volumes followed by a linear gradient to 90% ACN/DCM over 10 Column Volumes. 14 mL fractions of UV active eluent are collected. Fractions 6-9 are combined and evaporated by pumping to constant weight give white solid (0.1 g, 12%).

$^1$H NMR (DMSO-d6, 300 MHz): δ 1.21 (d, 6H), 3.23-3.58 (m, 4H), 5.33 (septet, 1H), 7.13 (dd, 1H), 7.20-7.26 (m, 4H), 8.17 (dd, 1H), 8.29 (dd, 1H), 8.77 (s, 1H) 13.77 (bs, 1H).

LC/MS (ES+) m/z=341.10.

Example 354

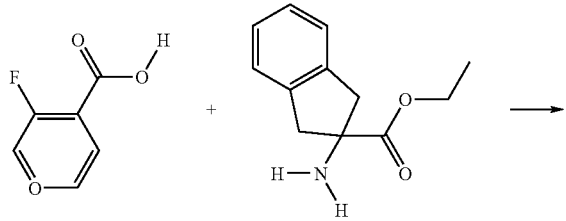

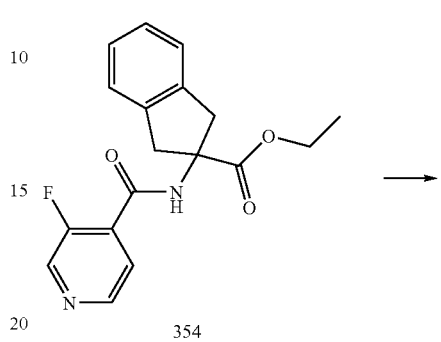

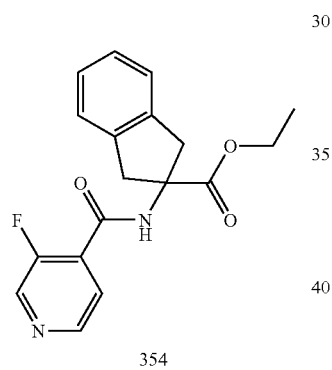

2-[(2-Fluoro-pyridine-4-carbonyl)-amino]-indan-2-carboxylic acid ethyl ester (354)

A 40 mL reaction vial which contains a stirring bar is charged with 3-fluoroisinicotinic acid (825 mg, 5.85 mmol) and dry DCM (15 mL). Stirring is initiated. After 2 min, the HTBU (2.22 g, 5.85 mmol) is added. After 5 min, 2-amino-indane-2-carboxylic acid ethyl ester (1.2 g, 5.25 mmol) is added followed by DIPEA (2.55 mL, 14.62 mmol). The reaction is allowed to stir for 7 days. Analysis by tlc of the reaction mixture (silica, 5% iPrOH/DCM) indicates complete consumption of the starting amine. The contents of the reaction flask are transferred to a reparatory funnel and diluted with EtOAc (75 mL). This is washed consecutively with brine (25 mL), saturated aqueous NaHCO$_3$ (25 mL) and brine (25 mL), and then dried over MgSO$_4$, filtered and evaporated in vacuo to provide 3.93 g of light yellow solid. This material is dissolved in 15 mL of DCM. This material is purified utilizing an ISCO Companion with a 40 g cartridge of silica. The gradient is 5% EtOAc in heptanes over 4 column volumes followed by a linear gradient to 65% EtOAc in heptanes over 10 column volumes. 14 mL fractions of UV active eluent are collected. Fractions 4 through 9 are combined and evaporated in vacuo. This yields white solid (1.5 g, 94%).

Example 355

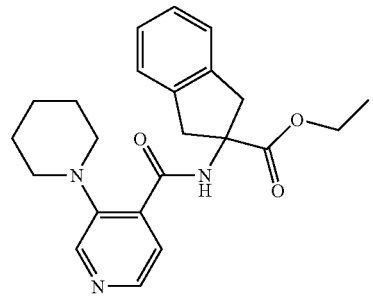

2-[(3,4,5,6-Tetrahydro-2H-[1,3']bipyridinyl-4'-carbonyl)-amino]-indan-2-carboxylic acid ethyl ester (355)

A 10 mL microwave reaction vessel is charged with 2-[(3-fluoro-pyridine-4-carbonyl)-amino]-indan-2-carboxylic acid ethyl ester (354, 500 mg, 1.52 mmol), 1,4-dioxane (1.5 mL) and piperidine (1.51 mL, 15.23 mmol). A stirring bar is added. The reaction vial is crimped sealed. The reaction vial is placed in a Smith Microwave reaction apparatus. The temperature is set for 150° C. with a fixed hold time of 10 min. Pre-stir time is set for 20 sec. The reaction vial is removed from the apparatus. The stirring bar is extracted. The contents of the flask are transferred to a round bottom flask and the solvent removed under reduced pressure. Pumping to a constant weight gives 1.2 g of yellow semi-solid. The residue is dissolved in DCM (10 mL) and applied to an ISCO Companion that is fitted with a 40 g column (silica). The column is eluted with EtOAc/heptanes (5%) for 4 column volumes followed by a linear gradient to 65% EtOAc/heptanes over 10 column volumes and then 90% EtOAc/heptanes for 2 column volumes. 14 mL fractions are collected. Fractions 42-50 are Example 356

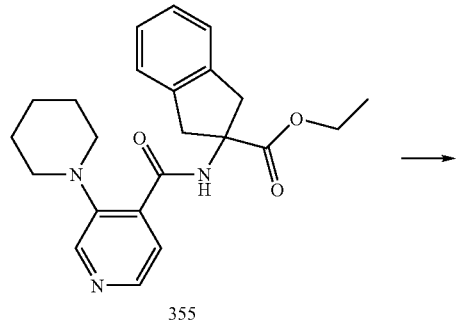

355

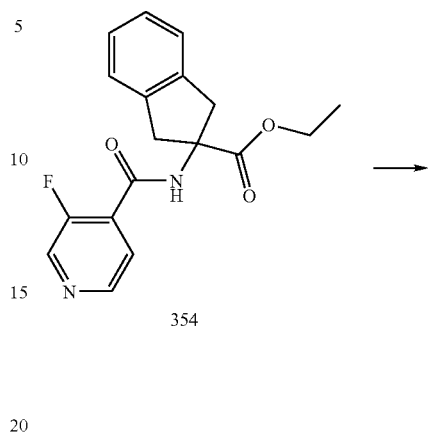

354

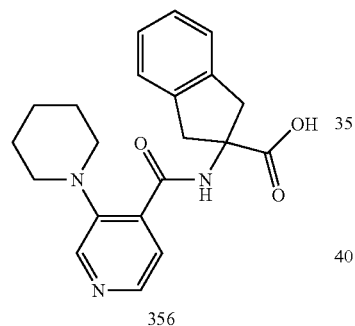

356

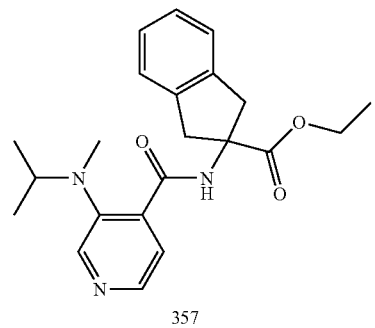

357

2-[(3,4,5,6-Tetrahydro-2H-[1,3']bipyridinyl-4'-carbonyl)-amino]-indan-2-carboxylic acid (356)

A 100 mL round bottom flask which contains 2-[(3,4,5,6-tetrahydro-2H-[1,3']bipyridinyl-4'-carbonyl)-amino]-indan-2-carboxylic acid ethyl ester (355, 370 mg, 0.94 mmol) is charged with 1,4-dioxane (4 mL) and MeOH (4 mL). A stirring bar is added and stirring is initiated. After dissolution, water (2 mL) is added followed by the LiOH monohydrate (100 mg, 2.38 mmol). After 68 h, tlc analysis (silica, 50% EtOAc/Heptanes) indicates that the starting material is completely consumed. Amberlyst highly acidic exchange resin (0.5 g) is added to the reaction vial. The reaction is capped and allowed to stir at ambient temperature. After 20 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides white solid (0.35 g, 96%).

$^1$H NMR (DMSO-d6, 300 MHz): δ 1.43 (m, 2H), 1.78 (m, 4H) 2.96 (m, 4H), 3.22-3.46 (m, 4H), 7.05-7.12 (m, 4H), 7.46 (d, 1H), 8.28 (d, 1H), 8.40 (s, 1H), 9.83 (bs, 1H).

LC/MS (ES+) m/z=366.16.

Example 357

2-{[3-(Isopropyl-methyl-amino)-pyridine-4-carbonyl]-amino}-indan-2-carboxylic acid ethyl ester (357)

A 10 mL microwave reaction vessel is charged with 2-[(3-fluoro-pyridine-4-carbonyl)-amino]-indan-2-carboxylic acid ethyl ester (354, 500 mg, 1.52 mmol), 1,4-dioxane (2 mL) and piperidine 2 mL, 29.5 mmol). A stirring bar is added. The reaction vial is crimped sealed. The reaction vial is placed in a Smith Microwave reaction apparatus. The temperature is set for 150° C. with a fixed hold time of 10 min. Pre-stir time is set for 20 sec. After this sequence is completed, the reaction vial is removed from the apparatus. The stirring bar is extracted. The contents of the flask are transferred to a round bottom flask and the solvent removed under reduced pressure. Pumping to a constant weight gives 0.71 g of brown syrup. This is dissolved in DCM (10 mL) and applied to an ISCO Companion that is fitted with a 40 g column (silica). The column is eluted with EtOAc/heptanes (5%) for 4 column volumes followed by a linear gradient to 65% EtOAc/heptanes over 10 column volumes and then 90% EtOAc/heptanes for 2 column volumes. 14 mL fractions of UV active eluent are collected. Fractions 5-11 are combined and evaporated by pumping to constant weight to give 0.29 g of an amorphous white solid (0.29 g, 51%).

Example 358

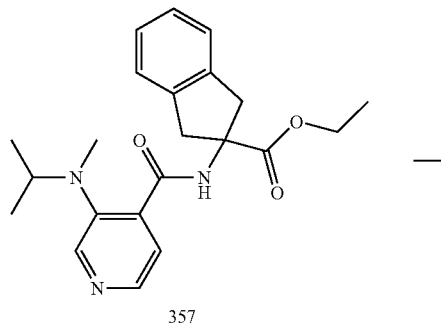

357

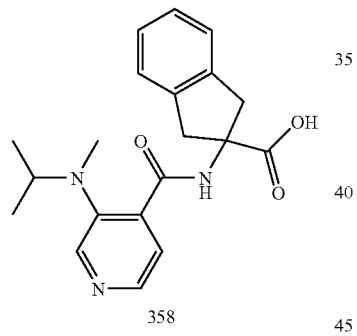

358

2-{[3-(Isopropyl-methyl-amino)-pyridine-4-carbonyl]-amino}-indan-2-carboxylic acid (358)

2-{[3-(Isopropyl-methyl-amino)-pyridine-4'-carbonyl]-amino}-indan-2-carboxylic acid ethyl ester 357, 270 mg, 0.71 mmol) is charged with 1,4-dioxane (3 mL) and MeOH (3 mL). A stirring bar is added and stirring is initiated. After dissolution, water (1.5 mL) is added followed by the LiOH monohydrate (75 mg, 1.94 mmol). After 4 days, tlc analysis (silica, 50% EtOAc/heptanes) indicates that the starting material is completely consumed. Amberlyst highly acidic exchange resin (0.5 g) is added to the reaction vial. The reaction is capped and allowed to stir at ambient temperature. After 3 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides white solid (0.22 g, 88%).

$^1$H NMR (DMSO-d6, 300 MHz): δ 1.03 (d, 6H), 2.69 (s, 3H), 3.77 (septet, 1H), 7.05-7.12 (m, 4H), 7.43 (d, 1H), 8.21 (d, 1H), 8.39 (s, 1H).
LC/MS (ES+) m/z=354.19.

Example 359

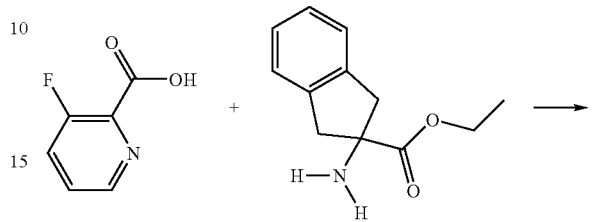

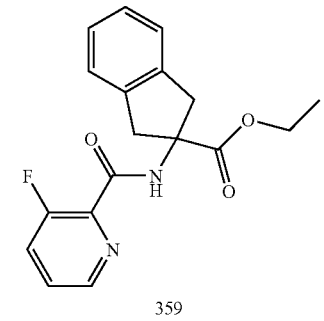

359

2-[(3-Fluoro-pyridine-2-carbonyl)-amino]-indan-2-carboxylic acid ethyl ester (359)

A 40 mL reaction vial which contains a stirring bar is charged with 3-Fluoropyridine-2-carboxylic acid (997 mg, 7.07 mmol) and dry DCM (15 mL). Stirring is initiated. After 2 min, the HTBU (2.7 g, 7.07 mmol) is added. After 5 min, 2-Amino-indan-2-carboxylic acid ethyl ester (1.45 g, 7.07 mmol) is added followed by DIPEA (2.50 mL, 14.5 mmol). The reaction is allowed to stir for 18 h. Analysis by tlc of the reaction mixture (silica, 5% iPrOH/DCM) indicates complete consumption of the starting amine. The contents of the reaction flask are transferred to a separatory funnel and diluted with EtOAc (50 mL). This is washed consecutively with water (3%, 25 mL), saturated aqueous NaHCO3 (2×25 mL) and brine (25 mL), and then dried over MgSO$_4$, filtered and evaporated in vacuo to provide 4.15 g of light orange solid. This material is dissolved in 20 mL of DCM. This material is purified utilizing an ISCO Companion with an 80 g cartridge of silica. The gradient is 5% EtOAc in heptanes for 4 column volumes followed by a linear gradient to 60% EtOAc in heptanes over 10 column volumes. 14 mL fractions of UV active elutant are collected. Fractions 6 through 14 are combined and evaporated in vacuo. This yields 2.04 g white solid (2.04 g, 88%).

Example 360

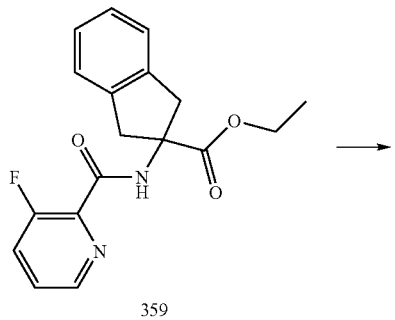

359

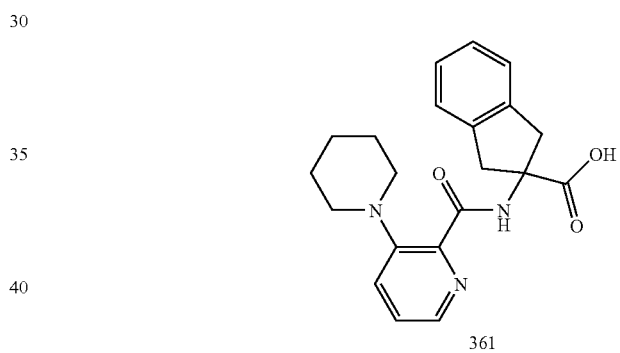

360

2-[(3,4,5,6-Tetrahydro-2H-[1,3']bipyridinyl-2'-carbonyl)-amino]-indan-2-carboxylic acid ethyl ester (360)

A 10 mL microwave reaction vessel is charged with 2-[(3-fluoro-pyridine-2-carbonyl)-amino]-indan-2-carboxylic acid ethyl ester (359, 488 mg, 1.49 mmol), 1,4-dioxane (1.5 mL) and piperidine (1.51 mL, 15.23 mmol). A stirring bar is added. The reaction vial is crimped sealed. The reaction vial is placed in a Smith Microwave reaction apparatus. The temperature is set for 150° C. with a fixed hold time of 10 min. Pre-stir time is set for 20 sec. The reaction vial is removed from the apparatus. The stirring bar is extracted. The contents of the flask are transferred to a round bottom flask and the solvent removed under reduced pressure. Pumping to a constant weight gives 1.02 g of off white solid. This is dissolved in DCM (10 mL) and applied to an ISCO Companion that is fitted with a 40 g column (silica). The column is eluted with EtOAc/heptanes (5%) for 4 column volumes followed by a linear gradient to 65% EtOAc/heptanes over 10 column volumes and then 90% EtOAc/heptanes for 2 column volumes.

14 mL fractions of UV Active eluent are collected. Fractions 2-10 are combined and evaporated by pumping to constant weight to give white solid (0.5 g, 86%).

Example 361

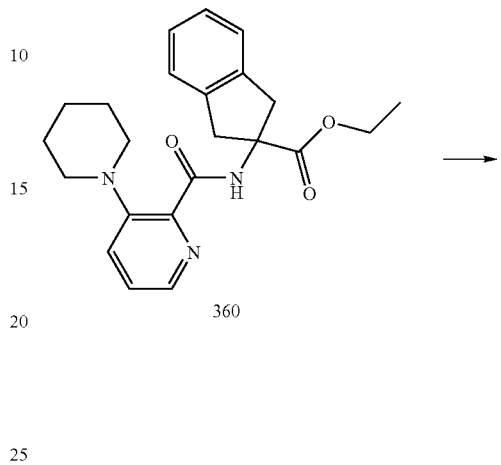

360

361

2-[(3,4,5,6-Tetrahydro-2H-[1,3']bipyridinyl-2'-carbonyl)-amino]-indan-2-carboxylic acid (361)

A 100 mL round bottom flask which contains 2-[(3,4,5,6-Tetrahydro-2H-[1,3']bipyridinyl-2'-carbonyl)-amino]-indan-2-carboxylic acid ethyl ester (360, 370 mg, 0.94 mmol) is charged with 1,4-dioxane (4 mL) and MeOH (4 mL). A stirring bar is added and stirring is initiated. After dissolution, water (2 mL) is added followed by LiOH monohydrate (100 mg, 2.38 mmol). After 38 h, tlc analysis (silica, 50% EtOAc/heptanes) indicates that the starting material has been completely consumed. Amberlyst highly acidic exchange resin (0.5 g) is added to the reaction vial. The reaction is capped and allowed to stir at ambient temperature. After 4 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides white solid (0.29, 84%).

$^1$H NMR 300 MHz): δ 1.43 (m, 2 HH), 1.78 (m, 4H), 2.96 (m, 4H), 3.22-3.46 (m, 4H), 7.05-7.12 (m, 4H), 7.46 (d, 1H), 8.28 (d, 1H), 8.40 (s, 1H), 9.83 (bs, 1H).

LC/MS (ES+) m/z=366.16.

Example 362

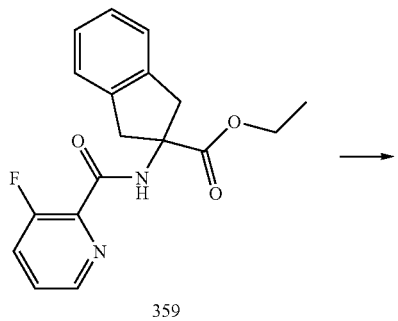

2-{[[3-Isopropylmethyl-amino)-pyridine-2-carbonyl]-amino}-indan-2-carboxylic acid ethyl ester (362)

A 10 mL microwave reaction vessel is charged with 2-[(3-fluoro-pyridine-2-carbonyl)-amino]-indan-2-carboxylic acid ethyl ester (359, 492 mg, 1.5 mmol), 1,4-dioxane (1.5 mL) and N-methylisopopyl amine (2 mL, 19.25 mmol) and DIPEA (2 mL, 11.48 mmol) are added. A stirring bar is added. The reaction vial is crimped sealed. The reaction vial is placed in a Smith Microwave reaction apparatus. The temperature is set for 155° C. with a fixed hold time of 90 min. Pre-stir time is set for 20 sec. The reaction vial is removed from the apparatus. The stirring bar is extracted. The contents of the flask are transferred to a round bottom flask and the solvent removed under reduced pressure. Pumping to a constant weight gives 0.75 g of brown syrup. This is dissolved in DCM (10 mL) and applied to an ISCO Companion which had been fitted with a 40 g column (silica). The column is eluted with EtOAc/heptanes (5%) for 4 column volumes followed by a linear gradient to 65% EtOAc/heptanes over 10 column volumes and then 90% EtOAc/heptanes for 2 column volumes. 14 mL fractions of UV Active eluent are collected. Fractions 7-15 are combined and evaporated by pumping to constant weight to give amorphous white solid (0.38 g, 67%).

Example 363

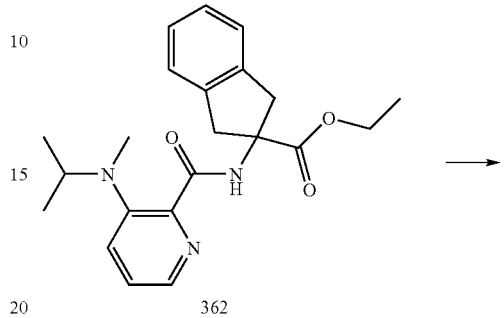

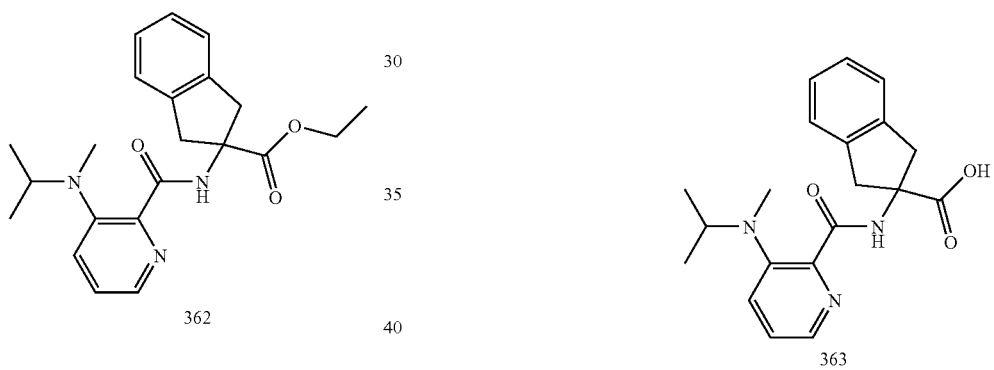

2-{[3-Isopropylmethyl-amino)-pyridine-2-carbonyl]-amino}-indan-2-carboxylic acid (363)

A 100 mL round bottom flask which contains 2-{[[3-isopropylmethyl-amino)-pyridine-2-carbonyl]-amino}-indan-2-carboxylic acid ethyl ester (362, 370 mg, 0.97 mmol) is charged with 1,4-dioxane (4 mL) and MeOH (4 mL). A stirring bar is added and stirring is initiated. After dissolution, water (2 mL) is added followed by LiOH monohydrate (103 mg, 2.46 mmol). After 62 h, tlc analysis (silica, 50% EtOAc/heptanes) indicates that the starting material has been completely consumed. Amberlyst highly acidic exchange resin (0.7 g) is added to the reaction vial. The reaction is capped and allowed to stir at ambient temperature. After 4 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provides a white solid (0.33, 96%).

$^1$H NMR 300 MHz): δ 1.04 (d, 6H), 2.39 (s, 3H), 3.18-3.53 (m, 4H), 3.64 (septet, 1H), 7.02-7.12 (m, 4H), 7.28 (dd, 1H), 7.36 (dd, 1H), 7.98 (dd, 1H), 8.84 (s, 1H).

LC/MS (ES+) m/z=354.17.

Example 364

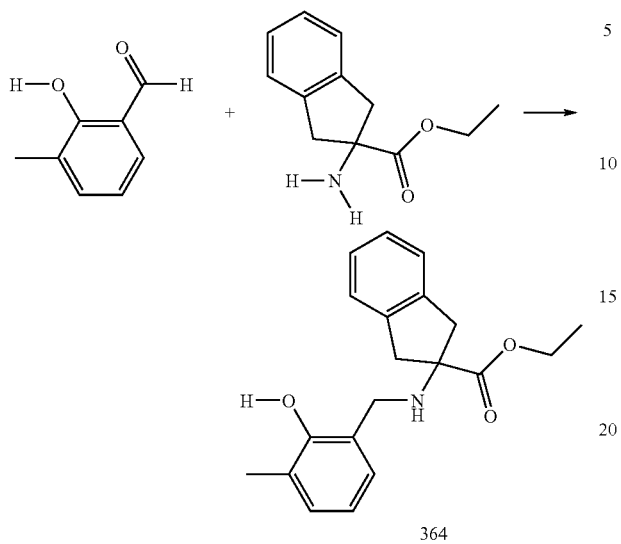

2-(2-Hydroxy-3-methyl-benzylamino)-indan-2-carboxylic acid ethyl ester (364)

A 10 mL microwave reaction vessel is charged with 2-amino-indan-2-carboxylic acid ethyl ester (500 mg, 2.44 mmol) and dry tetrahydrofuran (THF, 5 mL). A stirring bar is added and stirring is initiated. After dissolution, 2-hydroxy-3-methyl-benzaldehyde (0.3 mL, 2.43 mmol) is added. Stirring is continued. Phenylsilane (0.61 mL, 4.87 mmol) and dibutyltin dichloride (53 µL, 244 µM) are added. The reaction vial is crimped sealed and placed in a Smith Microwave Apparatus. The pre-stir time is set to 10 sec. Heating is set at 100° C. for 10 min. The contents of the reaction vial are transferred to a round bottom flask and evaporated by pumping to a constant weight yields 1.67 g of light yellow solid. This material is dissolved in DCM (10 mL) and applied to an ISCO Companion that is fitted with a 40 g Cartridge (silica). The column is eluted with 5% EtOAc/heptanes for 3 column volumes followed by a linear gradient to 50% EtOAc/heptanes over 10 column volumes and then 90% EtOAc/heptanes for 2 column volumes. 14 mL fractions of UV active eluent are collected. Fractions 5 to 8 are combined and evaporated by pumping to constant weight to give 0.59 g of white solid material (0.59 g, 74%).

Example 365

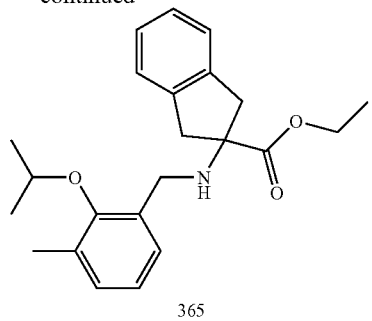

2-(2-Isopropoxy-3-methyl-benzylamino)-indan-2-carboxylic acid ethyl ester (365)

A 100 mL round bottom flask containing the 2-(2-hydroxy-3-methyl-benzylamino)-indan-2-carboxylic acid ethyl ester (364, 1.01 g, 3.10 mmol) is charged with dry tetrahydrofuran (THF, 10 mL). A stirring bar is added and stirring is initiated. After dissolution, iPrOH ([67-63-0], 0.47 mL, 6.21 mmol) and triphenylphosphine ([603-35-0], 1.63 g, 6.21 mmol) are added in turn. After dissolution of the triphenylphosphine, diisopropylazodicarboxylate (1.20 mL, 6.21 mmol) is added. The reaction flask is capped and allowed to stir at ambient temperature overnight. After 24 h, tlc analysis (silica, 1:2 EtOAc/Heptanes) indicates that the starting material is completely consumed and converted to a higher moving spot as visualized by UV. The stirring bar is removed from the reaction flask and the solvent removed under reduced pressure. Pumping to constant weight gives 2.06 g of viscous yellow oil. This is dissolved in DCM (10 mL) and applied to an ISCO Companion which had been fitted with a 40 g column (silica). The column is eluted with EtOAc/heptanes (5%) for 4 column volumes followed by a linear gradient to 60% EtOAc/heptanes over 10 column volumes and then 90% EtOAc/heptanes for 2 column volumes. 17 mL fractions of UV Active eluent are collected. Fractions 5-14 are combined and evaporated by pumping to constant weight to give viscous residue (0.42 g, 37%).

$^1$H NMR 300 MHz): δ 1.18 (d, 6H), 1.22 (t, 3H), 2.18 (s, 3H), 2.98-3.41 (m, 4H), 3.61 (d, 2H), 4.16 (q, 1H), 6.90 (dd, 1H), 7.04 (dd, 1H), 7.11-7.20 (m, 4H)

LC/MS (ES+) m/z=368.24.

Example 366

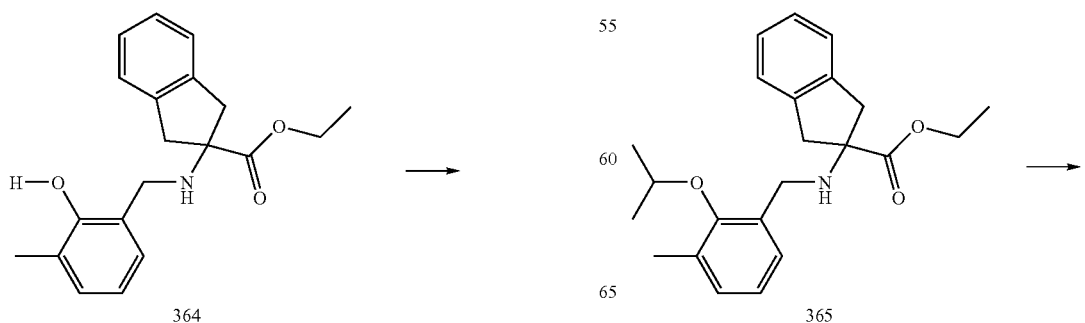

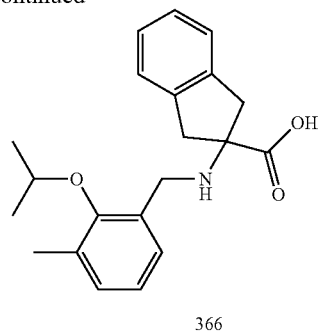

2-(2-Isopropoxy-3-methyl-benzylamino)-indan-2-carboxylic acid (366)

A 100 mL round bottom flask containing 2-(2-isopropoxy-3-methyl-benzylamino)-indan-2-carboxylic acid ethyl ester (365, 360 mg, 0.98 mmol) is charged with 1,4-dioxane (3 mL) and MeOH (3 mL). A stirring bar is added and stirring is initiated. After dissolution, water (1.5 mL) is added followed by the LiOH monohydrate (104 mg, 2.47 mmol). After 39 h, tlc analysis (silica, 50% EtOAc/Heptanes) indicates that the starting material is completely consumed. Amberlyst highly acidic exchange resin (0.5 g) is added to the reaction vial. The reaction is capped and allowed to stir at ambient temperature. After 15 days, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provided white solid (0.24 g, 72%).

$^1$H NMR (DMSO-d6, 300 MHz): δ 1.12 (d, 6H), 2.17 (s, 3H), 2.77-3.68 (m, 6H), 4.16 (septet, 1H), 6.84 (dd, 1H), 6.97-7.22 (m, 6H).

LC/MS (ES+) m/z=340.20.

Example 367

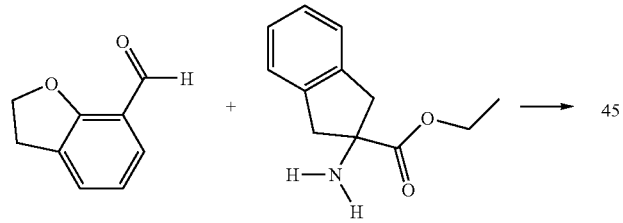

2-[(2,3-Dihydro-benzofuran-7-ylmethyl)-amino]-indan-2-carboxylic acid ethyl ester (367)

A 10 mL microwave reaction vessel is charged with 2-amino-indan-2-carboxylic acid ethyl ester (500 mg, 2.44 mmol) and dry tetrahydrofuran (THF, 5 mL). A stirring bar is added and stirring is initiated. After dissolution, 2,3-dihydro-1-benzofuran-7-carbaldehyde (361 mg, 2.43 mmol) is added. Stirring is continued. Phenylsilane ([694-18-1], 0.61 mL, 4.87 mmol) and dibutyltin dichloride (53 μL, 244 μM) are added. The reaction vial is crimped sealed and placed in a Smith Microwave Apparatus. The pre-stir time is set to 10 sec. Heating is set at 100° C. for 10 min. The contents of the reaction vial are transferred to a round bottom flask and evaporated by pumping to a constant weight yields 1.56 g of light yellow oil. This material is dissolved in DCM (10 mL) and applied to an ISCO Companion that is fitted with a 40 g Cartridge (silica). The column is eluted with 5% EtOAc/heptanes for 3 column volumes followed by a linear gradient to 50% EtOAc/heptanes over 10 column volumes and then 90% EtOAc/heptanes for 2 column volumes. 14 mL fractions of UV active eluent are collected. Fractions 7 to 11 are combined and evaporated by pumping to constant weight yields 0.59 g of white solid material (0.52 g, 63%).

Example 368

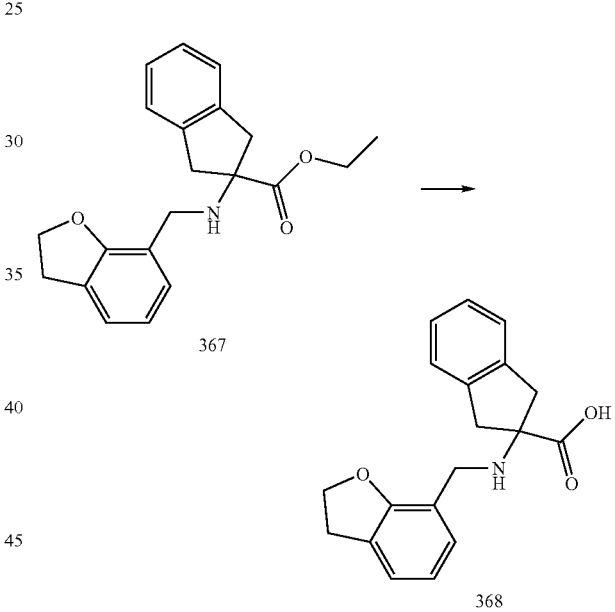

2-[(2,3-Dihydro-benzofuran-7-ylmethyl)-amino]-indan-2-carboxylic acid (368)

A 100 mL round bottom flask containing 2-[(2,3-Dihydro-benzofuran-7-ylmethyl)-amino]-indan-2-carboxylic acid ethyl ester (367, 350 mg, 1.037 mmol) is charged with 1,4-dioxane (3 mL) and MeOH (3 mL). A stirring bar is added and stirring is initiated. After dissolution, water (1.5 mL) is added followed by the LiOH monohydrate (110 mg, 2.52 mmol). After 16 h, tlc analysis (silica, 50% EtOAc/Heptanes) indicates that the starting material is completely consumed. Amberlyst highly acidic exchange resin (0.5 g) is added to the reaction vial. The reaction is capped and allowed to stir at ambient temperature. After 6 h, the contents of the flask are filtered through a pad of Celite. The solvent is removed from the filtrate. The residue is reconstituted with iPrOH/toluene (20+20 mL) and the solvent is removed. This process is repeated 1 time. Pumping to constant weight provided white solid (0.31 g, 99%).

¹H NMR (DMSO-d6, 300 MHz): δ 2.77-3.58 (m, 6H), 3.11 (t, 2H), 4.45 (t, 2H), 6.70 (dd, 1H), 7.02-7.11 (m, 6H).
LC/MS (ES+) m/z=310.14.

2-Amino-1,2,3,4-tetrahydro-naphthalene-2-carboxylic acid ethyl esters 369, 370, 371, 372 and 373 are synthesized according to the method of Michael Cox in Eur. Pat. Appl. EP 82-304382.

Example 369

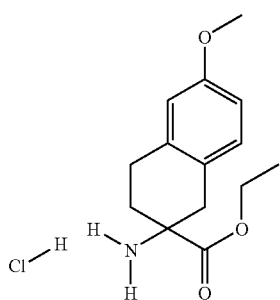

2-Amino-6-methoxy-1,2,3,4-tetrahydro-naphthalene-2-carboxylic acid ethyl ester hydrochloride salt (369)

LC/MS (ES+) m/z=250.18.

Example 370

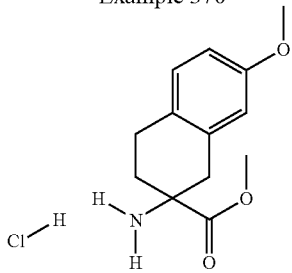

Example 370

2-Amino-7-methoxy-1,2,3,4-tetrahydro-naphthalene-2-carboxylic acid methyl ester; hydrochloride (370)

LC/MS (ES+) m/z=336.16.

Example 371

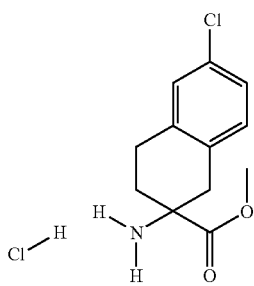

2-Amino-6-chloro-1,2,3,4-tetrahydro-naphthalene-2-carboxylic acid methyl ester hydrochloride salt (371)

LC/MS (ES+) m/z=340.11.

Example 372

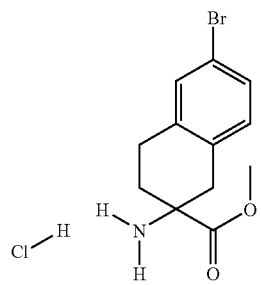

2-Amino-6-bromo-1,2,3,4-tetrahydro-naphthalene-2-carboxylic acid methyl ester hydrochloride salt (372)

LC/MS (ES+) m/z=340.11.

Example 373

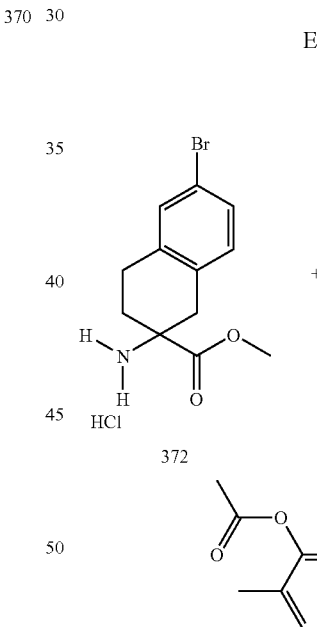

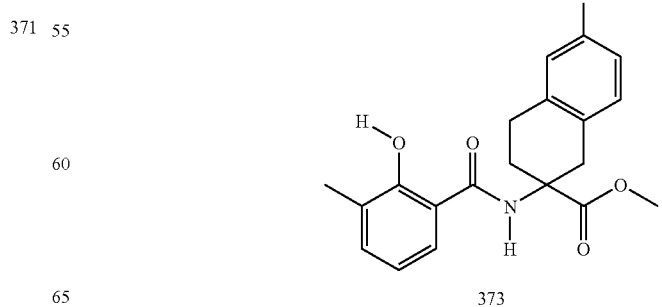

2-(2-Hydroxy-3-methyl-benzoyl)-6-bromo-1,2,3,4-tetrahydroisoquinoline-3-carboxylic acid methyl ester (373)

A 40 mL vial which contains a stirring bar is charged with 2-acetoxyl-3-methyl-benzoic acid ([2386-93-4], 1.69 g, 8.7 mmol) and dry DCM (10 mL). Stirring is initiated. After dissolution is complete, The HTBU (3.29 g, 8.7 mmol) is added. After 5 min, the 2-amino-6-bromo-1,2,3,4-tetrahydronaphthalene-2-carboxylic Acid hydrochloride Salt (372, 1.25 g, 3.9 mmol is added followed by DIPEA (3.4 mL, 19.5 mmol). An additional aliquot of dry DCM (4 mL) is added. The reaction is allowed to stir for 36 h. Analysis by tlc of the reaction mixture (silica, 50% EtOAc/heptanes) indicates complete consumption of the starting amine. The contents of the reaction flask are diluted with EtOAc (100 mL) and transferred to a reparatory funnel. This is washed consecutively with dilute aqueous $NaHCO_3$ (50 mL) and brine (50 mL), dried over $Na_2SO_4$, filtered and evaporated in vacuo to provide 5.2 g of thick brownish gum. This material is purified utilizing an ISCO Companion with a 120 g cartridge of silica. The gradient is 2% EtOAc in heptanes for 4 column volumes followed by a linear gradient to 30% EtOAc over 10 column volumes then to 100% EtOAc over 12 column volumes. 170 mL fractions of UV active eluent are collected. Fractions 13 through 23 are combined and evaporated in vacuo. This yields a foamy material (0.42 g, 26%).

Example 374

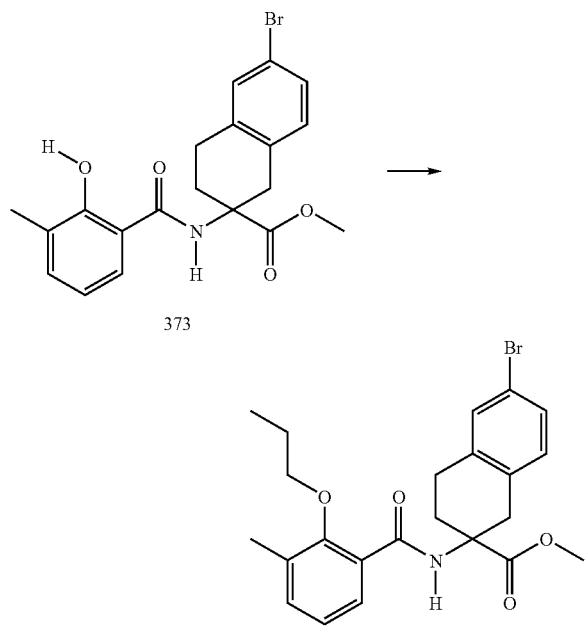

2-(2-Propoxy-3-methyl-benzoyl)-6-bromo-1,2,3,4-tetrahydroisoquinoline-3-carboxylic acid methyl ester (374)

A 100 mL round bottom flask which contains 6-bromo-(2-hydroxoxy-3-methyl-benzoylamino)-1,2,3,4-tetrahydronaphthalene-2-carboxylic acid methyl ester (373, 0.39 g, 0.932 mmol) and a stirring bar is charged with dry DMF (10 mL). Stirring is initiated. $K_2SO_4$ (0.258 g, 1.86 mmol), KI (1 mg, 6 μM), and 1-bromopropane (0.2 mL, 2.24 mmol) are added in turn. The reaction flask is immersed in an oil bath and fitted with a reflux condenser. The oil bath is heated to 79° C. The reaction is stirred for 2 h at this temperature then the oil bath is turned off. After 16 h at ambient temperature, heating is reinitiated at 53° C. for an additional hour. Analysis by ttlc (silica, 1:1 EtOAc:Heptanes), indicates consumption of starting material and appearance of a spot with a slightly lower $R_f$. The reaction is again allowed to cool to ambient temperature and filtered through a bed of Celite. The resulting solution is diluted with EtOAc (60 mL) and washed repeatedly with brine (4×40 mL), and then dried over $MgSO_4$, filtered and evaporated by pumping to a constant weight yields light yellow oil (0.42 g, 98%).

Example 375

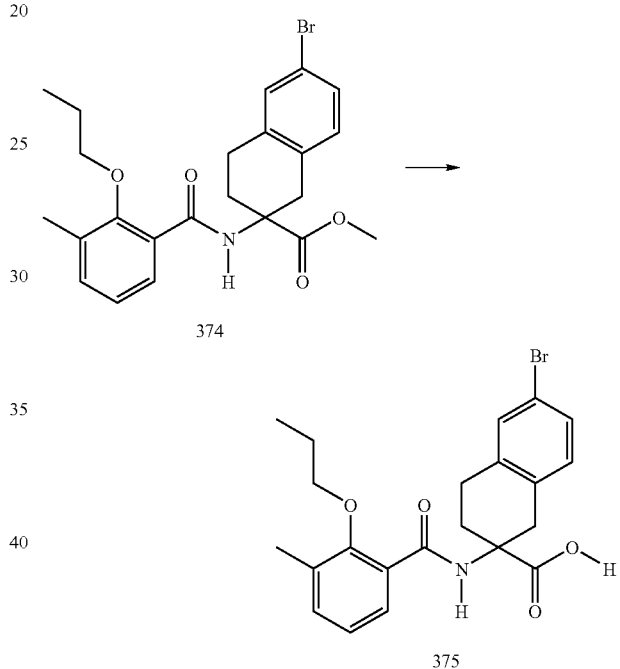

2-(2-Propoxy-3-methyl-benzoyl)-6-bromo-1,2,3,4-tetrahydroisoquinoline-3-carboxylic acid (375)

50 mL flask containing the 6-bromo-2-(2-propoxy-3-methyl-benzoylamino)-1,2,3,4-tetrahydro-naphthalene-2-carboxylic acid ethyl ester (374, 0.34 g, 0.74 mmol) is charged with 1,4-dioxane (5 mL) and MeOH (5 mL). A stirring bar is added and stirring is initiated. After dissolution, water (2.5 mL) is added followed by the LiOH monohydrate (77 mg, 1.44 mmol). After 16 hours, tlc analysis (silica, 5% i-PrOH/DCM) indicates that the starting material is completely consumed. The pH of the reaction mixture is carefully adjusted to pH 2 by slowly adding dilute aqueous HCl (3%, ~12 mL). The contents of the flask are poured into a separatory funnel that contains EtOAc (30 mL). The layers are separated. The aqueous layer is extracted with EtOAc (20 mL). The combined organic extracts are washed with water (20 mL) and brine (20 mL), and then dried over $MgSO_4$, filtered and concentrated. Pumping to constant weight gives off-white solid (0.30 g, 91%).

¹H NMR (300 MHz, DMSO-d6): δ 0.82 (t, 3H), 1.43 (m, 1H), 1.96-2.08 (m, 1H), 2.19 (s, 3H), 2.38-2.91 (m, 1H), 2.73-2.91 (m, 2H), 3.02-3.38 (m, 5H), 3.58-3.64 (m, 3H), 7.03-7.09 (m, 2H), 7.27-7.36 (m, 3H), 8.36 (s, 1H), 12.56 (bs, 1H).

LC/MS m/z=448.10.

Example 376

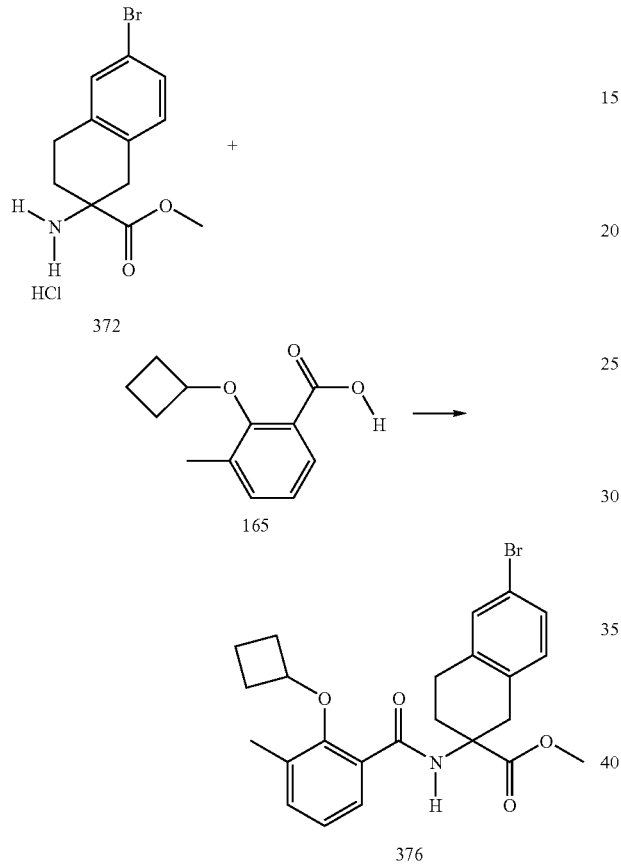

2-(2-cyclobutoxy-3-methyl-benzoylamino)-6-bromo-[(5,6,7,8-tetrahydro-naphthalene-1-carbonyl)-2-carboxylic acid methyl ester (376)

A 40 mL vial containing a stirring bar and the 2-cyclobutoxy-3-methylbenzoic acid (165, 447 mg, 2.17 mmol) is charged with dry DCM (6.5 mL). Stirring is initiated. HTBU (824 mg, 2.17 mmol) is added. 2-Amino-6-bromo-1,2,3,4-tertrahydronaphtahalene-2-carboxylic acid methyl ester; hydrochloride salt (372, 590 mg, 2.17 mmol) followed by the DIPEA (1.1 mL, 6.35 mmol) are added. The reaction is allowed to stir for 18 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous HCl (1N, 25 mL), saturated aqueous NaHCO₃ (25 mL) and brine (25 mL), dried over MgSO₄, filtered and evaporated in vacuo to provide 1.18 g of off-white solid. The material is dissolved in 10 mL of DCM. This material is purified utilizing an ISCO Companion with a 40 g cartridge of silica. The gradient is 10% EtOAC in heptanes over 3 column volumes followed by a linear gradient to 50% over 10 column volumes and then 90% EtOAc for 2 column volumes with ramp of 1 column volume. 25 mL fractions are collected. Fractions 9 through 15 are combined and evaporated in vacuo by pumping to a constant weight to give amorphous white solid (0.81 g, 79%).

Example 377

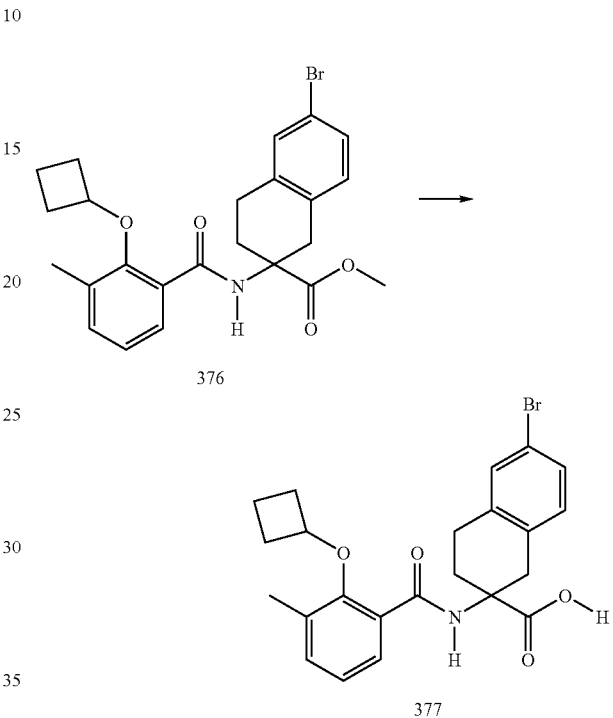

2-(2-cyclobutoxy-3-methyl-benzoylamino)-6-bromo-[(5,6,7,8-tetrahydro-naphthalene-1-carbonyl)-2-carboxylic acid (377)

A 50 mL flask containing the 2-(2-cyclobutoxy-3-methyl-benzoylamino)-6-bromo-[(5,6,7,8-tetrahydro-naphthalene-1-carbonyl)-2-carboxylic acid methyl ester (376, 0.44 g, 0.93 mmol) is charged with 1,4-dioxane (9 mL) and MeOH (9 mL). A stirring bar is added and stirring is initiated. After dissolution, water (4.5 mL) is added followed by the LiOH monohydrate (173 mg, 4.12 mmol). After 64 h, tlc analysis (silica, 5% i-PrOH/DCM) indicates that the starting material is completely consumed. The pH of the reaction mixture is carefully adjusted to pH 2 by slowly adding dilute aqueous HCl (3%, ~10 mL). The contents of the flask are poured into a separatory funnel containing EtOAc (30 mL). The layers are separated. The aqueous layer is extracted with EtOAc (20 mL). The combined organic extracts are washed with water (20 mL) and brine (20 mL), and then dried over MgSO₄, filtered and concentrated. Pumping to constant weight gives off-white solid (0.40 g, 98%).

¹H NMR (300 MHz, DMSO-d6): δ 1.17-1.34 (m, 1H), 1.39-1.57 (m, 1H), 1.78-2.16 (m, 4H), 2.21 (s, 3H), 2.37-2.42-(m, 1H), 2.74-2.98 (m, 2H), 3.15-3.27 (m, 3H), 4.34 (m, 1H), 7.01-7.11 (m, 2H), 7.25-7.35 (m, 3H), 8.34 (s, 1H), 12.53 (bs, 1H).

LC/MS m/z=460.05

Example 378

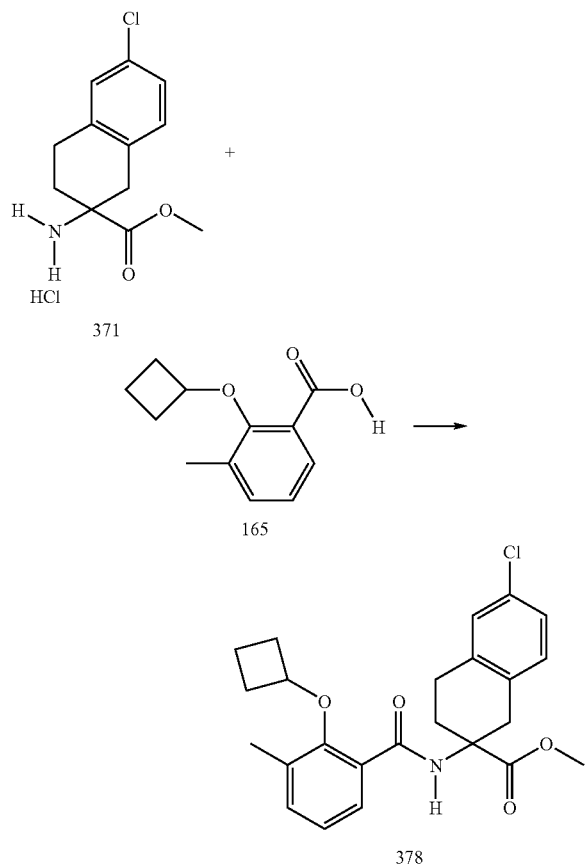

2-(2-cyclobutoxy-3-methyl-benzoylamino)-6-chloro-[(5,6,7,8-tetrahydro-naphthalene-1-carbonyl)-2-carboxylic acid methyl ester (375)

A 40 mL vial containing a stirring bar and the 2-cyclobutoxy-3-methylbenzoic acid (165, 447 mg, 2.17 mmol) is charged with dry DCM (6.5 mL). Stirring is initiated. HTBU (824 mg, 2.17 mmol) is added. 2-Amino-6-chloro-1,2,3,4-tertrahydronaphtahalene-2-carboxylic acid methyl ester; hydrochloride salt (371, 590 mg, 2.17 mmol) followed by the DIPEA (1.1 mL, 6.35 mmol) are added. The reaction is allowed to stir for 18 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous HCl (1 N, 25 mL), saturated aqueous NaHCO$_3$ (25 mL) and brine (25 mL), and then dried over MgSO$_4$, filtered and evaporated in vacuo to provide 1.18 g of off-white solid. The material is dissolved in 10 mL of DCM. This material is purified utilizing an ISCO Companion with a 40 g cartridge of silica. The gradient is 10% EtOAC in heptanes over 3 column volumes followed by a linear gradient to 50% over 10 column volumes and then 90% EtOAc for 2 column volumes with ramp of 1 column volume. 25 mL fractions of UV active eluent are collected. Fractions 2 through 11 are combined and evaporated in vacuo by pumping to a constant weight to give amorphous white solid (0.65 g, 70%).

Example 379

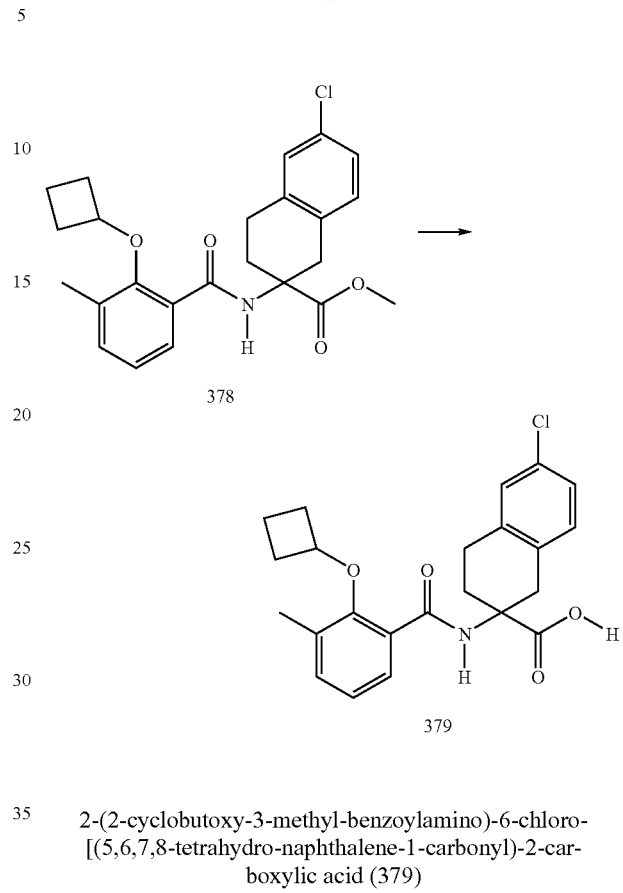

2-(2-cyclobutoxy-3-methyl-benzoylamino)-6-chloro-[(5,6,7,8-tetrahydro-naphthalene-1-carbonyl)-2-carboxylic acid (379)

A 50 mL flask containing the 2-(2-cyclobutoxy-3-methyl-benzoylamino)-6-chloro-[(5,6,7,8-tetrahydro-naphthalene-1-carbonyl)-2-carboxylic acid methyl ester (378, 0.42 g, 0.98 mmolg) is charged with 1,4-dioxane (5 mL) and MeOH (5 mL). A stirring bar is added and stirring is initiated. After dissolution, water (2.5 mL) is added followed by the LiOH monohydrate (103 mg, 2.45 mmol). After 260 h, tlc analysis (silica, 5% i-PrOH/DCM) indicates that the starting material has been completely consumed. The pH of the reaction mixture is carefully adjusted to pH 2 by slowly adding dilute aqueous HCl (3%, ~10 mL). The contents of the flask are poured into a reparatory funnel containing EtOAc (30 mL). The layers are separated. The aqueous layer is extracted with EtOAc (20 mL). The combined organic extracts are washed with water (20 mL) and brine (20 mL), and then dried over MgSO$_4$, filtered and concentrated. Pumping to constant weight gives off-white solid (0.38 g, 93%).

$^1$H NMR (300 MHz, DMSO-d6): δ 1.08-1.17 (m, 1H), 1.21-1.36 (m, 1H), 1.78-2.13 (m, 4H), 2.21 (s, 3H), 2.37-2.43-(m, 1H), 2.77-2.98 (m, 2H), 3.17-3.37 (m, 3H), 4.34 (m, 1H), 7.02 (dd, 1H), 7.10-7.35 (m, 5H), 8.35 (s, 1H), 12.57 (bs, 1H).

LC/MS m/z=414.15

Examples 380 and 381

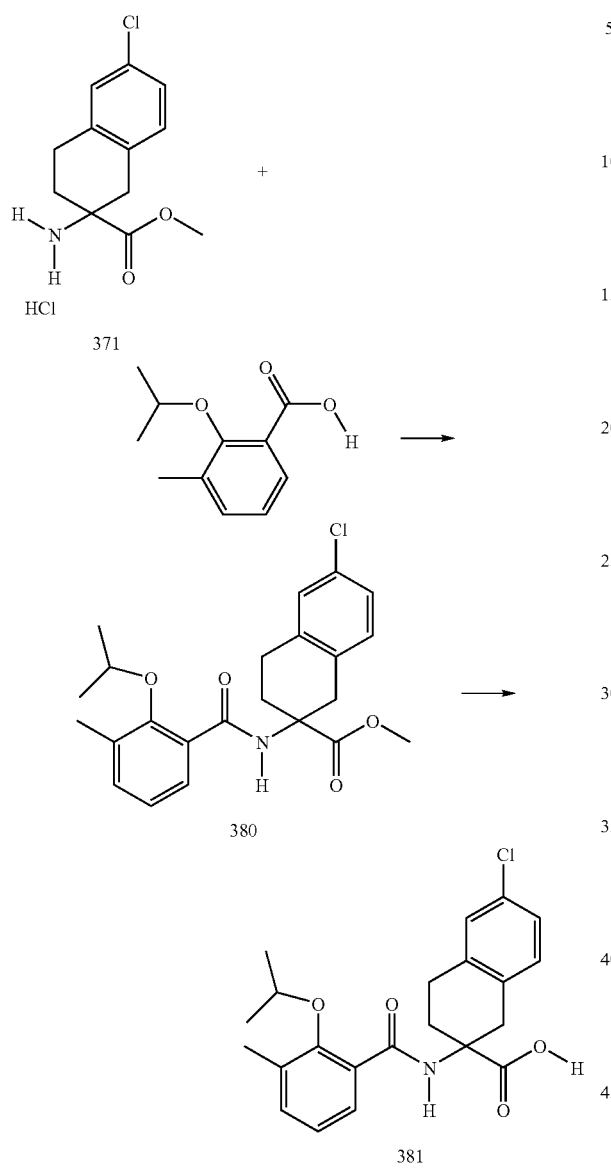

2-(2-Isopropoxy-3-methyl-benzoylamino)-6-chloro-[(5,6,7,8-tetrahydro-naphthalene-1-carbonyl)-2-carboxylic acid methyl ester (380)

2-(2-Isopropoxy-3-methyl-benzoylamino)-6-chloro-[(5,6,7,8-tetrahydro-naphthalene-1-carbonyl)-2-carboxylic acid (381)

2-(2-Isopropoxy-3-methyl-benzoylamino)-6-chloro-[(5,6,7,8-tetrahydro-naphthalene-1-carbonyl)-2-carboxylic acid (381) is synthesized according to the procedure for product 379 above excepting that 2-isopropoxy-3-methylbenzoic acid 2-cyclobutoxy-3-methylbenzoic acid is substituted for 2-cyclobutoxy-3-methylbenzoic acid in the amide bond formation step. Yield=94% for step one. Step 2 yields white solid material (0.43 g, 81%).

$^1$H NMR (300 MHz, DMSO-d6): δ 0.98 (d, 3H), 1.03 (d, 3H), 1.97-2.07 (m, 1H), 2.21 (s, 3H), 2.38-2.42-(m, 1H), 2.76-2.93 (m, 2H), 3.08-3.41 (m, 3H), 4.19 (m, 1H), 7.03 (dd, 1H), 7.11-7.20 (m, 3H), 7.27-7.35 (m, 2H), 8.35 (s, 1H), 12.52 (bs, 1H).

LC/MS m/z=414.15

Examples 382 and 383

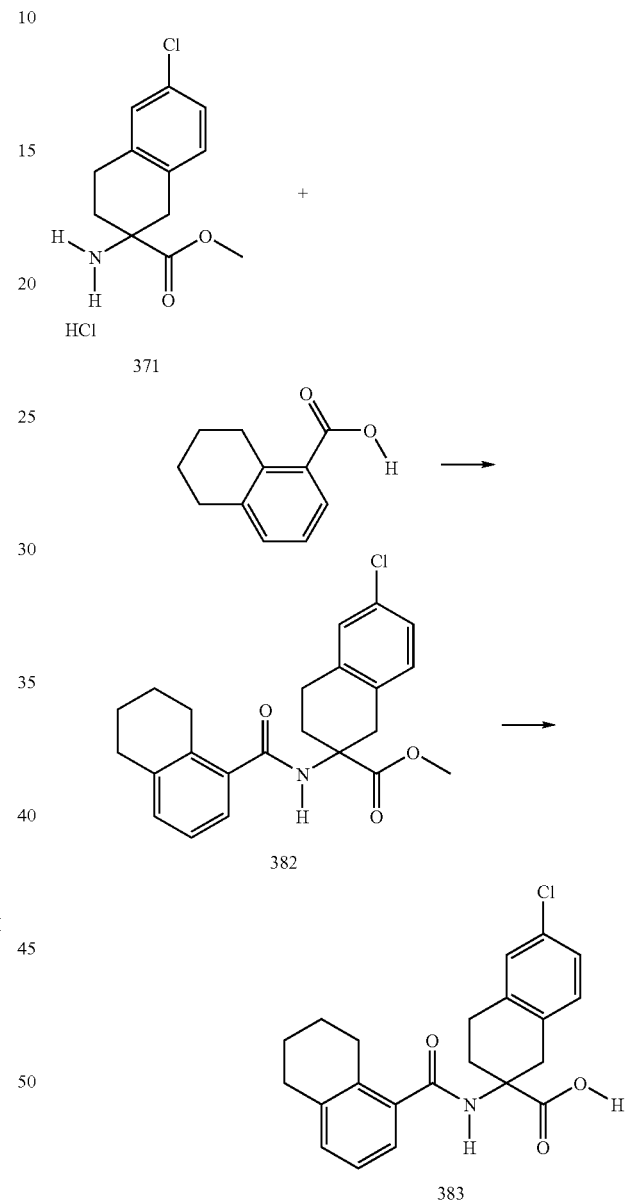

6-Chloro-2-[(5,6,7,8-tetrahydro-naphthalene-1-carbonyl)-amino]-1,2,3,4-tetrahydro-naphthalene-2-carboxylic acid (383)

6-Chloro-2-[(5,6,7,8-tetrahydronaphthalene-1-carbonyl)-amino]-1,2,3,4-tetrahydronaphthalene-2-carboxylic acid (383) is synthesized according to the procedure for product 379 above excepting that 5,6,7,8-tetrahydro-1-naphthalene carboxylic acid is substituted for 2-cyclobutoxy-3-methylbenzoic acid in the amide bond formation step. Yield=83% for step one. Step 2 yields a white solid material (0.42 g, 99%).

$^1$H NMR (300 MHz, DMSO-d6): δ 1.56-1.78 (m, 4H), 1.88-2.08 (m, 1H), 2.33-2.41-(m, 1H), 2.48-3.07 (m, 8H), 6.92 (dd, 1H), 7.03-7.18 (m, 5H), 8.72 (s, 1H), 12.49 (bs, 1H).
LC/MS m/z=384.11

Example 384

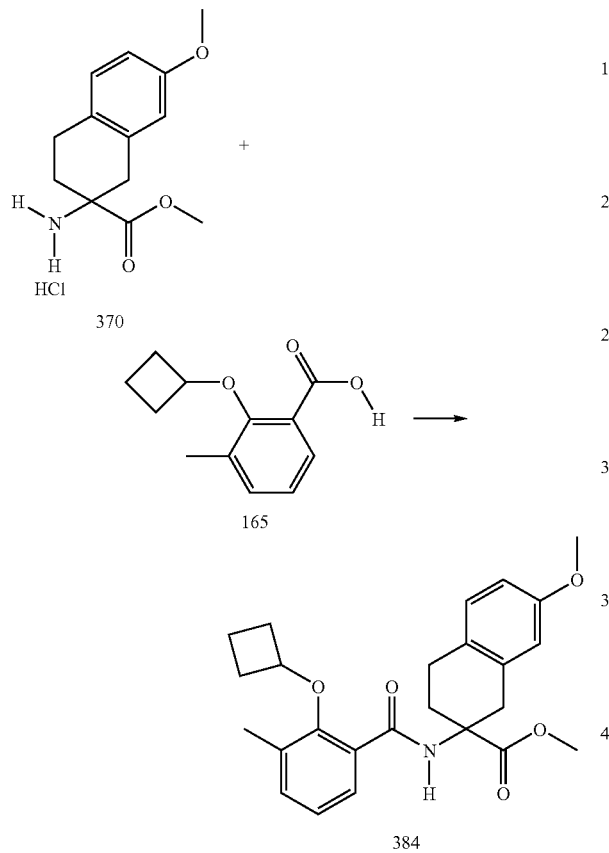

6-Methoxy-2-[(5,6,7,8-tetrahydro-naphthalene-1-carbonyl)-amino]-1,2,3,4-tetrahydro-naphthalene-2-carboxylic acid methyl ester (384)

A 40 mL vial containing a stirring bar and the 2-cyclobutoxy-3-methylbenzoic acid (165, 447 mg, 2.17 mmol) is charged with dry DCM (6.5 mL). Stirring is initiated. HTBU (824 mg, 2.17 mmol) is added. 2-Amino-7-methoxy-1,2,3,4-tertrahydronaphtahalene-2-carboxylic acid methyl ester hydrochloride salt (370, 590 mg, 2.17 mmol) followed by the DIPEA (1.1 mL, 6.35 mmol) are added. The reaction is allowed to stir for 18 h. Analysis by tlc of the reaction mixture (silica, 10% MeOH/DCM) indicates complete consumption of the starting amine. The contents of the reaction flask are diluted with EtOAc (50 mL) and transferred to a separatory funnel. This is washed consecutively with dilute aqueous HCl (1N, 25 mL), saturated aqueous NaHCO$_3$ (25 mL) and brine (25 mL), dried over MgSO$_4$, filtered and evaporated in vacuo to provide 1.2 g of off-white solid. The material is dissolved in 10 mL of DCM. This material is purified utilizing an ISCO Companion with a 40 g cartridge of silica. The gradient is 10% EtOAC in heptanes over 3 column volumes followed by a linear gradient to 50% over 10 column volumes and then 90% EtOAc for 2 column volumes with ramp of 1 column volume. 25 mL fractions of UV active eluent are collected. Fractions 9 through 15 are combined and evaporated in vacuo by pumping to a constant weight to give amorphous white solid (0.86 g, 83%).

Example 385

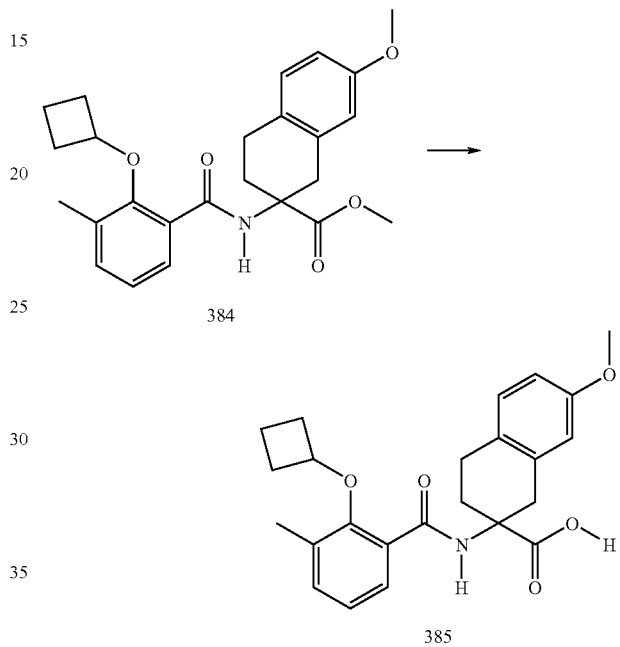

2-(2-cyclobutoxy-3-methyl-benzoylamino)-6-methoxy-[(5,6,7,8-tetrahydro-naphthalene-1-carbonyl)-2-carboxylic acid (385)

A 50 mL flask containing the 2-(2-cyclobutoxy-3-methyl-benzoylamino)-6-methoxy-[(5,6,7,8-tetrahydro-naphthalene-1-carbonyl)-2-carboxylic acid methyl ester (384, 0.45 g, 1.06 mmol) is charged with 1,4-dioxane (5 mL) and MeOH (5 mL). A stirring bar is added and stirring is initiated. After dissolution, water (2.5 mL) is added followed by the LiOH monohydrate (111 mg, 2.65 mmol). After 37 h, tlc analysis (silica, 5% i-PrOH/DCM) indicates that the starting material has been completely consumed. The pH of the reaction mixture is carefully adjusted to pH 2 by slowly adding dilute aqueous HCl (3%, ~10 mL). The contents of the flask are poured into a reparatory funnel containing EtOAc (30 mL). The layers are separated. The aqueous layer is extracted with EtOAc (20 mL). The combined organic extracts are washed with water (20 mL) and brine (20 mL), and then dried over MgSO$_4$, filtered and concentrated. Pumping to constant weight gives off-white solid (0.43 g, 99%).

$^1$H NMR (300 MHz, DMSO-d6): δ 1.18-1.33 (m, 1H), 1.41-1.57 (m, 1H), 1.79-2.11 (m, 4H), 2.21 (s, 3H), 2.37-2.43-(m, 1H), 2.63-2.91 (m, 2H), 3.07-3.37 (m, 3H), 3.41 (s, 3H), 4.37 (m, 1H), 6.69-6.72 (m, 2H), 7.00-7.05 (m, 2H), 7.26-7.35 (m, 2H), 8.31 (s, 1H), 12.49 (bs, 1H).
LC/MS m/z=410.15

Examples 386-389

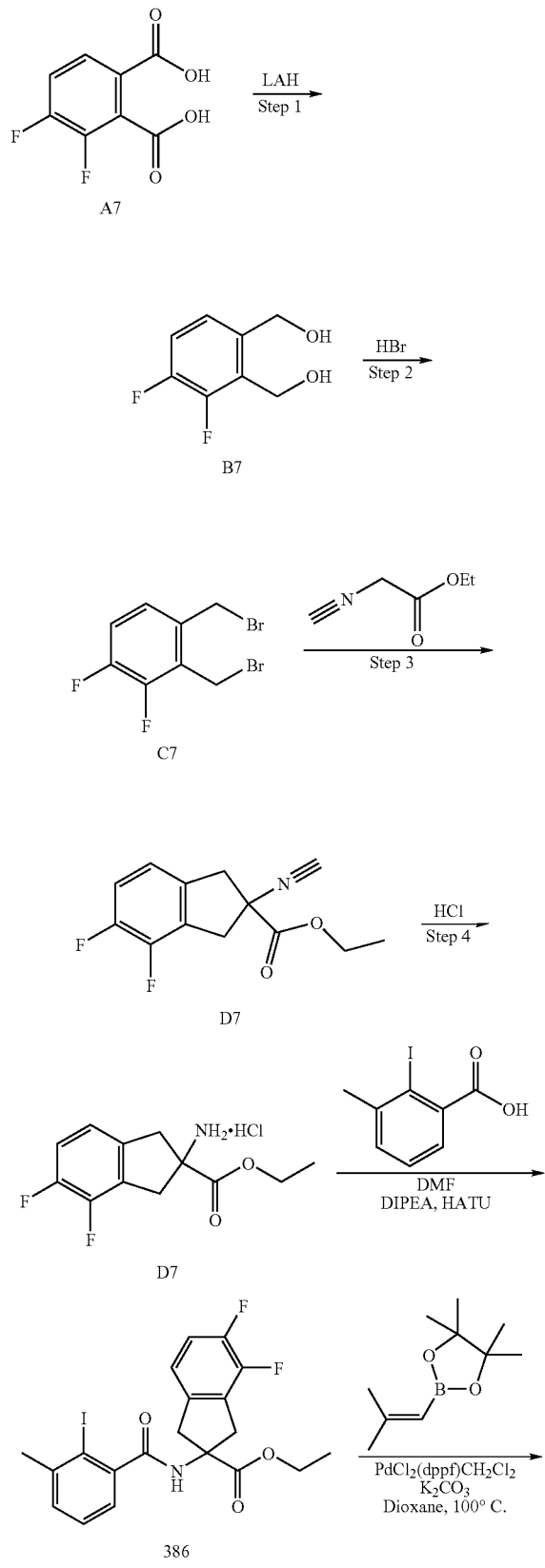

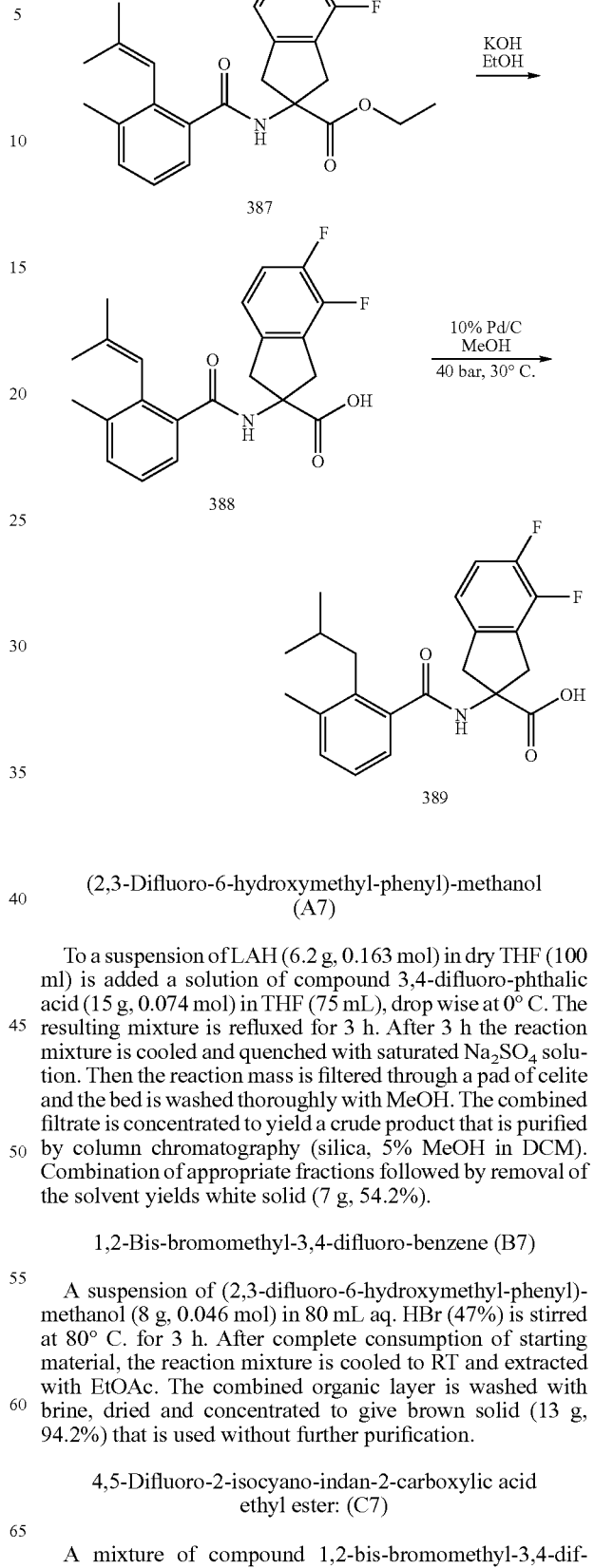

(2,3-Difluoro-6-hydroxymethyl-phenyl)-methanol (A7)

To a suspension of LAH (6.2 g, 0.163 mol) in dry THF (100 ml) is added a solution of compound 3,4-difluoro-phthalic acid (15 g, 0.074 mol) in THF (75 mL), drop wise at 0° C. The resulting mixture is refluxed for 3 h. After 3 h the reaction mixture is cooled and quenched with saturated $Na_2SO_4$ solution. Then the reaction mass is filtered through a pad of celite and the bed is washed thoroughly with MeOH. The combined filtrate is concentrated to yield a crude product that is purified by column chromatography (silica, 5% MeOH in DCM). Combination of appropriate fractions followed by removal of the solvent yields white solid (7 g, 54.2%).

1,2-Bis-bromomethyl-3,4-difluoro-benzene (B7)

A suspension of (2,3-difluoro-6-hydroxymethyl-phenyl)-methanol (8 g, 0.046 mol) in 80 mL aq. HBr (47%) is stirred at 80° C. for 3 h. After complete consumption of starting material, the reaction mixture is cooled to RT and extracted with EtOAc. The combined organic layer is washed with brine, dried and concentrated to give brown solid (13 g, 94.2%) that is used without further purification.

4,5-Difluoro-2-isocyano-indan-2-carboxylic acid ethyl ester: (C7)

A mixture of compound 1,2-bis-bromomethyl-3,4-difluoro-benzene (8 g, 0.027 mol), ethyl isocyanoacetate (3.01 g, 0.0266 mol), K$_2$CO$_3$ (22.07 g, 0.159 mol) and tetrabutylammonium hydrogen sulphate (5.45 g, 0.016 mol) in ACN (200 ml) is refluxed for overnight. After complete consumption of starting material the reaction mixture is cooled to RT and ACN is removed under reduced pressure. Water (300 mL) is added to the crude mass and then extracted with EtOAc (3×250 mL). The combined organic extracts are washed with water, dried and concentrated to give a crude product. The crude product is purified by column chromatography (silica, 3% EtOAc in hexane) and the solvent removed to give a viscous liquid (1.6 g, 23.7%).

4,5-Difluoro-2-amin-indan-2-carboxylic acid ethyl ester hydrochloride salt (D7)

A stirred solution of 4,5-difluoro-2-isocyano-indan-2-carboxylic acid ethyl ester (6 g, 0.0237 mol) in EtOH (100 mL) is immersed in an ice water bath and allowed to cool. After cooling, concentrated HCl (5 ml) is added. The reaction mixture is removed from the ice-water bath, allowed to come to ambient temperature and stirred at for 3 h. Then the reaction mixture is concentrated, diluted with water and extracted with ether (2×50 mL). The organic layer is discarded and the aqueous layer is cooled and pH is adjusted to 9-10 using aq. ammonia solution. The resulting solution is extracted with EtOAc (3×100 mL). The combined extracts are washed with water, dried and concentrated to give a viscous mass (4.5 g, 78%). This crude mass is immediately cooled to 5° C. and acidified with methanolic HCl and concentrated to give 4,5-difluoro-2-amin-indan-2-carboxylic acid ethyl ester hydrochloride salt.

4,5-Difluoro-2-(2-iodo-3-methyl-benzoylamino)-indan-2-carboxylic acid ethyl ester (386)

To a solution of 2-iodo-3-methyl-benzoic acid (1.31 g, 5 mmol), 2-amino-4,5-difluoro-indan-2-carboxylic acid ethyl ester HCl salt (D7, 1.38 g, 5 mmol), HATU [O-(7-Azabenzotriazol-1-yl)-N,N,N',N'-tetramethyluronium PF6, 3.8 g, 10 mmol) in anhydrous DMF (20 mL) is added DIPEA (N,N-diisopropylethylamine, 3.3 mL, 15 mmol). The resulting solution is stirred at room temperature for two days. After the removal of DMF in vacuo, the residue obtained is dissolved in ethyl acetate (200 mL) and washed with saturated NaHCO$_3$ (1×100 mL) and brine (2×100 mL). The organic layer is dried over anhydrous Na$_2$SO$_4$ and concentrated in vacuo. The obtained residue is purified by flash column chromatography (24 g silica gel, gradient elution: 0%-50% EtOAc in heptane) to give a pure product (386) as white solid (1.93 g, 79%).

$^1$H NMR (DMSO-d6, 300 MHz): δ 1.15 (t, 3H), 1.20 (s, 3H), 3.24 (d, 2H), 3.48 (d, 2H), 4.25 (m, 2H), 7.13-7.30 (m, 3H), 7.52 (m, 2H)

LC/MS (ES+) m/z=486.1

4,5-Difluoro-2-[3-methyl-2-(2-methyl-propenyl)-benzoylamino]-indan-2-carboxylic acid ethyl ester (387)

To a solution of 6-(4,5-difluoro-2-(2-iodo-3-methyl-benzoylamino)-indan-2-carboxylic acid ethyl ester (386) (2.55 g, 5.25 mmol) and 2-methyl-1-propenyl boronic acid pinacol ester (364 mg, 10.5 mmol) in dioxane (100 mL) is added dichloro[1,1'-bis(diphenylphosphino)ferrocene]palladium (II) dichloromethane adduct (350 mg, 8.2% mmol) and 2M aqueous solution of K$_2$CO$_3$ (7.87 mL, 15.75 mmol). The resulting reaction mixture is filled in with N$_2$, heated to 100° C. and stirred continuously for 6 h. Reaction mixture is filtered and concentrated in vacuo, and the resulting residue is purified by flash column chromatography (12 g silica gel, gradient elution: 0%-50% EtOAc in heptane) to give a pure product (387) as light brown solid (1.24 g, 57%).

$^1$H NMR (DMSO-d6, 300 MHz): δ 1.10 (t, 3H), 1.16 (s, 3H), 1.66 (s, 3H), 2.12 (s, 3H), 3.24 (d, 2H), 3.48 (d, 2H), 4.25 (m, 2H), 6.06 (s, 1H), 7.13-7.30 (m, 3H), 7.52 (m, 2H)

LC/MS (ES+) m/z=414.47

4,5-Difluoro-2-[3-methyl-2-(2-methyl-propenyl)-benzoylamino]-indan-2-carboxylic acid (388)

4,5-Difluoro-2-[3-methyl-2-(2-methyl-propenyl)-benzoylamino]-indan-2-carboxylic acid ethyl ester (387) (650 mg, 1.57 mmol) is dissolved in EtOH (50 mL) and set to stir at RT. To this solution is added 5M KOH (4 mL). The reaction mixture is stirred at RT overnight. After concentration in vacuo, the residue obtained is dissolved in water (20 mL) and washed with EtOAc (20 mL). The phases are separated and the aqueous phase is acidified with concentrated HCl to pH 2. The solid precipitate is collected via filtration, dried under vacuum, and then purified on an HPLC. The desired product (388) is obtained as white solid (440.0 mg, 73%).

$^1$H NMR (DMSO-d6, 300 MHz): δ 1.16 (s, 3H), 1.66 (s, 3H), 2.12 (s, 3H), 3.24 (d, 2H), 3.48 (d, 2H), 6.06 (s, 1H), 7.08-7.36 (m, 5H)

LC/MS (ES+) m/z=386.3

4,5-Difluoro-2-(2-isobutyl-3-methyl-benzoylamino)-indan-2-carboxylic acid (389)

A solution of 4,5-difluoro-2-[3-methyl-2-(2-methyl-propenyl)-benzoylamino]-indan-2-carboxylic acid (388) (220 mg, 0.57 mmol) in methanol (40 mL) is hydrogenated using 10% palladium/carbon catalyst at 40 bar and 30° C. using the Thales nanotechnology H-Cube for 24 hours. The methanol is concentrated to dryness in vacuo to give the product (389) as white solid powder.

$^1$H NMR (DMSO-d6, 300 MHz): δ 0.77 (d, 6H), 1.74 (m, 1H), 2.27 (s, 3H), 2.62 (d, 2H), 3.31 (d, 2H), 3.48 (d, 2H), 7.00-7.39 (m, 5H)

LC/MS (ES+) m/z=388.3

Examples 390-393

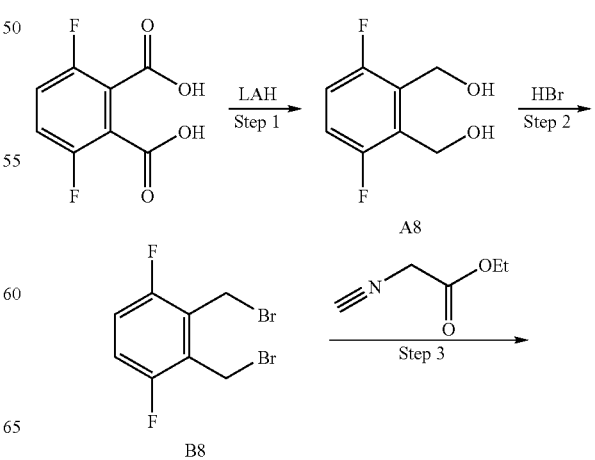

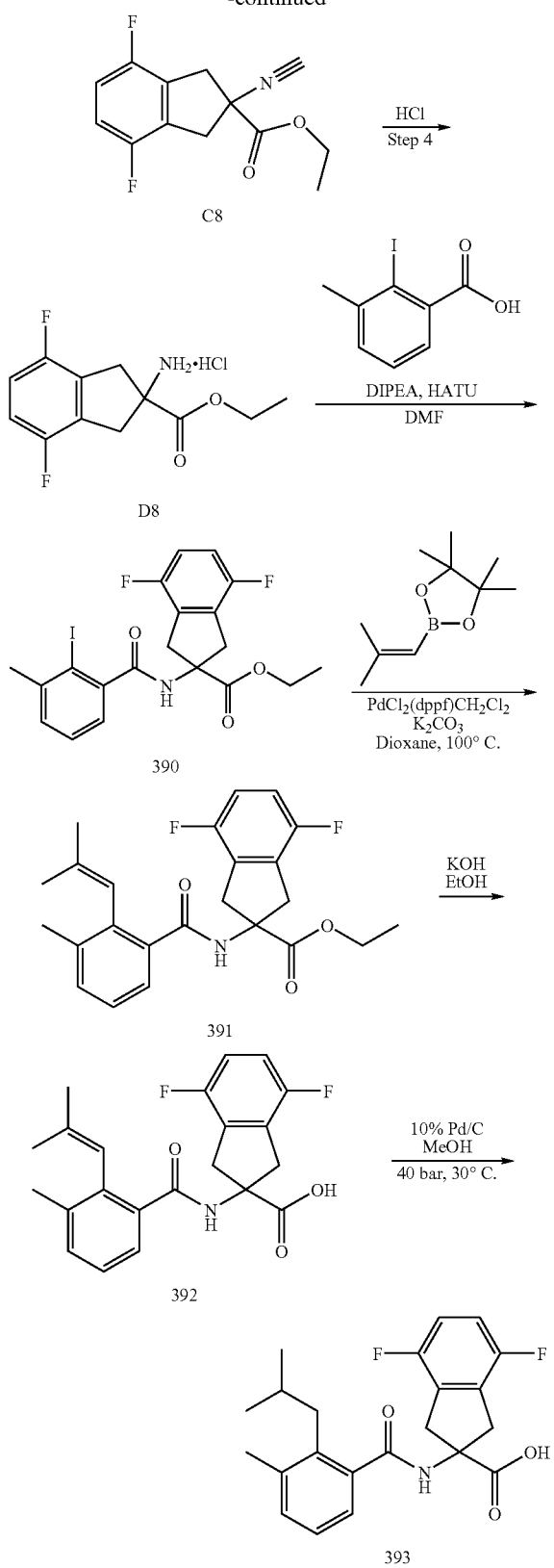

same procedures as for the synthesis of 2-amino-4,5-difluoro-indan-2-carboxylic acid ethyl ester HCl salt.

4,7-Difluoro-2-(2-iodo-3-methyl-benzoylamino)-indan-2-carboxylic acid ethyl ester (390)

To a solution of 2-iodo-3-methyl-benzoic acid (1.31 g, 5 mmol), 2-amino-4,7-difluoro-indan-2-carboxylic acid ethyl ester HCl salt (1.38 g, 5 mmol), HATU [O-(7-Azabenzotriazol-1-yl)-N,N,N',N'-tetramethyluronium PF6, 3.80 g, 10 mmol) in anhydrous DMF (20 mL) is added DIPEA (N,N-diisopropylethylamine, 3.3 mL, 15 mmol). The resulting solution is stirred at RT for two days. After the removal of DMF in vacuo, the residue obtained is dissolved in EtOAc (200 mL) and washed with saturated $NaHCO_3$ (1×100 mL) and brine (2×100 mL). The organic layer is dried over anhydrous $Na_2SO_4$ and concentrated in vacuo. The obtained residue is purified by flash column chromatography (40 g silica gel, gradient elution: 0%-50% EtOAc in heptane) to give a pure product (390) as white solid (1.83 g, 75%).

$^1$H NMR (DMSO-d6, 300 MHz): δ 1.15 (t, 3H), 1.20 (s, 3H), 3.24 (d, 2H), 3.48 (d, 2H), 4.25 (m, 2H), 7.13-7.30 (m, 5H)

LC/MS (ES+) m/z=486.1

4,7-Difluoro-2-[3-methyl-2-(2-methyl-propenyl)-benzoylamino]-indan-2-carboxylic acid ethyl ester (391)

To a solution of 4,7-difluoro-2-(2-iodo-3-methyl-benzoylamino)-indan-2-carboxylic acid ethyl ester (390) (451 mg, 1 mmol) and 2-methyl-1-propenyl boronic acid pinacol ester (364 mg, 2 mmol) in dioxane (20 mL) was added dichloro[1,1'-bis(diphenylphosphino)-ferrocene]palladium (II) dichloromethane adduct (65 mg, 8.2% mmol) and 2M aqueous solution of $K_2CO_3$ (1.5 mL, 3 mmol). The resulting reaction mixture is filled in with $N_2$, heated to 100° C. and stirred continuously for 4 h. The reaction mixture is filtered and concentrated in vacuo, and the resulting residue is purified by flash column chromatography (12 g silica gel, gradient elution: 0%-50% EtOAc in heptane) to give a pure product (391) as light brown oil (150 mg, 36%).

$^1$H NMR (DMSO-d6, 300 MHz): δ 1.10 (t, 3H), 1.16 (s, 3H), 1.66 (s, 3H), 2.12 (s, 3H), 3.24 (d, 2H), 3.48 (d, 2H), 4.25 (m, 2H), 6.06 (s, 1H), 7.13-7.30 (m, 5H)

LC/MS (ES+) m/z=414.47

4,7-Difluoro-2-[3-methyl-2-(2-methyl-propenyl)-benzoylamino]-indan-2-carboxylic acid (392)

4,7-Difluoro-2-[3-methyl-2-(2-methyl-propenyl)-benzoylamino]-indan-2-carboxylic acid ethyl ester (391) (133 mg, 0.32 mmol) is dissolved in EtOH (20 mL) and set to stir at RT. To this solution was added 5M KOH (2 ml). The reaction mixture was stirred at RT. After concentration in vacuo, the residue obtained is dissolved in water (20 mL) and washed with EtOAc (20 mL). The phases are separated and the aqueous phase is acidified with concentrated HCl to pH 2. The aqueous phase is washed with 100 mL EtOAc. The organic phases were collected, concentrated to dryness, and then the resulting residue is purified on an HPLC. The desired product (392) is obtained as white solid (38 mg, 28%).

$^1$H NMR (DMSO-d6, 300 MHz): δ 1.21 (s, 3H), 1.66 (s, 3H), 2.12 (s, 3H), 3.24 (d, 2H), 3.48 (d, 2H), 6.06 (s, 1H), 7.08-7.36 (m, 5H)

LC/MS (ES+) m/z=386.3

2-Amino-4,7-difluoro-indan-2-carboxylic acid ethyl ester HCl salt was prepared from 3,6-difluoro-phthalic acid as indicated by the scheme above regarding A7-D7 utilizing the

4,7-Difluoro-2-(2-isobutyl-3-methyl-benzoylamino)-indan-2-carboxylic acid (393)

A solution of 4,7-difluoro-2-[3-methyl-2-(2-methyl-propenyl)-benzoylamino]-indan-2-carboxylic acid (392) (82 mg, 0.21 mmol) in MeOH (40 mL) is hydrogenated using 10% palladium/carbon catalyst at 40 bar and 30° C. using the Thales nanotechnology H-Cube for 5 h. The MeOH is concentrated to dryness in vacuo to give the product (393) as white solid powder.

$^1$H NMR (DMSO-d6, 300 MHz): δ 0.76 (d, 6H), 1.72 (m, 1H), 2.28 (s, 3H), 2.61 (d, 2H), 3.42 (d, 2H), 3.51 (d, 2H), 6.93-7.30 (m, 5H)

LC/MS (ES+) m/z=388.3

Examples 394-395

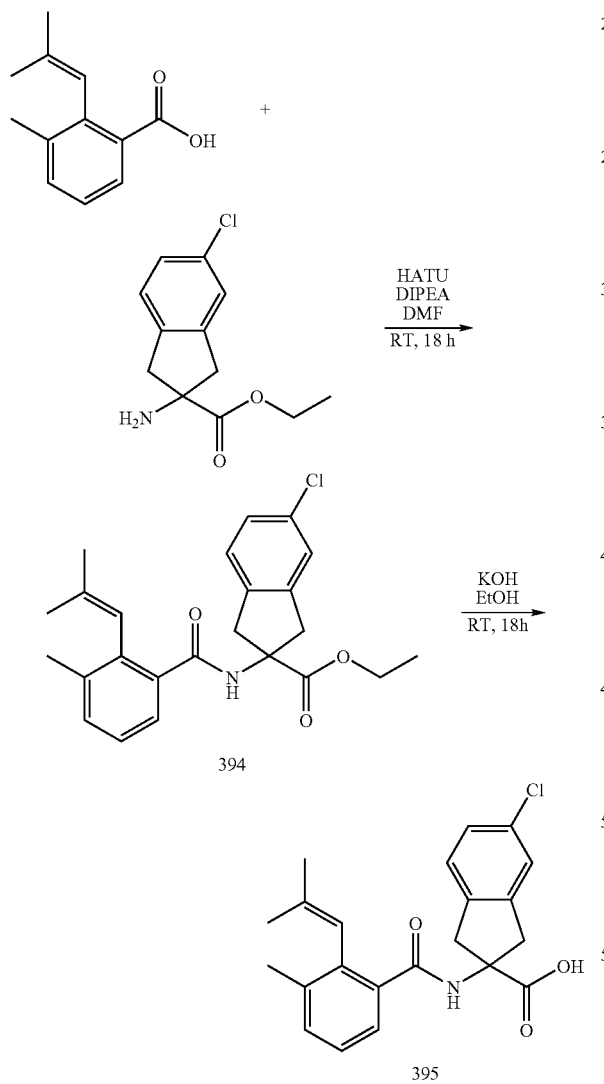

394

395

5-Chloro-2-[3-methyl-2-(2-methyl-propenyl)-benzoylamino]-indan-2-carboxylic acid ethyl ester (394)

To a solution of 3-methyl-2-(2-methyl-propenyl)-benzoic acid (95 mg, 0.50 mmol), 5-chloro-2-[3-methyl-2-(2-methyl-propenyl)-benzoylamino]-indan-2-carboxylic acid ethyl ester (120 mg, 0.5 mmol), HATU [O-(7-azabenzotriazol-1-yl)-N,N,N',N'-tetramethyluronium PF6, 380 mg, 1 mmol) in anhydrous DMF (10 mL) is added DIPEA (N,N-diisopropylethylamine, 0.25 mL, 1.5 mmol). The resulting solution is stirred at RT for 18 h. After the removal of DMF in vacuo, the resulting residue is dissolved in EtOAc (200 mL) and washed with saturated NaHCO$_3$ (1×100 mL) and brine (2×100 mL). The organic layer is dried over anhydrous Na$_2$SO$_4$ and concentrated in vacuo. The resulting residue is purified by flash column chromatography (40 g silica gel, gradient elution: 0%-50% EtOAc in heptane) to give a pure product (394) as white solid (120 mg, 58%).

$^1$H NMR (d-DMSO, 300 MHz): δ 1.10 (t, 3H), 1.16 (s, 3H), 1.66 (s, 3H), 2.12 (s, 3H), 3.24 (d, 2H), 3.48 (d, 2H), 4.25 (m, 2H), 6.06 (s, 1H), 7.13-7.30 (m, 6H)

LC/MS (ES+) m/z=411.93

5-Chloro-2-[3-methyl-2-(2-methyl-propenyl)-benzoylamino]-indan-2-carboxylic acid (395)

5-Chloro-2-[3-methyl-2-(2-methyl-propenyl)-benzoylamino]-indan-2-carboxylic acid ethyl ester (394) (120 mg, 0.3 mmol) is dissolved in EtOH (20 mL) and set to stir at RT. To this solution is added 5M KOH (2 mL). The reaction mixture is stirred at RT overnight. After concentration in vacuo, the resulting residue is dissolved in water (20 mL) and washed with EtOAc (20 mL). The phases are separated and the aqueous phase is acidified with concentrated HCl to pH 2. The aqueous phase is washed with 100 mL EtOAc. The organic phases are collected, concentrated to dryness, and then the resulting residue is purified on an HPLC. The desired product (395) is obtained as white solid (73 mg, 63%).

$^1$H NMR (d-DMSO, 300 MHz): δ 1.21 (s, 3H), 1.66 (s, 3H), 2.12 (s, 3H), 3.24 (d, 2H), 3.48 (d, 2H), 6.06 (s, 1H), 7.08-7.36 (m, 6H)

LC/MS (ES+) m/z=383.88

Examples 396-397

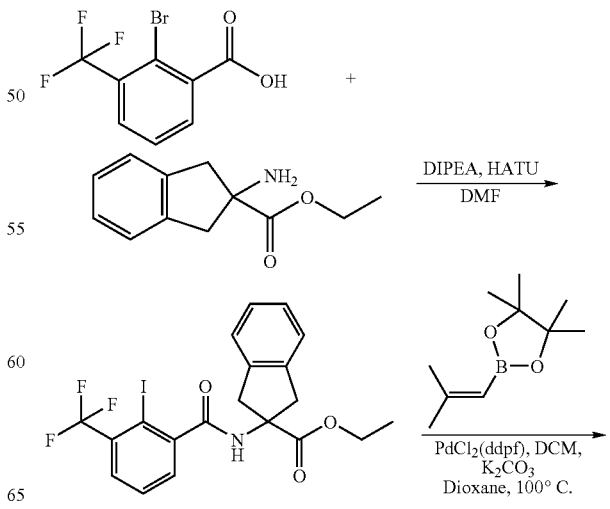

A8

-continued

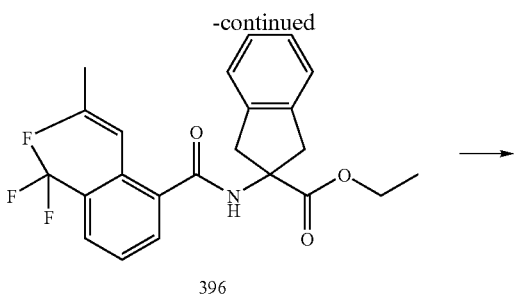

396

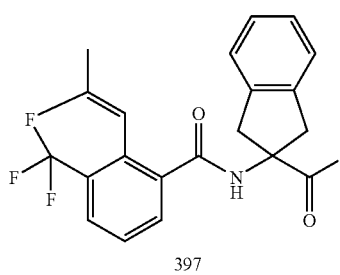

397

2-(2-Iodo-3-trifluoromethyl-benzoylamino)-indan-2-carboxylic acid ethyl ester (A8)

To a solution of 2-bromo-3-(trifluoromethyl)benzoic acid (5 g, 18.59 mmol), 2-amino-indan-2-carboxylic acid ethyl ester (3.82 g, 18.59 mmol), HATU (14.14 g, 37.19 mmol) in anhydrous DMF (75 mL) is added DIPEA (6.15 mL, 37.19 mmol). The resulting solution is stirred at RT overnight. After the removal of DMF in vacuo, the resulting residue is dissolved in EtOAc (100 mL) and washed with saturated NaHCO$_3$ (1×100 mL) and brine (2×100 mL). The organic layer is dried over anhydrous Na$_2$SO$_4$ and concentrated in vacuo. The obtained residue is purified by flash column chromatography (115 g silica gel, gradient elution: 0%-50% ethyl acetate in heptane) to give a pure product (A8) as a light brown solid (4.9 g, 58%).

$^1$H NMR (d-DMSO, 300 MHz): 1.15 (t, 3H), 1.20 (s, 3H), 3.24 (d, 2H), 3.48 (d, 2H), 4.25 (m, 2H), 0.12-7.28 (m, 4H), 7.55 (m, 2H), 7.75 (d, 1H)

LC/MS (ES+) m/z=455.1

2-[2-(2-Methyl-propenyl)-3-trifluoromethyl-benzoylamino]-indan-2-carboxylic acid ethyl ester (396)

To a solution of 42-(2-Iodo-3-trifluoromethyl-benzoylamino)-indan-2-carboxylic acid ethyl ester (A8) (500 mg, 1.10 mmol) and 2-methyl-1-propenyl boronic acid pinacol ester (400 mg, 2.20 mmol) in dioxane (20 mL) is added dichloro[1,1'-bis(diphenylphosphino)ferrocene]-palladium (II) DCM adduct (71.8 mg, 8.2% mmol) and 2M aqueous solution of K$_2$CO$_3$ (1.65 mL, 3.30 mmol). The resulting reaction mixture is filled in with N$_2$, heated to 100° C. and stirred continuously overnight. Reaction mixture is filtered and concentrated in vacuo, and the resulting residue is purified by flash column chromatography (12 g silica gel, gradient elution: 0%-50% EtOAc in heptane) to give a pure product (396) as light brown oil (100 mg, 21%).

$^1$H NMR (d-DMSO, 300 MHz): 1.10 (t, 3H), 1.66 (s, 3H), 2.12 (s, 3H), 3.24 (d, 2H), 3.48 (d, 2H), 4.25 (m, 2H), 6.06 (s, 1H), 0.12-7.28 (m, 4H), 7.55 (m, 2H), 7.75 (d, 1H)

LC/MS (ES+) m/z=431.27

2-[2-(2-Methyl-propenyl)-3-trifluoromethyl-benzoylamino]-indan-2-carboxylic acid (397)

2-[2-(2-Methyl-propenyl)-3-trifluoromethyl-benzoylamino]-indan-2-carboxylic acid ethyl ester (2) (100 mg, 0.32 mmol) is dissolved in EtOH (20 mL) and set to stir at RT. To this solution is added 5M KOH (2 mL). The reaction mixture is heated to reflux and stirred for 1 h. After concentration in vacuo, the resulting residue is dissolved in water (10 mL) and washed with EtOAc (20 mL). The phases are separated and the aqueous phase is acidified with concentrated HCl to pH 2. The aqueous phase is washed with 50 mL ether (3×). Organic phases are collected, concentrated to dryness, then the resulting residue is purified on an HPLC. The desired product (397) is obtained as white solid (40.0 mg, 43%).

$^1$H NMR (d-DMSO, 300 MHz): 1.21 (s, 3H), 1.66 (s, 3H), 2.12 (s, 3H), 3.24 (d, 2H), 3.48 (d, 2H), 6.06 (s, 1H), 7.12-7.28 (m, 4H), 7.55 (m, 2H), 7.75 (d, 1H)

LC/MS (ES+) m/z=403.13

What is claimed is:
1. A compound of the formula Ia

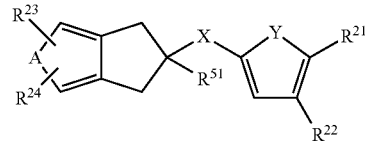

wherein:
A is CH=CH;
$R^{23}$ is hydrogen, halogen, $(C_1-C_4)$-alkyl, or $(C_1-C_4)$-alkyloxy;
$R^{24}$ is hydrogen or halogen;
X is N(H)C=O;
Y is $C(R^{12})=C(R^{13})$;
$R^{12}$ is $(C_1-C_6)$-alkyl, $(C_3-C_6)$-alkenyl, $(C_4-C_6)$-cycloalkyloxy, $(C_5-C_6)$-cycloalkyl, $(C_5-C_6)$-cycloalkenyl, $(C_3)$-cycloalkyl[$(C_2)$-alkyl or $(C_2)$-alkenyl], $(C_3)$-cycloalkyl$(C_1)$-alkyloxy, $(C_3-C_4)$-alkyloxy, $(C_3)$-alkenyloxy, $(C_1-C_3)$-alkyl-S—, or $(C_3)$-alkylcarbonyl;
$R^{13}$ is hydrogen, halogen, or $(C_1)$-alkyl;
$R^{21}$ is hydrogen;
$R^{22}$ is hydrogen, halogen, or $(C_1)$-alkyl; and
$R^{51}$ is COOH;
wherein all alkyl groups herein can independently of each other be optionally substituted by one or more fluorine atoms; or
a pharmaceutically acceptable ester thereof, a stereoisomeric form thereof, mixture of stereoisomeric forms thereof in any ratio, or a physiologically acceptable salt thereof.
2. The compound according to claim 1 wherein $R^{23}$ is hydrogen or halogen.
3. The compound according to claim 1 wherein $R^{12}$ is $(C_4-C_6)$-alkyl.
4. The compound according to claim 1 wherein $R^{12}$ is $(C_4)$-alkenyl.
5. The compound according to claim 1 wherein $R^{12}$ is $(C_4)$-cycloalkyloxy.

6. The compound according to claim 1 wherein $R^{12}$ is $(C_5-C_6)$-cycloalkyl.

7. The compound according to claim 1 wherein $R^{12}$ is $(C_5-C_6)$-cycloalkenyl.

8. The compound according to claim 1 wherein $R^{12}$ is $(C_3)$-cycloalkyl[$(C_2)$-alkyl or $(C_2)$-alkenyl].

9. The compound according to claim 1 wherein $R^{12}$ is $(C_3)$-cycloalkyl$(C_1)$-alkyloxy.

10. The compound according to claim 1 wherein $R^{12}$ is $(C_3-C_4)$-alkyloxy.

11. The compound according to claim 1 wherein $R^{12}$ is $(C_3)$-alkenyloxy.

12. The compound according to claim 1 wherein $R^{13}$ is halogen or $(C_1)$-alkyl.

13. The compound according to claim 1 wherein $R^{13}$ is $(C_1)$-alkyl wherein the alkyl is optionally substituted by 1-3 fluorine atoms.

14. The compound according to claim 1 wherein $R^{13}$ is unsubstituted $(C_1)$-alkyl.

15. The compound according to claim 1 wherein $R^{13}$ is $(C_1)$-alkyl that is substituted by 2-3 fluorine atoms.

16. The compound according to claim 1 wherein $R^{13}$ is halogen.

17. The compound (with Example number indicated parenthetically) according to claim 1 selected from:
- 2-(2-Allyloxy-3-methyl-benzoylamino)-indan-2-carboxylic acid (5),
- 2-(2-Isopropoxy-3-methyl-benzoylamino)-indan-2-carboxylic acid (7),
- 2-(2-Cyclobutoxy-3-methyl-benzoylamino)-indan-2-carboxylic acid (9),
- 2-(2-Cyclopropylmethoxy-3-methyl-benzoylamino)-indan-2-carboxylic acid (11),
- 2-(2-sec-Butoxy-3-methyl-benzoylamino)-indan-2-carboxylic acid (13),
- 2-(3-Chloro-2-isopropoxy-benzoylamino)-indan-2-carboxylic acid (16),
- 2-(2-Allyloxy-3-chloro-benzoylamino)-indan-2-carboxylic acid (18),
- 2-(3,5-Dichloro-2-cyclobutoxy-benzoylamino)-5-fluoro-indan-2-carboxylic acid (21),
- 2-(2-Isopropoxy-3-methyl-benzoylamino)-5-methoxy-indan-2-carboxylic acid (93),
- 2-(2-Isopropoxy-3-methyl-benzoylamino)-5-trifluoromethyl-indan-2-carboxylic acid (95),
- 5-Fluoro-2-(2-isopropoxy-3-methyl-benzoylamino)-indan-2-carboxylic acid (97),
- 2-(2-Cyclobutoxy-3-methyl-benzoylamino)-5-trifluoro-indan-2-carboxylic acid (99),
- 5-Bromo-2-(2-cyclobutoxy-3-methyl-benzoylamino)-indan-2-carboxylic acid (101),
- 2-(2-Cyclobutoxy-3-methyl-benzoylamino)-5-fluoro-indan-2-carboxylic acid (103),
- 2-(2-Cyclobutoxy-3-methyl-benzoylamino)-5,6-difluoro-indan-2-carboxylic acid (105),
- 2-[3-Methyl-2-((Z)-pent-1-enyl)-benzoylamino]-indan-2-carboxylic acid (125),
- 2-(3-Methyl-2-pentyl-benzoylamino)-indan-2-carboxylic acid (127),
- 2-[2-(-1-Ethyl-but-1-enyl)-3-methyl-benzoylamino]-indan-2-carboxylic acid (129),
- 2-[2-(1-Ethyl-butyl)-3-methyl-benzoylamino]-indan-2-carboxylic acid (130),
- 2-(Cyclopent-1-enyl-3-methyl-benzoylamino)-indan-2-carboxylic acid (132),
- 2-(2-Cyclopentyl-3-methyl-benzoylamino)-indan-2-carboxylic acid (133),
- 2-[3-Methyl-2-(2-methyl-propenyl)-benzoylamino]-indan-2-carboxylic acid (135),
- 2-(2-Isobutyl-3-methyl-benzoylamino)-indan-2-carboxylic acid (136),
- 2-[2-(-2-Cyclopropyl-vinyl)-3-methyl-benzoylamino]-indan-2-carboxylic acid (138),
- 2-[2-(2-Cyclopropyl-ethyl)-3-methyl-benzoylamino]-indan-2-carboxylic acid (139),
- 2-(2-Cyclohex-1-enyl-3-methyl-benzoylamino)-indan-2-carboxylic acid (141),
- 2-[3-Methyl-2-(1-propenyl)-benzoylamino]-indan-2-carboxylic acid (143),
- 2-(3-Methyl-2-propyl-benzoylamino)-indan-2-carboxylic acid (144),
- 2-[3-Methyl-2-((E)-pent-1-enyl)-benzoylamino]-indan-2-carboxylic acid (146),
- 5-Fluoro-2-[3-methyl-2-(2-methyl-propenyl)-benzoylamino]-indan-2-carboxylic acid (149),
- 5-Fluoro-2-(2-isobutyl-3-methyl-benzoylamino)-indan-2-carboxylic acid (150, 155),
- 2-(2-Cyclopent-1-enyl-3-methyl-benzoylamino)-5-fluoro-indan-2-carboxylic acid (152),
- 5-Fluoro-2-[3-methyl-2-((E)-propenyl)-benzoylamino]-indan-2-carboxylic acid (154),
- 5,6-Difluoro-2-[3-methyl-2-(2-methyl-propenyl)-benzoylamino]-indan-2-carboxylic acid (158),
- 5,6-Difluoro-2-(2-isobutyl-3-methyl-benzoylamino)-indan-2-carboxylic acid (159),
- 5,6-Difluoro-2-(3-methyl-2-propenyl-benzoylamino)-indan-2-carboxylic acid (160),
- 5,6-Difluoro-2-(3-methyl-2-propyl-benzoylamino)-indan-2-carboxylic acid (161),
- 5-Bromo-2-[3-methyl-2-((E)-propenyl)-benzoylamino]-indan-2-carboxylic acid (163),
- 2-(5-Chloro-2-cyclobutoxy-3-methyl-benzoylamino)-indan-2-carboxylic acid (212),
- 2-(2-Isobutyryl-3-methyl-benzoylamino)-indan-2-carboxylic acid (229),
- 2-[2-(1,1-Dimethyl-propyl)-benzoylamino]-indan-2-carboxylic acid (248),
- 2-(2-Cyclobutoxy-3-methyl-benzoylamino)-4,5-dichloro-indan-2-carboxylic acid (256),
- 2-(2-Cyclobutoxy-3-methyl-benzoylamino)-5-chloro-indan-2-carboxylic acid (262),
- 2-(2-Cyclobutoxy-3-methyl-benzoylamino)-4-fluoro-indan-2-carboxylic acid (267),
- 5-Bromo-2-(2-cyclobutoxy-3-methyl-benzoylamino)-indan-2-carboxylic acid (319),
- 2-(2-Isopropylsulfanyl-benzoylamino)-indan-2-carboxylic acid (327),
- 2-(5-Chloro-2-cyclobutoxy-3-methyl-benzoylamino)-5-fluoro-indan-2-carboxylic acid (329),
- 4,5-Difluoro-2-[3-methyl-2-(2-methyl-propenyl)-benzoylamino]-indan-2-carboxylic acid (388),
- 4,5-Difluoro-2-(2-isobutyl-3-methyl-benzoylamino)-indan-2-carboxylic acid (389),
- 4,7-Difluoro-2-[3-methyl-2-(2-methyl-propenyl)-benzoylamino]-indan-2-carboxylic acid (392),
- 4,7-Difluoro-2-(2-isobutyl-3-methyl-benzoylamino)-indan-2-carboxylic acid (393),
- 5-Chloro-2-[3-methyl-2-(2-methyl-propenyl)-benzoylamino]-indan-2-carboxylic acid (395), and
- 2-[2-(2-Methyl-propenyl)-3-trifluoromethyl-benzoylamino]-indan-2-carboxylic acid (397), or a pharmaceutically acceptable ester thereof, a stereoisomeric form thereof, mixture of stereoisomeric forms thereof in any ratio, or a physiologically acceptable salt thereof.

18. The compound according to claim 1 of the following structure

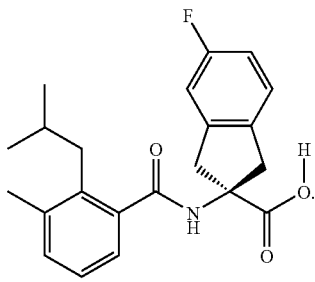

19. The compound according to claim 1 of the following structure

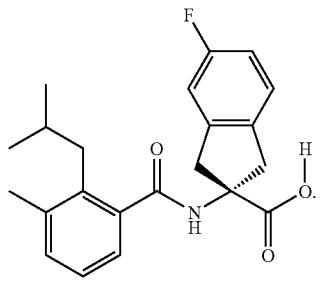

20. A pharmaceutical composition comprising a pharmaceutically acceptable amount of a compound according to claim 1 and at least one of a pharmaceutically acceptable excipient and pharmaceutically acceptable carrier.

* * * * *